(12) United States Patent
Sampson et al.

(10) Patent No.: US 10,358,436 B2
(45) Date of Patent: *Jul. 23, 2019

(54) KINASE INHIBITORS AND METHOD OF TREATING CANCER

(71) Applicant: University Health Network, Toronto (CA)

(72) Inventors: Peter Brent Sampson, Oakville (CA); Yong Liu, Oakville (CA); Sze-Wan Li, Toronto (CA); Bryan T. Forrest, Burlington (CA); Heinz W. Pauls, Oakville (CA); Louise G. Edwards, Mississauga (CA); Miklos Feher, New York, NY (US); Narendra Kumar B. Patel, Brampton (CA); Radoslaw Laufer, Oakville (CA)

(73) Assignee: University Health Network, Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/902,143

(22) Filed: Feb. 22, 2018

(65) Prior Publication Data

US 2018/0282306 A1 Oct. 4, 2018

Related U.S. Application Data

(60) Continuation of application No. 14/823,057, filed on Aug. 11, 2015, now Pat. No. 9,907,800, which is a continuation of application No. 13/935,021, filed on Jul. 3, 2013, now Pat. No. 9,139,563, which is a continuation of application No. 13/529,542, filed on Jun. 21, 2012, now Pat. No. 8,481,533, which is a division of application No. 13/081,254, filed on Apr. 6, 2011, now Pat. No. 8,263,596.

(60) Provisional application No. 61/321,332, filed on Apr. 6, 2010, provisional application No. 61/321,329, filed on Apr. 6, 2010.

(51) Int. Cl.
| | |
|---|---|
| *A61K 31/5377* | (2006.01) |
| *C07D 403/10* | (2006.01) |
| *C07D 403/04* | (2006.01) |
| *C07D 413/14* | (2006.01) |
| *C07D 231/56* | (2006.01) |
| *C07D 403/14* | (2006.01) |
| *A61K 45/06* | (2006.01) |

(52) U.S. Cl.
CPC ........ *C07D 403/10* (2013.01); *A61K 31/5377* (2013.01); *A61K 45/06* (2013.01); *C07D 231/56* (2013.01); *C07D 403/04* (2013.01); *C07D 403/14* (2013.01); *C07D 413/14* (2013.01)

(58) Field of Classification Search
None
See application file for complete search history.

(56) References Cited

U.S. PATENT DOCUMENTS

| | | |
|---|---|---|
| 4,642,309 A | 2/1987 | Michel et al. |
| 5,182,397 A | 1/1993 | Condon et al. |
| 6,506,763 B2 | 1/2003 | Tang et al. |
| 7,148,249 B2 | 12/2006 | Kley et al. |
| 7,205,328 B2 | 4/2007 | He et al. |
| 7,429,609 B2 | 9/2008 | Ohi et al. |
| 7,511,059 B2 | 3/2009 | Schulze et al. |
| 8,263,596 B2 | 9/2012 | Sampson et al. |
| 8,318,727 B2 | 11/2012 | Cao et al. |
| 8,481,525 B2 | 7/2013 | Sampson et al. |
| 8,481,533 B2 | 7/2013 | Sampson et al. |
| 8,765,748 B2 | 7/2014 | Pauls et al. |
| 8,921,545 B2 | 12/2014 | Cumming et al. |
| 8,933,070 B2 | 1/2015 | Pan et al. |
| 8,999,968 B2 | 4/2015 | Sampson et al. |
| 9,139,563 B2 | 9/2015 | Sampson et al. |
| 9,402,828 B2 | 8/2016 | Pan et al. |
| 9,579,327 B2 | 2/2017 | Cumming et al. |
| 9,642,856 B2 | 5/2017 | Hedley et al. |
| 9,796,703 B2 | 10/2017 | Cumming et al. |
| 9,884,855 B2 | 2/2018 | Sampson et al. |
| 2007/0135509 A1 | 6/2007 | Blackburn et al. |
| 2009/0054397 A1 | 2/2009 | Ohi et al. |

(Continued)

FOREIGN PATENT DOCUMENTS

| | | |
|---|---|---|
| CA | 2383623 A1 | 2/2000 |
| CA | 2498791 A1 | 4/2004 |

(Continued)

OTHER PUBLICATIONS

US 9,555,042 B2, 01/2017, Hedley et al. (withdrawn)

(Continued)

*Primary Examiner* — Samantha L Shterengarts
(74) *Attorney, Agent, or Firm* — McCarter & English, LLP; Steven G. Davis; Wei Song

(57) ABSTRACT

The invention is directed to a compound represented by the following structural formula and pharmaceutically acceptable salts thereof:

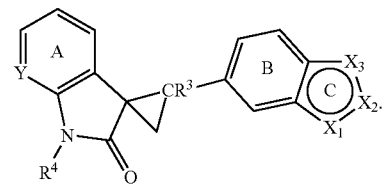

Compounds represented by this structural formula are kinase inhibitors and are therefore disclosed herein for the treatment of cancer. Definitions for the variables in the structural formula are provided herein.

6 Claims, 2 Drawing Sheets

(56) References Cited

U.S. PATENT DOCUMENTS

| | | |
|---|---|---|
| 2010/0016421 A1 | 1/2010 | Burger et al. |
| 2011/0065702 A1 | 3/2011 | Pauls et al. |
| 2011/0263598 A1 | 10/2011 | Sampson et al. |
| 2012/0149686 A1 | 6/2012 | Sampson et al. |
| 2012/0264800 A1 | 10/2012 | Sampson et al. |
| 2013/0096301 A1 | 4/2013 | Cumming et al. |
| 2013/0123273 A1 | 5/2013 | Pan et al. |
| 2014/0045822 A1 | 2/2014 | Sampson et al. |
| 2014/0045838 A1 | 2/2014 | Sampson et al. |
| 2015/0133677 A1 | 5/2015 | Cumming et al. |
| 2016/0045511 A1 | 2/2016 | Sampson et al. |
| 2016/0250220 A1 | 9/2016 | Hedley et al. |
| 2016/0264559 A1 | 9/2016 | Sampson et al. |

FOREIGN PATENT DOCUMENTS

| | | |
|---|---|---|
| CA | 2596967 A1 | 8/2006 |
| CA | 2631506 A1 | 1/2008 |
| CA | 2690567 A1 | 12/2008 |
| CA | 2706075 A1 | 5/2009 |
| CA | 2709536 A1 | 7/2009 |
| CA | 2732520 A1 | 2/2010 |
| CA | 2756568 A1 | 10/2010 |
| CA | 2781839 A1 | 6/2011 |
| JP | 2002-522452 A | 7/2002 |
| JP | 2003-535847 A | 12/2003 |
| JP | 2009-173629 A | 8/2009 |
| WO | 1996/032380 A1 | 10/1996 |
| WO | 1996/040116 A1 | 12/1996 |
| WO | 1998/007695 A1 | 2/1998 |
| WO | 1999/010325 A1 | 3/1999 |
| WO | 2000/056709 A1 | 9/2000 |
| WO | 2001/53268 A2 | 7/2001 |
| WO | 2002/10137 A2 | 2/2002 |
| WO | 2003/101968 A1 | 12/2003 |
| WO | 2004/037247 A1 | 5/2004 |
| WO | 2005/058309 A1 | 6/2005 |
| WO | 2007/008664 A1 | 1/2007 |
| WO | 2007/058626 A1 | 5/2007 |
| WO | 2007/109026 A2 | 9/2007 |
| WO | 2007/110559 A1 | 10/2007 |
| WO | 2009/065232 A1 | 5/2009 |
| WO | 2009/079767 A1 | 7/2009 |
| WO | 2009/111868 A1 | 9/2009 |
| WO | 2009/124692 A1 | 10/2009 |
| WO | 2009/132774 A1 | 11/2009 |
| WO | 2010/000518 A1 | 1/2010 |
| WO | 2010/115279 A1 | 10/2010 |
| WO | 2011/123946 A1 | 10/2011 |
| WO | 2011/123947 A1 | 10/2011 |
| WO | 2012/000103 A1 | 1/2012 |
| WO | 2012/048411 A1 | 4/2012 |
| WO | 2012/118812 A2 | 9/2012 |
| WO | 2012/121764 A1 | 9/2012 |
| WO | 2012/168721 A1 | 12/2012 |
| WO | 2013/053051 A1 | 4/2013 |
| WO | 2015/054781 A1 | 4/2015 |

OTHER PUBLICATIONS

U.S. Appl. No. 15/790,847, filed Oct. 23, 2017.
Aaltonen et al., Solid form screening—a review. EurJ Pharm Biopharm. Jan. 2009;71(1):23-37.
Adams et al., Mapping the kinase domain of Janus Kinase 3. Bioorg Med Chem Lett. Sep. 15, 2003;13(18):3105-10.
CAPLUS Accession No. 2002:594639. 2 pages (2013).
CAS RN 1247005-59-9, Spiro[cyclopropane-1,3'-[3H]indol]-2'[1'H]-one, 2-[3-[(1E)-2-[4-[[(2S,6S)-2,6-dimethyl-4-morpholinyl]methyl]phenyl]ethenyl]-1H-indazol-6-yl'-5'-methoxy-, (1R,2S)-(CA Index Name). 1 page, Oct. 26, 2010.
Chen et al., Crucial role of p53-dependent cellular senescence in suppression of Pten-deficient tumorigenesis. Nature. Aug. 4, 2005;436(7051):725-30.
Gao et al., Vicinal Diol Cyclic Sulfates: Like Epoxides Only More Reactive. J Am Chem Soc. 1988;110(22):7538-7539.
Golub et al., Molecular classification of cancer: class discovery and class prediction by gene expression monitoring. Science. Oct. 15, 1999;286(5439):531-7.
Guan et al., Design and synthesis of aminopropyl tetrahydroindole-based indolin-2-ones as selective and potent Inhibitors of Src and Yes tyrosine kinase. Bioorg Med Chem Lett. Jan. 5, 2004;14(1):187-90.
Hauf et al., The small molecule Hesperadin reveals a role for Aurora B in correcting kinetochore-microtubule attachment and in maintaining the spindle assembly checkpoint. J Cell Biol. Apr. 28, 2003;161(2):281-94.
Hollestelle et al., Distinct gene mutation profiles among luminal-type and basal-type breast cancer cell lines. Breast Cancer Res Treat. May 2010;121(1):53-64.
Howard et al., Synthesis and aldose reductase inhibitory activity of substituted 2(1H)-benzimidazolone- and oxindole-1-acetic acids. Eur J Med Chem. 1992;27:779-789.
Jiang et al., Design, synthesis, and biological evaluations of novel oxindoles as HIV-1 non-nucleoside reverse transcriptase inhibitors. Part 2. Bioorg Med Chem Lett. Apr. 15, 2006;16(8):2109-12.
Johnson et al., Pharmacological and functional comparison of the polo-like kinase family: insight into inhibitor and substrate specificity. Biochemistry. Aug. 21, 2007;46(33):9551-63.
Kazazian et al., Polo-like kinase 4 (Plk4) promotes cancer cell invasion. J Am Coll Surg. 2013;217(3):S128.
Kobayashi et al., Molecular pathogenesis of endometriosis-associated clear cell carcinoma of the ovary (review). Oncol Rep. Aug. 2009;22(2):233-40.
Lala et al., Role of nitric oxide in tumor progression: Lessons from experimental tumors. Cancer and Metastasis Reviews. 1998;17(1):91-106.
Lin et al., Synthesis and biological evaluation of 3-ethylidene-1,3-dihydro-indol-2-ones as novel checkpoint 1 inhibitors. Bioorg Med Chem Lett. Jan. 15, 2006;16(2):421-6.
Lohse et al., The PLK-4 inhibitor CFI-400945 reduces tumor growth in patient-derived pancreatic xenografts, AACR-NCI-EORTC International Conference on Molecular Targets and Cancer Therapeutics, Oct. 7, 2013, Boston, Abstract No. 282.
Lopiccolo et al., PTEN hamartomatous tumor syndromes (PHTS): rare syndromes with great relevance to common cancers and targeted drug development. Crit Rev Oncol Hematol. Sep. 2007;63(3):203-14.
Marti et al., Total synthesis of (−)-spirotryprostatin B: synthesis and related studies. J Am Chem Soc. Aug. 17, 2005;127(32)11505-15.
Mason et al., Functional characterization of CFI-400945, a Polo-like kinase 4 inhibitor, as a potential anticancer agent. Cancer Cell. Aug. 11, 2014;26(2):163-76.
Mohammadi et al., Structures of the tyrosine kinase domain of fibroblast growth factor receptor in complex with inhibitors. Science. May 9, 1997;276(5314):955-60.
Moldvai et al., Synthesis of Spiro[cyclopropone-1,3'[3H]indol]-2'(1'H)-ones with Antihypoxic Effects. Arch Pharm Pharm Med Chem. 1996;329:541-549.
Moshinsky et al., SU9516: biochemical analysis of cdk inhibition and crystal structure in complex with cdk2. Biochem Biophys Res Commun. Oct. 24, 2003;310(3):1026-31.
Pellegrino et al., Oncogenic and tumor suppressive roles of polo-like kinases in human hepatocellular carcinoma. Hepatology. Mar. 2010;51(3):857-68.
Rellos et al., Structure and regulation of the human Nek2 centrosomal kinase. J Biol Chem. Mar. 2, 2007;282 (9):6833-42.
Ribet et al., Conformational analysis and crystal structure of {[1-(3-chloro-4-fluorobenzoyl)-4-fluoropiperidin-4yl] methyl)}[(5-methylpyridin-2-yl)methyl]amine, fumaric acid salt. Spectrochim Acta A Mol Biomol Spectrosc. Nov. 2005;62 (1-3):353-63.
Sampson et al., The discovery of Polo-like kinase 4 inhibitors: design and optimization of spiro [cyclopropane-1,3?'[3H]indol]-2'(1'H).ones as orally bioavailable antitumor agents. J Med Chem. Jan. 8, 2015;58(1):130-46.
Sessa et al., Mechanism of Aurora B activation by INCENP and inhibition by hesperidin. Mol Cell. Apr. 29, 2005;18(3)379-91.

(56) References Cited

OTHER PUBLICATIONS

Song et al., Nuclear PTEN regulates the APC-CDH1 tumor-suppressive complex in a phosphatase-independent manner. Cell. Jan. 21, 2011;144(2):187-99.
Zhu et al., Discovery and SAR of oxindole-pyridine-based protein kinase B/Akt inhibitors for treating cancers. Bioorg Med Chem Lett. Jul. 1, 2006;16(13):3424-9.
International Preliminary Report on Patentability for Application No. PCT/CA2011/000387, dated Oct. 18, 2012.
International Search Report and Written Opinion for Application No. PCT/CA2014/050952, dated Dec. 9, 2014.
International Search Report for Application No. PCT/CA2008/002227, dated Apr. 6, 2009.
International Search Report for Application No. PCT/CA2010/000518, dated Jul. 8, 2010.
International Search Report for Application No. PCT/CA2011/000386, dated Aug. 2, 2011.
International Search Report for Application No. PCT/CA2011/000387, dated Jun. 23, 2011.

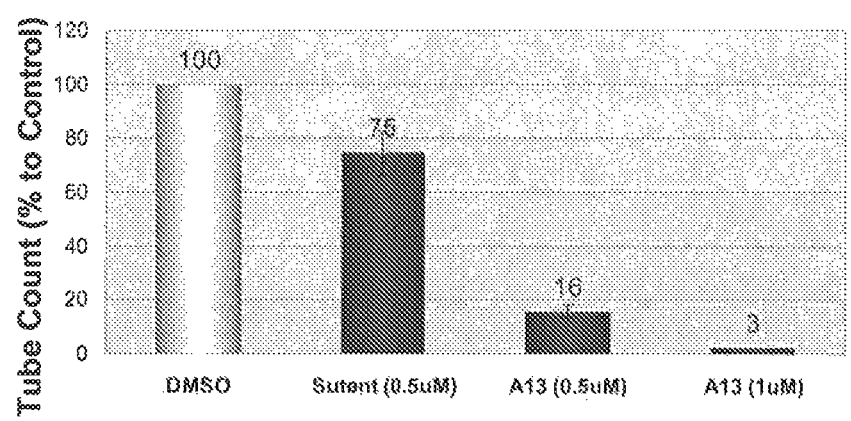
Figure 1. Compound example A13 in HUV-EC Cell Tube Formation Assay

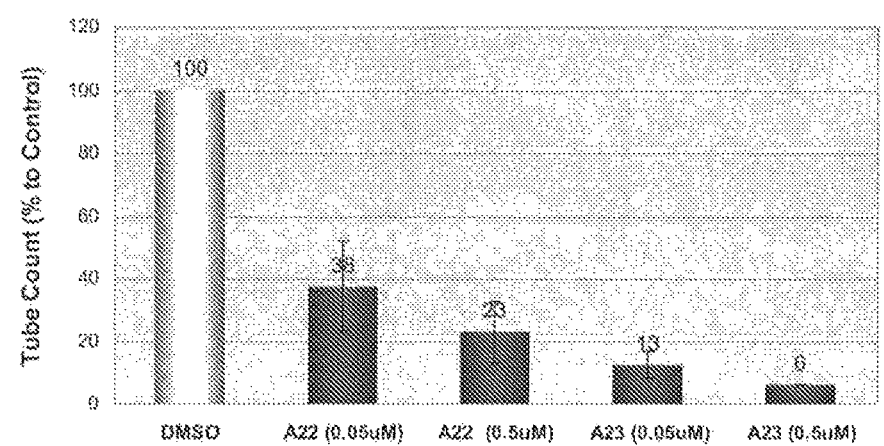
Figure 2. Compound examples A22 and A23 in HUV-EC Cell Tube Formation Assay

KINASE INHIBITORS AND METHOD OF TREATING CANCER

RELATED APPLICATIONS

This application is a continuation of U.S. application Ser. No. 14/823,057, filed Aug. 11, 2015, which is a continuation of U.S. application Ser. No. 13/935,021, filed Jul. 3, 2013; which is a continuation of Ser. No. 13/529,542, filed Jun. 21, 2012, which, in turn, is a divisional of U.S. application Ser. No. 13/081,254, filed Apr. 6, 2011, which claims the benefit of U.S. Provisional Application Nos. 61/321,332, filed Apr. 6, 2010 and 61/321,329, filed Apr. 6, 2010, which also claims the benefit of International Application No. PCT/CA2010/000518, filed Apr. 6, 2010. The entire teachings of each of the aforementioned applications are incorporated herein by reference.

BACKGROUND OF THE INVENTION

Protein kinases have been the subject of extensive study in the search for new therapeutic agents in various diseases, for example, cancer. Protein kinases are known to mediate intracellular signal transduction by effecting a phosphoryl transfer from a nucleoside triphosphate to a protein acceptor that is involved in a signaling pathway. There are a number of kinases and pathways through which extracellular and other stimuli cause a variety of cellular responses to occur inside the cell.

The polo-like kinase (PLK) family of serine/threonine kinases comprises at least four known members: PLK1, PLK2 (also known as Snk), PLK3 (also known as Fnk or Prk) and PLK4 (also known as Sak). PLK4 is the least understood and most divergent member of the PLK family The N-terminal catalytic domain of PLK4 has a different substrate specificity from that of PLK1-3. PLK4 also has a divergent C-terminus comprising only a single polo-box sequence, not the tandem PB sequences in PLK1-3, that appears to act as a homodimerization domain rather than a localization domain (Lowery et al., (2005) Oncogene 24: 248-259).

PLK4 is known to be involved in the control of mitotic entry and exit, and a regulator of centrosome duplication (Habedanck et al. Nature Cell Biology 7: 1140-1146, 2005). PLK4 transcripts increase from S through M phase, and the protein is ubiquitylated and destroyed by the anaphase promoting complex (APC) (Hudson et al. Curr. Biol. 11: 441-446, 2001; Fode et al. Mol. Cell. Biol. 16: 4665-4672, 1996). PLK4 is required for late mitotic progression (Fode et al. PNAS. 91: 6388-6392, 1994; Hudson et al. Curr. Biol. 11: 441-446, 2001), cell survival and postgastrulation embryonic development (Hudson et al. Curr. Biol. 11: 441-446, 2001). PLK4 knockout mice are embryonic lethal (E7.5), with a marked increase in mitotic and apoptotic cells (Hudson et al. Curr. Biol. 11: 441-446, 2001). PLK4 is transcriptionally repressed by p53 (Li et al. Neoplasia 7: 312-323, 2005). This repression is likely mediated through the recruitment of histone deacetylase (HDAC) repressors and repression appears to contribute to p53-induced apoptosis (Li et al. Neoplasia 7: 312-323, 2005).

PLK4 has been reported to be overexpressed in colorectal tumors with expression reported as low in adjacent normal intestinal mucosa (Macmillian et al. Ann. Surg. Oncol. 8: 729-740, 2001). In addition, PLK4 mRNA has been reported to be overexpressed in some tumor cell lines (Hitoshi, et al., U.S. Patent Application No. US 2003/0027756). In addition, Applicants described overexpression of PLK4 in basal-like tumors in a U.S. Provisional Application No. 61/003,825, filed on Nov. 20, 2007 (the entire teachings of which are incorporated herein by reference). PLK4 has been reported to be overexpressed in colorectal tumors with expression reported as low in adjacent normal intestinal mucosa (Macmillian et al. Ann. Surg. Oncol. 8: 729-740, 2001). In addition, PLK4 mRNA has been reported to be overexpressed in some tumor cell lines (Hitoshi, et al., U.S. Patent Application No. US 2003/0027756). In addition, Applicants described overexpression of PLK4 in basal-like tumors in a U.S. Provisional Application No. 61/003,825, filed on Nov. 20, 2007 (the entire teachings of which are incorporated herein by reference).

The human papillomavirus (HPV-16) E7 oncoproteins are overexpressed in HPV-associated anogenital and oropharyngeal cancers. The E7 oncoprotein triggers centrosome overduplication through a pathway that involves the concurrent formation of multiple daughters at single maternal centrioles. The HPV-16 E7 oncoprotein has been used as a tool to dissect abnormal centriole biogenesis and several lines of evidence identify PLK4 as a crucial player in this process (Duensing et al Environ. Mol. Mutagen. 50: 741-747, 2009). In addition, an increased level of PLK4 transcription is found in keratinocytes stably expressing HPV-16 E7. The ability of HPV-16 E7 to upregulate PLK4 mRNA was found to depend on its ability to degrade the retinoblastoma (pRb) protein, suggesting a role of E2F-mediated gene transcription in deregulation of PLK4 (Korzeniewski et al, AACR Meeting, Washington, 2010, Abstr. 5354). These results identify PLK4 as a target for small molecule inhibition to prevent centriole abnormalities, mitotic infidelity and malignant progression in HPV-associated cancers.

Therefore, agents which inhibit a protein kinase, in particular PLK4, have the potential to treat cancer. There is a need for additional agents which can act as protein kinase inhibitors, in particular PLK4 inhibitors.

SUMMARY OF THE INVENTION

Applicants have now discovered that certain spiro cyclopropyl indolinone compounds are potent kinase inhibitors, such as polo-like kinases 4 (PLK4) and Aurora Kinases (see Example B-F). Applicants have also now discovered that these spiro cyclopropyl indolinone compounds have potent anticancer activity (see Example J) and exhibit anti-angiogenic activity (example K). Based on these discoveries, spiro cyclopropyl indolinone compounds, pharmaceutical compositions thereof, and methods of treating cancer with the spiro cyclopropyl indolinone compounds are disclosed herein.

One embodiment of the invention is a compound represented by Structural Formula (I):

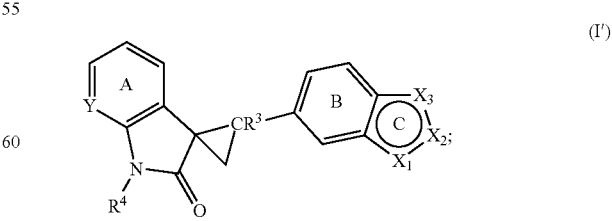

or a pharmaceutically acceptable salt thereof, wherein:

Ring A is optionally and independently substituted with one or more substituents represented by $R^a$ and ring B is optionally and independently substituted with one or more substituents represented by $R^b$;

ring C is a 5-membered heteroaromatic ring wherein one of $X_1$-$X_3$ is N, one of $X_1$-$X_3$ is $NR^5$, and one of $X_1$-$X_3$ is N or $CR^6$;

Y is independently N, CH or $CR^a$;

each of $R^a$ and $R^b$ independently is:

halogen, $-C(O)OR^1$, $-C(O)R^1$, $-C(S)R^1$, $-OC(O)R^1-$, $-C(O)NR^1R^2$, $-C(S)NR^1R^2$, $-OC(O)NR^1R^2$, $-S(O)R^1$, $-S(O)_2R^1$, $-SO_3R^1$, $-SO_2NR^1R^2$, $-OR^1$, $-SR^1$, $-NR^1R^2$, $-NR^2C(O)R^1$, $-NR^2S(O)R^1$, $-NR^2C(O)OR^1$, $-NR^2C(O)ONR^1R^2$, $-N(R^2)C(O)NR^1R^2$, $-NR^2SO_2NR^1R^2$, $-NR^2SO_2R^1$; $-NO_2$, $-CN$, $-NCS$; or two ortho $R^a$ groups taken together form $-O-[CH_2]_p-O-$, $-S-[CH_2]_p-S-$ or $-[CH_2]_q-$; or $C_{1-10}$ aliphatic group optionally substituted with one or more substituents selected from the group consisting halogen, nitro, cyano, $-N(R^{21})_2$, $-C(O)N(R^{21})_2$, $-C(O)N(R^{21})_2$, $-NR^{21}C(O)R^{21}$, $-SO_2R^{22}$, $-SO_2N(R^{21})_2$, $-NR^{21}SO_2R^{22}$, $-NR^{21}C(O)OR^{21}$, $-OC(O)N(R^{21})_2$, $-NR^{21}C(O)N(R^{21})_2$, $-NRC(O)ON(R)_2$, $-NR^{21}SO_2N(R^{21})_2$, $-OR^{21}$, $-SR^{21}$, $C_{1-10}$ haloalkoxy, $-C(O)R^{21}$, $-C(O)OR^{21}$ and $-OC(O)R^{21}$; or $(C_{0-10}$ alkylene)-$Ar^1$, $(C_{2-10}$ alkenylene)-$Ar^1$, wherein $Ar^1$ is a $C_{6-14}$ aryl group or a 5-14 membered heteroaryl group, each optionally and independently substituted with one or more substituents selected from the group consisting of halogen, nitro, cyano, $C_{1-10}$ alkyl, $C_{1-10}$ haloalkyl, $(C_{1-10}$ haloalkoxy)$C_{1-10}$ alkyl, $(C_{1-10}$ alkoxy)$C_{1-10}$ alkyl, $C_{1-10}$hydroxyalkyl, $C_{1-10}$aminoalkyl, $(C_{1-10}$ alkylamino)$C_{1-10}$alkyl, $(C_{1-10}$dialkylamino)$C_{1-10}$ alkyl, $-N(R^{21})_2$, $-C(O)N(R^{21})_2$, $-C(O)N(R^{21})_2$, $-NR^{21}C(O)R^{21}$, $-SO_2R^{22}$, $-SO_2N(R^{21})_2$, $-NR^{21}SO_2R^{22}$, $-NR^{21}C(O)N(R^{21})_2$, $-NRC(O)ON(R)_2$, $-NR^{21}SO_2N(R^{21})_2$, $-OR^{21}$, $-SR^{21}$, $C_{1-10}$ haloalkoxy, $-C(O)R^{21}$, $-C(O)OR^{21}$, $-OC(O)R^{21}$, phenyl and 5-6 membered heteroaryl, wherein said phenyl and said 5-6 membered heteroaryl are each independently and optionally substituted with one or more substituents selected from the group consisting of halogen, hydroxy, nitro, cyano, amino, $C_{1-3}$ alkyl, $C_{1-3}$ haloalkyl, $C_{1-3}$ alkoxy and $C_{1-3}$ haloalkoxy;

each $R^1$ independently is:

i) hydrogen;

ii) a $C_{6-14}$ aryl group or a 5-14 membered heteroaryl group, each optionally and independently substituted with one or more substituents selected from the group consisting of halogen, $-NO_2$, $-CN$, $-NCS$, $C_1$-$C_{10}$ aliphatic, $(C_{1-10}$ alkylene)-$Ar^{10}$ $(C_{2-10}$ alkenylene)-$Ar^{10}$, $-C(O)OR^{10}$, $-C(O)R^{10}$, $-C(S)R^{10}$, $-OC(O)R^{10}$, $-C(O)N(R^{11})_2$, $-C(S)N(R^{11})_2$, $-OC(O)N(R^{11})_2$, $-S(O)R^{12}$, $-S(O)_2R^{12}$, $-SO_3R^{12}$, $-SO_2N(R^{11})_2$, $-OR^{10}$, $-SR^{10}$, $-N(R^{11})_2$, $-NR^{11}C(O)R^{10}$, $-NR^{11}S(O)R^{12}$, $-NR^{11}C(O)OR^{12}$, $-N(R^{11})C(O)N(R^{11})_2$, $-NR^{11}SO_2N(R^{11})_2$ and $-NR^{11}SO_2R^{12}$; or iii) a $C_{1-10}$ aliphatic group optionally substituted with one or more substituents selected from the group consisting of halogen, $-NO_2$, $-CN$, $-NCS$, $Ar^{10}$, $-C(O)OR^{10}$, $-C(O)R^{10}$, $-C(S)R^{10}$, $-OC(O)R^{10}$, $-C(O)N(R^{11})_2$, $-C(S)N(R^{11})_2$, $-OC(O)N(R^{11})_2$, $-S(O)R^{12}$, $-S(O)_2R^{12}$, $-SO_3R^{12}$, $-SO_2N(R^{11})_2$, $-OR^{10}$, $-SR^{10}$, $-N(R^{11})_2$, $-NR^{11}C(O)R^{10}$, $-NR^{11}S(O)R^{12}$, $-NR^{11}C(O)OR^{12}$, $-N(R^{11})C(O)N(R^{11})_2$, $-NR^{11}SO_2N(R^{11})_2$ and $-NR^{11}SO_2R^{12}$, provided that $R^1$ is other than hydrogen when $R^a$ or $R^b$ is $-S(O)R^1$, $-S(O)_2R^1$, $-SO_3R^1$, $-NR^2S(O)R^1$ or $-NR^2SO_2R^1$; and each $R^2$ independently is $-H$ or $C_1$-$C_6$ alkyl, or, taken together with $NR^1$, forms a non-aromatic heterocyclic group optionally substituted with one or more substituents selected from the group consisting of $=O$, $=S$, halogen, nitro, cyano, hydroxy, $C_{1-6}$ alkyl, $C_{1-6}$ haloalkyl, $C_{1-6}$hydroxyalkyl, amino, $C_{1-6}$ alkylamino, $C_{1-6}$dialkylamino, $C_{1-6}$ aminoalkyl, $(C_{1-6}$ alkylamino)$C_{1-6}$ alkyl, $(C_{1-6}$dialkylamino)$C_{1-6}$ alkyl, (phenyl)$C_{1-6}$ alkyl, (5-6 membered heteroaryl)$C_{1-6}$ alkyl, $C_{1-6}$ alkoxy, $C_{1-6}$ haloalkoxy, $C_{1-6}$ alkylcarbonyloxy, $C_{1-6}$alkoxycarbonyl, $C_{1-6}$ alkylcarbonyl, phenyl and 5-6 membered heteroaryl;

$R^3$ is $-H$, halogen, $C_{1-6}$ alkyl or $C_{1-6}$ haloalkyl;

each of $R^4$ and $R^5$ independently is $-H$, $C_{1-6}$ alkyl, phenyl, $-C(O)(C_{1-6}$ alkyl), $-C(O)$(phenyl), $-C(O)O(C_{1-6}$ alkyl), $-C(O)O$(phenyl), $-S(O)_2(C_{1-6}$ alkyl) or $-S(O)_2$(phenyl), wherein each alkyl in the groups represented by $R^4$ and $R^5$ independently is optionally substituted with one or more substituents selected from the group consisting of halogen, hydroxy, nitro, cyano, amino, $-C(O)NH_2$, phenyl, 5-6 membered heteroaryl, $C_{1-6}$ alkoxy and $C_{1-6}$ haloalkoxy, and wherein each phenyl in the groups represented by $R^4$ and $R^5$ independently is optionally substituted with one or more substituents selected from the group consisting of halogen, hydroxy, nitro, cyano, amino, $C_{1-6}$ alkyl, $C_{1-6}$ haloalkyl, $C_{1-6}$ alkoxy and $C_{1-6}$ haloalkoxy;

$R^6$ is hydrogen, halogen, nitro, cyano, R', $-OR$, $-SR$, $-N(R)_2$, $-C(O)R$, $-C(O)OR$, $-OC(O)R$, $-C(O)N(R)_2$, $-OC(O)N(R)_2$, $-NRC(O)R$, $-NRC(O)OR$, $-SOR'$, $-SO_2R'$, $-SO_3R'$, $-SO_2N(R)_2$, $-NRS(O)R'$, $-NRSO_2R'$, $-NRC(O)N(R)_2$, $-NRC(O)ON(R)_2$, or $-NRSO_2N(R)_2$;

each $R^{10}$ independently is:

i) hydrogen;

ii) a $C_{6-14}$ aryl group or a 5-14 membered heteroaryl group, each optionally and independently substituted with one or more substituents selected from the group consisting of halogen, nitro, cyano, hydroxy, $C_{1-10}$ alkyl, $C_{1-10}$haloalkyl, $(C_{1-10}$ haloalkoxy)$C_{1-10}$ alkyl, $(C_{1-10}$ alkoxy)$C_{1-10}$ alkyl, $C_{1-10}$hydroxyalkyl, $C_{1-10}$ aminoalkyl, $(C_{1-10}$ alkylamino)$C_{1-10}$ alkyl, $(C_{1-10}$dialkylamino)$C_{1-10}$ alkyl, (phenyl)$C_{1-10}$ alkyl, (5-6 membered heteroaryl)$C_{1-10}$ alkyl, amino, $C_{1-10}$ alkylamino, $C_{1-10}$ dialkylamino, $C_{1-10}$ alkoxy, $C_{1-10}$ haloalkoxy, $C_{1-10}$ alkylcarbonyloxy, $C_{1-10}$ alkoxycarbonyl and $C_{1-10}$ alkylcarbonyl; or iii) a $C_{1-10}$ alkyl group optionally substituted with one or more substituents selected from the group consisting of halogen, nitro, cyano, hydroxy, $C_{1-10}$ haloalkyl, $C_{1-10}$ alkoxy, $C_{1-10}$ haloalkoxy, amino, $C_{1-10}$ alkylamino, $C_{1-10}$ dialkylamino, $C_{1-10}$ alkylcarbonyloxy, $C_{1-10}$ alkoxycarbonyl, $C_{1-10}$ alkylcarbonyl and phenyl, said phenyl being optionally substituted with one or more substituents selected from the group consisting of halogen, hydroxy, nitro, cyano, amino, $C_{1-3}$ alkyl, $C_{1-3}$ haloalkyl, $C_{1-3}$ alkoxy and $C_{1-3}$ haloalkoxy;

each $R^{11}$ independently is $R^{10}$, $-CO_2R^{10}$, $-SO_2R^{10}$ or $-C(O)R^{10}$, or $-N(R^{11})_2$ taken together is a non-aromatic heterocyclic group optionally substituted with one or more substituents selected from the group consisting of $=O$, $=S$, halogen, nitro, cyano, hydroxy, $C_{1-6}$ alkyl, $C_{1-6}$ haloalkyl, $C_{1-6}$ hydroxyalkyl, amino, $C_{1-6}$ alkylamino, $C_{1-6}$ dialkylamino, $C_{1-6}$ aminoalkyl, $(C_{1-6}$ alkylamino)$C_{1-6}$ alkyl, $(C_{1-6}$ dialkylamino)$C_{1-6}$ alkyl, $C_{1-6}$ alkoxy, $C_{1-6}$ haloalkoxy, $C_{1-6}$ alkylcarbonyloxy, $C_{1-6}$ alkoxycarbonyl and $C_{1-6}$ alkylcarbonyl; and each $R^{12}$ is independently is $R^{10}$ provided that $R^{12}$ is not hydrogen;

each $R^{21}$ independently is hydrogen, $C_{1-6}$ alkyl, phenyl or 5-6 membered heteroaryl, wherein each of the phenyl and heteroaryl groups represented by $R^{21}$ is independently and optionally substituted with one or more substituents selected from the group consisting of halogen, hydroxy, nitro, cyano, amino, $C_{1-3}$ alkyl, $C_{1-3}$ haloalkyl, $C_{1-3}$ alkoxy and $C_{1-3}$ haloalkoxy, and wherein the alkyl group represented by $R^{21}$ is optionally substituted with one or more substituents selected from the group consisting of halogen, hydroxy, nitro, cyano, amino, $C_{1-3}$ alkyl, $C_{1-3}$ haloalkyl, $C_{1-3}$ alkoxy and $C_{1-3}$ haloalkoxy; or $N(R^{21})_2$ forms a non-aromatic heterocyclic group optionally substituted with one or more substituents selected from the group consisting of halogen, hydroxy, nitro, cyano, =O, $C_{1-3}$ alkyl, $C_{1-3}$ haloalkyl, $C_{1-3}$ alkoxy, $C_{1-3}$ haloalkoxy and amino; and each $R^{22}$ independently $C_{1-6}$ alkyl, phenyl or 5-6 membered heteroaryl, wherein each of the phenyl and heteroaryl groups represented by $R^{22}$ is independently and optionally substituted with one or more substituents selected from the group consisting of halogen, hydroxy, nitro, cyano, amino, $C_{1-3}$ alkyl, $C_{1-3}$ haloalkyl, $C_{1-3}$ alkoxy and $C_{1-3}$ haloalkoxy, and wherein the alkyl group represented by $R^{22}$ is optionally substituted with one or more substituents selected from the group consisting of halogen, hydroxy, nitro, cyano, amino, $C_{1-3}$ alkyl, $C_{1-3}$ haloalkyl, $C_{1-3}$ alkoxy and $C_{1-3}$ haloalkoxy;

each R independently is hydrogen, $C_{1-10}$ aliphatic, phenyl or 5-6 membered heteroaryl, wherein the aliphatic group represented by R is optionally substituted with one or more substituents selected from the group consisting of halogen, hydroxy, nitro, cyano, amino, phenyl, 5-6 membered heteroaryl, $C_{1-6}$ alkoxy, $C_{1-6}$ haloalkoxy, and wherein each of the phenyl and heteroaryl groups represented by R, and the phenyl and heteroaryl substituents for the aliphatic group represented by R independently are optionally and independently substituted with one or more substituents selected from the group consisting of halogen, hydroxy, nitro, cyano, amino, $C_{1-6}$ alkyl, $C_{1-6}$ haloalkyl, $C_{1-6}$ alkoxy, $C_{1-6}$ haloalkoxy, or $N(R)_2$ forms a non-aromatic heterocyclic group optionally substituted with one or more substituents selected from the group consisting of =O, =S, halogen, nitro, cyano, hydroxy, $C_{1-6}$ alkyl, $C_{1-6}$ haloalkyl, $C_{1-6}$hydroxyalkyl, amino, $C_{1-6}$ alkylamino, $C_{1-6}$ dialkylamino, $C_{1-6}$ aminoalkyl, ($C_{1-6}$ alkylamino)$C_{1-6}$ alkyl, ($C_{1-6}$ dialkylamino)$C_{1-6}$ alkyl, (phenyl)$C_{1-6}$ alkyl, (5-6 membered heteroaryl)$C_{1-6}$ alkyl, $C_{1-6}$ alkoxy, $C_{1-6}$ haloalkoxy, $C_{1-6}$ alkylcarbonyloxy, $C_{1-6}$alkoxycarbonyl, $C_{1-6}$ alkylcarbonyl, phenyl and 5-6 membered heteroaryl; and each R' independently is $C_{1-10}$ aliphatic, phenyl, 5-12 membered heteroaryl or 9-12 membered heterocyclyl group, wherein the aliphatic group represented by R' is optionally substituted with one or more substituents selected from the group consisting of halogen, hydroxy, nitro, cyano, amino, phenyl, 5-12 membered heteroaryl, 9-12 membered heterocyclyl group, $C_1$-$C_6$ alkoxy, $C_1$-$C_6$ haloalkoxy, $C_{1-6}$ alkylamino, $C_{1-6}$ dialkylamino, —C(O)H, —C(O)($C_1$-$C_6$ alkyl), —C(O)($C_1$-$C_6$ haloalkyl), —C(O)(phenyl), —C(O)(non-aromatic heterocyclic group), —C(O)O(C1-C6 alkyl), —C(O)O(C1-C6 haloalkyl), —C(O)O(phenyl), —OC(O)($C_1$-$C_6$ alkyl), —OC(O)($C_1$-$C_6$ haloalkyl), —OC(O)(phenyl), —S(O)$_2$($C_1$-$C_6$ alkyl), —S(O)$_2$($C_1$-$C_6$ haloalkyl) and —S(O)$_2$(phenyl), and wherein each of the phenyl, heteroaryl and heterocyclyl groups represented by R', and the phenyl, heteroaryl and heterocyclyl groups in the substituents for the aliphatic group represented by R' independently are optionally substituted with one or more substituents selected from the group consisting of halogen, —OH, —SH, nitro, cyano, amino, $C_{1-6}$ alkylamino, $C_{1-6}$ dialkylamino, ($C_{1-6}$ dialkylamino)$C_{1-6}$ dialkylamino, $C_1$-$C_6$ alkyl, $C_1$-$C_6$ haloalkyl, —O($C_{1-6}$ alkyl), —O-(non-aromatic heterocyclic group), —S($C_{1-6}$ alkyl), —O($C_{1-6}$ haloalkyl), ($C_{1-6}$ haloalkoxy)$C_{1-6}$ alkyl, ($C_{1-6}$ alkoxy)$C_{1-6}$ alkyl, $C_{1-6}$ hydroxyalkyl, ($C_{1-6}$ aminoalkyl), ($C_{1-6}$ alkylamino)$C_{1-6}$ alkyl, ($C_{1-6}$ dialkylamino)$C_{1-6}$ alkyl, ($C_{1-6}$ dialkylamino)$C_{1-6}$ alkoxy, (phenyl)$C_{0-6}$ alkyl, (5-6 membered heteroaryl)$C_{0-6}$ alkyl, (non-aromatic heterocyclic group)$C_{0-6}$ alkyl (optionally substituted with halogen, —OH, $C_{1-6}$ hydroxyalkyl, $C_{1-6}$ alkyl, ($C_{1-6}$ alkoxy)$C_{1-6}$ alkyl, $C_{1-6}$ acyl, $C_{5-7}$ cycloalkyl, $C_{1-6}$ alkylamino, $C_{1-6}$ dialkylamino or non-aromatic heterocyclic group), (5-6 membered heteroaryl)$C_{1-6}$ alkoxy, (non-aromatic heterocyclic group)$C_{1-6}$ alkoxy, —C(O)($C_1$-$C_6$ alkyl), —C(O)($C_1$-$C_6$ haloalkyl), —C(O)(phenyl), —C(O)(non-aromatic heterocyclic group), —C(O)O($C_1$-C6 alkyl), —C(O)O($C_1$-$C_6$ haloalkyl), —C(O)O(phenyl), —OC(O)($C_1$-$C_6$ alkyl), —OC(O)($C_1$-$C_6$ haloalkyl), —OC(O)(phenyl), —S(O)$_2$NH$_2$, —S(O)$_2$($C_1$-$C_6$ alkyl), —S(O)$_2$($C_{1-6}$ haloalkyl), and —S(O)$_2$(phenyl);

each $Ar^{10}$ independently is a $C_{6-14}$ aryl group or a 5-14 membered heteroaryl group, each optionally and independently substituted with one or more substituents selected from the group consisting of halogen, nitro, cyano, —OH, —SH, —O($C_{1-10}$ alkyl), —S($C_{1-10}$ alkyl), $C_{1-10}$ alkyl, $C_{1-10}$ haloalkyl, ($C_{1-10}$ haloalkoxy)$C_{1-10}$ alkyl, ($C_{1-10}$ alkoxy)$C_{1-10}$ alkyl, $C_{1-10}$ hydroxyalkyl, ($C_{1-10}$ aminoalkyl), ($C_{1-10}$ alkylamino)$C_{1-10}$ alkyl, ($C_{1-10}$ dialkylamino)$C_{1-10}$ alkyl, (phenyl)$C_{1-10}$ alkyl, (5-6 membered heteroaryl)$C_{1-10}$ alkyl, amino, $C_{1-10}$ alkylamino, $C_{1-10}$ dialkylamino, $C_{1-10}$ haloalkoxy, $C_{1-10}$ alkylcarbonyloxy, $C_{1-10}$ alkoxycarbonyl and $C_{1-10}$ alkylcarbonyl;

each p is 1, 2 or 3; and each q is 2, 3, 4 or 5.

In another embodiment, the present invention is directed to a compound represented by the following Structural Formula:

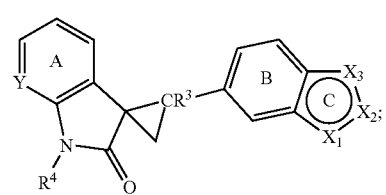

(I)

or a pharmaceutically acceptable salt thereof, wherein:

each of $R^4$ and $R^5$ independently is —H, $C_{1-6}$ alkyl, phenyl, —C(O)($C_{1-6}$ alkyl), —C(O)(phenyl), —C(O)O($C_{1-6}$ alkyl), —C(O)O(phenyl), —S(O)$_2$($C_{1-6}$ alkyl) or —S(O)$_2$(phenyl), wherein each alkyl in the groups represented by $R^4$ and $R^5$ independently is optionally substituted with one or more substituents selected from the group consisting of halogen, hydroxy, nitro, cyano, amino, phenyl, 5-6 membered heteroaryl, $C_{1-6}$ alkoxy, $C_{1-6}$ alkylamino, $C_{1-6}$ dialkylamino and $C_{1-6}$ haloalkoxy, and wherein each phenyl in the groups represented by $R^4$ and $R^5$ independently is optionally substituted with one or more substituents selected from the group consisting of halogen, hydroxy, nitro, cyano, amino, $C_{1-6}$ alkyl, $C_{1-6}$ haloalkyl, $C_{1-6}$ alkoxy and $C_{1-6}$ haloalkoxy; and each R' independently is $C_{1-10}$ aliphatic, phenyl or 5-12 membered heteroaryl, wherein the aliphatic group represented by R' is optionally substituted with one or more substituents selected from the group consisting of halogen, hydroxy, nitro, cyano, amino, phenyl, 5-12 membered heteroaryl, $C_1$-$C_6$ alkoxy, $C_1$-$C_6$ haloalkoxy, $C_{1-6}$ alkylamino, $C_{1-6}$ dialkylamino, —C(O)($C_1$-$C_6$ alkyl), —C(O)($C_1$-$C_6$ haloalkyl), —C(O)(phenyl), —C(O)(non-aromatic heterocyclic group), —C(O)O(C1-C6 alkyl), —C(O)O(C1-C6 haloalkyl), —C(O)O(phenyl), —OC(O)($C_1$-$C_6$ alkyl), —OC(O)($C_1$-$C_6$ haloalkyl), —OC(O)(phenyl), —S(O)$_2$($C_1$-$C_6$ alkyl), —S(O)$_2$($C_1$-$C_6$ haloalkyl) and —S(O)$_2$(phenyl), and wherein each of the phenyl and heteroaryl groups represented by R', and the phenyl and heteroaryl groups in the substituents for the aliphatic group represented by R' independently are optionally substituted with one or more substituents selected from the group consisting of halogen, —OH, —SH, nitro, cyano, amino, $C_{1-6}$ alkylamino, $C_{1-6}$ dialkylamino, $C_1$-$C_6$ alkyl, $C_1$-$C_6$ haloalkyl, —O($C_{1-6}$ alkyl), —S($C_{1-6}$ alkyl), —O($C_{1-6}$ haloalkyl), ($C_{1-6}$ haloalkoxy)$C_{1-6}$ alkyl, ($C_{1-6}$ alkoxy)$C_{1-6}$ alkyl, $C_{1-6}$hydroxyalkyl, ($C_{1-6}$ aminoalkyl), ($C_{1-6}$ alkylamino)$C_{1-6}$ alkyl, ($C_{1-6}$ dialkylamino)$C_{1-6}$ alkyl, (phenyl)$C_{0-6}$ alkyl, (5-6 membered heteroaryl)$C_{0-6}$ alkyl, (non-aromatic heterocyclic group)$C_{0-6}$ alkyl (optionally substituted with $C_{1-6}$ alkyl or $C_{1-6}$ acyl), —C(O)($C_1$-$C_6$ alkyl), —C(O)($C_1$-$C_6$ haloalkyl), —C(O)(phenyl), —C(O)(non-aromatic heterocyclic group), —C(O)O($C_1$-C6 alkyl), —C(O)O($C_1$-$C_6$ haloalkyl), —C(O)O(phenyl), —OC(O)($C_1$-$C_6$ alkyl), —OC(O)($C_1$-$C_6$ haloalkyl), —OC(O)(phenyl), —S(O)$_2$($C_1$-$C_6$ alkyl), —S(O)$_2$($C_1$-$C_6$ haloalkyl), and —S(O)$_2$(phenyl); and the remainder of the variables are as defined for Structural Formula (I').

In another embodiment, the present invention is a pharmaceutical composition comprising a compound represented by Structural Formula (I') or (I) described above or a pharmaceutically acceptable salt thereof, and a pharmaceutically acceptable carrier or diluent.

Another embodiment of the invention is a method of treating a subject having cancer comprising administering to the subject a therapeutically effective amount of a compound of Structural Formula (I') or (I) or a pharmaceutically acceptable salt thereof.

Another embodiment of the invention is a method of inhibiting Aurora B and/or PLK-4 in a subject in need of inhibition of Aurora B and/or PLK-4, comprising administering to the subject a therapeutically effective amount of a compound represented by Structural Formula (I') or (I) or a pharmaceutically acceptable salt thereof.

Another embodiment of the invention is the use of a compound represented by Structural Formula (I') or (I) or a pharmaceutically acceptable salt thereof in therapy. The therapy is for treating a subject with cancer. Alternatively, the therapy is for inhibiting Aurora B and/or PLK-4 in a subject in need of inhibition of Aurora B and/or PLK-4.

Another embodiment of the invention is the use of a compound represented by Structural Formula (I') or (I) or a pharmaceutically acceptable salt thereof for the manufacture of a medicament for treating a subject with cancer.

Another embodiment of the invention is the use of a compound represented by Structural Formula (I') or (I) or a pharmaceutically acceptable salt thereof for the manufacture of a medicament for inhibiting Aurora B and/or PLK-4 in a subject in need of inhibition of Aurora B and/or PLK-4.

BRIEF DESCRIPTION OF THE DRAWINGS

FIG. 1 shows anti-angiogenesis effect of compound A13.
FIG. 2 shows anti-angiogenesis effect of compounds A22 and A23.

DETAILED DESCRIPTION OF THE INVENTION

In one embodiment, the invention is directed to a spiro cyclopropyl indolinone compound represented by Structural Formula (I') or (I). Values and alternative values for the variables in Structural Formula (I') or (I) are provided in the following paragraphs:

Ring A and Ring B are optionally and independently substituted at any one or more substitutable ring carbon atoms, including the position represented by "Y" when "Y" is CH. Substituents for Ring A are represented by $R^a$ and substituents for Ring B are represented by $R^b$. Typically, Ring A has "n" substituents; whereas Ring B typically has "m" substituents. Definitions for $R^a$, $R^b$, "m" and "n" are provided below.

Ring C is a 5-membered heteroaromatic ring wherein one of $X_1$-$X_3$ is N, one of $X_1$-$X_3$ is $NR^5$, and one of $X_1$-$X_3$ is N or $CR^6$. Alternatively, $X_3$ is $CR^6$, $X_2$ is N and $X_1$ is $NR^5$. In another alternative, $X_3$ is $CR^6$, $X_2$ is N and $X_1$ is NH. In another alternative, $X_3$ is $NR^5$, $X_2$ is N and $X_1$ is $CR^6$. In another alternative, $X_3$ is NH, $X_2$ is N and $X_1$ is $CR^6$.

Y is independently CH or N. Alternatively, Y is CH.

Each $R^a$ and each $R^b$ are each independently halogen, —C(O)$OR^1$, —C(O)$R^1$, —C(S)$R^1$, —OC(O)$R^1$, —C(O)$NR^1R^2$, —C(S)$NR^1R^2$, —OC(O)$NR^1R^2$, —S(O)$R^1$, —S(O)$_2R^1$, —SO$_3R^1$, —SO$_2NR^1R^2$, —$OR^1$, —$SR^1$, —$NR^1R^2$, —$NR^2C(O)R^1$, —$NR^2S(O)R^1$, —$NR^2C(O)OR^1$, —$NR^2C(O)ONR^1R^2$, —$N(R^2)C(O)NR^1R^2$, —$NR^2SO_2NR^1R^2$, —$NR^2SO_2R^1$; —$NO_2$, —CN, —NCS; or two ortho $R^a$ groups taken together form —O—[CH$_2$]$_p$—O—, —S—[CH$_2$]$_p$—S— or —[CH$_2$]$_q$—; or a $C_{1-10}$ aliphatic group optionally substituted with one or more substituents selected from the group consisting halogen, nitro, cyano, —N($R^{21}$)$_2$, —C(O)N($R^{21}$)$_2$, —C(O)N($R^{21}$)$_2$, —$NR^{21}C(O)R^{21}$, —SO$_2R^{22}$, —SO$_2N(R^{21})_2$, —$NR^{21}SO_2R^{22}$, —$NR^{21}C(O)OR^{21}$, —OC(O)N($R^{21}$)$_2$, —$NR^{21}C(O)N(R^{21})_2$, —NRC(O)ON(R)$_2$, —$NR^{21}SO_2N(R^{21})_2$, —$SR^{21}$, $C_{1-10}$ haloalkoxy, —C(O)$R^{21}$, —C(O)$OR^{21}$ and —OC(O)$R^{21}$; or ($C_{0-10}$alkylene)-$Ar^1$, ($C_{2-10}$ alkenylene)-$Ar^1$. Alternatively, each $R^a$ and each $R^b$ is independently halogen, cyano, —$NR^1R^2$, —$NR^2C(O)R^1$, —C(O)$OR^1$, —OC(O)$R^1$, —C(O)$NR^1R^2$, —$NR^2C(O)OR^1$, —N($R^2$)C(O)$NR^1R^2$, —$OR^1$, —SO$_2NR^1R^2$, —$NR^2SO_2R^1$, $C_{1-6}$ alkyl, phenyl or 5-12 membered heteroaryl, wherein the $C_{1-6}$ alkyl represented by $R_a$ and $R_b$ is optionally and independently substituted with one or more substituents selected from the group consisting of halogen, nitro, cyano, —OH, —SH, —O($C_{1-6}$ alkyl), —S($C_{1-6}$ alkyl), $C_{1-6}$ haloalkoxy, amino, $C_{1-6}$ alkylamino, $C_{1-6}$ dialkylamino, $C_{1-6}$ alkylcarbonyloxy, $C_{1-6}$ alkoxycarbonyl and $C_{1-6}$ alkylcarbonyl; and the phenyl or the 5-12 membered heteroaryl (for example, pyridyl, thiazolyl, pyrazinyl, thiophenyl, indolyl, quinolinyl, pyrrolyl, pyrazolyl, or pyrimidinyl) represented by $R_a$ and $R_b$ is optionally substituted with one or more substituents selected from the group consisting of halogen, nitro, cyano, —OH, —SH, —O($C_{1-6}$ alkyl), —S($C_{1-6}$ alkyl), $C_{1-6}$ alkyl, $C_{1-6}$haloalkyl, ($C_{1-6}$ haloalkoxy)$C_{1-6}$ alkyl, ($C_{1-6}$ alkoxy)$C_{1-6}$ alkyl, $C_{1-6}$hydroxyalkyl, ($C_{1-6}$ aminoalkyl), ($C_{1-6}$ alkylamino)$C_{1-6}$ alkyl, ($C_{1-6}$dialkylamino)$C_{1-6}$ alkyl, (phenyl)$C_{1-6}$ alkyl, (5-6 membered heteroaryl)$C_{1-6}$ alkyl, amino, $C_{1-6}$ alkylamino, $C_{1-6}$ dialkylamino, $C_{1-6}$ haloalkoxy, $C_{1-6}$ alkylcarbonyloxy, $C_{1-6}$ alkoxycarbonyl and $C_{1-6}$ alkylcarbonyl. In another alternative, each $R^a$ is halogen, cyano, —$NR^1R^2$, —$NR^2C(O)R^1$, —$C(O)OR^1$, —$OC(O)R^1$, —$N(R^2)C(O)NR^1R^2$, $C_{1-6}$ alkyl, wherein the $C_{1-6}$ alkyl is optionally substituted with one or more substituents selected from the group consisting of halogen, —OH, —SH, —O($C_{1-6}$ alkyl), —S($C_{1-6}$ alkyl) and $C_{1-6}$ haloalkoxy. In another alternative, $R^a$ is halogen, cyano, —$NR^1R^2$, —$NR^2C(O)R^1$, —$N(R^2)C(O)NR^1R^2$, —$OR^1$ or $C_{1-6}$ alkyl, wherein the $C_{1-6}$ alkyl is optionally substituted with one or more substituents selected from the group consisting of halogen, —OH, —O($C_{1-6}$ alkyl), and $C_{1-6}$ haloalkoxy. In another alternative, $R^a$ is halogen, —$NH_2$, ($C_{1-6}$alkyl)amine or $C_{1-6}$ alkoxy. In another alternative, $R^b$ is —F, Cl or methyl. In another alternative, $R^a$ is —F, methoxy, methyl or ethyl.

Each $R^1$ independently is: i) hydrogen; ii) a $C_{6-14}$ aryl group or a 5-14 membered heteroaryl group, each optionally and independently substituted with one or more substituents selected from the group consisting of halogen, —$NO_2$, —CN, —NCS, $C_1$-$C_{10}$ aliphatic, ($C_{1-10}$ alkylene)-$Ar^{10}$, ($C_{2-10}$ alkenylene)-$Ar^{10}$, —$C(O)OR^{10}$, —$C(O)R^{10}$, —$C(S)R^{10}$, —$OC(O)R^{10}$, —$C(O)N(R^{11})_2$, —$C(S)N(R^{11})_2$, —$OC(O)N(R^{11})_2$, —$S(O)R^{12}$, —$S(O)_2R^{12}$, —$SO_3R^{12}$, —$SO_2N(R^{11})_2$, —$OR^{10}$, —$SR^{10}$, —$N(R^{11})_2$, —$NR^{11}C(O)R^{10}$, —$NR^{11}S(O)R^{12}$, —$NR^{11}C(O)OR^{12}$, —$N(R^{11})C(O)N(R^{11})_2$, —$NR^{11}SO_2N(R^{11})_2$ and —NR or iii) a $C_{1-10}$ aliphatic group optionally substituted with one or more substituents selected from the group consisting of halogen, —$NO_2$, —CN, —NCS, $Ar^{10}$, —$C(O)OR^{10}$, —$C(O)R^{10}$, —$C(S)R^{10}$, —$OC(O)R^{10}$, —$C(O)N(R^{11})_2$, —$C(S)N(R^{11})_2$, —$OC(O)N(R^{11})_2$, —$S(O)R^{12}$, —$S(O)_2R^{12}$, —$SO_3R^{12}$, —$SO_2N(R^{11})_2$, —$OR^{10}$, —$SR^{10}$, —$N(R^{11})_2$, —$NR^{11}C(O)R^{10}$, —$NR^{11}S(O)R^{12}$, —$NR^{11}C(O)OR^{12}$, —$N(R^{11})C(O)N(R^{11})_2$, —$NR^{11}SO_2N(R^{11})_2$ and —$NR^{11}SO_2R^{12}$, provided that $R^1$ is other than hydrogen when $R^a$ or $R^b$ is —$S(O)R^1$, —$S(O)_2R^1$, —$SO_3R^1$, —$NR^2S(O)R^1$ or —$NR^2SO_2R^1$. Alternatively, each $R^1$ is independently —H or $C_{1-6}$ alkyl, wherein the $C_{1-6}$ alkyl is optionally substituted with one or more substituents independently selected from the group consisting of halogen, —OH, —SH, —O($C_{1-3}$ alkyl), —S($C_{1-3}$ alkyl) and $C_{1-6}$ haloalkoxy.

Each $R^2$ independently is H or $C_1$-$C_6$ alkyl, or, taken together with $NR^1$, forms a non-aromatic heterocyclic group optionally substituted with one or more substituents selected from the group consisting of =O, =S, halogen, nitro, cyano, hydroxy, $C_{1-6}$ alkyl, $C_{1-6}$haloalkyl, $C_{1-6}$hydroxyalkyl, amino, $C_{1-6}$alkylamino, $C_{1-6}$dialkylamino, $C_{1-6}$ aminoalkyl, ($C_{1-6}$ alkylamino)$C_{1-6}$ alkyl, ($C_{1-6}$ dialkylamino)$C_{1-6}$ alkyl, (phenyl)$C_{1-6}$ alkyl, (5-6 membered heteroaryl)$C_{1-6}$ alkyl, $C_{1-6}$ alkoxy, $C_{1-6}$ haloalkoxy, $C_{1-6}$ alkylcarbonyloxy, $C_{1-6}$alkoxycarbonyl, $C_{1-6}$ alkylcarbonyl, phenyl and 5-6 membered heteroaryl. Alternatively, $R^2$ is H or $C_{1-6}$ alkyl.

$R^3$ is H, halogen, $C_{1-6}$ alkyl or $C_{1-6}$ haloalkyl. Alternatively, $R^3$ is H.

$R^4$ is —H, $C_{1-6}$, phenyl, —$C(O)(C_{1-6}$ alkyl), —$C(O)$(phenyl), —$C(O)O(C_{1-6}$ alkyl), —$C(O)O$(phenyl), —$S(O)_2(C_{1-6}$ alkyl) or —$S(O)_2$(phenyl), wherein each alkyl in the groups represented by $R^4$ independently is optionally substituted with one or more substituents selected from the group consisting of halogen, hydroxy, nitro, cyano, amino, phenyl, 5-6 membered heteroaryl, $C_{1-6}$ alkoxy and $C_{1-6}$ haloalkoxy, and wherein each phenyl in the groups represented by $R^4$ independently is optionally substituted with one or more substituents selected from the group consisting of halogen, hydroxy, nitro, cyano, amino, $C_{1-6}$ alkyl, $C_{1-6}$ haloalkyl, $C_{1-6}$ alkoxy and $C_{1-6}$ haloalkoxy. Alternatively, $R^4$ is —H, $C_{1-6}$ alkyl, phenyl, —$C(O)(C_{1-6}$ alkyl), —$C(O)$(phenyl), —$C(O)O(C_{1-6}$ alkyl), —$C(O)O$(phenyl), —$S(O)_2(C_{1-6}$ alkyl) or —$S(O)_2$(phenyl), wherein each phenyl in the group represented by $R^4$ is optionally substituted with one or more substituents independently selected from the group consisting of halogen, $C_{1-6}$ alkyl, —$O(C_{1-6}$ alkyl), $C_{1-6}$ haloalkyl, $C_{1-6}$ haloalkoxy, cyano and nitro. In another alternative, $R^4$ is H, methyl, ethyl, 2-methoxyethyl or —$CH_2CONH_2$. In another alternative, $R^4$ is H or methyl. In another alternative, $R^4$ is H.

$R^5$ is —H, $C_{1-6}$, phenyl, —$C(O)(C_{1-6}$ alkyl), —$C(O)$(phenyl), —$C(O)O(C_{1-6}$ alkyl), —$C(O)O$(phenyl), —$S(O)_2(C_{1-6}$ alkyl) or —$S(O)_2$(phenyl), wherein each alkyl in the groups represented by $R^5$ independently is optionally substituted with one or more substituents selected from the group consisting of halogen, hydroxy, nitro, cyano, amino, phenyl, 5-6 membered heteroaryl, $C_{1-6}$ alkoxy and $C_{1-6}$ haloalkoxy, and wherein each phenyl in the groups represented by $R^5$ independently is optionally substituted with one or more substituents selected from the group consisting of halogen, hydroxy, nitro, cyano, amino, $C_{1-6}$ alkyl, $C_{1-6}$ haloalkyl, $C_{1-6}$ alkoxy and $C_{1-6}$ haloalkoxy. Alternatively, $R^5$ is —H, $C_{1-6}$ alkyl, phenyl, —$C(O)(C_{1-6}$ alkyl), —$C(O)$(phenyl), —$C(O)O(C_{1-6}$ alkyl), —$C(O)O$(phenyl), —$S(O)_2(C_{1-6}$ alkyl) or —$S(O)_2$(phenyl), wherein each phenyl in the group represented by $R^5$ is optionally substituted with one or more substituents independently selected from the group consisting of halogen, $C_{1-6}$ alkyl, —$O(C_{1-6}$ alkyl), $C_{1-6}$ haloalkyl, $C_{1-6}$ haloalkoxy, cyano and nitro. In another alternative, $R^5$ is H.

$R^6$ is hydrogen, halogen, nitro, cyano, R', —OR, —SR, —$N(R)_2$, —$C(O)R$, —$C(O)OR$, —$OC(O)R$, —$C(O)N(R)_2$, —$OC(O)N(R)_2$, —$NRC(O)R$, —$NRC(O)OR$, —SOR', —$SO_2R'$, —$SO_3R'$, —$SO_2N(R)_2$, —$NRS(O)R'$, —$NRSO_2R'$, —$NRC(O)N(R)_2$, —$NRC(O)ON(R)_2$, or —$NRSO_2N(R)_2$. Alternatively, $R^6$ is optionally substituted phenyl, optionally substituted 5-12 membered heteroaryl, —$CH_2$-(optionally substituted phenyl), —$CH_2$-(optionally substituted 5-12 membered heteroaryl), —$CH_2$—$CH_2$-(optionally substituted phenyl), —$CH_2$—$CH_2$-(optionally substituted 5-12 membered heteroaryl), —CH=CH-(optionally substituted phenyl), —CH=CH-(optionally substituted 5-12 membered heteroaryl), C≡C-(optionally substituted phenyl) or —C≡C-(optionally substituted 5-12 membered heteroaryl). Exemplary 5-12 membered heteroaryls in the group represented by $R^6$ include pyridyl, thiazolyl, pyrazinyl, thiophenyl, indolyl, quinolinyl, pyrrolyl, pyrazolyl, and pyrimidinyl, each of which is optionally substituted. In another alternative, exemplary 5-12 membered heteroaryls in the group represented by $R^6$ include optionally substituted pyridinyl, pyrimidinyl or pyrazinyl. In another alternative, $R^6$ is optionally substituted phenyl, —CH=CH-(optionally substituted phenyl) or —C≡C-(optionally substituted phenyl). Exemplary substituents for the phenyl or 5-12 membered heteroaryl in the group represented by $R^6$ include halogen, nitro, cyano, —OH, —SH, —O($C_{1-6}$ alkyl), —S($C_{1-6}$ alkyl), $C_{1-6}$ alkyl, $C_{1-6}$ haloalkyl, ($C_{1-6}$ haloalkoxy)$C_{1-6}$ alkyl, ($C_{1-6}$ alkoxy)$C_{1-6}$ alkyl, $C_{1-6}$ hydroxyalkyl, ($C_{1-6}$ aminoalkyl), ($C_{1-6}$ alkylamino)$C_{1-6}$ alkyl, ($C_{1-6}$ dialkylamino)$C_{1-6}$ alkyl, (phenyl)$C_{1-6}$ alkyl, (5-6 membered heteroaryl)$C_{1-6}$ alkyl, amino, $C_{1-6}$ alkylamino, $C_{1-6}$dialkylamino, $C_{1-6}$ haloalkoxy, $C_{1-6}$ alkylcarbonyloxy, $C_{1-6}$ alkoxycarbonyl, $C_{1-6}$ alkylcarbonyl, —$(CH_2)_{0-3}$—N-piperidinyl, —$(CH_2)_{0-3}$—N-morpholinyl, —$(CH_2)_{0-3}$—N-pyrrolidinyl and —$(CH_2)_{0-3}$—N—$(CH_2)_{0-3}$-piperazinyl, wherein the N-piperazinyl is optionally substituted with $C_{1-6}$ alkyl or $C_{1-6}$ acyl. Alternatively, exemplary substituents for the phenyl or 5-12 membered heteroaryl in the group represented by $R^6$ include halogen, $C_{1-6}$ alkyl, $C_{1-6}$ haloalkyl, ($C_{1-6}$ aminoalkyl), ($C_{1-6}$ alkylamino)$C_{1-6}$ alkyl, ($C_{1-6}$ dialkylamino)$C_{1-6}$ alkyl, (phenyl)$C_{1-6}$ alkyl, amino, $C_{1-6}$ alkylamino, $C_{1-6}$ dialkylamino, —(CH$_2$)$_{0-3}$—N-piperidinyl, —(CH$_2$)$_{0-3}$—N-morpholinyl, —(CH$_2$)$_{0-3}$—N-pyrrolidinyl and —(CH$_2$)$_{0-3}$—N-piperazinyl, wherein the N-piperazinyl is optionally substituted with $C_{1-6}$ alkyl or $C_{1-6}$ acyl. In another alternative, exemplary substituents for the phenyl or 5-12 membered heteroaryl in the group represented by $R^6$ include halogen, $C_{1-6}$ alkyl, $C_{1-6}$ haloalkyl, ($C_{1-6}$ aminoalkyl), ($C_{1-6}$ alkylamino)$C_{1-6}$ alkyl, ($C_{1-6}$dialkylamino)$C_{1-6}$ alkyl, (phenyl)$C_{1-6}$ alkyl, amino, $C_{1-6}$ alkylamino, $C_{1-6}$ dialkylamino, —(CH$_2$)$_{0-3}$—N-piperidinyl, —(CH$_2$)$_{0-3}$—N-morpholinyl, —(CH$_2$)$_{0-3}$—N-pyrrolidinyl, —(CH$_2$)$_{0-3}$—N-piperazinyl and —(CH$_2$)$_{0-3}$—N-oxazepanyl, wherein the N-piperazinyl is optionally N'-substituted with $C_{1-6}$ alkyl or $C_{1-6}$ acyl. When substituted, the phenyl and 5-12 membered heteroaryl group represented by $R^6$ can have one or more substituents. In another alternative, $R^6$ is CH=CH-(phenyl); wherein the phenyl in CH=CH-(phenyl) is optionally substituted with one or more substituents independently selected from the group consisting of halogen, $C_{1-6}$ alkyl, $C_{1-6}$ haloalkyl, ($C_{1-6}$ aminoalkyl), ($C_{1-6}$ alkylamino)$C_{1-6}$ alkyl, ($C_{1-6}$ dialkylamino)$C_{1-6}$ alkyl, (phenyl)$C_{1-6}$ alkyl, amino, $C_{1-6}$ alkylamino, $C_{1-6}$ dialkylamino, —(CH$_2$)$_{0-3}$—N-piperidinyl, —(CH$_2$)$_{0-3}$—N-morpholinyl, —(CH$_2$)$_{0-3}$—N-pyrrolidinyl, —(CH$_2$)$_{0-3}$—N-piperazinyl and (CH$_2$)$_{0-3}$—N-oxazepanyl, wherein the N-piperazinyl is optionally N'-substituted with $C_{1-6}$ alkyl or $C_{1-6}$ acyl. In yet another alternative, $R^6$ is phenyl optionally substituted with —(CH$_2$)$_{0-3}$—N-piperazinyl, wherein the N-piperazinyl is optionally N'-substituted with $C_{1-6}$ alkyl or ($C_{1-6}$ alkoxy)$C_{1-6}$ alkyl.

Each $R^{10}$ independently is: i) hydrogen; ii) a $C_{6-14}$ aryl group or a 5-14 membered heteroaryl group, each optionally and independently substituted with one or more substituents selected from the group consisting of halogen, nitro, cyano, hydroxy, $C_{1-10}$ alkyl, $C_{1-10}$ haloalkyl, ($C_{1-10}$ haloalkoxy) $C_{1-10}$ alkyl, ($C_{1-10}$ alkoxy)$C_{1-10}$ alkyl, $C_{1-10}$ hydroxyalkyl, $C_{1-10}$ aminoalkyl, ($C_{1-10}$ alkylamino)$C_{1-10}$ alkyl, ($C_{1-10}$dialkylamino)$C_{1-10}$ alkyl, (phenyl)$C_{1-10}$ alkyl, (5-6 membered heteroaryl)$C_{1-10}$ alkyl, amino, $C_{1-10}$ alkylamino, $C_{1-10}$dialkylamino, $C_{1-10}$ alkoxy, $C_{1-10}$ haloalkoxy, $C_{1-10}$ alkylcarbonyloxy, $C_{1-10}$ alkoxycarbonyl and $C_{1-10}$ alkylcarbonyl; or iii) a $C_{1-10}$ alkyl group optionally substituted with one or more substituents selected from the group consisting of halogen, nitro, cyano, hydroxy, $C_{1-10}$ haloalkyl, $C_{1-10}$ alkoxy, $C_{1-10}$ haloalkoxy, amino, $C_{1-10}$ alkylamino, $C_{1-10}$dialkylamino, $C_{1-10}$ alkylcarbonyloxy, $C_{1-10}$ alkoxycarbonyl, $C_{1-10}$ alkylcarbonyl and phenyl, said phenyl being optionally substituted with one or more substituents selected from the group consisting of halogen, hydroxy, nitro, cyano, amino, $C_{1-3}$ alkyl, $C_{1-3}$ haloalkyl, $C_{1-3}$ alkoxy and $C_{1-3}$ haloalkoxy.

Each $R^{11}$ independently is $R^{10}$, —CO$_2R^{10}$, —SO$_2R^{10}$ or —C(O)$R^{10}$, or —N($R^{11}$)$_2$ taken together is a non-aromatic heterocyclic group optionally substituted with one or more substituents selected from the group consisting of =O, =S, halogen, nitro, cyano, hydroxy, $C_{1-6}$ alkyl, $C_{1-6}$ haloalkyl, $C_{1-6}$hydroxyalkyl, amino, $C_{1-6}$ alkylamino, $C_{1-6}$ dialkylamino, $C_{1-6}$ aminoalkyl, ($C_{1-6}$ alkylamino)$C_{1-6}$ alkyl, ($C_{1-6}$ dialkylamino)$C_{1-6}$ alkyl, $C_{1-6}$ alkoxy, $C_{1-6}$ haloalkoxy, $C_{1-6}$alkylcarbonyloxy, $C_{1-6}$ alkoxycarbonyl and $C_{1-6}$ alkylcarbonyl.

Each $R^{12}$ is independently is $R^{10}$ provided that $R^{12}$ is not hydrogen;

Each $R^{21}$ independently is hydrogen, $C_{1-6}$ alkyl, phenyl or 5-6 membered heteroaryl, wherein each of the phenyl and heteroaryl groups represented by $R^{21}$ is independently and optionally substituted with one or more substituents selected from the group consisting of halogen, hydroxy, nitro, cyano, amino, $C_{1-3}$ alkyl, $C_{1-3}$ haloalkyl, $C_{1-3}$ alkoxy and $C_{1-3}$ haloalkoxy, and wherein the alkyl group represented by $R^{21}$ is optionally substituted with one or more substituents selected from the group consisting of halogen, hydroxy, nitro, cyano, amino, $C_{1-3}$ alkyl, $C_{1-3}$ haloalkyl, $C_{1-3}$ alkoxy and $C_{1-3}$ haloalkoxy; or N($R^{21}$)$_2$ forms a non-aromatic heterocyclic group optionally substituted with one or more substituents selected from the group consisting of halogen, hydroxy, nitro, cyano, =O, $C_{1-3}$ alkyl, $C_{1-3}$ haloalkyl, $C_{1-3}$ alkoxy, $C_{1-3}$ haloalkoxy and amino; and Each $R^{22}$ independently $C_{1-6}$ alkyl, phenyl or 5-6 membered heteroaryl, wherein each of the phenyl and heteroaryl groups represented by $R^{22}$ is independently and optionally substituted with one or more substituents selected from the group consisting of halogen, hydroxy, nitro, cyano, amino, $C_{1-3}$ alkyl, $C_{1-3}$ haloalkyl, $C_{1-3}$ alkoxy and $C_{1-3}$ haloalkoxy, and wherein the alkyl group represented by $R^{22}$ is optionally substituted with one or more substituents selected from the group consisting of halogen, hydroxy, nitro, cyano, amino, $C_{1-3}$ alkyl, $C_{1-3}$ haloalkyl, $C_{1-3}$ alkoxy and $C_{1-3}$ haloalkoxy;

Each R independently is hydrogen, $C_{1-10}$ aliphatic, phenyl or 5-6 membered heteroaryl. The aliphatic group represented by R is optionally substituted with one or more substituents selected from the group consisting of halogen, hydroxy, nitro, cyano, amino, phenyl, 5-6 membered heteroaryl, $C_{1-6}$ alkoxy, $C_{1-6}$ haloalkoxy, and wherein each of the phenyl and heteroaryl groups represented by R, and the phenyl and heteroaryl substituents for the aliphatic group represented by R independently are optionally and independently substituted with one or more substituents selected from the group consisting of halogen, hydroxy, nitro, cyano, amino, $C_{1-6}$ alkyl, $C_{1-6}$ haloalkyl, $C_{1-6}$ alkoxy, $C_{1-6}$ haloalkoxy, or N(R)$_2$ forms a non-aromatic heterocyclic group optionally substituted with one or more substituents selected from the group consisting of =O, =S, halogen, nitro, cyano, hydroxy, $C_{1-6}$ alkyl, $C_{1-6}$ haloalkyl, $C_{1-6}$hydroxyalkyl, amino, $C_{1-6}$ alkylamino, $C_{1-6}$ dialkylamino, $C_{1-6}$ aminoalkyl, ($C_{1-6}$ alkylamino)$C_{1-6}$ alkyl, ($C_{1-6}$ dialkylamino)$C_{1-6}$ alkyl, (phenyl)$C_{1-6}$ alkyl, (5-6 membered heteroaryl)$C_{1-6}$ alkyl, $C_{1-6}$ alkoxy, $C_{1-6}$ haloalkoxy, $C_{1-6}$ alkylcarbonyloxy, $C_{1-6}$ alkoxycarbonyl, $C_{1-6}$ alkylcarbonyl, phenyl and 5-6 membered heteroaryl.

Each R' independently is $C_{1-10}$ aliphatic, phenyl or 5-12 membered heteroaryl. The aliphatic group represented by R' is optionally substituted with one or more substituents selected from the group consisting of halogen, hydroxy, nitro, cyano, amino, phenyl, 5-12 membered heteroaryl, $C_1$-$C_6$ alkoxy, $C_1$-$C_6$ haloalkoxy, $C_{1-6}$ alkylamino, $C_{1-6}$ dialkylamino, —C(O)($C_1$-$C_6$ alkyl), —C(O)($C_1$-$C_6$ haloalkyl), —C(O)(phenyl), —C(O)(non-aromatic heterocyclic group), —C(O)O(C1-C6 alkyl), —C(O)O(C1-C6 haloalkyl), —C(O)O(phenyl), —OC(O)($C_1$-$C_6$ alkyl), —OC(O)($C_1$-$C_6$ haloalkyl), —OC(O)(phenyl), —S(O)$_2$($C_1$-$C_6$ alkyl), —S(O)$_2$($C_1$-$C_6$ haloalkyl) and —S(O)$_2$(phenyl); and each of the phenyl and heteroaryl groups represented by R', and the phenyl and heteroaryl groups in the substituents for the aliphatic group represented by R' independently are optionally substituted with one or more substituents selected from the group consisting of halogen, —OH, —SH, nitro, cyano, amino, $C_{1-6}$ alkylamino, $C_{1-6}$ dialkylamino, $C_1$-$C_6$ alkyl, $C_1$-$C_6$ haloalkyl, —O($C_{1-6}$ alkyl), —S($C_{1-6}$ alkyl), —O($C_{1-6}$ haloalkyl), ($C_{1-6}$ haloalkoxy)$C_{1-6}$ alkyl, ($C_{1-6}$ alkoxy)$C_{1-6}$ alkyl, $C_{1-6}$hydroxyalkyl, ($C_{1-6}$ aminoalkyl), ($C_{1-6}$ alkylamino) $C_{1-6}$ alkyl, ($C_{1-6}$ dialkylamino)$C_{1-6}$ alkyl, (phenyl)$C_{0-6}$ alkyl, (5-6 membered heteroaryl)$C_{0-6}$ alkyl, (non-aromatic heterocyclic group)$C_{0-6}$ alkyl (optionally substituted with $C_{1-6}$ alkyl or $C_{1-6}$ acyl), —C(O)($C_1$-$C_6$ alkyl), —C(O)($C_1$-$C_6$ haloalkyl), —C(O)(phenyl), —C(O)(non-aromatic heterocyclic group), —C(O)O($C_1$-C6 alkyl), —C(O)O($C_1$-$C_6$ haloalkyl), —C(O)O(phenyl), —OC(O)($C_1$-$C_6$ alkyl), —OC(O)($C_1$-$C_6$ haloalkyl), —OC(O)(phenyl), —S(O)$_2$($C_1$-$C_6$ alkyl), —S(O)$_2$($C_1$-$C_6$ haloalkyl), and —S(O)$_2$(phenyl). Alternatively, suitable substituents for the each of the aliphatic, phenyl and heteroaryl groups represented by R, and the phenyl and heteroaryl groups in the substituents for the aliphatic group represented by R independently are as described for the phenyl and 5-12 membered heteroaryl groups represented by $R^6$.

$Ar^1$ is a $C_{6-14}$ aryl group or a 5-14 membered heteroaryl group, each optionally and independently substituted with one or more substituents selected from the group consisting of halogen, nitro, cyano, $C_{1-10}$ alkyl, $C_{1-10}$haloalkyl, ($C_{1-10}$ haloalkoxy)$C_{1-10}$ alkyl, ($C_{1-10}$ alkoxy)$C_{1-10}$ alkyl, $C_{1-10}$hydroxyalkyl, $C_{1-10}$ aminoalkyl, ($C_{1-10}$ alkylamino)$C_{1-10}$ alkyl, ($C_{1-10}$dialkylamino)$C_{1-10}$ alkyl, —N($R^{21}$)$_2$, —C(O)N($R^{21}$)$_2$, —C(O)N($R^{21}$)$_2$, —NR$^{21}$C(O)R$^{21}$, —SO$_2$R$^{22}$, —SO$_2$N($R^{21}$)$_2$, —NR$^{21}$SO$_2$R$^{22}$, —NR$^{21}$C(O)N($R^{21}$)$_2$, —NRC(O)ON(R)$_2$, —NR$^{21}$SO$_2$N($R^{21}$)$_2$, —OR$^{21}$, —SR$^{21}$, $C_{1-10}$ haloalkoxy, —C(O)R$^{21}$, —C(O)OR$^{21}$, —OC(O)R$^{21}$, phenyl and 5-6 membered heteroaryl, wherein said phenyl and said 5-6 membered heteroaryl are each independently and optionally substituted with one or more substituents selected from the group consisting of halogen, hydroxy, nitro, cyano, amino, $C_{1-3}$ alkyl, $C_{1-3}$ haloalkyl, $C_{1-3}$ alkoxy and $C_{1-3}$ haloalkoxy.

Each $Ar^{10}$ independently is a $C_{6-14}$ aryl group or a 5-14 membered heteroaryl group, each optionally and independently substituted with one or more substituents selected from the group consisting of halogen, nitro, cyano, —OH, —SH, —O($C_{1-10}$ alkyl), —S($C_{1-10}$ alkyl), $C_{1-10}$ alkyl, $C_{1-10}$ haloalkyl, ($C_{1-10}$ haloalkoxy)$C_{1-10}$ alkyl, ($C_{1-10}$ alkoxy)$C_{1-10}$ alkyl, $C_{1-10}$hydroxyalkyl, ($C_{1-10}$ aminoalkyl, ($C_{1-10}$ alkylamino)$C_{1-10}$ alkyl, ($C_{1-10}$ dialkylamino)$C_{1-10}$ alkyl, (phenyl)$C_{1-10}$ alkyl, (5-6 membered heteroaryl)$C_{1-10}$ alkyl, amino, $C_{1-10}$ alkylamino, $C_{1-10}$dialkylamino, $C_{1-10}$ haloalkoxy, $C_{1-10}$alkylcarbonyloxy, $C_{1-10}$ alkoxycarbonyl and $C_{1-10}$ alkylcarbonyl.

Each n is 0, 1, 2, 3 or 4. Alternatively, each n is 0, 1 or 2.

Each m is 0, 1, 2 or 3. Alternatively, each m is 0 or 1. In another alternative, m is 0.

Each p is 1, 2 or 3; and

Each q is 2, 3, 4 or 5.

Another embodiment of the invention is a compound represented by any one of following structural formulas (Ia)-(Id), (II)-(XIII), (IIa)-(XIIIa), (IIb)-(XIIIb), (IIc)-(XIIIc) and (IId)-(XIIId), or a pharmaceutically acceptable salt thereof:

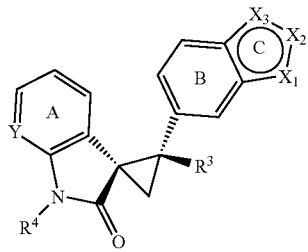
(Ia)

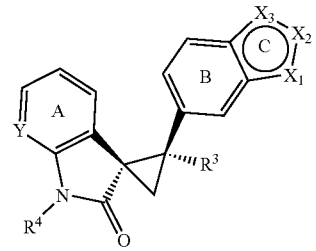
(Ib)

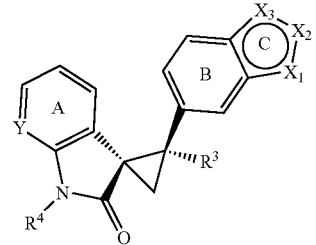
(Ic)

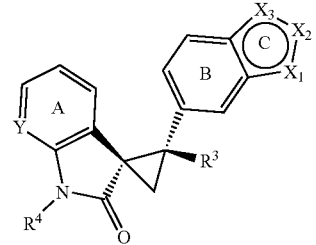
(Id)

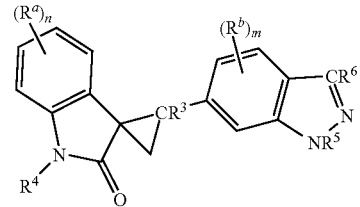
(II)

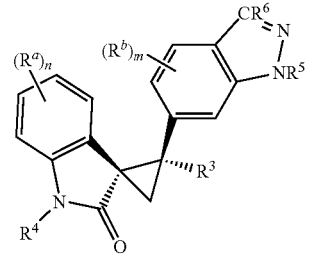
(IIa)

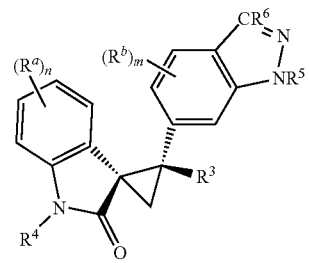
(IIb)

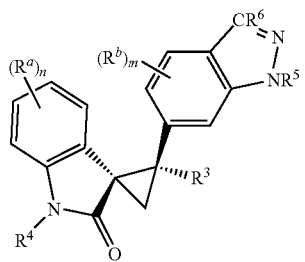
(IIc)
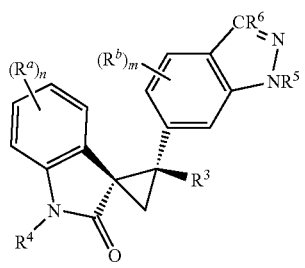
(IId)
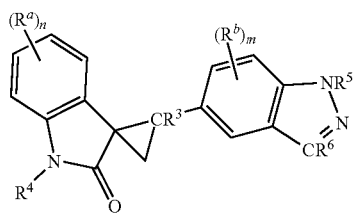
(III)
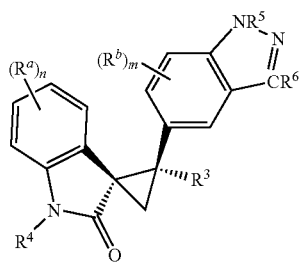
(IIIa)
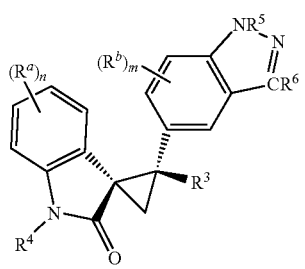
(IIIb)
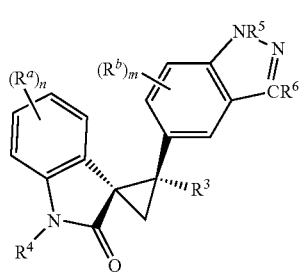
(IIIc)
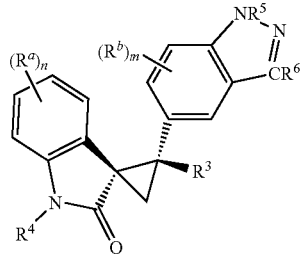
(IIId)
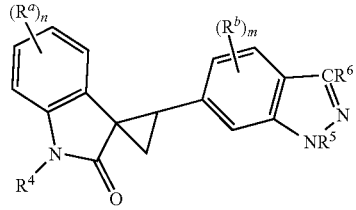
(IV)
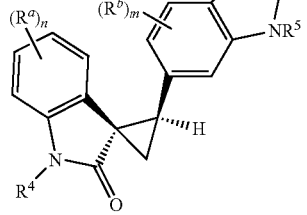
(IVa)
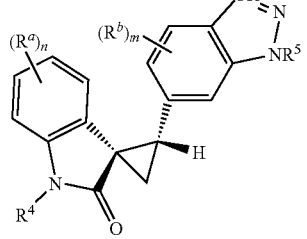
(IVb)
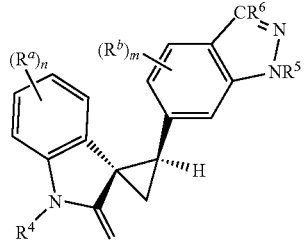
(IVc)
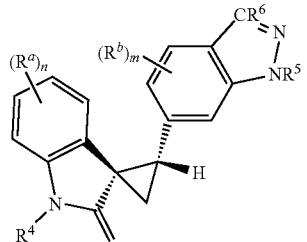
(IVd)

(V)
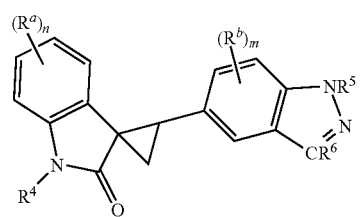
(Va)
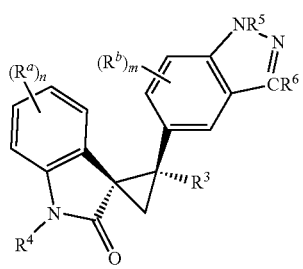
(Vb)
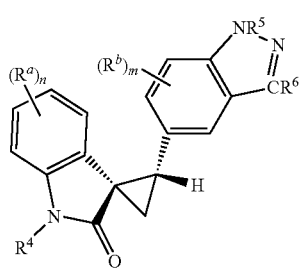
(Vc)
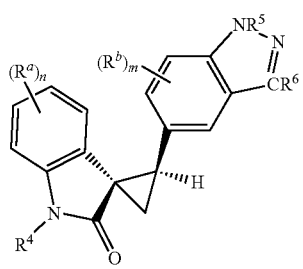
(Vd)
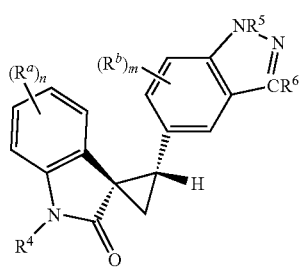
(VI)
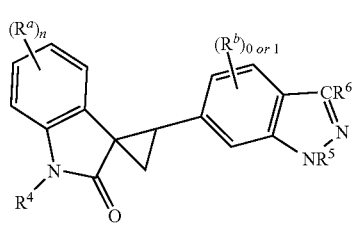
(VIa)
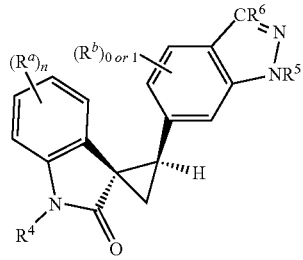
(VIb)
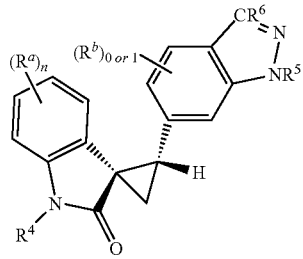
(VIc)
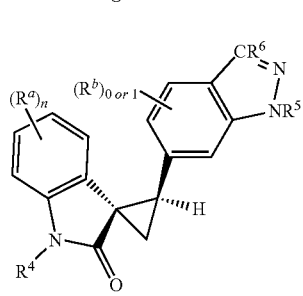
(VId)
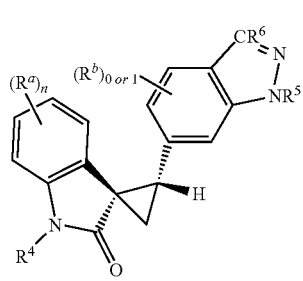
(VII)
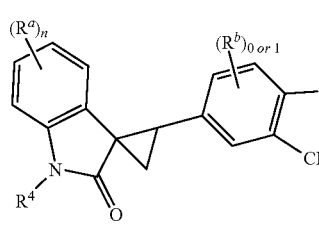
(VIIa)
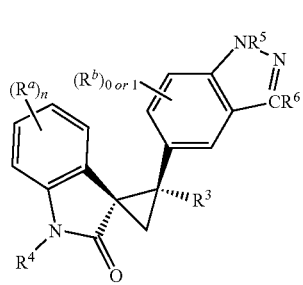

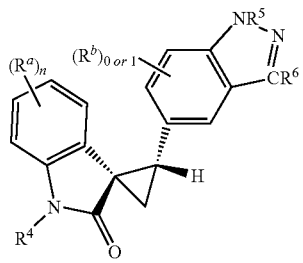 (VIIb)
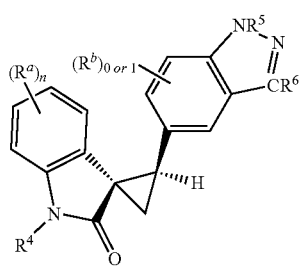 (VIIc)
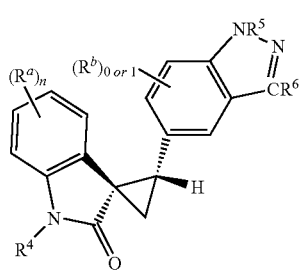 (VIId)
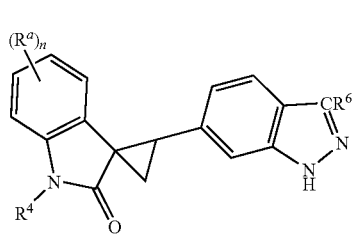 (VIII)
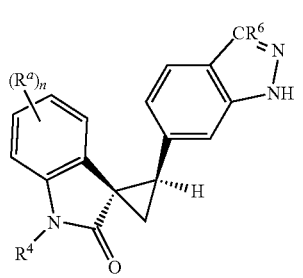 (VIIIa)
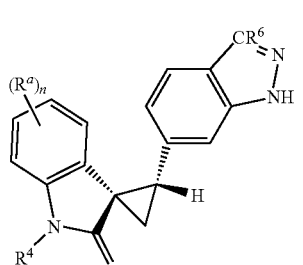 (VIIIb)
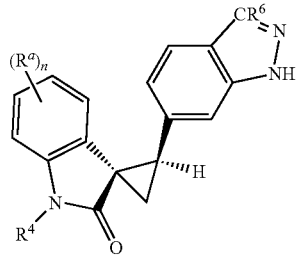 (VIIIc)
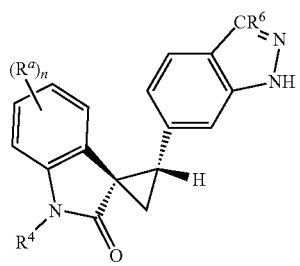 (VIIId)
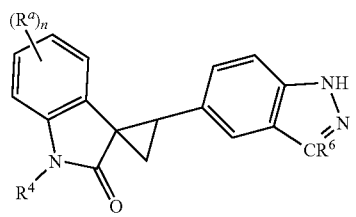 (IX)
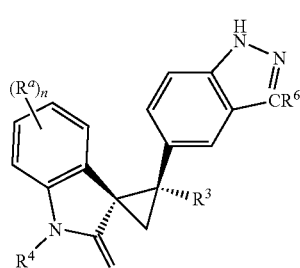 (IXa)
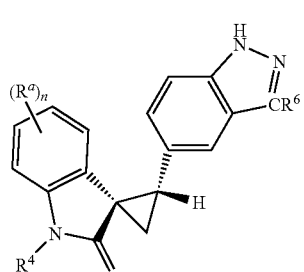 (IXb)
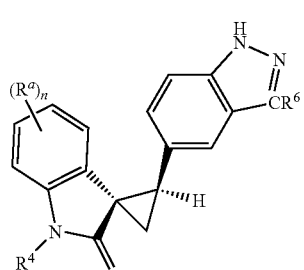 (IXc)

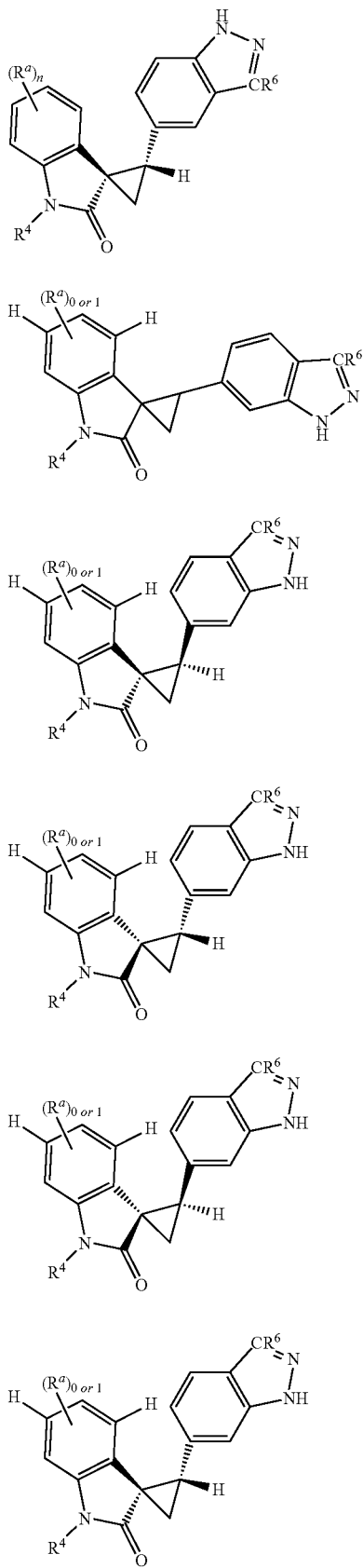
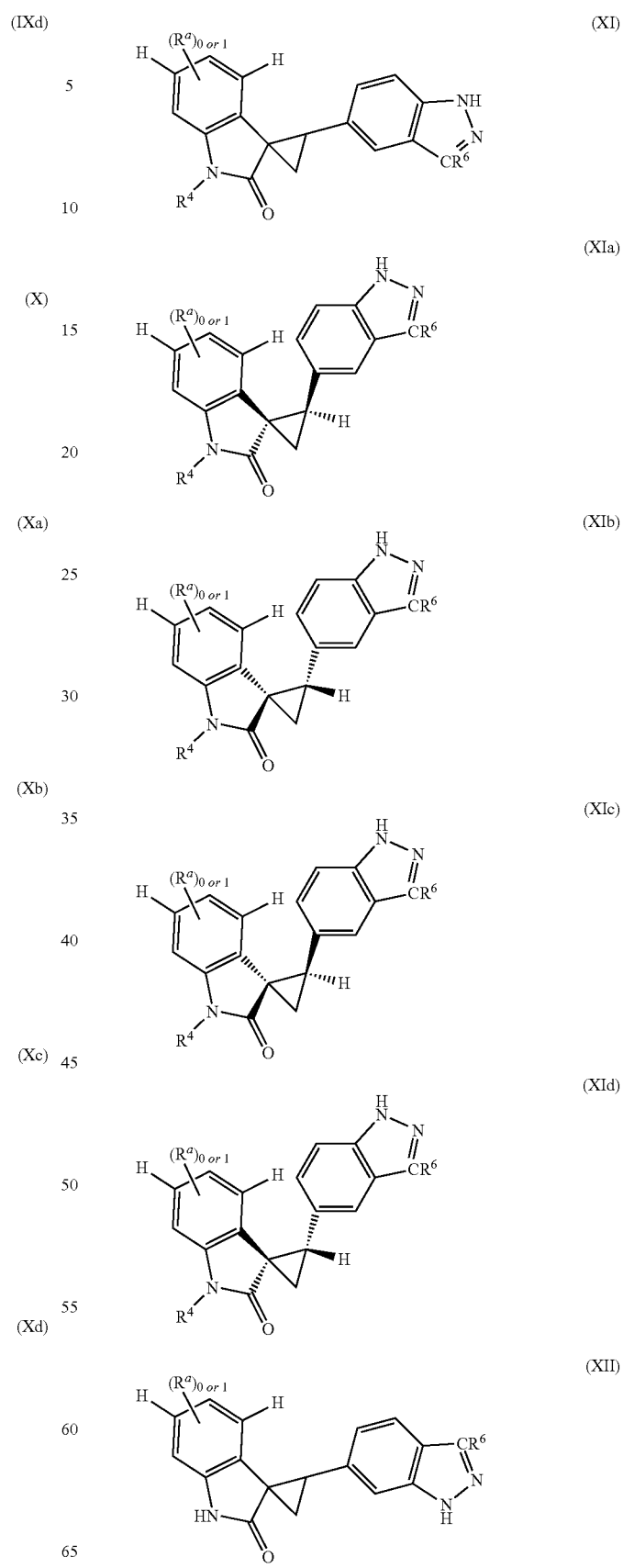

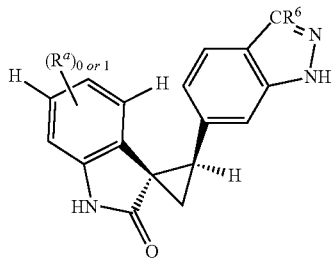
(XIIa)

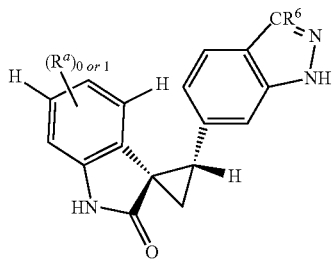
(XIIb)

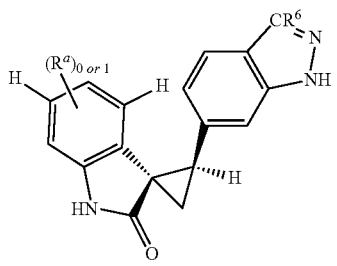
(XIIc)

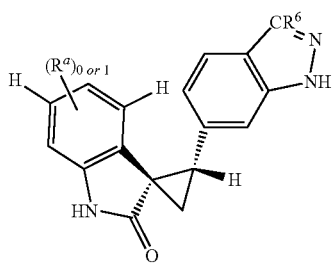
(XIId)

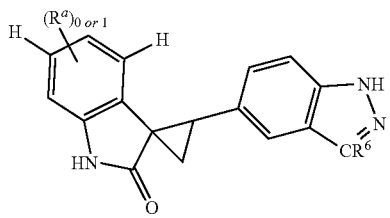
(XIII)

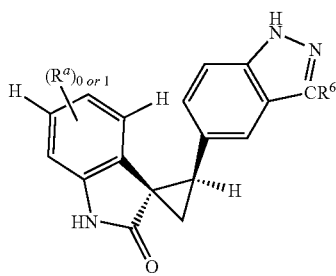
(XIIIa)

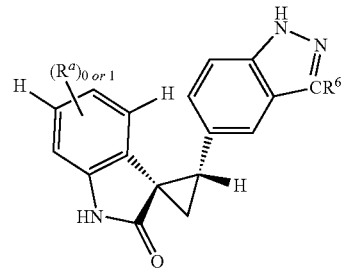
(XIIIb)

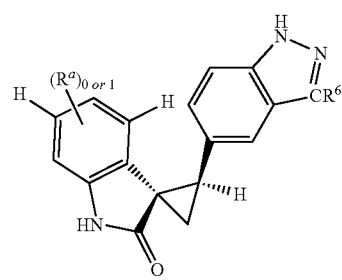
(XIIIc)

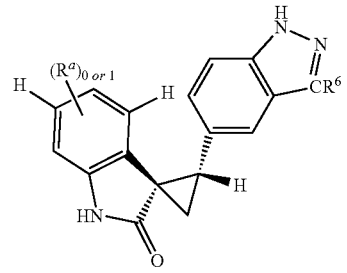
(XIIId)

Values and alternative values for Structural Formulas (Ia)-(Id), (II)-(XIII), (IIa)-(XIIIa), (IIb)-(XIIIb), (IIc)-(XIIIc) and (IId)-(XIIId) are as described for Structural Formulas (I') or (I) above.

In a second embodiment, the invention is directed to a compound represented by any one of Structural Formulas (Ia)-(Id), (II)-(VII), (IIa)-(VIIa), (IIb)-(XIIIb), (IIc)-(VIIc) and (IId)-(VIId) or a pharmaceutically acceptable salt thereof, wherein $R^5$ is —H, C1-C6 alkyl, phenyl, —C(O)(C1-C6 alkyl), —C(O)(phenyl), —C(O)O(C1-C6 alkyl), —C(O)O(phenyl), —S(O)$_2$(C1-C6 alkyl) or —S(O)$_2$(phenyl), wherein each phenyl in the group represented by $R^5$ is optionally substituted with one or more substituents independently selected from the group consisting of halogen, $C_{1-6}$ alkyl, —O($C_{1-6}$ alkyl), $C_{1-6}$haloalkyl, $C_{1-6}$haloalkoxy, cyano and nitro; and values and alternative values for the remainder of the variables are as described above for Structural Formula (I') or (I).

In a third embodiment, the invention is directed to a compound represented by any one of Structural Formulas (Ia)-(Id), (II)-(XI), (IIa)-(XIa), (IIb)-(XIb), (IIc)-(XIc) and (IId)-(XId) or a pharmaceutically acceptable salt thereof, wherein $R^4$ is —H, C1-C6 alkyl, phenyl, —C(O)(C1-C6 alkyl), —C(O)(phenyl), —C(O)O(C1-C6 alkyl), —C(O)O(phenyl), —S(O)$_2$(C1-C6 alkyl) or —S(O)$_2$(phenyl), wherein each phenyl in the group represented by $R^4$ is optionally substituted with one or more substituents independently selected from the group consisting of halogen, $C_{1-6}$ alkyl, —O($C_{1-6}$ alkyl), $C_{1-6}$haloalkyl, $C_{1-6}$haloalkoxy, cyano and nitro; $R^5$, when present (as in Structural Formulas (Ia)-(Id), (II)-(VII), (IIa)-(VIIa), (IIb)-(VIIIb), (IIc)-(VIIc)

and (IId)-(VIId)), is selected from the same list of values as $R^4$, but is independently selected with respect to $R^4$; and values and alternative values for the remainder of the variables are as described above for Structural Formula (I') or (I).

In a fourth embodiment, the invention is directed to a compound represented by any one of Structural Formulas (Ia)-(Id), (II)-(XIII), (IIa)-(XIIIa), (IIb)-(XIIIb), (IIc)-(XIIIc) and (IId)-(XIIId) or a pharmaceutically acceptable salt thereof, wherein $R^4$, when present (as in Structural Formulas (Ia)-(Id), (II)-(XI), (IIa)-(XIa), (IIb)-(XIb), (IIc)-(XIc) and (IId)-(XId)), and $R^5$, when present (as in Structural Formulas (Ia)-(Id), (II)-(VII), (IIa)-(VIIa), (IIb)-(VIIb), (IIc)-(VIIc) and (IId)-(VIId)), are independently —H, C1-C6 alkyl, phenyl, —C(O)(C1-C6 alkyl), —C(O)(phenyl), —C(O)O(C1-C6 alkyl), —C(O)O(phenyl), —S(O)$_2$(C1-C6 alkyl) or —S(O)$_2$(phenyl), wherein each phenyl in the group represented by $R^5$ is optionally substituted with one or more substituents independently selected from the group consisting of halogen, $C_{1-6}$ alkyl, —O($C_{1-6}$ alkyl), $C_{1-6}$haloalkyl, $C_{1-6}$haloalkoxy, cyano and nitro; $R^6$ is optionally substituted phenyl, optionally substituted 5-12 membered heteroaryl, —CH$_2$-(optionally substituted phenyl), —CH$_2$-(optionally substituted 5-12 membered heteroaryl), —CH$_2$—CH$_2$-(optionally substituted phenyl), —CH$_2$—CH$_2$-(optionally substituted 5-12 membered heteroaryl), —CH=CH-(optionally substituted phenyl), —CH=CH-(optionally substituted 5-12 membered heteroaryl), —C≡C-(optionally substituted phenyl) or —C≡C-(optionally substituted 5-12 membered heteroaryl); and values and alternative values for the remainder of the variables are as described above for Structural Formula (I') or (I). Exemplary 5-12 membered heteroaryls in the group represented by $R^6$ include pyridyl, thiazolyl, pyrazinyl, thiophenyl, indolyl, quinolinyl, pyrrolyl, pyrazolyl, and pyrimidinyl, each of which is optionally substituted. An alternative group of exemplary 5-12 membered heteroaryls in the group represented by $R^6$ include optionally substituted pyridinyl, pyrimidinyl or pyrazinyl.

In a fifth embodiment, for Structural Formulas (Ia)-(Id), (II)-(XI), (IIa)-(XIa), (IIb)-(XIb), (IIc)-(XIc) and (IId)-(XId), $R^4$ is H, methyl, ethyl, 2-methoxyethyl or —CH$_2$CONH$_2$. Values and alternative values for the remainder of the variables are as described above for Structural Formula (I') or (I)

In a sixth embodiment, $R^6$ is optionally substituted phenyl, —CH=CH-(optionally substituted phenyl) or —C≡C-(optionally substituted phenyl). Values and alternative values for the remainder of the variables are as described above for Structural Formula (I') or (I) or in the fifth embodiment.

Exemplary substituents for the phenyl and 5-12 membered heteroaryl group represented by $R^6$ in the fourth or sixth embodiment include halogen, nitro, cyano, —OH, —SH, —O($C_{1-6}$ alkyl), —S($C_{1-6}$ alkyl), $C_{1-6}$ alkyl, $C_{1-6}$ haloalkyl, ($C_{1-6}$ haloalkoxy)$C_{1-6}$ alkyl, ($C_{1-6}$ alkoxy)$C_{1-6}$ alkyl, $C_{1-6}$ hydroxyalkyl, ($C_{1-6}$ aminoalkyl), ($C_{1-6}$ alkylamino)$C_{1-6}$ alkyl, ($C_{1-6}$ dialkylamino)$C_{1-6}$ alkyl, (phenyl)$C_{1-6}$ alkyl, (5-6 membered heteroaryl)$C_{1-6}$ alkyl, amino, $C_{1-6}$ alkylamino, $C_{1-6}$ dialkylamino, $C_{1-6}$ haloalkoxy, $C_{1-6}$ alkylcarbonyloxy, $C_{1-6}$ alkoxycarbonyl, $C_{1-6}$ alkylcarbonyl, —(CH$_2$)$_{0-3}$—N-piperidinyl, —(CH$_2$)$_{0-3}$—N-morpholinyl, —(CH$_2$)$_{0-3}$—N-pyrrolidinyl and —(CH$_2$)$_{0-3}$—N—(CH$_2$)$_{0-3}$-piperazinyl, wherein the N-piperazinyl is optionally substituted with $C_{1-6}$ alkyl or $C_{1-6}$ acyl. An alternative list of exemplary substituents for the phenyl and 5-12 membered heteroaryl group represented by $R^6$ in the fourth or sixth embodiment include halogen, $C_{1-6}$ alkyl, $C_{1-6}$ haloalkyl, ($C_{1-6}$ aminoalkyl), ($C_{1-6}$ alkylamino)$C_{1-6}$ alkyl, ($C_{1-6}$ dialkylamino)$C_{1-6}$ alkyl, (phenyl)$C_{1-6}$ alkyl, amino, $C_{1-6}$ alkylamino, $C_{1-6}$ dialkylamino, —(CH$_2$)$_{0-3}$—N-piperidinyl, —(CH$_2$)$_{0-3}$—N-morpholinyl, —(CH$_2$)$_{0-3}$—N-pyrrolidinyl and —(CH$_2$)$_{0-3}$—N-piperazinyl, wherein the N-piperazinyl is optionally substituted with $C_{1-6}$ alkyl or $C_{1-6}$ acyl. In a seventh embodiment, the invention is directed to a compound represented by any one of (Ia)-(Id), (II)-(XIII), (IIa)-(XIIIa), (IIb)-(XIIIb), (IIc)-(XIIIc) and (IId)-(XIIId), wherein $R^a$ and $R^b$, when present (as in (Ia)-(Id), (II)-(VII), (IIa)-(VIIa), (IIb)-(VIIb), (IIc)-(VIIc) and (IId)-(VIId)), are independently halogen, cyano, —NR$^1$R$^2$, —NR$^2$C(O)R$^1$, —C(O)OR$^1$, —OC(O)R$^1$, —C(O)NR$^1$R$^2$, —NR$^2$C(O)OR$^1$, —N(R$^2$)C(O)NR$^1$R$^2$, —OR$^1$, —SO$_2$NR$^1$R$^2$, —NR$^2$SO$_2$R$^1$, $C_{1-6}$ alkyl, phenyl or 5-12 membered heteroaryl (for example, pyridyl, thiazolyl, pyrazinyl, thiophenyl, indolyl, quinolinyl, pyrrolyl, pyrazolyl, or pyrimidinyl), wherein the $C_{1-6}$ alkyl represented by $R^a$ and $R_b$ is optionally and independently substituted with one or more substituents selected from the group consisting of halogen, nitro, cyano, —OH, —SH, —O($C_{1-6}$ alkyl), —S($C_{1-6}$ alkyl), $C_{1-6}$ haloalkoxy, amino, $C_{1-6}$ alkylamino, $C_{1-6}$ dialkylamino, $C_{1-6}$ alkylcarbonyloxy, $C_{1-6}$ alkoxycarbonyl and $C_{1-6}$ alkylcarbonyl; and the phenyl or the 5-12 membered heteroaryl represented by $R^a$ and $R_b$ is optionally substituted with one or more substituents selected from the group consisting of halogen, nitro, cyano, —OH, —SH, —O($C_{1-6}$ alkyl), —S($C_{1-6}$ alkyl), $C_{1-6}$ alkyl, $C_{1-6}$ haloalkyl, ($C_{1-6}$ haloalkoxy)$C_{1-6}$ alkyl, ($C_{1-6}$ alkoxy)$C_{1-6}$ alkyl, $C_{1-6}$ hydroxyalkyl, ($C_{1-6}$ aminoalkyl), ($C_{1-6}$ alkylamino)$C_{1-6}$ alkyl, ($C_{1-6}$ dialkylamino)$C_{1-6}$ alkyl, (phenyl)$C_{1-6}$ alkyl, (5-6 membered heteroaryl)$C_{1-6}$ alkyl, amino, $C_{1-6}$ alkylamino, $C_{1-6}$ dialkylamino, $C_{1-6}$ haloalkoxy, $C_{1-6}$ alkylcarbonyloxy, $C_{1-6}$ alkoxycarbonyl and $C_{1-6}$ alkylcarbonyl; each $R^1$ is independently —H or $C_{1-6}$ alkyl, wherein the $C_{1-6}$ alkyl is optionally substituted with one or more substituents independently selected from the group consisting of halogen, —OH, —SH, —O($C_{1-3}$ alkyl), —S($C_{1-3}$ alkyl) and $C_{1-6}$haloalkoxy; and the remainder of the variables are defined as in the first, second, third, fourth, fifth or sixth embodiment. In a eighth embodiment, the invention is directed to a compound represented by any one of (Ia)-(Id), (II)-(XIII), (IIa)-(XIIIa), (IIb)-(XIIIb), (IIc)-(XIIIc) and (IId)-(XIIId), wherein $R^a$ and $R^b$, when present (as in (Ia)-(Id), (II)-(VII), (IIa)-(VIIa), (IIb)-(VIIb), (IIc)-(VIIc) and (IId)-(VIId)), are independently halogen, cyano, —NR$^1$R$^2$, —NR$^2$C(O)R$^1$, —C(O)OR$^1$, —OC(O)R$^1$, —N(R$^2$)C(O)NR$^1$R$^2$, —OR$^1$ or $C_{1-6}$ alkyl, wherein the $C_{1-6}$ alkyl is optionally substituted with one or more substituents selected from the group consisting of halogen, —OH, —SH, —O($C_{1-6}$ alkyl), —S($C_{1-6}$ alkyl) and $C_{1-6}$ haloalkoxy; each $R^1$ is independently —H or $C_{1-6}$ alkyl, wherein the $C_{1-6}$ alkyl is optionally substituted with one or more substituents independently selected from the group consisting of halogen, —OH, —SH, —O($C_{1-3}$ alkyl), —S($C_{1-3}$ alkyl) and $C_{1-6}$haloalkoxy; and the remainder of the variables are defined as in the first, second, third, fourth, fifth or sixth embodiment.

In a ninth embodiment, the invention is directed to a compound represented by any one of (Ia)-(Id), (II)-(XIII), (IIa)-(XIIIa), (IIb)-(XIIIb), (IIc)-(XIIIc) and (IId)-(XIIId), wherein $R^a$ and $R^b$, when present (as in (Ia)-(Id), (II)-(VII), (IIa)-(VIIa), (IIb)-(VIIb), (IIc)-(VIIc) and (IId)-(VIId)), are independently halogen, —NH$_2$, ($C_{1-6}$ alkyl)amine or $C_{1-6}$ alkoxy; and the remainder of the variables are defined as in the first, second, third, fourth, fifth or sixth embodiment.

In a tenth embodiment, the invention is directed to a compound represented by any one of (Ia)-(Id), (II)-(XIII), (IIa)-(XIIIa), (IIb)-(XIIIb), (IIc)-(XIIIc) and (IId)-(XIIId), wherein $R^a$ and $R^b$, when present (as in (Ia)-(Id), (II)-(VII), (IIa)-(VIIa), (IIb)-(VIIb), (IIc)-(VIIc) and (IId)-(VIId)), are independently F, methyl, ethyl or methoxy; and the remainder of the variables are defined as in the first, second, third, fourth, fifth or sixth embodiment.

In a eleventh embodiment, the invention is directed to compound represented by any one of (Ia)-(Id), (II)-(XIII), (IIa)-(XIIIa), (IIb)-(XIIIb), (IIc)-(XIIIc) and (IId)-(XIIId), wherein $R^6$ is CH=CH-(phenyl); wherein the phenyl in CH=CH-(phenyl) is optionally substituted with one or more substituents independently selected from the group consisting of halogen, $C_{1-6}$ alkyl, $C_{1-6}$ haloalkyl, ($C_{1-6}$ aminoalkyl), ($C_{1-6}$ alkylamino)$C_{1-6}$ alkyl, ($C_{1-6}$ dialkylamino)$C_{1-6}$ alkyl, (phenyl)$C_{1-6}$ alkyl, amino, $C_{1-6}$ alkylamino, $C_{1-6}$ dialkylamino, —$(CH_2)_{0-3}$—N-piperidinyl, —$(CH_2)_{0-3}$—N-morpholinyl, —$(CH_2)_{0-3}$—N-pyrrolidinyl, —$(CH_2)_{0-3}$—N-piperazinyl and $(CH_2)_{0-3}$—N-oxazepanyl, wherein the N-piperazinyl is optionally N'-substituted with $C_{1-6}$ alkyl or $C_{1-6}$acyl. Values and alternative values for the remainder of the variables are defined as in the first, second, third, fourth, fifth, sixth, seventh, eighth, ninth or tenth embodiment.

In a twelfth embodiment, the invention is directed to compound represented by any one of (Ia)-(Id), (II)-(XIII), (IIa)-(XIIIa), (IIb)-(XIIIb), (IIc)-(XIIIc) and (IId)-(XIIId), wherein $R^6$ is phenyl optionally substituted with —$(CH_2)_{0-3}$—N-piperazinyl, wherein the N-piperazinyl is optionally N'-substituted with $C_{1-6}$ alkyl or ($C_{1-6}$ alkoxy) $C_{1-6}$ alkyl. Values and alternative values for the remainder of the variables are defined as in the first, second, third, fourth, fifth, sixth, seventh, eighth, ninth or tenth embodiment.

In a thirteenth embodiment, the invention is directed to compound represented by any one of (Ia)-(Id), (II)-(XIII), (IIa)-(XIIIa), (IIb)-(XIIIb), (IIc)-(XIIIc) and (IId)-(XIIId), IV is —F, methyl, ethyl or methoxy; and $R^4$, when present, (as in Structural Formulas (Ia)-(Id), (II)-(XI), (IIa)-(XIa), (IIb)-(XIb), (IIc)-(XIc) and (IId)-(XId)) is H or methyl. Values and alternative values for the remainder of the variables are defined as in the eleventh or twelfth embodiment.

Specific examples of compounds of the invention include those exemplified in the examples below, stereoisomers thereof, and pharmaceutically acceptable salts thereof.

The recitation "the phenyl and the 5-12 membered heteroaryl in the group represented by $R^6$" refers to the phenyl and 5-12 membered heteroaryl in any value for the variable $R^6$ which consists of phenyl or a 5-12 membered heteroaryl or which comprises phenyl or a 5-12 membered heteroaryl. For example, when $R^6$ is defined to be "optionally substituted phenyl, optionally substituted 5-12 membered heteroaryl, —$CH_2$-(optionally substituted phenyl), —$CH_2$-(optionally substituted 5-12 membered heteroaryl), —$CH_2$—$CH_2$-(optionally substituted phenyl), —$CH_2$—$CH_2$-(optionally substituted 5-12 membered heteroaryl), —CH=CH-(optionally substituted phenyl), —CH=CH-(optionally substituted 5-12 membered heteroaryl), —C≡C-(optionally substituted phenyl) or —C≡C-(5-12 optionally substituted membered heteroaryl)", then the language "the phenyl and the 5-12 membered heteroaryl in the group represented by $R^6$" refers to the phenyl and the 5-12 membered heteroaryl represented by $R^6$ as well as to the phenyl moiety and the 5-12 membered heteroaryl moiety in the groups —$CH_2$-(optionally substituted phenyl), —$CH_2$-(optionally substituted 5-12 membered heteroaryl), —$CH_2$—$CH_2$-(optionally substituted phenyl), —$CH_2$—$CH_2$-(optionally substituted 5-12 membered heteroaryl), —CH=CH-(optionally substituted phenyl), —CH=CH-(optionally substituted 5-12 membered heteroaryl), —C≡C-(optionally substituted phenyl) or —C≡C-(optionally substituted 5-12 membered heteroaryl).

In Structural Formulas described herein, when a hydrogen atom(s) is depicted at a particular position(s) of the aromatic ring(s) of the structural formula(s), no substitution is permitted at that (those) particular position(s).

Tautomeric forms exist when a compound is a mixture of two or more structurally distinct compounds that are in rapid equilibrium. Certain compounds of the invention exist as tautomeric forms. For example, the following compound represented by Structural Formula (I') or (I) include at least the following tautomeric forms:

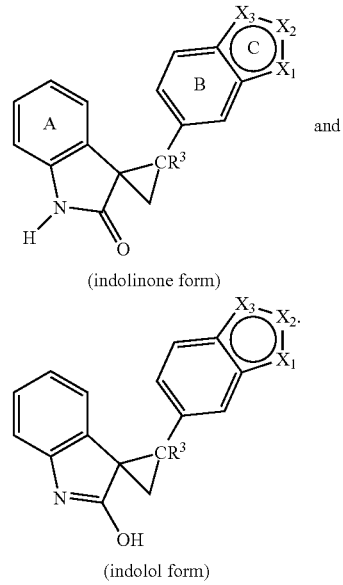

(indolinone form)

(indolol form)

It is to be understood that when one tautomeric form of a compound is depicted by name or structure, all tautomeric forms of the compound are included.

The compounds of the invention contain at least two chiral centers and a cyclopropane and, therefore, exist as stereoisomers, such as isomers about the cyclopropane (i.e., cis/trans isomers), enantiomers, and/or diastereomers. When compounds of the invention are depicted or named without indicating the stereochemistry, it is to be understood that both stereomerically pure forms (e.g., pure cis or pure trans, enantiomerically pure, or diastereomerically pure) and stereoisomeric mixtures are encompassed. For example, compounds represented by Structural Formula (I') or (I) have "cis" and "trans" isomers shown below:

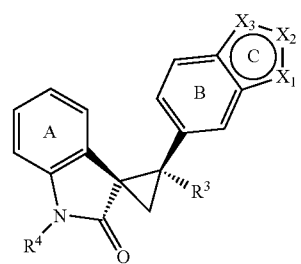

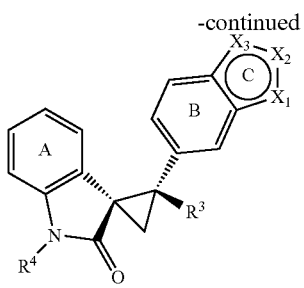

Ring A and Ring B are cis and

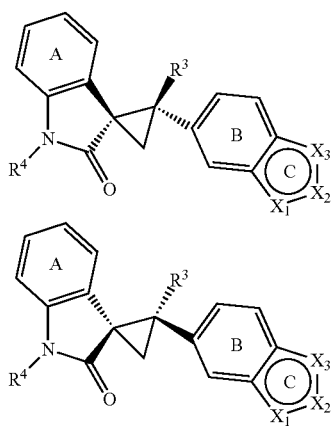

Ring A and Ring B are trans.

The language "Ring A and Ring B are cis" means Ring A and Ring B are both on the same side of the cyclopropane whereas the language "Ring A and Ring B are trans" means Ring A and Ring B are on different sides of the cyclopropane. Stereoisomers of the cis/trans variety are also referred to as geometric isomers. Accordingly, the compounds of the invention depicted by Structural Formula (I)-(XIII) include the pure cis isomer, the pure trans isomer, and mixtures thereof, including cis/trans mixtures enriched in the cis geometric isomer and cis/trans mixtures enriched in the trans geometric isomer. For example, Structural Formulas (Ia)-(XIIIa) and (Ib)-(XIIIb), depict a cis relationship between Ring A and B, whereas in, for example, Structural Formulas (Ic)-(XIIIc) and (Id)-(XIIId) the relationship between Ring A and B is trans. It is to be understood that both cis and trans forms of Structural Formulas (I)-(XIII) with respect to Rings A and B are encompassed within the invention.

When a geometric isomer is depicted by name or structure, it is to be understood that the geometric isomeric purity of the named or depicted geometric isomer is at least 60%, 70%, 80%, 90%, 99% or 99.9% pure by weight. Geometric isomeric purity is determined by dividing the weight of the named or depicted geometric isomer in the mixture by the total weight of both geomeric isomers in the mixture.

Racemic mixture means 50% of one enantiomer and 50% of is corresponding enantiomer. The invention encompasses all enantiomerically-pure, enantiomerically-enriched, diastereomerically pure, diastereomerically enriched, and racemic mixtures, and diastereomeric mixtures of the compounds of the invention.

Enantiomeric and diastereomeric mixtures can be resolved into their component enantiomers or stereoisomers by well known methods, such as chiral-phase gas chromatography, chiral-phase high performance liquid chromatography, crystallizing the compound as a chiral salt complex, or crystallizing the compound in a chiral solvent. Enantiomers and diastereomers can also be obtained from diastereomerically- or enantiomerically-pure intermediates, reagents, and catalysts by well known asymmetric synthetic methods.

When a compound is designated by a name or structure that indicates a single enantiomer, unless indicated otherwise, the compound is at least 60%, 70%, 80%, 90%, 99% or 99.9% optically pure (also referred to as "enantiomerically pure"). Optical purity is the weight in the mixture of the named or depicted enantiomer divided by the total weight in the mixture of both enantiomers.

When the stereochemistry of a disclosed compound is named or depicted by structure, and the named or depicted structure encompasses more than one stereoisomer (e.g., as in a diastereomeric pair), it is to be understood that one of the encompassed stereoisomers or any mixture of the encompassed stereoisomers are included. It is to be further understood that the stereoisomeric purity of the named or depicted stereoisomers at least 60%, 70%, 80%, 90%, 99% or 99.9% by weight. The stereoisomeric purity in this case is determined by dividing the total weight in the mixture of the stereoisomers encompassed by the name or structure by the total weight in the mixture of all of the stereoisomers.

Included in the invention are pharmaceutically acceptable salts of the compounds disclosed herein. The disclosed compounds have basic amine groups and therefore can form pharmaceutically acceptable salts with pharmaceutically acceptable acid(s). Suitable pharmaceutically acceptable acid addition salts of the compounds of the invention include salts of inorganic acids (such as hydrochloric acid, hydrobromic, phosphoric, metaphosphoric, nitric, and sulfuric acids) and of organic acids (such as, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic, and tartaric acids). Compounds of the invention with acidic groups such as carboxylic acids can form pharmaceutically acceptable salts with pharmaceutically acceptable base(s). Suitable pharmaceutically acceptable basic salts include ammonium salts, alkali metal salts (such as sodium and potassium salts) and alkaline earth metal salts (such as magnesium and calcium salts). Compounds with a quaternary ammonium group also contain a counteranion such as chloride, bromide, iodide, acetate, perchlorate and the like. Other examples of such salts include hydrochlorides, hydrobromides, sulfates, methanesulfonates, nitrates, maleates, acetates, citrates, fumarates, tartrates [e.g. (+)-tartrates, (−)-tartrates or mixtures thereof including racemic mixtures], succinates, benzoates and salts with amino acids such as glutamic acid.

The term "halo" as used herein means halogen and includes chloro, fluoro, bromo and iodo.

An "aliphatic group" is acyclic, non-aromatic, consists solely of carbon and hydrogen and may optionally contain one or more units of unsaturation, e.g., double and/or triple bonds. An aliphatic group may be straight chained or branched. An aliphatic group typically contains between about one and about twenty carbon atoms, typically between about one and about ten carbon atoms, more typically between about one and about six carbon atoms. A "substituted aliphatic group" is substituted at any one or more "substitutable carbon atoms". A "substitutable carbon atom" in an aliphatic group is a carbon in the aliphatic group that is bonded to one or more hydrogen atoms. One or more hydrogen atoms can be optionally replaced with a suitable substituent group. A "haloaliphatic group" is an aliphatic group, as defined above, substituted with one or more halogen atoms.

The term "alkyl" used alone or as part of a larger moiety, such as "alkoxy", "haloalkyl", "arylalkyl", "alkylamine", "dialkyamine", "alkylamino", "dialkyamino" "alkylcarbonyl", "alkoxycarbonyl" and the like, means saturated straight-chain or branched aliphatic group. As used herein, a C1-C6 alkyl group is referred to "lower alkyl." Similarly, the terms "lower alkoxy", "lower haloalkyl", "lower arylalkyl", "lower alkylamine", lower dialkyamine", "lower alkylamino", "lower dialkyamino" "lower alkylcarbonyl", "lower alkoxycarbonyl" include straight and branched, saturated chains containing one to six carbon atoms.

The term "alkenyl" means straight-chain or branched aliphatic group having at least one double bond.

The term "alkynyl" means straight-chain or branched aliphatic group having at least one triple bond.

The term "alkoxy" means O-alkyl; "hydroxyalkyl" means alkyl substituted with hydroxy; "aralkyl" means alkyl substituted with an aryl group; "alkoxyalkyl" mean alkyl substituted with an alkoxy group; "alkylamine" means amine substituted with an alkyl group; "cycloalkylalkyl" means alkyl substituted with cycloalkyl; "dialkylamine" means amine substituted with two alkyl groups; "alkylcarbonyl" means —C(O)—R, wherein R is alkyl; "alkoxycarbonyl" means —C(O)—OR, wherein R is alkyl; and where alkyl is as defined above.

The terms "haloalkyl" and "haloalkoxy" means alkyl or alkoxy, as the case may be, substituted with one or more halogen atoms. The term "halogen" means F, Cl, Br or I. Preferably the halogen in a haloalkyl or haloalkoxy is F.

The term "acyl group" means C(O)R, wherein R is an optionally substituted alkyl group or aryl group (e.g., optionally substituted phenyl). R is preferably an unsubstituted alkyl group or phenyl.

An "alkylene group" is represented by —[CH$_2$]$_z$—, wherein z is a positive integer, preferably from one to eight, more preferably from one to four.

An "alkenylene" is an alkylene group in which one methylene has been replaced with a double bond.

The term "aryl group" used alone or as part of a larger moiety as in "aralkyl", "aralkoxy", or "aryloxyalkyl", means a carbocyclic aromatic ring. The term "aryl" may be used interchangeably with the terms "aryl ring" "carbocyclic aromatic ring", "aryl group" and "carbocyclic aromatic group". An aryl group typically has six to fourteen ring atoms. Examples includes phenyl, naphthyl, anthracenyl, 1,2-dihydronaphthyl, 1,2,3,4-tetrahydronaphthyl, fluorenyl, indanyl, indenyl and the like. A "substituted aryl group" is substituted at any one or more substitutable ring atom, which is a ring carbon atom bonded to a hydrogen.

The term "cycloalkyl" refers to a monocyclic or polycyclic saturated hydrocarbon ring system. For example, a $C_{5-7}$ cycloalkyl includes, but is not limited to cyclopentyl, cyclohexyl or cyclopentyl, each of which is optionally substituted.

The term "heteroaryl", "heteroaromatic", "heteroaryl ring", "heteroaryl group", "heteroaromatic ring", and "heteroaromatic group", used alone or as part of a larger moiety as in "heteroaralkyl" or "heteroarylalkoxy", refers to aromatic ring groups having five to fourteen ring atoms selected from carbon and at least one (typically 1 to 4, more typically 1 or 2) heteroatoms (e.g., oxygen, nitrogen or sulfur). "Heteroaryl" includes monocyclic rings and polycyclic rings in which a monocyclic heteroaromatic ring is fused to one or more other carbocyclic aromatic or heteroaromatic rings. As such, "5-14 membered heteroaryl" includes monocyclic, bicyclic or tricyclic ring systems.

Examples of monocyclic 5-6 membered heteroaryl groups include furanyl (e.g., 2-furanyl, 3-furanyl), imidazolyl (e.g., N-imidazolyl, 2-imidazolyl, 4-imidazolyl, 5-imidazolyl), isoxazolyl (e.g., 3-isoxazolyl, 4-isoxazolyl, 5-isoxazolyl), oxadiazolyl (e.g., 2-oxadiazolyl, 5-oxadiazolyl), oxazolyl (e.g., 2-oxazolyl, 4-oxazolyl, 5-oxazolyl), pyrazolyl (e.g., 3-pyrazolyl, 4-pyrazolyl), pyrrolyl (e.g., 1-pyrrolyl, 2-pyrrolyl, 3-pyrrolyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl), thiazolyl (e.g., 2-thiazolyl, 4-thiazolyl, 5-thiazolyl), triazolyl (e.g., 2-triazolyl, 5-triazolyl), tetrazolyl (e.g., tetrazolyl), thienyl (e.g., 2-thienyl, 3-thienyl), pyrimidinyl, pyridinyl and pyridazinyl. Examples of polycyclic aromatic heteroaryl groups include carbazolyl, benzimidazolyl, benzothienyl, benzofuranyl, indolyl, quinolinyl, benzotriazolyl, benzothiazolyl, benzoxazolyl, benzimidazolyl, isoquinolinyl, indolyl, isoindolyl, acridinyl, or benzisoxazolyl. A "substituted heteroaryl group" is substituted at any one or more substitutable ring atom, which is a ring carbon or ring nitrogen atom bonded to a hydrogen.

The term "heterocyclyl group" or "heterocyclic group" means a monocyclic, non-aromatic ring with 3 to 10-members containing from 1-3 ring heteroatoms or a polycyclic ring with ring with 7 to 20-members and from 1 to 4 ring heteroatoms, wherein the polycyclic ring having one or more monocyclic non-aromatic heterocyclic ring fused with one or more aromatic or heteroaromatic ring. In one embodiment, the heterocyclyl group is a bicyclic ring having a monocyclic non-aromatic heterocyclic ring fused with a phenyl group. Exemplary polycyclic heterocyclic group includes tetrahydroisoquinolinyl (such as 1,2,3,4-tetrahydroisoquinolin-7-yl, 2-methyl-1,2,3,4-tetrahydroisoquinolin-7-yl, 1,2,3,4-tetrahydroisoquinolin-6-yl and 2-methyl-1, 2,3,4-tetrahydroisoquinolin-6-yl), isoindolinyl (such as 2-ethylisoindolin-5-yl, 2-methylisoindolin-5-yl), indolinyl, tetrahydrobenzo[f]oxazepinyl (such as 2,3,4,5-tetrahydrobenzo[f][1,4]oxazepin-7-yl).

The term "non-aromatic heterocyclic group" means a monocyclic, non-aromatic ring with 3 to 10-members containing from 1-3 ring heteroatoms or a polycyclic non-aromatic ring with 7 to 20-members and from 1 to 4 ring heteroatoms. Each heteroatom is independently selected from nitrogen, quaternary nitrogen, oxidized nitrogen (e.g., NO); oxygen; and sulfur, including sulfoxide and sulfone. The substituted non-aromatic heterocylic group may be attached via a suitable heteroatom or carbon atom. Representative non-aromatic heterocyclic groups include morpholinyl, thiomorpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, tetrahydropyrindinyl, tetrahydropyrimidinyl, tetrahydrothiophenyl, tetrahydrothiopyranyl, and the like. A "substituted non-aromatic heterocylic group" is substituted at any one or more substitutable ring atom, which is a ring carbon or ring nitrogen atom bonded to a hydrogen.

Unless otherwise indicated, suitable substituents for a substituted aliphatic group, aryl group, heteroaryl group and non-aromatic heteroaryl groups include the groups represented by $R^a$. Other examples include halogen, nitro, cyano, hydroxy, $C_{1-20}$ alkyl, $C_{2-20}$ alkenyl, $C_{2-20}$ alkynyl, amino, $C_{1-20}$ alkylamino, $C_{1-20}$dialkylamino, $C_{1-20}$ alkoxy, $(C_{1-10}$alkoxy$)C_{1-20}$ alkyl, $C_{1-20}$haloalkoxy, $(C_{1-10}$haloalkoxy$)C_{1-20}$ alkyl and $C_{1-20}$haloalkyl.

Spiro cyclopropyl indolinone compounds of the invention can inhibit various kinases, including the PLK4, PLK1, PLK2, Aurora A, Aurora B and FLT-3 (see Examples B-G). Thus, generally, the spiro cyclopropyl indolinone compounds of the invention are useful in the treatment of diseases or conditions associated with such kinases. For example, PLK4, PLK1, Aurora A and Aurora B are believed to be involved in cellular miotic progression. Thus, small molecule inhibitors of these enzymes can be potential anti-tumor agents.

In a specific embodiment, the compounds of the invention are PLK, Aurora A, Aurora B and/or FLT-3 inhibitors, and are useful for treating diseases, such as cancer, associated with such a kinase(s). In another specific embodiment, the compounds of the invention are PLK inhibitors and are useful for treating diseases associated with PLK, such as cancer. Typically, the PLK is PLK4, PLK2 and PLK 1. In one example, the PLK is PLK1 and PLK4. In another example, the PLK is PLK4. In another specific embodiment, the compounds of the invention are Aurora A and/or B inhibitors and are useful in inhibiting Aurora A and/or B activity for the treatment of various conditions such as cancers. In yet another specific embodiment, the compounds of the invention are FLT-3 inhibitors and are useful in inhibiting FLT-3 activity for the treatment of various conditions such as cancers.

Another aspect of the invention relates to a method of treating a subject with cancer comprising administering to the subject an effective amount of a compound of the invention. In one embodiment, the compounds of the invention inhibit the growth of a tumor. Specifically, the compounds of the invention inhibit the growth of a tumor that overexpresses at least one of PLK, Aurora A, Aurora B, and FLT-3. More specifically, the compounds of the invention inhibit the growth of a tumor that overexpresses PLK, for example, PLK1, PLK2 and/or PLK4. Even more specifically, the compounds of the invention inhibit the growth of a tumor that overexpresses PLK4. In another embodiment, the compounds of the invention inhibit the growth of the tumor by inducing apoptosis of the tumor cells or by inhibiting proliferation of the tumor cells.

Cancers that can be treated or prevented by the methods of the present invention include lung cancer, breast cancer, colon cancer, brain cancer, neuroblastoma, prostate cancer, melanoma, glioblastoma multiform, ovarian cancer, lymphoma, leukemia, melanoma, sarcoma, paraneoplasia, osteosarcoma, germinoma, glioma and mesothelioma. In one specific embodiment, the cancer is lung cancer, colon cancer, brain cancer, neuroblastoma, prostate cancer, melanoma, glioblastoma multiform or ovarian cancer. In another specific embodiment, the cancer is lung cancer, breast cancer, colon cancer, brain cancer, neuroblastoma, prostate cancer, melanoma, glioblastoma multiform or ovarian cancer. In yet another specific embodiment, the cancer is a breast cancer. In yet another specific embodiment, the cancer is a basal sub-type breast cancer or a luminal B sub-type breast cancer. In one embodiment, the basal sub-type breast cancer is ER (estrogen receptor), HER2 and PR (progesterone receptor) negative breast cancer. In yet another specific embodiment, the cancer is a soft tissue cancer. A "soft tissue cancer" is an art-recognized term that encompasses tumors derived from any soft tissue of the body. Such soft tissue connects, supports, or surrounds various structures and organs of the body, including, but not limited to, smooth muscle, skeletal muscle, tendons, fibrous tissues, fatty tissue, blood and lymph vessels, perivascular tissue, nerves, mesenchymal cells and synovial tissues. Thus, soft tissue cancers can be of fat tissue, muscle tissue, nerve tissue, joint tissue, blood vessels, lymph vessels, and fibrous tissues. Soft tissue cancers can be benign or malignant. Generally, malignant soft tissue cancers are referred to as sarcomas, or soft tissue sarcomas. There are many types of soft tissue tumors, including lipoma, lipoblastoma, hibernoma, liposarcoma, leiomyoma, leiomyosarcoma, rhabdomyoma, rhabdomyosarcoma, neurofibroma, schwannoma (neurilemoma), neuroma, malignant schwannoma, neurofibrosarcoma, neurogenic sarcoma, nodular tenosynovitis, synovial sarcoma, hemangioma, glomus tumor, hemangiopericytoma, hemangioendothelioma, angiosarcoma, Kaposi sarcoma, lymphangioma, fibroma, elastofibroma, superficial fibromatosis, fibrous histiocytoma, fibrosarcoma, fibromatosis, dermatofibrosarcoma protuberans (DFSP), malignant fibrous histiocytoma (MFH), myxoma, granular cell tumor, malignant mesenchymomas, alveolar soft-part sarcoma, epithelioid sarcoma, clear cell sarcoma, and desmoplastic small cell tumor. In a particular embodiment, the soft tissue cancer is a sarcoma selected from the group consisting of a fibrosarcoma, a gastrointestinal sarcoma, a leiomyosarcoma, a dedifferentiated liposarcoma, a pleomorphic liposarcoma, a malignant fibrous histiocytoma, a round cell sarcoma, and a synovial sarcoma.

The invention further relates to a method of treating a subject with tumor cells, comprising administering to the subject, an amount of a compound disclosed herein that is effective to reduce effectively PLK activity, such as PLK 2 or PLK4 activity, in the subject. In a specific embodiment, the PLK is PLK4.

The term a "effective amount" means an amount when administered to the subject which results in beneficial or desired results, including clinical results, e.g., reduces the likelihood of developing the cancer or inhibits, suppresses or reduces the cancer (e.g., as determined by clinical symptoms or the amount of cancer cells) in a subject as compared to a control. Specifically, "treating a subject with a cancer" includes achieving, partially or substantially, one or more of the following: arresting the growth or spread of a cancer, reducing the extent of a cancer (e.g., reducing size of a tumor or reducing the number of affected sites), inhibiting the growth rate of a cancer, and ameliorating or improving a clinical symptom or indicator associated with a cancer (such as tissue or serum components). It also reduces the likelihood of reoccurrence of the cancer.

Generally, an effective amount of a compound of the invention varies depending upon various factors, such as the given drug or compound, the pharmaceutical formulation, the route of administration, the type of disease or disorder, the identity of the subject or host being treated, and the like, but can nevertheless be routinely determined by one skilled in the art. An effective amount of a compound of the present invention may be readily determined by one of ordinary skill by routine methods known in the art.

In an embodiment, an effective amount of a compound of the invention ranges from about 0.01 to about 1000 mg/kg body weight, alternatively about 0.05 to about 500 mg/kg body weight, alternatively about 0.1 to about 100 mg/kg body weight, alternatively about 0.1 to about 15 mg/kg body weight, alternatively about 1 to about 5 mg/kg body weight, and in another alternative, from about 2 to about 3 mg/kg body weight. The skilled artisan will appreciate that certain factors may influence the dosage required to effectively treat a subject suffering from cancer and these factors include, but are not limited to, the severity of the disease or disorder, previous treatments, the general health and/or age of the subject and other diseases present.

Moreover, a "treatment" regime of a subject with an effective amount of the compound of the present invention may consist of a single administration, or alternatively comprise a series of applications. For example, the compound of the present invention may be administered at least once a week. However, in another embodiment, the compound may be administered to the subject from about one time per week to once daily for a given treatment. The length of the treatment period depends on a variety of factors, such as the severity of the disease, the age of the patient, the concentration and the activity of the compounds of the present invention, or a combination thereof. It will also be appreciated that the effective dosage of the compound used for the treatment or prophylaxis may increase or decrease over the course of a particular treatment or prophylaxis regime. Changes in dosage may result and become apparent by standard diagnostic assays known in the art. In some instances, chronic administration may be required.

As used herein, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, reducing the likelihood of the spread of the disease, delay or slowing of disease progression, amelioration or palliation of the disease state, and remission (whether partial or total), whether detectable or undetectable. "Treatment" can also mean prolonging survival as compared to expected survival if not receiving treatment. "Treatment" also includes reducing the likelihood of developing the disease or reducing the likelihood of reoccurrence of the disease.

A "subject" is a mammal, preferably a human, but can also be an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

In one embodiment, the method of the present invention is a mono-therapy where the pharmaceutical compositions of the invention are administered alone. Accordingly, in this embodiment, the compound of the invention is the only pharmaceutically active ingredient in the pharmaceutical compositions or the only pharmaceutically active ingredient administered to the subject.

In another embodiment, the method of the invention is a co-therapy with one or more of other therapeutically active drugs or therapies known in the art for treating the desired diseases or indications. In one example, one or more other anti-proliferative or anticancer therapies are combined with the compounds of the invention. In another example, the compounds disclosed herein are co-administered with one or more of other anticancer drugs known in the art. Anticancer therapies that may be used in combination with the compound of the invention include surgery, radiotherapy (including, but not limited to, gamma-radiation, neutron beam radiotherapy, electron beam radiotherapy, proton therapy, brachytherapy, and systemic radioactive isotopes) and endocrine therapy. Anticancer agents that may be used in combination with the the compounds of the invention include biologic response modifiers (including, but not limited to, interferons, interleukins, and tumor necrosis factor (TNF)), hyperthermia and cryotherapy, agents to attenuate any adverse effects (e.g., antiemetics), and other approved chemotherapeutic drugs (e.g. taxol and analogs thereof).

When the compounds of the invention are combined with other anticancer drugs, they can be administered contemporaneously. As used herein, "administered contemporaneously" means that two substances are administered to a subject such that they are both biologically active in the subject at the same time. The exact details of the administration will depend on the pharmacokinetics of the two substances in the presence of each other, and can include administering one substance within a period of time of one another, e.g., 24 hours of administration of the other, if the pharmacokinetics are suitable. Designs of suitable dosing regimens are routine for one skilled in the art. In particular embodiments, two substances will be administered substantially simultaneously, i.e. within minutes of each other, or in a single composition that comprises both substances. Alternatively, the two agents can be administered separately, such that only one is biologically active in the subject at the same time.

The compounds of the invention can be administered to a patient in a variety of forms depending on the selected route of administration, as will be understood by those skilled in the art. The compounds of the invention may be administered, for example, by oral, parenteral, buccal, sublingual, nasal, rectal, patch, pump or transdermal administration and the pharmaceutical compositions formulated accordingly. Parenteral administration includes intravenous, intraperitoneal, subcutaneous, intramuscular, transepithelial, nasal, intrapulmonary, intrathecal, rectal and topical modes of administration. Parenteral administration can be by continuous infusion over a selected period of time.

The compounds of the invention can be suitably formulated into pharmaceutical compositions for administration to a subject. The pharmaceutical compositions of the invention optionally include one or more pharmaceutically acceptable carriers and/or diluents therefor, such as lactose, starch, cellulose and dextrose. Other excipients, such as flavoring agents; sweeteners; and preservatives, such as methyl, ethyl, propyl and butyl parabens, can also be included. More complete listings of suitable excipients can be found in the Handbook of Pharmaceutical Excipients ($5^{th}$ Ed., Pharmaceutical Press (2005)). A person skilled in the art would know how to prepare formulations suitable for various types of administration routes. Conventional procedures and ingredients for the selection and preparation of suitable formulations are described, for example, in Remington's Pharmaceutical Sciences (2003—20th edition) and in The United States Pharmacopeia: The National Formulary (USP 24 NF19) published in 1999. The carriers, diluents and/or excipients are "acceptable" in the sense of being compatible with the other ingredients of the pharmaceutical composition and not deleterious to the recipient thereof.

Typically, for oral therapeutic administration, a compound of the invention may be incorporated with excipient and used in the form of ingestible tablets, buccal tablets, troches, capsules, elixirs, suspensions, syrups, wafers, and the like.

Typically for parenteral administration, solutions of a compound of the invention can generally be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms.

Typically, for injectable use, sterile aqueous solutions or dispersion of, and sterile powders of, a compound of the invention for the extemporaneous preparation of sterile injectable solutions or dispersions.

For nasal administration, the compounds of the invention can be formulated as aerosols, drops, gels and powders.

Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as fluorochlorohydrocarbon. The aerosol dosage forms can also take the form of a pump-atomizer.

For buccal or sublingual administration, the compounds of the invention can be formulated with with a carrier such as sugar, acacia, tragacanth, or gelatin and glycerine, as tablets, lozenges or pastilles.

For rectal administration, the compounds of the invention can be formulated in the form of suppositories containing a conventional suppository base such as cocoa butter.

The compounds of the invention, can be formulated alone or for contemporaneous administration with other agents for treating cancer. Therefore, in another aspect, a pharmaceutical composition of the invention comprises a pharmaceutically acceptable carrier or diluent, a compound disclosed herein or a pharmaceutically acceptable salt thereof and another anti-cancer agent, for example, but not limited to a glucose metabolism inhibitor or taxol.

In accordance with another aspect of the present invention, the compounds of the invention can be prepared by processes analogous to those established in the art. By way of illustration, compounds of Formula (I), wherein Rings A and B are as defined herein may be prepared by the methods outlined in Scheme 1. Reaction of an appropriately substituted Indazolylmethyleneindolinone 1 (wherein ring A is as defined herein and ring B and C together are an indazole) is reacted with a suitable methylene source, such as trimethylsulfonium iodide, or trimethylsulfoxonium iodide in the presence of a base (such as sodium hydride, LDA or NaHMDS), in a polar solvent (such as DMF, THF or DMSO). The reaction is conveniently effected at the appropriate temperature (generally in the range of 20° to 60° C.). The vinyl linkage, wherein Ar is a phenyl and heteroaryl group as defined herein, and $P^1$ represents suitable indazole protecting group (such as Boc, acetyl or SEM) and X is a halide can be installed under typical Heck reaction conditions. Alternatively, wherein Ar is a phenyl and heteroaryl group as defined herein, and $P^1$ represents suitable indazole protecting group (such as Boc, acetyl or SEM) and X is a halide can be installed under typical Suzuki reaction conditions, using either a boronic acid or boronate ester. The reaction is preferably effected under microwave irradiation conditions, advantageously in the range, for example of 100 to 150° C., or generally at about 120° C. Removal of the protecting group may be effected by any of the procedures known to effect such a transformation. For example, when the protecting group $P^1$ is SEM, the transformation can be effected by treatment with tetrabutylammonium fluoride in a polar solvent, such as THF, at reflux, or by stepwise treatment with boron trifluoride etherate and 2N HCl in ethanol.

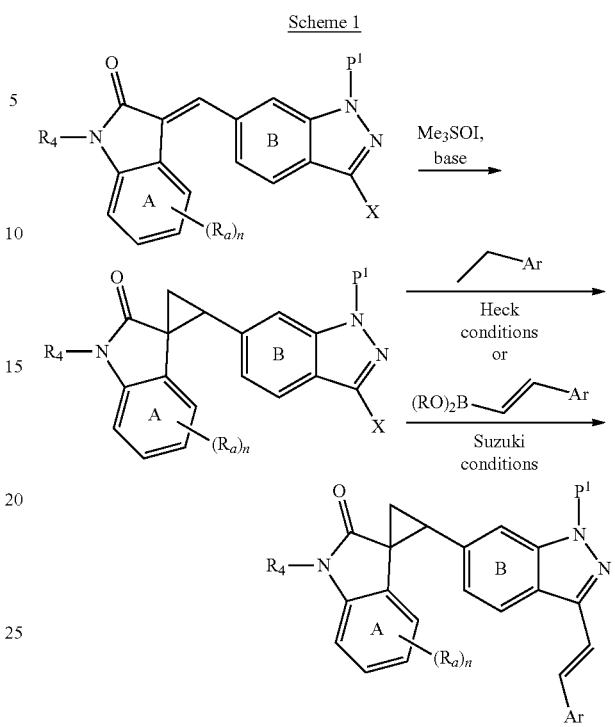

In another aspect of the invention (SCHEME 2), the aryl linkage wherein $R_6$ is as defined herein, $P^1$ is either H or a suitable indazole protecting group (such as Boc, acetyl or SEM) and X is a halide, can be installed under typical Suzuki reaction conditions, using either a boronic acid or boronate ester. The reaction is preferably effected under microwave irradiation conditions, advantageously in the range, for example of 100 to 150° C., or generally at about 120° C. Removal of the protecting group may be effected by any of the procedures known to effect such a transformation. For example, when the protecting group $P^1$ is SEM, the transformation can be effected by treatment with tetrabutylammonium fluoride in a polar solvent, such as THF, at reflux, or by stepwise treatment with boron trifluoride etherate and 2N HCl in ethanol.

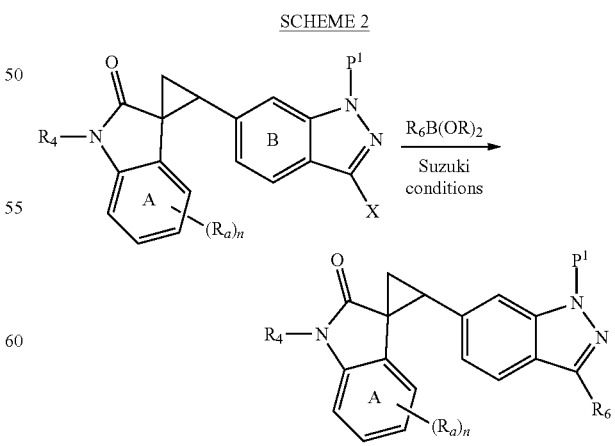

In another aspect of the invention (SCHEME 3), the alkyne linkage, wherein Ar is a phenyl and heteroaryl group, $P^1$ is either H, or a suitable indazole protecting group (such as Boc, acetyl or SEM) and X is a halide, can be installed under typical Sonagashira reaction conditions. The reaction is preferably effected under microwave irradiation conditions, advantageously in the range, for example of 100 to 150° C., or generally at 120° C. Removal of the protecting group may be effected by any of the procedures known to effect such a transformation. For example, when the protecting group P¹ is SEM, the transformation can be effected by treatment with tetrabutylammonium fluoride in a polar solvent, such as THF, at reflux, or by stepwise treatment with boron trifluoride etherate and 2N HCl in ethanol.

SCHEME 3

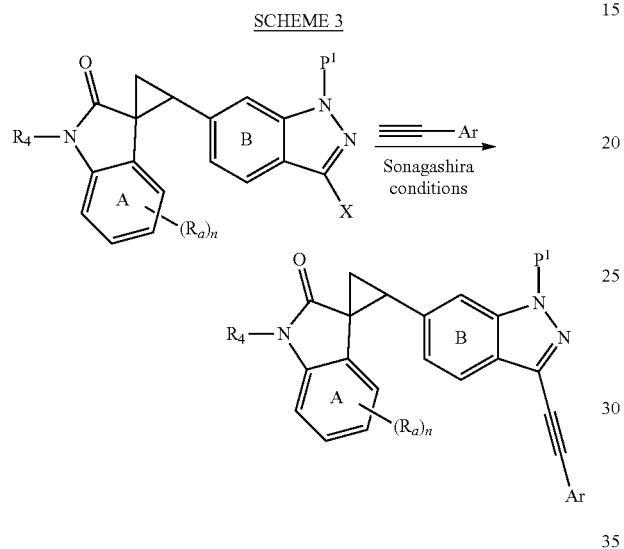

In another aspect of the invention (SCHEME 4), the cyclopropanation can be effected on compounds such as (I), wherein $R_5$ is as defined herein and $R_6$ is as defined herein, is reacted with a suitable methylene source, such as trimethylsulfonium iodide, or trimethylsulfoxonium iodide in the presence of a base (such as sodium hydride, LDA or NaHMDS), in a polar solvent (such as DMF, THF or DMSO). The reaction is conveniently effected at the appropriate temperature (generally in the range of 20° to 60° C.).

SCHEME 4

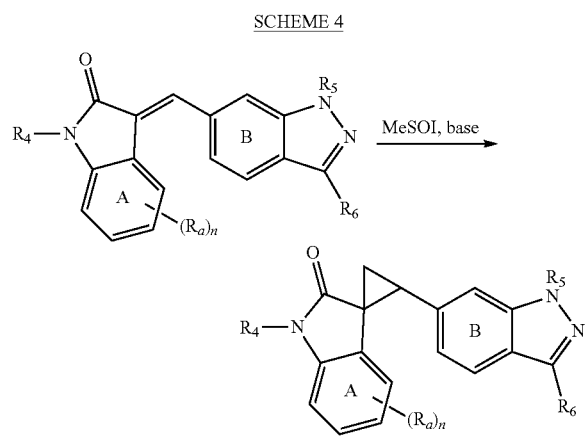

In another aspect of the invention, indazolyl-spiro-cyclopropane-indolinones 3 may be obtained from reaction of the dianions generated by treating substituted oxindoles 1 with a strong base such as sodium hydride in a suitable solvent such as THF, with bis-electrophiles 2 (Scheme 5). When the (S) dimesylate is employed, the desired (1R,2S) enantiomer form almost exclusively, with little to none of the undesired (1S,2S) diastereomer detectable.

SCHEME 5

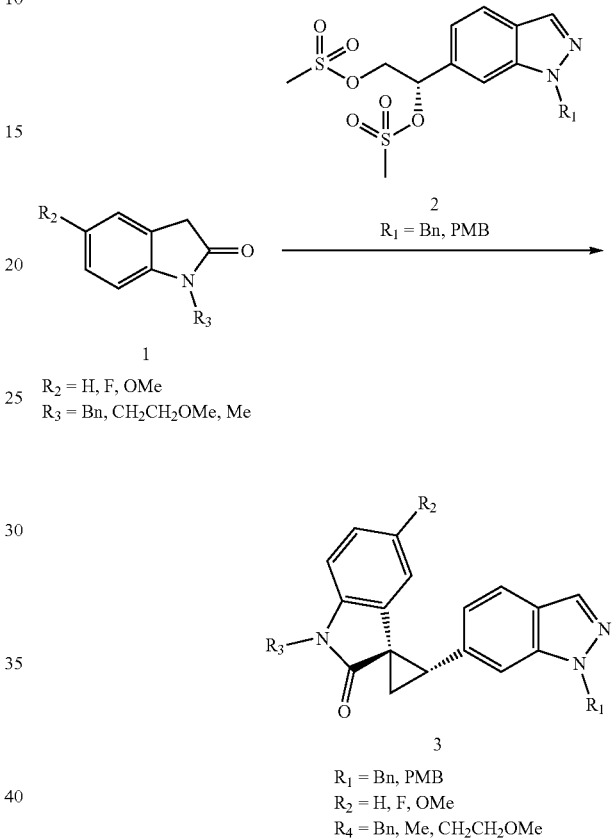

Indazolyl-spiro-cyclopropane-indolinones 3 which contain a Bn or PMB moiety may be deprotected by employment of suitable reaction conditions. Compounds 3 which contain more than one such protecting group may be deprotected at both sites in a one-pot reaction to provide compounds 4 (Scheme 6). Compounds 3 containing a PMB or Bn group may be deprotected by treatment with a strong base, such as KO'Bu or 'BuLi, and oxygen donor such as $O_2$, MoOPH or MoOPD, in a suitable solvent such as THF, with DMSO or DMS to reduce the hydroperoxide intermediate formed in situ (A. A. Haddach, A. Kelleman, and M. V. Deaton-Rewolinski, *Tetrahedron Lett.*, 2002, 43, 399-402; R. M. Williams and E. Kwast, *Tetrahedron Lett.*, 1989, 30, 451-454). Compounds 3 containing a PMB group may alternatively be deprotected by treatment with an acid such as TFA, TfOH or a mixture of such acids, at temperatures between 50° C. 130° C. to provide indazolyl-spiro-cyclopropane-indolinones 4.

SCHEME 6

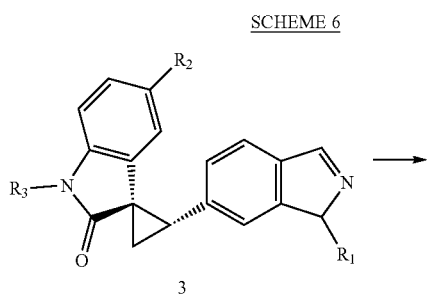

3
R₁ = Bn, PMB
R₂ = H, F, OMe
R₄ = Bn, Me, CH₂CH₂OMe

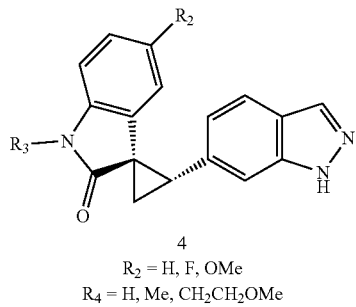

4
R₂ = H, F, OMe
R₄ = H, Me, CH₂CH₂OMe

Indazolyl-spiro-cyclopropane-indolinones 4 may be iodinated to provide compounds of 5 (Scheme 7) by treatment with an iodinating agent such as iodine or N-iodosuccinimide, in the presence of a base such as Na₂CO₃, K₂CO₃, NaOH or KO'Bu, in a suitable solvent such as acetone, ACN, DMF, DMSO, dioxane, NMP, THF, with or in the absence of water.

SCHEME 7

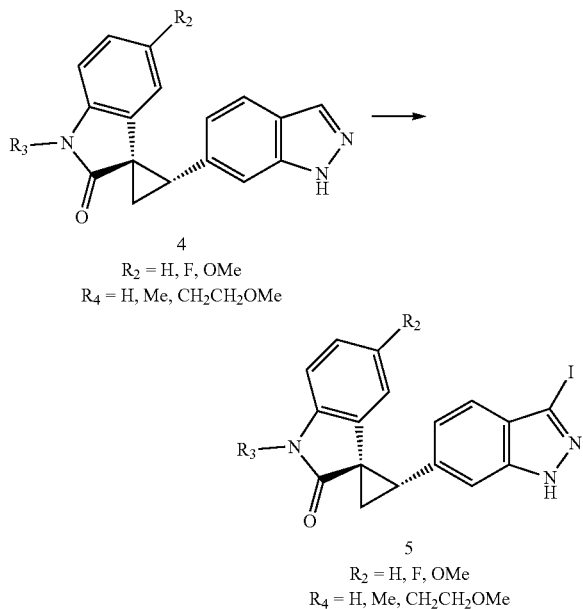

The relative stereochemistry of the cyclopropane ring may be assigned as (1R*,2S*) by comparison to the minor diastereomer produced in the synthesis of the racemic reference standards by use of HCOSY NMR experiment to assign the signals for each proton in the ¹H NMR followed by NOESY experiment to determine the through space interaction between the cyclopropane protons and the proton at position 4 of the indolinone following (I. Moldvai, E. Gacs-Baitz, M. Incze and C. Szantay; *Arch. Pharm. Pharm. Med. Chem.* 1996, 329, 541-549). The absolute stereochemistry of the product may be assigned as (1R,2S), based upon application of the Sharpless mnemonic to predict diol configuration as (S) and assuming an $S_N2$ coupling process to form the cyclopropane resulting in inversion of the (S) stereocenter of the diol with preservation of e.e.

The invention is illustrated by the following examples which are not intended to be limiting in any way. Exemplary syntheses are also described in the International Application Publication No. WO2011/123947, entitled SYNTHESIS OF CHIRAL 2-(1H-INDAZOL-6-YL)-SPIRO[CYCLOPROPANE-1,3'-INDOLIN]-2'-ONES, filed Apr. 6, 2011, the entire teachings of which are incorporated herein by reference.

EXEMPLIFICATION

A. Syntheses of Compounds of the Invention

General Experimental Methods:

Commercially available starting materials, reagents, and solvents were used as received, with the exception of N,N-dimethyl-1-(4-vinylphenyl)methanamine which was purified by chromatography on silica gel prior to use in Heck reactions. In general, anhydrous reactions were performed under an inert atmosphere such as nitrogen or argon. Microwave reactions were performed with a Biotage Initiator microwave reactor. Reaction progress was generally monitored by TLC using Merck silica gel plates with visualization by UV at 254 nm, by analytical HPLC or by LCMS (Bruker Exquire 4000). Flash column chromatographic purification of intermediates or final products was performed using 230-400 mesh silica gel 60 from EMD chemicals. Final products were sometimes purified by preparative reverse-phase HPLC. Purification was performed on a Varian PrepStar model SD-1 HPLC system with a Varian Monochrom 10u C-18 reverse-phase column using a gradient of about 5-30% acetonitrile/0.05% TFA water to 70-100% acetonitrile/0.05% TFA water over a 20-40-min period at a flow rate of 30-50 ml/min. Fractions containing the desired material were concentrated and lyophilized to obtain the final products. Proton NMRs were recorded on a Bruker 400 MHz spectrometer, and mass spectra were obtained using a Bruker Esquire 4000 spectrometer. Optical Rotations were measured at the sodium D-line (589.44 nM) using an AA-55 Polarimeter from Optical Activity Ltd with a 2.5×100 mm unjacketed stainless steel tube at given sample concentrations (c, units of g/100 mL).

Compound names were generated using the software built into ChemBioDraw Ultra version 11.0 with the following exception. Racemic compounds with known relative stereochemistry were named using the R*/S* system as described by North (Principles and Applications of Stereochemistry, CRC Press, 1998), wherein the lower numbered atom is arbitrarily defined as R*, and the higher numbered atoms are defined relative to that center. Thus a racemic mixture of enantiomers of a compound with two chiral centers is designated as (1R*,2S*) or (1R*,2R*) depending on the known relative stereochemistry. The standard R and S nomenclature is used to describe single enantiomers or enantiomerically enriched compounds of greater than 95% e.e.

Abbreviations:
aq. aqueous
BF$_3$.OEt$_2$ borontrifluoride etherate
br. Broad
dba dibenzylideneacetone
DCM dichloromethane
DCM dichloromethane
(DHQ)$_2$PHAL hydroquinine 1,4-phthalazinediyl diether
(DHQD)$_2$PHAL hydroquinidine 1,4-phthalazinediyl diether
DME 1,2-dimethoxyethane
DMF N,N-dimethylformamide
DMSO dimethylsulfoxide
dppf 1,1'-bis(diphenylphosphino)ferrocene
Et$_2$O diethyl ether
Et$_3$N triethylamine
EtOAc ethyl acetate
EtOH ethanol
h hours
Hex hexane
AcOH acetic acid
HPLC high performance liquid chromatography
LC-MS liquid chromatography coupled to mass spectroscopy
MeCN acetonitrile
MeOH methanol
min minutes
MsCl methanesulfonyl chloride
MS ESI mass spectra, electrospray ionization
NMO N-methyl morpholine N-oxide
NMR nuclear magnetic resonance
O/N overnight
Pd(OAc)$_2$ palladium acetate
PPh$_3$ triphenylphosphine
prepHPLC preparative scale high pressure liquid chromatography
prepTLC preparative scale thin layer chromatography
RBF round bottomed flask
rt room temperature
sat. saturated
SEM 2-(trimethylsilyl)ethoxy)methyl
tBuOOH tert-butyl hydroperoxide
TBAF tetrabutylammonium fluoride
$^t$BuOK potassium tert-butoxide
temp. temperature
THF tetrahydrofuran
wt % percent by weight Preparation of Starting Materials Synthesis of 5-methoxyoxindole

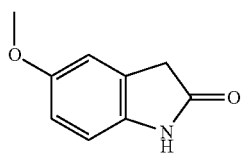

To a solution of 5-methoxyisatin (10.62 g, 60 mmol) in DMSO (30 mL) was added N$_2$H$_4$.H$_2$O (hydrazine hydrate, 6 mL, 120 mmol) dropwise over 5 min (exothermic). After addition, the resulting mixture was heated at 140° C. (oil temp.) for 2 h and then cooled to rt. After diluting with H$_2$O (30 mL), 6 M HCl (12 mL, 72 mmol) was added and the resulting mixture was stirred for 1 h at rt. Ice (30 mL) was added and the reaction mixture was stirred O/N at rt. The precipitate formed was collected by suction filtration, rinsed with H$_2$O, then dried to give the 5-methoxyoxindole (6.523 g) as a brown solid. (about 10% impurity being the oxime from starting material 5-methoxyisatin) $^1$H NMR (400 MHz, d$_6$-DMSO) 6.78 (s, 1H), 6.85 (s, 1H), 6.72-6.79 (m, 2H), 3.39 (s, 3H); ESI 164.0 [M+H]$^+$, calcd for [C$_9$H$_9$NO$_2$+H]$^+$ 164.1.

Synthesis of (E and Z)-3-((3-iodo-1H-indazol-6-yl)methylene)-5-methoxyindolin-2-one

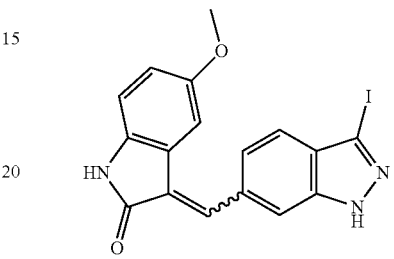

To a mixture of 3-iodo-1H-indazole-6-carbaldehyde (1.360 g, 5 mmol) and 5-methoxyoxindole (1.06 g, 6.5 mmol) in methanol (50 mL) was added piperidine (0.1 mL, 1 mmol). The resulting mixture was refluxed (oil temp. 75° C.) for 3 h, then cooled to rt and stirred for 2 h at rt. The resulting precipitates were collected by suction filtration and dried to give (E/Z)-3-((3-iodo-1H-indazol-6-yl)methylene)-5-methoxyindolin-2-one (E/Z=2:1) as dark brick orange solid (1.966 g, 94%). The mixture was used as an intermediate without purification of the isomers.

This intermediate was also prepared using these conditions: A round bottom flask was charged with 5-methoxyoxindole (commercial reagent from Prime Organics, 300 mg, 1.84 mmol), 3-iodo-1H-indazole-6-carbaldehyde (500 mg, 1.84 mmol), piperidine (20 uL, 0.18 mmol) and MeOH (7 mL). The reaction was then heated to 60° C. for 4 h. A bright red precipitate formed which was further precipitated by cooling to room temperature. The red powder was then filtered and washed with MeOH giving 658 mg, 86% of the title compound. A mixture of (E)- and (Z)-isomers (84:16 by NMR) was obtained. $^1$H NMR (400 MHz, DMSO-d$_6$) 13.78 (br. s, 1H), 10.50 (s, 1H), 9.01 (s, 1H), 8.00 (s, 1H), 8.00 (d, J=8.3 Hz, 1H), 7.48 (d, J=8.3 Hz, 1H), 7.45 (d, J=2.1 Hz, 1H), 6.81 (dd, J=4.1, 2.2 Hz, 1H), 6.73 (d, J=8.4 Hz, 1H), 3.77 (s, 3H); MS ESI 418.0 [M+H]$^+$, calcd for [C$_{17}$H$_{12}$IN$_3$O$_2$+H]$^+$ 418.00.

Synthesis of (E)-3-((3-iodo-1H-indazol-6-yl)methylene)indolin-2-one

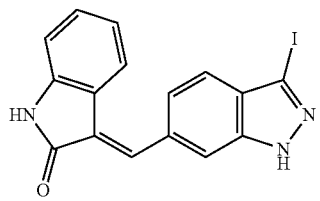 [SMILES: O=C1Nc2ccccc2/C1=C\c1ccc2c(I)n[nH]c2c1]

To a mixture of 3-iodo-1H-indazole-6-carbaldehyde (1.360 g, 5 mmol) and 2-oxindole (732 g, 5.5 mmol) in MeOH (25 mL) was added piperidine (0.1 mL, 1 mmol). The resulting mixture was refluxed (oil temp. 75° C.) for 90 min, then cooled to rt. The resulting precipitates were collected by suction filtration and dried to give (E/Z)-3-((3-iodo-1H-indazol-6-yl)methylene)-indolin-2-one as yellow solid (E:Z=5:1, 1.86 g). The mixture was used as an intermediate without purification of the isomers, or alternatively the pure E isomer could be purified by dissolving in THF (1.57 g in 46.85 mL) at room temperature. Hexane (146.8 mL) was added to the clear solution with stirring to give a yellow precipitate. The solid suspension was heated to 70° C. for 30 min & then cooled to room temperature. The yellow solid was filtered and washed with hexane (3.14 mL) to give the title compound (1.22 g, 79%). $^1$H NMR (400 MHz, DMSO-$d_6$) δ 13.71 (s, 1H), 10.64 (s, 1H), 7.88 (s, 1H), 7.77 (s, 1H), 7.57-7.46 (m, 3H), 7.23 (t, 1H, J=7.6 Hz), 6.87 (d, 1H, J=8.0 Hz), 6.83 (d, 1H, J=7.6 Hz); MS ESI 388.0 [M+H]$^+$, calcd for [$C_{16}H_{10}IN_3O$+H]$^+$ 387.99.

Synthesis of (E)-3-((3-iodo-1-((2-(trimethylsilyl)ethoxy)methyl)-1H-indazol-6-yl)methylene)-indolin-2-one

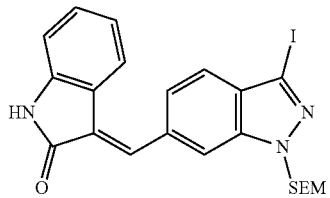 [SMILES: C[Si](C)(C)CCOCn1nc(I)c2ccc(/C=C3/C(=O)Nc4ccccc43)cc21]

Oxindole (665 mg, 5 mmol) and 3-iodo-1-((2-(trimethylsilyl)ethoxy)methyl)-1H-indazole-6-carbaldehyde (2 g, 5 mmol) were dissolved into ethanol (25 mL). Piperidine (0.1 mL) was added and the solution was heated to 70° C. for 2 h, cooled to rt and stirred overnight. The solvent was removed in vacuo to give an orange solid which was triturated with ethanol to give the title compound in quantitative yield. $^1$H NMR (400 MHz, CDCl$_3$) δ 7.95 (s, 1H), 7.86 (s, 1H), 7.62-7.55 (m, 3H), 7.24 (d, 1H, J=7.8 Hz), 6.91 (d, 1H, J=7.8 Hz), 6.86 (t, 1H, J=7.6 Hz), 5.75 (s, 2H), 3.62-3.58 (m, 2H), 0.93-0.89 (m, 2H), −0.04 (s, 9H); MS ESI 518.0 [M+H]$^+$, calcd for [$C_{22}H_{24}IN_3O_2S_{11}$+H]$^+$ 518.4.

Synthesis of (1R*,2S*)-2-(3-iodo-1-((2-(trimethylsilyl)ethoxy)methyl)-1H-indazol-6-yl)spiro[cyclopropane-1,3'-indolin]-2'-one

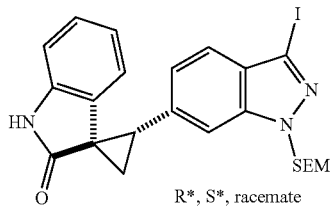
R*, S*, racemate

To a solution of trimethylsulfoxonium iodide (1.89 g, 8.6 mmol) in anhydrous DMF (40 mL) was added sodium hydride (60% dispersion in oil) (1.03 g, 25.8 mmol) at 0° C. The mixture was stirred for 15 min after which time (E)-3-((3-iodo-1-((2-(trimethylsilyl)ethoxy)methyl)-1H-indazol-6-yl)methylene)indolin-2-one (2.2 g, 4.3 mmol) was added. The solution was stirred overnight at rt. The reaction was quenched with sat. NH$_4$Cl solution (50 mL), extracted with EtOAc (4×100 mL), dried over MgSO$_4$ and concentrated to dryness. The title compound was isolated by silica gel chromatography (CH$_2$Cl$_2$/MeOH 98:2) as a yellow solid (1.5 g, 66%). $^1$H NMR (400 MHz, CDCl$_3$) δ 7.46 (s, 1H), 7.39 (d, 1H J=8.3 Hz), 7.09 (t, 1H, J=7.5 Hz), 7.04 (d, 1H, J=8.0 Hz), 6.92 (d, 1H, J=7.8 Hz), 6.61 (t, 1H, J=8.0 Hz), 5.90 (d, 1H, 8.0 Hz), 5.70 (s, 2H), 3.57-3.53 (m, 2H), 3.49-3.44 (m, 1H), 2.31-2.28 (m, 1H), 2.12-2.09 (m, 1H), 0.89-0.84 (m, 2H), −0.05 (s, 9H); MS ESI 532.1 [M+H]$^+$, calcd for [$C_{23}H_{26}IN_3O_2Si$+H]$^+$ 532.4.

Synthesis of (Z)-5-fluoro-3-((3-iodo-1H-indazol-6-yl)methylene)indolin-2-one

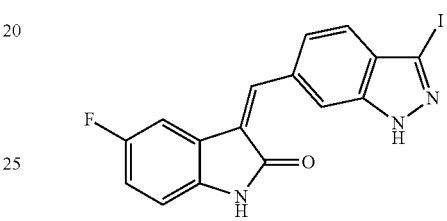

A round bottom flask was charged with 5-fluoroindolin-2-one (100 mg, 0.661 mmol), 3-iodo-1H-indazole-6-carbaldehyde (180 mg, 0.661 mmol), piperidine (13 uL, 0.027 mmol) and methanol (7.5 mL). The reaction was then heated to 60° C. for 3 h prior to cooling the reaction mass to room temperature. Filtration and washing with methanol (0.50 mL×2) gave the title compound as a yellow solid (260 mg, 96%). $^1$H NMR (400 MHz, DMSO-$d_6$) δ 13.82 (s, 1H), 10.72 (s, 1H), 9.00 (s, 1H), 8.06 (s, 1H), 7.98 (d, J=8.8 Hz, 1H), 7.71 (s, J=8.8 Hz, 1H), 7.48 (d, J=8.8 Hz, 1H), 7.07-7.02 (m, 1H), 6.81 (d, J=4.4 Hz, 1H).

Synthesis of (E)-5-fluoro-3-((3-iodo-1-((2-(trimethylsilyl)ethoxy)methyl)-1H-indazol-6-yl)methylene)indolin-2-one

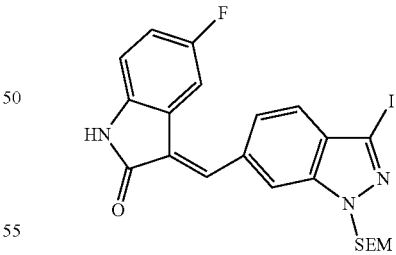

A round bottom flask was charged with 5-fluoroindolin-2-one (100 mg, 0.661 mmol), 3-iodo-1-((2-(trimethylsilyl)ethoxy)methyl)-1H-indazole-6-carbaldehyde (266.18 mg, 0.661 mmol), piperidine (13 uL, 0.013 mmol) and methanol (7.5 mL). The reaction was then heated to 55° C. for 4 h prior to cooling the reaction mass to room temperature. Filtration and washing with methanol (0.50 mL×2) gave the title compound as a yellow solid (273 mg, 77%). $^1$H NMR (400 MHz, CDCl$_3$) δ 8.14 (s, 1H), 8.00 (s, 1H), 7.85 (s, 1H), 7.62 (d, J=8.4 Hz, 1H), 7.50 (d, J=8.4 Hz, 1H), 7.34 (dd, J=8.0, 2.4 Hz, 1H), 6.97 (td, J=6.4, 2.4 Hz, 1H), 6.85 (dd, J=8.4, 4.4 Hz, 1H), 5.80 (s, 2H), 3.58 (t, J=8.4 Hz, 2H), 0.92 (t, J=8.4 Hz, 2H), 0.03 (s, 9H).

Synthesis of (1R*,2S*)-5'-fluoro-2-(3-iodo-1-((2-(trimethylsilyl)ethoxy)methyl)-1H-indazol-6-yl)spiro[cyclopropane-1,3'-indolin]-2'-one

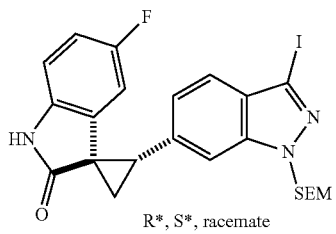

R*, S*, racemate

Trimethylsulfoxonium iodide (164.4 mg, 0.747 mmol) was added to a suspension of sodium hydride (89.6 mg, 2.24 mmol) (60% dispersion in oil) in DMF (2.0 mL) at room temperature. The mixture was stirred for 15 min after which time a solution of (E)-5-fluoro-3-((3-iodo-1-((2-(trimethylsilyl)ethoxy)methyl)-1H-indazol-6-yl)methylene)indolin-2-one (200 mg, 0.373 mmol) in DMF (1.25 ml) was added. The solution was stirred at 55° C. for 7.0 h prior to quenching reaction mass over 25% NH$_4$Cl solution (10 mL) at room temperature. The product was extracted using ethyl acetate (15 mL×2) and the organic layer was dried over MgSO$_4$ and evaporated in vacuo. The crude product was purified using silica gel column chromatography (hexane:acetone 80:20 as an eluent) to yield a creamy semi-solid, which was then triturated with hexanes (2.0 mL) to give the title compound as an off-white powder (94 mg, 46%). $^1$H NMR (400 MHz, CDCl$_3$) δ 8.48 (s, 1H), 7.46 (s, 1H), 7.41 (d, J=8.8 Hz, 1H), 7.03 (d, J=8.8 Hz, 1H), 6.86 (s, 1H), 6.78 (m, 1H), 5.72 (s, 2H), 5.68 (d, J=8 Hz, 1H), 3.54-3.48 (m, 3H), 2.34 (br s, 1H), 2.13 (br s, 1H), 0.88 (m, 2H), 0.03 (s, 9H).

Synthesis of 3-iodo-1H-indazole-6-carbaldehyde

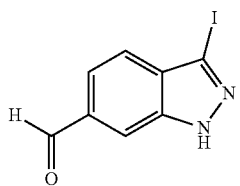 [SMILES: O=Cc1ccc2c(I)n[nH]c2c1]

To a solution of 1H-indazole-6-carbaldehyde (2.00 g, 13.7 mmol), K$_2$CO$_3$ (3.79 g, 27.4 mmol) in DMF (15 mL) was added dropwise a solution of I$_2$ (5.91 g, 23.3 mmol) in DMF (15 mL) and the reaction allowed to stir for two h. An aqueous solution consisting of Na$_2$S$_2$O$_4$ (3.30 g)/K$_2$CO$_3$ (0.20 g)/H$_2$O (30 mL) was then added and the solution stirred for one h. The product was then precipitated by pouring the solution over ice-water (300 mL) and collected by vacuum filtration to give after drying 3.02 g, 81% of a beige powder. $^1$H NMR (400 MHz, CD$_3$OD) δ 10.11 (s, 1H), 8.11 (s, 1H), 7.74 (d, J=8.34 Hz, 1H), 7.62 (d, J=8.34 Hz, 1H); MS ESI 272.9 [M+H]$^+$, calcd for [C$_8$H$_5$IN$_2$O+H]$^+$ 272.95.

Synthesis of 3-iodo-1-((2-(trimethylsilyl)ethoxy)methyl)-1H-indazole-6-carbaldehyde and 3-iodo-2-((2-(trimethylsilyl)ethoxy)methyl)-2H-indazole-6-carbaldehyde

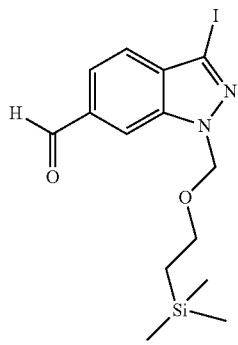

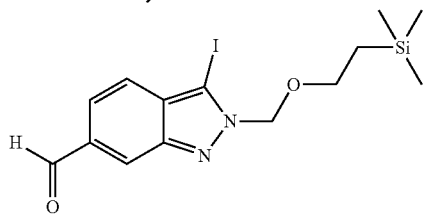

To a suspension of 3-iodo-1H-indazole-6-carbaldehyde (3.01 g, 11.1 mmol) in CH$_2$Cl$_2$ (70 mL) and 50% aq. KOH (20 mL) was added tetrabutylammonium bromide (36 mg, 0.111 mmol) and the solution cooled to 0° C. (2-(Chloromethoxy)ethyl)trimethylsilane (2.3 mL, 13.3 mmol) was then added dropwise and the reaction stirred at 0° C. for 3 hours. The solution was then transferred to a sep. funnel containing CH$_2$Cl$_2$ (200 mL) and the organic layer was washed with brine (2×100 mL), dried (MgSO$_4$) and the solvent removed in vacuo. The resulting residue was purified by column chromatography (100% CH$_2$Cl$_2$) to give 2.88 g, 65% of the N-1 isomer (higher eluting spot) and 757 mg, 17% of the N-2 isomer (lower eluting spot). N-1 isomer: $^1$H NMR (400 MHz, CDCl$_3$) δ 10.18 (s, 1H), 8.11 (s, 1H), 7.81 (d, J=8.4 Hz, 1H), 7.65 (d, J=8.4 Hz, 1H), 5.82 (s, 2H), 3.60 (m, 2H), 0.91 (m, 2H), −0.042 (s, 9H); MS ESI 425.0 [M+Na]$^+$, calcd for [C$_{14}$H$_{19}$IN$_2$O$_2$Si+Na]$^+$ 425.02.

N-2 isomer: $^1$H NMR (400 MHz, CD$_3$OD) 10.09 (s, 1H), 8.31 (s, 1H), 7.62 (m, 2H), 5.91 (s, 2H), 3.71 (m, 2H), 0.92 (m, 2H), −0.039 (s, 9H); MS ESI 425.0 [M+Na]$^+$, calcd for [C$_{14}$H$_{19}$IN$_2$O$_2$Si+Na]$^+$ 425.02.

Synthesis of 3-formyl-1H-indazole-6-carbonitrile

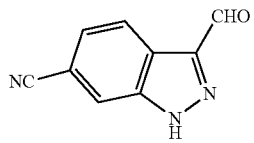 [SMILES: N#Cc1ccc2c(C=O)n[nH]c2c1]

To a solution of NaNO$_2$ (11.04 g, 160 mmol) in H$_2$O (200 mL) was added 6-cyanoindole (5.68 g, 40 mmol) in one portion slowly. The resulting suspension was stirred for 5 min at rt. HCl (32 mL, 192 mmol 6N) was added dropwise via a dropping funnel over 30 min and the pH was about 1.

The resulting suspension was stirred for 4.5 h at rt before of EtOAc (400 mL) was added. After stirring for additional 10 min to dissolve the precipitate, the two layers were separated and the aqueous layer was extracted with EtOAc (150 mL). Combined extracts were dried over $Na_2SO_4$. Removal of solvents afforded 6.864 g (100%) of title compound as brown (coffee color) solid. $^1H$ NMR (400 MHz, DMSO-$d_6$) δ 14.70 (s, 1H, NH), 10.22 (s, 1H, CHO), 8.38 (s, 1H), 8.28 (d, J=8.4 Hz, 1H), 7.69 (d, J=8.4 Hz, 1H). MS ESI 172.0 $[M+H]^+$, calcd for $[C_9H_5N_3O+H]^+$ 172.0.

Synthesis of (E)-3-(2-(pyridin-3-yl)vinyl)-1H-indazole-6-carbaldehyde

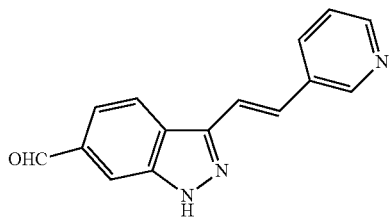 [SMILES: O=Cc1ccc2c(/C=C/c3cccnc3)n[nH]c2c1]

a) (E)-3-(2-(pyridin-3-yl)vinyl)-1H-indazole-6-carbonitrile

To a suspension of 3-chloromethylpyridine hydrochloride (6.54 g, 40 mmol) in benzene (75 mL) was added 40% NaOH (2.7 mL). The resulting mixture was sonicated for 10 min and filtered. The residue was treated with additional benzene (25 ml), sonicated and filtered. The combined benzene layers were dried ($Na_2SO_4$) to give a solution of 3-chloromethylpyridine in benzene.

To a solution of diethyl phosphate (6.06 g, 44 mmol) in benzene (50 mL) was added freshly cut Na (1.02 g, 44 mmol). The resulting mixture was refluxed (oil temp. 95° C.) for 30 min then cooled to 0° C. The solution of 3-chloromethylpyridine in benzene obtained above was added dropwise to this solution via dropping funnel over 15 min. After addition, the resulting mixture was refluxed for 2 h (oil temp. 100° C.) and LC-MS indicated the completion of reaction. After cooling to rt, the insoluble white precipitate (NaCl) was filtered off and rinsed with benzene (50 mL). The filtrate was concentrated and dried under high vacuum to give 6.30 g of diethyl pyridin-3-ylmethylphosphonate as a light yellow liquid.

Diethyl pyridin-3-ylmethylphosphonate was redissolved in DMF (50 mL), cooled to 0° C. and treated with $^t$BuOK (6.72 g, 60 mmol) portion wise over 3 min; the reaction turned a dark reddish brown. After stirring for 3 min at 0° C., a solution of 3-formyl-1H-indazole-6-carbonitrile (3.42 g, 20 mmol) in DMF (25 mL) was added dropwise by pipette over 5 min. After addition, the resulting mixture was stirred for 1 h at 0° C. before quenching with ice (100 mL). The reaction mixture was cooled to 0° C. and slowly acidified with 2M HCl until pH 5. During this addition, a copious amount of precipitate was formed. After stirring for 2 min at this temperature, sat $NaHCO_3$ was added slowly until pH 8 and the mixture was stirred for an additional 2 min. Water was added until the total volume reached 600 mL. After stirring for 10 min, the resulting precipitate was collected by suction filtration and rinsed thoroughly with water, then dried under high vacuum to give the title compound (3.30 g, 67%) as a beige solid. $^1H$ NMR (400 MHz, DMSO-$d_6$) δ 13.80 (s, 1H, NH), 8.89 (s, 1H), 8.48 (d, J=4.4 Hz, 1H), 4.42 (d, J=8.4 Hz, 1H), 8.22-8.17 (m, 2H), 7.74 (d, J=16.8 Hz, 1H), 7.59 (d, J=18.0 Hz, 1H, partially overlapping with the doublet at 7.55 ppm), 7.55 (d, J=10.0 Hz, 1H, partially overlapping with the doublet at 7.59 ppm), 7.43 (dd, J=8.0 Hz, 5.6 Hz, 1H); MS ESI 247.0 $[M+H]^+$, calcd for $[C_{15}H_{10}N_4+H]^+$ 247.1.

b) (E)-3-(2-(pyridin-3-yl)vinyl)-1H-indazole-6-carbaldehyde

To a suspension of (E)-3-(2-(pyridin-3-yl)vinyl)-1H-indazole-6-carbonitrile (984 mg, 3 mmol) in pyridine (30 mL) was added HOAc (8 mL), followed by DMF (30 mL). The resulting mixture was heated and sonicated to make a clear solution. After cooling to 0° C., a solution of sodium hypophosphite (1.408 g, 16 mmol) in $H_2O$ (8 mL) was added, followed by Raney-Nickel 2400 (slurry in $H_2O$, 0.8 mL). The resulting mixture was heated at 60° C. (oil temp.) for 1 h before cooling to rt. $H_2O$ (50 mL) was added and the mixture was extracted with EtOAc (100 mL+50 mL×2). The combined extracts were dried ($Na_2SO_4$). Removal of low boiling point solvents gave a yellow solution in DMF (30 mL); $H_2O$ (500 mL) was added with swirling and a yellow precipitate formed. After standing 10 min, the resulting precipitate was collected by suction filtration, rinsed with $H_2O$ and dried under high vacuum to give the title compound (500 mg, 50%) as a yellow solid. $^1H$ NMR (400 MHz, DMSO-$d_6$) δ 13.79 (s, 1H, NH), 10.14 (s, 1H, CHO), 8.90 (s, 1H), 8.48 (d, J=4.8 Hz, 1H), 8.39 (d, J=8.0 Hz, 1H), 8.19 (d, J=9.2 Hz, 1H, partially overlapping with the singlet at 8.18 ppm), 8.18 (s, 1H, partially overlapping with the doublet at 8.19 ppm), 7.75 (d, J=16.4 Hz, 1H), 7.69 (d, J=8.4 Hz, 1H), 7.59 (d, J=16.8 Hz, 1H), 7.43 (dd, J=8.0 Hz, 5.2 Hz, 1H); MS ESI 250.0 $[M+H]^+$, calcd for $[C_{15}H_{11}N_3O+H]^+$ 250.1.

Synthesis of (E)-3-((1H-indazol-5-yl)methylene)indolin-2-one

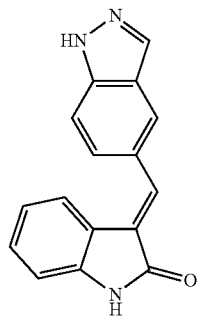 [SMILES: O=C1Nc2ccccc2/C1=C\c1ccc2[nH]ncc2c1]

A scintillation vial was charged with indolin-2-one (67 mg, 0.500 mmol), 1H-indazole-5-carbaldehyde (73 mg, 0.550 mmol), piperidine (5.0 uL, 0.076 mmol) and EtOH (2 mL). The reaction was then heated to 90° C. for 2 hrs. The EtOH was removed and the product purified by preparatory reverse-phase HPLC to give 10 mg, 7.6% of the title compound. $^1H$ NMR (400 MHz, $CD_3OD$) δ 8.20-8.18 (m, 2H), 7.89 (s, 1H), 7.76 (d, J=7.9 Hz, 1H), 7.71-7.67 (m, 2H), 7.24 (t, J=7.4 Hz, 1H), 6.93 (d, J=7.7 Hz, 1H), 6.90 (t, J=7.5 Hz, 1H); MS ESI 262.0 $[M+H]^+$, calcd for $[C_{16}H_{11}N_3O+H]^+$ 262.10.

Synthesis of (E)-3-((1H-indazol-6-yl)methylene)indolin-2-one

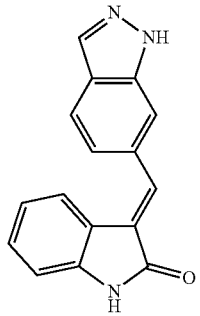 [SMILES: O=C1Nc2ccccc2/C1=C\c1ccc2cn[nH]c2c1]

The title compound was synthesized according to the method described for (E)-3-((1H-indazol-5-yl)methylene)indolin-2-one except reacting oxindole (67 mg, 0.216 mmol) with 1H-indazole-6-carbaldehyde (73 mg, 0.238 mmol) to obtain 32 mg, 51%. $^1$H NMR (400 MHz, CD$_3$OD) δ 8.14 (s, 1H), 7.91 (d, J=8.5 Hz, 1H), 7.89 (s, 2H), 7.65 (d, J=7.6 Hz, 1H), 7.47 (d, J=8.4 Hz, 1H), 7.25 (t, J=7.7 Hz, 1H), 6.93 (d, J=7.8 Hz, 1H), 6.87 (t, J=7.6 Hz, 1H); MS ESI 262.0 [M+H]$^+$, calcd for [C$_{16}$H$_{11}$N$_3$O+H]$^+$ 262.10.

Synthesis of (E and Z)-3-((1H-indazol-6-yl)methylene)-5-bromo-1H-pyrrolo[2,3-b]pyridin-2(3H)-one

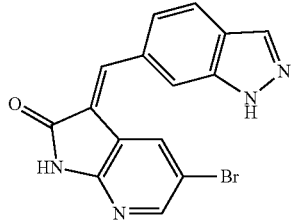 [SMILES: O=C1Nc2ncc(Br)cc2/C1=C\c1ccc2cn[nH]c2c1]

The title compound (50 mg, 95%) was synthesized as a green solid according to the method described for (E/Z)-3-((3-iodo-1H-indazol-6-yl)methylene)-5-methoxyindolin-2-one using 5-bromo-1H-pyrrolo[2,3-b]pyridin-2(3H)-one (21.3 mg, 0.1 mmol) and 1H-indazole-6-carbaldehyde (14.6 mg, 0.1 mmol). $^1$H NMR indicated 56:44 mixture of E/Z isomers. E isomer: $^1$H NMR (400 MHz, DMSO-d$_6$) δ 13.38 (s, 1H, NH), 11.45 (s, 1H, NH), 8.38 (d, J=2.0 Hz, 1H), 8.25 (d, J=2.0 Hz, 1H), 8.19 (s, 1H), 8.01 (s, 1H), 7.93 (s, 1H), 7.90 (d, J=2.0 Hz, 1H), 7.45 (dd, J=8.4 Hz, 2.0 Hz, 1H); Z isomer: δ 13.46 (s, 1H, NH), 11.45 (s, 1H, NH), 8.94 (s, 1H), 8.21 (d, J=2.0 Hz, 1H), 8.19 (s, 1H), 8.15 (s, 1H), 7.99 (dd, J=8.8 Hz, 1.6 Hz, 1H), 7.94 (d, J=8.4 Hz, 1H), 7.85 (d, J=8.0 Hz, 1H); MS ESI 341.0 [M+H]$^+$, calcd for [C$_{15}$H$_9$BrN$_4$O+H]$^+$ 341.1.

Synthesis of (E and Z)-3-((3-(6-(4-methylpiperazin-1-yl)pyridin-3-yl)-1H-indazol-6-yl)methylene)indolin-2-one

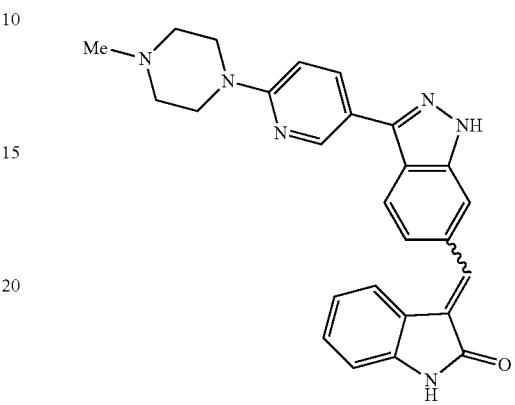

A. 3-(6-(4-methylpiperazin-1-yl)pyridin-3-yl)-1H-indazole-6-carbaldehyde

According to the procedure example A12A, except substituting 3-iodo-1H-indazole-6-carbaldehyde and 1-methyl-4-(5-(4,4,5,5-tetramethyl-1,3,2-dioxa-borolan-2-yl)pyridin-2-yl)piperazine (67 mg, 0.22 mmol), the title compound was obtained as a beige solid (57 mg, 99%). $^1$H NMR (400 MHz, CD$_3$OD) δ ppm 10.11 (s, 1H), 8.73 (d, J=2.3 Hz, 1H), 8.16 (dd, J=8.8, 2.3 Hz, 1H), 8.14 (s, 1H), 8.09 (d, J=8.3 Hz, 1H), 7.72 (d, J=8.5 Hz, 1H), 7.05 (d, J=8.8 Hz, 1H), 3.83-3.78 (m, 4H), 3.01 (t, J=5.0 Hz, 4H), 2.67 (s, 3H); MS ESI 322.1 (100) [M+H]$^+$, calcd for [C$_{18}$H$_{19}$N$_5$O+H]$^+$ 322.16.

B. (E and Z)-3-((3-(6-(4-methylpiperazin-1-yl)pyridin-3-yl)-1H-indazol-6-yl)methylene)indolin-2-one According to the procedure for the synthesis of (E)-3-((1H-indazol-6-yl)methylene)indolin-2-one, except substituting 3-(6-(4-methylpiperazin-1-yl)pyridin-3-yl)-1H-indazole-6-carbaldehyde (40 mg, 0.12 mol), the title compound was prepared as a yellow solid (4.9 mg, 9%). A mixture of (E)- and (Z)-isomers (79:21 by NMR) was obtained. $^1$H NMR (400 MHz, DMSO-d$_6$) δ 13.34 (br. s, 1H), 10.64 (br. s, 1H), 8.76 (d, J=2.3 Hz, 1H), 8.14 (dd, J=8.8, 2.5 Hz, 2H), 7.91 (s, 1H), 7.79 (s, 1H), 7.62 (d, J=7.8 Hz, 1H), 7.48 (d, J=8.0 Hz, 1H), 7.24 (t, J=7.5 Hz, 1H), 6.99 (d, J=9.0 Hz, 1H), 6.89 (d, J=7.8 Hz, 1H), 6.85 (t, J=7.3 Hz, 1H), 3.57 (t, J=4.5 Hz, 4H), 2.42 (t, J=5.0 Hz, 4H), 2.23 (s, 3H); MS ESI 437.2 [M+H]$^+$, calcd for [C$_{26}$H$_{24}$N$_6$O+H]$^+$ 437.20.

Synthesis of (E and Z)-5-methoxy-3-((3-(6-(4-methylpiperazin-1-yl)pyridin-3-yl)-1H-indazol-6-yl)methylene)indolin-2-one

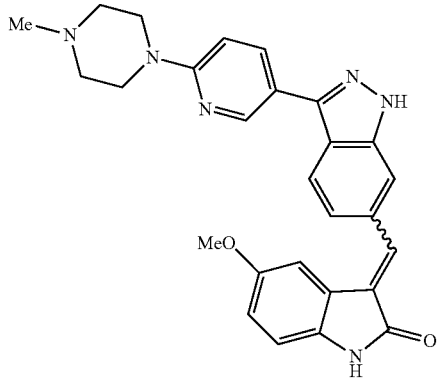 [SMILES: COc1ccc2c(c1)C(=Cc1ccc3c(-c4ccc(N5CCN(C)CC5)nc4)n[nH]c3c1)C(=O)N2]

According to the procedure for the synthesis of 3-((3-(6-(4-methylpiperazin-1-yl)pyridin-3-yl)-1H-indazol-6-yl)methylene)indolin-2-one, except substituting 5-methoxyoxindole (28 mg, 0.087 mol), the title compound was prepared as a yellow solid (14.4 mg, 35%). A mixture of (E)- and (Z)-isomers (83:17 by NMR) was obtained. $^1$H NMR (400 MHz, CD$_3$OD) 8.74 (d, J=2.3 Hz, 1H), 8.14 (dd, J=8.8, 2.3 Hz, 1H), 8.07 (d, J=8.5 Hz, 1H), 7.87 (d, J=10.0 Hz, 2H), 7.49 (d, J=8.3 Hz, 1H), 7.26 (s, 1H), 7.01 (d, J=8.8, 1H), 6.83 (s, 2H), 3.75-3.69 (br. m, 4H), 3.62 (s, 3H), 2.82-2.76 (br. m, 4H), 2.51 (s, 3H); MS ESI 467.2 [M+H]$^+$, calcd for [C$_{27}$H$_{26}$N$_6$O$_2$+H]$^+$ 467.21.

Synthesis of (E)-3-((3-((E)-2-(pyridin-3-yl)vinyl)-1H-indazol-6-yl)methylene)-indolin-2-one

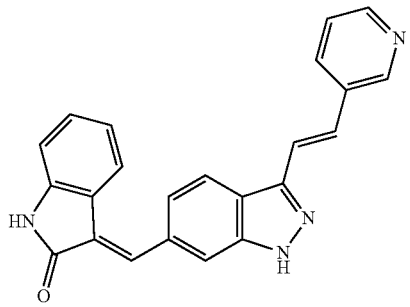 [SMILES: O=C1Nc2ccccc2/C1=C\c1ccc2c(/C=C/c3cccnc3)n[nH]c2c1]

The title compound (61 mg, 84%) was synthesized as a yellow solid according to the method described for (E/Z)-3-((3-iodo-1H-indazol-6-yl)methylene)-5-methoxyindolin-2-one (oil temp 75° C., reflux 90 min) using oxindole (26.6 mg, 0.2 mmol) and (E)-3-(2-(pyridin-3-yl)vinyl)-1H-indazole-6-carbaldehyde (49.8 mg, 0.2 mmol). $^1$H NMR (400 MHz, DMSO-d$_6$) δ 13.46 (s, 1H, NH), 10.64 (s, 1H, NH), 8.91 (s, 1H), 8.48 (d, J=4.4 Hz, 1H), 8.36 (d, J=8.4 Hz, 1H), 8.20 (d, J=8.4 Hz, 1H), 7.90 (s, 1H), 7.80 (s, 1H), 7.73 (d, J=16.8 Hz, 1H), 7.61 (d, J=7.2 Hz, 1H, partially overlapping with the peak at 7.60 ppm), 7.60 (d, J=17.2 Hz, 1H, partially overlapping with the peak at 7.61 ppm), 7.54 (d, J=8.4 Hz, 1H), 7.43 (dd, J=7.8 Hz, 4.8 Hz, 1H), 7.24 (t, J=7.8 Hz, 1H), 6.89 (d, J=7.6 Hz, 1H), 6.85 (t, J=7.8 Hz, 1H); MS ESI 365.1 [M+H]$^+$, calcd for [C$_{23}$H$_{16}$N$_4$O+H]$^+$ 365.1.

Synthesis of (E and Z)-5-methoxy-3-((3-((E)-2-(6-(4-methylpiperazin-1-yl)pyridin-3-yl)vinyl)-1H-indazol-6-yl)methylene)indolin-2-one dihydrochloride

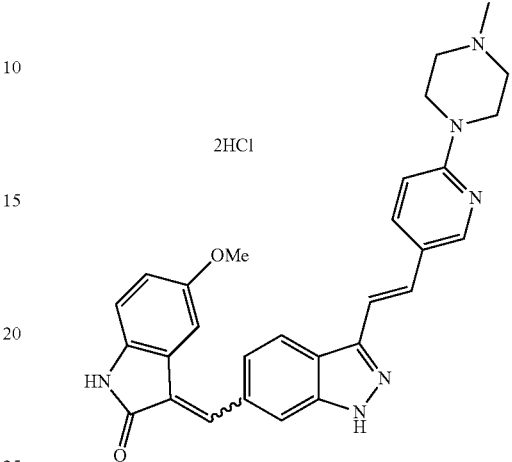

A. 1-Methyl-4-(5-vinylpyridin-2-yl)piperazine

A sealed, degassed mixture of powdered KOH (123 mg, 2.2 mmol) and 1,2-dibromoethane (0.05 mL, 0.6 mmol) in anh THF (2 mL) under Ar was heated under microwave irradiation at 95° C. for 70 min. The reaction mixture was then cooled to rt and treated with Pd(OAc)$_2$ (5.0 mg, 0.022 mmol), PPh$_3$ (11.5 mg, 0.044 mmol), 1-methyl-4-(5-(4,4,5,5-tetramethyl-1,3,2-dioxaborolan-2-yl)pyridin-2-yl)piperazine (120 mg, 0.39 mmol) and degassed MeOH (2 mL). The sealed reaction mixture was heated again under microwave irradiation at 95° C. for 60 min. The crude mixture was concentrated under reduced pressure and purified by prepTLC (SiO$_2$ 10% MeOH/DCM) to provide the title compound a colorless gum (0.18 g, quantitative): $^1$H NMR (400 MHz, CD$_3$OD) δ ppm 8.07 (d, J=2.26 Hz, 1H), 7.73 (dd, J=8.91, 2.38 Hz, 1H), 6.82 (d, J=9.03 Hz, 1H), 6.62 (dd, J=17.82, 11.04 Hz, 1H), 5.63 (d, 1H), 5.12 (d, J=10.79 Hz, 4H), 3.52-3.66 (m, 4H), 2.50-2.61 (m, 4H), 2.35 (s, 3H); MS ESI 204.0 [M+H]$^+$, calcd for [C$_{12}$H$_{17}$N$_3$+H]$^+$ 204.3.

B. (E)-3-(2-(6-(4-methylpiperazin-1-yl)pyridin-3-yl)vinyl)-1-((2-(trimethylsilyl)-ethoxy)methyl)-1H-indazole-6-carbaldehyde The title compound was synthesized according to the method of Example A15A, utilizing 1-methyl-4-(5-vinylpyridin-2-yl)piperazine (65 mg, 0.32 mmol) and 3-iodo-1-((2-(trimethylsilyl)ethoxy)methyl)-1H-indazole-6-carbaldehyde (100 mg, 0.25 mmol), with heating in a sealed tube at 90° C. overnight instead of with microwave irradiation. Purified by prepTLC (SiO$_2$ 10% MeOH/DCM) to provide the title compound to as a pale orange material (46 mg, 39%). $^1$H NMR (400 MHz, CD$_3$OD) δ ppm 10.14 (s, 1H), 8.34 (d, J=2.26 Hz, 1.0H), 8.24-8.28 (m, 2H), 8.00 (dd, J=8.91, 2.38 Hz, 1H), 7.80 (d, J=8.78 Hz, 1H), 7.51 (d, J=16.56 Hz, 1H), 7.36 (d, J=16.56 Hz, 1H), 6.97 (d, J=9.29 Hz, 1H), 5.85 (s, 2H), 3.77-3.87 (m, 4H), 3.63 (t, J=7.91 Hz, 2H), 3.06-3.15 (m, 4H), 2.75 (s, 3H), 0.88 (t, J=8.03 Hz, 2H), −0.09 (s, 9H); MS ESI 478.3 [M+H]$^+$, calcd for [C$_{26}$H$_{35}$N$_5$O$_2$Si+H]$^+$ 478.7.

C. 5-methoxy-3-(E & Z)-((3-((E)-2-(6-(4-methyl-piperazin-1-yl)-pyridin-3-yl)vinyl)-1-((2-(trimethyl-silyl)ethoxy)methyl)-1H-indazol-6-yl)methylene)indolin-2-one The title compound was synthesized according to the method described for (E)-3-((1H-indazol-5-yl)methylene)indolin-2-one, utilizing 5-methoxyindolin-2-one (14.7 mg, 0.090 mmol) and (E)-3-(2-(6-(4-methylpiperazin-1-yl)pyridine-3-yl)vinyl)-1-((2-(trimethylsilyl)ethoxy)methyl)-1H-indazole-6-carbaldehyde (41 mg, 0.086 mmol). The crude mixture was concentrated under reduced pressure and purified by prepTLC (SiO$_2$ 5% MeOH/DCM) to provide the title compound as a (E:Z) mixture of isomers: a yellow solid (11.5 mg, 21%); $^1$H NMR (400 MHz, CD$_3$OD) δ ppm 8.29 (d, J=2.26 Hz, 1H), 8.22 (d, J=8.03 Hz, 1H), 7.92-7.97 (m, 2H), 7.86 (s, 1H), 7.57 (d, J=8.53 Hz, 1H), 7.50 (d., J=16.6 Hz, 1H), 7.30 (d., J=16.6 Hz, 1H), 7.20 (br. s, 1H), 6.89 (d, J=9.03 Hz, 1H), 6.84 (s, 2H), 5.77 (s, 2H), 3.58-3.67 (m, 9H), 2.55-2.62 (m, 4H), 2.37 (s, 3H), 0.88 (t, J=8.16 Hz, 2H), −0.09 (s, 9H); MS ESI [M+2H—CH$_2$CH$_2$SiMe$_3$]$^+$ 523.4, calcd for [C$_{35}$H$_{42}$N$_6$O$_3$Si+H]$^+$ 623.8.

D. (E and Z)-5-methoxy-3-((3-((E)-2-(6-(4-methyl-piperazin-1-yl)pyridin-3-yl)vinyl)-1H-indazol-6-yl)methylene)indolin-2-one dihydrochloride To a DCM (50 mL) solution of 5-methoxy-3-(E & Z)-((3-((E)-2-(6-(4-methylpiperazin-1-yl)-pyridin-3-yl)vinyl)-1-((2-(trimethylsilyl)ethoxy)methyl)-1H-indazol-6-yl)methylene)indolin-2-one (0.85 g, 1.36 mmol) was added BF$_3$.OEt$_2$ (1.7 mL, 13.6 mmol) at 0° C. The cooling bath was removed and the reaction mixture was stirred for 4 h. After removal of the solvent under reduced pressure, the residue was heated in EtOH (40 mL) and 2 M aq HCl (20 mL) at 60° C. overnight. The reaction was then stored at 5° C. overnight. A red precipitate was collected and washed separately with EtOAc, MeCN and Et$_2$O to provide the title compound as as a 3.3:1 (E:Z) mixture of isomers: an orange-red powder (0.32 g, 42%). $^1$H NMR (400 MHz, CD$_3$OD) δ ppm 8.87 (s, 0.3H), 8.53-8.61 (m, 1.0H), 8.28-8.32 (m, 1H), 8.26 (d, J=8.53 Hz, 0.7H), 8.13 (d, J=8.28 Hz, 0.3H), 8.00 (t, J=7.99 Hz, 0.3H), 7.95-8.02 (m, 1.5H), 7.83-7.90 (m, 3.3H), 7.30 (d, J=2.3 Hz, 0.3H), 7.24 (s, 0.7H), 6.84 (s, 1.4H), 6.76-6.84 (m, 0.4H), 4.39-4.59 (br.s, 2H), 3.64-3.85 (br.s., 4H), 3.63 (s, 3H), 3.32-3.60 (br.s., 2H), 3.03 (s, 3H); MS ESI [M+H]$^+$ 493.3, calcd for [C$_{29}$H$_{28}$N$_6$O$_2$+H]$^+$ 493.6.

Synthesis of (E and Z)-3-((3-(4-((dimethylamino)methyl)-1H-indazol-6-yl)-methylene)-5-methoxyindolin-2-one 2,2,2-trifluoroacetate

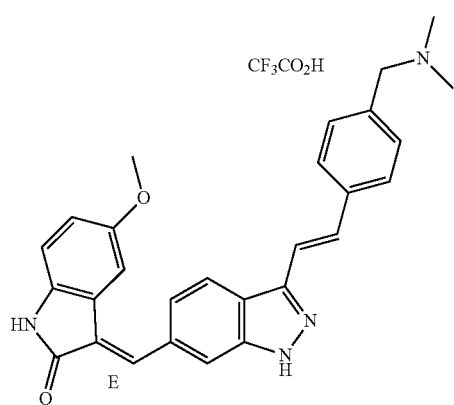

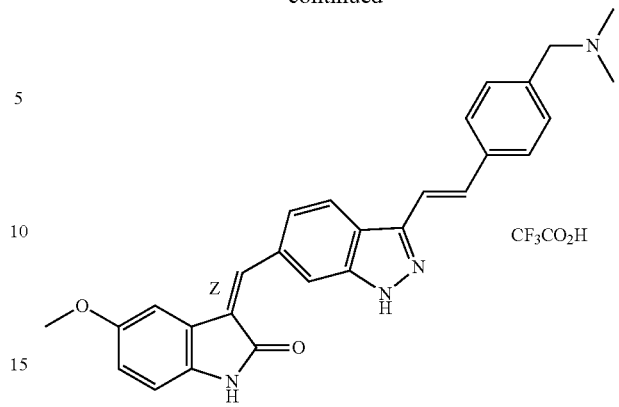

A. (E)-3-(4-((dimethylamino)methyl)styryl)-1-((2-(trimethylsilyl)ethoxy)methyl)-1H-indazole-6-carbaldehyde The title compound was synthesized according to the method of Example A22A, utilizing N,N-dimethyl-1-(4-vinylphenyl)methanamine (42 mg, 0.26 mmol) and 3-iodo-1-((2-(trimethylsilyl)ethoxy)methyl)-1H-indazole-6-carbaldehyde (70 mg, 0.17 mmol) with heating in a sealed tube at 90° C. overnight instead of with microwave irradiation. Purified by prepTLC (SiO$_2$ 10% MeOH/DCM) to provide the title compound to as a pale orange gum (33.4 mg, 44%). $^1$H NMR (400 MHz, CD$_3$OD) δ ppm 10.13 (s, 1H), 8.27 (m, 2H), 7.81 (d, J=9.29 Hz, 1H), 7.69 (d, J=8.28 Hz, 2H), 7.61 (d, J=16.6 Hz, 1H), 7.50 (d, J=16.6 Hz, 1H), 7.43 (d, J=8.28 Hz, 2H), 5.86 (s, 2H), 3.82 (s, 2H), 3.62 (t, J=8.03 Hz, 1H), 2.50 (s, 6H), 0.87 (t, J=8.03 Hz, 2H), −0.09 (s, 9H); MS ESI 436.3 [M+H]$^+$, calcd for [C$_{25}$H$_{33}$N$_3$O$_2$Si+H]$^+$ 436.6.

B. (E)-3-((3-(4-((dimethylamino)methyl)styryl)-1-((2-(trimethylsilyl)ethoxy)methyl)-1H-indazol-6-yl)methylene)-5-methoxyindolin-2-one Piperidine (0.01 mL, 0.1 mmol) was added to a solution of 5-methoxyoxindole (52 mg, 0.32 mmol) and (E)-3-(4-((dimethylamino)methyl)styryl)-1-((2-(trimethylsilyl)ethoxy)-methyl)-1H-indazole-6-carbaldehyde (contaminated with TBAF from previous deprotection attempt, 95.5 mg, 0.22 mmol) in EtOH (5 mL). The reaction was then heated to 75° C. for 25 hrs. The solvent was evaporated in vacuo. Chromatography (5 g silica SPE tube, Silicycle, 5-10% MeOH in CH$_2$Cl$_2$) gave a brown oil (105 mg, contained product and TBAF by NMR). The residue was dissolved in EtOAc (100 mL) and washed with brine (3×15 mL), dried over Na$_2$SO$_4$ and the solvent was evaporated in vacuo to give the title compound as a brown oil (110 mg, used without further purification).

C. (E & Z)-3-((3-(4-((dimethylamino)methyl)styryl)-1H-indazol-6-yl)-methylene)-5-methoxyindolin-2-one According to the method of Example A22B, 3-((3-(4-((dimethylamino)methyl)styryl)-1-((2-(trimethylsilyl)ethoxy)methyl)-1H-indazol-6-yl)methylene)-5-methoxyindolin-2-one (19 mg, 0.033 mmol) was treated with boron trifluoride etherate, followed by 2 N HCl (water/EtOH) treatment. The solvents were removed in vacuo using additional EtOH to azeotropically remove water. The residue was dissolved in MeOH/EtOAc and filtered to remove solid, then the solvent was evaporated in vacuo. Purification by prep-HPLC gave the title compound (E isomer, first eluting fraction, 94% by HPLC) as an orange solid (11 mg, 60%,). $^1$H NMR (400 MHz, CD$_3$OD) δ ppm 8.26 (d, J=8.5 Hz, 1H), 7.88 (d, J=9.3 Hz, 2H), 7.80 (d, J=8.3 Hz, 2H), 7.61 (s, 2H), 7.51-7.58 (m, 3H), 7.26 (s, 1H), 6.84 (s, 2H), 4.34 (s, 2H), 3.63 (s, 3H), 2.89 (s, 6H); MS ESI 451.2 [M+H]$^+$, calcd for [C$_{28}$H$_{26}$N$_4$O$_2$+H]$^+$ 451.22. The second eluting fraction was the Z-isomer (5 mg, 30%). $^1$H NMR (400 MHz, CD$_3$OD) δ ppm 8.89 (s, 1H), 8.15 (d, J=9.0 Hz, 1H), 7.99 (dd, J=9.0, 1.3 Hz, 1H), 7.90 (s, 1H), 7.81 (d, J=8.3 Hz, 2H), 7.57-7.61 (m, 2H), 7.53 (d, J=8.3 Hz, 2H), 7.33 (d, J=2.0 Hz, 1H), 6.85 (dd, J=8.4, 2.4 Hz, 1H), 6.80 (d, J=8.4 Hz, 1H), 4.34 (s, 2H), 3.84 (s, 3H), 2.89 (s, 6H); MS ESI 451.2 [M+H]$^+$, calcd for [C$_{28}$H$_{26}$N$_4$O$_2$+H]$^+$ 451.22.

Synthesis of (E and Z)-5-bromo-3-((3-(6-(4-methyl-piperazin-1-yl)pyridin-3-yl)-1H-indazol-6-yl)methylene)indolin-2-one

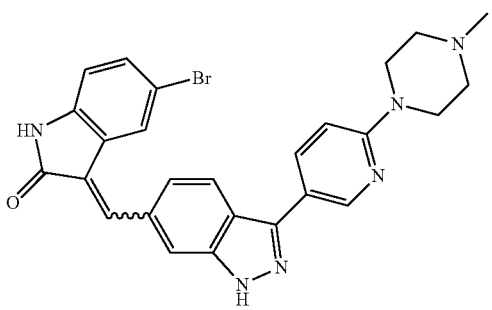 [SMILES: CN1CCN(c2ccc(-c3n[nH]c4cc(C=C5C(=O)Nc6ccc(Br)cc65)ccc34)cn2)CC1]

The title compound (E/Z=3:4, 65 mg, 88%) was synthesized as an orange solid according to the method described for (E/Z)-3-((3-iodo-1H-indazol-6-yl)methylene)-5-methoxyindolin-2-one-(oil temp 75° C., reflux 3 h) using 5-bromoindolin-2-one (32 mg, 0.15 mmol) and 3-(6-(4-methylpiperazin-1-yl)pyridin-3-yl)-1H-indazole-6-carbaldehyde (46 mg, 0.143 mmol). $^1$H NMR (400 MHz, DMSO-d$_6$) E isomer: δ 13.41 (s, 1H), 10.80 (s, 1H), 8.76 (s, 1H), 8.20-8.03 (m, 2H), 7.91 (s, 1H), 7.87 (s, 1H), 7.67 (d, 1H), 7.48-7.40 (m, 2H), 7.99 (d, J=8.8 Hz, 1H), 6.86 (d, J=8.0 Hz, 1H), 3.57 (t, 4H), 2.41 (t, 4H), 2.23 (s, 3H); Z isomer: δ 13.48 (s, 1H), 10.84 (s, 1H), 9.02 (s, 1H), 8.76 (s, 1H), 8.20-8.03 (m, 5H), 7.38 (d, J=8.0 Hz, 1H), 6.98 (d, J=9.6 Hz, 1H), 6.80 (d, J=8.0 Hz, 1H), 3.57 (t, 4H), 2.41 (t, 4H), 2.23 (s, 3H); MS ESI 515.4 [M+H]$^+$, calcd for [C$_{26}$H$_{23}$BrN$_6$O+H]$^+$ 515.1.

Synthesis of (E)-1-methyl-4-(5-(2-(4,4,5,5-tetramethyl-1,3,2-dioxaborolan-2-yl)vinyl)pyridin-2-yl)piperazine

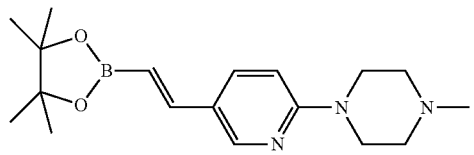

A mixture of 1-(5-bromopyridin-2-yl)-4-methylpiperazine (501.7 mg, 1.96 mmol), PdCl$_2$(PPh$_3$)$_2$ (51.1 mg, 0.073 mmol) and copper(I) iodide (39.9 mg, 0.21 mmol) was flushed with argon for 10 min prior to addition of piperidine (1.25 mL, 12.7 mmol) and trimethylsilylacetylene (1.40 mL, 9.9 mmol). The resulting mixture was heated at 90° C. in a sealed vial for 3 d. The reaction mixture was cooled to room temperature and the volatiles were removed in vacuo. Chromatography on Biotage (silica, SNAP-25 g, 5-15% MeOH in DCM) yielded an impure product. A second chromatography on Biotage (silica, SNAP-25 g, 0-3% Et$_3$N in Et$_2$O) gave 1-methyl-4-(5-((trimethylsilyl)ethynyl)pyridin-2-yl)piperazine (325.7 mg, 61%). $^1$H NMR (400 MHz, CDCl$_3$) δ ppm 8.29 (d, J=1.3 Hz, 1H), 7.53 (dd, J=8.9, 2.4 Hz, 1H), 6.55 (d, J=8.8 Hz, 1H), 3.67-3.52 (m, 4H), 2.57-2.44 (m, 4H), 2.35 (s, 3H); MS ESI [M+H]$^+$ 274.0, calcd for [C$_{15}$H$_{23}$N$_3$Si+H]$^+$ 274.2.

Potassium carbonate (1M aq., 1.5 mL, 1.5 mmol) was added in a drop-wise manner to a solution of 1-methyl-4-(5-((trimethylsilyl)ethynyl)pyridin-2-yl)piperazine (325 mg, 1.19 mmol) in MeOH (5.0 mL) at room temperature, and the resulting mixture was stirred for 2 h. After removal of the solvent in vacuo, water (5 mL) and brine (10 mL) were added and the product was extracted with DCM (150 mL, then 3×10 mL). The combined organic layers were washed with brine (15 mL), dried over Na$_2$SO$_4$ and filtered. Evaporation of the solvent gave 1-(5-ethynylpyridin-2-yl)-4-methylpiperazine (239 mg, quantitative yield), which was used in the next step without purification. $^1$H NMR (400 MHz, CDCl$_3$) δ ppm 8.32 (s, 1H), 7.55 (dd, J=8.9, 2.1 Hz, 1H), 6.58 (d, J=8.8 Hz, 1H), 3.54-3.67 (m, 4H), 3.08 (s, 1H), 2.46-2.58 (m, 4H), 2.35 (s, 3H); MS ESI [M+H]$^+$ 201.9, calcd for [C$_{12}$H$_{15}$N$_3$+H]$^+$ 202.1.

The title compound was prepared in a similar manner to Example A42A using 1-(5-ethynylpyridin-2-yl)-4-methylpiperazine (239 mg, 1.19 mmol). Attempted purification on Biotage (KP-NH, SNAP-28 g column, 10-40% EtOAc in hexane) resulted in a crude product, which was triturated with 50% Et$_2$O in hexane to give the title compound (off-white solid, 53.8 mg, 13%). A second crop was obtained by evaporation of the mother liquor and trituration with 20% Et$_2$O in hexane (off-white solid, 90.3 mg, 22%). Evaporation and chromatography on Biotage (silica, SNAP-10 g, with 10-100% EtOAc in DCM, followed by 0-100% Acetone in EtOAc) gave a third crop (orange solid, 92.6 mg, 23%, ~90% pure by $^1$H NMR, used without further purification). $^1$H NMR (400 MHz, CDCl$_3$) δ ppm 8.25 (s, 1H), 7.70 (d, J=9.0 Hz, 1H), 7.30 (d, J=18.3 Hz, 1H), 6.65 (d, J=8.3 Hz, 1H), 5.99 (d, J=18.3 Hz, 1H), 3.78 (br. s., 4H), 2.74 (br. s., 4H), 2.51 (br. s., 3H), 1.32 (s, 12H).

Synthesis of 1-(5-(4,4,5,5-tetramethyl-1,3,2-dioxaborolan-2-yl)pyridin-2-yl)piperidin-4-yl acetate

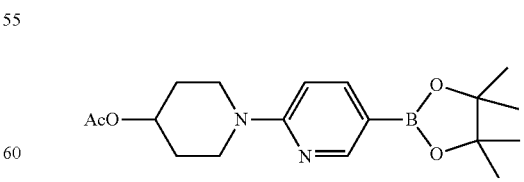

A. 1-(5-bromopyridin-2-yl)piperidin-4-ol

A mixture of 2,5-dibromopyridine (100 mg, 0.42 mmol), 4-hydroxypiperidine (49 mg, 0.46 mmol) and K$_2$CO$_3$ (64 mg, 0.46 mmol) in ethanol (4 mL) was heated to 110° C. for 52 h. The crude reaction mixture was concentrated under reduced pressure to dryness and the residue was treated with water. Crude product was collected by vacuum filtration and purified by flash chromatography using EtOAc/hexanes (1:4 to 2:3) to give the title compound as a white solid (533 mg, 41%). $^1$H NMR (400 MHz, CDCl$_3$) δ 8.18 (d, J=2.2 Hz, 1H), 7.53 (dd, J=9.0, 2.3 Hz, 1H), 6.59 (d, J=9.0 Hz, 1H), 4.04-3.94 (m, 3H), 3.18 (t, J=11 Hz, 2H), 2.00-1.95 (m, 2H), 1.63-1.54 (m, 2H); MS ESI 256.9 [M+H]$^+$, calcd for [C$_{10}$H$_{13}$BrN$_2$O+H]$^+$ 257.02.

B. 1-(5-bromopyridin-2-yl)piperidin-4-yl acetate

A mixture of 1-(5-bromopyridin-2-yl)piperidin-4-ol (200 mg, 0.78 mmol), acetic anhydride (0.16 mL, 1.7 mmol), DMAP (10 mg, 0.08 mmol), and Et$_3$N (0.24 mL, 1.7 mmol) in CH$_2$Cl$_2$ (4 mL) was stirred at rt for 17 h. Brine was added and extracted with CH$_2$Cl$_2$, dried over MgSO$_4$, filtered and concentrated to dryness. The crude product was triturated with water and the title compound was collected by vacuum filtration (203 mg, 88%). $^1$H NMR (400 MHz, CDCl$_3$) δ 8.17 (d, J=2.2 Hz, 1H), 7.52 (dd, J=9.0 Hz, 2.5 Hz, 1H), 6.57 (d, 9.0 Hz, 1H), 5.01-4.95 (m, 1H), 3.9-3.85 (m, 2H), 3.35-3.28 (m, 2H), 2.07 (s, 3H), 1.99-1.92 (m, 2H), 1.74-1.65 (m, 2H); MS ESI 300.9 [M+H]$^+$, calcd for [C$_{12}$H$_{15}$BrN$_2$O$_2$+H]$^+$ 299.03.

C. 1-(4-(4,4,5,5-tetramethyl-1,3,2-dioxaborolan-2-yl)phenyl)piperidin-4-yl acetate A mixture of 1-(5-bromopyridin-2-yl)piperidin-4-yl acetate (170 mg, 0.57 mmol), bis(pinacolato)diboron (290 mg, 1.14 mmol), KOAc (170 mg, 1.7 mmol) and DMF (4 mL) was purged with argon for 10 min. [1,1'-Bis(diphenylphosphine)ferrocene] dichloropalladium(II) (13 mg, 0.017 mmol) was added, the vial sealed and heated at 90° C. for 2 h. The crude reaction mixture was concentrated under reduced pressure to dryness and the residue was dissolved with EtOAc. The mixture was filtered through a cake of Celite and the filtrate was concentrated to give the crude product. Crude product was purified by flash chromatography using EtOAc/hexanes (3:7 to 2:3) to give the title compound as a yellow solid (107 mg, 54%). $^1$H NMR (400 MHz, CDCl$_3$) δ 8.54 (s, 1H), 7.84 (dd, J=8.6 Hz, 1.7 Hz, 1H), 6.63 (d, 8.7 Hz, 1H), 5.04-4.98 (m, 1H), 4.04-3.94 (m, 2H), 3.42-3.36 (m, 2H), 2.08 (s, 3H), 1.97-1.94 (m, 2H), 1.73-1.65 (m, 2H), 1.33 (s, 12H).

Synthesis of 1-(4-(4,4,5,5-tetramethyl-1,3,2-dioxaborolan-2-yl)phenyl)piperidin-4-yl acetate

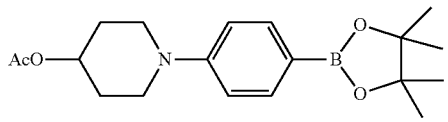 [SMILES: CC(=O)OC1CCN(c2ccc(B3OC(C)(C)C(C)(C)O3)cc2)CC1]

A. 1-(4-bromophenyl)piperidin-4-ol

To a mixture of 1-(4-bromophenyl)piperidin-4-one (600 mg, 2.36 mmol) in EtOH (10 mL) was added NaBH$_4$ (134 mg, 3.54 mmol) slowly at 0° C. The resulting mixture was stirred at rt for 1 h. The reaction was quenched with sat. NH$_4$Cl solution, extracted with EtOAc, dried over MgSO$_4$, filtered, and concentrated to dryness. The title compound was isolated by silica gel chromatography (EtOAc/hexanes, 2:3 to 3:2) as a yellow solid (606 mg, 100%). $^1$H NMR (400 MHz, CDCl$_3$) δ 7.33 (d, J=8.9 Hz, 2H), 6.81 (d, J=8.9 Hz, 2H), 3.89-3.84 (m, 1H), 3.55-3.49 (m, 2H), 2.95-2.89 (m, 2H), 2.06-1.99 (m, 2H), 1.72-1.64 (m, 2H); MS ESI 255.9 [M+H]$^+$, calcd for [C$_{11}$H$_{14}$BrNO+H]$^+$ 256.03.

B. 1-(4-bromophenyl)piperidin-4-yl acetate

The title compound was synthesized according to the method described for the synthesis of 1-(5-bromopyridin-2-yl)piperidin-4-yl acetate, except substituting 1-(4-bromophenyl)piperidin-4-ol (606 mg, 2.37 mmol). Crude product was purified by flash chromatography using EtOAc/hexanes as eluent (1:9 to 1:4) to give the title compound as a white solid (648 mg, 92%). $^1$H NMR (400 MHz, CDCl$_3$) δ 7.33 (d, J=9.0 Hz, 2H), 6.80 (d, J=9.0 Hz, 2H), 4.92-4.89 (m, 1H), 3.47-3.41 (m, 2H), 3.06-3.00 (m, 2H), 2.08 (s, 3H), 2.04-1.99 (m, 2H), 1.84-1.76 (m, 2H); MS ESI 297.9 [M+H]$^+$, calcd for [C$_{13}$H$_{16}$BrNO$_2$+H]$^+$ 298.04.

C. 1-(4-(4,4,5,5-tetramethyl-1,3,2-dioxaborolan-2-yl)phenyl)piperidin-4-yl acetate The title compound was synthesized according to the method described for the synthesis of 1-(4-(4,4,5,5-tetramethyl-1,3,2-dioxaborolan-2-yl)phenyl)piperidin-4-yl acetate, except substituting 1-(4-bromophenyl)piperidin-4-yl acetate (200 mg, 0.67 mmol) and the reaction was heated to 120° C. for 3 h. Crude product was purified by flash chromatography using EtOAc/hexanes as eluent (1:19 to 1:4) to give the title compound as a yellow solid (67 mg, 29%). $^1$H NMR (400 MHz, CD$_3$OD) δ 7.61 (d, J=8.5 Hz, 2H), 6.92 (d, J=8.6 Hz, 2H), 4.94-4.88 (m, 1H), 3.61-3.55 (m, 2H), 3.14-3.08 (m, 2H), 2.05 (s, 3H), 2.01-1.97 (m, 2H), 1.78-1.70 (m, 2H), 1.33 (s, 12H); MS ESI 346.1 [M+H]$^+$, calcd for [C$_{19}$H$_{28}$BNO$_4$+H]$^+$ 346.21.

Synthesis of N,N-dimethyl-1-(4-(4,4,5,5-tetramethyl-1,3,2-dioxaborolan-2-yl)phenyl)piperidin-4-amine

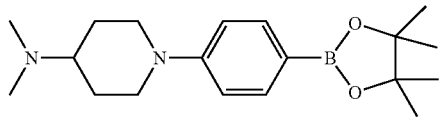

A. 1-(4-bromophenyl)-N,N-dimethylpiperidin-4-amine

To a mixture of 1-(4-bromophenyl)piperidin-4-one (200 mg, 0.79 mmol), dimethylamine (0.80 mL, 1.57 mmol, 2M in THF), and acetic acid (0.20 mL, 3.15 mmol) in DCE (8 mL) was added sodium triacetoxyborohydride (250 mg, 1.18 mmol) at rt. The resulting mixture was stirred at rt for 2.5 h. The reaction was quenched with sat. NaHCO$_3$ solution, extracted with CH$_2$Cl$_2$, dried over MgSO$_4$, filtered, and concentrated to give a yellow oil. The title compound was isolated by silica gel chromatography (EtOAc to MeOH/CH$_2$Cl$_2$, 35:100) as a yellow solid (139 mg, 63%). $^1$H NMR (400 MHz, CD$_3$OD) δ 7.31 (d, J=9.0 Hz, 2H), 6.88 (d, J=9.0

Hz, 2H), 3.76-3.73 (m, 2H), 2.69 (t, J=12.3 Hz, 2H), 2.53-2.45 (m, 1H), 2.41 (s, 6H), 2.01-1.98 (m, 2H), 1.67-1.57 (m, 2H); MS ESI 283.0 [M+H]$^+$, calcd for [C$_{13}$H$_{19}$BrN$_2$+H]$^+$ 283.07.

B. N,N-dimethyl-1-(4-(4,4,5,5-tetramethyl-1,3,2-dioxaborolan-2-yl)phenyl)piperidin-4-amine The title compound was synthesized according to the method described for the synthesis of 1-(4-(4,4,5,5-tetramethyl-1,3,2-dioxaborolan-2-yl)phenyl)piperidin-4-yl acetate, except substituting 1-(4-bromophenyl)-N,N-dimethylpiperidin-4-amine (139 mg, 0.49 mmol) and the reaction was heated to 120° C. for 4 h. Crude product was purified by flash chromatography using EtOAc/Et$_3$N as eluent (1:0 to 98:2) to give the title compound as a yellow solid (37 mg, 23%). $^1$H NMR (400 MHz, MeOD) δ 7.61 (d, J=8.6 Hz, 2H), 6.92 (d, J=8.5 Hz, 2H), 3.89-3.86 (m, 2H), 2.75-2.69 (m, 2H), 2.36-2.30 (m, 1H), 2.30 (s, 6H), 1.96-1.64 (m, 2H), 1.65-1.48 (m, 2H), 1.32 (s, 12H); MS ESI 331.1 [M+H]$^+$, calcd for [C$_{19}$H$_{31}$BN$_2$O$_2$+H]$^+$ 331.25.

Synthesis of 4-(4-isopropylpiperazin-1-yl)phenylboronic acid

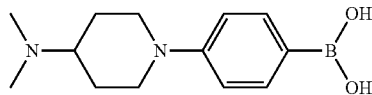

To a solution of sec-BuLi (4.7 mL, 6.5 mmol) in THF at −78° C. was added a solution of 1-(4-bromophenyl)-N,N-dimethylpiperidin-4-amine (230 mg, 0.81 mmol) in THF (2 mL). The resulting yellow mixture was stirred at −78° C. for 1 h followed by the addition of triisopropylborate (0.23 mL, 0.97 mmol). The reaction mixture was warmed to rt for 30 min, and water (5 mL) was added. The reaction was stirred at rt for 1 h and concentrated under reduced pressure to dryness. Crude product was purified by flash chromatography using MeOH/CH$_2$Cl$_2$ as eluent (2:98 to 1:4) to give the title compound as a yellow solid (48 mg, 24%). $^1$H NMR (400 MHz, MeOD) δ 7.60 (br s, 2H), 6.95 (d, J=8.0 Hz, 2H), 3.94-3.91 (m, 2H), 2.84-2.74 (m, 1H), 2.77 (s, 6H), 2.19-2.11 (m, 2H), 1.86-1.68 (m, 2H), 1.65-1.48 (m, 2H), 1.32 (s, 12H); MS ESI 248.9 [M+H]$^+$, calcd for [C$_{13}$H$_{21}$BN$_2$O$_2$+H]$^+$ 249.17.

Synthesis of 4-(4-morpholinopiperidin-1-yl)phenylboronic acid

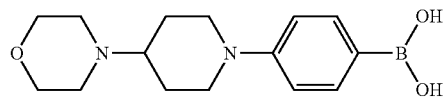 [SMILES: OB(O)c1ccc(N2CCC(N3CCOCC3)CC2)cc1]

A. 4-(1-(4-bromophenyl)piperidin-4-yl)morpholine

The title compound was synthesized according to the synthesis of 1-(4-bromophenyl)-N,N-dimethylpiperidin-4-amine, except reacting 1-(4-bromophenyl)piperidin-4-one (500 mg, 1.97 mmol) with morpholine (0.21 mL, 2.36 mmol) for 25 h to give the title compound as a yellow solid (620 mg, 97%). $^1$H NMR (400 MHz, MeOD) δ 7.31 (d, J=8.2 Hz, 2H), 6.89 (d, J=8.6 Hz, 2H), 3.87-3.67 (m, 6H), 2.71 (t, J=12.5 Hz, 2H), 2.67-2.62 (m, 4H), 2.37-2.36 (m, 1H), 2.04-1.97 (m, 2H), 1.72-1.56 (m, 2H); MS ESI 325.2 [M+H]$^+$, calcd for [C$_{15}$H$_{21}$BrN$_2$O+H]$^+$ 325.08.

B. 4-(4-morpholinopiperidin-1-yl)phenylboronic acid

The title compound was synthesized according to the synthesis of 4-(4-isopropylpiperazin-1-yl)phenylboronic acid, except substituting 4-(1-(4-bromophenyl)piperidin-4-yl)morpholine (250 mg, 0.77 mmol). The aqueous layer was washed with EtOAc and concentrated. The residue was triturated with THF and the filtrate was concentrated to give the title compound as a yellow solid (87 mg, 40%). $^1$H NMR (400 MHz, MeOD) δ 7.58 (br s, 2H), 6.93 (d, J=7.5 Hz, 2H), 3.85-3.82 (m, 2H), 3.72 (br s, 4H), 2.72 (t, J=12.3 Hz, 2H), 2.63 (br s, 4H), 2.40-2.34 (m, 1H), 2.01-1.98 (m, 2H), 1.62-1.54 (m, 2H); MS ESI 291.1 [M+H]$^+$, calcd for [C$_{15}$H$_{23}$BN$_2$O$_3$+H]$^+$ 291.18.

Synthesis of tert-butyl 4-(4-(4,4,5,5-tetramethyl-1,3,2-dioxaborolan-2-yl)phenyl)piperidine-1-carboxylate

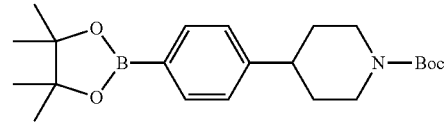 [SMILES: CC(C)(C)OC(=O)N1CCC(c2ccc(B3OC(C)(C)C(C)(C)O3)cc2)CC1]

A. 4-(4-Bromophenyl)-5,6-dihydropyridine

A solution of 4-(4-bromophenyl)piperidin-4-ol (500 mg, 1.95 mmol) in TFA (4 mL) was heated to 90° C. for 2 h. The crude reaction mixture was concentrated under reduced pressure to dryness, to give a yellow solid (460 mg, used without further purification). MS ESI 237.9 [M+H]$^+$, calcd for [C$_{11}$H$_{12}$BrN+H]$^+$ 238.02.

B. Tert-butyl 4-(4-bromophenyl)-5,6-dihydropyridine-1(2H)-carboxylate

A solution of 4-(4-bromophenyl)-5,6-dihydropyridine (460 mg, 1.93 mmol), di-tert-butyl dicarbonate (510 mg, 2.32 mmol), DMAP (5 mg, 0.39 mmol), and Et$_3$N (0.67 mL, 2.5 mmol) in CH$_2$Cl$_2$ was stirred at rt for 17 h. The reaction was extracted with CH$_2$Cl$_2$, dried over MgSO$_4$ and concentrated to give the title compound as a yellow solid (592 mg, 91%). $^1$H NMR (400 MHz, CDCl$_3$) δ 7.41 (d, J=8.5 Hz, 2H), 7.20 (d, J=8.4 Hz, 2H), 6.01 (br s, 1H), 4.05-4.04 (m, 2H), 3.61 (t, J=5.6 Hz, 2H), 2.46 (br s, 2H), 1.48 (s, 9H); MS ESI 359.9 [M+Na]$^+$, calcd for [C$_{16}$H$_{20}$BrNO$_2$+Na]$^+$ 360.06.

C. tert-Butyl 4-(4-bromophenyl)piperidine-1-carboxylate

To a solution of tert-butyl 4-(4-bromophenyl)-5,6-dihydropyridine-1(2H)-carboxylate (100 mg, 0.30 mmol) in EtOAc was added Rh/C (8 mg, 0.03 mmol). The resulting reaction mixture was stirred at rt in a hydrogen atmosphere for 17 h. The mixture was filtered through a cake of Celite and the filtrate was concentrated to give the title compound as a colourless oil (558 mg, 94%). $^1$H NMR (400 MHz, CDCl$_3$) δ 7.43 (d, J=8.4 Hz, 2H), 7.08 (d, J=8.3 Hz, 2H), 4.27-4.23 (m, 2H), 2.79 (t, J=12.9 Hz, 2H), 2.65-2.58 (m, 1H), 1.82-1.79 (m, 2H), 1.64-1.56 (m, 2H), 1.49 (s, 9H); MS ESI 361.9 [M+Na]$^+$, calcd for [C$_{16}$H$_{22}$BrNO$_2$+Na]$^+$ 362.07.

D. tert-Butyl 4-(4-(4,4,5,5-tetramethyl-1,3,2-dioxaborolan-2-yl)phenyl)piperidine-1-carboxylate The title compound was synthesized according to the method described for the synthesis of 1-(4-(4,4,5,5-tetramethyl-1,3,2-dioxaborolan-2-yl)phenyl)piperidin-4-yl acetate, except substituting tert-butyl 4-(4-bromophenyl)piperidine-1-carboxylate (200 mg, 0.59 mmol). Crude product was purified by flash chromatography using EtOAc/hexanes as eluent (2:98 to 15:85) to give the title compound as a colourless oil (239 mg, 80%). $^1$H NMR (400 MHz, CDCl$_3$) δ 7.75 (d, J=7.9 Hz, 2H), 7.21 (d, J=7.9 Hz, 2H), 4.25-4.22 (m, 2H), 2.78 (t, J=12.5 Hz, 2H), 2.67-2.61 (m, 1H), 1.82-1.78 (m, 2H), 1.67-1.57 (m, 2H), 1.48 (s, 9H), 1.32 (s, 12H); MS ESI 410.1 [M+Na]$^+$, calcd for [C$_{11}$H$_{34}$BNO$_4$+Na]$^+$ 410.25.

Synthesis of 1-methyl-4-(4-(4,4,5,5-tetramethyl-1,3,2-dioxaborolan-2-yl)phenyl)piperidine

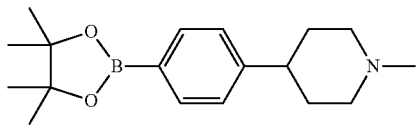

A. 4-(4-(4,4,5,5-tetramethyl-1,3,2-dioxaborolan-2-yl)phenyl)piperidine2,2,2-trifluoroacetate To a solution of tert-butyl 4-(4-bromophenyl)-5,6-dihydropyridine-1(2H)-carboxylate (316 mg, 0.93 mmol) in CH$_2$Cl$_2$ (10 mL) was added TFA (2 mL, 28 mmol). The resulting reaction mixture was stirred at rt for 90 min. The crude reaction mixture was concentrated under reduced pressure to dryness, to give a yellow oil (223 mg, used without further purification). MS ESI 240.1 [M+H]$^+$, calcd for [C$_{11}$H$_{14}$BrN+H]$^+$ 240.3.

B. 4-(4-bromophenyl)-1-methylpiperidine

To a reaction mixture of 4-(4-(4,4,5,5-tetramethyl-1,3,2-dioxaborolan-2-yl)phenyl)piperidine2,2,2-trifluoroacetate (223 mg, 0.93 mmol), formalin (0.08 mL, 0.98 mmol), and MgSO$_4$ (0.5 g) in DCE (8 mL) was added sodium triacetoxyborohydride (600 mg, 2.8 mmol). The reaction was stirred at rt for 17 h. The reaction was quenched with sat. NaHCO$_3$ solution, extracted with CH$_2$Cl$_2$, dried over MgSO$_4$, filtered, and concentrated to give the title compound as a yellow solid (236 mg, used without further purification). $^1$H NMR (400 MHz, MeOD) δ 7.41 (d, J=7.8 Hz, 2H), 7.15 (d, J=7.9 Hz, 2H), 3.00-2.98 (m, 2H), 2.53-2.51 (m, 1H), 2.33 (s, 3H), 2.16 (t, J=11.8 Hz, 2H), 1.82-1.68 (m, 4H); MS ESI 254.0 [M+H]$^+$, calcd for [C$_{12}$H$_{16}$BrN+H]$^+$ 254.05.

C. 1-methyl-4-(4-(4,4,5,5-tetramethyl-1,3,2-dioxaborolan-2-yl)phenyl)piperidine The title compound was synthesized according to the method described for the synthesis of 1-(4-(4,4,5,5-tetramethyl-1,3,2-dioxaborolan-2-yl)phenyl)piperidin-4-yl acetate, except substituting 4-(4-bromophenyl)-1-methylpiperidine (236 mg, 0.93 mmol). The reaction was then allowed to cool to rt and was diluted with EtOAc and water was added. The resulting mixture was extracted with EtOAc and the combined organic extracts were washed with brine, dried over MgSO$_4$ and concentrated to give a viscous brown solid (236 mg, used without further purification). $^1$H NMR (400 MHz, MeOD) δ 7.70 (d, J=7.5 Hz, 2H), 7.25 (d, J=7.5 Jz, 2H), 3.26-3.23 (m, 2H), 2.69-2.64 (m, 1H), 2.60-2.54 (m, 5H), 1.92-1.91 (m, 4H), 1.33 (s, 12H); MS ESI 302.2 [M+Na]$^+$, calcd for [C$_{18}$H$_{28}$BNO$_2$+Na]$^+$ 302.22.

Synthesis of 4-fluoro-1-methyl-4-(4-(4,4,5,5-tetramethyl-1,3,2-dioxaborolan-2-yl)phenyl)piperidine

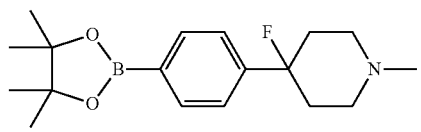

A. 4-(4-bromophenyl)-1-methylpiperidin-4-ol

A reaction mixture of 4-(4-bromophenyl)piperidin-4-ol (1.5 g, 5.9 mmol), methyl iodide (0.4 mL, 6.4 mmol), and K$_2$CO$_3$ (1.2 g, 8.8 mmol) in acetone was stirred at rt for 90 min. The reaction was diluted with EtOAc and water was added. The resulting mixture was extracted with EtOAc and the combined organic extracts were dried over MgSO$_4$ and concentrated to give the title compound as a yellow solid (1.5 g, used without further purification). $^1$H NMR (400 MHz, CDCl$_3$) δ 7.40 (d, J=8.1 Hz, 2H), 7.29 (d, J=8.1 Hz, 2H), 3.20 (br s, 1H), 2.64-2.61 (m, 2H), 2.39 (t, J=11.8 Hz, 2H), 2.21 (s, 3H), 2.03-1.96 (m, 2H), 1.64-1.61 (m, 2H); MS ESI 270.0 [M+H]$^+$, calcd for [C$_{12}$H$_{16}$BrNO+H]$^+$ 270.04.

B. 4-(4-bromophenyl)-4-fluoro-1-methylpiperidine

To a solution of DAST (0.50 g, 3.8 mmol) in CH$_2$Cl$_2$ was added a solution of 4-(4-bromophenyl)-1-methylpiperidin-4-ol (0.507 g, 1.88 mmol) in CH$_2$Cl$_2$ at −78° C. The resulting mixture was warmed to rt over a period of 3 h. The reaction was then allowed to cool to 0° C. and quenched with saturated NaHCO$_3$. The resulting mixture was extracted with CH$_2$Cl$_2$ and the combined organic extracts were dried over MgSO$_4$ and concentrated to give a yellow oil. The crude product was purified by silica gel chromatography (95:5 EtOAc/NH$_3$ to 10:8:2 CH$_2$Cl$_2$/MeOH/NH$_3$) to yield an inseparable mixture of the title compound and 4-(4-bromophenyl)-1-methyl-1,2,3,6-tetrahydropyridine (280 mg, used without further purification).

To a round bottom flask containing tBuOH/H$_2$O (4 mL each) was added AD-mix α (700 mg, 0.50 mmol). The mixture was stirred at rt for 5 min followed by the addition of a mixture of 4-(4-bromophenyl)-4-fluoro-1-methylpiperidine and 4-(4-bromophenyl)-1-methyl-1,2,3,6-tetrahydropyridine (280 mg) in tBuOH/H$_2$O (1 mL each). The resulting reaction was stirred at rt for 2 d. The reaction was then allowed to cool to 0° C. and quenched with solid Na$_2$CO$_3$ (0.75 g). The mixture was stirred at rt for 30 min. The resulting mixture was extracted with EtOAc and the combined organic extracts were dried over MgSO$_4$ and concentrated to give an orange oil. The crude product was purified by silica gel chromatography (93:5:2 to 83:15:2 CH$_2$Cl$_2$/MeOH/NH$_3$) to give the title compound as a yellow solid (133 mg, 26%). $^1$H NMR (400 MHz, MeOD) δ 7.52 (d, J=8.1 Hz, 2H), 7.33 (d, J=8.2 Hz, 2H), 2.85-2.82 (m, 2H), 2.46 (t, J=12.0 Hz, 2H), 2.37 (s, 3H), 2.21-2.11 (m, 1H), 2.10-2.04 (m, 1H), 1.98-1.91 (m, 2H); $^{19}$F NMR (400 MHz, MeOD) δ −161.51; MS ESI 272.1 [M+H]$^+$, calcd for [C$_{12}$H$_{15}$BrFN+H]$^+$ 272.16.

C. 4-fluoro-1-methyl-4-(4-(4,4,5,5-tetramethyl-1,3,2-dioxaborolan-2-yl)phenyl)piperidine The title compound was synthesized according to the method described for the synthesis of 1-(4-(4,4,5,5-tetramethyl-1,3,2-dioxaborolan-2-yl)phenyl)piperidin-4-yl acetate, except substituting 4-(4-bromophenyl)-4-fluoro-1-methylpiperidine (133 mg, 0.49 mmol). The reaction was then allowed to cool to room temperature and was diluted with EtOAc and water was added. The resulting mixture was extracted with EtOAc and the combined organic extracts were washed with brine, dried over MgSO$_4$ and concentrated to give the title compound as a brown solid (281 mg, used without further purification). $^1$H NMR (400 MHz, MeOD) δ 7.76 (d, J=7.7 Hz, 2H), 7.41 (d, J=7.8 Hz, 2H), 2.94-2.91 (m, 2H), 2.59 (t, J=12.0 Hz, 2H), 2.45 (s, 3H), 2.30-2.22 (m, 1H), 2.20-2.12 (m, 1H), 2.01-1.95 (m, 2H); $^{19}$F NMR (400 MHz, MeOD) δ −162.38; MS ESI 320.1 [M+H]$^+$, calcd for [C$_{18}$H$_{27}$BFNO$_2$+H]$^+$ 320.21.

Synthesis of 4-((3S,5R)-3,5-dimethylpiperazin-1-yl)phenylboronic acid

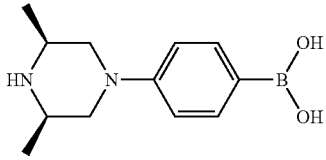

A. 1-(4-bromophenyl)-cis-3,5-dimethylpiperazine

A microwave vial was charged with 1-bromo-4-iodobenzene (1.0 g, 3.5 mmol), CuI (0.135 g, 0.707 mmol), BINOL (0.202 g, 0.707 mmol), and K$_3$PO$_4$ (1.5 g. 7.1 mmol). The vial was capped and then evacuated and backfilled with Ar. Cis-2,6-dimethylpiperazine (0.605 g, 5.30 mmol) and DMF (4 mL) were then added. The resulting mixture was stirred at rt for 4 d. The mixture was diluted with EtOAc, filtered through a cake of Celite and the filtrate was concentrated to give the crude product. Crude product was purified by flash chromatography using MeOH/CH$_2$Cl$_2$ (2:98 to 15:85) to give the title compound as a red solid (567 mg, 59%). $^1$H NMR (400 MHz, MeOD) δ 7.33 (d, J=8.8 Hz, 2H), 6.89 (d, J=8.8 Hz, 2H), 3.63-3.60 (m, 2H), 3.18-3.07 (m, 2H), 2.40 (t, J=11.6 Hz, 2H), 1.23 (d, J=6.4 Hz, 6H); MS ESI 269.0 [M+H]$^+$, calcd for [C$_{12}$H$_{17}$BrN$_2$+H]$^+$ 269.06.

B. 4-(cis-3,5-dimethylpiperazin-1-yl)phenylboronic acid

The title compound was synthesized according to the synthesis of 4-(4-isopropylpiperazin-1-yl)phenylboronic acid, except substituting 1-(4-bromophenyl)-cis-3,5-dimethylpiperazine (300 mg, 1.11 mmol). The reaction was quenched with sat. NH$_4$Cl solution, extracted with EtOAc, dried over MgSO$_4$, filtered, and concentrated to dryness. The title compound was isolated by silica gel chromatography (MeOH/CH$_2$Cl$_2$, 6:94 to 1:4) as a yellow solid (59 mg, 23%). $^1$H NMR (400 MHz, MeOD) δ 7.59 (d, J=6.2 Hz, 2H), 6.91 (d, J=8.2 Hz, 2H), 3.67-3.63 (m, 2H), 3.09-3.01 (m, 2H), 2.32 (t, J=11.6 Hz, 2H), 1.18 (d, J=6.4 Hz, 6H); MS ESI 235.1 [M+H]$^+$, calcd for [C$_{12}$H$_{19}$BN$_2$O$_2$+H]$^+$ 235.15.

Synthesis of N,N,N'-trimethyl-N'-(4-(4,4,5,5-tetramethyl-1,3,2-dioxaborolan-2-yl)phenyl)ethane-1,2-diamine

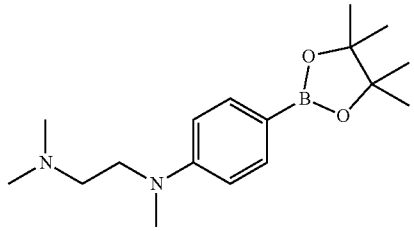

A. N-(4-Iodophenyl)-N,N',N'-trimethylethane-1,2-diamine

The title compound was synthesized according to the synthesis of 1-(4-bromophenyl)-cis-3,5-dimethylpiperazine, except reacting 1,4-diiodobenzene (1.06 g, 3.21 mmol) with N,N,N'-trimethylethylenediamine (0.5 mL, 3.9 mmol). The title compound was purified by silica gel chromatography (MeOH/CH$_2$Cl$_2$, 5:95 to 1:5) to give a pale orange solid (0.62 g, 64%). $^1$H NMR (400 MHz, CDCl$_3$) δ 7.50 (d, J=8.0 Hz, 2H), 6.55 (d, J=8.2 Hz, 2H), 3.77-3.76 (m, 2H), 2.99 (s, 3H), 2.99-2.92 (m, 2H), 2.65 (s, 6H); MS ESI 305.0 [M+H]$^+$, calcd for [C$_{11}$H$_{17}$IN$_2$+H]$^+$ 305.04.

B. N,N,N'-trimethyl-N'-(4-(4,4,5,5-tetramethyl-1,3,2-dioxaborolan-2-yl)phenyl)ethane-1,2-diamine A mixture of N-(4-Iodophenyl)-N,N',N'-trimethylethane-1,2-diamine (150 mg, 0.49 mmol), bis(pinacolato)diboron (150 mg, 0.59 mmol), KOAc (145 mg, 1.5 mmol) and DMSO (4 mL) was purged with argon for 10 min. [1,1'-Bis(diphenylphosphine)ferrocene]dichloropalladium(II) (20 mg, 0.025 mmol) was added, the vial sealed and heated at 85° C. for 2 h. The reaction was then allowed to cool to rt and quenched with saturated NaHCO$_3$. The resulting mixture was extracted with EtOAc and the combined organic extracts were dried over MgSO$_4$ and concentrated. The crude product was purified by silica gel chromatography (95:5 to 85:15 CH$_2$Cl$_2$/MeOH) to yield the title compound as a brown solid (51 mg, 34%). $^1$H NMR (400 MHz, CDCl$_3$) δ 7.59 (d, J=8.0 Hz, 2H), 6.73 (d, J=8.1 Hz, 2H), 3.60 (t, J=7.4 Hz, 2H), 3.00 (s, 3H), 2.76 (t, J=7.6 Hz, 2H), 2.50 (s, 6H), 1.32 (s, 12H); MS ESI 305.1 [M+H]$^+$, calcd for [C$_{17}$H$_{29}$BN$_2$O$_2$+H]$^+$ 305.23.

Synthesis of (R)—N,N-dimethyl-1-(4-(4,4,5,5-tetramethyl-1,3,2-dioxaborolan-2-yl)phenyl)pyrrolidin-3-amine

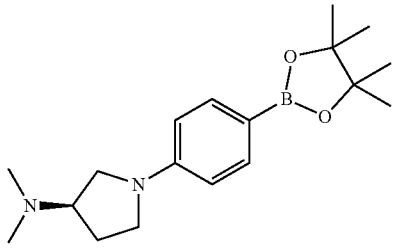

A. (R)-1-(4-iodophenyl)-N,N-dimethylpyrrolidin-3-amine

The title compound was synthesized according to the synthesis of 1-(4-bromophenyl)-cis-3,5-dimethylpiperazine, except reacting 1,4-diiodobenzene (2.41 g, 7.30 mmol) with (R)—N,N-dimethylpyrrolidin-3-amine (1.0 g, 8.8 mmol). The title compound was purified by silica gel chromatography (MeOH/CH$_2$Cl$_2$, 2:98 to 12:88) as a yellow solid (1.17 g, 51%). $^1$H NMR (400 MHz, MeOD) δ 7.42 (d, J=8.2 Hz, 2H), 6.39 (d, J=8.0 Hz, 2H), 3.51-3.47 (m, 1H), 3.44-3.39 (m, 1H), 3.29-3.24 (m, 1H), 3.13-3.09 (m, 2H), 3.00-2.87 (m, 1H), 2.35 (s, 6H), 2.35-2.26 (m, 1H), 1.96-1.86 (m, 1H); MS ESI 317.0 [M+H]$^+$, calcd for [C$_{12}$H$_{17}$IN$_2$+H]$^+$ 317.04.

B. (R)—N,N-dimethyl-1-(4-(4,4,5,5-tetramethyl-1,3,2-dioxaborolan-2-yl)phenyl)pyrrolidin-3-amine The title compound was synthesized according to the synthesis of N,N,N'-trimethyl-N'-(4-(4,4,5,5-tetramethyl-1,3,2-dioxaborolan-2-yl)phenyl)ethane-1,2-diamine, substituting (R)-1-(4-iodophenyl)-N,N-dimethylpyrrolidin-3-amine (300 mg, 0.95 mmol). The title compound was purified by silica gel chromatography (MeOH/CH$_2$Cl$_2$, 2:98 to 12:88) as a yellow solid (95 mg, 32%). $^1$H NMR (400 MHz, MeOD) δ 7.58 (d, J=7.6 Hz, 2H), 6.52 (d, J=7.8 Hz, 2H), 3.55-3.51 (m, 1H), 3.48-3.43 (m, 1H), 3.32-3.26 (m, 1H), 3.15-3.11 (m, 1H), 2.92-2.86 (m, 1H), 2.55 (s, 3H), 2.32 (s, 6H), 2.28-2.22 (m, 1H), 1.94-1.86 (m, 1H); MS ESI 317.2 [M+H]$^+$, calcd for [C$_{18}$H$_{29}$BN$_2$O$_2$+H]$^+$ 317.23.

Synthesis of (S)—N,N-dimethyl-1-(4-(4,4,5,5-tetramethyl-1,3,2-dioxaborolan-2-yl)phenyl)pyrrolidin-3-amine

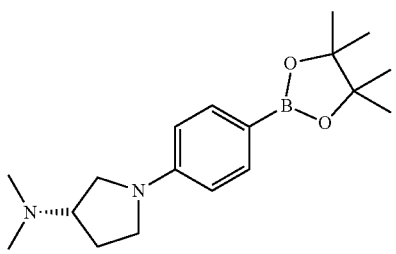

A. (S)-1-(4-iodophenyl)-N,N-dimethylpyrrolidin-3-amine

The title compound was synthesized according to the synthesis of 1-(4-bromophenyl)-cis-3,5-dimethylpiperazine, except reacting 1,4-diiodobenzene (2.41 g, 7.30 mmol) with (S)—N,N-dimethylpyrrolidin-3-amine (1.0 g, 8.8 mmol). The title compound was purified by silica gel chromatography (MeOH/CH$_2$Cl$_2$, 2:98 to 1:9) as a yellow solid (1.27 g, 55%). $^1$H NMR (400 MHz, CDCl$_3$) δ 7.46 (d, J=8.7 Hz, 2H), 6.33 (d, J=8.0 Hz, 2H), 3.47-3.38 (m, 2H), 3.32-3.26 (m, 1H), 3.16-3.12 (m, 1H), 2.89-2.83 (m, 1H), 2.33 (s, 6H), 2.26-2.21 (m, 1H), 1.99-1.89 (m, 1H); MS ESI 317.0 [M+H]$^+$, calcd for [C$_{12}$H$_{17}$IN$_2$+H]$^+$ 317.04.

B. (S)—N,N-dimethyl-1-(4-(4,4,5,5-tetramethyl-1,3,2-dioxaborolan-2-yl)phenyl)pyrrolidin-3-amine The title compound was synthesized according to the synthesis of N,N,N'-trimethyl-N'-(4-(4,4,5,5-tetramethyl-1,3,2-dioxaborolan-2-yl)phenyl)ethane-1,2-diamine, except substituting (S)-1-(4-iodophenyl)-N,N-dimethylpyrrolidin-3-amine (500 mg, 1.58 mmol). The title compound was purified by silica gel chromatography (MeOH/CH$_2$Cl$_2$, 5:95 to 15:85) followed by passing a solution of the desired product (20 mL MeOH) through a PoraPak Rxn CX ionic exchange column as a yellow solid (125 mg, 25%). $^1$H NMR and LCMS were identical to the enantiomer, (R)—N,N-dimethyl-1-(4-(4,4,5,5-tetramethyl-1,3,2-dioxaborolan-2-yl)phenyl)pyrrolidin-3-amine.

Synthesis of (4-bromophenyl)(4-methylpiperazin-1-yl)methanone

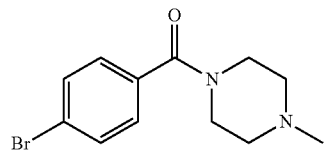

To a mixture of N-methylpiperizine (1.00 g, 10 mmol) and Et$_3$N (2.1 mL, 15 mmol) in CH$_2$Cl$_2$ (50 mL) at rt was added 4-bromobenzoyl chloride (2.195 g, 10 mmol) in one portion. The reaction was heated to reflux briefly and cooled. The resulting mixture was stirred O/N at rt. The reaction was quenched with H$_2$O (30 mL) and sat. NaHCO$_3$ (10 mL), separated and dried (Na$_2$SO$_4$). Evaporation of solvents afforded the title compound as a pale yellowish white solid (2.69 g, 95%). $^1$H NMR (400 MHz, CDCl$_3$) δ 7.64 (d, J=8.4 Hz, 2H), 7.33 (d, J=8.4 Hz, 2H), 3.70-3.20 (m, 4H), 2.40-2.15 (m, 7H; s, 3H at 2.18 ppm and m, 4H overlapping); MS ESI 283.0 [M+H]$^+$, calcd. for [C$_{12}$H$_{15}$BrN$_2$O+H]$^+$ 283.0.

Synthesis of 2-(4-(4-iodophenyl)piperazin-1-yl)ethanol

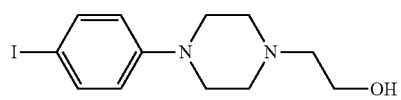 [SMILES: OCCN1CCN(c2ccc(I)cc2)CC1]

To a mixture of 1-(4-iodophenyl)piperazine (2.25 g, 7.8 mmol) and $^iPr_2NEt$ (3.4 mL, 19.5 mmol, 2.5 equiv.) in $CH_3CN$ was added 2-chloroethanol (995 mg, 11.7 mmol, 1.5 equiv.). The resulting mixture was refluxed 7 h (oil temp. 91° C.), then O/N (15 h, oil temp. 83° C.) and 6 h (oil temp. 90° C.) before cooling to rt. After diluting with $H_2O$ (30 mL) and sat. $NaHCO_3$ (30 mL), it was extracted with EtOAc (60 mL×2) and washed with $H_2O$ and brine. Removal of solvents followed by trituration with MeOH (15 mL) afforded the title compound as a beige solid (1.340 g, 81%). A second trituration of the concentrated mother liquor gave additional 602 mg of crude product as a light brown solid. $^1H$ NMR (400 MHz, DMSO-$d_6$) δ 7.46 (d, J=8.4 Hz, 2H), 6.76 (d, J=8.8 Hz, 2H), 4.43 (t, J=5.0 Hz, 1H), 3.51 (q, J=5.6 Hz, 2H), 3.12-3.07 (m, 4H), 2.55-2.49 (m, 4H, partially overlapping with DMSO signal), 2.41 (t, J=6.0 Hz, 2H); MS ESI 332.9 [M+H]$^+$, calcd. for $[C_{12}H_{17}IN_2O+H]^+$ 333.0.

Synthesis of 1-cyclopentyl-4-(4-iodophenyl)piperazine

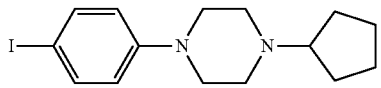 [SMILES: Ic1ccc(N2CCN(C3CCCC3)CC2)cc1]

To a mixture of 1-(4-iodophenyl)piperazine (1.44 g, 5 mmol) and cyclopentanone (840 mg, 10 mmol) in DCE/THF (40 mL/20 mL) was added $NaBH(OAc)_3$ (1.484 g, 7 mmol), followed by AcOH (0.5 mL). After addition, the resulting mixture was stirred 22 h at rt. After quenching with sat. $NaHCO_3$ (20 mL), $H_2O$ (20 mL) and brine (20 mL), the solution was extracted with EtOAc (60 mL+30 mL). Removal of solvents, followed by trituration with MeOH afforded the crude title compound as a pale yellow solid (1.46 g, 82%). $^1H$ NMR (400 MHz, DMSO-$d_6$) δ 7.52 (d, J=8.4 Hz, 2H), 6.70 (d, J=8.4 Hz, 2H), 3.20 (t, J=4.8 Hz, 4H), 2.66 (t, J=4.6 Hz, 4H), 2.54 (p, J=7.6 Hz, 1H), 1.96-1.87 (m, 2H), 1.78-1.52 (m, 4H), 1.50-1.38 (m, 2H); MS ESI 357.0 [M+H]$^+$, calcd. for $[C_{15}H_{21}IN_2+H]^+$ 357.1.

Synthesis of 1-cyclohexyl-4-(4-iodophenyl)piperazine

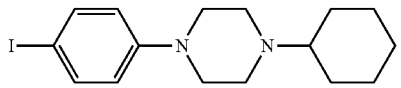

The title compound was obtained as a pale yellow solid (1.398 g, 76%) from 1-(4-iodophenyl)piperazine (1.44 g, 5 mmol) and cyclohexanone (980 mg, 10 mmol) using the method for the preparation of 1-cyclopentyl-4-(4-iodophenyl)piperazine. $^1H$ NMR (400 MHz, DMSO-$d_6$) δ 7.46 (d, J=8.0 Hz, 2H), 7.40 (d, J=8.0 Hz, 2H), 3.10-3.03 (m, 4H), 2.62-2.56 (m, 4H), 2.28-2.18 (m, 1H), 1.80-1.68 (m, 4H), 1.27-1.00 (m, 5H); MS ESI 371.0 [M+H]$^+$, calcd. for $[C_{16}H_{23}IN_2+H]^+$ 371.1.

Synthesis 1-ethyl-4-(4-iodophenyl)piperazine

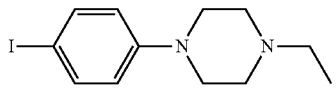

To a stirred mixture of 1-(4-iodophenyl)piperazine (5.76 g, 20 mmol) and $K_2CO_3$ (5.44 g, 40 mmol) in acetone (200 mL) was added iodoethane (2.58 mL, 32 mmol) dropwise over 1 min. After addition, the resulting mixture was stirred at rt for 21 h. The resulting precipitate was filtered off and rinsed with EtOAc (2×60 mL). The filtrate was concentrated to dryness to give a whitish yellow solid. Trituration with MeOH (10 mL) and $H_2O$ (250 mL), followed by suction filtration (rinsed with $H_2O$) gave the title compound as a yellow solid (5.37 g, 85%) after drying. $^1H$ NMR (400 MHz, DMSO-$d_6$) δ 7.46 (d, J=7.6 Hz, 2H), 6.76 (d, J=8.0 Hz, 2H), 3.13-3.07 (m, 4H), 2.48-2.43 (m, 4H), 2.34 (q, J=7.2 Hz, 2H), 1.01 (t, J=7.2 Hz, 3H); MS ESI 317.0 [M+H]$^+$, calcd. for $[C_{12}H_{17}IN_2+H]^+$ 317.0.

Synthesis of 1-(4-iodophenyl)-4-isopropylpiperazine

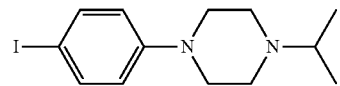 [SMILES: CC(C)N1CCN(c2ccc(I)cc2)CC1]

To a mixture of 1-(4-iodophenyl)piperazine (1.44 g, 5 mmol) and acetone (1.47 mL, 20 mmol) in DCE/THF (45 mL/15 mL) was added $NaBH(OAc)_3$ (1.38 g, 6.5 mmol), followed by AcOH (0.5 mL). After addition, the resulting mixture was stirred O/N at rt. The reaction as quenched with sat. $NaHCO_3$ (10 mL) and $H_2O$ (20 mL), and was then extracted with EtOAc (2×60 mL), dried over $MgSO_4$ and concentrated to give the crude title compound as a light yellow solid (1.396 g, 85%). $^1H$ NMR (400 MHz, DMSO-$d_6$) δ 7.46 (d, J=8.4 Hz, 2H), 6.75 (d, J=8.8 Hz, 2H), 3.12-3.07 (m, 4H), 2.65 (p, J=6.5 Hz, 1H), 2.56-2.52 (m, 4H), 0.98 (d, J=6.4 Hz, 6H); MS ESI 330.9 [M+H]$^+$, calcd. for $[C_{13}H_{19}IN_2+H]^+$ 331.1.

Synthesis of 1-(4-bromophenyl)-4-ethylpiperazine

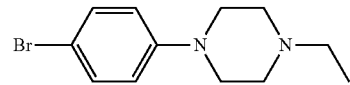

To a stirred mixture of 1-(4-bromophenyl)piperazine (4.82 g, 20 mmol) and $K_2CO_3$ (5.44 g, 40 mmol) in acetone (200 mL) was added iodoethane (2.58 mL, 32 mmol) dropwise over 1 min After addition, the resulting mixture was stirred at rt for 24 h. The resulting precipitate was filtered off and rinsed with EtOAc (2×30 mL). The filtrate was concentrated to dryness to give a white solid which was treated with $H_2O$ (60 mL). Extraction with EtOAc (100 mL+60 mL) followed by concentration gave the crude title compound as a white solid. Trituration with MeOH (40 mL) gave first crop as a white solid (1.30 g). The mother liquor was concentrated to dryness and the trituration was repeated with MeOH, hexane and $H_2O$ to give additional 3.60 g as white solid. Total: 4.90 g (91%). $^1H$ NMR (400 MHz, DMSO-$d_6$) δ 7.20 (d, J=7.6 Hz, 2H), 6.87 (d, J=7.6 Hz, 2H), 3.13-3.03 (m, 4H), 2.49-2.40 (m, 4H, partially overlapping with DMSO signal), 2.34 (q, J=6.8 Hz, 2H), 1.01 (t, J=6.8 Hz, 3H); MS ESI 269.0 [M+H]$^+$, calcd. for $[C_{12}H_{17}BrN_2+H]^+$ 269.1.

Synthesis of 1-(4-bromophenyl)-4-isopropylpiperazine

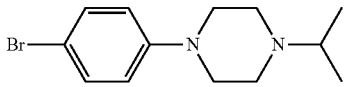

To a mixture of 1-(4-bromophenyl)piperazine (1.20 g, 5 mmol) and acetone (1.47 mL, 20 mmol) in DCE/THF (45 mL/15 mL) was added NaBH(OAc)$_3$ (1.38 g, 6.5 mmol), followed by AcOH (0.5 mL). After addition, the resulting mixture was stirred O/N at rt. The reaction as quenched with NaHCO$_3$ (10 mL) and H$_2$O (10 mL), and was extracted with EtOAc (60 mL×2). The solvents were removed in vacuo to give the crude title compound as a white solid (1.40 g, 99%). $^1$H NMR (400 MHz, DMSO-d$_6$) δ 7.45 (d, J=7.2 Hz, 2H), 7.21 (d, J=7.2 Hz, 2H), 3.64-3.55 (m, 2H), 3.44 (s, 2H), 2.68 (d, J=11.6 Hz, 2H), 1.75 (t, J=11.0 Hz, 2H), 1.54 (d, J=6.0 Hz, 6H); MS ESI 282.9 [M+H]$^+$, calcd. for [C$_{13}$H$_{19}$BrN$_2$+H]$^+$ 283.1.

Synthesis of 4-((4-bromothiophen-2-yl)methyl)morpholine

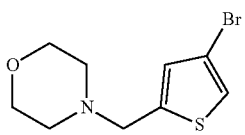 [SMILES: Brc1csc(CN2CCOCC2)c1]

To a mixture of 4-bromothiophene-2-carbaldehyde (1.91 g, 10 mmol) morpholine (0.96 mL, 11 mmol) in DCE (30 mL) was added NaBH(OAc)$_3$ (2.65 g, 12.5 mmol), followed by AcOH (0.5 mL). After addition, the resulting mixture was stirred O/N at rt. Aqueous workup followed by flash chromatography (gradient: MeOH/DCM 0 to 10%) afforded the title compound as a white crystalline solid (1.58 g, 50%). $^1$H NMR (400 MHz, CDCl$_3$) δ 7.16 (s, 1H), 6.87 (s, 1H), 3.78-3.72 (m, 4H), 3.68 (s, 2H), 2.55-2.45 (m, 4H); MS ESI 261.8 [M+H]$^+$, calcd. for [C$_9$H$_{12}$BrNOS+H]$^+$ 262.0.

Synthesis of 1-(4-bromothiophen-2-yl)-N,N-dimethylmethanamine

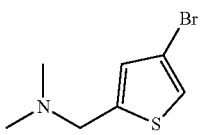

To a mixture of 4-bromothiophene-2-carbaldehyde (1.91 g, 10 mmol) and dimethylamine (2 M in THF, 7.5 mL, 15 mmol) in DCE (30 mL) was added NaBH(OAc)$_3$ (2.65 g, 12.5 mmol), followed by AcOH (0.2 mL). After addition, the resulting mixture was stirred O/N at rt. The reaction was quenched with sat. NaHCO$_3$ (20 mL) and brine, and was then extracted with EtOAc (100 mL+30 mL). The solvents were removed in vacuo to afford the crude title compound as a light yellow liquid (1.70 g, 77%). $^1$H NMR (400 MHz, CDCl$_3$) δ 7.15 (s, 1H), 6.84 (s, 1H), 3.60 (s, 2H), 2.29 (s, 6H); MS ESI 219.7 [M+H]$^+$, calcd for [C$_7$H$_{10}$BrNS+H]$^+$ 220.0.

Synthesis of 5-bromo-2-ethylisoindoline-1,3-dione

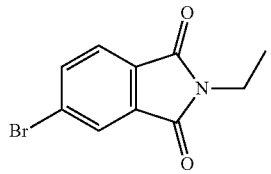

To a solution of 5-bromo-2-ethylisoindoline-1,3-dione (2.26 g, 10 mmol) in DMF (25 mL) at 0° C. was added 60% NaH (600 mg, 15 mmol). After addition, the resulting mixture was stirred for 10 min at 0° C. before iodoethane (0.97 mL, 12 mmol) was added. After addition, the resulting mixture was stirred for 1 h at 0° C. before quenching with ice, sat. NH$_4$Cl, H$_2$O to a total volume about 100 mL. The precipitate was collected by suction filtration to give the title compound as an off-white flaky solid (2.049 g, 81%). $^1$H NMR (400 MHz, DMSO-d$_6$) δ 8.04 (s, 1H), 8.02 (d, J=8.0 Hz, 1H), 7.78 (d, J=8.0 Hz, 1H), 3.58 (q, J=7.2 Hz, 2H), 1.15 (t, J=7.2 Hz, 3H); MS ESI 253.9 [M+H]$^+$, calcd for [C$_{10}$H$_8$BrNO$_2$+H]$^+$ 254.0.

Synthesis of 4-(4-bromobenzyl)-cis-2,6-dimethylmorpholine

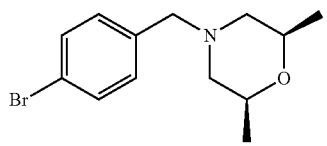 [SMILES: C[C@@H]1CN(Cc2ccc(Br)cc2)C[C@H](C)O1]

To a mixture of 4-bromobenzaldehyde (3.70 g, 20 mmol) and cis-2,6-dimethylmorpholine (2.52 g, 22 mmol) in DCE (100 mL) was added NaBH(OAc)$_3$ (5.30 g, 25 mmol), followed by AcOH (0.5 mL). After addition, the resulting mixture was stirred O/N at rt. The reaction as quenched with sat. NaHCO$_3$ (30 mL) and H$_2$O (30 mL), and was extracted with DCM (30 mL×2). Concentration of the solvents afforded the crude title compound as a pale yellow liquid (6.41 g, quantitative yield). $^1$H NMR (400 MHz, CDCl$_3$) δ 7.45 (d, J=7.2 Hz, 2H), 7.21 (d, J=7.2 Hz, 2H), 3.64-3.55 (m, 2H), 3.44 (s, 2H), 2.68 (d, J=11.6 Hz, 2H), 1.75 (t, J=11.0 Hz, 2H), 1.54 (d, J=6.0 Hz, 6H); MS ESI 284.0 [M+H]$^+$, calcd for [C$_{13}$H$_{18}$BrNO+H]$^+$ 284.1.

Synthesis of 4-(4-bromobenzyl)-cis-2,6-dimethylpiperidine

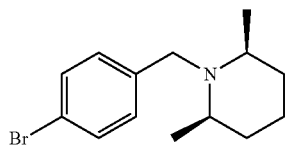

To a solution of 1-bromo-4-(bromomethyl)benzene (5.00 g, 20 mmol) in CH$_2$Cl$_2$ (40 mL) was added cis-2,6-dimethylpiperidine (2.49 g, 22 mmol) dropwise. After addition, the resulting mixture was stirred for 30 min before quenching with sat. NaHCO$_3$ (20 mL) and H$_2$O (20 mL). Extraction with DCM followed by flash chromatography (gradient: MeOH/DCM 0 to 20%) afforded the title compound as a colorless oil which turned orange upon standing (1.17 g, 21%). $^1$H NMR (400 MHz, CDCl$_3$) δ 7.10 (d, J=8.0 Hz, 2H), 7.28 (d, J=8.0 Hz, 2H), 3.73 (s, 2H), 2.52-2.43 (m, 2H), 1.68-1.64 (m, 1H), 1.62-1.55 (m, 2H), 1.36-1.26 (m, 3H), 1.03 (d, J=6.4 Hz, 6H); MS ESI 282.0 [M+H]$^+$, calcd for [C$_{14}$H$_{20}$BrN+H]$^+$ 282.1.

Synthesis of 1-isopentylindolin-2-one

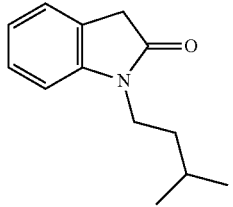

To a solution of isatin (4.41 g, 30 mmol) in DMF (60 mL) at 0° C. was added 60% NaH (1.50 g, 37.5 mmol) portionwise. After addition, the resulting mixture was stirred for 15 min at 0° C. and 1-bromo-3-methylbutane (4.7 mL, 37.5 mmol) was added dropwise over 2 min. The resulting mixture was stirred for 1 h at 0° C. followed by 6 h at rt. The reaction was cooled to 0° C., quenched with sat. NH$_4$Cl, ice, H$_2$O, extracted with EtOAc (200 mL×2), dried over Na$_2$SO$_4$ and concentrated to give crude 1-isopentylisatin as a dark orange red liquid which was used without further purification. $^1$H NMR (400 MHz, DMSO-d$_6$) δ 7.66 (t, J=7.6 Hz, 1H), 7.54 (d, J=7.2 Hz, 1H), 7.15 (d, J=8.8 Hz, 1H, partially overlapping with the peak at 7.12 ppm), 7.12 (t, J=7.6 Hz, 1H, partially overlapping with the peak at 7.15 ppm), 3.66 (t, J=7.6 Hz, 2H), 1.67-1.57 (m, 1H), 1.48 (q, J=7.2 Hz, 1H), 0.92 (d, J=6.4 Hz, 6H); MS ESI 217.9 [M+H]$^+$, calcd for [C$_{13}$H$_{15}$NO$_2$+H]$^+$ 218.1.

The above 1-isopentylisatin was redissolved in DMSO (15 mL). N$_2$H$_4$-xH$_2$O (3 mL) was added dropwise over 10 min After addition, the reaction mixture was stirred for 5 min at rt, then 2 h at 140° C. (oil temp.) before cooling to rt. Ice/H$_2$O (30 mL) was added, followed by 6 M HCl (10 mL, 60 mmol) and the resulting mixture was stirred for 30 min at rt. Additional ice/H$_2$O (50 mL) was added and the mixture was extracted with EtOAc (3×50 mL). The crude product was purified by flash chromatography (gradient: EtOAc/hex 0 to 20%) to afford the title compound as an orange red liquid (4.30 g, 71% over two steps). $^1$H NMR (400 MHz, DMSO-d$_6$) δ 7.27-7.22 (m, 2H), 7.02-6.95 (m, 2H), 3.65 (t, J=7.4 Hz, 2H), 3.33 (s, 2H), 1.60-1.52 (m, 1H), 1.44 (q, J=7.2 Hz, 2H), 0.92 (d, J=6.4 Hz, 6H); MS ESI 203.9 [M+H]$^+$, calcd for [C$_{13}$H$_{17}$NO+H]$^+$ 204.1.

Synthesis of 1-(2-methoxyethyl)indolin-2-one

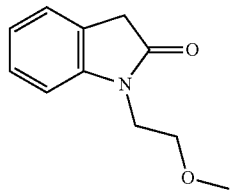

To a solution of isatin (2.94 g, 20 mmol) in DMF (40 mL) at 0° C. was added 60% NaH (1.00 g, 25 mmol) portionwise. After addition, the resulting mixture was stirred for 15 min at 0° C. and 1-bromo-2-methoxyethane (2.35 mL, 25 mmol) was added dropwise over 2 min. The resulting mixture was stirred for 10 min at 0° C., warmed to rt and stirred O/N. The reaction was then cooled to 0° C., quenched with sat. NH$_4$Cl, ice, H$_2$O, extracted with EtOAc (150 mL×2), dried over Na$_2$SO$_4$ and concentrated to give a dark orange red liquid which was redissolved in DMSO (10 mL). N$_2$H$_4$-xH$_2$O (2 mL) was added dropwise over 7 min. After addition, the reaction mixture was stirred for 5 min at rt, then 2 h at 140° C. (oil temp.) before cooling to rt. Ice/H$_2$O (20 mL) was added, followed by 6 M HCl (7 mL, 42 mmol) and the resulting mixture was stirred for 30 min at rt. Additional ice/H$_2$O (40 mL) was added and the mixture was extracted with EtOAc (50 mL×3). The crude product was purified by flash chromatography (gradient: EtOAc/hex 0 to 40%) to afford the title compound as an orange liquid (2.32 g, 61% over 2 steps). $^1$H NMR (400 MHz, DMSO-d$_6$) δ 7.26-7.20 (m, 2H), 7.03 (d, J=8.0 Hz, 1H), 6.98 (t, J=7.4 Hz, 1H), 3.82 (t, J=5.6 Hz, 2H), 3.55 (s, 2H), 3.52 (t, J=5.8 Hz, 2H), 3.22 (s, 3H); MS ESI 191.8 [M+H]$^+$, calcd for [C$_{11}$H$_{13}$NO$_2$+H]$^+$ 192.1.

Synthesis of 2-(2-oxoindolin-1-yl)acetamide

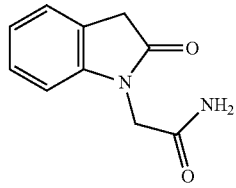 [SMILES: NC(=O)CN1C(=O)Cc2ccccc21]

To a mixture of isatin (5.0 g, 35 mmol), K$_2$CO$_3$ (5.5 g, 40 mmol) and chloroacetamide (3.74 g, 40 mmol) in a 100 mL of flask was added DMF (25 mL). The resulting mixture was heated at 90° C. (oil temp.) for 2 h. After cooling to rt, it was poured onto ice/H$_2$O (200 mL) and the resulting precipitate was collected by suction filtration to give 2-(2,3-dioxoindolin-1-yl)acetamide (4.32 g) after drying. $^1$H NMR (400 MHz, DMSO-d$_6$) δ 7.72 (s, 1H), 7.65 (t, J=7.6 Hz, 1H), 7.58 (d, J=7.2 Hz, 1H), 7.30 (s, 1H), 7.14 (t, J=7.4 Hz, 1H), 7.02 (d, J=8.0 Hz, 1H), 4.25 (s, 2H).

The above 2-(2,3-dioxoindolin-1-yl)acetamide (4.32 g) was redissolved in DMSO (20 mL) and N$_2$H$_4$-xH$_2$O (2.5 mL) was added dropwise over 10 min After addition, the resulting mixture was stirred for 5 min at rt, then 2 h at 140° C. before cooling to rt. The reaction was quenched with ice (20 mL) and 6 M HCl (8 mL), then stirred for 30 min at rt. Suction filtration gave crude title compound (2.92 g) as a light yellow solid. The product was suspended in EtOAc (120 mL) and H$_2$O (60 mL) was added, followed by 2 M HCl (30 mL). The mixture was separated and suction filtration of aqueous layer afforded the title compound as a light beige solid (1.78 g, 27% over 2 steps) after drying. $^1$H NMR (400 MHz, DMSO-d$_6$) δ 7.59 (s, 1H, NH), 7.28-7.08 (m, 4H), 6.99 (t, J=7.4 Hz, 1H), 6.81 (d, J=8.0 Hz, 1H), 4.22 (s, 2H), 3.56 (s, 2H); MS ESI 191.0 [M+H]$^+$, calcd for [C$_{10}$H$_{10}$N$_2$O$_2$+H]$^+$ 191.1; MS ESI 174.0 [M−NH$_2$]$^+$, calcd for [C$_{10}$H$_{10}$N$_2$O$_2$—NH$_2$]$^+$ 174.1; MS ESI 146.0 [M−CONH$_2$]$^+$, calcd for [C$_{10}$H$_{10}$N$_2$O$_2$—CONH$_2$]$^+$ 146.1.

Synthesis of (1R*,2S*)-2-(3-vinyl-1H-indazol-6-yl)spiro[cyclopropane-1,3'-indolin]-2'-one

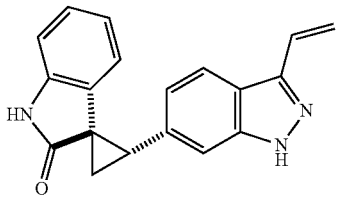

To a mixture of (1R*,2S*)-2-(3-iodo-1H-indazol-6-yl)-spiro [cyclopropane-1,3'-indolin]-2'-one (802 mg, 2 mmol) and 4,4,5,5-tetramethyl-2-vinyl-1,3,2-dioxaborolane (462 mg, 3 mmol) in a 20 mL microwave vial was added PhCH$_3$/EtOH (8 mL/4 mL), followed by 1 M Na$_2$CO$_3$ (3 mL, 3 mmol) and Ph(PPh$_3$)$_4$ (46 mg, 0.04 mmol, 2 mol %) was added and the resulting mixture was purged with argon, then microwaved 3 h at 120° C. After aqueous workup, the solution was extracted with EtOAc and was purified by flash chromatography (Hex/EtOAc 1:1) to give the crude title compound as a light yellow foam (512 mg) which was used without further purification. $^1$H NMR (400 MHz, CDCl$_3$) δ 7.74 (d, J=8.4 Hz, 1H), 7.35 (s, 1H), 7.10-6.88 (m, 5H), 6.54 (t, J=7.4 Hz, 1H), 6.06 (d, J=18.0 Hz, 1H), 5.92 (d, J=7.6 Hz, 1H), 5.49 (d, J=7.6 Hz, 1H), 3.46 (d, J=8.2 Hz, 1H), 2.30-2.18 (m, 2H); MS ESI 302.0 [M+H]$^+$, calcd for [C$_{19}$H$_{15}$N$_3$O+H]$^+$ 302.1.

Synthesis of (1R*,2S*)-5'-methoxy-2-(3-vinyl-1H-indazol-6-yl)spiro[cyclopropane-1,3'-indolin]-2'-one

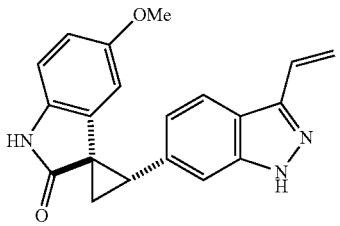

To a mixture of (1R*,2S*)-2-(3-iodo-1H-indazol-6-yl)-5'-methoxyspiro [cyclopropane-1,3'-indolin]-2'-one (1.00 g, 2.32 mmol) and 4,4,5,5-tetramethyl-2-vinyl-1,3,2-dioxaborolane (500 mg, 3.25 mmol) in a 20 mL microwave vial was added PhCH$_3$/EtOH (7 mL/3.5 mL), followed by 1 M Na$_2$CO$_3$ (3 mL, 3 mmol). After stirring for 1 min at rt, Ph(PPh$_3$)$_4$ (50 mg, 0.043 mmol, 1.9 mol %) was added and the resulting mixture was purged with argon, and microwaved 3 h at 120° C. This reaction was repeated twice on the same scale and the resulting mixtures were combined. Aqueous workup gave the crude title compound as a dark orange solid/foam (3.10 g) which was used without further purification. A sample of pure compound can be obtained by flash chromatography (Hex/EtOAc 1:1). $^1$H NMR (400 MHz, CDCl$_3$) δ 7.89 (d, J=8.4 Hz, 1H), 7.45 (s, 1H), 7.01 (dd, J=18.2 Hz, J=11.4 Hz, 1H overlapping with d, J=6.8 Hz, 1H; total 2H), 6.83 (d, J=8.4 Hz, 1H), 6.61 (dd, J=8.4 Hz, J=2.4 Hz, 1H), 6.09 (d, J=18.0 Hz, 1H), 5.56 (d, J=1.6 Hz, 1H), 5.52 (d, J=11.6 Hz, 1H), 3.56 (t, J=7.6 Hz, 1H, partially overlapping with MeOH residue), 3.26 (s, 3H), 2.24 (dd, J=7.8 Hz, J=5.0 Hz, 1H), 2.18 (dd, J=9.2 Hz, J=4.8 Hz, 1H); MS ESI 332.0 [M+H]$^+$, calcd for [C$_{20}$H$_{17}$N$_3$O$_2$+H]$^+$ 332.1.

Synthesis of (1R*,2S*)-5'-ethyl-2-(3-iodo-1H-indazol-6-yl)spiro[cyclopropane-1,3'-indolin]-2'-one

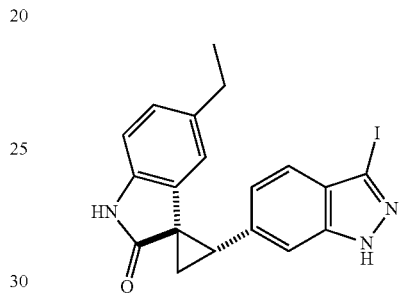

The title compound, as a single diastereomer, (710 g, 33% over 2 steps, triturated from hex/MeOH) was obtained as a light orange solid from 5-ethylindolin-2-one (885 mg, 5.5 mmol) and 3-iodo-1H-indazole-6-carbaldehyde (1.36 g, 5 mmol) using the method for the preparation of (1R*,2S*)-2-(3-vinyl-1H-indazol-6-yl)spiro[cyclopropante-1,3'-indolin]-2'-one. $^1$H NMR (400 MHz, DMSO-d$_6$) δ 13.44 (s, 1H), 10.51 (s, 1H), 7.44 (s, 1H), 7.30 (d, J=8.4 Hz, 1H), 6.99 (d, J=8.8 Hz, 1H), 6.80 (d, J=7.2 Hz 1H), 6.72 (d, J=7.6 Hz, 1H), 5.76 (s, 1H), 3.17 (t, J=7.8 Hz, 1H), 2.29 (dd, J=8.0 Hz, J=4.8 Hz, 1H), 2.18-2.04 (m, 2H), 1.98 (dd, J=8.6 Hz, J=4.8 Hz, 1H), 0.60 (t, J=7.4 Hz, 1H); MS ESI 430.0 [M+H]$^+$, calcd for [C$_{19}$H$_{16}$IN$_3$O+H]$^+$ 430.0.

Synthesis of (1R*,2S*)-2-(3-iodo-1H-indazol-6-yl)-5',6'-dimethoxyspiro[cyclopropane-1,3'-indolin]-2'-one

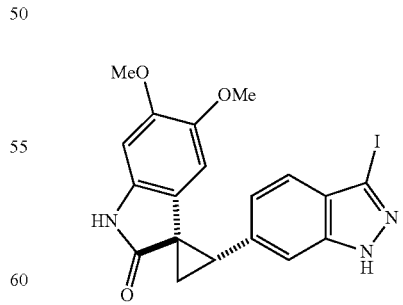

The crude title compound (1.765 g, 77% over 2 steps) was obtained as an orange solid from 5,6-dimethoxyindolin-2-one (1.01 g, 5.25 mmol) and 3-iodo-1H-indazole-6-carbaldehyde (1.36 g, 5 mmol) using the method for the preparation of (1R*,2S*)-2-(3-vinyl-1H-indazol-6-yl)spiro

[cyclopropane-1,3'-indolin]-2'-one. MS ESI 462.1 [M+H]+, calcd for [C19H16IN3O3+H]+ 462.0.

Synthesis of (1R*,2S*)-2-(3-iodo-1H-indazol-6-yl)-5'-methylspiro[cyclopropane-1,3'-indolin]-2'-one

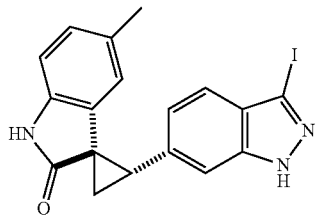

The crude title compound (2.06 g, 99% over 2 steps) was obtained as a yellow solid from 5-methylindolin-2-one (772 mg, 5.25 mmol) and 3-iodo-1H-indazole-6-carbaldehyde (1.36 g, 5 mmol) using the method for the preparation of (1R*,2S*)-2-(3-vinyl-1H-indazol-6-yl)spiro[cyclopropane-1,3'-indolin]-2'-one. NMR indicated a 6:1 mixture of the title compound and the minor diasteromer. $^1$H NMR (400 MHz, DMSO-$d_6$) δ 13.43 (s, 1H), 10.51 (s, 1H), 7.47 (s, 1H), 7.32 (d, J=8.4 Hz, 1H), 7.02 (d, J=8.8 Hz, 1H), 6.81 (d, J=8.4 Hz, 1H), 6.73 (d, J=7.6 Hz, 1H), 5.86 (s, 1H), 3.18 (t, J=8.2 Hz, 1H), 2.30-2.20 (m 1H), 2.00-1.90 (m, 1H), 1.85 (s, 3H); MS ESI 416.1 [M+H]+, calcd for [C18H14IN3O+H]+ 416.0.

Synthesis of (1R*,2S*)-5'-chloro-2-(3-iodo-1H-indazol-6-yl)spiro[cyclopropane-1,3'-indolin]-2'-one

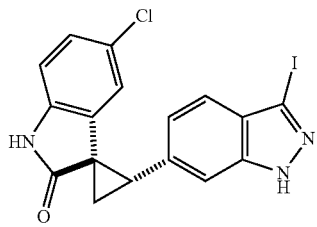

The crude title compound (2.29 g, quantitative yields over 2 steps) was obtained as a light beige solid from 5-chloroindolin-2-one (880 mg, 5.25 mmol) and 3-iodo-1H-indazole-6-carbaldehyde (1.36 g, 5 mmol) using the method for the preparation of (1R*,2S*)-2-(3-vinyl-1H-indazol-6-yl)spiro[cyclopropane-1,3'-indolin]-2'-one. NMR indicated a mixture of the title compound and minor diasteromer. $^1$H NMR (400 MHz, DMSO-$d_6$) δ 13.51 (s, 1H), 10.76 (s, 1H), 7.52 (s, 1H), 7.33 (d, J=8.0 Hz, 1H), 7.04 (t, J=8.8 Hz, 2H), 6.84 (d, J=8.4 Hz, 1H), 6.03 (s, 1H), 3.23 (t, J=8.0 Hz, 1H), 2.06-1.97 (m, 1H); MS ESI 436.2 [M+H]+, calcd for [C17H11ClIN3O+H]+ 436.0.

Synthesis of (1R*,2S*)-2-(3-iodo-1H-indazol-6-yl) spiro[cyclopropane-1,3'-pyrrolo[2,3-b]pyridin]-2' (1'H)-one

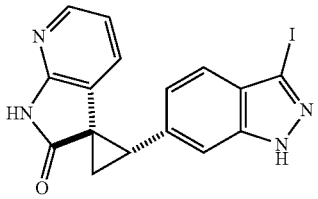

The crude title compound (1.075 g, quantitative yields over 2 steps) was obtained as a light beige solid from 1H-pyrrolo[2,3-b]pyridin-2(3H)-one (352 mg, 2.625 mmol) and 3-iodo-1H-indazole-6-carbaldehyde (680 g, 2.5 mmol) using the method for the preparation of (1R*,2S*)-2-(3-vinyl-1H-indazol-6-yl)spiro[cyclopropane-1,3'-indolin]-2'-one. $^1$H NMR (400 MHz, DMSO-$d_6$) δ 13.50 (s, 1H), 11.23 (s, 1H), 7.90 (d, J=8.4 Hz, 1H), 7.51 (s, 1H), 7.31 (d, J=8.0 Hz, 1H), 7.03 (d, J=8.4 Hz, 1H), 6.58 (t, J=6.2 Hz, 1H), 6.27 (d, J=7.2 Hz, 1H), 3.28 (t, J=8.6 Hz, 1H), 2.50-2.40 (m, 1H), 2.08-2.03 (m, 1H); MS ESI 403.0 [M+H]+, calcd for [C16H11IN4O+H]+ 403.0.

Synthesis of (1R*,2S*)-2-(3-iodo-1H-indazol-6-yl)-5'-(trifluoromethyl)spiro[cyclopropane-1,3'-indolin]-2'-one

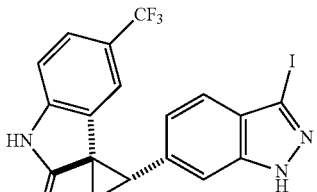

The crude title compound (1.234 g, quantitative yields over 2 steps) was obtained as a light beige solid from 5-(trifluoromethyl)indolin-2-one (528 mg, 2.625 mmol) and 3-iodo-1H-indazole-6-carbaldehyde (680 g, 2.5 mmol) using the method (cyproanation: 65° C., 30 min) for the preparation of (1R*,2S*)-2-(3-vinyl-1H-indazol-6-yl)spiro[cyclopropane-1,3'-indolin]-2'-one. NMR indicated a 8:1 mixture of the title compound and minor diasteromer. $^1$H NMR (400 MHz, DMSO-$d_6$) δ 13.49 (s, 1H), 11.02 (s, 1H), 7.53 (s, 1H), 7.37 (d, J=8.0 Hz, 1H), 7.10 (d, J=8.8 Hz, 1H), 7.01 (t, J=8.2 Hz, 2H), 6.22 (s, 1H), 3.29 (t, J=8.8 Hz, 1H, partially overlapping with H2O peak), 2.63-2.57 (m, 1H), 2.30-2.25 (m, 1H); MS ESI 470.1 [M+H]+, calcd for [C18H11F3IN3O+H]+ 470.0.

Synthesis of 2-((1R*,2S*)-2-(3-iodo-1H-indazol-6-yl)-2'-oxospiro[cyclopropane-1,3'-indoline]-1'-yl)acetamide

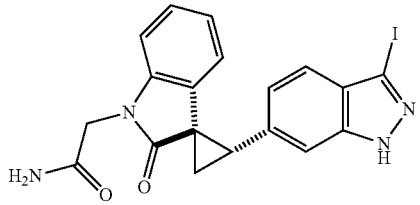

To a mixture of 2-(2-oxoindolin-1-yl)acetamide (380 mg, 2 mmol) and 3-iodo-1H-indazole-6-carbaldehyde (544 mg, 2 mmol) in MeOH (20 mL) was added piperidine (0.04 mL). The resulting mixture was heated at 75° C. (oil temp.) for 90 min. After cooling to rt, the resulting precipitate was collected by suction filtration to give a yellow solid (850 mg).

To a mixture of trimethylsulfoxonium iodide (880 mg, 4 mmol) and 60% NaH (486 mg, 12 mmol) in a 100 mL of flask was added DMF (5 mL). The resulting mixture was stirred for 5 min at rt, before a suspension of the above yellow solid (850 mg) in DMF (20 mL) was added via a pipet. After addition, the resulting pink mixture was stirred for 2 h at rt and cooled to 0° C. The reaction was quenched with ice/H$_2$O, sat. NH$_4$Cl (15 mL), followed by ice/H$_2$O to a total volume of 100 mL. After stirring for 2 min at rt, the resulting precipitate was collected by suction filtration to give the crude title compound as a pink solid (805 mg, 88% over 2 steps) after drying. $^1$H NMR (400 MHz, DMSO-d$_6$) δ 13.50 (s, 1H), 7.94 (s, 1H), 7.70 (s, 1H, NH), 7.49 (s, 1H), 7.31 (d, J=8.4 Hz, 1H), 7.26 (s, 1H), 7.06 (t, J=7.6 Hz, 1H, partially overlapping with the peak at 7.03 ppm), 7.03 (d, J=8.8 Hz, 1H, partially overlapping with the peak at 7.06 ppm), 6.86 (d, J=7.6 Hz, 1H), 6.60 (t, J=7.6 Hz, 1H), 4.38 (t, J=18.4 Hz, 2H), 3.26 (t, J=8.8 Hz, 1H), 2.40-2.35 (m, 1H), 2.10-2.04 (m, 1H); MS ESI 459.1 [M+H]$^+$, calcd for [C$_{19}$H$_{15}$IN$_4$O$_2$+H]$^+$ 459.0.

Synthesis of (1R*,2S*)-2-(3-iodo-1H-indazol-6-yl)-1'-isopentylspiro[cyclopropane-1,3'-indolin]-2'-one

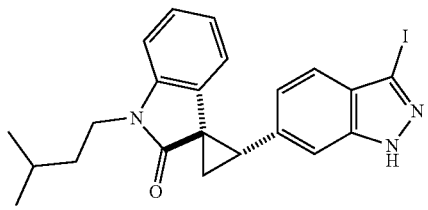

To a mixture of 1-isopentylindolin-2-one (406 mg, 2 mmol) and 3-iodo-1H-indazole-6-carbaldehyde (544 mg, 2 mmol) in MeOH (12 mL) was added piperidine (0.04 mL). The resulting mixture was heated at 70° C. (oil temp.) for 3 h. After cooling to rt, the precipitate was collected by suction filtration to give a yellow solid.

To a mixture of trimethylsulfoxonium iodide (880 mg, 4 mmol) and 60% NaH (400 mg, 10 mmol) in a 100 mL of flask was added DMF (6 mL). The resulting mixture was stirred for 5 min at rt, before a solution of the above yellow solid in DMF (10 mL) was added. After addition, the resulting pink mixture was stirred for 10 min at rt and cooled to 0° C. The reaction was quenched with sat. NH$_4$Cl (15 mL), followed by ice/H$_2$O to a total volume of 80 mL. Suction filtration gave the crude title compound as a light beige solid (770 mg, 82% over 2 steps) after drying. $^1$H NMR (400 MHz, DMSO-d$_6$) δ 13.45 (s, 1H), 7.47 (s, 1H), 7.30 (d, J=8.5 Hz, 1H), 7.10 (t, J=7.6 Hz, 1H), 7.20 (d, J=7.8 Hz, 1H), 6.97 (d, J=8.4 Hz, 1H), 6.60 (t, J=7.4 Hz, 1H), 6.02 (d, J=7.3 Hz, 1H), 3.79 (t, J=7.2 Hz, 2H), 3.24 (t, J=8.1 Hz, 1H), 2.36 (t, J=6.2 Hz, 1H), 2.04 (dd, J=9.0 Hz, J=4.8 Hz, 1H), 1.66-1.45 (m, 3H), 0.94 (d, J=6.4 Hz, 6H); MS ESI 472.2 [M+H]$^+$, calcd for [C$_{22}$H$_{22}$IN$_3$O+H]$^+$ 472.1.

Synthesis of (1R,2S)-2-(3-iodo-1H-indazol-6-yl)-1'-(2-methoxyethyl)spiro[cyclopropane-1,3'-indolin]-2'-one

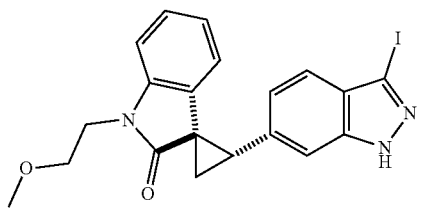

The crude title compound (750 mg, 82% over 2 steps) was obtained as a light beige solid from 1-(2-methoxyethyl)indolin-2-one (382 mg, 2 mmol) and 3-iodo-1H-indazole-6-carbaldehyde (544 mg, 2 mmol) using the method for the preparation of (1R*,2S*)-2-(3-vinyl-1H-indazol-6-yl)spiro[cyclopropane-1,3'-indolin]-2'-one. NMR indicated a 6:1 mixture of the title compound and minor diastereomer. $^1$H NMR (400 MHz, DMSO-d$_6$) δ 13.48 (s, 1H), 7.47 (s, 1H), 7.30 (d, J=7.8 Hz, 1H), 7.10-7.05 (m, 2H), 6.98 (d, J=8.3 Hz, 1H), 6.64-6.56 (m, 1H), 6.01 (d, J=7.3 Hz, 1H), 3.98-3.92 (m, 2H), 3.63-3.57 (m, 2H), 3.25 (s, 3H and t, J=8.6 Hz, 1H overlapping; total 4H), 2.37 (t, J=6.1 Hz, 1H), 2.05 (dd, J=9.0 Hz, J=5.0 Hz, 1H); MS ESI 460.1 [M+H]$^+$, calcd for [C$_{20}$H$_{18}$IN$_3$O$_2$+H]$^+$ 460.0.

Synthesis of 1-cyclopentyl-4-(4-(4,4,5,5-tetramethyl-1,3,2-dioxaborolan-2-yl)phenyl)piperazine

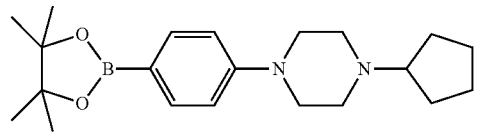 [SMILES: CC1(C)OB(c2ccc(N3CCN(C4CCCC4)CC3)cc2)OC1(C)C]

To a mixture of 1-cyclopentyl-4-(4-iodophenyl)piperazine (712 mg, 2 mmol), bis(pinacolato)diborane (559 mg, 2.2 mmol) and KOAc (588 mg, 6 mmol) in a 20 mL microwave vial was added DMSO (12 mL), followed by Pd(dppf)Cl$_2$—CH$_2$Cl$_2$ (32.7 mg, 0.04 mmol). The resulting mixture was purged with argon, and then microwaved 2 h at 85° C. After cooling to rt, the mixture was diluted with H$_2$O (60 mL) and extracted with EtOAc (30 mL). The combined extracts were washed with H$_2$O, brine, dried over Na$_2$SO$_4$ and purified by flash chromatography (gradient: MeOH/DCM 0 to 10%) to afford the title compound as a beige solid (373 mg, 52%). $^1$H NMR (400 MHz, CDCl$_3$) δ 7.66 (d, J=8.0 Hz, 2H), 6.82 (d, J=8.4 Hz, 2H), 3.26-3.20 (m, 4H), 2.65-2.55 (m, 4H), 1.87-1.77 (m, 2H), 1.72-1.60 (m, 2H), 1.56-1.34 (m, 4H), 1.26 (s, 12H); MS ESI 357.2 [M+H]$^+$, calcd for [C$_{21}$H$_{33}$BN$_2$O$_2$H]$^+$ 357.3.

Synthesis of 2-(4-(4-(4,4,5,5-tetramethyl-1,3,2-dioxaborolan-2-yl)phenyl)piperazin-1-yl)ethanol

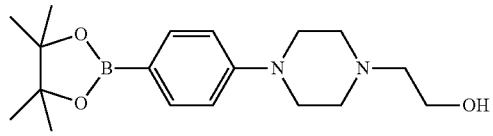 [SMILES: CC1(C)OB(c2ccc(N3CCN(CCO)CC3)cc2)OC1(C)C]

The title compound (189 mg, 31%) was obtained as a brown solid from 2-(4-(4-iodophenyl)piperazin-1-yl)ethanol (602 mg, 1.81 mmol) using the method for the preparation of 1-cyclopentyl-4-(4-(4,4,5,5-tetramethyl-1,3,2-dioxaborolan-2-yl)phenyl) piperazine. $^1$H NMR (400 MHz, CDCl$_3$) δ 7.64 (d, J=8.0 Hz, 2H), 6.81 (d, J=8.4 Hz, 2H), 3.64-3.57 (m, 2H), 3.20 (t, J=4.4 Hz, 4H), 2.60-2.56 (m, 4H), 2.52 (t, J=5.6 Hz, 2H), 1.26 (s, 12H); MS ESI 333.2 [M+H]$^+$, calcd for [C$_{18}$H$_{29}$BN$_2$O$_3$+H]$^+$ 333.2.

Synthesis of 1-cyclohexyl-4-(4-(4,4,5,5-tetramethyl-1,3,2-dioxaborolan-2-yl)phenyl)piperazine

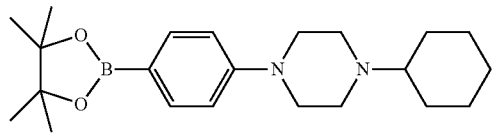 [SMILES: CC1(C)OB(c2ccc(N3CCN(C4CCCCC4)CC3)cc2)OC1(C)C]

The title compound (431 mg, 58%) was obtained as a beige solid from 1-cyclohexyl-4-(4-iodophenyl)piperazine (740 mg, 2 mmol) using the method for the preparation of 1-cyclopentyl-4-(4-(4,4,5,5-tetramethyl-1,3,2-dioxaborolan-2-yl)phenyl) piperazine. $^1$H NMR (400 MHz, CDCl$_3$) δ 7.66 (d, J=8.0 Hz, 2H), 6.83 (d, J=8.0 Hz, 2H), 3.23 (t, J=4.4 Hz, 4H), 2.68 (t, J=4.4 Hz, 4H), 2.32-2.23 (m, 1H), 1.92-1.72 (m, 4H), 1.63-1.55 (m, 1H), 1.27 (s, 12H), 1.20-1.00 (m, 5H); MS ESI 314.2 [M+H]$^+$, calcd for [C$_{18}$H$_{27}$BN$_2$O$_2$+H]$^+$ 314.2; MS ESI 371.0 [M+H]$^+$, calcd for [C$_{22}$H$_{35}$BN$_2$O$_2$+H]$^+$ 371.3.

Synthesis of (E)-N,N-dimethyl-1-(4-(2-(4,4,5,5-tetramethyl-1,3,2-dioxaborolan-2-yl)vinyl)phenyl)methanamine

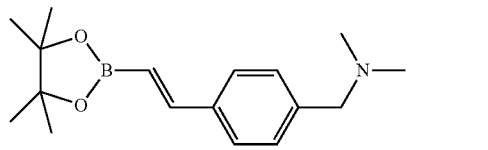

Glacial acetic acid (3 drops) was added to a mixture of 4-ethynylbenzaldehyde (250.7 mg, 1.93 mmol), dimethylamine (2M in THF, 1.5 mL, 3.0 mmol) and NaBH(OAc)$_3$ (617 mg, 2.91 mmol) in DCE (6.5 mL). The resulting mixture was stirred for 2.5 h at rt. The reaction was quenched with saturated aqueous NaHCO$_3$ (~40 mL). The product was extracted into CH$_2$Cl$_2$ (100 mL, then 2×50 mL), and the combined organic layer was washed with brine (25 mL), dried (Na$_2$SO$_4$) and evaporated in vacuo. Purification on Biotage Isolera (silica, 0-3% 2M NH$_3$-methanol/CH$_2$Cl$_2$) gave 1-(4-ethynylphenyl)-N,N-dimethylmethanamine (280.1 mg, 92%). $^1$H NMR (400 MHz, CDCl$_3$) δ 7.46 (d, J=8 Hz, 2H), 7.28 (d, J=8 Hz, 2H), 3.42 (s, 2H), 3.07 (s, 1H), 2.24 (s, 6H).

4,4,5,5-Tetramethyl-1,3,2-dioxaborolane (1.20 mL, 8.23 mmol) was added to an argon-purged solution of 1-(4-ethynylphenyl)-N,N-dimethylmethanamine (262 mg, 1.65 mmol) and HRuCl(CO)(PPh$_3$)$_3$ (104.1 mg, 0.11 mmol) in toluene (9.0 mL). The resulting mixture was heated at 50° C. for 12 h. The product was extracted into Et$_2$O (250 mL), and the organic layer was washed sequentially with water (3×20 mL) and brine (20 mL), dried (Na$_2$SO$_4$) and evaporated in vacuo. Purification by column chromatography (silica gel, 50-100% CH$_2$Cl$_2$ in Et$_2$O) gave (E)-N,N-dimethyl-1-(4-(2-(4,4,5,5-tetramethyl-1,3,2-dioxaborolan-2-yl)vinyl)phenyl)methanamine (402 mg, containing 20% pinacol impurity by $^1$H NMR, 68% yield). $^1$H NMR (400 MHz, CDCl$_3$) δ 7.46 (d, J=8 Hz, 2H), 7.4 (d, 1H), 7.28 (d, 2H), 6.16 (d, 1H), 3.42 (s, 2H), 2.24 (s, 6H), 1.32 (s, 12H); MS ESI 288.0 [M+H]$^+$, calcd for [C$_{17}$H$_{26}$BNO$_2$+H]$^+$ 288.2.

Synthesis of ((E)-1-(4-(2-(4,4,5,5-tetramethyl-1,3,2-dioxaborolan-2-yl)vinyl)benzyl)pyrrolidine

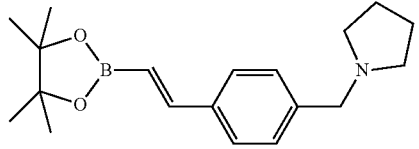 [SMILES: CC1(C)OB(/C=C/c2ccc(CN3CCCC3)cc2)OC1(C)C]

Glacial acetic acid (0.2 mL) was added to a mixture of 4-ethynylbenzaldehyde (1 g, 7.5 mmol), pyrrolidine (1.2 mL, 15 mmol) and NaBH(OAc)$_3$ (2.5 g, 11.5 mmol) in DCE (35 mL). The resulting mixture was stirred for 2 h at rt. The reaction was quenched with saturated aqueous NaHCO$_3$ (50 mL). The product was extracted into CH$_2$Cl$_2$ (2×100 mL), and the combined organic layer was washed with brine (25 mL), dried (MgSO$_4$) and evaporated in vacuo to give 1-(4-ethynylphenyl)pyrrolidine in quantitative yield. $^1$H NMR (CDCl$_3$) δ: 7.45 (d, J=7.8 Hz, 2H), 7.30 (d, J=8.3 Hz, 2H), 3.62 (s, 2H), 3.06 (s, 1H), 2.51 (bs, 4H), 1.80 (bs, 4H).

To a solution of 4,4,5,5-Tetramethyl-1,3,2-dioxaborolane (1.9 g, 15 mmol) in toluene (20 mL) was added 1-(4-ethynylphenyl)pyrrolidine (1 g, 5 mmol) and HRuCl(CO)(PPh$_3$)$_3$ (120 mg, 0.11 mmol) under argon. The resulting mixture was heated at 50° C. for 4 h. The product was extracted into EtOAc (250 mL), and the organic layer was washed sequentially with water (3×20 mL) and brine (20 mL), dried (MgSO$_4$) and evaporated in vacuo. Purification by column chromatography (silica gel, 0-20% MeOH/EtOAc) gave the title compound (1.2 g, 77%). $^1$H NMR (400 MHz, CDCl$_3$) δ 7.45 (d, J=7.8 Hz, 2H), 7.39 (d, J=18.6 Hz, 1H), 7.33-7.29 (m, 2H), 6.15 (d, J=18.6 Hz, 1H), 3.61 (s, 2H), 2.51 (bs, 4H), 1.79 (bs, 4H), 1.32 (s, 12H).

Synthesis of (E)-4-(4-(2-(4,4,5,5-tetramethyl-1,3,2-dioxaborolan-2-yl)vinyl)benzyl)morpholine

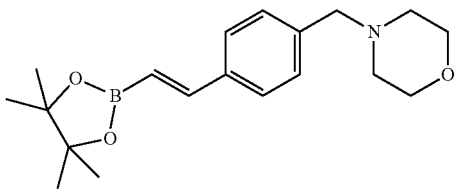 [SMILES: CC1(C)OB(/C=C/c2ccc(CN3CCOCC3)cc2)OC1(C)C]

The title compound (4.35 g, 71%) was obtained as a white to yellow solid from 4-(4-bromobenzyl)morpholine (4.18 g, 16.3 mmol) and 4,4,5,5-tetramethyl-2-vinyl-1,3,2-dioxaborolane (3 mL, 17.7 mmol, 1.1 eq.) using the method for the preparation of Example A51A (PhCH$_3$=30 mL, 1 mol % Pd(P$^t$Bu$_3$)$_2$, 80° C., 1 h). $^1$H NMR (400 MHz, CDCl$_3$) δ 7.45 (d, J=8.0 Hz, 2H), 7.40 (d, J=18.4 Hz, 1H), 7.31 (d, J=8.0 Hz, 2H), 6.16 (d, J=18.0 Hz, 1H), 3.72 (t, J=4.4 Hz, 4H), 3.50 (s, 2H), 2.47-2.42 (m, 4H), 1.32 (s, 12H); MS ESI 330.1 [M+H]$^+$, calcd for [C$_{19}$H$_{28}$BNO$_3$+H]$^+$ 330.2.

Synthesis of (E)-4-(2-(4,4,5,5-tetramethyl-1,3,2-dioxaborolan-2-yl)vinyl)benzaldehyde

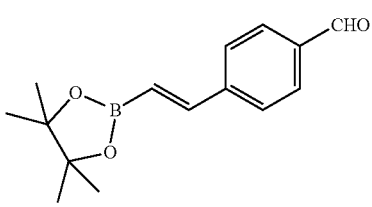 [SMILES: CC1(C)OB(/C=C/c2ccc(C=O)cc2)OC1(C)C]

The title compound (498 mg, 71%) was obtained as a light yellow solid from 4-bromobenzaldehyde (500 mg, 2.71 mmol) and 4,4,5,5-tetramethyl-2-vinyl-1,3,2-dioxaborolane (0.5 mL, 2.95 mmol, 1.1 eq.) using the method for the preparation of Example A51A (PhCH$_3$=8 mL, 2 mol % Pd(P$^t$Bu$_3$)$_2$, 80° C., O/N). $^1$H NMR (400 MHz, CDCl$_3$) δ 10.01 (s, 1H), 7.88 (d, J=8.0 Hz, 2H), 7.64 (d, J=8.4 Hz, 2H), 7.43 (d, J=18.4 Hz, 1H), 6.34 (d, J=18.4 Hz, 1H), 1.34 (s, 12H); MS ESI 258.9 [M+H]$^+$, calcd for [C$_{15}$H$_{19}$BO$_3$+H]$^+$ 259.1.

Synthesis of (E)-4-(3-(2-(4,4,5,5-tetramethyl-1,3,2-dioxaborolan-2-yl)vinyl)benzyl)morpholine

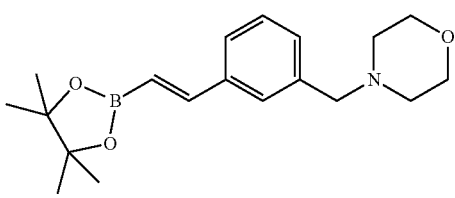 [SMILES: CC1(C)OB(/C=C/c2cccc(CN3CCOCC3)c2)OC1(C)C]

To a mixture of 3-ethynylbenzaldehyde (650 mg, 5 mmol) and morpholine (0.87 mL, 10 mmol) in DCE (15 mL) was added NaBH(OAc)$_3$ (1.325 g, 6.25 mmol), followed by AcOH (0.2 mL). The resulting mixture was stirred for 2 h at rt. Aqueous workup followed by extraction with EtOAc gave crude 4-(3-ethynylbenzyl)morpholine (0.98 g) as a light brown oil. The title compound (1.75 g, quantitative yield over 2 steps) was obtained as a light brown oil using the method (PhCH$_3$=12 mL, 1 mol % HRuCl(CO)(PPh$_3$)$_3$, 50° C., 2 h) for the preparation of Example A42A. $^1$H NMR (400 MHz, CDCl$_3$) δ 7.47 (s, 1H), 7.46-7.37 (m, 2H), 7.35-7.27 (m, 2H), 6.19 (d, J=18.4 Hz, 1H), 3.78-3.68 (m, 4H), 3.52 (s, 2H), 2.52-2.42 (m, 4H), 1.32 (s, 12H); MS ESI 330.1 [M+H]$^+$, calcd for [C$_{19}$H$_{28}$BNO$_3$+H]$^+$ 330.2.

Synthesis of (E)-N,N-dimethyl-1-(3-(2-(4,4,5,5-tetramethyl-1,3,2-dioxaborolan-2-yl)vinyl)phenyl)methanamine

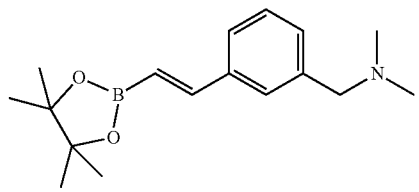

The title compound (1.36 g, quantitative yield over 2 steps) was obtained as a yellow oil from 3-ethynylbenzaldehyde (520 mg, 4 mmol) and Me$_2$NH (2 M in THF, 3 mL, 6 mol) using the method (PhCH$_3$=12 mL, 2 mol % HRuCl(CO)(PPh$_3$)$_3$, 50° C., 2 h) for the preparation of (E)-4-(3-(2-(4,4,5,5-tetramethyl-1,3,2-dioxaborolan-2-yl)vinyl)benzyl) morpholine. $^1$H NMR (400 MHz, CDCl$_3$) δ 7.47 (s, 1H), 7.45-7.38 (m, 2H), 7.35-7.27 (m, 2H), 6.19 (d, J=18.4 Hz, 1H), 3.68-3.58 (m, 4H), 3.52 (s, 2H), 2.53-2.43 (m, 4H), 1.32 (s, 12H); MS ESI 288.1 [M+H]$^+$, calcd for [C$_{17}$H$_{26}$BNO$_2$+H]$^+$ 288.2.

Synthesis of (E)-4-((4-(2-(4,4,5,5-tetramethyl-1,3,2-dioxaborolan-2-yl)vinyl)thiophen-2-yl)methyl)morpholine

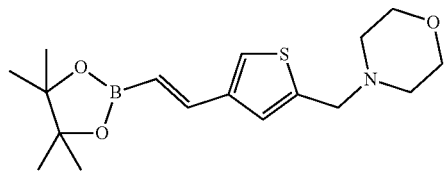 [SMILES: CC1(C)OB(/C=C/c2csc(CN3CCOCC3)c2)OC1(C)C]

The title compound (909 mg, quantitative yield) was obtained as a light red liquid (solidified to orange solid after sitting in fridge) from 4-((4-bromothiophen-2-yl)methyl)morpholine (710 mg, 2.71 mmol) and 4,4,5,5-tetramethyl-2-vinyl-1,3,2-dioxaborolane (0.5 mL, 2.95 mmol, 1.1 eq.) using the method for the preparation of Example A51A (PhCH$_3$=12 mL, 2 mol % Pd(P$^t$Bu$_3$)$_2$, 80° C., 2 h). $^1$H NMR (400 MHz, CDCl$_3$) δ 7.30 (d, J=18.0 Hz, 1H, partially overlapping with CHCl$_3$ residue), 7.22 (s, 1H), 7.12 (s, 1H), 5.88 (d, J=18.0 Hz, 1H), 3.72 (t, J=4.4 Hz, 4H), 3.49 (s, 2H), 3.06-2.97 (m, 4H), 1.30 (s, 12H); MS ESI 336.0 [M+H]$^+$, calcd for [C$_{17}$H$_{26}$BNO$_3$S+H]$^+$ 336.2.

Synthesis of (E)-N,N-dimethyl-1-(4-(2-(4,4,5,5-tetramethyl-1,3,2-dioxaborolan-2-yl)vinyl)thiophen-2-yl)methanamine

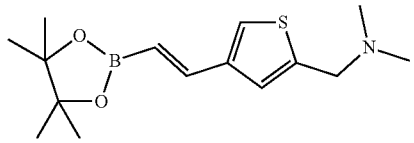

The title compound (338 mg, 46%) was obtained as a light yellow oil from 1-(4-bromothiophen-2-yl)-N,N-dimethylmethanamine (630 mg, 2.85 mmol) and 4,4,5,5-tetramethyl-2-vinyl-1,3,2-dioxaborolane (0.5 mL, 2.95 mmol) using the method for the preparation of Example A51A (PhCH$_3$=12 mL, 2 mol % Pd(P$^t$Bu$_3$)$_2$, 80° C., 1 h). The title compound was used without further purification. $^1$H NMR (400 MHz, CDCl$_3$) δ 7.31 (d, J=18.4 Hz, 1H), 7.23 (s, 1H), 7.12 (s, 1H), 5.89 (d, J=18.4 Hz, 1H), 3.63 (s, 2H), 2.30 (s, 6H), 1.31 (s, 12H); MS ESI 294.0 [M+H]$^+$, calcd for [C$_{15}$H$_{24}$BNO$_2$S+H]$^+$ 294.2.

Synthesis of (E)-1-(4-(2-(4,4,5,5-tetramethyl-1,3,2-dioxaborolan-2-yl)vinyl)phenyl)piperazine

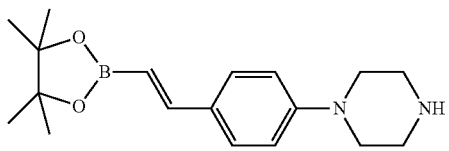

The title compound (267 mg, 68%) was obtained as yellow solid from 1-(4-bromophenyl)piperazine (653 mg, 2.71 mmol) and 4,4,5,5-tetramethyl-2-vinyl-1,3,2-dioxaborolane (0.5 mL, 2.95 mmol, 1.1 eq.) using the method for the preparation of Example A51A (PhCH$_3$=12 mL, 2 mol % Pd(P$^t$Bu$_3$)$_2$, 80° C., 2 h). $^1$H NMR (400 MHz, DMSO-d$_6$) δ 7.41 (d, J=8.0 Hz, 2H), 7.09 (d, J=18.4 Hz, 1H), 6.89 (d, J=8.0 Hz, 2H), 5.86 (d, J=18.8 Hz, 1H), 3.17-3.11 (m, 4H), 2.90-2.84 (m, 4H), 1.22 (s, 12H); MS ESI 315.0 [M+H]$^+$, calcd for [C$_{18}$H$_{27}$BN$_2$O$_2$+H]$^+$ 315.2.

Synthesis of Cis-2,6-dimethyl-4-(4-((E)-2-(4,4,5,5-tetramethyl-1,3,2-dioxaborolan-2-yl)vinyl)benzyl)morpholine

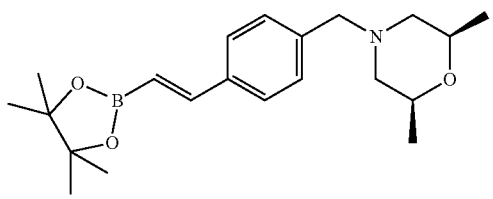

The title compound (2.52 g, 71%) was obtained as white solid from 4-(4-bromobenzyl)-cis-2,6-dimethylmorpholine (2.82 g, 10 mmol) and 4,4,5,5-tetramethyl-2-vinyl-1,3,2-dioxaborolane (1.85 mL, 11 mmol, 1.1 eq.) using the method for the preparation of Example A51A (PhCH$_3$=25 mL, 1 mol % Pd(P$^t$Bu$_3$)$_2$, 80° C., 2 h). $^1$H NMR (400 MHz, CDCl$_3$) δ 7.46 (d, J=8.0 Hz, 2H), 7.40 (d, J=18.4 Hz, 1H), 7.30 (d, J=7.6 Hz, 2H), 6.16 (d, J=18.4 Hz, 1H), 3.75-3.65 (m, 2H), 3.47 (s, 2H), 2.70 (d, J=10.8 Hz, 2H), 1.75 (t, J=10.2 Hz, 2H), 1.32 (s, 12H), 1.14 (d, J=6.4 Hz, 6H); MS ESI 358.2 [M+H]$^+$, calcd for [C$_{21}$H$_{32}$BNO$_3$+H]$^+$ 358.2.

Synthesis of (E)-1-methyl-4-(4-(2-(4,4,5,5-tetramethyl-1,3,2-dioxaborolan-2-yl)vinyl)phenyl)piperazine

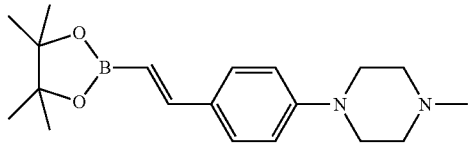

The title compound (674 mg, 76%) was obtained as a light yellow solid from 1-(4-bromophenyl)-4-methylpiperazine (691 mg, 2.71 mmol) and 4,4,5,5-tetramethyl-2-vinyl-1,3,2-dioxaborolane (0.5 mL, 2.95 mmol, 1.1 eq.) using the method for the preparation of Example A51A (PhCH$_3$=10 mL, 2 mol % Pd(P$^t$Bu$_3$)$_2$, 80° C., 2 h). $^1$H NMR (400 MHz, CDCl$_3$) δ 7.41 (d, J=8.4 Hz, 2H), 7.34 (d, J=18.4 Hz, 1H), 6.87 (d, J=8.4 Hz, 2H), 5.99 (d, J=18.4 Hz, 1H), 3.26-3.33 (m, 4H), 2.65-2.59 (m, 4H), 2.40 (s, 3H), 1.31 (s, 12H); MS ESI 329.1 [M+H]$^+$, calcd for [C$_{19}$H$_{29}$BN$_2$O$_2$+H]$^+$ 329.2.

Synthesis of (E)-1-ethyl-4-(4-(2-(4,4,5,5-tetramethyl-1,3,2-dioxaborolan-2-yl)vinyl)phenyl)piperazine

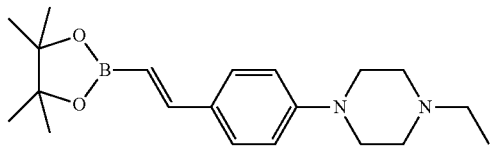 [SMILES: CCN1CCN(c2ccc(/C=C/B3OC(C)(C)C(C)(C)O3)cc2)CC1]

The title compound (601 mg, 65%) was obtained as a light yellow solid from 1-(4-bromophenyl)-4-ethylpiperazine (729 mg, 2.71 mmol) and 4,4,5,5-tetramethyl-2-vinyl-1,3,2-dioxaborolane (0.5 mL, 2.95 mmol, 1.1 eq.) using the method for the preparation of Example A51A (PhCH$_3$=12 mL, 2 mol % Pd(P$^t$Bu$_3$)$_2$, 80° C., 2 h). $^1$H NMR (400 MHz, CDCl$_3$) δ 7.41 (d, J=8.4 Hz, 2H), 7.34 (d, J=18.0 Hz, 1H), 6.88 (d, J=8.4 Hz, 1H), 6.99 (d, J=18.0 Hz, 1H), 3.28 (t, J=4.8 Hz, 4H), 2.61 (t, J=4.8 Hz, 4H), 2.48 (q, J=7.2 Hz, 2H), 1.32 (s, 12H), 1.14 (t, J=7.2 Hz, 3H); MS ESI 343.1 [M+H]$^+$, calcd for [C$_{20}$H$_{31}$BN$_2$O$_2$+H]$^+$ 343.2.

Synthesis of (E)-1-isopropyl-4-(4-(2-(4,4,5,5-tetramethyl-1,3,2-dioxaborolan-2-yl)vinyl)phenyl)piperazine

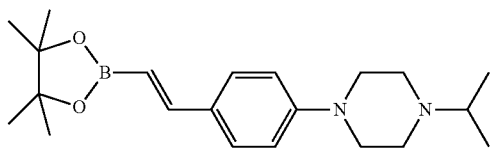 [SMILES: CC(C)N1CCN(c2ccc(/C=C/B3OC(C)(C)C(C)(C)O3)cc2)CC1]

The title compound (504 mg, 52%) was obtained as a light orange solid from 1-(4-iodophenyl)-4-isopropylpiperazine (894 mg, 2.71 mmol) and 4,4,5,5-tetramethyl-2-vinyl-1,3,2-dioxaborolane (0.5 mL, 2.95 mmol, 1.1 eq.) using the method for the preparation of Example A51A (PhCH$_3$=10 mL, 2 mol % Pd(P$^t$Bu$_3$)$_2$, 80° C., O/N). $^1$H NMR (400 MHz, CDCl$_3$) δ 7.41 (d, J=8.4 Hz, 2H), 7.34 (d, J=18.4 Hz, 1H), 6.87 (d, J=8.4 Hz, 2H), 5.98 (d, J=18.4 Hz, 1H), 3.26 (t, J=4.8 Hz, 4H), 2.76-2.66 (m, 5H), 1.32 (s, 12H), 1.10 (d, J=6.4 Hz, 6H); MS ESI 357.2 [M+H]$^+$, calcd for [C$_{21}$H$_{33}$BN$_2$O$_2$+H]$^+$ 357.3.

Synthesis of (E)-2-ethyl-5-(2-(4,4,5,5-tetramethyl-1,3,2-dioxaborolan-2-yl)vinyl)isoindoline

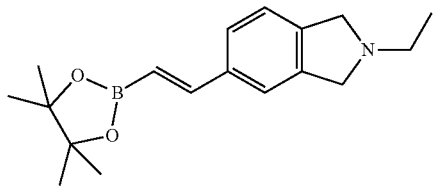 [SMILES: CCN1Cc2ccc(/C=C/B3OC(C)(C)C(C)(C)O3)cc2C1]

To a solution of 5-bromo-2-ethylisoindoline-1,3-dione (1.27 g, 5 mmol) in THF (10 mL) was added LAH (1 M in THF, 12.5 mL, 12.5 mmol) dropwise over 10 min. The reaction was exothermic. After addition, the resulting mixture was stirred for 30 min at rt. LC-MS showed over reduction. The reaction was quenched with sat. NH$_4$Cl, basified with sat. NaHCO$_3$ and the product was extracted with EtOAc. The mixture was purified by flash chromatography (gradient: MeOH/DCM 0 to 15%) to give the crude 5-bromo-2-ethylisoindoline as a light yellow oil (120 mg). The crude material was converted to the title compound (73 mg, impure, 5% over 2 steps) as a light brown oil using the method for the preparation of Example A51A. $^1$H NMR (400 MHz, CDCl$_3$) δ 7.37 (d, J=18.4 Hz, 1H), 7.31 (s, 1H, partially overlapping with the peak at 7.30 ppm), 7.30 (d, J=8.0 Hz, 1H, partially overlapping with the peak at 7.31 ppm), 7.13 (d, J=7.6 Hz, 1H), 6.10 (d, J=18.4 Hz, 1H), 3.88 (s, 4H), 1.29 (s, 12H).

Synthesis of (E)-4-(2-(4-(2-(4,4,5,5-tetramethyl-1,3,2-dioxaborolan-2-yl)vinyl)phenoxy)ethyl)morpholine

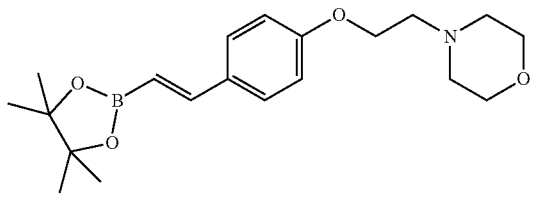 [SMILES: CC1(C)OB(/C=C/c2ccc(OCCN3CCOCC3)cc2)OC1(C)C]

The title compound (902 g, 72%) was obtained as a white solid from 4-(2-(4-bromophenoxy)ethyl)morpholine (1 g, 3.50 mmol) and 4,4,5,5-tetramethyl-2-vinyl-1,3,2-dioxaborolane (0.6 mL, 3.58 mmol, 1.02 eq.) using the method for the preparation of Example A51A (PhCH$_3$=12 mL, 2 mol % Pd(P$^t$Bu$_3$)$_2$, 80° C., O/N). $^1$H NMR (400 MHz, CDCl$_3$) δ 7.28 (d, J=8.0 Hz, 2H), 7.22 (d, J=18.4 Hz, 1H), 6.70 (d, J=8.0 Hz, 2H), 5.88 (d, J=18.4 Hz, 1H), 3.90 (t, J=4.8 Hz, 2H), 3.60-3.50 (m, 4H), 2.59 (t, J=4.8 Hz, 2H), 2.42-2.32 (m, 4H), 1.15 (s, 12H); MS ESI 360.2 [M+H]$^+$, calcd for [C$_{20}$H$_{30}$BNO$_4$+H]$^+$ 360.2.

Synthesis of (E)-3-(2-(4,4,5,5-tetramethyl-1,3,2-dioxaborolan-2-yl)vinyl)pyridine

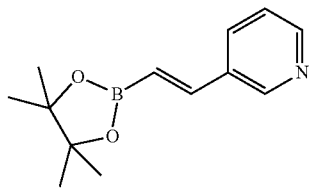 [SMILES: CC1(C)OB(/C=C/c2cccnc2)OC1(C)C]

The title compound (1.18 g, 52%) was obtained as a light yellow solid from 3-brompyridine (856 mg, 5.42 mmol) and 4,4,5,5-tetramethyl-2-vinyl-1,3,2-dioxaborolane (1 mL, 5.9 mmol, 1.1 eq.) using the method for the preparation of Example A51A (PhCH$_3$=10 mL, 1 mol % Pd(P$^t$Bu$_3$)$_2$, 80° C., O/N). $^1$H NMR (400 MHz, CDCl$_3$) δ 8.69 (s, 1H), 8.53 (d, J=4.8 Hz, 1H), 7.81 (d, J=8.8 Hz, 1H), 7.38 (d, J=18.4 Hz, 1H), 7.30-7.27 (m, 1H, partially overlapping with CHCl$_3$ signal), 6.26 (d, J=18.4 Hz, 1H), 1.33 (s, 12H); MS ESI 232.0 [M+H]$^+$, calcd for [C$_{13}$H$_{18}$BNO$_2$+H]$^+$ 232.1.

Synthesis of (E)-2-fluoro-4-(2-(4,4,5,5-tetramethyl-1,3,2-dioxaborolan-2-yl)vinyl)benzaldehyde

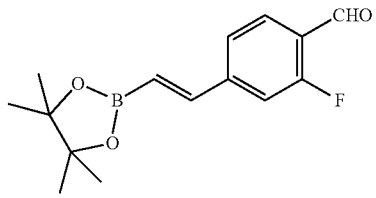 [SMILES: CC1(C)OB(/C=C/c2ccc(C=O)c(F)c2)OC1(C)C]

The title compound (610 mg, 55%) was obtained as yellow solid from 4-bromo-2-fluorobenzaldehyde (812 mg, 4 mmol) and 4,4,5,5-tetramethyl-2-vinyl-1,3,2-dioxaborolane (0.8 mL, 4.8 mmol) using the method for the preparation of Example A51A (PhCH$_3$=10 mL, 1 mol % Pd(P$^t$Bu$_3$)$_2$, 80° C., 1.5 h). $^1$H NMR (400 MHz, CDCl$_3$) δ 10.34 (s, 1H), 7.85 (t, J=7.6 Hz, 1H), 7.36 (d, J=8.8 Hz, 1H, partially overlapping with the peak at 7.35 ppm), 7.35 (d, J=17.2 Hz, 1H, partially overlapping with the peak at 7.36 ppm), 7.26 (d, J=11.2 Hz, 1H, partially overlapping with CDCl$_3$ residue), 6.32 (d, J=18.4 Hz, 1H), 1.33 (s, 12H).

Synthesis of (E)-4-(2-fluoro-4-(2-(4,4,5,5-tetramethyl-1,3,2-dioxaborolan-2-yl)vinyl)benzyl)morpholine

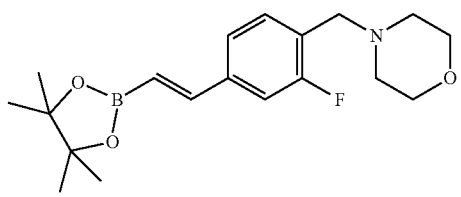 [SMILES: CC1(C)OB(/C=C/c2ccc(CN3CCOCC3)c(F)c2)OC1(C)C]

To a mixture of (E)-2-fluoro-4-(2-(4,4,5,5-tetramethyl-1,3,2-dioxaborolan-2-yl)vinyl)benzaldehyde (0.61 g, 2.2 mmol) and morpholine (0.3 mL) in DCE (20 mL) was added NaBH(OAc)$_3$ (636 mg, 3 mmol), followed by AcOH (0.5 mL). The resulting mixture was stirred for 2 h at rt. The reaction was quenched with sat. NaHCO$_3$ (10 mL), H$_2$O (10 mL), and extracted with EtOAc (2×30 mL). The solvents were removed in vacuo to afford the title compound as a white solid (0.72 g, 94%). $^1$H NMR (400 MHz, CDCl$_3$) δ 7.20-7.12 (m, 2H), 7.04 (d, J=7.6 Hz, 1H), 6.99 (d, J=10.8 Hz, 1H), 5.98 (d, J=18.4 Hz, 1H), 3.55-3.45 (m, 4H), 3.36 (s, 2H), 2.33-2.23 (m, 4H), 1.14 (s, 12H); MS ESI 348.2 [M+H]$^+$, calcd for [C$_{19}$H$_{27}$BFNO$_3$+H]$^+$ 348.2.

Synthesis of Cis-2,6-dimethyl-1-(4-((E)-2-(4,4,5,5-tetramethyl-1,3,2-dioxaborolan-2-yl)vinyl)benzyl) piperidine

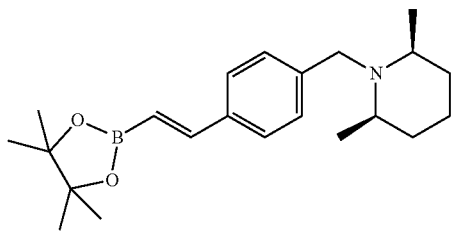 [SMILES: C[C@@H]1CCC[C@H](C)N1Cc1ccc(/C=C/B2OC(C)(C)C(C)(C)O2)cc1]

The title compound (0.45 g, 55%) was obtained as light yellow oil from 4-(4-bromobenzyl)-cis-2,6-dimethylpiperidine (0.60 g, 2.13 mmol) and 4,4,5,5-tetramethyl-2-vinyl-1,3,2-dioxaborolane (0.44 mL, 2.6 mmol) using the method for the preparation of Example A51A (PhCH$_3$=10 mL, 2.5 mol % Pd(P$^t$Bu$_3$)$_2$, 80° C., 75 min). $^1$H NMR (400 MHz, CDCl$_3$) δ 7.43 (d, J=8.0 Hz, 2H, partially overlapping with the peak at 7.40 ppm), 7.40 (d, J=18.8 Hz, 1H, partially overlapping with the peaks at 7.43 ppm and 7.36 ppm), 7.36 (d, J=8.4 Hz, 2H, partially overlapping with the peak at 7.40 ppm), 6.14 (d, J=18.4 Hz, 1H), 3.78 (s, 2H), 2.53-2.44 (m, 2H), 1.68-1.55 (m, 3H), 1.40-1.28 (m, 3H), 1.05 (d, J=6.4 Hz, 6H); MS ESI 356.2 [M+H]$^+$, calcd for [C$_{22}$H$_{34}$BNO$_2$+H]$^+$ 356.3.

Synthesis of N-Benzyl-oxindole

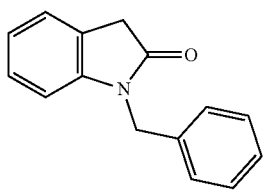 [SMILES: O=C1Cc2ccccc2N1Cc1ccccc1]

Prepared according to literature procedure (C. Martin and E. M. Carreira, *J. Am. Chem. Soc.*, 2005, 127, 11505-11515). A stirred solution of isatin (10.0 g, 68 mmol) in dry DMF (125 mL) was cooled in an ice bath before addition of sodium hydride (60 wt % in mineral oil, 2.86 g, 71.5 mmol) in 10 portions, the orange solution turning quickly purple. When no further evolution of gas was observed, benzyl bromide (13.4 g, 78.0 mmol) was added by syringe. A colour change back to orange was observed within 20 min. Water (300 mL) was added with stirring, and the resulting orange-red precipitate collected by filtration and washed with water and a little cold ethanol. The solid was then recrystallized from boiling ethanol (300 mL) to afford N-benzylisatin (13.7 g, 85%) as long, red needles.

N-benzylisatin (13.0 g, 55 mmol) was mixed with hydrazine hydrate (60 mL) and placed in an oil bath. The mixture was heated in stages to 125° C., becoming first a green sludge, then yellow with clumps of a sticky solid. After a total of 5 h at 125° C., the mixture was cooled and extracted with EtOAc (2×100 mL). The combined organic portions were washed twice with 1.0 M aq. H$_2$SO$_4$, and once each with half-saturated brine then brine, dried over MgSO$_4$, filtered and concentrated to afford a pale yellow solid. Re-precipitation from ether/pentane gave the title compound as an off-white solid (9.6 g, 75%). Spectral data matches literature values (C. Martin and E. M. Carreira, *J. Am. Chem. Soc.*, 2005, 127, 11505-11515).

Synthesis of 1-Benzyl-5-fluoroindolin-2-one

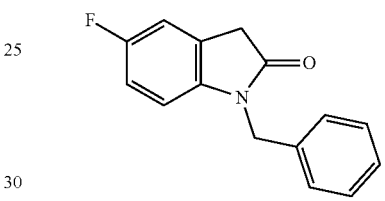

In a manner similar to the method of N-benzylisatin, 5-fluoroisatin (10.0 g, 60.5 mmol) yielded 5-fluoro-N-benzylisatin as an orange red powder (14.5 g, 93%). The crude product was used for the next step without purification. $^1$H NMR (400 MHz, CDCl$_3$) δ 7.33-7.21 (m, 5H), 6.95 (d, J=7.6 Hz, 1H), 6.84 (t, 1H), 6.60 (m, 1H), 4.89 (s, 2H); MS ESI 255.9 [M+H]$^+$, calcd for [C$_{15}$H$_{10}$FNO$_2$+H]$^+$ 255.07.

The title compound was prepared in a manner similar to the method of N-Benzyl-oxindole using 5-fluoro-N-benzylisatin (14.5 g, 56.8 mmol). Trituration using Et$_2$O:hexane yielded the title compound as a pale yellow solid (10.3 g, 75%). $^1$H NMR (400 MHz, CDCl$_3$) δ 7.30-7.26 (m, 5H), 7.00 (d, J=7.6 Hz, 1H), 6.87 (t, 1H), 6.63 (m, 1H), 4.91 (s, 2H), 3.63 (s, 2H); MS ESI 241.9 [M+H]$^+$, calcd for [C$_{15}$H$_{10}$FNO$_2$+H]$^+$ 241.09.

Synthesis of 1-Benzyl-5-methylindolin-2-one

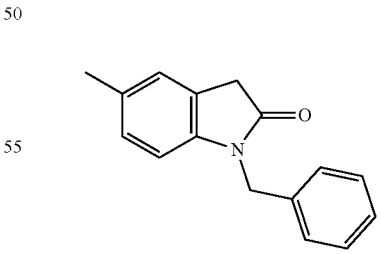

To a mixture of 5-methylisatin (8.05 g, 50 mmol) and K$_2$CO$_3$ (8.16 g, 60 mmol) in DMF (100 mL) was added BnBr (6.5 mL, 55 mmol) dropwise over 2 min After addition, the resulting mixture was heated in an oil bath at 75° C. for 1.5 h. After cooling to rt, the reaction mixture was poured onto ice/cold water (250 mL), rinsed with H$_2$O (50 mL) and stirred for 5 min. The resulting precipitates were collected by suction filtration and air dried to give 1-benzyl-5-methylisatin as dark red solid. MS ESI 252.0 [M+H]+, calcd for [C16H13NO2+H]+ 252.1.

1-Benzyl-5-methylisatin was suspended in DMSO (100 mL) and cooled to 0° C. Hydrazine hydrate (5 mL) was added dropwise over 5 min. After addition, the resulting clear red solution was heated at 120° C. for 2 h then 140° C. for 5 h. After cooling to rt, it was poured into a 1 L Erlenmeyer flask, rinsed with H2O (50 mL) and ice was added until a total volume about 300 mL. 2 M HCl (50 mL) was added and the mixture was extracted with EtOAc (200 mL×2, then 100 mL), and the organic layer was dried (Na2SO4). Removal of solvents followed by drying under high vacuum for 2 days gave the title compound as a dark red solid (12.53 g, quantitative yield over 2 steps, contained some DMSO residue). $^1$H NMR (400 MHz, CDCl3) δ 7.35-7.29 (m, 5H), 7.09 (s, 1H), 6.97 (d, J=7.6 Hz, 1H), 6.61 (d, J=8.0 Hz, 1H), 4.91 (s, 2H), 3.60 (s, 2H), 2.31 (s, 3H); MS ESI 238.0 [M+H]+, calcd for [C16H15NO+H]+ 238.1.

Synthesis of 1-Benzyl-5-methoxyindolin-2-one

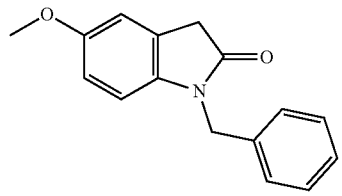 [SMILES: COc1ccc2c(c1)CC(=O)N2Cc1ccccc1]

A stirred solution of 5-methoxyisatin (5.0 g, 28 mmol) in dry DMF (40 mL) was cooled in an ice bath before addition of sodium hydride (60 wt % in mineral oil, 1.7 g, 42 mmol) slowly, the dark red solution turning quickly black. After stirring for 20 min, BnBr (3.7 mL, 31 mmol) was added to the reaction mixture by syringe and the resulting mixture was stirred for 1 h. Water (150 mL) was added with stirring, and the resulting dark red precipitate collected by filtration and washed with water to give 1-benzyl-5-methoxyindoline-2,3-dione as a dark red solid (6.1 g, 81%). $^1$H NMR (400 MHz, CDCl3) δ 7.39-7.31 (m, 5H), 7.17 (s, 1H), 7.03 (d, J=8.1 Hz, 1H), 6.68 (d, J=8.6 Hz, 1H), 4.92 (s, 2H), 3.79 (s, 3H). MS ESI 268.1 [M+H]+, calcd for [C16H13NO3+H]+ 268.09.

A solution of 1-benzyl-5-methoxyindoline-2,3-dione (6.1 g, 23 mmol) and hydrazine hydrate (50-60% grade, 2.9 mL, ca. 2 eq) in DMSO (15 mL) is heated to 140° C. in an oil bath. After 3 h, the mixture was cooled, diluted with water and EtOAc, the layers separated and the aqueous extracted with EtOAc three times (30 mL). The combined organic portions were washed with 2M H2SO4, brine, and dried over MgSO4, filtered and concentrated to afford the crude product as a viscous brown oil. The crude product was purified by silica gel chromatography (20-50% EtOAc in hexane) to yield the title compound as a brown oil (5.0 g, 85%). $^1$H NMR (400 MHz, CDCl3) δ 7.34-7.23 (m, 5H), 6.89 (s, 1H), 6.69 (d, J=8.3 Hz, 1H), 6.61 (d, J=8.5 Hz, 1H), 4.91 (s, 2H), 3.76 (s, 3H), 3.62 (s, 2H). MS ESI 254.0 [M+H]+, calcd for [C16H15NO2+H]+ 254.1.

Synthesis of N1-Benzyl-6-vinyl-1H-indazole

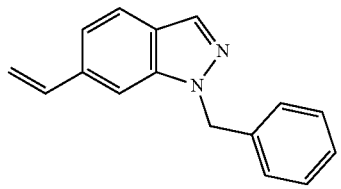 [SMILES: C=Cc1ccc2cnn(Cc3ccccc3)c2c1]

Method 1: A mixture of N1-Benzyl-6-bromo-1H-indazole (10.2 g, 35.5 mmol) and NaOH (4.3 g, 107 mmol) in THF/water (9:1, 350 mL) was purged with nitrogen. In a separate flask, Pd(OAc)2 (0.16 g, 0.7 mmol, 2 mol %) and PPh3 (0.37 g, 1.4 mmol, 4 mol %) were stirred together in nitrogen-purged dry THF (35 mL) for 10 min, forming a red solution with some suspended solids. Vinylboronic acid pinacol ester (7.5 mL, 44.4 mmol) and the catalyst solution were added to the reaction mixture, and the resulting solution purged once more with nitrogen. The mixture was warmed in an oil bath set to 65° C.; TLC indicated consumption of starting material within 7 h. The mixture was concentrated under reduced pressure to remove most of the THF, then diluted with water (50 mL), brine (50 mL) and EtOAc (250 mL). The layers were separated and the aqueous phase extracted with further EtOAc (4×50 mL). The combined organic portions were washed with brine, dried over Na2SO4, filtered and concentrated (at 70° C./20 mbar) to afford the crude product. This was chromatographed on silica using 10-20% EtOAc in cyclohexane to afford the title compound (7.5 g, 90%) as a yellow oil that solidified on standing. $^1$H NMR (400 MHz, CDCl3) δ 7.98 (s, 1H), 7.63 (d, J=8.4 Hz, 1H), 7.29-7.19 (m, 5H), 7.18-7.13 (m, J=7.0 Hz, 2H), 6.75 (dd, J=17.6, 10.9 Hz, 1H), 5.76 (d, J=17.5 Hz, 1H), 5.53 (s, 2H), 5.26 (d, J=10.9 Hz, 1H). MS (ES+): 235 ([M+H]+); calcd for [C16H14N2+H]+ 235.1.

Method 2: using 4,4,6-Trimethyl-2-vinyl-1,3,2-dioxaborinane: A mixture of N1-Benzyl-6-bromo-1H-indazole (1.44 g, 5.0 mmol) and NaOH (0.4 g, 10.0 mmol) in THF/water (5:1, 15 mL) was purged with nitrogen. In a separate flask, Pd(OAc)2 (11 mg, 0.05 mmol, 1 mol %) and PPh3 (26 mg, 0.1 mmol, 2 mol %) were stirred together in nitrogen-purged THF (2.5 mL) for 10 min, forming a red solution with some suspended solids. The THF used was of HPLC grade and inhibitor free; the effect of lower grade or stabilized THF is not known. 4,4,6-Trimethyl-2-vinyl-1,3,2-dioxaborinane (1.12 mL, 6.5 mmol) and the catalyst solution were added to the reaction mixture, and the resulting solution purged once more with nitrogen. The mixture was warmed in an oil bath set to 65° C.; heating was continued for 24 h but the reaction is probably complete in fewer than 8 h. The crude mixture was then combined with a second, parallel reaction of the same scale where higher dilution had been used. The mixture was concentrated under reduced pressure to remove most of the THF, then diluted with water, brine and cyclohexane. The layers were separated and the aqueous phase extracted with further cyclohexane until TLC indicated all the desired product had been extracted (3-4 extracts). The combined organic portions were washed with brine, dried over MgSO4, and then passed through a 1 cm pad of silica to remove baseline material. Any product remaining on the silica was eluted using 10% EtOAc in cyclohexane (Rf. 0.15 in this eluent). The combined eluate was concentrated to afford the title compound (2.05 g, 88%) as a yellow oil that solidified on standing and was of sufficient purity to use in subsequent reactions.

Method 3: N1-Benzyl-6-bromo-1H-indazole (half of the crude material obtained in method 3 above) was processed in two batches as follows: a mixture of crude N1-Benzyl-6-bromo-1H-indazole (153 g, containing a maximum of 0.5 mol assuming 100% yield in benzylation/equilibration) and NaOH (40 g, 1.0 mol) in THF/water (5:1, 1.5 L; HPLC grade inhibitor-free THF) was purged with nitrogen. In a separate flask, Pd(OAc)$_2$ (1.13 g, 5.0 mmol, 1 mol %) and PPh$_3$ (2.6 g, 10.0 mmol, 2 mol %) were stirred together in nitrogen-purged THF (250 mL) for 10 min, forming a red solution with some suspended solids. 4,4,6-Trimethyl-2-vinyl-1,3,2-dioxaborinane (112 mL, 0.65 mol) and the catalyst solution were added to the reaction mixture, and the resulting solution purged once more with nitrogen. The mixture was heated overnight in an oil bath set to 60° C. $^1$H NMR of a sample indicated that some starting material remained, and so additional vinyl donor (30 mL) was added to push to completion. Both batches of mixture were combined and the mixture was concentrated under reduced pressure to remove most of the THF, then diluted with water, brine and cyclohexane. The layers were separated and the aqueous phase extracted with further cyclohexane until TLC indicated all of the desired product had been extracted (total 3.5 L cyclohexane). The combined organic portions were washed with brine, dried over MgSO$_4$, and then passed through a 2 cm pad of silica to remove baseline material. Any product remaining on the silica was eluted using 10% EtOAc in cyclohexane (Rf. 0.15 in this eluent). The combined eluate was concentrated to afford 309 g of a crude oil comprising the title compound, a little of the diol derived from the vinyl donor, and a number of benzyl-containing impurities.

Method 4: A further reaction carried out using distilled N1-Benzyl-6-bromo-1H-indazole (64.3 g, 0.144 moles) afforded full conversion without the need for additional portion of vinyl donor, and gave semi-crude N1-Benzyl-6-vinyl-1H-indazole (55.5 g, quantitative) which was used without further purification below.

Synthesis of (S)-1-(N1-Benzyl-1H-indazol-6-yl)-ethane-1,2-diol

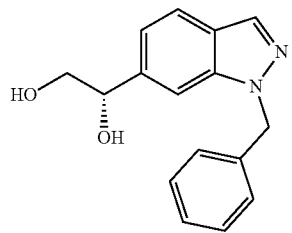 [SMILES: OC[C@@H](O)c1ccc2cnn(Cc3ccccc3)c2c1]

Method 1: K$_3$Fe(CN)$_6$ (16.7 g, 51.0 mmol), K$_2$CO$_3$ (7.05 g, 51.0 mmol), (DHQ)$_2$PHAL (0.13 g, 0.17 mmol, 1 mol %) and K$_2$OsO$_4$.2H$_2$O (12.8 mg, 0.034 mmol, 0.2 mol %) were placed in a roundbottomed flask. A mixture of $^t$BuOH and water (1:1, 160 mL) was added, forming a clear, biphasic mixture on stirring. The mixture was cooled in an ice bath, resulting in partial precipitation, before addition of powdered N1-benzyl-6-vinyl-1H-indazole (4.0 g, 17.1 mmol). The resulting mixture was vigorously stirred in the ice bath for 5 h, at which point no further solid was visible and TLC indicated consumption of starting material. The reaction was quenched by addition of sodium metabisulfite (40 g), with the resulting effervescence causing the reaction mixture to overspill into the ice bath. The remaining material was added to the ice bath and the resulting mixture (containing approximately 1 L of water and ice) was stirred overnight, warming slowly. Celite and CH$_2$Cl$_2$ (200 mL) were added, the mixture thoroughly stirred and then filtered. The solids were washed thoroughly with further CH$_2$Cl$_2$ (2×50 mL). The biphasic filtrate was separated, and the aqueous layer extracted with CHCl$_3$ (4×50 mL). The combined organic portions were washed with brine, dried over MgSO$_4$, filtered and concentrated. The residue was taken up in EtOAc and filtered through a pad of silica (1 cm depth×8 cm diameter), eluting with further EtOAc, to remove baseline material. The eluate was concentrated and stripped with toluene to remove traces of $^t$BuOH. Finally, the residue was recrystallized from hot toluene (10 mL/g) to afford the title compound as white needles (3.87 g, 84%, 98.8% ee) with the major (S) enantiomer eluting at 16.8 min (Daicel Chiralpak IB (250×4.6 mm); isocratic 10% EtOH in n-heptane; 1 mL/min; ambient temperature (ca. 22° C.); Detection: 254, 230, 210 nm); From the racemic reference standard, the retention time of the (R) enantiomer was 14.8 min using this method and N1-benzyl-6-vinyl-1H-indazole eluted at 5.4 min. $^1$H NMR and mass spectral data were identical to racemic 1-(1-Benzyl-1H-indazol-6-yl)-ethane-1,2-diol obtained above. Optical Rotation: $[\alpha]^{22}_D$=13° (c 1.018, MeOH).

Method 2: Semi-crude N1-Benzyl-6-vinyl-1H-indazole (Method 4 above, 55.5 g) was dihydroxylated in a similar manner to afford, after recrystallization to obtain 2 crops of solid, pure (S)-1-(N1-Benzyl-1H-indazol-6-yl)-ethane-1,2-diol (38 g, quantitative).

Method 3: K$_3$Fe(CN)$_6$ (0.98 kg, 3 mol), K$_2$CO$_3$ (0.55 kg, 3 mol), (DHQ)$_2$PHAL (3.9 g, 5.0 mmol) and K$_2$OsO$_4$.2H$_2$O (0.37 g, 1 mmol) were placed in a 10 L clamp-top reaction vessel equipped with overhead stirrer. A mixture of $^t$BuOH and water (1:1, 7.5 L) was added, forming a clear, biphasic mixture on stirring. The mixture was cooled using a Haake EK90 chiller, resulting in partial precipitation, before addition of crude N1-benzyl-6-vinyl-1H-indazole (ca. 0.7-0.8 mol). The resulting mixture was vigorously stirred, but set solid as insufficient space was available for proper circulation in the cooling bath and the actual temperature dropped to around 20° C. when left over the weekend. Little conversion was evident. To speed up the reaction, further (DHQ)$_2$PHAL (2.5 mmol) and K$_2$OsO$_4$.2H$_2$O (0.5 mmol) were added, and the mixture let warm to approx. 10° C.; the reaction then proceeded satisfactorily. The reaction was quenched by portion-wise addition of sodium metabisulfite (1.5 kg). The mixture was stirred for 1 h at rt, becoming almost clear, then filtered through a pad of celite to remove precipitated OsO$_2$. The filtrate was extracted with CH$_2$Cl$_2$ (4 extracts, final volume 7 L), and the combined organic portions dried over MgSO$_4$, filtered and concentrated. The crude product was recrystallized from hot toluene (10 mL/g); two crops of the title compound were collected, of 98.7% and 98.0% e.e., totalling 163.7 g (55% from 6-bromo-1H-indazole).

Synthesis of (S)-Methanesulfonic acid 2-(N1-benzyl-1H-indazol-6-yl)-2-methanesulfonyloxy-ethyl ester

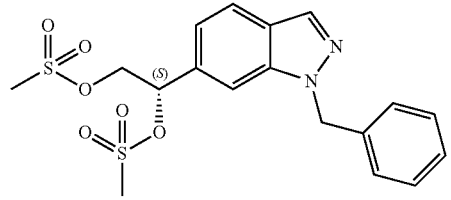

Method 1: A solution of (S)-1-(N1-Benzyl-1H-indazol-6-yl)-ethane-1,2-diol (3.75 g, 14.0 mmol, 98.8% ee) and Et$_3$N (4.9 mL, 35.0 mmol) in dry CH$_2$Cl$_2$ (350 mL) was cooled in an ice bath before dropwise addition of MsCl (2.17 mL, 28.0 mmol) over 10 min. The resulting mixture was left to stir for 30 min. After dilution with further CH$_2$Cl$_2$ (250 mL), the solution was washed with cold 1.0 M aq. HCl (2×50 mL), sat. aq. NaHCO$_3$ (50 mL) and brine (50 mL), then dried over Na$_2$SO$_4$. The solution was poured onto a short silica pad (1 cm depth×8 cm diameter) under suction. The initial filtrate did not contain any of the product; this was subsequently eluted with 1:1 Et$_2$O/CH$_2$Cl$_2$. The eluate was concentrated under reduced pressure to afford the title compound (5.98 g, quant.) as a white solid. $^1$H NMR and mass spectral data were identical to racemic methanesulfonic acid 2-(1-benzyl-1H-indazol-6-yl)-2-methanesulfonyloxy-ethyl ester obtained above. The e.e. of this batch of material was not determined at this stage but was carried forward to the next step. Optical Rotation: $[\alpha]^{22}_D$=58° (c 0.73, CHCl$_3$).

Method 2: A solution of (S)-1-(N1-benzyl-1H-indazol-6-yl)-ethane-1,2-diol (134 g, 0.5 mol, 98% e.e.) and Et$_3$N (174 mL, 1.25 mol) in CH$_2$Cl$_2$ (2.5 L) was cooled in an ice bath before slow addition of MsCl (81.3 mL, 1.05 mol) over approx. 1 h. The internal temperature increased to a maximum of 11° C. The resulting mixture was left to stir for 30 min. The reaction was quenched with cold 1.0 M aq. HCl (400 mL), the phases separated, and the organic phase washes with further cold 1.0 M aq. HCl, aq. NaHCO$_3$ and brine, then dried over MgSO$_4$. The solution was poured onto a short silica pad under suction. Some of the product eluted from the silica during this filtration, and the remainder was eluted using 1:1 Et$_2$O/CH$_2$Cl$_2$ (2 L). The eluate was concentrated under reduced pressure to afford a hard white solid. This was triturated with Et$_2$O (800 mL) overnight. The fine white powder was collected by filtration and washed with further Et$_2$O (2×100 mL) to yield the title compound (184.2 g, 87%, 99% e.e.) with the major (S) enantiomer eluting at 13.4 min (Daicel Chiralpak IB (250×4.6 mm); isocratic 30% EtOH in n-heptane; 1 mL/min; ambient temperature (ca. 22° C.); Detection: 254, 230, 210 nm); From the racemic reference standard, the retention time of the (R) enantiomer was 14.4 min using this method. The filtrate contained only a small quantity of product of low e.e. and was discarded.

Synthesis of (1R,2S)-1'-benzyl-2-(1-benzyl-1H-indazol-6-yl)spiro[cyclopropante-1,3'-indolin]-2'-one

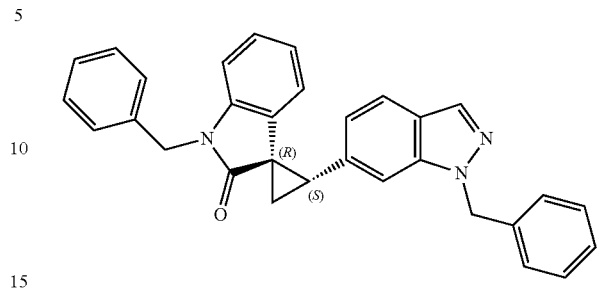

Method 1: A solution of N-benzyl-oxindole (3.57 g) in dry THF (120 mL) was cooled in an ice bath before addition of NaH (60 wt % in mineral oil, 1.92 g, 48.0 mmol) in four portions; the solution quickly became a deep purple. After 30 min, a solution of (S)-methane sulfonic acid 2-(N1-benzyl-1H-indazol-6-yl)-2-methanesulfonyloxy-ethyl ester (6.79 g, 16.0 mmol, 98.5% ee, previously stripped twice with dry THF) in dry THF (80 mL) was added by syringe pump over a period of 1 h. TLC indicated rapid conversion to a single compound with Rf 0.45 (25% EtOAc in cyclohexane, eluted twice; starting materials Rf 0.5 & Rf 0.2). After stirring for 2 h, the mixture was poured into sat. aq. NH$_4$Cl (50 mL), diluted with water (50 mL), and EtOAc (100 mL). The phases were separated and the aqueous layer extracted with further portions of EtOAc (4×50 mL). The combined organic portions were washed with brine, dried over Na$_2$SO$_4$, filtered and concentrated to afford a crude product that, by $^1$H NMR, appeared to consist almost exclusively of the title compound. The crude product was passed through a short silica pad (1 cm depth×5 cm diameter), eluting with 1:1 EtOAc in cyclohexane. The residue was triturated with n-heptane (3×50 mL) to remove mineral oil, and stripped with toluene to afford the title compound (7.0 g, up to 90% yield) as a glassy solid that contained some solvent. HPLC indicated an optical purity of 98% e.e. with the major (1R,2S) enantiomer eluting at 13.3 min (Daicel Chiralpak IA, 250×4.6 mm; isocratic 10% EtOH in n-heptane; 1 mL/min; ambient temperature (ca. 22° C.); Detection: 254, 230, 210 nm); From the racemic reference standard, the retention time of the (1S,2R) enantiomer was 12.1 min using this method. $^1$H NMR (400 MHz, CDCl$_3$) δ 7.99 (s, 1H), 7.60 (d, J=8.3 Hz, 1H), 7.36-7.20 (m, 8H), 7.19 (s, 1H), 7.15-7.10 (m, J=6.4 Hz, 2H), 6.99 (td, J=7.8, 0.9 Hz, 1H), 6.92 (d, J=8.3 Hz, 1H), 6.74 (d, J=7.8 Hz, 1H), 6.50 (t, J=7.4 Hz, 1H), 5.76 (d, J=7.3 Hz, 1H), 5.61 (d, J=15.8 Hz, 1H), 5.53 (d, J=15.8 Hz, 1H), 5.08 (d, J=15.6 Hz, 1H), 4.97 (d, J=15.7 Hz, 1H), 3.48 (t, J=8.5 Hz, 1H), 2.28 (dd, J=9.0, 4.5 Hz, 1H), 2.02 (dd, J=8.0, 4.6 Hz, 1H). MS (ES+): 456 ([M+H]$^+$), calcd for [C$_{31}$H$_{25}$N$_3$O+H]$^+$ 456.2.

Method 2: In a separate set of individual experiments carried out in a similar manner as Method 1 but not performing any column chromatography, using between on 20-45 g of (S)-methanesulfonic acid 2-(N1-benzyl-1H-indazol-6-yl)-2-methanesulfonyloxy-ethyl ester per batch, a total of 133.8 g, 315 mmol was carried forward. Some batches were combined and passed through a silica plug to remove traces of baseline material before use, but this didn't seem to make any difference in subsequent reactions. The crude product was isolated as a foamy solid (174.1 g, containing mineral oil from the sodium hydride accounting for approximately 10% of each crude product, as well as Synthesis of (1R,2S)-1'-benzyl-2-(1-benzyl-1H-indazol-6-yl)spiro[cyclopropane-1,3'-indolin]-2'-one

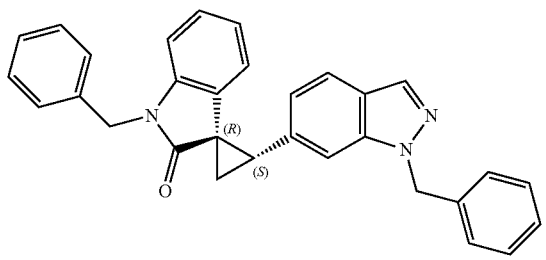

Method 1: A solution of N-benzyl-oxindole (3.57 g) in dry THF (120 mL) was cooled in an ice bath before addition of NaH (60 wt % in mineral oil, 1.92 g, 48.0 mmol) in four portions; the solution quickly became a deep purple. After 30 min, a solution of (S)-methanesulfonic acid 2-(N1-benzyl-1H-indazol-6-yl)-2-methanesulfonyloxy-ethyl ester (6.79 g, 16.0 mmol, ~98.5% ee, previously stripped twice with dry THF) in dry THF (80 mL) was added by syringe pump over a period of 1 h. TLC indicated rapid conversion to a single compound with Rf 0.45 (25% EtOAc in cyclohexane, eluted twice; starting materials Rf 0.5 & Rf 0.2). After stirring for 2 h, the mixture was poured into sat. aq. NH$_4$Cl (50 mL), diluted with water (50 mL), and EtOAc (100 mL). The phases were separated and the aqueous layer extracted with further portions of EtOAc (4×50 mL). The combined organic portions were washed with brine, dried over Na$_2$SO$_4$, filtered and concentrated to afford a crude product that, by $^1$H NMR, appeared to consist almost exclusively of the title compound. The crude product was passed through a short silica pad (1 cm depth×5 cm diameter), eluting with 1:1 EtOAc in cyclohexane. The residue was triturated with n-heptane (3×50 mL) to remove mineral oil, and stripped with toluene to afford the title compound (7.0 g, up to 90% yield) as a glassy solid that contained some solvent. HPLC indicated an optical purity of 98% e.e. with the major (1R,2S) enantiomer eluting at 13.3 min (Daicel Chiralpak IA, 250×4.6 mm; isocratic 10% EtOH in n-heptane; 1 mL/min; ambient temperature (ca. 22° C.); Detection: 254, 230, 210 nm); From the racemic reference standard, the retention time of the (1S,2R) enantiomer was 12.1 min using this method. $^1$H NMR (400 MHz, CDCl$_3$) δ 7.99 (s, 1H), 7.60 (d, J=8.3 Hz, 1H), 7.36-7.20 (m, 8H), 7.19 (s, 1H), 7.15-7.10 (m, J=6.4 Hz, 2H), 6.99 (td, J=7.8, 0.9 Hz, 1H), 6.92 (d, J=8.3 Hz, 1H), 6.74 (d, J=7.8 Hz, 1H), 6.50 (t, J=7.4 Hz, 1H), 5.76 (d, J=7.3 Hz, 1H), 5.61 (d, J=15.8 Hz, 1H), 5.53 (d, J=15.8 Hz, 1H), 5.08 (d, J=15.6 Hz, 1H), 4.97 (d, J=15.7 Hz, 1H), 3.48 (t, J=8.5 Hz, 1H), 2.28 (dd, J=9.0, 4.5 Hz, 1H), 2.02 (dd, J=8.0, 4.6 Hz, 1H). MS (ES+): 456 ([M+H]$^+$), calcd for [C$_{31}$H$_{25}$N$_3$O+H]$^+$ 456.2.

Synthesis of (1R,2S)-1'-benzyl-2-(1-benzyl-1H-indazol-6-yl)-5'-fluorospiro[cyclopropane-1,3'-indolin]-2'-one

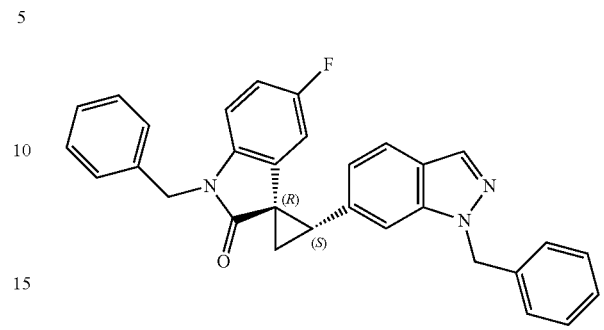

The title compound was prepared in a manner similar to the method of (1R,2S)-1'-benzyl-2-(1-benzyl-1H-indazol-6-yl)spiro[cyclopropane-1,3'-indolin]-2'-one using (S)-1-(1-benzyl-1H-indazol-6-yl)ethane-1,2-diyl dimethanesulfonate (501.4 mg, 1.181 mmol) and 1-benzyl-5-fluoroindolin-2-one (285.0 mg, 1.181 mmol). Purification using Biotage Isolera (SNAP 25 g column, 25-100% EtOAc in hexane) yielded the title compound as a cream solid (352 mg, 63%; 97% ee) with the major (1R,2S) enantiomer eluting at 7.03 min (Phenomenex Lux 5μ, Cellulose-1 (150×4.6 mm), 1.0 mL/min isocratic at 80% EtOH in hexane for 1.0 min, then gradient 80-90% EtOH in hexane over 10 min). From the racemic reference standard, the retention time of the (1S,2R) enantiomer was 5.95 min using this method. $^1$H NMR (400 MHz, CDCl$_3$) δ 8.04 (s, 1H), 7.67 (d, J=8.8 Hz, 1H), 7.40-7.27 (m, 8H), 7.17 (s, 1H), 7.11 (d, J=7.2 Hz, 2H), 6.92 (d, J=8.4 Hz, 1H), 6.67-6.62 (m, 2H), 5.62 (d, J=15.6 Hz, 1H), 5.55 (d, J=15.6 Hz, 1H), 5.51 (t, J=6.0 Hz, 1H), 5.10 (d, J=15.6 Hz, 1H), 4.94 (d, J=16.0 Hz, 1H), 3.53 (t, J=8.4 Hz, 1H), 2.32 (dd, J=9.2, 4.4 Hz, 1H), 2.02 (dd, J=8.0, 3.2 Hz, 1H), MS ESI 474.3 [M+H]$^+$, calcd for [C$_{31}$H$_{24}$FN$_3$O+H]$^+$ 474.2.

Synthesis of (1R,2S)-5'-fluoro-2-(1H-indazol-6-yl)spiro[cyclopropane-1,3'-indolin]-2'-one

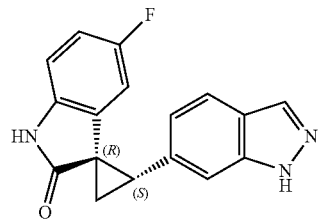

The title compound was prepared in a manner similar to the chiral synthetic method of Example A4 using (1R,2S)-1'-benzyl-2-(1-benzyl-1H-indazol-6-yl)-5'-fluorospiro [cyclopropane-1,3'-indolin]-2'-one (560 mg, 1.18 mmol). Purification by using silica gel column chromatography with 5-95% EtOAc in hexane to give the title compound as a creamy solid (179 mg, 52%). $^1$H NMR (400 MHz, CD$_3$OD) δ 8.03 (s, 1H), 7.71 (d, J=8.0 Hz, 1H), 7.62-7.46 (m, 2H), 6.94 (d, J=8.4 Hz, 1H), 6.88 (t, J=4.8 Hz, 1H), 5.69 (d, J=9.2 Hz, 1H), 3.39 (t, J=8.0 Hz, 1H), 2.30-2.71 (m, 1H), 2.23-2.18 (m, 1H); MS ESI 294.1 [M+H]$^+$, calcd for [C$_{17}$H$_{12}$FN$_3$O+H]$^+$ 294.10.

Synthesis of (1R,2S)-5'-fluoro-2-(3-iodo-1H-indazol-6-yl)spiro[cyclopropane-1,3'-indolin]-2'-one

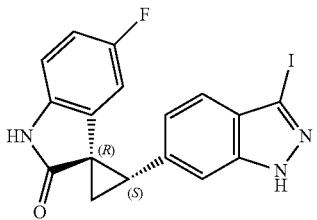

The title compound was prepared in a manner similar to the chiral synthetic method of Example A10 using (1R,2S)-5'-fluoro-2-(1H-indazol-6-yl)spiro[cyclopropane-1,3'-indolin]-2'-one (240 mg, 0.818 mmol). Purification using Biotage Isolera with SNAP 25 g column with 5-90% EtOAc in hexane yielded the title compound as a cream solid (195 mg, 57%; 97% ee) with the major (1R,2S) enantiomer eluting at 3.7 min (Phenomenex Lux 5µ, Cellulose-2 (150× 4.6 mm); isocratic 25% EtOH in n-hexane; 1.5 mL/min; 24° C.; Detection: 254 nm). From the racemic reference standard, the retention time of the (1S,2R) enantiomer was 3.2 min using this method. $^1$H NMR (400 MHz, CD$_3$OD) δ 7.47 (s, 1H), 7.38 (d, J=8.4 Hz, 1H), 7.01 (d, J=8.8 Hz, 1H), 6.88 (dd, J=8.8, 4.4 Hz, 1H), 6.79 (t, J=8.8 Hz, 1H), 5.69 (d, J=8.4 Hz, 1H), 3.38 (t, J=8.8 Hz, 1H), 2.28 (dd, J=8.8, 4.2 Hz, 1H), 2.21 (dd, J=9.2, 4.4 Hz, 1H); MS ESI 420.0 [M+H]$^+$, calcd for [C$_{17}$H$_{11}$FIN$_3$O+H]$^+$ 420.0.

Synthesis of (1R,2S)-1'-benzyl-2-(1-benzyl-1H-indazol-6-yl)-5'-methylspiro[cyclopropane-1,3'-indolin]-2'-one

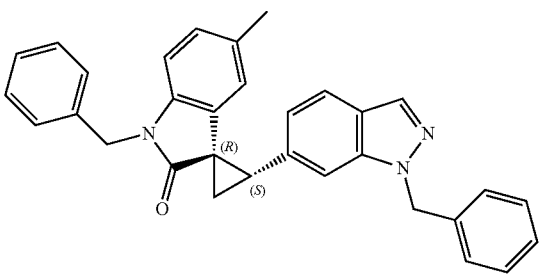

To a 250 mL round bottom flask charged with 60% NaH (1.20 g, 30 mmol) was added anhydr. THF (20 mL) and the resulting mixture was cooled to 0° C. A solution of 1-benzyl-5-methylindolin-2-one (2.37 g, 10 mmol) in dry THF (25 mL) was added over 2 min, followed by rinsing with THF (5 mL). After stirring for 20 min at 0° C., a solution of (S)-1-(1-benzyl-1H-indazol-6-yl)ethane-1,2-diyl dimethanesulfonate (4.24 g, 10 mmol) in dry THF (45 mL) was added dropwise through dropping funnel over 40 min, followed by rinsing with THF (5 mL). After addition, the resulting mixture was stirred for 30 min at 0° C. (TLC showed completion) then left O/N at rt. After cooling to 0° C., the reaction mixture was poured into an Erlenmeyer flask containing ice (100 mL) and sat. NH$_4$Cl (30 mL) and extracted with EtOAc (150 mL×2), dried (Na$_2$SO$_4$). After removal of solvents, the residue was transferred to a 100 mL RBF using 30 mL of EtOAc and crystals formed. Suction filtration gave the title compound as a beige solid (1.537 g). The filtrate was concentrated and purified by Biotage Isolera (20-30% EtOAc in hexane) and triturated with EtOAc/hexane to give 2nd crop as off white solid (1.560 g). The filtrate was purified using the above procedure to give 3rd crop as a beige solid (115 mg). Total 3.212 g (68%). $^1$H NMR (400 MHz, CDCl$_3$) δ 8.02 (s, 1H), 7.63 (d, J=8.0 Hz, 1H), 7.36-7.20 (m, 9H), 7.14 (d, J=6.0 Hz, 2H), 6.94 (d, J=8.4 Hz, 1H), 6.80 (d, J=8.0 Hz, 1H), 6.64 (d, J=7.2 Hz, 1H), 5.62 (d, J=16.8 Hz, 1H, partially overlapping with s at 5.59), 5.59 (s, 1H, partially overlapping with d at 5.62), 5.55 (d, J=16.8 Hz, 1H), 5.08 (d, J=16.0 Hz, 1H), 4.97 (d, J=15.6 Hz, 1H), 3.48 (t, J=8.4 Hz, 1H), 2.30-2.25 (m, 1H), 2.02-1.96 (m, 1H), 1.85 (s, 3H); MS ESI 470.3 [M+H]$^+$, calcd for [C$_{32}$H$_{27}$N$_3$O+H]$^+$ 470.2.

Synthesis of (1R,2S)-2-(1H-indazol-6-yl)-5'-methylspiro[cyclopropane-1,3'-indolin]-2'-one

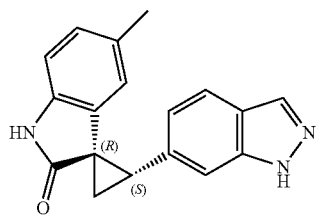

To a 100 mL flask charged with (1R,2S)-1'-benzyl-2-(1-benzyl-1H-indazol-6-yl)-5'-methylspiro[cyclopropane-1,3'-indolin]-2'-one (469 mg, 1 mmol) was added dry THF (2 mL) and the resulting mixture was stirred at 0° C. before KO$^t$Bu (1 M in THF, 18 mL, 18 mmol) was added over 2 min After addition, the resulting mixture was stirred for 15 min at 0° C. and DMSO (1.85 mL) was added. Oxygen was bubbled through for 1 h and reaction turned from homogeneous to heterogeneous. LC-MS showed good conversion at 50 min. It was quenched with sat. NH$_4$Cl.

The above reaction was repeated on a larger scale using (1R,2S)-1'-benzyl-2-(1-benzyl-1H-indazol-6-yl)-5'-methylspiro[cyclopropane-1,3'-indolin]-2'-one (1.41 g, 3 mmol). After quenching with saturated NH$_4$Cl, two reactions were combined, diluted with H$_2$O and extracted with EtOAc (100 mL×2). Purification by Biotage Isolera (10-95% EtOAc in hexane) gave the title compound as a light solid (680 mg, 53%). $^1$H NMR (400 MHz, CD$_3$OD) δ 8.02 (s, 1H), 7.67 (d, J=8.4 Hz, 1H), 7.46 (s, 1H), 6.94 (d, J=8.4 Hz, 1H), 6.85 (d, J=8.0 Hz, 1H), 6.81 (d, J=7.6 Hz, 1H), 5.78 (s, 1H), 3.32 (t, overlapping with MeOH residue), 2.20-2.12 (m, 2H), 1.87 (s, 3H); MS ESI 290.1 [M+H]$^+$, calcd for [C$_{18}$H$_{15}$N$_3$O+H]$^+$ 290.1.

Synthesis of (1R,2S)-2-(3-iodo-1H-indazol-6-yl)-5'-methylspiro[cyclopropane-1,3'-indolin]-2'-one

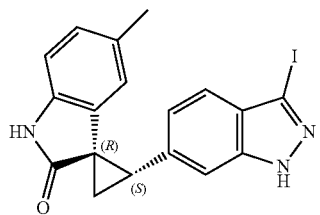

To a solution of (1R,2S)-2-(1H-indazol-6-yl)-5'-methylspiro[cyclopropane-1,3'-indolin]-2'-one (680 mg, 2.35 mmol) in DMF (16 mL) was added $K_2CO_3$ (544 mg, 4 mmol), followed by iodine (851 mg, 3.2 mmol). The resulting mixture was stirred for 3 h at rt, cooled to 0° C., quenched with sat. $Na_2S_2O_3$, diluted with $H_2O$, extracted with EtOAc (50 mL×3) and dried ($Na_2SO_4$). Evaporation of solvents and purification by Biotage Isolera (EtOAc/hexane gradient: 10-90%) gave the title compound as a light yellow solid (794 mg, 81%; >98% e.e.). The major (1R,2S)-enantiomer eluted at 9.6 min (Phenomenex Lux 5u Cellulose-2 (150×4.6 mm); isocratic 10% EtOH in n-hexane 1.75 L/min; ambient temperature; Detection: 254, 214 nm). From the racemic reference standard, the retention time of the (1S,2R)-enantiomer was 7.7 min using this method. $^1H$ NMR (400 MHz, DMSO-d6) δ 13.46 (s, 1H), 10.51 (s, 1H), 7.47 (s, 1H), 7.32 (d, J=8.8 Hz, 1H), 7.02 (d, J=8.0 Hz, 1H), 6.81 (d, J=7.6 Hz, 1H), 6.73 (d, J=7.6 Hz, 1H), 5.86 (s, 1H), 3.16 (t, overlapping with trace MeOH residue), 2.32-2.25 (m, 1H), 2.00-1.93 (m, 1H), 1.85 (s, 3H); MS ESI 416.0 $[M+H]^+$, calcd for $[C_{18}H_{14}IN_3O+H]^+$ 416.0.

Synthesis of (1R,2S)-2-(1-benzyl-1H-indazol-6-yl)-1'-methylspiro[cyclopropane-1,3'-indolin]-2'-one

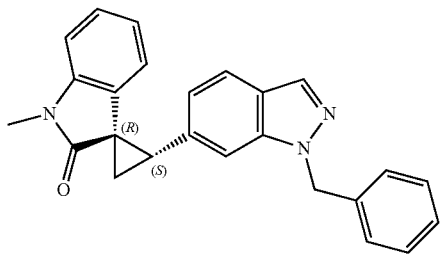

The title compound was prepared in a manner similar to the method of (1R,2S)-1'-benzyl-2-(1-benzyl-1H-indazol-6-yl)spiro[cyclopropane-1,3'-indolin]-2'-one using (S)-1-(1-benzyl-1H-indazol-6-yl)ethane-1,2-diyl dimethanesulfonate (6.70 g, 15.8 mmol) and 1-methylindolin-2-one (2.33 g, 15.8 mmol). Purification via column chromatography (silica gel, 25-50% EtOAc in hexane) yielded the title compound as a pale-orange crystalline solid (5.01 g, 84%); $^1H$ NMR (400 MHz, $CDCl_3$) δ 8.00 (s, 1H), 7.60 (d, J=8.3 Hz, 1H), 7.30-7.25 (m, 3H), 7.18 (s, 1H), 7.13-7.10 (m, 3H), 6.92 (d, J=8.6 Hz, 1H), 6.85 (d, J=7.6 Hz, 1H), 6.55 (t, J=7.0 Hz, 1H), 5.76 (d, J=7.2 Hz, 1H), 5.63-5.49 (m, 2H), 3.41 (t, J=8.8 Hz, 1H), 3.33 (s, 3H), 2.22-2.18 (m, 1H), 2.00-1.96 (m, 1H); MS ESI 380.2 $[M+H]^+$, calcd for $[C_{25}H_{21}N_3O+H]^+$ 380.18.

Synthesis of (1R,2S)-2-(1H-indazol-6-yl)-1'-methylspiro[cyclopropane-1,3'-indolin]-2'-one

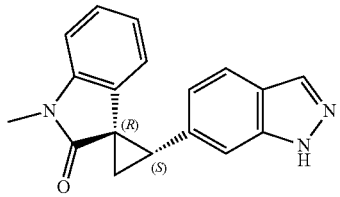

The title compound was prepared in a manner similar to the chiral synthetic method of Example A4 using (1R,2S)-2-(1-benzyl-1H-indazol-6-yl)-1'-methylspiro[cyclopropane-1,3'-indolin]-2'-one (1.16 g, 3.06 mmol). Purification via column chromatography (silica gel, 3-6% MeOH in $CH_2Cl_2$) yielded the title compound as a pale-yellow solid (656 mg, 74%); $^1H$ NMR (400 MHz, $CDCl_3$) δ 10.06 (br. s, 1H), 8.05 (s, 1H), 7.64 (d, 1H, J=7.6 Hz), 7.36 (s, 1H), 7.14 (t, J=8.7 Hz, 1H), 6.97 (d, J=8.7 Hz, 1H), 6.87 (d, J=8.2 Hz, 1H), 6.62 (t, J=7.6 Hz, 1H), 5.91 (d, J=7.9 Hz, 1H), 3.46 (t, J=7.8 Hz, 1H), 3.34 (s, 3H), 2.26-2.23 (m, 1H), 2.08-2.04 (m, 1H); MS ESI 290.1 $[M+H]^+$, calcd for $[C_{18}H_{15}N_3O+H]^+$ 290.13.

Synthesis of (1R,2S)-2-(3-iodo-1H-indazol-6-yl)-1'-methylspiro[cyclopropane-1,3'-indolin]-2'-one

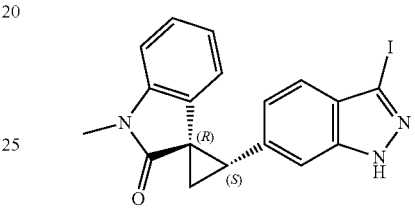

The title compound was prepared in a manner similar to the chiral synthetic method of Example A10 using (1R,2S)-2-(1H-indazol-6-yl)-1'-methylspiro[cyclopropane-1,3'-indolin]-2'-one (930 mg, 3.21 mmol). Precipitation with EtOAc followed by filtration and rinsing with EtOAc gave the title compound (970 mg, 73%; >98% ee) with the major enantiomer eluting at 2.4 min (Phenomenex Lux 5μ, Amylose-2 150×4.6 mm, 2.5 mL/min with isocratic at 20% EtOH in hexane for 0.5 min, then gradient 20-50% EtOH in hexane over 2.5 min, then isocratic at 50% for 1 min). From the racemic reference standard, the retention time of the (1S,2R) enantiomer was 3.0 min using this method. $^1H$ NMR (400 MHz, $CDCl_3$) δ 10.96 (br. s, 1H), 7.43-7.39 (m, 2H), 7.16 (t, J=7.6 Hz, 1H), 7.05 (d, J=8.0 Hz, 1H), 6.89 (d, J=7.8 Hz, 1H), 6.66 (t, J=7.2 Hz, 1H), 5.91 (d, J=8.0 Hz, 1H), 3.47 (t, J=8.4 Hz, 1H), 3.35 (s, 3H), 2.30-2.26 (m, 1H), 2.08-2.04 (m, 1H); MS ESI 416.0 $[M+H]^+$, calcd for $[C_{18}H_{14}IN_3O+H]^+$ 416.03. Optical Rotation: $[\alpha]^{23}_D=-210°$ (c 0.4, MeOH).

Synthesis of (1R,2S)-1'-benzyl-2-(1-benzyl-1H-indazol-6-yl)-5'-methoxy-1'-methylspiro[cyclopropane-1,3'-indolin]-2'-one

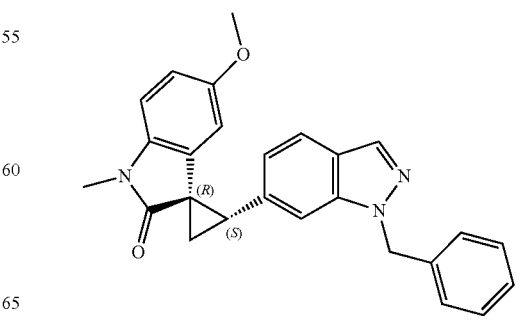

The title compound was prepared in a manner similar to the method of (1R,2S)-1'-benzyl-2-(1-benzyl-1H-indazol-6-yl)spiro[cyclopropane-1,3'-indolin]-2'-one using (S)-1-(1-benzyl-1H-indazol-6-yl)ethane-1,2-diyl dimethanesulfonate (1.44 g, 3.39 mmol) and 5-methoxy-1-methylindolin-2-one (0.601 g, 3.39 mmol). Purification using Biotage Isolera (1-50% EtOAc in hexane, SNAP 25 g column) yielded the title compound (light brown solid, 1.05 g, 76%). $^1$H NMR (400 MHz, CDCl$_3$) δ 8.03 (s, 1H), 7.67 (d, J=8.8 Hz, 1H), 7.50 (s, 1H), 7.26-7.23 (m, 3H), 7.11 (d, J=7.6 Hz, 2H), 6.95 (d, J=8.4 Hz, 1H), 6.89 (d, J=8.4 Hz, 1H), 6.67 (d, J=8.4 Hz, 1H), 5.63 (d, J=16.4 Hz, 1H), 5.58 (d, J=16.0 Hz, 1H), 5.41 (s, 1H), 3.37 (t, J=8.8 Hz, 1H), 3.15 (s, 3H), 2.23-2.19 (m, 1H), 2.18-2.14 (m, 1H), —OCH$_3$ proton is obscured by methanol peak. MS ESI 410.2 [M+H]$^+$, calcd for [C$_{26}$H$_{23}$N$_3$O$_2$+H]$^+$ 410.2.

Synthesis of (1R,2S)-2-(1H-indazol-6-yl)-5'-methoxy-1'-methylspiro[cyclopropane-1,3'-indolin]-2'-one

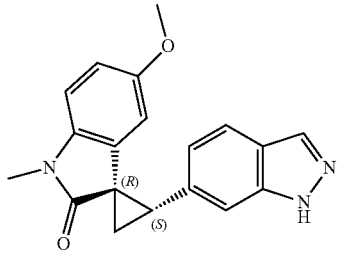

A solution of potassium-t-butoxide (1M, 19.23 mL, 0.19 mol) was added to a solution of (1R,2S)-1'-benzyl-2-(1-benzyl-1H-indazol-6-yl)-5'-methoxy-1'-methylspiro [cyclopropane-1,3'-indolin]-2'-one (0.875 g, 2.1 mmol) in anhydrous THF (2.62 mL) at 0° C. and the mixture was stirred for 15 min at the same temperature. Then anhydrous DMSO (1.97 mL, 27 mmol) was added via syringe to the mixture at 0° C. and stirring was continued for 5 min. The reaction mixture was purged O$_2$ gas for 1.5 hr at 0° C. After stirring at 0° C. for a further 15 min, the reaction mixture was quenched with 25% aq. NH$_4$Cl (20 mL). The product was extracted using EtOAc (40 mL×2), and the combined EtOAc layer was washed with water (10 mL) and dried (Na$_2$SO$_4$) and concentrated under vacuum at 40° C./125 mbar. The resultant pale yellow residue was purified by silica gel column chromatography using 5-10% EtOAc in hexane to give the title compound as an off-white solid (445 mg, 65%). $^1$H NMR (400 MHz, CD$_3$OD) δ 8.02 (s, 1H), 7.67 (d, J=8.4 Hz, 1H), 7.47 (s, 1H), 6.95-6.90 (m, 2H), 6.68 (d, J=8.8 Hz, 1H), 5.58 (s, 1H), 3.38 (t, J=8.4 Hz, 1H), 3.20 (s, 3H), 2.28 (dd, J=9.2, 4.4 Hz, 1H), 2.06 (dd, J=8.4, 4.8 Hz, 1H), —OCH$_3$ proton is merged with Methanol peak. MS ESI 320.1 [M+H]$^+$, calcd for [C$_{19}$H$_{17}$N$_3$O$_2$+H]$^+$ 320.2.

Synthesis of (1R,2S)-2-(3-iodo-1H-indazol-6-yl)-5'-methoxy-1'-methylspiro[cyclopropane-1,3'-indolin]-2'-one

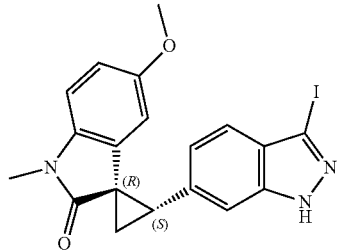

In a manner similar to the chiral synthetic method of Example A10 using (1R,2S)-2-(1H-indazol-6-yl)-5'-methoxy-1'-methylspiro[cyclopropane-1,3'-indolin]-2'-one (1.34 g, 4.19 mmol), the title compound was obtained as a cream color solid (1.71 g, 91%; 98% ee) with the major (1R,2S) enantiomer eluting at 2.6 min (Phenomenex Lux 5µ, Amylose-2 150×4.6 mm, 2.5 mL/min with isocratic at 20% EtOH in hexane for 0.5 min, then gradient 20-50% EtOH in hexane over 2.5 min, then isocratic at 50% for 1 min). From the racemic reference standard, the retention time of the (1S,2R) enantiomer was 3.25 min using this method. $^1$H NMR (400 MHz, CDCl$_3$) δ 10.38 (s, 1H), 7.42 (d, J=8.4 Hz, 1H), 7.35 (s, 1H), 7.04 (d, J=8.8 Hz, 1H), 6.77 (d, J=8.4 Hz, 1H), 6.66 (d, J=8.4 Hz, 1H), 5.53 (s, 1H), 3.46 (t, J=8.0 Hz, 1H), 3.38 (s, 3H), 3.32 (s, 3H), 2.24 (dd, J=8.4, 4.8 Hz, 1H), 2.04 (dd, J=12.4, 4.8 Hz, 1H); MS ESI 446.1 [M+H]$^+$, calcd for [C$_{19}$H$_{16}$IN$_3$O$_2$+H]$^+$ 446.0. Optical Rotation: [α]$^{22}_D$=−134° (c 0.238, MeOH).

Synthesis of (1R,2S)-1'-benzyl-2-(1-benzyl-1H-indazol-6-yl)-1'-(2-methoxyethyl)spiro[cyclopropane-1,3'-indolin]-2'-one

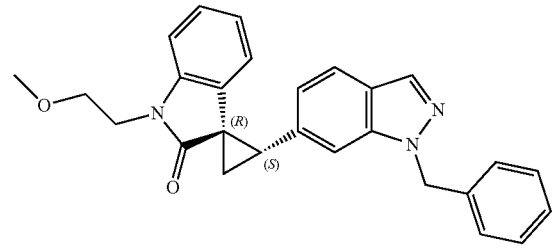

The title compound was prepared in a manner similar to the method of (1R,2S)-1'-benzyl-2-(1-benzyl-1H-indazol-6-yl)spiro[cyclopropane-1,3'-indolin]-2'-one using (S)-1-(1-benzyl-1H-indazol-6-yl)ethane-1,2-diyl dimethanesulfonate (1.22 g, 2.87 mmol) and 1-(2-methoxyethyl)indolin-2-one (550.0 mg, 2.87 mmol). Purification on Biotage Isolera (0-60% EtOAc in hexane, SNAP 25 g column) yielded the title compound as a pale brown solid (774 mg, 64%). $^1$H NMR (400 MHz, CDCl$_3$) δ 8.01 (s, 1H), 7.60 (d, J=8.0 Hz, 1H), 7.29-7.27 (m, 3H), 7.19 (s, 1H), 7.14-7.09 (m, 3H), 6.98 (d, J=7.6 Hz, 1H), 6.92 (d, J=8.4 Hz, 1H), 6.54 (t, J=7.2 Hz, 1H), 5.75 (d, J=7.6 Hz, 1H), 5.60 (t, J=16.0 Hz, 1H), 5.51 (d, J=16.0 Hz, 1H), 4.08-4.03 (m, 1H), 4.00-3.95 (m, 1H), 3.69 (t, J=5.6 Hz, 2H), 3.43 (t, J=8.0 Hz, 1H), 3.38 (s, 3H), 2.24 (dd, J=9.2, 4.8 Hz, 1H), 2.00 (dd, J=8.4, 5.6 Hz, 1H); MS ESI 424.2 [M+H]⁺, calcd for [C₂₇H₂₅N₃O₂+H]⁺ 424.2.

Synthesis of (1R,2S)-2-(1H-indazol-6-yl)-1'-(2-methoxyethyl)spiro[cyclopropane-1,3'-indolin]-2'-one

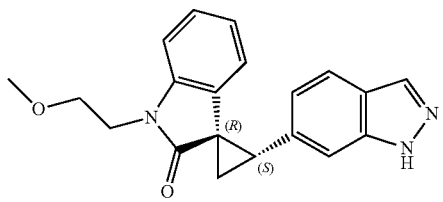

A solution of KO^tBu (1M, 11.97 mL, 11.9 mmol) was added to a solution of (1R,2S)-2-(1H-indazol-6-yl)-1'-(2-methoxyethyl)spiro[cyclopropane-1,3'-indolin]-2'-one (390 mg, 0.92 mmol) in anhydrous THF (1.95 mL) at 0° C. and the mixture was stirred for 15 min at the same temperature. Then anhydrous DMSO (1.18 mL, 16.6 mmol) was added via syringe to the mixture in single lot at 0° C. and stirring was continued for 5 min. Then, reaction mixture was purged with O₂ gas for 1.5 h at 0° C. After stirring at 0° C. for a further 15 min, reaction mixture was quenched with 25% aq. NH₄Cl (10 mL). The product was extracted using EtOAc (20 mL×2), and the combined EtOAc layer was washed with water (10 mL) and dried over an. sodium sulfate and concentrated under vacuum at 40° C./125 mbar. The resultant pale yellowish residue was purified by flash chromatography on Biotage Isolera (using 5-10% EtOAc in hexane, SNAP 25 g column) to give the title compound as a white solid (205 mg, 67%). ¹H NMR (400 MHz, CDCl₃) δ 8.08 (s, 1H), 7.65 (d, J=8.4 Hz, 1H), 7.42 (s, 1H), 7.12 (t, J=7.6 Hz, 1H), 7.00 (t, J=8.0 Hz, 2H), 6.60 (t, J=7.6 Hz, 1H), 5.90 (d, J=7.2 Hz, 1H), 4.10-3.97 (m, 2H), 3.70 (t, J=5.6 Hz, 2H), 3.47 (t, J=8.4 Hz, 1H), 3.38 (s, 3H), 2.29 (dd, J=8.8, 4.4 Hz, 1H), 2.08 (dd, J=6.8, 4.4 Hz, 1H); MS ESI 334.2 [M+H]⁺, calcd for [C₂₀H₁₉N₃O₂+H]⁺ 334.2.

Synthesis of (1R,2S)-2-(3-iodo-1H-indazol-6-yl)-1'-(2-methoxyethyl)spiro[cyclopropane-1,3'-indolin]-2'-one

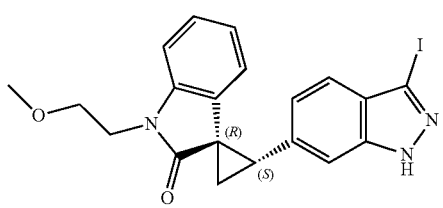

The title compound was prepared in a manner similar to the chiral synthetic method of Example A10 using (1R,2S)-2-(1H-indazol-6-yl)-1'-(2-methoxyethyl)spiro [cyclopropane-1,3'-indolin]-2'-one (260 mg, 0.779 mmol). Purification using 0-30% EtOAc in hexane on Biotage Isolera with SNAP 25 g column yielded the title compound as a white solid (235 mg, 66%; 98% ee) with the major (1R,2S) enantiomer eluting at 2.6 min (Phenomenex Lux 5μ, Amy-lose-2 150×4.6 mm, 2.5 mL/min with isocratic at 20% EtOH in hexane for 0.5 min, then gradient 20-50% EtOH in hexane over 2.5 min, then isocratic at 50% for 1 min). From the racemic reference standard, the retention time of the (1S,2R) enantiomer was 3.2 min using this method. ¹H NMR (400 MHz, CDCl₃) δ 10.39 (s, 1H), 7.40 (d, J=8.8 Hz, 1H), 7.34 (s, 1H), 7.14 (t, J=7.6 Hz, 1H), 7.06-7.01 (m, 2H), 6.63 (t, J=7.2 Hz, 1H), 5.87 (d, J=7.6 Hz, 1H), 4.14-3.97 (bm, 2H), 3.70 (t, J=5.6 Hz, 2H), 3.46 (t, J=7.6 Hz, 1H), 3.39 (s, 3H), 2.28-2.26 (m, 1H), 2.05-2.01 (m, 1H); MS ESI 460.1 [M+H]⁺, calcd for [C₂₀H₁₈IN₃O₂+H]⁺ 460.0. Optical Rotation: [α]²²_D=−239° (c 0.243, MeOH).

Preparation of Compounds of the Invention

Example A1. (1R*,2S*)-2-(1H-indazol-5-yl)spiro[cyclopropane-1,3'-indolin]-2'-one

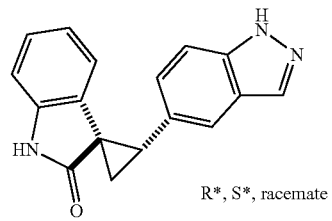

To a solution of trimethylsulfoxonium iodide (33 mg, 0.15 mmol) in anhydrous DMF (1 mL) was added sodium hydride (60% dispersion in oil) (16 mg, 0.4 mmol) at 0° C. The mixture was stirred for 15 min after which time (E)-3-((1H-indazol-5-yl)methylene)indolin-2-one (26 mg, 0.1 mmol) was added. The solution was stirred overnight at rt. The reaction was quenched with sat. NH₄Cl solution (2 mL), extracted with EtOAc (50 mL), dried over MgSO₄ and concentrated to dryness. The title was compound isolated by preparative HPLC as a white solid (5 mg, 18%). ¹H NMR (400 MHz, d₆-DMSO) δ 13.03 (s, 1H), 10.58 (d, 1H, J=8.3 Hz), 8.02 (s, 1H), 7.74 (s, 1H), 7.40 (d, 1H, J=8.9 Hz), 7.11 (d, 1H, J=8.6 Hz), 6.98 (t, 1H, J=7.7 Hz), 6.83 (d, 1H, J=7.6 Hz), 6.50 (t, 1H, J=7.3 Hz), 5.94 (d, 1H, 7.5 Hz), 3.17-3.13 (m, 1H), 2.27-2.23 (m, 1H), 1.98-1.95 (m, 1H); MS ESI 276.1 [M+H]⁺, calcd for [C₁₇H₁₃N₃O+H]⁺ 276.3.

Example A2. (1R*,2S*)-2-(1H-indazol-6-yl)spiro[cyclopropane-1,3'-indolin]-2'-one

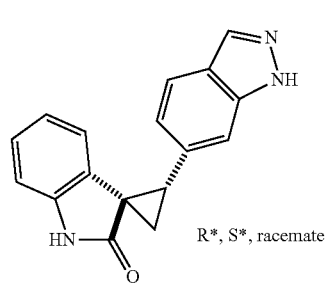

To a solution of trimethylsulfoxonium iodide (264 mg, 1.2 mmol) in anhydrous DMF (40 mL) was added sodium hydride (60% dispersion in oil) (140 mg, 3.48 mmol) at 0° C. The mixture was stirred for 15 min after which time (E)-3-((1H-indazol-6-yl)methylene)indolin-2-one (151 mg, 0.58 mmol) was added. The solution was stirred overnight at rt. The reaction was quenched with sat. NH$_4$Cl solution (10 mL), extracted with EtOAc (4×50 mL), dried over MgSO$_4$ and concentrated to dryness. The major diastereomer was isolated by silica gel chromatography (EtOAc/Hex 1:1) as a beige solid (44 mg, 28%). $^1$H NMR (400 MHz, d$_6$-DMSO) δ 13.01 (s, 1H), 10.61 (d, 1H J=8.3 Hz), 8.01 (s, 1H), 7.63 (d, 1H, J=8.3 Hz), 7.44 (s, 1H), 6.99 (t, 1H, J=7.5 Hz), 6.92 (d, 1H, J=8.0 Hz), 6.84 (d, 1H, J=8.0 Hz), 6.51 (t, 1H, J=7.0 Hz), 5.98 (d, 1H, 8.0 Hz), 3.20-3.17 (m, 1H), 2.30-2.26 (m, 1H), 2.00-1.95 (m, 1H); MS ESI 276.1 [M+H]$^+$, calcd for [C$_{17}$H$_{13}$N$_3$O+H]$^+$ 276.3.

Example A3. (1S,2R)-2-(1H-indazol-6-yl)spiro-[cyclopropane-1,3'-indolin]-2'-one

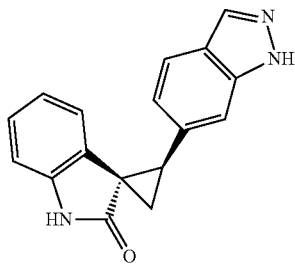 [SMILES: O=C1Nc2ccccc2[C@@]12C[C@@H]2c1ccc2cn[nH]c2c1]

Racemic (1R*,2S*)-2-(1H-indazol-6-yl)spiro[cyclopropane-1,3'-indolin]-2'-one (25 mg, prepared in example A2) was separated using chiral HPLC: Chiralpak 1A (3×15 cm), (30% methanol (0.1% DEA)/CO$_2$, 70 mL/min) to give a white solid (11.8 mg)

Analytical HPLC: Chiralpak 1A (15×0.46 cm), (40% methanol (0.1% DEA)/CO$_2$, 3 mL/min) 98% e.e., Rt=2.7 min.

Example A4. (1R,2S)-2-(1H-indazol-6-yl)spiro[cyclopropane-1,3'-indolin]-2'-one

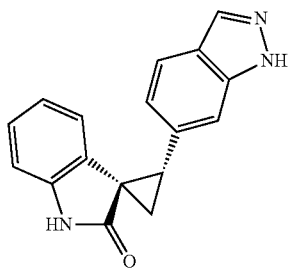 [SMILES: O=C1Nc2ccccc2[C@]12C[C@H]2c1ccc2cn[nH]c2c1]

HPLC Resolution:

Racemic (1R*,2S*)-2-(1H-indazol-6-yl)spiro[cyclopropane-1,3'-indolin]-2'-one (25 mg, prepared in example A2) was separated using chiral HPLC: Chiralpak 1A (3×15 cm), (30% methanol (0.1% DEA)/CO$_2$, 70 mL/min) to give a white solid (11.5 mg)

Analytical HPLC: Chiralpak 1A (15×0.46 cm), (40% methanol (0.1% DEA)/CO$_2$, 3 mL/min) 97% e.e., Rt=5.2 min).

Chiral Synthesis:

A solution of (1R,2S)-2-(N1-benzyl-1H-indazol-6-yl) spiro-[N-benzyl-cyclopropane-1,3-indolin]-2'-one (6.5 g, up to 14 mmol; contains some solvent) in a mixture of DMSO (20 mL, 286 mmol) and THF (200 mL) was cooled in ice before addition of KO$^t$Bu (10.0 g, 89 mmol). The mixture darkened immediately. The mixture was purged gently with oxygen from balloons, warming slowly to rt. NMR of a sample after 5 h showed approx. 30% conversion, and so the mixture was let stir overnight under a balloon of oxygen (no purge). No further conversion had occurred, and so further KO$^t$Bu (20.0 g, 178 mmol) was added. Uptake of oxygen was immediately evident, suggesting that this large excess of base is required for effective deprotection. After a further 5 h, the mixture was poured into sat. aq. NH$_4$Cl (100 mL). Most of the THF was removed under reduced pressure, and the resulting mixture was extracted with portions of EtOAc (4×50 mL). The combined organic portions were washed with sat. aq. sodium thiosulfate (50 mL) and brine (50 mL), dried over Na$_2$SO$_4$, filtered and concentrated. The residue was slurried in CH$_2$Cl$_2$ (100 mL) and poured onto a short silica pad (2 cm depth×5 cm diameter) under suction. The major byproduct (Rf 0.6 in 1:1 EtOAc/cyclohexane, Rf 0.15 in CH$_2$Cl$_2$) was eluted using CH$_2$Cl$_2$ (ca. 1 L). The product (Rf 0.25 in 1:1 EtOAc/cyclohexane) was eluted using 2% then 5% MeOH/EtOAc. An impurity co-eluted with the product, as the latter 'streaked' badly. Concentrating the product containing fractions afforded the title compound (2.5 g, 64%) as a pale brown solid, contaminated with a second cyclopropane-containing compound (<10%; possibly a monobenzylated compound). HPLC indicated an optical purity of 94% e.e. (although the presence of a co-eluting impurity is suspected), with the major (1R,2S) enantiomer eluting at 14.3 min (Daicel Chiralpak AS-H (250×4.6 mm); isocratic 40% EtOH in n-heptane; 1 ml/min; 35° C.; Detection: 254, 230, 210 nm). From the racemic reference standard, the retention time of the (1S,2R) enantiomer was 9.9 min using this method. Analytical data was identical for that obtained in Example A2.

Example A5. (1R*,2R*)-2-(1H-indazol-6-yl)spiro[cyclopropane-1,3'-indolin]-2'-one

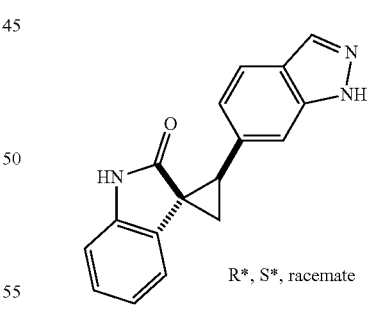

R*, S*, racemate

The minor diastereomer from the reaction of Example A2 was isolated as beige solid (3.5 mg, 2%). $^1$H NMR (400 MHz, DMSO-d$_6$) δ 12.97 (s, 1H), 10.33 (d, 1H J=8.3 Hz), 7.99 (s, 1H), 7.59 (d, 1H, J=8.2 Hz), 7.41 (s, 1H), 7.18-7.12 (m, 2H), 6.99-6.94 (m, 2H), 6.86 (d, 1H, J=7.8 Hz), 3.32 (t, 1H, J=8.3 Hz), 2.27-2.23 (m, 1H), 2.18-2.15 (m, 1H); MS ESI 276.1 [M+H]$^+$, calcd for [C$_{17}$H$_{13}$N$_3$O+H]$^+$ 276.3.

Example A6. (1R*,2S*)- and (1R*,2R*)-2-(3-iodo-1H-indazol-6-yl)-5'-methoxyspiro-[cyclopropane-1,3'-indolin]-2'-one

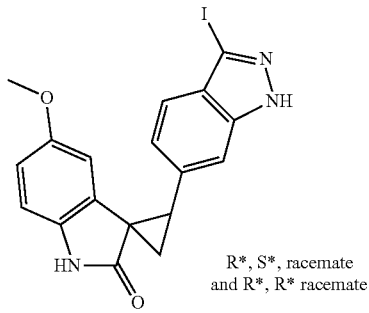 [SMILES: COc1ccc2c(c1)C1(CC1c1ccc3c(I)n[nH]c3c1)C(=O)N2]

R*, S*, racemate
and R*, R* racemate

To a solution of NaH (380 mg, 9.5 mmol) in DMF (8 mL) at 0° C. was added trimethylsulfoxonium iodide (694 mg, 3.15 mmol). The resulting mixture was stirred at rt for 30 min followed by the addition of (E/Z)-3-((3-iodo-1H-indazol-6-yl)methylene)-5-methoxyindolin-2-one (658 mg, 1.6 mmol, E/Z ratio 84:16) in DMF (2 mL). The reaction mixture was stirred at rt for 18 h. The reaction was cooled to 0° C. and quenched with saturated NH$_4$Cl. The mixture was extracted with EtOAc and the combined organic extracts were washed with brine, dried over MgSO$_4$ and concentrated to give a yellow viscous oil. The crude product was purified by silica gel chromatography (95:5 CH$_2$Cl$_2$/MeOH) to yield a yellow solid, which was then triturated with a 1:1 mixture of hexanes and EtOAc to give the title compound as a white powder (471 mg, 69%). A mixture of diastereomers (7:1 by NMR) was obtained. In repeated runs, the ratio of diastereomers varied from 6:1 to 10:1 in favor of the 1R*,2S* diastereomer. The material was used without further purification as an intermediate for subsequent reactions. Alternatively the material was recrystallized from methanol to yield the title compound as a 12:1 mixture in favour of the 1R*,2S* diastereomer. Analytical data for the major isomer: $^1$H NMR (400 MHz, d$_6$-DMSO) δ 13.48 (s, 1H), 10.43 (s, 1H), 7.49 (s, 1H), 7.33 (d, J=8.4 Hz, 1H), 7.02 (d, J=8.4 Hz, 1H), 6.74 (d, J=8.4 Hz, 1H), 6.57 (dd, J=8.4 Hz, J=2.4 Hz, 1H), 5.62 (d, J=2.4 Hz, 1H), 3.29 (s, 3H), 3.18 (t, J=8.2 Hz, 1H), 2.34 (dd, J=7.8 Hz, J=4.6 Hz, 1H), 1.98 (dd, J=9.2 Hz, J=4.8 Hz, 1H); MS ESI 432.1 [M+H]$^+$, calcd for [C$_{18}$H$_{14}$IN$_3$O$_2$+H]$^+$ 432.0.

Example A7. (1R,2S)-2-(3-iodo-1H-indazol-6-yl)-5'-methoxyspiro[cyclopropane-1,3'-indolin]-2'-one

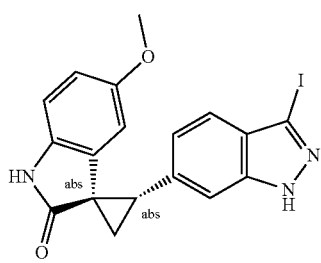 [SMILES: COc1ccc2c(c1)[C@]1(C[C@H]1c1ccc3c(I)n[nH]c3c1)C(=O)N2]

HPLC Resolution:

Racemic (1R*,2S*)-2-(3-iodo-1H-indazol-6-yl)-5'-methoxyspiro spiro[cyclopropane-1,3'-indolin]-2'-one (15 g, prepared in example A6) was separated using chiral HPLC: Chiralcel OJ-H (3×15 cm), (30% methanol (0.1% DEA)/CO$_2$, 75 mL/min) to give a white solid (6.75 g)

Analytical HPLC: Chiralpak 1A (15×0.46 cm), (40% isopropanol (0.1% DEA)/CO$_2$, 3 mL/min) 99% e.e., Rt=2.1 min).

Chiral Synthesis:

A. (1R,2S)-1'-benzyl-2-(1-benzyl-1H-indazol-6-yl)-5'-methoxyspiro[cyclopropane-1,3'-indolin]-2'-one The title compound was prepared in a manner similar to the method of (1R,2S)-1'-benzyl-2-(1-benzyl-1H-indazol-6-yl)spiro[cyclopropane-1,3'-indolin]-2'-one using (S)-1-(1-benzyl-1H-indazol-6-yl)ethane-1,2-diyl dimethanesulfonate (3.35 g, 7.90 mmol) and 1-benzyl-5-methoxyindolin-2-one (2.00 g, 7.90 mmol). The crude product was purified by silica gel chromatography (15-40% EtOAc in hexane) followed by trituration (EtOAc) to give the title compound as a white solid (1.97 g, 52%). $^1$H NMR (400 MHz, CDCl$_3$) δ 8.01 (s, 1H), 7.64 (d, J=8.2 Hz, 1H), 7.36-7.23 (m, 10H), 7.14 (d, J=7.2 Hz, 2H), 6.94 (d, J=8.3 Hz, 1H), 6.63 (d, J=8.3 Hz, 1H), 6.53 (d, J=8.4 Hz, 1H), 5.61 (d, J=15.1 Hz, 1H), 5.54 (d, J=15.4 Hz, 1H), 5.37 (s, 1H), 5.07 (d, J=15.4 Hz, 1H), 4.95 (d, J=15.7 Hz, 1H), 3.51 (t, J=8.1 Hz, 1H), 3.18 (s, 3H), 2.32-2.29 (m, 1H), 2.09-2.00 (m, 1H). MS ESI 486.3 [M+H]$^+$, calcd for [C$_{32}$H$_{27}$N$_3$O$_2$+H]$^+$ 486.2.

B. (1R,2S)-2-(1H-indazol-6-yl)-5'-methoxyspiro[cyclopropane-1,3'-indolin]-2'-one The title compound was prepared in a manner similar to the chiral synthetic method of Example A4 using (1R,2S)-1'-benzyl-2-(1-benzyl-1H-indazol-6-yl)-5'-methoxy spiro[cyclopropane-1,3'-indolin]-2'-one (1.0 g, 2.1 mmol). Purification via column chromatography (silica gel, 30-80% EtOAc in hexane) yielded the title compound as a white solid (0.50 g, 80%). $^1$H NMR (400 MHz, DMSO-d$_6$) δ 13.02 (br s, 1H), 10.42 (br s, 1H), 8.02 (s, 1H), 7.64 (d, J=8.3 Hz, 1H), 7.45 (s, 1H), 6.94 (d, J=7.8 Hz, 1H), 6.73 (d, J=8.2 Hz, 1H), 6.55 (d, J=8.6 Hz, 1H), 5.62 (s, 1H), 3.20 (s, 3H), 3.18 (t, J=8.7 Hz, 1H), 2.34-2.28 (m, 1H), 1.98-1.95 (m 1H). MS ESI 306.1 [M+H]$^+$, calcd for [C$_{18}$H$_{15}$N$_3$O$_2$+H]$^+$ 306.12. Optical Rotation: [α]$^{23}_D$=−225° (c 0.441, MeOH)

C. (1R,2S)-2-(3-iodo-1H-indazol-6-yl)-5'-methoxyspiro[cyclopropane-1,3'-indolin]-2'-one The title compound was prepared in a manner similar to the chiral synthetic method for Example A10 using (1R,2S)-2-(1H-indazol-6-yl)-5'-methoxyspiro[cyclopropane-1,3'-indolin]-2'-one (0.40 g, 1.3 mmol). Crude product was triturated with EtOAc (5 mL) to yield the title compound as a white solid (0.52 g, 93%, >98% e.e.) with the major (1R,2S) enantiomer eluting at 8.5 min (Phenomenex Lux 5µ, Cellulose-2 (150×4.6 mm); 1.0 mL/min; isocratic at 10% $^i$PrOH in n-hexane for 1.0 min, then gradient 10-90% $^i$PrOH in n-hexane over 10 min, then isocratic at 90% $^i$PrOH in n-hexane for 2.0 min; 1.0 ml/min; 24° C.; Detection: 254 nm). From the racemic reference standard, the retention time of the (1S,2R) enantiomer was 6.2 min using this method. $^1$H NMR (400 MHz, DMSO-d$_6$) δ 13.48 (br s, 1H), 10.43 (br s, 1H), 7.49 (s, 1H), 7.31 (d, J=8.6 Hz, 1H), 7.02 (d, J=8.1 Hz, 1H), 6.73 (d, J=8.4 Hz, 1H), 6.57 (d, J=8.6 Hz, 1H), 5.62 (s, 1H), 3.29 (s, 3H), 3.19 (t, J=8.4 Hz, 1H), 2.36-2.32 (m, 1H), 1.99-1.96 (m 1H). MS ESI 432.1 [M+H]⁺, calcd for [C₁₈H₁₄IN₃O₂+H]⁺ 432.0. Optical Rotation: [α]²²_D=−143° (c 0.399, MeOH).

Example A8. (1S,2R)-2-(3-iodo-1H-indazol-6-yl)-5'-methoxyspiro[cyclopropane-1,3'-indolin]-2'-one

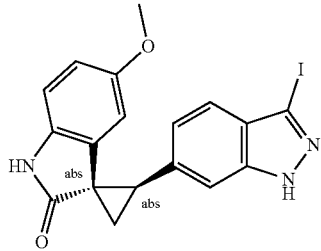 [SMILES: COc1ccc2c(c1)[C@@]1(C[C@@H]1c1ccc3c(I)n[nH]c3c1)C(=O)N2]

Racemic (1R*,2S*)-2-(3-iodo-1H-indazol-6-yl)-5'-methoxyspiro spiro[cyclopropane-1,3'-indolin]-2'-one (15 g, prepared in example A6) was separated using chiral HPLC: Chiralcel OJ-H (3×15 cm), (30% methanol (0.1% DEA)/CO₂, 75 ml/min) to give a white solid (6.6 g).

Analytical HPLC: Chiralpak 1A (15×0.46 cm), (40% isopropanol (0.1% DEA)/CO₂, 3 mL/min) 99% e.e., Rt=3.4 min).

Example A9. (1R*,2S*)-2-(3-iodo-1H-indazol-6-yl)spiro[cyclopropane-1,3'-indolin]-2'-one

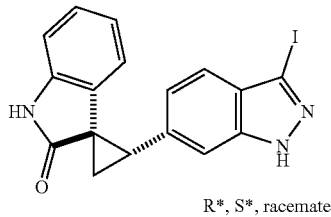

R*, S*, racemate

A. (1R*,2S*)- and (1R*,2R*)-2-(3-iodo-1H-indazol-6-yl)spiro[cyclopropane-1,3'-indolin]-2'-one The compound was used without further purification as an intermediate, or the pure diastereomer was obtained in the following procedure. Sodium hydride (309.9 mg, 7.75 mmol) (60% dispersion in oil) added to anhydrous DMF (2.5 mL) at room temperature. Then trimethylsulfoxonium iodide (568.4 mg, 2.58 mmol) was added to the suspension at the same temperature. The mixture was stirred for 15 min after which time a solution of (E/Z)-3-((3-iodo-1H-indazol-6-yl)methylene)-indolin-2-one (500 mg, 1.29 mmol) in DMF (2.0 ml) was added. The solution was stirred at 55° C. for 5 h prior to quenching the reaction over methanol solution (1 mL) at room temperature for 15 min before addition of water (50 mL). The product was extracted with ethyl acetate (2×50 mL), dried over anhydrous Na₂SO₄ and concentrated to dryness. The solid was suspended in toluene (21 mL) and collected to give the title compound (331 mg, 64%). as a 9:1 mixture in favor of the R*,S* diastereomer. This white solid was used without further purification as an intermediate in subsequent reactions. ¹H NMR (400 MHz, d₆-DMSO) δ 13.47 (s, 0.9H), 13.41 (s, 0.1H), 10.62 (s, 0.9H), 10.35 (s, 0.1H), 7.47 (s, 0.9H), 7.43 (s, 0.1H), 7.30 (d, J=8.0 Hz, 0.9H), 7.26 (d, J=8.0 Hz, 0.1H), 7.23 (m, 0.1H), 7.15 (m, 0.3H), 7.05-6.98 (m, 2H), 6.85 (m, 1H), 6.53 (t, J=7.6 Hz, 0.9H), 5.97 (d, J=7.6 Hz, 0.9H), 3.33 (m, 0.1H, partially obscured by water signal), 3.18 (t, J=8.4 Hz, 0.9H), 2.31 (dd, J=7.2, 4.8 Hz, 0.9H), 2.26 (m 0.1H), 2.16 (dd, J=8.8, 4.0 Hz, 0.1H), 1.98 (dd, J=8.8, 4.8 Hz, 0.9H).

B. (1R*,2S*)-2-(3-iodo-1H-indazol-6-yl)spiro[cyclopropane-1,3'-indolin]-2'-one

The diastereomeric mixture (100 mg) obtained above was treated with THF (1 mL) at 55° C. for 15 min then cooled to room temperature for 30 min. The off-white solid was collected by filtration to give the title compound (32 mg, 32%). ¹H NMR (400 MHz, DMSO-d₆) δ 13.47 (s, 1H), 10.62 (s, 1H), 7.47 (s, 1H), 7.30 (d, J=8.0 Hz, 1H), 7.02-6.98 (m, 2H), 6.84 (d, J=7.6 Hz, 1H), 6.53 (t, J=7.6 Hz, 1H), 5.97 (d, J=7.6 Hz, 1H), 3.18 (t, J=8.4 Hz, 1H), 2.31 (dd, J=7.2 Hz, J=4.8 Hz, 1H), 1.98 (dd, J=8.8 Hz, J=4.8 Hz, 1H); MS ESI 402.0 [M+H]⁺, calcd for [C₁₇H₁₂IN₃O+H]⁺ 402.0.

Example A10. (1R,2S)-2-(3-iodo-1H-indazol-6-yl)spiro[cyclopropane-1,3'-indolin]-2'-one

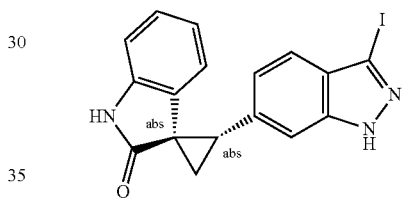

HPLC Resolution:
Racemic (1R*,2S*)-2-(3-iodo-1H-indazol-6-yl)spiro[cyclopropane-1,3'-indolin]-2'-one (35 mg, prepared in example A9) was separated using chiral HPLC: Lux Cellulose AXIA (150×21.2 mm), (Gradient 10% isopropanol/Hexane to 90% isopropanol/hexane 20 ml/min) to give a white solid (8.8 mg).

Analytical HPLC: Lux Cellulose AXIA (150×4.6 mm), (Gradient 10% isopropanol/Hexane to 90% isopropanol/hexane 1 ml/min) 98% e.e., Rt=7.8 min).

Chiral Synthesis:
A mixture of (1R,2S)-2-(1H-indazol-6-yl)spiro-[cyclopropane-1,3'-indolin]-2'-one (2.20 g, 8.0 mmol, ca. 94% ee) and K₂CO₃ (2.21 g, 16.0 mmol) in dry DMF (20 mL) was treated with a solution of I₂ (3.45 g, 13.6 mmol) in dry DMF (15 mL), adding the latter by syringe pump over 45 min. The mixture was stirred for 1.5 h and then poured into a mixture of water (400 mL) and sat. aq. Na₂S₂O₃. The resulting mixture was triturated in an ultrasound bath for 30 min to break up the sticky clumps of solid, then filtered. The solids were washed with water (2×50 mL), partially dried under suction, then stripped twice with acetone to remove residual water. HPLC of the crude mixture indicated an optical purity of 95% e.e. with the major (1R,2S) enantiomer eluting at 14.1 min (Daicel Chiralpak AS-H (250×4.6 mm); isocratic 40% EtOH in n-heptane; 1 mL/min; 35° C.; Detection: 254, 230, 210 nm). From the racemic reference standard, the retention time of the (1S,2R) enantiomer was 8.4 min using this method, and both enantiomers of the minor diastereomer product were also detected at 6.0 min and 6.9 min.

Baseline material was removed by passing an EtOAc solution of the product through a short silica pad (2 cm depth×4 cm diameter), eluting with further EtOAc. Further purification was then attempted by trituration. Et$_2$O and toluene removed some of the impurities, but no enhancement of optical purity was observed. Recrystallization from THF/cyclohexane and EtOAc/cyclohexane were also unsuccessful, and so the material was purified by column chromatography on silica (20 cm depth×4 cm diameter) using 1:1 EtOAc/cyclohexane to afford the title compound (1.47 g, 46%) as an off-white powder. Analytical data was identical to that obtained in Example A9.

Example A11. (1S,2R)-2-(1H-indazol-6-yl)spiro [cyclopropane-1,3'-indolin]-2'-one

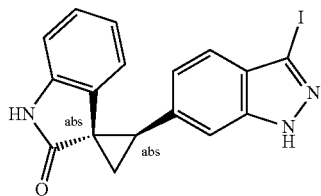 [SMILES: O=C1Nc2ccccc2[C@@]12C[C@@H]2c1ccc2c(I)n[nH]c2c1]

Racemic (1R*,2S*)-2-(3-iodo-1H-indazol-6-yl)spiro[cyclopropane-1,3'-indolin]-2'-one (35 mg, prepared in example A9) was separated using chiral HPLC: Lux Cellulose AXIA (150×21.2 mm), (Gradient 10% isopropanol/Hexane to 90% isopropanol/hexane 20 ml/min) to give a white solid (7.7 mg).

Analytical HPLC: Lux Cellulose AXIA (150×4.6 mm), (Gradient 10% isopropanol/Hexane to 90% isopropanol/hexane 1 ml/min) 98% e.e., Rt=6.7 min).

Example A12. (1R*,2S*)-5'-bromo-2-(1H-indazol-6-yl)spiro[cyclopropane-1,3'-pyrrolo[2,3-b]pyridin]-2'(1'H)-one

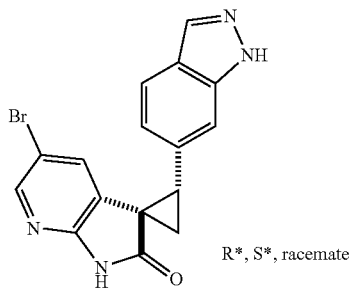

To a mixture of trimethylsulfoxonium iodide (220 mg, 1 mmol) and 60% NaH (120 mg, 3 mmol) in a RBF was added DMF (5 mL). The resulting mixture was stirred for 5 min at rt. A solution of (E & Z)-3-((1H-indazol-6-yl)methylene)-5-bromo-1H-pyrrolo[2,3-b]pyridin-2(3H)-one (170 mg, 0.5 mmol) in DMF (5 mL) was added. After addition, the resulting mixture was heated at 55° C. (oil temp.) for 2.5 h. Upon cooling to 0° C., it was quenched with ice, sat. NH$_4$Cl, extracted with EtOAc (50 mL×2). Combined extracts were dried (Na$_2$SO$_4$) and concentrated to give light brown liquid. The residue was purified by flash chromatography (eluent: CH$_2$Cl$_2$/MeOH/Et$_3$N 100:5:1 to 100:10:1) to give the title compound as a pale yellow oil which was triturated with CH$_2$Cl$_2$. The resulting precipitates were collected by suction filtration and dried to give the title compound (66 mg, 37%) as a white solid. $^1$H NMR (400 MHz, DMSO-d$_6$) δ 13.07 (s, 1H), 11.42 (s, 1H), 8.04 (s, 1H), 8.02 (d, J=2.0 Hz, 1H), 7.68 (d, J=8.4 Hz, 1H), 7.51 (s, 1H), 6.98 (d, J=8.0 Hz, 1H), 6.44 (d, J=2.0 Hz, 1H), 2.60 (dd, J=8.0 Hz, J=4.4 Hz, 1H), 2.10 (dd, J=8.8 Hz, J=4.8 Hz, 1H); MS ESI 355.1 [M+H]$^+$, calcd for [C$_{16}$H$_{11}$BrN$_4$O+H]$^+$ 355.0.

Example A13. (1R*,2S*)-5'-Methoxy-2-(3-(6-(4-methylpiperazin-1-yl)pyridin-3-yl)-1H-indazol-6-yl) spiro[cyclopropane-1,3'-indolin]-2'-one

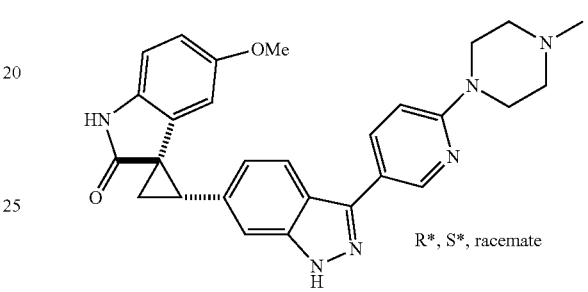

To a solution of NaH (260 mg, 6.5 mmol) in DMF (10 mL) at 0° C. was added trimethylsulfoxonium iodide (475 mg, 2.2 mmol). The resulting mixture was stirred at rt for 30 min followed by the addition of 5-methoxy-3-((3-(6-(4-methylpiperazin-1-yl)pyridin-3-yl)-1H-indazol-6-yl)methylene)indolin-2-one (504 mg, 1.1 mmol) in DMF (2 mL). The reaction mixture was stirred at rt for 24 h. Additional portion of NaH (130 mg, 3.3 mmol) and trimethylsulfoxonium iodide (238 mg, 1.1 mmol) were added to the reaction mixture and the reaction was stirred at rt for another 19 h. The reaction was cooled to 0° C. and quenched with saturated NH$_4$Cl. The mixture was extracted with EtOAc and the combined organic extracts were washed with brine, dried over MgSO$_4$ and concentrated to give a yellow viscous oil. The crude product was purified by silica gel chromatography (95:5 to 90:10 CH$_2$Cl$_2$/MeOH) to yield a viscous yellow oil. MeOH was added and the resulting suspension was sonicated for 5 min and the title compound was collected by vacuum filtration as a pale yellow powder (224 mg, 43%). $^1$H NMR (400 MHz, DMSO-d$_6$) δ 13.08 (br s, 1H), 10.44 (br s, 1H), 8.70 (d, J=2.4 Hz, 1H), 8.08 (dd, J=8.8, 2.3 Hz, 1H), 7.91 (d, J=8.5 Hz, 1H), 7.49 (s, 1H), 7.00 (d, J=8.8, 1H), 6.96 (d, J=8.9 Hz, 1H), 6.74 (d, J=8.4 Hz, 1H), 6.57 (dd, J=8.4, 2.4 Hz, 1H), 5.70 (d, J=2.5, 1H), 3.54 (t, J=4.6 Hz, 4H), 3.29 (s, 3H), 3.19 (t, J=8.3 Hz, 1H), 2.41 (t, J=4.9 Hz, 4H), 2.34 (dd, J=8.0, 4.8 Hz, 1H), 2.22 (s, 3H), 1.99 (dd, J=8.7, 4.7 Hz, 1H); MS ESI 481.3 [M+H]$^+$, calcd for [C$_{28}$H$_{28}$N$_6$O$_2$+H]$^+$ 481.23.

Example A14. (1R*,2S*)-5'-Methoxy-2-(3-(6-(4-methylpiperazin-1-yl)pyridin-3-yl)-1H-indazol-6-yl)spiro[cyclopropane-1,3'-indolin]-2'-one dihydrochloride

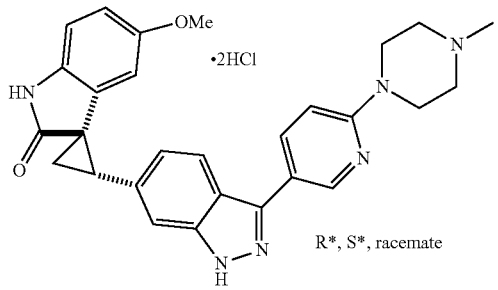

R*, S*, racemate

HCl (4M in dioxane, 0.20 mL, 0.80 mmol) was added in a dropwise manner to a solution of (1R*,2S*)-5'-methoxy-2-(3-(6-(4-methylpiperazin-1-yl)pyridin-3-yl)-1H-indazol-6-yl)spiro[cyclopropane-1,3'-indolin]-2'-one (92 mg, 0.19 mmol) in MeOH (1 mL) and DCM (4 mL). The mixture was stirred for 1 h at rt prior to evaporation of the solvent in vacuo. MeOH (5 mL) and EtOAc (3 mL) were added, and filtration yielded the title compound as a beige solid (92.7 mg, 88%). $^1$H NMR (400 MHz, d$_6$-DMSO) δ ppm 13.24 (br. s, 1H), 10.78 (br. s, 1H), 10.46 (s, 1H), 8.72 (s, 1H), 8.22 (dd, J=9.2, 2.0 Hz, 1H), 7.92 (d, J=8.0 Hz, 1H), 7.52 (s, 1H), 7.15 (d, J=8.8 Hz, 1H), 7.03 (d, J=8.4 Hz, 1H), 6.74 (d, J=8.4 Hz, 1H), 6.57 (dd, J=8.4, 2.4 Hz, 1H), 5.71 (d, J=2.4 Hz, 1H), 4.48 (d, J=14 Hz, 2H), 3.50 (d, J=11.6 Hz, 2H), 3.33 (t, J=12.8 Hz, 2H), 3.29 (s, 3H), 3.20 (t, J=8.4 Hz, 1H), 3.09 (m, 2H), 2.80 (d, J=4.4 Hz, 3H), 2.35 (m, 1H), 1.99 (m, 1H).

Example A15. (1S,2R)-5'-methoxy-2-(3-(6-(4-methylpiperazin-1-yl)pyridin-3-yl)-1H-indazol-6-yl)spiro[cyclopropane-1,3'-indolin]-2'-one Racemic (1R*,2S*)-5'-methoxy-2-(3-(6-(4-methylpiperazin-1-yl)pyridin-3-yl)-1H-indazol-6-yl)spiro[cyclopropane-1,3'-indolin]-2'-one (100 mg, prepared in example A13) was separated using chiral HPLC: Chiralcel OJ-H (2×25 cm) (40% methanol/5% DCM (0.1% DEA)/CO$_2$, 65 mL/min) to give a yellow solid (48 mg).

Analytical HPLC: Chiralcel OJ-H (2×0.46 cm) (40% methanol (0.1% DEA)/CO$_2$, 3 mL/min)) 99% e.e., Rt=2.0 min).

Example A16. (1S,2R)-5'-methoxy-2-(3-(6-(4-methylpiperazin-1-yl)pyridin-3-yl)-1H-indazol-6-yl)spiro[cyclopropane-1,3'-indolin]-2'-one

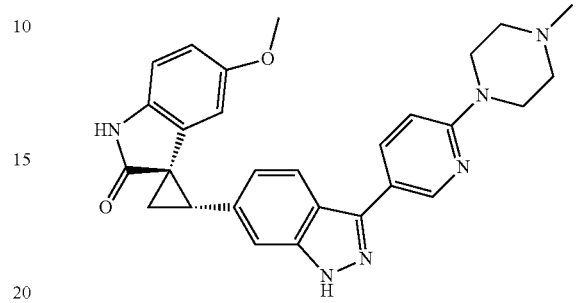

Racemic (1R*,2S*)-5'-methoxy-2-(3-(6-(4-methylpiperazin-1-yl)pyridin-3-yl)-1H-indazol-6-yl)spiro[cyclopropane-1,3'-indolin]-2'-one (100 mg, prepared in example A13) was separated using chiral HPLC: Chiralcel OJ-H (2×25 cm) (40% methanol/5% DCM (0.1% DEA)/CO$_2$, 65 mL/min) to give a yellow solid (45 mg).

Analytical HPLC: Chiralcel OJ-H (2×0.46 cm) (40% methanol (0.1% DEA)/CO$_2$, 3 mL/min)) 99% e.e., Rt=3.5 min).

Example A17. (1R*,2R*)-5'-Methoxy-2-(3-(6-(4-methylpiperazin-1-yl)pyridin-3-yl)-1H-indazol-6-yl)spiro[cyclopropane-1,3'-indolin]-2'-one

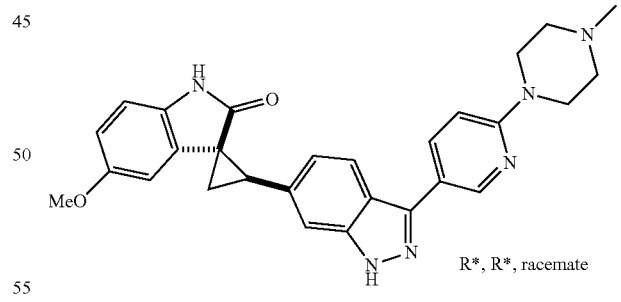

R*, R*, racemate

According to procedure for the synthesis of example A13, the title compound was isolated as a minor diastereomer. $^1$H NMR (400 MHz, DMSO-d$_6$) δ 13.01 (br. s, 1H), 10.15 (br. s, 1H), 8.70 (s, 1H), 8.07 (dd, J=9.0, 2.0 Hz, 1H), 7.84 (d, J=8.5 Hz, 1H), 7.42 (s, 1H), 7.01 (d, J=8.5 Hz, 1H), 6.96 (d, J=8.8 Hz, 1H), 6.82 (s, 1H), 6.77-6.72 (m, 2H), 3.73 (s, 3H), 3.54 (br s, 4H), 3.16-3.15 (m, 1H), 2.41 (t, J=4.2 Hz, 4H), 2.32-2.16 (m, 2H), 2.22 (s, 3H); MS ESI 481.3 [M+H]$^+$, calcd for [C$_{28}$H$_{28}$N$_6$O$_2$+H]$^+$ 481.23.

Example A18. (1R*,2S*)-2-(3-(6-(4-Methylpiperazin-1-yl)pyridin-3-yl)-1H-indazol-6-yl)spiro[cyclopropane-1,3'-indolin]-2'-one

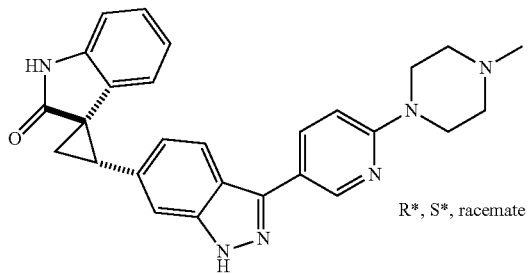

R*, S*, racemate

According to procedure for the synthesis of example A13, except substituting (E)-3-((3-(6-(4-methylpiperazin-1-yl)pyridin-3-yl)-1H-indazol-6-yl)methylene)indolin-2-one (52 mg, 0.122 mmol) to give the title compound as a yellow powder (9 mg, 17%). $^1$H NMR (400 MHz, DMSO-d$_6$) δ 13.07 (br. s, 1H), 10.62 (br. s, 1H), 8.69 (d, J=1.9 Hz, 1H), 8.07 (dd, J=8.7, 2.0 Hz, 1H), 7.89 (d, J=8.4 Hz, 1H), 7.47 (s, 1H), 7.02-6.94 (m, 3H), 6.85 (d, J=7.6 Hz, 1H), 6.54 (t, J=7.3 Hz, 1H), 6.05 (d, J=7.4 Hz, 1H), 3.54 (br. t, J=4.5 Hz, 4H), 3.21-3.16 (m, 1H), 2.40 (t, J=4.4 Hz, 4H), 2.33-2.30 (m, 1H), 2.22 (s, 3H), 2.01-1.98 (m, 1H); MS ESI 451.3 [M+H]$^+$, calcd for [C$_{27}$H$_{26}$N$_6$O+H]$^+$ 451.22.

Example A19. (1R*,2S*)-5'-bromo-2-(3-(6-(4-methylpiperazin-1-yl)pyridin-3-yl)-1H-indazol-6-yl)spiro[cyclopropane-1,3'-indolin]-2'-one

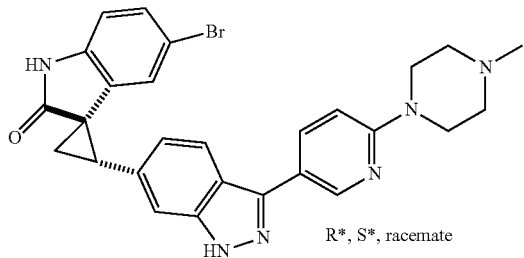

R*, S*, racemate

To a mixture of trimethylsulfoxonium iodide (48.4 mg, 0.22 mmol) and 60% NaH (26.4 mg, 0.66 mmol) in a RBF was added DMF (2 mL). The resulting mixture was stirred for 5 min at rt. A solution of (E/Z)-5-bromo-3-((3-(6-(4-methylpiperazin-1-yl)pyridin-3-yl)-1H-indazol-6-yl)methylene)indolin-2-one (E/Z=3:4, 56.6 mg, 0.11 mmol) in DMF (5 mL) was added. After addition, the resulting mixture was heated at 55° C. (oil temp.) for 2.5 h. Upon cooling to 0° C., it was quenched with ice and sat. NH$_4$Cl, and the product was extracted with EtOAc (30 mL×2). The combined extracts were dried (Na$_2$SO$_4$) and concentrated to give a light yellow liquid. The residue was purified by flash chromatography (eluent: CH$_2$Cl$_2$/MeOH/Et$_3$N 100:5:0.5 to 100:15:0.5) to give the title compound as a light yellow oil which was triturated with methanol. The resulting precipitates were collected by suction filtration and dried to give the title compound (23 mg, 40%) as a white solid. NMR indicated a mixture of two diastereomers (9:1). $^1$H NMR (400 MHz, CD$_3$OD) δ 8.70 (d, J=2.0 Hz, 1H), 8.14 (dd, J=8.8 Hz, J=2.4 Hz, 1H), 7.91 (d, J=8.8 Hz, 1H), 7.50 (s, 1H), 7.20 (dd, J=8.4 Hz, J=2.0 Hz, 1H), 7.03 (d, J=9.6 Hz, 1H), 6.99 (d, J=9.2 Hz, 1H), 6.86 (d, J=8.4 Hz, 1H), 6.13 (d, J=2.0 Hz, 1H), 3.68-3.63 (m, 4H), 3.40 (t, J=8.0 Hz, 1H), 2.62 (t, J=4.8 Hz, 4H), 2.38 (s, 3H), 2.31 (dd, J=8.0 Hz, J=5.2 Hz, 1H), 2.22 (dd, J=8.8 Hz, J=4.8 Hz, 1H); MS ESI 529.5 [M+H]$^+$, calcd for [C$_{27}$H$_{25}$BrN$_6$O+H]$^+$ 529.1.

Example A20. (1R*,2S*)*-5'-Methoxy-2-(3-(6-morpholinopyridin-3-yl)-1H-indazol-6-yl)spiro[cyclopropane-1,3'-indolin]-2'-one

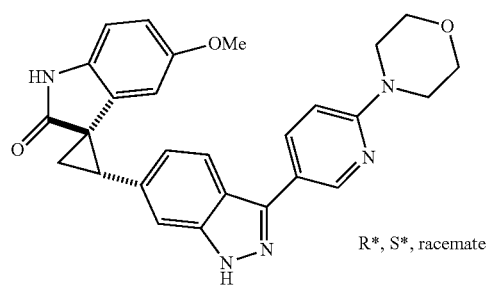

R*, S*, racemate

A. 3-(6-Morpholinopyridin-3-yl)-1-((2-(trimethylsilyl)ethoxy)methyl)-1H-indazole-6-carbaldehyde A mixture 3-iodo-1-((2-(trimethylsilyl)ethoxy)methyl)-1H-indazole-6-carbaldehyde (25 mg, 0.62 mmol), 4-(5-(4,4,5,5-tetramethyl-1,3,2-dioxaborolan-2-yl)pyridin-2-yl)morpholine (22 mg, 0.75 mmol), PdCl$_2$(PPh$_3$)$_2$ (4 mg, 0.006 mmol) and 2M Na$_2$CO$_3$ (0.31 mL, 0.62 mmol) in DME/H$_2$O/EtOH (2.8 mL/0.8 mL/0.4 mL) was sealed and heated with stirring under microwave irradiation at 125° C. for 4 h. Solvent was removed and the crude product was purified by silica gel chromatography (95:5 CH$_2$Cl$_2$/MeOH) to yield a bright yellow foam (266 mg, 97%). $^1$H NMR (400 MHz, CD$_3$OD) δ 10.02 (s, 1H), 8.60 (d, J=2.3 Hz, 1H), 8.13 (s, 1H), 7.99 (dd, J=8.9, 2.5 Hz, 1H), 7.94 (d, J=8.6 Hz, 1H), 7.64 (dd, J=8.7, 1.1 Hz, 1H), 6.80 (d, J=9.1 Hz, 1H), 5.78 (s, 2H), 3.76 (t, J=4.7 Hz, 4H), 3.61 (t, J=8.0 Hz, 2H), 3.49 (t, J=5.1 Hz, 4H), 0.84 (t, J=8.0 Hz, 2H), −0.12 (s, 9H); MS ESI 439.3 [M+H]$^+$, calcd for [C$_{23}$H$_{30}$N$_4$O$_3$Si+H]$^+$ 439.21.

B. (E)-5-Methoxy-3-((3-(6-morpholinopyridin-3-yl)-1-((2-(trimethylsilyl)ethoxy)methyl)-1H-indazol-6-yl)methylene)indolin-2-one A round bottom flask was charged with 5-methoxyoxindole (100 mg, 0.61 mmol), 3-(6-Morpholinopyridin-3-yl)-1-((2-(trimethylsilyl)ethoxy)methyl)-1H-indazole-6-carbaldehyde (266 mg, 0.61 mmol), piperidine (6 uL, 0.06 mmol) and MeOH (4 mL). The reaction was then heated to 60° C. for 4 h. An orange precipitate formed which was further precipitated by cooling to room temperature. The orange powder was then filtered and washed with MeOH to give the title compound (224 mg, 63%). $^1$H NMR (400 MHz, DMSO-d$_6$) 10.46 (s, 1H), 8.79 (d, J=1.5 Hz, 1H), 8.20 (d, J=8.5, 1H), 8.17-8.13 (m, 2H), 7.77 (s, 1H), 7.57 (d, J=8.3 Hz, 1H), 7.13 (s, 1H), 7.01 (d, J=8.5 Hz, 1H), 6.85 (d, J=8.5 Hz, 1H), 6.80 (d, J=8.5 Hz, 1H), 5.82 (s, 2H), 3.73 (t, J=4.3 Hz, 4H), 3.62-3.53 (m, 9H), 0.82 (t, J=8.2 Hz, 2H), −0.12 (s, 9H); MS ESI 584.3 [M+H]$^+$, calcd for [C$_{32}$H$_{37}$N$_5$O$_4$Si+H]$^+$ 584.26.

C. (1R*,2S*)-5'-Methoxy-2-(3-(6-morpholinopyridin-3-yl)-1-((2-(trimethylsilyl)ethoxy)-methyl)-1H-indazol-6-yl)spiro[cyclopropane-1,3'-indolin]-2'-one To a solution of NaH (84 mg, 2.1 mmol) in DMF (5 mL) at 0° C. was added trimethylsulfoxonium iodide (154 mg, 0.70 mmol). The resulting mixture was stirred at rt for 30 min followed by the addition of (E)-5-Methoxy-3-((3-(6-morpholinopyridin-3-yl)-1-((2-(trimethylsilyl)ethoxy)methyl)-1H-indazol-6-yl)methylene)indolin-2-one in DMF (2 mL). The reaction mixture was then heated to 55° C. for 3 h. The reaction was cooled to 0° C. and quenched with saturated NH$_4$Cl. The mixture was extracted with EtOAc and the combined organic extracts were washed with brine, dried over MgSO$_4$ and concentrated to give yellow viscous oil. The crude product was purified by silica gel chromatography (95:5 CH$_2$Cl$_2$/MeOH) to yield a bright yellow powder, which was triturated with EtOAc to give the title compound as a pale yellow powder (93 mg, 44%). $^1$H NMR (400 MHz, CD$_3$OD) δ 10.45 (br. s, 1H), 8.71 (s, 1H), 8.10 (d, J=8.5 Hz, 1H), 7.93 (d, J=7.2 Hz, 1H), 7.84 (s, 1H), 7.08 (d, J=7.2 Hz, 1H), 6.98 (d, J=7.2 Hz, 1H), 6.73 (d, J=5.4 Hz, 1H), 6.56 (d, J=6.0 Hz, 1H), 5.86-5.75 (m, 3H), 3.71 (br s, 4H), 3.52 (br s, 4H), 3.40-3.16 (m, 6H), 2.42 (br. s, 1H), 2.00 (br. s, 1H), 0.79 (br s, 2H), −0.13 (s, 9H); MS ESI 598.4 [M+H]$^+$, calcd for [C$_{33}$H$_{39}$N$_5$O$_4$Si+H]$^+$ 598.28.

D. (1R*,2S*)-5'-Methoxy-2-(3-(6-morpholinopyridin-3-yl)-1H-indazol-6-yl)spiro[cyclopropane-1,3'-indolin]-2'-one A solution of (1R*,2S*)-5'-methoxy-2-(3-(6-morpholinopyridin-3-yl)-1-((2-(trimethylsilyl)ethoxy)methyl)-1H-indazol-6-yl)spiro[cyclopropane-1,3'-indolin]-2'-one (10 mg, 0.02 mmol) in THF (2.0 mL) was treated with TBAF (0.10 mL, 1M in THF) and refluxed for 3 h. The reaction was diluted with EtOAc and the organic layer was washed with brine (4×) and then dried over MgSO$_4$. The solvent was removed and the crude product was purified by silica gel chromatography using EtOAc as eluent followed by trituration (EtOAc: Hexanes, 1:1) to give the title compound as a yellow powder (5 mg, 13%). $^1$H NMR (400 MHz, CD$_3$OD) δ 8.70 (d, J=2.4 Hz, 1H), 8.14 (dd, J=8.8, 2.4 Hz, 1H), 7.89 (d, J=8.5 Hz, 1H), 7.50 (s, 1H), 7.04 (d, J=7.5 Hz, 1H), 6.98 (d, J=8.9 Hz, 1H), 6.83 (d, J=8.5 Hz, 1H), 6.62 (dd, J=8.5, 2.6 Hz, 1H), 5.61 (d, J=2.5, 1H), 4.63 (s, 1H), 3.84 (t, J=4.8 Hz, 4H), 3.58 (t, J=5.0 Hz, 4H), 3.40-3.35 (m, 1H), 3.29 (s, 3H), 2.28-2.25 (m, 1H), 2.21-2.18 (m, 1H); MS ESI 468.3 [M+H]$^+$, calcd for [C$_{27}$H$_{25}$N$_5$O$_3$+H]$^+$ 468.20.

Example A21. 4-(5-(6-((1R*,2S*)-5'-Methoxy-2'-oxospiro[cyclopropane-1,3'-indoline]-2-yl)-1H-indazol-3-yl)pyridinium-2-yl)piperazine bis(2,2,2-trifluoroacetate)

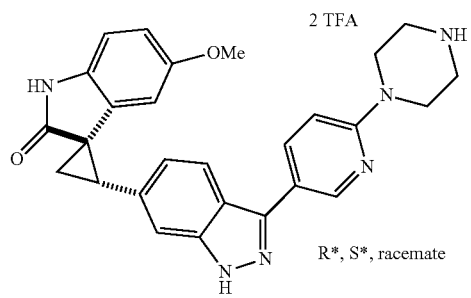

A mixture of (1R*,2S*)- and (1R*,2R*)-2-(3-Iodo-1H-indazol-6-yl)-5'-methoxyspiro[cyclopropane-1,3'-indolin]-2'-one (50 mg, 0.12 mmol), 2-(piperazin-1-yl)pyridine-5-boronic acid pinacol ester (40 mg, 0.13 mmol), PdCl$_2$(PPh$_3$)$_2$ (8 mg, 0.01 mmol) and 2M Na$_2$CO$_3$ (60 uL, 0.12 mmol) in DME/H$_2$O/EtOH (2.8 mL/0.8 mL/0.4 mL) was sealed and heated with stirring under microwave irradiation at 125° C. for 120 min. The reaction mixture was diluted with EtOAc and saturated NaHCO$_3$ was added. The resulting mixture was extracted with EtOAc and the combined organic extracts were washed with brine twice, dried over MgSO$_4$ and concentrated to give an orange solid. The title compound was purified by preparatory HPLC to give a yellow solid (26 mg, 48%). $^1$H NMR (400 MHz, CD$_3$OD) δ 8.41 (d, J=1.9 Hz, 1H), 8.28 (dd, J=8.9, 2.0 Hz, 1H), 7.87 (d, J=8.4 Hz, 1H), 7.51 (s, 1H), 7.17 (d, J=9.0 Hz, 1H), 7.03 (d, J=8.6 Hz, 1H), 6.83 (d, J=8.4 Hz, 1H), 6.61 (dd, J=8.3, 2.3 Hz, 1H), 5.60 (d, J=2.3 Hz, 1H), 3.93 (t, J=5.1 Hz, 4H), 3.41-3.34 (m, 5H), 3.27 (s, 3H), 2.26-2.23 (m, 1H), 2.20-2.17 (m, 1H); MS ESI 467.2 [M+H]$^+$, calcd for [C$_{27}$H$_{26}$N$_6$O$_2$+H]$^+$ 467.21.

Example A22. 1R*,2S*)-(E)-2-(3-(2-(pyridin-4-yl)vinyl)-1H-indazol-6-yl)spiro-[cyclo-propane-1,3'-indolin]-2'-one

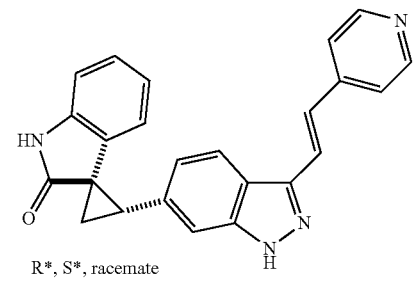

Method 1

A. (1R*,2S*)-(E)-2-(3-(2-(pyridin-4-yl)vinyl)-1-((2-(trimethylsilyl)ethoxy)methyl)-1H-indazol-6-yl)spiro[cyclopropane-1,3'-indolin]-2'-one To a solution of (1R*,2S*)-2-(3-iodo-1-((2-(trimethylsilyl)ethoxy)methyl)-1H-indazol-6-yl)spiro[cyclopropane-1,3'-indolin]-2'-one (375 mg, 0.7 mmol), 4-vinylpyridine (110 mg, 1.05 mmol), diisopropylethylamine (0.25 mL, 1.4 mmol) and DMF (2.5 mL) was added Pd(OAc)$_2$ (8 mg, 0.035 mmol) and P(o-Tol)$_3$ (22 mg, 0.07 mmol). The mixture was heated under microwave irradiation (130° C.) for 2 h. Ethyl acetate (150 mL) was added and the solution was washed with water (2×20 mL) and brine (20 mL), dried over MgSO$_4$ and concentrated. The residue was purified by silica gel chromatography (1:1 Hexane/EtOAc to 100% EtOAc) to give the title compound as a beige solid (320 mg, 90%). MS ESI 509.3 [M+H]$^+$, calcd for [C$_{30}$H$_{32}$N$_4$O$_2$Si+H]$^+$ 509.7.

B. (1R*,2S*)-(E)-2-(3-(2-(pyridin-4-yl)vinyl)-1H-indazol-6-yl)spiro[cyclo-propane-1,3'-indolin]-2'-one A dry-round bottom was charged with (1R*,2S*)-(E)-2-(3-(2-(pyridin-4-yl)vinyl)-1-((2-(trimethylsilyl)ethoxy)methyl)-1H-indazol-6-yl)spiro[cyclopropane-1,3'-indolin]-2'-one (320 mg, 0.62 mmol), and CH$_2$Cl$_2$ (15 mL) under an atmosphere of $N_2$. Boron trifluoride etherate (1 mL) was added dropwise and the reaction was stirred for 2 h. Methylene chloride was removed in vacuo, and then 5 mL of a 2:1 mixture of EtOH/2M HCl was added and the reaction heated to 50° C. for 2 h. The reaction was cooled with an ice-bath and neutralized with $NH_4OH$ to pH-8, the EtOH was removed and the resulting precipitate was collected. The product was purified by silica gel chromatography (85:15 $CH_2Cl_2$/MeOH) to give the title compound as a yellow solid (220 mg, 90%). $^1$H NMR (400 MHz, DMSO-$d_6$) δ 13.31 (s, 1H), 10.63 (s, 1H), 8.57-8.50 (m, 2H), 8.10 (d, J=8.1 Hz, 1H), 7.80 (d, 1H, J=16.6 Hz), 7.75-7.70 (m, 2H), 7.50-7.42 (m, 2H), 7.09-6.99 (m, 2H), 6.85 (d, 1H, J=7.6 Hz), 6.53 (t, 1H, J=7.5 Hz), 6.01 (d, 1H, J=7.8 Hz) 3.23-3.19 (m, 1H), 2.35-2.31 (m, 1H), 2.02-1.98 (m, 1H); MS ESI 379.2 $[M+H]^+$, calcd for $[C_{24}H_{18}N_4O+H]^+$ 379.4.
Method 2

A. (E)-3-(2-(pyridin-4-yl)vinyl)-1H-indazole-6-carbonitrile

To a mixture of 3-formyl-1H-indazole-6-carbonitrile (1.14 g, 6.67 mmol) and 4-picoline (2 mL) was added acetic anhydride (2 mL). The resulting mixture was stirred to make a homogeneous solution and then irradiated 10 min at 100° C. by microwave. After cooling to rt, the mixture was poured onto ice/$H_2O$ (50 mL) and stirred for 10 min, sonicated for 2 min, then stirred for 10 min and suction filtered to give the crude (E)-1-acetyl-3-(2-(pyridin-4-yl)vinyl)-1H-indazole-6-carbonitrile as a dark brown solid.

This crude amide was suspended in DMSO (5 mL) and 2 M NaOH (15 mL, 30 mmol) was added and the resulting mixture was heated at 50° C. for 30 min before cooling down to 0° C. 2 M HCl was added dropwise to acidify until pH about 6. The resulting precipitates were collected by suction filtration to give crude (E)-3-(2-(pyridin-4-yl)vinyl)-1H-indazole-6-carbonitrile as a dark brown solid. MS ESI 247.1 $[M+H]^+$, calcd for $[C_{23}H_{16}N_4O+H]^+$ 246.9.

B. (E)-3-(2-(pyridin-4-yl)vinyl)-1H-indazole-6-carbaldehyde

The crude (E)-3-(2-(pyridin-4-yl)vinyl)-1H-indazole-6-carbonitrile was dissolved in DMF (10 mL). Pyridine (10 mL) and acetic acid (5 mL) were added, followed by $NaH_2PO_2/H_2O$ (1.76 g, 20 mmol/5 mL) and Raney-Nickel 2400 (slurry in $H_2O$, 1 mL). The resulting mixture was heated at 60° C. for 1 h before cooling to rt. The mixture was diluted with $H_2O$ and extracted with EtOAc (50 mL×3). The combined extracts were dried ($Na_2SO_4$) and concentrated to give an orange liquid. $H_2O$ (50 mL) was added and the resulting suspension was sonicated, suction filtered, rinsed with $H_2O$ and dried to give crude (E)-3-(2-(pyridin-4-yl)vinyl)-1H-indazole-6-carbaldehyde (540 mg) as a brown solid. $^1$H NMR (400 MHz, DMSO-$d_6$) δ 13.90 (s, 1H), 10.15 (s, 1H), 8.57 (d, 2H, J=4.0 Hz), 8.40 (d, 1H, J=8.0 Hz), 8.20 (s, 1H), 7.89 (d, 1H, J=16.4 Hz), 7.73-7.68 (m, 3H), 7.55 (d, 1H, J=16.8 Hz); MS ESI 249.9 $[M+H]^+$, calcd for $[C_{23}H_{16}N_4O+H]^+$ 250.1.

C. (E/Z)-3-((3-((E)-2-(pyridin-4-yl)vinyl)-1H-indazol-6-yl)methylene)indolin-2-one To a mixture of (E)-3-(2-(pyridin-4-yl)vinyl)-1H-indazole-6-carbonitrile (533 mg, 2.14 mmol) and 2-oxindole (313 mg, 2.35 mmol) in MeOH (50 mL) was added piperidine (0.1 mL, 1 mmol). The resulting mixture was refluxed (oil temp. 75° C.) for 2 h and kept at 0° C. for 30 min. The resulting precipitates were collected by suction filtrated. Filtrate was concentrated and triturated with MeOH to give more (E/Z)-3-((3-((E)-2-(pyridin-4-yl)vinyl)-1H-indazol-6-yl)methylene)indolin-2-one (total: 547 mg). MS ESI 365.1 $[M+H]^+$, calcd for $[C_{23}H_{16}N_4O+H]^+$ 365.1.

D. (1R*,2S*)-(E)-2-(3-(2-(pyridin-4-yl)vinyl)-1H-indazol-6-yl)spiro[cyclo-propane-1,3'-indolin]-2'-one DMF (5 mL) was added to a mixture of trimethylsulfoxonium iodide (660 mg, 3 mmol) and 60% NaH (360 mg, 9 mmol). The resulting mixture was stirred for 1 min at rt. A solution of (E/Z)-3-((3-((E)-2-(pyridin-4-yl)vinyl)-1H-indazol-6-yl)methylene)-indolin-2-one (540 mg, 1.5 mmol)) in DMF (20 mL) was added via a pipet. After addition, the resulting dark red mixture was heated at 60° C. (oil temp.) for 1 h. Upon cooling to 0° C., it was quenched with ice and sat. $NH_4Cl$, and the product was extracted with EtOAc (100 mL×2). The combined extracts were dried ($Na_2SO_4$) and concentrated to give a light yellow solution. $H_2O$ (100 mL) was added and the resulting yellow solid was collected by suction filtration. The solid was suspended in MeOH (6 mL), sonicated, suction filtered and dried to give the title compound as a yellow solid (145 mg, 26%). $^1$H NMR (400 MHz, DMSO-$d_6$) δ 13.31 (s, 1H), 10.63 (s, 1H), 8.54 (d, J=2.8 Hz, 2H), 8.10 (d, J=8.0 Hz, 1H), 7.80 (d, J=16.0 Hz, 1H), 7.67 (d, J=4.8 Hz, 2H), 7.48 (s, 1H, partially overlapping with the peak at 7.46 ppm), 7.46 (d, J=16.8 Hz, 1H, partially overlapping with the peak at 7.48 ppm), 7.06 (d, J=7.6 Hz, 1H), 7.00 (t, J=7.6 Hz, 1H), 6.87 (d, J=7.6 Hz, 1H), 6.53 (t, J=7.6 Hz, 1H), 6.01 (d, J=6.8 Hz, 1H), 3.21 (t, J=8.2 Hz, 1H), 2.35-2.31 (m, 1H), 2.00 (dd, J=8.4 Hz, J=4.4 Hz, 1H); MS ESI 379.1 $[M+H]^+$, calcd for $[C_{24}H_{18}N_4O+H]^+$ 379.1.

Example A23. (1R*,2S*)-(E)-2-(3-(4-((dimethylamino)methyl)styryl)-1H-indazol-6-yl)spiro[cyclopropane-1,3'-indolin]-2'-one 2,2,2-trifluoroacetate

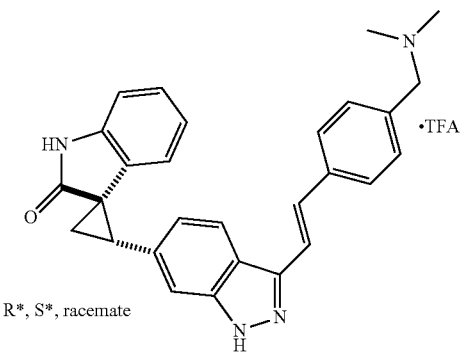

R*, S*, racemate

A. (E)-2-(3-(4-((dimethylamino)methyl)styryl)-1-((2-(trimethylsilyl)ethoxy)methyl)-1H-indazol-6-yl)spiro[cyclopropane-1,3'-indolin]-2'-one The title compound was synthesized according to the method of Example A22, Method 1A, using N,N-dimethyl-1-(4-vinylphenyl)methanamine (80 mg, 0.15 mmol). The title compound was isolated by silica gel chromatography (3:1 $CH_2Cl_2$/MeOH) to give the title compound as a beige solid (38 mg, 45%). MS ESI 565.4 $[M+H]^+$, calcd for $[C_{34}H_{40}N_4O_2Si+H]^+$ 565.7.

B. (1R*,2S*)-2-(3-(4-((dimethylamino)methyl) styryl)-1H-indazol-6-yl)spiro[cyclopropane-1,3'-indolin]-2'-one 2,2,2-trifluoroacetate The title compound was synthesized according to the method of Example A22, Method 1B, using (E)-2-(3-(4-((dimethylamino)methyl)styryl)-1-((2-(trimethylsilyl)-ethoxy)methyl)-1H-indazol-6-yl)spiro[cyclopropane-1,3'-indolin]-2'-one (38 mg, 0.052 mmol). The crude reaction mixture was concentrated under reduced pressure to dryness, and purified by reverse phase preparative HPLC to give the title compound as a white solid and as the TFA salt (11 mg, 31%). $^1$H NMR (400 MHz, CD$_3$OD) δ ppm 8.02 (d, J=8.3 Hz, 1H), 7.78 (d, 2H, J=8.3 Hz), 7.56-7.48 (m, 5H), 7.08-7.04 (m, 2H), 6.94 (d, 1H, J=8.3 Hz), 6.59 (t, 1H, J=7.8 Hz), 6.00 (d, 1H, J=8.0 Hz), 4.38 (s, 2H) 3.39-3.33 (m, 1H), 2.90 (s, 6H), 2.28-2.22 (m, 1H), 2.22-2.17 (m, 1H); MS ESI 435.2 [M+H]$^+$, calcd for [C$_{28}$H$_{26}$N$_4$O+H]$^+$ 435.5.

Example A24. (1R,2S)-(E)-2-(3-(4-((dimethylamino)methyl)styryl)-1H-indazol-6-yl)spiro[cyclopropane-1,3'-indolin]-2'-one 2,2,2-trifluoroacetate

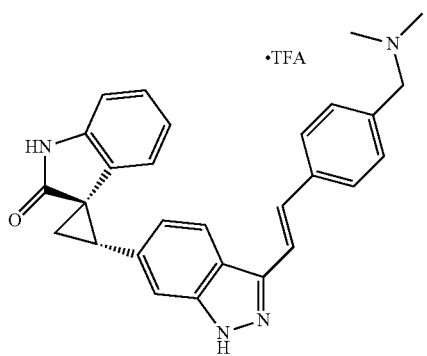 [SMILES: CN(C)Cc1ccc(/C=C/c2n[nH]c3cc([C@@H]4C[C@@]45C(=O)Nc4ccccc45)ccc23)cc1]

To a solution of (1R,2S)-2-(3-iodo-1H-indazol-spiro[cyclopropane-1,3'-indolin]-2'-one (20 mg, 0.05 mmol) in DMF (0.4 mL) and water (0.1 mL) was added (E)-N,N-dimethyl-1-(4-(2-(4,4,5,5-tetramethyl-1,3,2-dioxaborolan-2-yl)vinyl) phenyl) methanamine (25 mg, 0.08 mmol) potassium fluoride (6 mg, 0.1 mmol) and Pd(PPh$_3$)$_4$ (3 mg, 0.002 mmol). The mixture was heated to 120° C. for 2 h under microwave irradiation. Ethyl acetate (50 mL) was added and the solution was washed with water (2×5 mL), brine (5 mL) and dried over MgSO$_4$. Purification by reverse phase preparatory HPLC gave the title compound as a yellow solid (12 mg, 44%).

Example A25. (1S,2R)-(E)-2-(3-(4-((dimethylamino)methyl)styryl)-1H-indazol-6-yl)spiro[cyclopropane-1,3'-indolin]-2'-one 2,2,2-trifluoroacetate

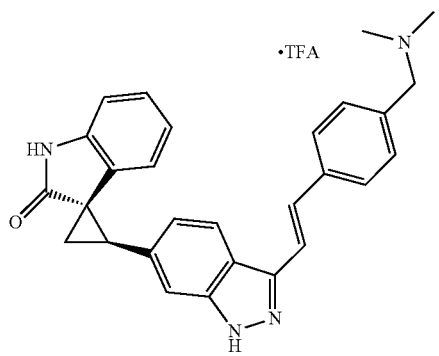 [SMILES: CN(C)Cc1ccc(/C=C/c2n[nH]c3cc([C@H]4C[C@]45C(=O)Nc4ccccc45)ccc23)cc1]

To a solution of (1S,2R)-2-(3-iodo-1H-indazol-spiro[cyclopropane-1,3'-indolin]-2'-one (20 mg, 0.05 mmol) in DMF (0.4 mL) and water (0.1 mL) was added (E)-N,N-dimethyl-1-(4-(2-(4,4,5,5-tetramethyl-1,3,2-dioxaborolan-2-yl)vinyl) phenyl) methanamine (25 mg, 0.08 mmol) potassium fluoride (6 mg, 0.1 mmol) and Pd(PPh$_3$)$_4$ (3 mg, 0.002 mmol). The mixture was heated to 120° C. for 2 h under microwave irradiation. Ethyl acetate (50 mL) was added and the solution was washed with water (2×5 mL), brine (5 mL) and dried over MgSO$_4$. Purification by reverse phase preparatory HPLC gave the title compound as a yellow solid (4 mg, 15%).

Example A26. (1R*,2R*)-(E)-2-(3-(4-((dimethylamino)methyl)styryl)-1H-indazol-6-yl)spiro[cyclopropane-1,3'-indolin]-2'-one 2,2,2-trifluoroacetate

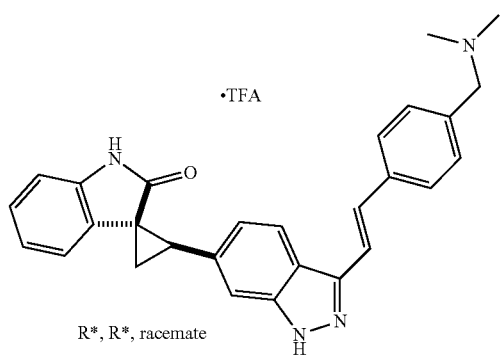 [SMILES: CN(C)Cc1ccc(/C=C/c2n[nH]c3cc([C@H]4C[C@@]45C(=O)Nc4ccccc45)ccc23)cc1]

R*, R*, racemate

During a larger scale preparation of Example A23 (obtained as a pale yellow solid, 63 mg), the corresponding minor diastereomer, i.e. the title compound, was obtained as a white solid by reverse phase preparative HPLC (4.6 mg). $^1$H NMR (400 MHz, CD$_3$OD) δ ppm 8.00 (d, 1H, J=8.0 Hz), 7.77 (d, 2H, J=8.4 Hz), 7.56-7.50 (m, 5H), 7.23 (t, 1H, J=7.6 Hz), 7.16-7.05 (m, 3H), 6.96 (d, 1H, J=7.6 Hz), 4.33 (s, 2H) 3.44-3.38 (m, 1H), 2.88 (s, 6H), 2.43-2.40 (m, 1H), 2.25-2.23 (m, 1H); MS ESI 435.2 [M+H]$^+$, calcd for [C$_{28}$H$_{26}$N$_4$O+H]$^+$ 435.5.

Example A27. (1R*,2S*)-5'-bromo-2-(3-((E)-2-(pyridin-3-yl)vinyl)-1H-indazol-6-yl)spiro[cyclopropane-1,3'-pyrrolo[2,3-b]pyridin]-2'(1'H)-one

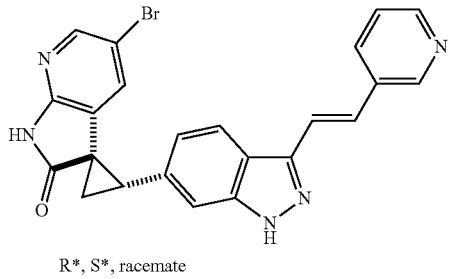

R*, S*, racemate

A. (E/Z)-5-bromo-3-((3-((E)-2-(pyridin-3-yl)vinyl)-1H-indazol-6-yl)methylene)-1H-pyrrolo[2,3-b]pyridin-2(3H)-one To a mixture of (E)-3-(2-(pyridin-3-yl)vinyl)-1H-indazole-6-carbaldehyde (498 mg, 2 mmol) and 5-bromo-1H-pyrrolo[2,3-b]pyridin-2(3H)-one (469 mg, 2.2 mmol) in MeOH (30 mL) was added piperidine (0.02 mL, 0.2 mmol). The resulting mixture was heated at 70° C. (oil temp.) for 2 h. After cooling to rt, the precipitates were collected by suction filtration and dried to give (E/Z)-5-bromo-3-((3-((E)-2-(pyridin-3-yl)vinyl)-1H-indazol-6-yl)methylene)-1H-pyrrolo[2,3-b]pyridin-2(3H)-one (850 mg) as a yellow solid. MS ESI 444.4 [M+H]$^+$, calcd for [$C_{23}H_{16}BrN_5O$+H]$^+$ 444.0.

B. (1R*,2S*)-5'-bromo-2-(3-((E)-2-(pyridin-3-yl)vinyl)-1H-indazol-6-yl)spiro[cyclo-propane-1,3'-pyrrolo[2,3-b]pyridin]-2'(1'H)-one To a mixture of trimethylsulfoxonium iodide (880 m g, 4 mmol) and 60% NaH (480 mg, 12 mmol) in a 50 mL RBF was added DMF (8 mL). The resulting mixture was stirred for 2 min at rt. A suspension of (E/Z)-5-bromo-3-((3-((E)-2-(pyridin-3-yl)vinyl)-1H-indazol-6-yl)methylene)-1H-pyrrolo[2,3-b]pyridin-2(3H)-one (850 mg) in DMF (20 mL) was added via a pipet over 1 min. After addition, the resulting mixture was stirred for 1 min at rt, then heated at 60° C. (oil temp.) for 90 min. Upon cooling to 0° C., it was quenched with ice (20 mL), sat. NH$_4$Cl (10 mL) and H$_2$O (20 mL), and the product was extracted with EtOAc (100 mL×2). The combined extracts were dried (Na$_2$SO$_4$) and concentrated to give a light yellow liquid. H$_2$O (100 mL) was added and the suspension was sonicated, suction filtered to give the crude title compound as a white solid. It was suspended in MeOH (10 mL), sonicated, suction filtered, air dried and then suspended in hexane (20 mL) and repeated the process to give the title compound as a light beige solid (645 mg) after drying. NMR indicated a mixture of two diastereomers (96:4). $^1$H NMR (400 MHz, DMSO-d$_6$) δ 13.27 (s, 1H) 11.45 (s, 1H), 8.87 (s, 1H), 8.45 (s, 1H), 8.15 (t, J=9.6 Hz, 2H), 8.03 (s, 1H), 7.68 (d, J=16.8 Hz, 1H), 7.54 (s, 1H, partially overlapping with the peak at 7.52 ppm), 7.52 (d, J=16.8 Hz, 1H, partially overlapping with the peak at 7.54 ppm), 7.41 (br. s, 1H), 7.09 (d, J=8.0 Hz, 1H), 6.48 (s, 1H), 2.67-2.61 (m, 1H), 2.15-1.99 (m, 1H); MS ESI 458.4 [M+H]$^+$, calcd for [$C_{23}H_{16}BrN_5O$+H]$^+$ 458.1.

Example A28. (1R*,2S*)-2-(3-((E)-2-(pyridin-3-yl)vinyl)-1H-indazol-6-yl)spiro-[cyclopropane-1,3'-indolin]-2'-one

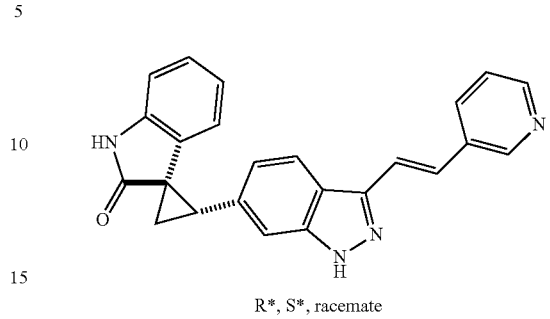

R*, S*, racemate

To a mixture of trimethylsulfoxonium iodide (176 mg, 0.8 mmol) and 60% NaH (96 mg, 2.4 mmol) in a RBF was added DMF (5 mL). The resulting mixture was stirred for 2 min at rt then cooled to 0° C. A solution of (E)-3-((3-((E)-2-(pyridin-3-yl)vinyl)-1H-indazol-6-yl)methylene)indolin-2-one (122 mg, 0.33 mmol)) in DMF (20 mL) was added via a pipet. After addition, the resulting mixture was heated at 55° C. (oil temp.) for 2 h and cooled to rt. Additional trimethylsulfoxonium iodide (176 mg, 0.8 mmol) and 60% NaH (96 mg, 2.4 mmol) were added and the resulting mixture was stirred O/N at rt and poured onto ice (80 mL). It was acidified with sat. NH$_4$Cl and extracted with EtOAc (40 mL×3). The combined extracts were dried (Na$_2$SO$_4$) and concentrated to give a light brown liquid. This residue was purified by flash chromatography (eluent: CH$_2$Cl$_2$ to CH$_2$Cl$_2$/MeOH/Et$_3$N=200:10:1) to give the crude title compound as a light yellow solid which was triturated with MeOH (5 mL) and suction filtered to give the title compound as a yellow solid (43 mg, 34%). $^1$H NMR (400 MHz, DMSO-d6) δ 13.21 (s, 1H), 10.64 (s, 1H), 8.86 (s, 1H), 8.45 (d, J=3.2 Hz, 1H), 8.15 (d, J=8.0 Hz, 1H), 8.09 (d, J=8.4 Hz, 1H), 7.65 (d, J=16.8 Hz, 1H), 7.49 (d, J=16.8 Hz, 1H, partially overlapping with the peak at 7.47 ppm), 7.47 (s, 1H, partially overlapping with the peak at 7.49 ppm), 7.40 (dd, J=8.0 Hz, J=4.8 Hz, 1H), 7.03 (d, J=8.4 Hz, 1H), 6.99 (d, J=7.2 Hz, 1H), 6.86 (d, J=7.6 Hz, 1H), 6.53 (t, J=7.4 Hz, 1H), 6.01 (d, J=7.6 Hz, 1H), 3.21 (t, J=8.4 Hz, 1H), 2.32 (dd, J=7.6 Hz, J=4.8 Hz, 1H), 2.00 (dd, J=9.0 Hz, J=4.8 Hz, 1H); MS ESI 379.1 [M+H]$^+$, calcd for [$C_{24}H_{18}N_4O$+H]$^+$ 379.1.

Example 29

(1R,2S)-2-(3-((E)-2-(pyridin-3-yl)vinyl)-1H-indazol-6-yl)spiro[cyclopropane-1,3'-indolin]-2'-one

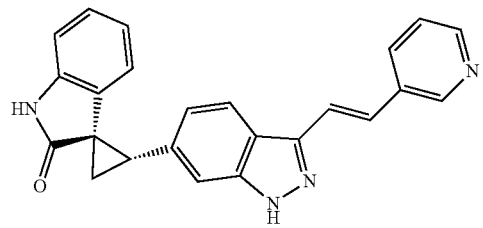 [SMILES: O=C1Nc2ccccc2[C@]12C[C@H]2c1ccc2c(/C=C/c3cccnc3)n[nH]c2c1]

A. (E)-3-(2-(4,4,5,5-tetramethyl-1,3,2-dioxaborolan-2-yl)vinyl)pyridine

An oven-dried round-bottom flask was cooled under N₂ (g) and then charged with 3-ethynyl pyridine (104 mg, 1 mmol), toluene (4 mL), and 4,4,5,5-tetramethyl-1,3,2-dioxaborolane (0.73 mL, 5 mmol). The mixture was purged with argon for 15 min. HRuCl(CO)(PPh₃)₃ (73 mg, 0.05 mmol) was then added and the reaction heated to 50° C. for 18 h. The reaction was quenched with NaHCO₃ (sat.) (10 mL), extracted with EtOAc, and the organic layer washed with brine (10 mL) and then dried over MgSO₄. The solvent was removed and the resulting residue purified by column chromatography (silica gel, Hexanes/EtOAc, 1:1) to give the title compound as a white solid (115 mg, 50%). ¹H NMR (400 MHz, CDCl₃) δ 8.69 (s, 1H) 8.52 (d, 1H, J=4.8 Hz), 7.81 (d, 1H, J=7.8 Hz), 7.38 (d, J=18.6 Hz, 1H), 7.28-7.26 (m, 1H), 6.26 (d, 1H, J=18.5 Hz), 1.33 (s, 12H).

B. (1R,2S)-2-(3-((E)-2-(pyridin-3-yl)vinyl)-1H-indazol-6-yl)spiro[cyclopropane-1,3'-indolin]-2'-one To a solution of (1R,2S)-2-(3-iodo-1H-indazol-spiro[cyclopropane-1,3'-indolin]-2'-one (50 mg, 0.12 mmol) in DMF (0.4 mL) and water (0.1 mL) was added (E)-3-(2-(4,4,5,5-tetramethyl-1,3,2-dioxaborolan-2-yl)vinyl)pyridine (50 mg, 0.2 mmol) potassium fluoride (14 mg, 0.24 mmol) and Pd(PPh₃)₄ (7 mg, 0.006 mmol). The mixture was heated to 120° C. for 2 h under microwave irradiation. Ethyl acetate (50 mL) was added and the solution was washed with water (2×5 mL), brine (5 mL) and dried over MgSO₄. Purification by reverse phase preparatory HPLC gave the title compound as a yellow solid (20 mg, 44%).

Example A30. (1S,2R)-2-(3-((E)-2-(pyridin-3-yl)vinyl)-1H-indazol-6-yl)spiro[cyclopropane-1,3'-indolin]-2'-one

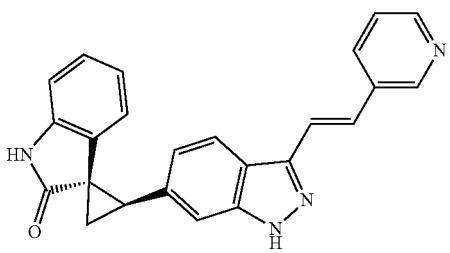 [SMILES: O=C1Nc2ccccc2[C@@]12C[C@@H]2c1ccc2c(/C=C/c3cccnc3)n[nH]c2c1]

Prepared according to the method of Example 31B, except substituting (1S,2R)-2-(3-iodo-1H-indazol-spiro[cyclopropane-1,3'-indolin]-2'-one. Purification by reverse phase preparatory HPLC gave the title compound as a yellow solid (23 mg, 52%). Analytical data was identical to that obtained for Example A29.

Example A31. (1R*,2S*)-5'-methoxy-2-(3-((E)-2-(6-(4-methylpiperazin-1-yl)pyridin-3-yl)vinyl)-1H-indazol-6-yl)spiro[cyclopropane-1,3'-indolin]-2'-one

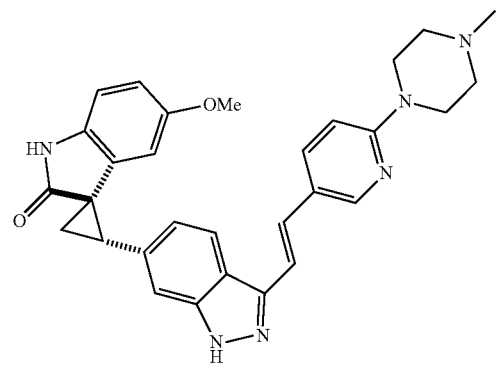

R*, S*, racemate

DMF (3 mL) was added to a mixture of NaH (60%, 171.5 mg, 4.29 mmol) and trimethylsulfoxonium iodide (246.2 mg, 1.12 mmol). The resulting mixture was stirred at rt for 10 min followed by the addition of 5-methoxy-3-((E)-2-(6-(4-methylpiperazin-1-yl)pyridin-3-yl)vinyl)-1H-indazol-6-yl)methylene)indolin-2-one dihydrochloride (E:Z mixture, 155.5 mg, 0.275 mmol) as a suspension in DMF (9 mL, divided for transfer and vial rinse). The reaction mixture was then heated to 55° C. for 6 h, then stirred at rt for 18 h prior to quenching by addition of water (15 mL) and brine (15 mL). The mixture was extracted with EtOAc (225 mL) and the organic layer was washed with brine (2×15 mL), dried over Na₂SO₄ and concentrated in vacuo. Co-evaporation of DMF with toluene (2×10 mL) in vacuo gave a viscous oil, which was triturated with hexane (3×5 mL) to give a sticky solid. The crude product was purified by silica gel chromatography (5-7.5% 2M NH₃-MeOH in DCM) to yield an 85:15 mixture of the title compound and the (1R*,2R*) diastereomer. The major isomer was isolated by silica gel chromatography (3-5% MeOH and 2% Et₃N in CHCl₃) to yield a sticky yellow solid which was triturated with Et₂O to give the title compound as a yellow powder (57.4 mg, 41%). ¹H NMR (400 MHz, CD₃OD) δ ppm 8.26 (s, 1H), 8.00 (d, J=8.4 Hz, 1H), 7.92 (d, J=9.2 Hz, 1H), 7.45 (s, 1H), 7.40 (d, J=16.8 Hz, 1H), 7.28 (d, J=16.8 Hz, 1H), 7.03 (d, J=7.6 Hz, 1H), 6.87 (d, J=9.2 Hz, 1H), 6.83 (d, J=8.4 Hz, 1H), 6.61 (dd, J=8.4, 2.4 Hz, 1H), 5.58 (d, J=2.0 Hz, 1H), 3.61 (m, 4H), 3.38 (m, 1H), 3.26 (s, 3H), 2.57 (m, 4H), 2.36 (s, 3H), 2.21 (m, 2H); MS ESI [M+H]⁺ 507.2, calcd for [C₃₀H₃₀N₆O₂+H]⁺ 507.2.

Example A32. (1S,2R)-5'-methoxy-2-(3-((E)-2-(6-(4-methylpiperazin-1-yl)pyridin-3-yl)vinyl)-1H-indazol-6-yl)spiro[cyclopropane-1,3'-indolin]-2'-one

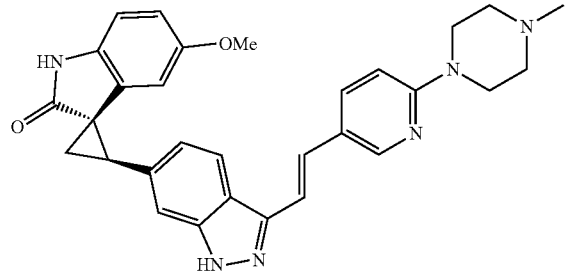 [SMILES: COc1ccc2c(c1)[C@@]1(C[C@@H]1c1ccc3c(/C=C/c4ccc(N5CCN(C)CC5)nc4)n[nH]c3c1)C(=O)N2]

From two repeated batches of Example A31 using 5-methoxy-3-((3-((E)-2-(6-(4-methylpiperazin-1-yl)pyridin-3-yl)vinyl)-1H-indazol-6-yl)methylene)indolin-2-one (combined 491 mg, 1.0 mmol), purification using flash chromatography (silica gel, 1% Et₃N in CHCl₃/MeOH 96:4 to 92:8), followed by trituration with 1:1 Et₂O/CH₂Cl₂ gave the minor diastereomer title compound as a pale yellow solid (18 mg, 4%). $^1$H NMR (400 MHz, CDCl₃ with a few drops of CD₃OD) δ ppm 8.21 (s, 1H), 7.82 (d, J=8.5 Hz, 1H), 7.75 (d, J=8.5 Hz, 1H), 7.39 (s, 1H), 7.27 (d, J=17.3 Hz, 1H), 7.16 (d, J=17.3 Hz, 1H), 7.05 (d, J=8.8 Hz, 1H), 6.80 (d, J=8.3 Hz, 1H), 6.72 (d, J=8.8 Hz, 1H), 6.67 (d, J=9.3 Hz, 1H), 6.54 (s, 1H), 3.77 (s, 3H), 3.58 (bs, 4H), 3.18-3.27 (m, 1H), 2.57 (bs, 4H), 2.40 (dd, J=8.5, 5.3 Hz, 1H), 2.35 (bs, 3H), 2.09 (dd, J=9.0, 5.0 Hz, 1H); MS ESI 507.3 [M+H]⁺, calcd for [C₃₀H₃₀N₆O₂+H]⁺ 507.2.

Example A33. (1R,2S)-5'-methoxy-2-(3-((E)-2-(6-(4-methylpiperazin-1-yl)pyridin-3-yl)vinyl)-1H-indazol-6-yl)spiro[cyclopropane-1,3'-indolin]-2'-one 2,2,2-trifluoroacetate

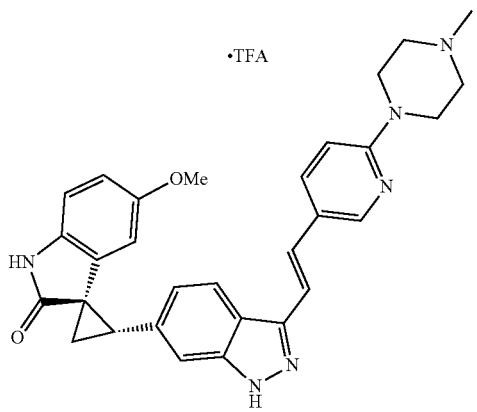 [SMILES: COc1ccc2c(c1)[C@]1(C[C@H]1c1ccc3c(/C=C/c4ccc(N5CCN(C)CC5)nc4)n[nH]c3c1)C(=O)N2]

The title compound was prepared in a similar manner to Example A45 using (1R,2S)-2-(3-iodo-1H-indazol-6-yl)-5'-methoxyspiro[cyclopropane-1,3'-indolin]-2'-one (130.0 mg, 0.30 mmol) with (E)-1-methyl-4-(5-(2-(4,4,5,5-tetramethyl-1,3,2-dioxaborolan-2-yl)vinyl)pyridin-2-yl)piperazine (118.9 mg, 0.36 mmol). The reaction mixture was diluted with MeOH (12.5 mL) and filtered through a plug of silica (5 g), eluting with 2M NH₃:MeOH (100 mL). After removal of the solvents in vacuo, the title compound was purified by preparative HPLC to yield the title compound as the TFA salt (yellow solid, 104 mg, 34%). $^1$H NMR and LCMS were identical to corresponding racemate given in Example A31.

Example A34. (1R*,2S*)-(E)-2-(3-(4-((dimethylamino)methyl)styryl)-1H-indazol-6-yl)-5'-methoxyspiro[cyclopropane-1,3'-indolin]-2'-one

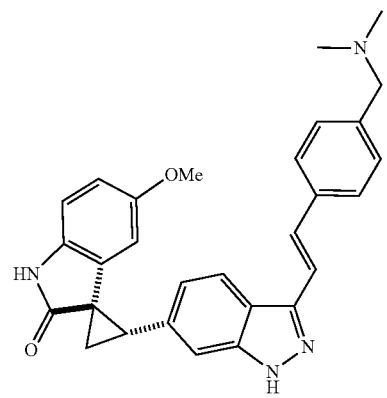

R*, S*, racemate

A. DMF (3 mL) was added to a mixture of NaH (60%, 85.2 mg, 2.1 mmol) and trimethylsulfoxonium iodide (131.5 mg, 0.60 mmol). The resulting mixture was stirred at rt for 10 min followed by the addition of (E)-3-((3-(4-((dimethylamino)methyl)-styryl)-1H-indazol-6-yl)methylene)-5-methoxyindolin-2-one 2,2,2-trifluoroacetate (163 mg, 0.29 mmol) as a solution in DMF (6 mL, divided for transfer and vial rinse). The reaction mixture was not complete after stirring at rt for 24 h. The mixture was heated at 55° C. for 1 h but was still not complete. After cooling to rt, NaH (60%, 44 mg, 1.1 mmol) and trimethylsulfoxonium iodide (69.5 mg, 0.31 mmol) was added and the mixture was heated at 55° C. for 1 h prior to quenching by addition of water (25 mL) and brine (25 mL). The mixture was extracted with EtOAc (300 mL) and the organic layer was washed with brine (2×25 mL), dried over Na₂SO₄ and concentrated in vacuo. The crude product was purified by silica gel chromatography (5-7.5% 2M NH₃-MeOH in DCM) to yield the title compound as a yellow solid (42.8 mg, 32%). $^1$H NMR (400 MHz, DMSO-d₆) δ ppm 13.11 (s, 1H), 10.43 (s, 1H), 8.07 (d, J=8.8 Hz, 1H), 7.64 (d, J=7.6 Hz, 2H), 7.47 (m, 3H), 7.29 (d, J=8.0 Hz, 2H), 7.03 (d, J=8.8 Hz, 1H), 6.74 (d, J=8.4 Hz, 1H), 6.57 (dd, J=8.4, 2.4 Hz, 1H), 5.65 (d, J=2.4 Hz, 1H), 3.38 (s, 2H), 3.28 (s, 3H), 3.20 (t, J=7.6 Hz, 1H), 2.34 (m, 1H), 2.14 (s, 6H), 1.99 (m, 1H); MS ESI [M+H]⁺ 465.2, calcd for [C₂₉H₂₈N₄O₂+H]⁺ 465.2.

B. Larger scale, TFA salt: NaH (60%, 491 mg, 12.29 mmol) was added in 3 portions to an ice cooled mixture of trimethylsulfoxonium iodide (959.3 mg, 4.36 mmol) in DMF (12 mL). The resulting mixture was stirred at 0° C. for 10 min followed by the addition of (E)-3-((3-(4-((dimethylamino)methyl)-styryl)-1H-indazol-6-yl)methylene)-5-methoxyindolin-2-one hydrochloride (984.4 mg, 2.02 mmol) as a suspension in DMF (12 mL, divided for transfer and vial rinse). The reaction mixture was warmed to room temperature over 10 min, then heated at 55° C. for 17 h prior to quenching by addition of water (25 mL) and

Example A35. (1R,2S)-(E)-2-(3-(4-((dimethyl-amino)methyl)styryl)-1H-indazol-6-yl)-5'-methoxyspiro[cyclopropane-1,3'-indolin]-2'-one hydrochloride

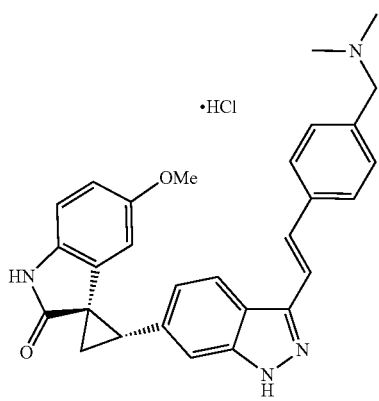 [SMILES: COc1ccc2c(c1)[C@]1(C[C@H]1c1ccc3c(/C=C/c4ccc(CN(C)C)cc4)n[nH]c3c1)C(=O)N2 ; Cl]

The title compound was prepared in a similar manner to Example A51B using (1R,2S)-2-(3-iodo-1H-indazol-6-yl)-5'-methoxyspiro[cyclopropane-1,3'-indolin]-2'-one (251.3 mg, 0.58 mmol) and (E)-N,N-dimethyl-1-(4-(2-(4,4,5,5-tetramethyl-1,3,2-dioxaborolan-2-yl)vinyl)phenyl)methanamine (191.5 mg, 0.67 mmol). The product was extracted using EtOAc (40 mL) with a Varian 3 mL ChemElut cartridge. After removal of the solvents in vacuo, the title compound was purified by chromatography on Biotage (silica, SNAP-25 g, 5-20% MeOH in DCM). Trituration with with 1:1 Et$_2$O/DCM yielded the title compound (92.1 mg, 34%). HCl (1M in Et$_2$O, 0.25 mL, 0.25 mmol) was added in a drop-wise manner to an ice cooled solution of the free base (92 mg, 0.20 mmol) in THF (10 mL), and the resulting mixture was allowed to stir in ice for 40 minutes, then Et$_2$O (10 mL) was added to the mixture. Filtration under vacuum yielded the title compound as the hydrochloride salt (orange-red solid, 79 mg, 79%). $^1$H NMR (400 MHz, CD$_3$OD) δ ppm 8.05 (d, J=8.5 Hz, 1H), 7.77 (d, J=8.0 Hz, 2H), 7.48-7.63 (m, 5H), 7.09 (d, J=8.3 Hz, 1H), 6.84 (d, J=8.5 Hz, 1H), 6.61 (dd, J=8.3, 2.3 Hz, 1H), 5.61 (d, J=2.3 Hz, 1H), 4.36 (s, 2H), 3.35 (m, 1H), 3.28 (s, 3H), 2.89 (s, 6H), 2.26 (dd, J=7.7, 5.1 Hz, 1H), 2.18 (dd, J=8.8, 4.8 Hz, 1H); MS ESI [M+H]$^+$ 465.3, calcd for [C$_{29}$H$_{28}$N$_4$O$_2$+H]$^+$ 465.2. Optical Rotation: [α]$^{24}_D$=−70° (c 0.445, MeOH).

Example A36. (1S,2R)-(E)-2-(3-(4-((dimethyl-amino)methyl)styryl)-1H-indazol-6-yl)-5'-methoxyspiro[cyclopropane-1,3'-indolin]-2'-one 2,2,2-trifluoroacetate

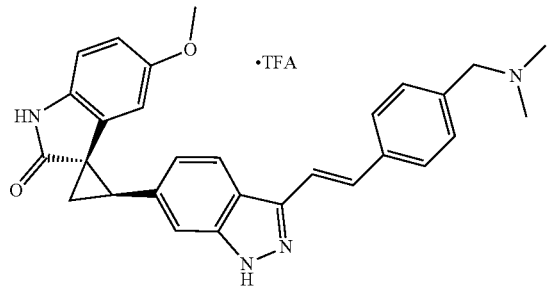 [SMILES: COc1ccc2c(c1)[C@@]1(C[C@@H]1c1ccc3c(/C=C/c4ccc(CN(C)C)cc4)n[nH]c3c1)C(=O)N2]

The title compound was synthesized according to the method of Example A51B, by using (1S,2R)-2-(3-iodo-1H-indazol-6-yl)-5'-methoxyspiro[cyclopropane-1,3'-indolin]-2'-one (40 mg, 0.092 mmol) and (E)-N,N-dimethyl-1(4-(2-(4,4,5,5-tetramethyl-1,3,2-dioxa borolan-2-yl)vinyl)benzyl)methanamine (33.3 mg, 0.115 mmol). Purification by preparative HPLC gave the title compound as a cream solid (22 mg, 39%). $^1$H NMR (400 MHz, CD$_3$OD) δ 8.02 (d, J=8.4 Hz, 1H), 7.75 (d, J=7.6 Hz, 2H), 7.54-7.49 (m, 5H), 7.04 (d, J=8.4 Hz, 1H), 6.83 (d, J=8.4 Hz, 1H), 6.60 (d, J=8.4 Hz, 1H), 5.58 (s, 1H), 4.33 (s, 2H), 3.37 (t, J=8.4 Hz, 1H), 3.26 (s, 3H), 2.88 (s, 6H), 2.25-2.23 (m, 1H), 2.20-2.21 (m, 1H); MS ESI 465.3 [M+H]$^+$, calcd for [C$_{29}$H$_{28}$N$_4$O$_2$+H]$^+$ 465.2. Optical Rotation: [α]$^{23}_D$=85° (c 0.542, Methanol).

Example A37. (1R*,2S*)-5'-Methoxy-2-(3-(2-(4-methylpiperazin-1-yl)pyridin-4-yl)-1H-indazol-6-yl)spiro[cyclopropane-1,3'-indolin]-2'-one

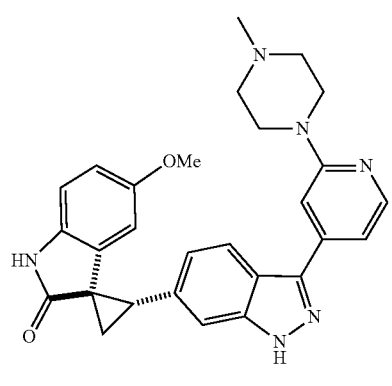

R*, S*, racemate

According to procedure for the synthesis of example A21, except substituting 1-methyl-4-(4-(4,4,5,5-tetramethyl-1,3,2-dioxaborolan-2-yl)pyridin-2-yl)piperazine (0.033 g, 0.11 mmol). The reaction mixture was concentrated and the crude product was purified by flash chromatography using CH$_2$Cl$_2$/MeOH as eluent (95:5 to 90:10). The title compound was isolated as pale yellow powder (0.013 g, 28%). $^1$H NMR (400 MHz, CD$_3$OD) δ 8.68 (d, J=1.7 Hz, 1H), 8.09 (dd, J=8.9, 2.1 Hz, 1H), 7.85 (d, J=8.6 Hz, 1H), 7.48 (s, 1H), 7.01 (d, J=8.5 Hz, 1H), 6.96 (d, J=8.9 Hz, 1H), 6.82 (d, J=8.5

Hz, 1H), 6.60 (dd, J=8.4, 2.3 Hz, 1H), 5.60 (d, J=2.2 Hz, 1H), 3.67 (br t, 4H), 3.38-3.34 (m, 1H), 3.26 (s, 3H), 2.69 (t, J=4.7 Hz, 4H), 2.43 (s, 3H), 2.26-2.23 (m, 1H), 2.20-2.16 (m, 1H); MS ESI 481.2 [M+H]$^+$, calcd for [C$_{28}$H$_{28}$N$_6$O$_2$+H]$^+$ 481.23.

Example A38. (1R*,2S*)-5'-Methoxy-2-(3-(4-(4-methylpiperazin-1-yl)phenyl)-1H-indazol-6-yl)spiro[cyclopropane-1,3'-indolin]-2'-one

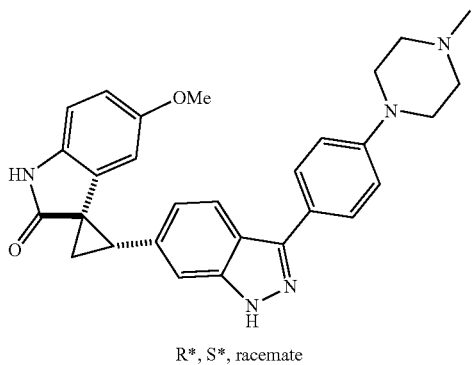

R*, S*, racemate

According to procedure for the synthesis and purification of example A21, except substituting 1-methyl-4-(4-(4,4,5,5-tetramethyl-1,3,2-dioxaborolan-2-yl)phenyl) piperazine (0.039 g, 0.13 mmol). The title compound was isolated as pale yellow powder (0.010 g, 18%). $^1$H NMR (400 MHz, CD$_3$OD) δ 7.87 (d, J=8.4 Hz, 1H), 7.79 (d, J=8.7 Hz, 2H), 7.46 (s, 1H), 7.07 (d, J=8.8 Hz, 2H), 6.98 (d, J=8.5 Hz, 1H), 6.82 (d, J=8.5 Hz, 1H), 6.59 (dd, J=8.5, 2.4 Hz, 1H), 5.60 (d, J=2.3 Hz, 1H), 3.38-3.28 (m, 5H), 3.24 (s, 3H), 2.69 (t, J=4.7 Hz, 4H), 2.41 (s, 3H), 2.25-2.21 (m, 1H), 2.19-2.15 (m, 1H); MS ESI 480.3 [M+H]$^+$, calcd for [C$_{29}$H$_{29}$N$_5$O$_2$+H]$^+$ 480.23.

Example A39. (1R,2S)-5'-methoxy-2-(3-(4-(4-methylpiperazin-1-yl)phenyl)-1H-indazol-6-yl)spiro[cyclopropane-1,3'-indolin]-2'-one hydrochloride

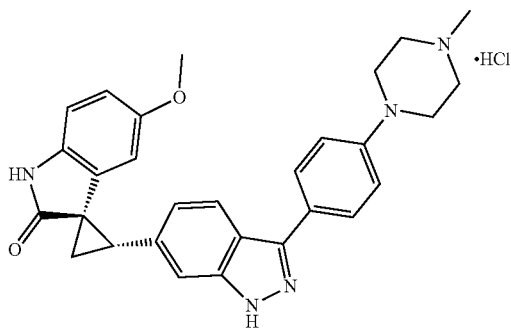 [SMILES: COc1ccc2c(c1)[C@]1(C[C@H]1c1ccc3c(-c4ccc(N5CCN(C)CC5)cc4)n[nH]c3c1)C(=O)N2 ; Cl]

A mixture of (1R,2S)-2-(3-iodo-1H-indazol-6-yl)-5'-methoxyspiro[cyclopropane-1,3'-indolin]-2'-one (540 mg, 1.25 mmol), 1-methyl-4-(4-(4,4,5,5-tetramethyl-1,3,2-dioxaborolan-2-yl)phenyl)piperazine (416 mg, 1.38 mmol), Pd(PPh$_3$)$_4$ (7 mg, 0.06 mmol), LiCl (159 mg, 3.75 mmol) and 1M Na$_2$CO$_3$ (6.3 mL, 6.3 mmol) in dioxane (20 mL) was heated to reflux in an oil bath until the iodide had been consumed as determined by LCMS. The reaction was then allowed to cool to room temperature and was diluted with EtOAc and water was added. The resulting mixture was extracted with EtOAc and the combined organic extracts were washed with brine, dried over MgSO$_4$ and concentrated to give an orange solid. The title compound was purified by silica gel chromatography (95:3:2 to 85:13:2 CH$_2$Cl$_2$/MeOH/NH$_3$) to yield a yellow solid. HCl (1M in diethyl ether, 3.1 mL, 3.1 mmol) was added in a dropwise manner to a solution of (1R,2S)-5'-methoxy-2-(3-(4-(4-methylpiperazin-1-yl)phenyl)-1H-indazol-6-yl)spiro [cyclopropane-1,3'-indolin]-2'-one (240 mg, 0.500 mmol) in THF (1 mL). A yellow precipitate formed and the solid was then filtered and washed with ether (2 mL) giving the title compound (256 mg, 42%). $^1$H NMR (400 MHz, CD$_3$OD) δ 7.94 (d, J=8.2 Hz, 1H), 7.88 (d, J=8.4 Hz, 2H), 7.52 (s, 1H), 7.19 (d, J=8.6 Hz, 2H), 7.05 (d, J=8.2 Hz, 1H), 6.84 (d, J=8.4 Hz, 1H), 6.62 (d, J=7.7 Hz, 1H), 5.62 (s, 1H), 4.01-3.98 (m, 2H), 3.67-3.64 (m, 2H), 3.39-3.32 (m, 3H), 3.28 (s, 3H), 3.18-3.11 (m, 2H), 3.00 (s, 3H), 2.28-2.25 (m, 1H), 2.21-2.18 (m, 1H); MS ESI 480.4 [M+H]$^+$, calcd for [C$_{29}$H$_{29}$N$_5$O$_2$+H]$^+$ 480.23.

Optical Rotation: [α]$^{22}_D$=–126° (c 0.40, MeOH).

Example A40. (1R*,2S*)-5'-fluoro-2-(3-iodo-1H-indazol-6-yl)spiro[cyclopropane-1,3'-indolin]-2'-one

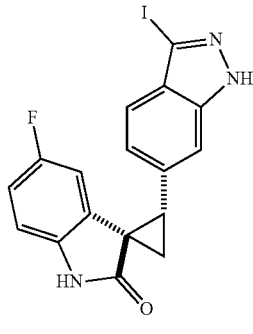

R*, S*, racemate

Trimethylsulfoxonium iodide (173.8 mg, 0.789 mmol) was added to a suspension of sodium hydride (94.76 mg, 4.12 mmol) (60% dispersion in oil) in THF (4.0 mL) at room temperature. The mixture was stirred for 15 min after which time a solution of (Z)-5-fluoro-3-((3-iodo-1H-indazol-6-yl)methylene)indolin-2-one (160 mg, 0.394 mmol) in THF (2.4 mL) was added. The solution was stirred at 50° C. for 7 h prior to quenching the reaction mass over 10% NH$_4$Cl solution (15 mL) at room temperature. The product was extracted using ethyl acetate (15 mL×2) and the organic layer was dried over Na$_2$SO$_4$ and evaporated in vacuo. Trituration with hexane (5 mL) gave the title compound as a cream solid (89 mg, 54%). $^1$H NMR (400 MHz, DMSO-d$_6$) δ 13.50 (s, 1H), 10.65 (s, 1H), 7.50 (s, 1H), 7.31 (d, 1H, J=8.4 Hz), 7.00 (d, 1H, J=8.4 Hz), 6.85-6.81 (m, 2H), 5.81 (d, 1H, J=8.4 Hz), 3.22 (m, 1H), 2.43 (m, 1H), 2.01 (m, 1H); MS ESI 420.0 [M+H]$^+$, calcd for [C$_{17}$H$_{11}$FIN$_3$O+H]$^+$ 420.0.

135

Example A41. (1R*,2S*)-(E)-5'-methoxy-2-(3-(4-(morpholinomethyl)styryl)-1H-indazol-6-yl)spiro[cyclopropane-1,3'-indolin]-2'-one 2,2,2-trifluoroacetate

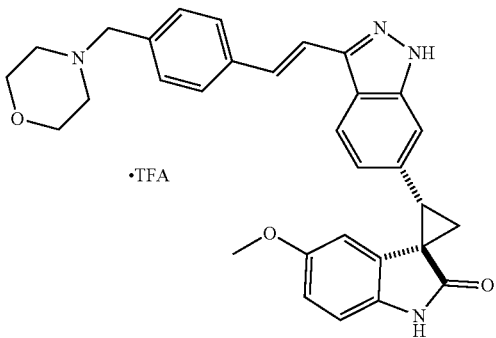

The title compound was synthesized according to the method of Example A45, except substituting (1R*,2S*)-2-(3-iodo-1H-indazol-6-yl)-5'-methoxyspiro[cyclopropane-1,3'-indolin]-2'-one (30 mg, 0.070 mmol) and (E)-4-(4-(2-(4,4,5,5-tetramethyl-1,3,2-dioxaborolan-2-yl)vinyl)benzyl)morpholine (30 mg, 0.091 mmol). Purification by column chromatography (silica gel, CH$_2$Cl$_2$/MeOH, 95:5 to 94:6) gave crude material which was 85% pure by LC-MS. This material was further purified by prep-HPLC to give a white solid (18 mg, 51%); Spectral was data identical to that obtained in Example A42B.

Example A42. (1R,2S)-(E)-5'-methoxy-2-(3-(4-(morpholinomethyl)styryl)-1H-indazol-6-yl)spiro[cyclopropane-1,3'-indolin]-2'-one hydrochloride

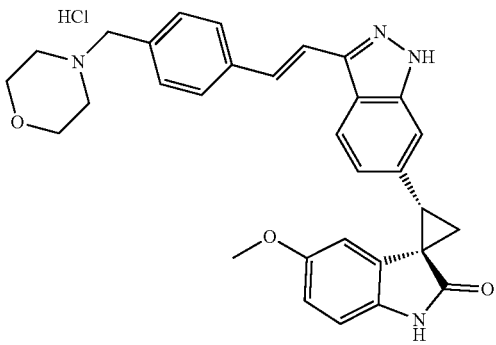 [SMILES: COc1ccc2c(c1)[C@]1(C[C@H]1c1ccc3c(/C=C/c4ccc(CN5CCOCC5)cc4)n[nH]c3c1)C(=O)N2 ; Cl]

A. (E)-4-(4-(2-(4,4,5,5-tetramethyl-1,3,2-dioxaborolan-2-yl)vinyl)benzyl)morpholine

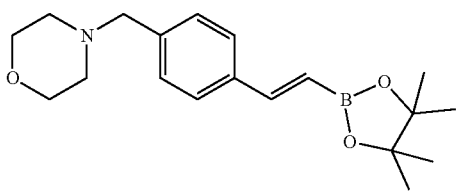 [SMILES: CC1(C)OB(/C=C/c2ccc(CN3CCOCC3)cc2)OC1(C)C]

136

An oven-dried round-bottom flask was cooled under N$_2$ $_{(g)}$ and then charged with 4-(4-ethynylbenzyl)morpholine (120 mg, 0.596 mmol), toluene (2.5 mL), and 4,4,5,5-tetramethyl-1,3,2-dioxaborolane (0.43 mL, 2.98 mmol). The mixture was stirred for 15 min while purging the solution with N$_2$ $_{(g)}$. HRuCl(CO)(PPh$_3$)$_3$ (29 mg, 0.030 mmol) was then added and the reaction heated to 50° C. for 18 h. The reaction was quenched with NaHCO$_3$ (sat.) (10 mL), extracted with EtOAc, and the organic layer washed with brine (2×) and then dried over MgSO$_4$. The solvent was removed and the resulting residue purified by column chromatography (silica gel, Hexanes/EtOAc, 2:3 to 1:2) to give a white solid (155 mg, 79%). $^1$H NMR (400 MHz, CDCl$_3$) δ 7.44 (d, 2H, J=8.0 Hz), 7.38 (d, 1H, J=18.8 Hz), 7.30 (m, 2H), 6.15 (d, 1H, J=18.5 Hz), 3.72 (bs, 4H), 3.49 (bs, 2H), 2.45 (bs, 4H), 1.31 (s, 12H); MS ESI 330.1 [M+H]$^+$, calcd for [C$_{19}$H$_{28}$BNO$_3$+H]$^+$ 330.22.

B. (1R,2S)-5'-methoxy-2-(3-(4-(morpholinomethyl)styryl)-1H-indazol-6-yl)spiro[cyclopropane-1,3'-indolin]-2'-one hydrochloride

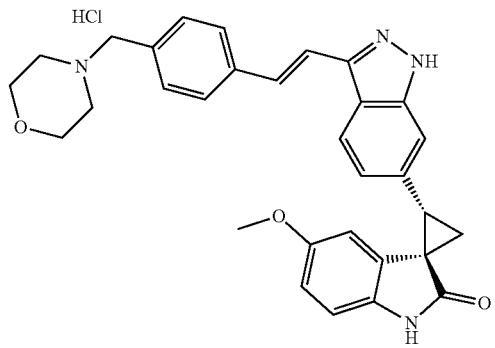 [SMILES: Cl ; COc1ccc2c(c1)[C@]1(C[C@H]1c1ccc3c(/C=C/c4ccc(CN5CCOCC5)cc4)n[nH]c3c1)C(=O)N2]

A round-bottom flask was charged with (1R,2S)-2-(3-iodo-1H-indazol-6-yl)-5'-methoxyspiro[cyclopropane-1,3'-indolin]-2'-one (255 mg, 0.592 mmol), (E)-4-(4-(2-(4,4,5,5-tetramethyl-1,3,2-dioxaborolan-2-yl)vinyl)benzyl)morpholine (260 mg, 0.710 mmol), LiCl (75 mg, 1.78 mmol), dioxane (6.0 mL), and Na$_2$CO$_3$ (3.0 mL of a 1M aqueous solution). The mixture was purged with a balloon of Ar$_{(g)}$ for 15 min and then Pd(PPh$_3$)$_4$ (21 mg, 0.0178 mmol) was added and the reaction heated to 100° C. for 18 h. The reaction was cooled, EtOAc and NaHCO$_3$ (sat.) were added, and the mixture transferred to a separatory funnel. The organic layer was washed with NaHCO$_3$ (sat.), Brine and then dried over MgSO$_4$. The solvent was removed and the residue purified by column chromatography (silica gel, CH$_2$Cl$_2$/MeOH, 9:1) to give a solid which was sonicated with Et$_2$O and filtered to give 183 mg, 61% of a white solid. The HCl salt was prepared by dissolving the free base (183 mg, 0.361 mmol) into THF (2 mL) and then HCl (0.72 mL of a 1M solution in Et$_2$O) was added. A precipitate immediately formed which was further precipitated with Et$_2$O (10 mL). The solid was quickly filtered and washed with Et$_2$O to give, after drying, an off-white solid (153 mg, 78%). $^1$H NMR (400 MHz, CD$_3$OD) δ 8.04 (d, 1H, J=8.4 Hz), 7.78 (d, 2H, J=8.2 Hz), 7.57-7.50 (m, 5H), 7.07 (d, 1H, J=8.6 Hz), 6.83 (d, 1H, J=8.5 Hz), 6.61 (dd, 1H, J$_1$=8.5 Hz, J$_2$=2.2 Hz), 5.58 (d, 1H, J=2.2 Hz), 4.39 (s, 2H), 4.09-4.04 (m, 2H), 3.78-3.72 (m, 2H), 3.43-3.33 (m, 3H), 3.27-3.20 (m, 5H), 2.27-2.23 (m, 1H), 2.21-2.16 (m, 1H); MS ESI 507.3 [M+H]+, calcd for [C31H30N4O3+H]+ 507.24.

Example A43. (1R*,2S*)-2-(3-(3-(hydroxymethyl)phenyl)-1H-indazol-6-yl)-5'-methoxy spiro[cyclopropane-1,3'-indolin]-2'-one 2,2,2-trifluoroacetate

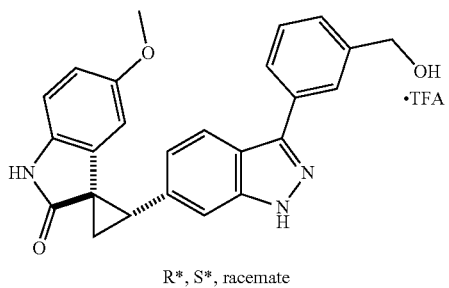

R*, S*, racemate

A mixture of (1R,2S)- and (1S, 2R)-2-(3-Iodo-1H-indazol-6-yl)-5'-methoxyspiro[cyclopropane-1,3'-indolin]-2'-one (50 mg, 0.12 mmol), 3-(hydroxymethyl)phenylboronic acid (20 mg, 0.13 mmol), PdCl2(PPh3)2 (8 mg, 0.01 mmol) and 2M Na2CO3 (60 uL, 0.12 mmol) in DME/H2O/EtOH (2.1 mL/0.6 mL/0.3 mL) was sealed and heated with stirring under microwave irradiation at 125° C. for 120 min. The crude reaction mixture was concentrated under reduced pressure to dryness, and purified by preparative HPLC to give the title compound as a white solid and as the TFA salt (22 mg, 46%). 1H NMR (400 MHz, CD3OD) δ 7.95-7.93 (m, 2H), 7.81 (d, J=7.7 Hz, 1H), 7.50-7.46 (m, 2H), 7.40 (d, J=7.6 Hz, 1H), 7.01 (d, J=8.5 Hz, 1H), 6.82 (d, J=8.5 Hz, 1H), 6.59 (dd, J=8.4, 2.5 Hz, 1H), 5.60 (d, J=2.4 Hz, 1H), 4.71 (s, 2H), 3.39-3.34 (m, 1H), 3.25 (s, 3H), 2.25-2.22 (m, 1H), 2.19-2.16 (m, 1H); MS ESI 412.2 [M+H]+, calcd for [C25H21N3O3+H]+ 412.16.

Example A44. (1R*,2S*)-5'-methoxy-2-(3-(3-(piperidin-1-ylmethyl)phenyl)-1H-indazol-6-yl)spiro[cyclopropane-1,3'-indolin]-2'-one 2,2,2-trifluoroacetate

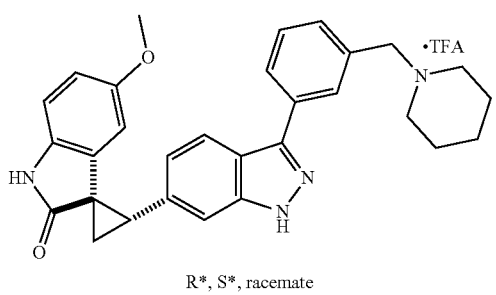

R*, S*, racemate

The title compound was synthesized according to the method of Example A43, using 1-(3-(4,4,5,5-tetramethyl-1,3,2-dioxaborolan-2-yl)benzyl)piperidine hydrochloric salt (44 mg, 0.13 mmol) and 2M Na2CO3 (180 uL, 0.35 mmol). The crude reaction mixture was concentrated under reduced pressure to dryness, and purified by preparative HPLC to give the title compound as a yellow solid and as the TFA salt (25 mg, 45%). 1H NMR (400 MHz, CD3OD) δ 8.10-8.08 (m, 2H), 7.99 (d, J=8.5 Hz, 1H), 7.65 (t, J=7.7 Hz, 1H), 7.57-7.53 (m, 2H), 7.05 (d, J=8.9 Hz, 1H), 6.84 (d, J=8.4 Hz, 1H), 6.61 (dd, J=8.5, 2.5 Hz, 1H), 5.60 (d, J=2.4 Hz, 1H), 4.40 (s, 2H), 3.54-3.48 (m, 2H), 3.39-3.35 (m, 1H), 3.28 (s, 3H), 3.03 (t, J=10.6 Hz, 2H), 2.27-2.24 (m, 1H), 2.22-2.18 (m, 1H), 1.98-1.95 (m, 2H), 1.86-1.70 (m, 3H), 1.54-1.52 (m, 1H); MS ESI 479.3 [M+H]+, calcd for [C30H30N4O2+H]+ 479.24.

Example A45. (1R*,2S*)-2-(3-(4-(hydroxymethyl)phenyl)-1H-indazol-6-yl)-5'-methoxyspiro[cyclopropane-1,3'-indolin]-2'-one 2,2,2-trifluoroacetate

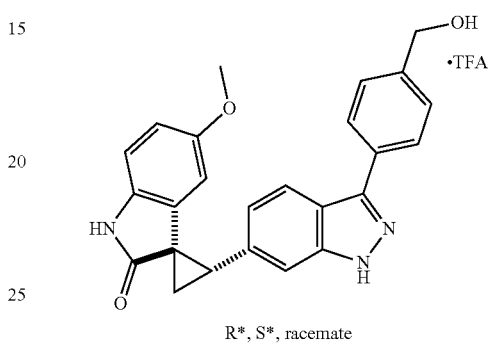

R*, S*, racemate

A mixture of (1R,2S)- and (1S,2R)-2-(3-Iodo-1H-indazol-6-yl)-5'-methoxyspiro[cyclopropane-1,3'-indolin]-2'-one (50 mg, 0.12 mmol), 4-(hydroxymethyl)phenylboronic acid (20 mg, 0.13 mmol), Pd(PPh3)4 (11 mg, 0.01 mmol) and KF (14 mg, 0.23 mmol) in DMF/H2O (2 mL/0.5 mL) was sealed and heated with stirring under microwave irradiation at 120° C. for 120 min. The crude reaction mixture was concentrated under reduced pressure to dryness, and purified by preparative HPLC to give the title compound as a white solid and as the TFA salt (16 mg, 33%). 1H NMR (400 MHz, CDCl3) δ 9.03 (s, 1H), 7.95 (d, J=8.6, 1H), 7.87 (d, J=8.0 Hz, 2H), 7.56 (d, J=7.8 Hz, 2H), 7.52 (s, 1H), 7.11 (d, J=8.7 Hz, 1H), 6.91 (d, J=8.5 Hz, 1H), 6.66 (dd, J=8.4, 2.3 Hz, 1H), 5.59 (d, J=2.1 Hz, 1H), 4.83 (s, 2H), 3.52 (t, J=8.4 Hz, 1H), 3.40 (s, 3H), 2.40-2.36 (m, 1H), 2.18-2.15 (m, 1H); MS ESI 412.2 [M+H]+, calcd for [C25H21N3O3+H]+ 412.16.

Example A46. (1R*,2S*)-2-(3-(3-(2-hydroxyethyl)phenyl)-1H-indazol-6-yl)-5'-methoxy spiro[cyclopropane-1,3'-indolin]-2'-one

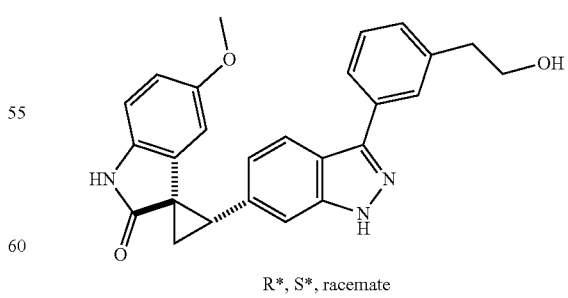

R*, S*, racemate

The title compound was synthesized according to the method of Example A45, using 3-(2-hydroxyethyl)phenylboronic acid (21 mg, 0.13 mmol). The crude reaction mixture was concentrated under reduced pressure to dryness, and purified by flash chromatography using hexanes/EtOAc as eluent (20:80 to 0:100), followed by preparative HPLC to give the title compound as a white solid (10 mg, 20%). ¹H NMR (400 MHz, CD$_3$OD) δ 7.93 (d, J=8.4 Hz, 1H), 7.81 (s, 1H), 7.75 (d, J=7.8 Hz, 1H), 7.50 (s, 1H), 7.44 (t, J=7.6 Hz, 1H), 7.30 (d, J=7.5 Hz, 1H), 7.03 (d, J=8.5 Hz, 1H), 6.83 (d, J=8.5 Hz, 1H), 6.61 (dd, J=8.4, 2.4 Hz, 1H), 5.60 (d, J=2.3 Hz, 1H), 3.84 (t, J=6.9 Hz, 2H), 3.37 (t, J=8.4 Hz, 1H), 3.26 (s, 3H), 3.93 (t, J=6.9 Hz, 2H), 2.27-2.24 (m, 1H), 2.21-2.17 (m, 1H); MS ESI 426.2 [M+H]$^+$, calcd for [C$_{26}$H$_{23}$N$_3$O$_3$+H]$^+$ 426.17.

Example A47. (1R*,2S*)-5'-methoxy-2-(3-(3-(piperazin-1-yl)phenyl)-1H-indazol-6-yl)spiro[cyclopropane-1,3'-indolin]-2'-one 2,2,2-trifluoroacetate

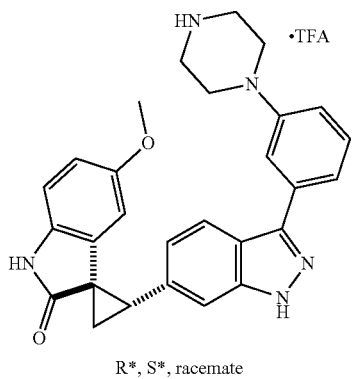

R*, S*, racemate

A mixture of (1R,2S)- and (1S,2R)-2-(3-Iodo-1H-indazol-6-yl)-5'-methoxyspiro[cyclopropane-1,3'-indolin]-2'-one (50 mg, 0.12 mmol), tert-butyl 4-(3-(4,4,5,5-tetramethyl-1,3,2-dioxaborolan-2-yl)phenyl)piperazine-1-carboxylate (50 mg, 0.13 mmol), PdCl$_2$(PPh$_3$)$_2$ (8 mg, 0.01 mmol) and 2M Na$_2$CO$_3$ (60 uL, 0.12 mmol) in DME/H$_2$O/EtOH (2.1 mL/0.6 mL/0.3 mL) was sealed and heated with stirring under microwave irradiation at 125° C. for 120 min. The crude reaction mixture was concentrated under reduced pressure to dryness, and purified by flash chromatography using hexanes/EtOAc as eluent (60:40 to 20:80) to give a pale yellow solid.

The intermediate was dissolved in CH$_2$Cl$_2$ (3 mL) and TFA (30 uL) was added. The resulting mixture was stirred at rt for 4 h. The crude reaction mixture was concentrated under reduced pressure to dryness, and purified by preparative HPLC to give the title compound as a yellow powder and as the TFA salt (25 mg, 37%). ¹H NMR (400 MHz, DMSO-d$_6$) δ 13.21 (s, 1H), 10.45 (s, 1H), 8.68 (br s, 1), 7.92 (d, J=8.4 Jz. 1H), 7.53-7.45 (m, 3H), 7.39 (t, J=8.0 Hz, 1H), 7.04-7.02 (m, 2H), 6.74 (d, J=8.4 Hz, 1H), 6.57 (dd, J=8.4, 2.4 Hz, 1H), 5.71 (d, J=2.5 Hz, 1H), 3.43-3.34 (m, 1H), 3.29 (s, 3H), 3.29-3.24 (m, 3H), 3.23-3.16 (m 2H), 2.36-2.32 (m, 1H), 2.02-1.98 (m, 1H); MS ESI 466.3 [M+H]$^+$, calcd for [C$_{28}$H$_{27}$N$_5$O$_2$+H]$^+$ 466.22.

Example A48. (1R*,2S*)-5'-methoxy-2-(3-(4-(piperazin-1-yl)phenyl)-1H-indazol-6-yl)spiro[cyclopropane-1,3'-indolin]-2'-one 2,2,2-trifluoroacetate

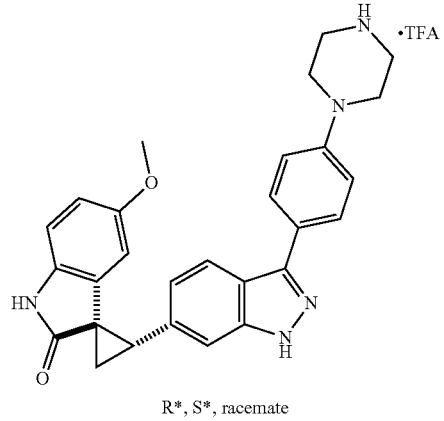

R*, S*, racemate

The title compound was synthesized according to the method of Example A47, using tert-butyl 4-(4-(4,4,5,5-tetramethyl-1,3,2-dioxaborolan-2-yl)phenyl)piperazine-1-carboxylate (99 mg, 0.26 mmol). The crude reaction mixture was concentrated under reduced pressure to dryness, and purified by flash chromatography using hexanes/EtOAc as eluent (50:50 to 0:100) to give a pale yellow solid.

The intermediate was dissolved in CH$_2$Cl$_2$ (3 mL) and TFA (20 uL) was added. The resulting mixture was stirred at rt for 4 h. The crude reaction mixture was concentrated under reduced pressure to dryness, and purified by preparative HPLC to give the title compound as a yellow powder and as the TFA salt (41 mg, 30%). ¹H NMR (400 MHz, CD$_3$OD) δ 7.88-7.84 (m, 3H), 7.47 (s, 1H), 7.14 (d, J=8.7 Hz, 2H), 6.98 (d, J=8.5 Hz, 1H), 6.82 (d, J=8.4 Hz, 1H), 6.60 (dd, J=8.4, 2.4 Hz, 1H), 5.60 (d, J=2.3 Hz, 1H), 3.51-3.48 (m, 4H), 3.41-3.36 (m, 4H), 3.33-3.31 (m 1H), 3.25 (s, 3H), 2.25-3.22 (m, 1H), 2.19-2.16 (m, 1H); MS ESI 466.2 [M+H]$^+$, calcd for [C$_{28}$H$_{27}$N$_5$O$_2$+H]$^+$ 466.22.

Example A49. (1R,2S)-5'-methoxy-2-(3-(4-(piperazin-1-yl)phenyl)-1H-indazol-6-yl)spiro[cyclopropane-1,3'-indolin]-2'-oneone 2,2,2-trifluoroacetate

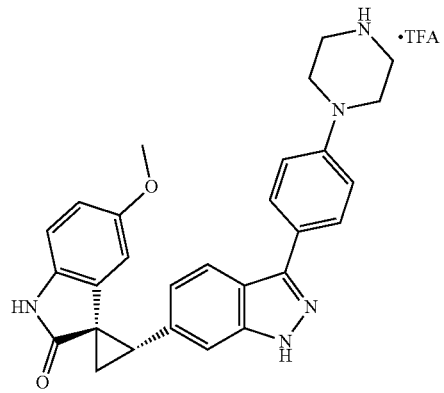 [SMILES: COc1ccc2c(c1)[C@]1(C[C@H]1c1ccc3c(-c4ccc(N5CCNCC5)cc4)n[nH]c3c1)C(=O)N2]

The title compound was synthesized according to the method of Example A48, except using (1R,2S-2-(3-iodo- 1H-indazol-6-yl)-5'-methoxyspiro[cyclopropane-1,3'-indolin]-2'-one (43 mg, 0.1 mmol) and tert-butyl 4-(4-(4,4,5,5-tetramethyl-1,3,2-dioxaborolan-2-yl)phenyl)piperazine-1-carboxylate (47 mg, 0.12 mmol). The title compound was isolated by reversed phase HPLC as a yellow solid (24 mg, 58%). Spectral was data identical to that obtained in Example A48.

Example A50. (1S,2R)-5'-methoxy-2-(3-(4-(piperazin-1-yl)phenyl)-1H-indazol-6-yl)spiro[cyclopropane-1,3'-indolin]-2'-one 2,2,2-trifluoroacetate

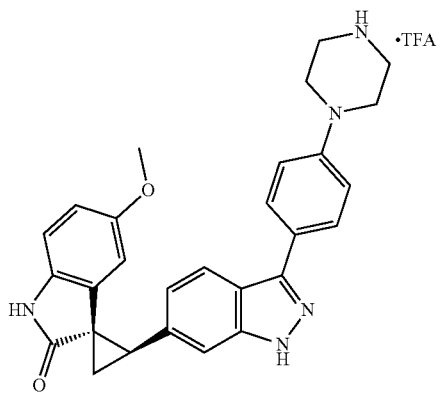 [SMILES: COc1ccc2c(c1)[C@@]1(C[C@@H]1c1ccc3c(-c4ccc(N5CCNCC5)cc4)n[nH]c3c1)C(=O)N2]

The title compound was synthesized according to the method of Example A48, except using (1S,2R)-2-(3-iodo-1H-indazol-6-yl)-5'-methoxyspiro[cyclopropane-1,3'-indolin]-2'-one (43 mg, 0.1 mmol) and tert-butyl 4-(4-(4,4,5,5-tetramethyl-1,3,2-dioxaborolan-2-yl)phenyl)piperazine-1-carboxylate (47 mg, 0.12 mmol). The title compound was isolated by reversed phase HPLC as a yellow solid (14 mg, 34%). Spectral was data identical to that obtained in Example A48.

Example A51. Synthesis of (1R,2S)-(E)-5'-methoxy-2-(3-(4-(2-morpholinoethyl)styryl)-1H-indazol-6-yl)spiro[cyclopropane-1,3'-indolin]-2'-one 2,2,2-trifluoroacetate

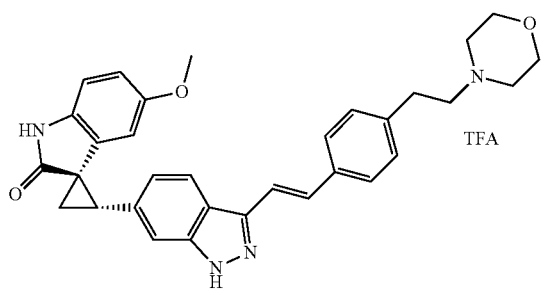 [SMILES: COc1ccc2c(c1)[C@]1(C[C@H]1c1ccc3c(/C=C/c4ccc(CCN5CCOCC5)cc4)n[nH]c3c1)C(=O)N2]

A. (E)-4-(4-(2-(4,4,5,5-tetramethyl-1,3,2-dioxaborolan-2-yl)vinyl)phenethyl)morpholine To a mixture of 4-(4-bromophenethyl)morpholine (731 mg, 2.71 mmol) and 4,4,5,5-tetramethyl-2-vinyl-1,3,2-dioxaborolane (0.5 mL, 2.95 mmol, 1.1 eq.) and toluene (10 mL) in a 20 mL microwave vial was added Et$_3$N (0.76 mL, 5.4 mmol, 2 eq.), followed by Pd(P$^t$Bu$_3$)$_2$ (14 mg, 0.027 mmol, 1 mol %). The resulting mixture was purged with argon, then capped and heated at 80° C. (oil temp.) for 2 h. After cooling to rt, it was quenched with sat. NaHCO$_3$ (10 mL), H$_2$O (10 mL), extracted with EtOAc (30 mL×2) and dried (Na$_2$SO$_4$). After evaporation of the solvents, the residue was purified by Biotage column system (EtOAc/hex gradient: 0-100%) to give (E)-4-(4-(2-(4,4,5,5-tetramethyl-1,3,2-dioxaborolan-2-yl)vinyl)phenethyl)morpholine as a white solid (714 mg, 77%). $^1$H NMR (400 MHz, CDCl$_3$) δ 7.42 (d, J=8.0 Hz, 2H), 7.38 (d, J=19.0 Hz, 1H), 7.19 (d, J=7.8 Hz, 2H), 6.13 (d, J=18.3 Hz, 1H), 3.75 (t, J=4.4 Hz, 4H), 2.84-2.77 (m, 2H), 2.63-2.56 (m, 2H), 2.53 (br, pseudo s, 4H), 1.32 (s, 12H).

B. Synthesis of (1R,2S)-5'-methoxy-2-(3-(4-(2-morpholinoethyl)styryl)-1H-indazol-6-yl)spiro[cyclopropane-1,3'-indolin]-2'-one To a mixture of (1R,2S)-2-(3-iodo-1H-indazol-6-yl)-5'-methoxyspiro [cyclopropane-1,3'-indolin]-2'-one (172 mg, 0.4 mmol) and (E)-4-(4-(2-(4,4,5,5-tetramethyl-1,3,2-dioxaborolan-2-yl)vinyl)phenethyl)morpholine (138 mg, 0.4 mmol) in PhCH$_3$/EtOH (8 mL/4 mL) in a 20 mL microwave vial was added 1 M Na$_2$CO$_3$ (0.8 mL, 0.8 mmol), followed by Pd(PPh$_3$)$_4$ (23 mg, 0.02 mmol, 5 mol %). The resulting mixture was purged with argon, then microwaved for 2 h at 125° C. After cooling to rt, the mixture was diluted with H$_2$O (20 mL), extracted with EtOAc (30 mL×2) and dried (Na$_2$SO$_4$). After removal of solvents, the residue was redissolved in DMF (4 mL) and purified by preparatory HPLC to give the title compound (TFA salt, 115 mg, 45%) as a pale yellow solid. $^1$H NMR (400 MHz, CD$_3$OD) δ 7.90 (d, J=8.4 Hz, 1H), 7.53 (d, J=7.2 Hz, 2H), 7.43 (s, 1H), 7.37 (d, J=6.4 Hz, 2H), 7.28 (d, J=7.2 Hz, 2H), 6.95 (d, J=7.6 Hz, 1H), 6.81 (d, J=8.4 Hz, 1H), 6.57 (d, J=7.6 Hz, 1H), 5.57 (s, 1H), 4.06 (d, J=11.2 Hz, 2H), 3.80 (t, J=11.2 Hz, 2H), 3.56 (d, J=11.2 Hz, 2H), 3.38 (t, J=7.6 Hz, 2H), 3.27-3.12 (m, 5H), 3.07 (t, 2H), 2.20-2.10 (m, 2H); MS ESI 521.4 [M+H]$^+$, calcd for [C$_{32}$H$_{32}$N$_4$O$_3$+H]$^+$ 521.2.

Example A52. (1R*,2S*)- and (1R*,2S*)-5'-methoxy-2-(3-(pyridin-3-ylethynyl)-1H-indazol-6-yl)spiro[cyclopropane-1,3'-indolin]-2'-one

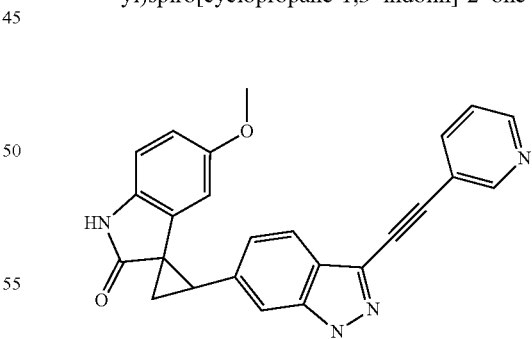

R*, S*, racemate and
R*, R*, racemate

To a mixture of 3-ethnylpyridine (12.4 mg, 0.12 mmol, 1.2 equiv.), (1R*,2S*)- and (1R*,2R*)-2-(3-iodo-1H-indazol-6-yl)-5'-methoxyspiro-[cyclopropane-1,3'-indolin]-2'-one (43.1 mg, 0.1 mmol), Pd(PPh$_3$)$_2$Cl$_2$ (3.5 mg, 0.005 mmol, 5 mol %) and CuI (1.9 mg, 0.01 mmol, 10 mol %) in DMF (3 mL) was adde Et$_3$N (5 mL). The resulting mixture was heated at 100° C. under argon for 2 h. After cooling to rt, Et$_3$N was removed by rotary evaporator and the residue was purified by flash chromatography (eluent: EtOAc/hexane 1:3 to 1:1 then EtOAc) to give the crude product as a liquid. H$_2$O (30 mL) was added and the resulting precipitates were collected by suction filtration and dried to give the title compound (25 mg, 61%) as a light beige solid. The $^1$H NMR indicated a mixture of two diastereomers (87:13) in favor of the (1R*,2S*) isomer. $^1$H NMR (400 MHz, CD$_3$OD) δ 8.81 (s, 1H), 8.57 (s, 1H), 8.08 (d, J=8.8 Hz, 1H), 7.89 (d, J=9.2 Hz, 1H), 7.60-7.47 (m, 2H), 7.10 (d, J=8.0 Hz, 1H), 6.84 (d, J=7.6 Hz, 1H), 6.63 (d, J=8.8 Hz, 1H), 5.56 (s, 1H), 2.30-2.15 (m, 2H) (note: 2 signals for methoxy and one cyclopropyl were obscured by methanol solvent signal); MS ESI 407.2 [M+H]$^+$, calcd for [C$_{25}$H$_{18}$N$_4$O$_2$+H]$^+$ 407.2.

Example A53. (1R*,2S*)-2-(3-((E)-2-(pyridin-2-yl)vinyl)-1H-indazol-6-yl)spiro[cyclopropane-1,3'-indolin]-2'-one

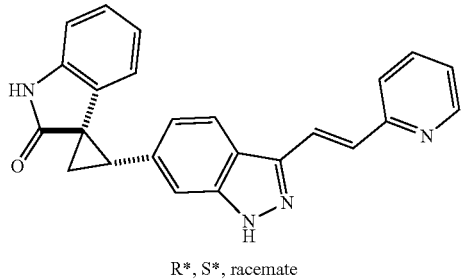

R*, S*, racemate

A. (1R*,2S*)-2-(3-((E)-2-(pyridin-2-yl)vinyl)-1-((2-(trimethylsilyl)ethoxy)methyl)-1H-indazol-6-yl)spiro[cyclopropane-1,3'-indolin]-2'-one The title compound was synthesized according to the method of Example A22, Method 1A, using 2-vinylpyridine (60 mg, 0.58 mmol). The title compound was isolated by silica gel chromatography (1:1 EtOAc/Hex) to give the title compound as a beige solid (127 mg, 66%). MS ESI 509.2 [M+H]$^+$, calcd for [C$_{30}$H$_{32}$N$_4$O$_2$Si+H]$^+$ 509.3.

B. (1R*,2S*)-2-(3-((E)-2-(pyridin-2-yl)vinyl)-1H-indazol-6-yl)spiro[cyclopropane-1,3'-indolin]-2'-one The title compound was synthesized according to the method of Example A15, Method 1B, using (1R,2S)-2-(3-((E)-2-(pyridin-2-yl)vinyl)-1-((2-(trimethylsilyl)ethoxy)methyl)-1H-indazol-6-yl)spiro[cyclopropane-1,3'-indolin]-2'-one (60 mg, 0.1 mmol). The crude reaction mixture was concentrated under reduced pressure to dryness, and purified by reverse phase preparative HPLC to give the title compound as a white solid (8 mg, 21%). $^1$H NMR (400 MHz, CD$_3$OD) δ 8.71 (d, J=6.3 Hz, 1H), 8.52 (t, J=8.7 Hz, 1H), 8.45 (d, J=8.2 Hz, 1H), 8.22 (d, J=16.6 Hz, 1H), 8.03 (d, J=8.0 Hz, 1H), 7.86-7.84 (m, 1H), 7.66 (d, J=17.0 Hz, 1H), 7.56 (s, 1H), 7.13 (d, J=8.2 Hz, 1H), 7.07-7.04 (m, 1H), 6.95 (d, J=7.5 Hz, 1H), 6.57 (t, J=7.5 Hz, 1H), 5.97 (d, J=7.0 Hz, 1H), 3.40-3.33 (m, 1H), 2.29-2.17 (m, 2H); MS ESI 379.2 [M+H]$^+$, calcd for [C$_{24}$H$_{18}$N$_4$O+H]$^+$ 379.4.

Example A54. 4-((E)-2-(6-((1R*,2S*)-2'-oxospiro[cyclopropane-1,3'-indoline]-2-yl)-1H-indazol-3-yl)vinyl)benzonitrile

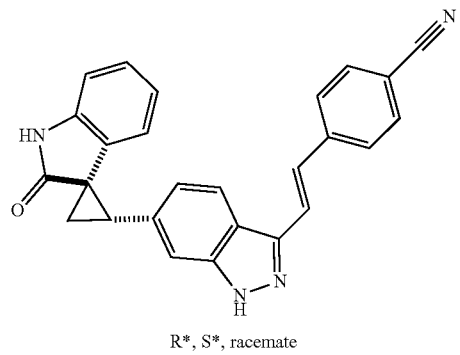

R*, S*, racemate

A. 6-formyl-1H-indazole-3-carbonitrile

To a solution of 3-iodo-1H-indazole-6-carbaldehyde (3 g, 10.8 mmol) in DMF (25 mL) was added Copper cyanide (1.9 g, 21 mmol). The solution was heated by microwave irradiation at 185° C. for 10 min Water (100 mL) was added and a white precipitate was collected. The precipitate was dissolved in EtOAc (250 mL), washed with water (2×25 mL), dried over MgSO$_4$ and concentrated to give the title compound as a white solid (1.1 g, 73%). $^1$H NMR (400 MHz, DMSO-d$_6$) δ 14.92 (bs, 1H), 10.17 (s, 1H), 8.39 (s, 1H), 8.06 (d, J=8.3 Hz, 1H), 7.83 (d, J=8.5 Hz, 1H).

B. (E)-6-((2-oxoindolin-3-ylidene)methyl)-1H-indazole-3-carbonitrile

To a mixture of 6-formyl-1H-indazole-3-carbonitrile (1.10 g, 6.4 mmol) and 2-oxindole (871 mg, 6.5 mmol) in EtOH (25 mL) was added piperidine (0.1 mL, 1 mmol). The resulting mixture was refluxed (oil temp. 75° C.) for 90 min, then cooled to rt. The resulting precipitate was collected by suction filtration and dried to give the title compound as an orange solid (1.5 g, 82%) $^1$H NMR (400 MHz, DMSO-d$_6$) δ 14.6 (s, 1H), 10.66 (s, 1H), 8.09 (s, 1H), 8.01 (d, J=8.5 Hz, 1H) 7.78 (s, 1H), 7.67 (d, J=8.5 Hz, 1H), 7.48 (d, 1H, J=7.8 Hz), 7.24 (t, J=7.6 Hz, 1H), 6.88 (d, J=7.8 Hz, 1H), 6.83 (t, J=7.8 Hz, 1H).

C. 6-((1R*,2S*)-2'-oxospiro[cyclopropane-1,3'-indoline]-2-yl)-1H-indazole-3-carbonitrile The title compound was synthesized according to the method of Example A1, using (E)-6-((2-oxoindolin-3-ylidene)methyl)-1H-indazole-3-carbonitrile (1.5 g, 5.2 mmol) to give the title compound as a yellow solid (1.3 g, 83%). $^1$H NMR (400 MHz, CD$_3$OD) δ 7.73 (d, J=8.3 Hz, 1H), 7.61 (s, 1H), 7.18 (d, J=8.5 Hz, 1H) 7.08-7.04 (m, 1H), 6.94 (d, J=8.0 Hz, 1H), 6.58 (t, J=7.6 Hz, 1H), 5.93 (d, J=7.8 Hz, 1H), 3.38-3.34 (m, 1H), 2.27-2.18 (m, 1H).

D. 6-((1R*,2S*)-2'-oxospiro[cyclopropane-1,3'-indoline]-2-yl)-1H-indazole-3-carbaldehyde To a solution of 6-((1R*,2S*)-2'-oxospiro[cyclopropane-1,3'-indoline]-2-yl)-1H-indazole-3-carbonitrile (1 g, 3.3 mmol) in pyridine (30 mL) acetic acid (8 mL) and water (8 mL) and Raney Nickel (1 g). Sodium hypophosphite (1.8 g, 21 mmol) was dissolved in water (10 mL) and added dropwise and the reaction was stirred overnight. The product was extracted into ethyl acetate (300 mL), washed with brine (50 mL), dried over MgSO$_4$ and concentrated to dryness. The residue was purified by silica gel chromatography (95:5 CH$_2$Cl$_2$/MeOH) to give the title compound as a yellow solid (300 mg, 30%). $^1$H NMR (400 MHz, CD$_3$OD) δ 10.17 (s, 1H), 8.10 (d, J=8.3 Hz, 1H), 7.55 (s, 1H), 7.17 (d, J=8.5 Hz, 1H) 7.08-7.04 (m, 1H), 6.94 (d, J=8.3 Hz, 1H), 6.56 (t, J=7.6 Hz, 1H), 5.93 (d, J=7.5 Hz, 1H), 3.38-3.34 (m, 1H), 2.27-2.17 (m, 1H).

E. 4-((E)-2-(6-((1R*,2S*)-2'-oxospiro[cyclopropane-1,3'-indoline]-2-yl)-1H-indazol-3-yl)vinyl)benzonitrile Diethyl 4-cyanobenzylphosphonate (600 mg, 2.4 mmol) was dissolved into DMF (5 mL) at 0° C. Potassium tert-butoxide (540 mg, 4.8 mmol) was added and the mixture was stirred for 5 min. Compound A54D (200 mg, 0.66 mmol) was dissolved into DMF (5 mL) and added dropwise to the solution and the mixture was stirred for 90 min. The reaction was quenched with HCl (0.1 N) and the resulting precipitate collected. The precipitate was dissolved into EtOAc (100 mL) and washed with H$_2$O (2×10 mL), brine (10 mL), dried over MgSO$_4$ and concentrated to dryness. The residue was purified by silica gel chromatography to give the title compound as a white solid (100 mg, 38%). $^1$H NMR (400 MHz, CD$_3$OD) δ 8.04 (d, J=8.5 Hz, 1H), 7.82 (d, J=8.6 Hz, 2H), 7.74 (d, J=8.6 Hz, 2H), 7.66-7.53 (m, 2H), 7.48 (s, 1H), 7.08-7.04 (m, 2H), 6.94 (d, J=8.3 Hz, 1H), 6.59 (t, J=7.6 Hz, 1H), 5.99 (d, J=7.5 Hz, 1H), 3.38-3.34 (m, 1H), 2.27-2.18 (m, 2H); MS ESI 403.1 [M+H]$^+$, calcd for [C$_{26}$H$_{18}$N$_4$O+H]$^+$ 403.1.

Example A55. (1R*,2S*)-(E)-2-(3-(4-(morpholinomethyl)styryl)-1H-indazol-6-yl)spiro[cyclopropane-1,3'-indolin]-2'-one 2,2,2-trifluoroacetate

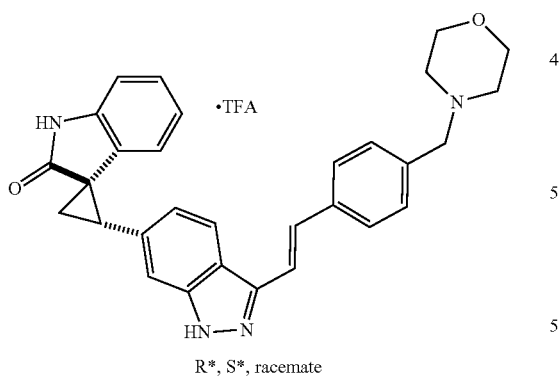

R*, S*, racemate

A. 4-((E)-2-(6-((1R*,2S*)-2'-oxospiro[cyclopropane-1,3'-indoline]-2-yl)-1H-indazol-3-yl)vinyl)benzaldehyde The title compound was synthesized according to the method of Example A54D, except substituting 4-((E)-2-(6-((1R*,2S*)-2'-oxospiro[cyclopropane-1,3'-indoline]-2-yl)-1H-indazol-3-yl)vinyl)benzonitrile (100 mg, 0.25 mmol).

Purification by silica gel chromatography (99:1 CH$_2$Cl$_2$/MeOH) gave the title compound as an orange solid (95 mg, 94%). MS ESI 406.2 [M+H]$^+$, calcd for [C$_{26}$H$_{19}$N$_3$O$_2$+H]$^+$ 406.2.

B. (1R*,2S*)-2-(3-(4-(morpholinomethyl)styryl)-1H-indazol-6-yl)spiro[cyclopropane-1,3'-indolin]-2'-one 2,2,2-trifluoroacetate To a solution of Example A54A (40 mg, 0.1 mmol) in THF (3 mL) was added morpholine (43 mg, 0.5 mmol) and titanium isopropoxide (57 mg, 0.2 mmol) and the reaction was stirred 30 min Sodium borohydride (13 mg, 0.2 mmol) was added and the mixture was heated to 50° C. overnight. The reaction was quenched with water (2 mL) and extracted with ethyl acetate (25 mL) dried over MgSO$_4$ and concentrated to dryness. The residue was purified by reversed phase preparatory HPLC to give the title compound as the TFA salt (5 mg, 9%). $^1$H NMR (400 MHz, CD$_3$OD) δ 8.02 (d, J=8.5 Hz, 1H), 7.78 (d, J=8.6 Hz, 2H), 7.75-7.48 (m, 5H), 7.08-7.05 (m, 2H), 6.94 (d, J=8.3 Hz, 1H), 6.59 (t, J=7.6 Hz, 1H), 5.99 (d, J=7.5 Hz, 1H) 4.39 (s, 2H) 4.12-4.04 (m, 2H), 3.79-3.68 (m, 2H) 3.44-3.34 (m, 3H), 3.30-3.19 (m, 2H) 2.28-2.16 (m, 2H); MS ESI 477.3 [M+H]$^+$, calcd for [C$_{30}$H$_{28}$N$_4$O$_2$+H]$^+$ 477.2.

Example A56. (1R,2S)-(E)-2-(3-(4-(morpholinomethyl)styryl)-1H-indazol-6-yl)spiro[cyclopropane-1,3'-indolin]-2'-one 2,2,2-trifluoroacetate

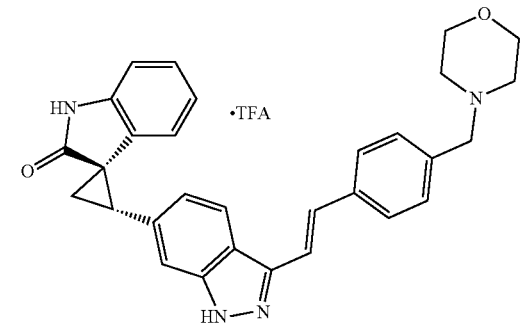 [SMILES: O=C1Nc2ccccc2[C@]12C[C@H]2c1ccc2c(/C=C/c3ccc(CN4CCOCC4)cc3)n[nH]c2c1]

The title compound was synthesized according to the method of Example A51B, except substituting (1R,2S)-2-(3-iodo-1H-indazol-6-yl) [cyclopropane-1,3'-indolin]-2'-one (150 mg, 0.37 mmol) and (E)-4-(4-(2-(4,4,5,5-tetramethyl-1,3,2-dioxaborolan-2-yl)vinyl)benzyl)morpholine (160 mg, 0.48 mmol). Purification by reverse phase preparatory HPLC gave the title compound as a yellow TFA salt (122 mg, 58%). [α]$^{23.8°}_D$=−79° (c 0.33, Methanol). Spectral was data identical to that obtained in Example A55.

Example A57. (1R*,2S*)-(E)-2-(3-(4-(piperidin-1-ylmethyl)styryl)-1H-indazol-6-yl)spiro[cyclopropane-1,3'-indolin]-2'-one 2,2,2-trifluoroacetate

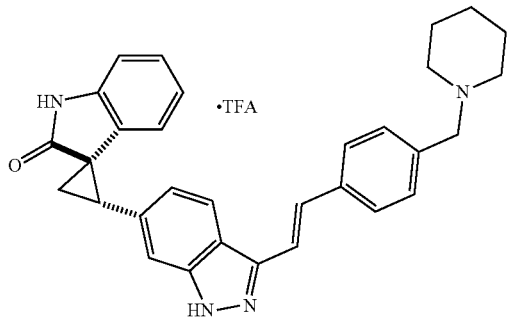

The title compound was synthesized according to the method of Example A55, method B, except substituting piperidine (43 mg, 0.5 mmol). Purification by reverse phase preparatory HPLC gave the title compound as a yellow TFA salt (8 mg, 28%). $^1$H NMR (400 MHz, CD$_3$OD) δ 8.02 (d, J=8.8 Hz, 1H), 7.77 (d, J=8.6 Hz, 2H), 7.75-7.48 (m, 5H), 7.08-7.05 (m, 2H), 6.94 (d, J=7.5 Hz, 1H), 6.59 (t, J=7.7 Hz, 1H), 5.99 (d, J=7.3 Hz, 1H) 4.31 (s, 2H) 3.53-3.45 (m, 2H), 3.39-3.34 (m, 1H), 3.04-2.93 (m, 2H) 2.27-2.17 (m, 2H), 2.02-1.95 (m, 2H), 1.88-1.71 (m, 3H), 1.57-1.45 (m, 1H); MS ESI 475.3 [M+H]$^+$, calcd for [C$_{31}$H$_{30}$N$_4$O+H]$^+$ 475.2.

Example A58. (1R,2S)-(E)-2-(3-(4-(piperidin-1-ylmethyl)styryl)-1H-indazol-6-yl)spiro[cyclopropane-1,3'-indolin]-2'-one 2,2,2-trifluoroacetate

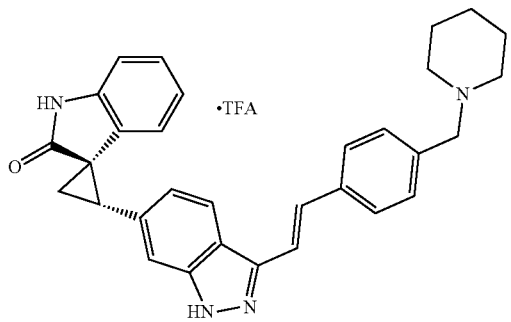 [SMILES: O=C1Nc2ccccc2[C@]12C[C@H]2c1ccc2c(/C=C/c3ccc(CN4CCCCC4)cc3)n[nH]c2c1]

The title compound was synthesized according to the method of Example A51B, except substituting (1R,2S)-2-(3-iodo-1H-indazol-6-yl) [cyclopropane-1,3'-indolin]-2'-one (50 mg, 0.12 mmol) and (E)-4-(4-(2-(4,4,5,5-tetramethyl-1,3,2-dioxaborolan-2-yl)vinyl)benzyl)piperidine (59 mg, 0.18 mmol). Purification by reverse phase preparatory HPLC gave the title compound as a yellow TFA salt (13 mg, 20%). [α]$^{23.6°}_D$=−109° (c 0.35, Methanol). Spectral was data identical to that obtained in Example A57.

Example A59. (1R,2S)-(E)-5'-methoxy-2-(3-(4-(piperidin-1-ylmethyl)styryl)-1H-indazol-6-yl)spiro[cyclopropane-1,3'-indolin]-2'-one 2,2,2-trifluoroacetate salt

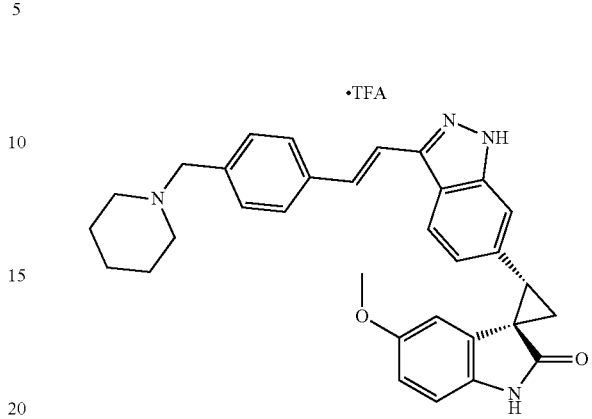

The title compound was synthesized according to the method of Example A51B, except substituting (E)-4-(4-(2-(4,4,5,5-tetramethyl-1,3,2-dioxaborolan-2-yl)vinyl)benzyl)piperidine (59 mg, 0.18 mmol). Purification by reverse phase preparatory HPLC gave the title compound as a yellow TFA salt (17 mg, 23%). $^1$H NMR (400 MHz, CD$_3$OD) δ 8.02 (d, J=8.3 Hz, 1H), 7.75 (d, J=8.6 Hz, 2H), 7.53-7.49 (m, 5H), 7.05 (d, J=8.5 Hz, 1H), 6.84 (d, J=8.5 Hz, 1H), 6.61 (dd, J=8.4, 2.3 Hz, 1H), 5.58 (d, J=2.3 Hz, 1H) 4.30 (s, 2H), 3.52-3.44 (m, 2H), 3.38-3.34 (m, 1H), 3.26 (s, 3H), 3.01-2.93 (m, 2H), 2.26-2.17 (m, 4H), 2.00-1.91 (m, 2H), 1.89-1.67 (m, 3H), 1.58-1.46 (m, 1H); MS ESI 505.3 [M+H]$^+$, calcd for [C$_{32}$H$_{32}$N$_4$O$_2$+H]$^+$ 505.3. [α]$^{22.6°}_D$=−69° (c 0.29, Methanol).

Example A60. (1R*,2S*)-(E)-2-(3-(4-(pyrrolidin-1-ylmethyl)styryl)-1H-indazol-6-yl)spiro[cyclopropane-1,3'-indolin]-2'-one 2,2,2-trifluoroacetate

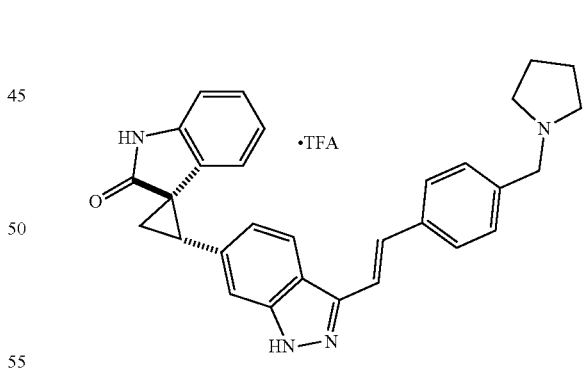

The title compound was synthesized according to the method of Example A55, except substituting pyrrolidine (71 mg, 0.86 mmol). Purification by reverse phase preparatory HPLC gave the title compound as a yellow TFA salt (34 mg, 35%). $^1$H NMR (400 MHz, CD$_3$OD) δ 8.02 (d, J=8.6 Hz, 1H), 7.76 (d, J=8.6 Hz, 2H), 7.55-7.48 (m, 5H), 7.08-7.05 (m, 2H), 6.94 (d, J=7.8 Hz, 1H), 6.59 (t, J=7.5 Hz, 1H), 5.99 (d, J=7.5 Hz, 1H) 4.40 (s, 2H), 3.55-3.46 (m, 2H), 3.38-3.34 (m, 1H), 3.27-3.16 (m, 2H), 2.27-2.17 (m, 4H), 2.06-1.98 (m, 2H); MS ESI 461.3 [M+H]$^+$, calcd for [C$_{30}$H$_{28}$N$_4$O+H]$^+$ 461.2.

Example A61. (1R,2S)-(E)-2-(3-(4-(pyrolidin-1-ylmethyl)styryl)-1H-indazol-6-yl)spiro[cyclopropane-1,3'-indolin]-2'-one 2,2,2-trifluoroacetate

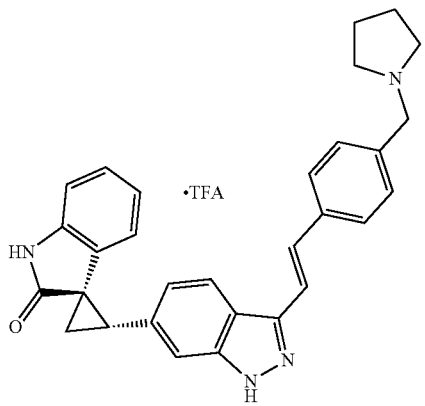 [SMILES: O=C1Nc2ccccc2[C@]12C[C@H]2c1ccc2c(/C=C/c3ccc(CN4CCCC4)cc3)n[nH]c2c1]

The title compound was synthesized according to the method of Example A51B, except substituting (1R,2S)-2-(3-iodo-1H-indazol-6-yl) [cyclopropane-1,3'-indolin]-2'-one (175 mg, 0.43 mmol) and (E)-4-(4-(2-(4,4,5,5-tetramethyl-1,3,2-dioxaborolan-2-yl)vinyl)benzyl)pyrrolidine (225 mg, 0.64 mmol). Purification by reverse phase preparatory HPLC gave the title compound as a yellow TFA salt (123 mg, 51%). Spectral was data identical to that obtained in Example A60.

Example A62. (1R,2S)-(E)-5'-methoxy-2-(3-((E)-2-(6-(piperidin-1-ylmethyl)pyridin-3-yl)vinyl)-1H-indazol-6-yl)spiro[cyclopropane-1,3'-indolin]-2'-one 2,2,2-trifluoroacetate salt

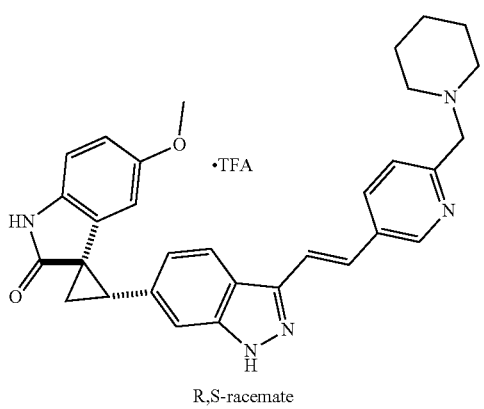

R,S-racemate

A. 5-((trimethylsilyl)ethynyl)picolinaldehyde

A solution of 5-bromopicolinaldehyde (1 g, 5.3 mmol), TMS-acetylene (1.04 g, 10.6 mmol) and triethylamine (4 mL) in THF (10 mL) was purged with argon for 10 min Copper iodide (76 mg, 0.4 mmol), Pd(PPh$_3$)$_2$Cl$_2$ (141 mg, 0.4 mmol) and triphenylphosphine (0.1 g, 0.4 mmol) was added and the mixture was heated to 100° C. under microwave irradiation for 10 min. Ethyl acetate (200 mL) was added at the solution was washed with water (2×25 mL), dried over MgSO$_4$ and concentrated to dryness. The residue was filtered through silica gel with CH$_2$Cl$_2$ to give the title compound as a yellow oil (1 g, 95%). $^1$H NMR (400 MHz, CDCl$_3$) δ 10.08 (s, 1H), 8.82 (s, 1H), 7.91 (s, 2H), 0.29 (s, 9H).

B. 5-ethynylpicolinaldehyde

To a solution of Example A62A (1 g, 4.9 mmol) in methanol (50 mL) was added potassium carbonate (68 mg, 0.44 mmol). The mixture was stirred at rt for 3 h. Ethyl acetate (200 mL) was added and the solution was washed with water (2×25 mL), brine (25 mL), dried over MgSO$_4$ and concentrated to dryness. The residue was filtered through silica gel with CH$_2$Cl$_2$ to give the title compound as a yellow oil (400 g, 62%). MS ESI 131.8 [M+H]$^+$, calcd for [C$_8$H$_5$NO+H]$^+$ 132.0.

C. 5-ethynyl-2-(piperidin-1-ylmethyl)pyridine

To a solution of Example A62B (150 mg, 0.14 mmol) in dichloroethane (4 mL) was added piperidine (144 mg, 1.7 mmol) and acetic acid (2 drops). Sodium triacetoxyborohydride (360 mg, 1.7 mmol) was added and the reaction was stirred overnight. The reaction was quenched with sat. NH$_4$Cl (50 mL). Ethyl acetate (100 mL) was added and the solution was washed with sat. NaHCO$_3$ (2×10 mL), brine (10 mL), dried over MgSO$_4$ and concentrated to dryness. The residue was flushed through a CX column with methanol and 1% NH$_3$/Methanol to give the title compound as a colorless oil (200 mg, 88%). $^1$H NMR (400 MHz, CDCl$_3$) δ 8.66 (s, 1H), 7.75 (d, J=8.0 Hz, 1H), 7.51-7.45 (m, 1H), 3.67 (s, 2H) 3.20 (s, 1H), 2.48 (bs, 4H), 1.64 (bs, 4H), 1.52-1.42 (m, 2H).

D. (E)-2-(piperidin-1-ylmethyl)-5-(2-(4,4,5,5-tetramethyl-1,3,2-dioxaborolan-2-yl)vinyl)pyridine The title compound was synthesized according to the method of Example A42A, except substituting 5-ethynyl-2-(piperidin-1-ylmethyl)pyridine (200 mg, 1 mmol). The title compound was purified by silica gel chromatography (95:5 CH$_2$Cl$_2$/MeOH) to give the title compound as a brown solid (140 mg, 43%). $^1$H NMR (400 MHz, CDCl$_3$) δ 8.62 (s, 1H), 7.79 (d, J=7.8 Hz, 1H), 7.51-7.45 (m, 1H), 7.38 (d, J=18.6 Hz, 1H), 6.23 (d, J=18.6 Hz, 1H), 3.68 (s, 2H), 2.50 (bs, 4H), 1.65 (bs, 4H), 1.47 (bs, 2H).

E. (1R*,2S*)-5'-methoxy-2-(3-((E)-2-(6-(piperidin-1-ylmethyl)pyridin-3-yl)vinyl)-1H-indazol-6-yl)spiro[cyclopropane-1,3'-indolin]-2'-one The title compound was synthesized according to the method of Example A51B, except substituting (E)-2-(piperidin-1-ylmethyl)-5-(2-(4,4,5,5-tetramethyl-1,3,2-dioxaborolan-2-yl)vinyl)pyridine (65 mg, 0.2 mmol). Purification by reverse phase preparatory HPLC gave the title compound as a yellow TFA salt (15 mg, 21%). $^1$H NMR (400 MHz, CD$_3$OD) δ 8.90 (d, J=1.2 Hz, 1H), 8.19 (dd, J=8.2, 1.8 Hz, 1H) 8.05 (d, J=8.0 Hz, 1H), 7.67-7.51 (m, 5H), 7.07 (d, J=8.3 Hz, 1H), 6.84 (d, J=8.3 Hz, 1H), 6.62 (dd, J=8.5, 2.5 Hz, 1H), 5.58 (d, J=2.3 Hz, 1H), 4.45 (s, 2H) 3.39-3.10 (m, 3H) 3.27 (s, 3H), 2.27-2.17 (m, 2H), 1.95-1.80 (m, 5H), 1.80-1.60 (m, 3H); MS ESI 506.3 [M+H]$^+$, calcd for [C$_{31}$H$_{31}$N$_5$O$_2$+H]$^+$ 506.2.

Example A63. (1R*,2S*)-(E)-2-(3-((E)-2-(6-(piperidin-1-ylmethyl)pyridin-3-yl)vinyl)-1H-indazol-6-yl)spiro[cyclopropane-1,3'-indolin]-2'-one 2,2,2-trifluoroacetate salt

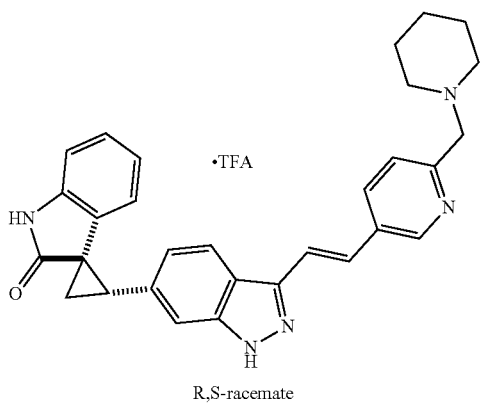

R,S-racemate

The title compound was synthesized according to the method of Example A51B, except substituting (1R*,2S*)-2-(3-iodo-1H-indazol-6-yl)[cyclopropane-1,3'-indolin]-2'-one (50 mg, 0.12 mmol) and (E)-2-(piperidin-1-ylmethyl)-5-(2-(4,4,5,5-tetramethyl-1,3,2-dioxaborolan-2-yl)vinyl)pyridine (65 mg, 0.2 mmol). Purification by reverse phase preparatory HPLC gave the title compound as a yellow TFA salt (9 mg, 15%). $^1$H NMR (400 MHz, CD$_3$OD) δ 8.91 (s, 1H), 8.20 (dd, J=8.2, 2.0 Hz, 1H) 8.04 (d, J=8.0 Hz, 1H), 7.68-7.49 (m, 4H), 7.08-7.04 (m, 2H), 6.95 (d, J=7.8 Hz, 1H), 6.60-6.56 (m, 1H), 5.99 (d, J=7.5 Hz, 1H), 4.45 (s, 2H) 3.39-3.10 (m, 3H), 2.27-2.18 (m, 2H), 1.95-1.60 (m, 8H); MS ESI 476.4 [M+H]$^+$, calcd for [C$_{30}$H$_{29}$N$_5$O+H]$^+$ 476.2.

Example A64. (1R,2S)-5'-methoxy-2-(3-((E)-2-(2-methyl-1,2,3,4-tetrahydroisoquinolin-7-yl)vinyl)-1H-indazol-6-yl)spiro[cyclopropane-1,3'-indolin]-2'-one 2,2,2-trifluoroacetate salt

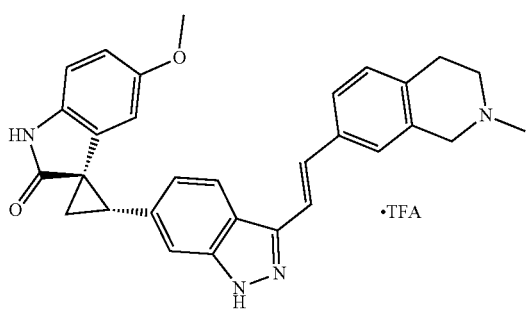 [SMILES: COc1ccc2c(c1)[C@]1(C[C@H]1c1ccc3c(/C=C/c4ccc5c(c4)CN(C)CC5)n[nH]c3c1)C(=O)N2]

A. 7-bromo-2-methyl-1,2,3,4-tetrahydroisoquinoline

To a solution of 7-bromo-1,2,3,4-tetrahydroisoquinoline (1 g, 4.7 mmol) in formic acid (20 mL) was added formalin (1.2 mL, 15 mmol). The solution was heated to 150° C. for 5 min under microwave irradiation. The solvent was removed in vacuo and the residue was dissolved into ethyl acetate (100 mL), washed with sat. sodium bicarbonate (2×10 mL), brine (10 mL) and dried over MgSO$_4$. Removal of the solvent gave the title compound as a white solid (800 mg, 78%). $^1$H NMR (400 MHz, CDCl$_3$) δ 7.73 (d, J=8.3 Hz, 1H), 7.70 (s, 1H), 7.50 (d, J=8.0 Hz, 1H), 4.11 (s, 2H), 3.37-3.34 (m, 2H), 3.27-3.24 (m, 2H) 2.95 (s, 3H); MS ESI 225.9, 227.9 [M+H]$^+$, calcd for [C$_{10}$H$_{12}$BrN+H]$^+$ 226.0, 228.0.

B. (E)-2-methyl-7-(2-(4,4,5,5-tetramethyl-1,3,2-dioxaborolan-2-yl)vinyl)-1,2,3,4-tetrahydroisoquinoline The title compound was synthesized according to the method of Example A51A, except substituting 7-bromo-2-methyl-1,2,3,4-tetrahydroisoquinoline (720 mg, 3.2 mmol). The title compound isolated as an orange oil (700 mg, 73%). $^1$H NMR (400 MHz, CDCl$_3$) δ 7.37 (d, J=18.6 Hz, 1H), 7.29-7.26 (m, 1H), 7.13 (s, 1H), 7.08 (d, J=7.3 Hz, 1H), 6.10 (d, J=18.6 Hz, 1H), 3.57 (s, 2H), 2.93-2.90 (m, 2H), 2.70-2.67 (m, 2H), 2.46 (s, 3H), 1.32 (s, 12H); MS ESI 300.2 [M+H]$^+$, calcd for [C$_{18}$H$_{26}$BNO$_2$+H]$^+$ 300.2.

C. (1R,2S)-5'-methoxy-2-(3-((E)-2-(2-methyl-1,2,3,4-tetrahydroisoquinolin-7-yl)vinyl)-1H-indazol-6-yl)spiro[cyclopropane-1,3'-indolin]-2'-one The title compound was synthesized according to the method of Example A51B, except substituting (E)-2-methyl-7-(2-(4,4,5,5-tetramethyl-1,3,2-dioxaborolan-2-yl)vinyl)-1,2,3,4-tetrahydroisoquinoline (80 mg, 0.3 mmol) Purification by reverse phase preparatory HPLC gave the title compound as a yellow TFA salt (32 mg, 38%). $^1$H NMR (400 MHz, CD$_3$OD) δ 8.01 (d, J=8.3 Hz, 1H), 7.64-7.60 (m, 1H), 7.49-7.45 (m, 4H), 7.32 (d, J=8.3 Hz, 1H), 7.05 (d, J=8.5 Hz, 1H), 6.84 (d, J=8.5 Hz, 1H), 6.63-6.59 (m, 1H), 5.99-5.98 (m, 1H), 4.65-4.58 (m, 1H) 4.42-4.34 (m, 1H), 3.84-3.75 (m, 1H), 3.49-3.40 (m, 1H), 3.39-3.33 (m, 1H), 3.27 (s, 3H), 3.24-3.17 (m, 2H), 3.09 (s, 3H), 2.27-2.18 (m, 2H); MS ESI 477.3 [M+H]$^+$, calcd for [C$_{30}$H$_{28}$N$_4$O$_2$+H]$^+$ 477.2. $[\alpha]^{24.2°}_D$=−85° (c 0.40, Methanol).

Example A65. (1R,2S)-2-(3-((E)-2-(2-methyl-1,2,3,4-tetrahydroisoquinolin-7-yl)vinyl)-1H-indazol-6-yl)spiro[cyclopropane-1,3'-indolin]-2'-one 2,2,2-trifluoroacetate salt

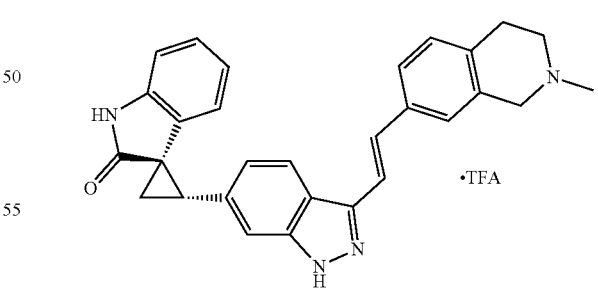

The title compound was synthesized according to the method of Example A51B, except substituting (1R,2S)-2-(3-iodo-1H-indazol-6-yl)[cyclopropane-1,3'-indolin]-2'-one (150 mg, 0.37 mmol) and (E)-2-methyl-7-(2-(4,4,5,5-tetramethyl-1,3,2-dioxaborolan-2-yl)vinyl)-1,2,3,4-tetrahydroisoquinoline (150 mg, 0.55 mmol). Purification by reverse phase preparatory HPLC gave the title compound as a yellow TFA salt (35 mg, 17%). $^1$H NMR (400 MHz, CD$_3$OD) δ 7.97 (d, J=8.3 Hz, 1H), 7.60 (d, J=8.5 Hz, 1H), 7.45 (bs, 4H), 7.30 (d, J=8.0 Hz, 1H), 7.08-6.93 (m, 2H), 6.94 (d, J=7.8 Hz, 1H), 6.57 (t, J=7.40 Hz, 1H), 5.98 (d, J=7.3 Hz, 1H), 4.64-4.59 (m., 1H), 4.39-4.32 (m, 1H), 3.82-3.77 (m, 1H), 3.49-3.37 (m, 1H), 3.37-3.33 (m, 1H), 3.30-3.20 (m, 2H), 3.08 (s, 3H), 2.27-2.17 (m, 2H); MS ESI 447.3 [M+H]$^+$, calcd for [C$_{29}$H$_{26}$N$_4$O+H]$^+$ 447.2. [α]$^{23.4°}_D$=−124° (c 0.25, Methanol).

Example A66. (1R,2S)-5'-methoxy-2-(3-((E)-2-(1,2,3,4-tetrahydroisoquinolin-7-yl)vinyl)-1H-indazol-6-yl)spiro[cyclopropane-1,3'-indolin]-2'-one 2,2,2-trifluoroacetate salt

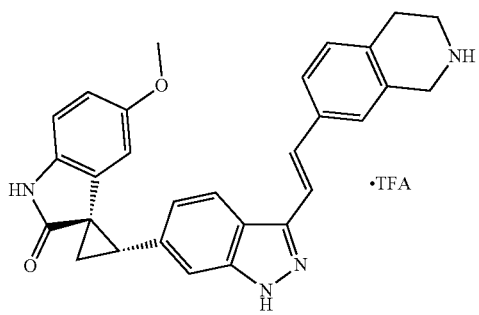 [SMILES: COc1ccc2c(c1)[C@]1(C[C@H]1c1ccc3c(/C=C/c4ccc5c(c4)CNCC5)n[nH]c3c1)C(=O)N2]

A. (E)-2,2,2-trifluoro-1-(7-(2-(4,4,5,5-tetramethyl-1,3,2-dioxaborolan-2-yl)vinyl)-3,4-dihydroisoquinolin-2(1H)-yl)ethanone The title compound was synthesized according to the method of Example A51A, except substituting 1-(7-bromo-3,4-dihydroisoquinolin-2(1H)-yl)-2,2,2-trifluoroethanone (415 mg, 1.32 mmol). The title compound was purified by silica gel chromatography (3:2 hexanes/EtOAC) to give the title compound as a white solid (300 mg, 58%). MS ESI 382.2 [M+H]$^+$, calcd for [C$_{19}$H$_{23}$BF$_3$NO$_3$+H]$^+$ 382.2.

B. (1R,2S)-5'-methoxy-2-(3-((E)-2-(1,2,3,4-tetrahydroisoquinolin-7-yl)vinyl)-1H-indazol-6-yl)spiro[cyclopropane-1,3'-indolin]-2'-one The title compound was synthesized according to the method of Example A51B, except substituting (E)-2,2,2-trifluoro-1-(7-(2-(4,4,5,5-tetramethyl-1,3,2-dioxaborolan-2-yl)vinyl)-3,4-dihydroisoquinolin-2(1H)-yl)ethanone (80 mg, 0.21 mmol) Purification by reverse phase preparatory HPLC gave the title compound as a yellow TFA salt (26 mg, 31%). $^1$H NMR (400 MHz, CD$_3$OD) δ 8.02 (d, J=8.5 Hz, 1H), 7.60 (d, J=8.8 Hz, 1H), 7.48 (bs, 4H), 7.29 (d, J=8.0 Hz, 1H), 7.05 (d, J=8.8 Hz, 1H), 6.84 (d, J=8.5 Hz, 1H), 6.62 (d, J=7.8 Hz, 1H), 5.58 (s, 1H), 4.41 (s, 2H), 3.54 (t, J=6.0 Hz, 2H), 3.40-3.33 (m, 1H), 3.27 (s, 3H), 3.19-3.11 (m, 2H), 2.29-2.14 (m, 2H); MS ESI 463.3 [M+H]$^+$, calcd for [C$_{29}$H$_{26}$N$_4$O$_2$+H]$^+$ 463.2.

Example A67. (1R,2S)-5'-methoxy-2-(3-(4-(2-(piperidin-1-yl)ethoxy)phenyl)-1H-indazol-6-yl)spiro[cyclopropane-1,3'-indolin]-2'-one 2,2,2-trifluoroacetate salt

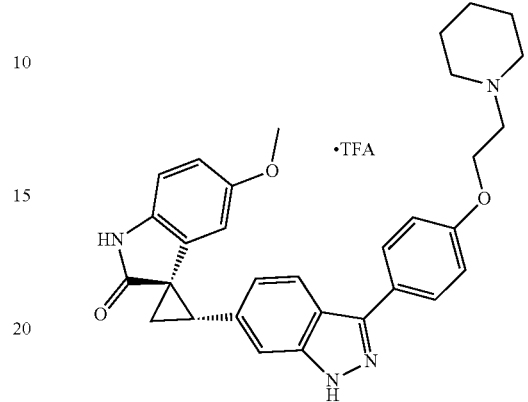

The title compound was synthesized according to the method of Example A42B, except substituting 1-(2-(4-(4,4,5,5-tetramethyl-1,3,2-dioxaborolan-2-yl)phenoxy)ethyl)piperidine (90 mg, 0.27 mmol) Purification by reverse phase preparatory HPLC gave the title compound as a yellow TFA salt (26 mg, 31%). $^1$H NMR (400 MHz, CD$_3$OD) δ 7.93-7.88 (m, 3H), 7.50 (s, 1H), 7.17 (d, J=8.5 Hz, 2H), 7.02 (d, J=8.2 Hz, 1H), 6.84 (d, J=8.2 Hz, 1H), 6.62-6.60 (m, 1H), 5.61 (s, 1H), 4.47-4.44 (m, 2H), 3.71-3.60 (m, 4H), 3.42-3.34 (m, 1H), 3.26 (s, 3H), 3.15-3.05 (m, 2H), 2.29-2.15 (m, 2H), 2.05-1.98 (m, 2H), 1.90-1.82 (m, 3H), 1.64-1.52 (m, 1H); MS ESI 509.3 [M+H]$^+$, calcd for [C$_{31}$H$_{32}$N$_4$O$_3$+H]$^+$ 509.2.

Example A68. (1R,2S)-5'-methoxy-2-(3-(4-(2-morpholinoethoxy)phenyl)-1H-indazol-6-yl)spiro[cyclopropane-1,3'-indolin]-2'-one 2,2,2-trifluoroacetate salt

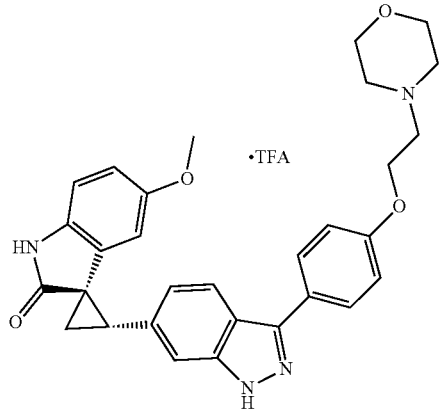 [SMILES: COc1ccc2c(c1)[C@]1(C[C@H]1c1ccc3c(-c4ccc(OCCN5CCOCC5)cc4)n[nH]c3c1)C(=O)N2]

The title compound was synthesized according to the method of Example A42B, except substituting 1-(2-(4-(4,4,5,5-tetramethyl-1,3,2-dioxaborolan-2-yl)phenoxy)ethyl)morpholine (60 mg, 0.18 mmol) Purification by reverse phase preparatory HPLC gave the title compound as a yellow TFA salt (33 mg, 37%). $^1$H NMR (400 MHz, CD$_3$OD) δ 7.93-7.88 (m, 3H), 7.50 (s, 1H), 7.22-7.17 (m, 2H), 7.05-7.02 (m, 1H), 6.86-6.83 (m, 1H), 6.63-6.60 (m, 1H), 5.61 (s, 1H), 4.49-4.44 (m, 2H), 4.18-4.05 (m, 2H), 3.91-3.80 (m, 2H), 3.73-3.58 (m, 4H), 3.40-3.33 (m, 3H), 3.27 (s, 3H), 2.29-2.15 (m, 2H); MS ESI 511.3 [M+H]$^+$, calcd for [C$_{30}$H$_{30}$N$_4$O$_4$+H]$^+$ 511.2.

Example A69. (1R,2S)-2-(3-(4-(2-(dimethylamino)ethoxy)phenyl)-1H-indazol-6-yl)-5'-methoxyspiro[cyclopropane-1,3'-indolin]-2'-one 2,2,2-trifluoroacetate salt

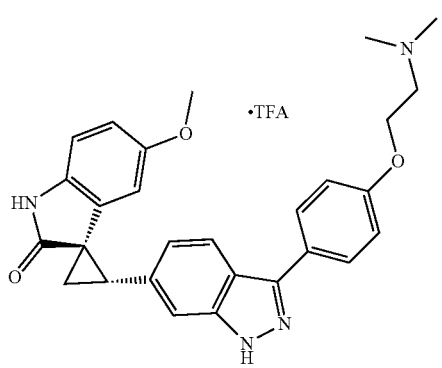 [SMILES: COc1ccc2c(c1)[C@]1(C[C@H]1c1ccc3c(-c4ccc(OCCN(C)C)cc4)n[nH]c3c1)C(=O)N2]

A. N,N-dimethyl-2-(4-(4,4,5,5-tetramethyl-1,3,2-dioxaborolan-2-yl)phenoxy)ethanamine To a solution of 2-(4-bromophenoxy)-N,N-dimethylethanamine (700 mg, 2.8 mmol), Bispinacolatodiboron (1.44 g, 5.7 mmol) and potassium acetate (823 mg, 8.4 mmol) in DMF (5 mL) was added PdCl$_2$(dppf) (61 mg, 0.084 mmol). The solution was heated to 100° C. for 2 h under microwave irradiation. Ethyl acetate (100 mL) was added and the mixture was washed with water (2×10 mL), brine (10 mL), dried over MgSO$_4$ and concentrated to dryness. Purification by Biotage silica column (gradient 2-20% MeOH in CH$_2$Cl$_2$) gave the title compound as a white solid (175 mg, 22%). $^1$H NMR (400 MHz, CDCl$_3$) δ 7.75 (d, J=8.0 Hz, 2H), 6.90 (d, J=7.8 Hz, 2H), 4.21 (t, J=5.2 Hz, 2H), 2.95 (t, J=5.1 Hz, 2H), 2.49 (s, 6H), 1.34 (s, 12H) MS ESI 292.1 [M+H]$^+$, calcd for [C$_{16}$H$_{26}$BNO$_3$+H]$^+$ 292.2.

B. (1R,2S)-2-(3-(4-(2-(dimethylamino)ethoxy)phenyl)-1H-indazol-6-yl)-5'-methoxyspiro[cyclopropane-1,3'-indolin]-2'-one The title compound was synthesized according to the method of Example A42B, except substituting N,N-dimethyl-2-(4-(4,4,5,5-tetramethyl-1,3,2-dioxaborolan-2-yl)phenoxy) ethanamine (156 mg, 0.45 mmol) Purification by reverse phase preparatory HPLC gave the title compound as a yellow TFA salt (82 mg, 32%). $^1$H NMR (400 MHz, CD$_3$OD) δ 7.93-7.90 (m, 3H), 7.50 (s, 1H), 7.19 (d, J=8.8 Hz, 2H), 7.04-7.02 (m, 1H), 6.84 (d, J=8.3 Hz, 1H), 6.63-6.61 (m, 1H), 5.61 (s, 1H), 4.43 (t, J=4.3 Hz, 2H), 3.68-3.62 (m, 2H), 3.39-3.36 (m, 1H), 3.27 (s, 3H), 3.02 (s, 6H), 2.30-2.15 (m, 2H); MS ESI 469.1 [M+H]$^+$, calcd for [C$_{28}$H$_{28}$N$_4$O$_3$+H]$^+$ 469.2.

Example A70. (1R,2S)-5'-methoxy-2-(3-(2-methyl-1,2,3,4-tetrahydroisoquinolin-7-yl)-1H-indazol-6-yl)spiro[cyclopropane-1,3'-indolin]-2'-one 2,2,2-trifluoroacetate salt

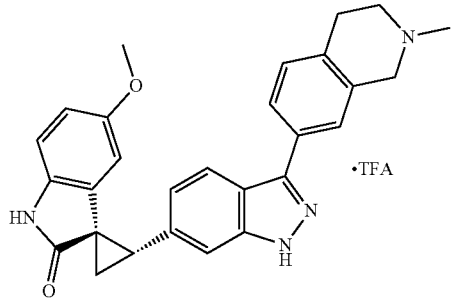 [SMILES: COc1ccc2c(c1)[C@]1(C[C@H]1c1ccc3c(-c4ccc5c(c4)CN(C)CC5)n[nH]c3c1)C(=O)N2]

A. 2-methyl-7-(4,4,5,5-tetramethyl-1,3,2-dioxaborolan-2-yl)-1,2,3,4-tetrahydro isoquinoline The title compound was synthesized according to the method of Example A69 method A, except substituting 7-bromo-2-methyl-1,2,3,4-tetrahydroisoquinoline (450 mg, 2 mmol). Trituration with hexane gave the title compound as a brown solid (300 mg, 55%). MS ESI 274.1.1 [M+H]$^+$, calcd for [C$_{16}$H$_{26}$BNO$_3$+H]$^+$ 274.2.

B. (1R,2S)-5'-methoxy-2-(3-(2-methyl-1,2,3,4-tetrahydroisoquinolin-7-yl)-1H-indazol-6-yl)spiro[cyclopropane-1,3'-indolin]-2'-one The title compound was synthesized according to the method of Example A42B, except substituting 2-methyl-7-(4,4,5,5-tetramethyl-1,3,2-dioxaborolan-2-yl)-1,2,3,4-tetrahydroisoquinoline (80 mg, 0.29 mmol). Purification by reverse phase preparatory HPLC gave the title compound as a yellow TFA salt (32 mg, 40%). $^1$H NMR (400 MHz, CD$_3$OD) δ 7.94 (t, J=8.9 Hz, 2H), 7.79 (s, 1H), 7.53 (s, 1H), 7.44 (d, J=8.0 Hz, 1H), 7.05 (d, J=9.0 Hz, 1H), 6.84 (d, J=9.3 Hz, 1H), 6.62 (d, J=7.0 Hz, 1H), 5.60 (s, 1H), 4.73-4.63 (m, 1H), 4.47-4.42 (m, 1H), 3.85-3.78 (m, 1H), 3.52-3.42 (m, 1H), 3.41-3.28 (m, 3H), 3.27 (s, 3H), 3.11 (s, 3H), 2.29-2.18 (m, 2H); MS ESI 451.3 [M+H]$^+$, calcd for [C$_{28}$H$_{26}$N$_4$O$_2$+H]$^+$ 451.2.

Example A71. (1R,2S)-5'-methoxy-2-(3-(1,2,3,4-tetrahydroisoquinolin-7-yl)-1H-indazol-6-yl)spiro[cyclopropane-1,3'-indolin]-2'-one 2,2,2-trifluoroacetate salt

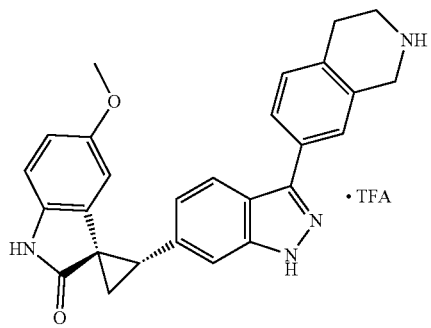 [SMILES: COc1ccc2c(c1)[C@]1(C[C@H]1c1ccc3c(-c4ccc5c(c4)CNCC5)n[nH]c3c1)C(=O)N2]

A. 2,2,2-trifluoro-1-(7-(4,4,5,5-tetramethyl-1,3,2-dioxaborolan-2-yl)-3,4-dihydroisoquinolin-2(1H)-yl)ethanone The title compound was synthesized according to the method of Example A69 method A, except substituting 1-(7-bromo-3,4-dihydroisoquinolin-2(1H)-yl)-2,2,2-trifluoroethanone (450 mg, 2 mmol). Silica gel chromatography (3:2 hexane/EtOAc) gave the title compound as a white (320 mg, 90%). MS ESI 356.1 [M+H]$^+$, calcd for [C$_{17}$H$_{21}$BF$_3$NO$_3$+H]$^+$ 356.2.

B. (1R,2S)-5'-methoxy-2-(3-(1,2,3,4-tetrahydroisoquinolin-7-yl)-1H-indazol-6-yl)spiro[cyclopropane-1,3'-indolin]-2'-one The title compound was synthesized according to the method of Example A42B, except substituting 2,2,2-trifluoro-1-(7-(4,4,5,5-tetramethyl-1,3,2-dioxaborolan-2-yl)-3,4-dihydroisoquinolin-2(1H)-yl)ethanone (100 mg, 0.2 mmol). Purification by reverse phase preparatory HPLC gave the title compound as a yellow TFA salt (18 mg, 17%). $^1$H NMR (400 MHz, CD$_3$OD) δ 7.95 (t, J=8.3 Hz, 1H), 7.90 (d, J=6.78 Hz, 1H), 7.80 (s, 1H), 7.53 (s, 1H), 7.42 (d, J=8.0 Hz, 1H), 7.05 (d, J=8.0 Hz, 1H), 6.84 (d, J=8.3 Hz, 1H), 6.62 (d, J=8.3 Hz, 1H), 5.60 (s, 1H), 4.48 (s, 2H), 3.60-3.53 (m, 2H), 3.41-3.33 (m, 1H), 3.27 (s, 3H), 3.20 (t, J=6.6 Hz, 2H), 2.29-2.18 (m, 2H); MS ESI 437.1 [M+H]$^+$, calcd for [C$_{27}$H$_{24}$N$_4$O$_2$+H]$^+$ 437.2.

Example A72. (1R,2S)-(E)-2-(3-(4-((1,4-oxazepan-4-yl)methyl)styryl)-1H-indazol-6-yl)spiro[cyclopropane-1,3'-indolin]-2'-one 2,2,2-trifluoroacetate salt

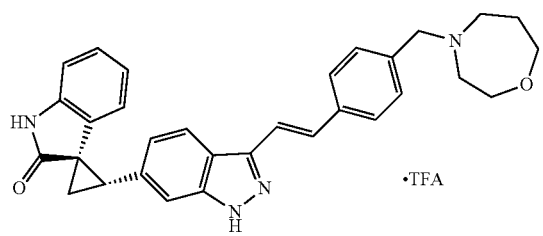 [SMILES: O=C1Nc2ccccc2[C@]12C[C@H]2c1ccc2c(/C=C/c3ccc(CN4CCCOCC4)cc3)n[nH]c2c1]

A. 4-(4-bromobenzyl)-1,4-oxazepane

To a solution of 4-bromobenzaldehyde (616 mg, 3.3 mmol) in dichloroethane (50 mL) was added homomorpholine hydrochloride (548 mg, 4 mmol) and acetic acid (0.1 mL). Sodium triacetoxyborohydride (3.4 g, 16 mmol) was added and the reaction was stirred overnight. The reaction was quenched with sat. NH$_4$Cl (30 mL). Ethyl acetate (250 mL) was added and the solution was washed with sat. NaHCO$_3$ (2×50 mL), brine (50 mL), dried over MgSO$_4$ and concentrated to dryness. The residue was flushed through a silica plug with (5% MeOH/CH$_2$Cl$_2$) to give a white solid (850 mg, 85%). $^1$H NMR (400 MHz, CDCl$_3$) δ 7.28 (d, J=7.3 Hz, 2H), 7.10 (d, J=7.3 Hz, 2H), 3.66-3.57 (m, 2H), 3.55-3.50 (m, 2H), 3.46-3.42 (m, 2H), 3.16-3.10 (m, 2H), 2.55-2.45 (m, 4H), 1.75-1.65 (m, 2H).

B. (E)-4-(4-(2-(4,4,5,5-tetramethyl-1,3,2-dioxaborolan-2-yl)vinyl)benzyl)-1,4-oxazepane The title compound was synthesized according to the method of Example A51A, except substituting 4-(4-bromobenzyl)-1,4-oxazepane (500 mg, 1.86 mmol). The title compound isolated as an orange oil (560 mg, 88%). MS ESI 344.2 [M+H]$^+$, calcd for [C$_{20}$H$_{30}$BNO$_3$+H]$^+$ 344.2.

C. (1R,2S)-2-(3-(4-((1,4-oxazepan-4-yl)methyl)styryl)-1H-indazol-6-yl)spiro[cyclopropane-1,3'-indolin]-2'-one The title compound was synthesized according to the method of Example A51B, except substituting (1R,2S)-2-(3-iodo-1H-indazol-6-yl) [cyclopropane-1,3'-indolin]-2'-one (100 mg, 0.25 mmol) and (E)-4-(4-(2-(4,4,5,5-tetramethyl-1,3,2-dioxaborolan-2-yl)vinyl)benzyl)-1,4-oxazepane (103 mg, 0.30 mmol). Purification by reverse phase preparatory HPLC gave the title compound as a yellow TFA salt (38 mg, 26%).

$^1$H NMR (400 MHz, MeOD) δ 8.02 (d, J=9.0 Hz, 1H), 7.78 (d, J=8.3 Hz, 2H), 7.61-7.53 (m, 4H), 7.48 (s, 1H), 7.08-7.04 (m, 2H), 6.94 (d, J=7.5 Hz, 1H), 6.60-6.56 (m, 1H), 5.99 (d, J=7.8 Hz, 1H), 4.45 (s, 2H), 4.02-3.80 (m, 4H), 3.65-3.60 (m, 1H), 3.57-3.35 (m, 4H), 2.29-2.12 (m, 4H); MS ESI 491.3 [M+H]$^+$, calcd for [C$_{31}$H$_{30}$N$_4$O$_2$+H]$^+$ 490.2. [α]$^{23.4°}_D$=−146° (c 0.39, Methanol).

Example A73. (1R,2S)-(E)-2-(3-(4-((1,4-oxazepan-4-yl)methyl)styryl)-1H-indazol-6-yl)-5'-methoxyspiro[cyclopropane-1,3'-indolin]-2'-one 2,2,2-trifluoroacetate salt

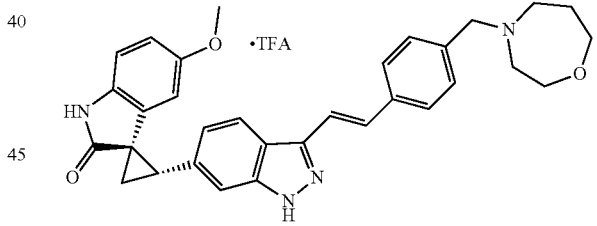

The title compound was synthesized according to the method of Example A51B, except substituting (E)-4-(4-(2-(4,4,5,5-tetramethyl-1,3,2-dioxaborolan-2-yl)vinyl)benzyl)-1,4-oxazepane (103 mg, 0.30 mmol). Purification by reverse phase preparatory HPLC gave the title compound as a yellow TFA salt (48 mg, 31%). $^1$H NMR (400 MHz, CD$_3$OD) δ 8.02 (d, J=8.3 Hz, 1H), 7.76 (d, J=7.8 Hz, 2H), 7.57-7.49 (m, 5H), 7.05 (d, J=8.28 Hz, 1H), 6.84 (d, J=8.3 Hz, 1H), 6.61 (d, J=8.3 Hz, 1H), 5.58 (s, 1H), 4.44 (s, 2H), 3.99-3.75 (m, 4H), 3.69-3.55 (m, 1H), 3.55-3.34 (m, 4H), 3.26 (s, 3H) 2.28-2.11 (m, 4H); MS ESI 521.3 [M+H]$^+$, calcd for [C$_{32}$H$_{32}$N$_4$O$_3$+H]$^+$ 520.2. [α]$^{22.8°}_D$=−76° (c 0.33, Methanol).

Example A74. (1R,2S)-2-(3-((E)-2-(2-methyl-1,2,3,4-tetrahydroisoquinolin-6-yl)vinyl)-1H-indazol-6-yl)spiro[cyclopropane-1,3'-indolin]-2'-one 2,2,2-trifluoroacetate salt

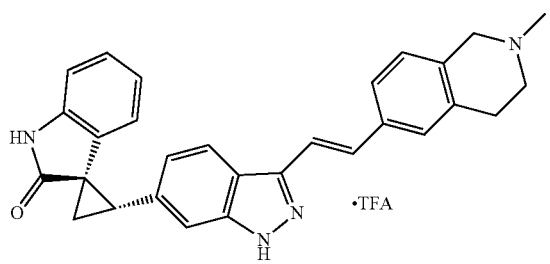 [SMILES: CN1CCc2cc(/C=C/c3n[nH]c4cc([C@@H]5C[C@@]56C(=O)Nc5ccccc56)ccc34)ccc2C1]

A. 6-bromo-2-methylisoquinolinium trifluoromethanesulfonate

A solution of 6-bromoisoquinoline (618 mg, 3 mmol) in CH$_2$Cl$_2$ (35 mL) was cooled to 0° C. under argon. Methyl triflate (0.38 mL, 3.3 mmol) was added dropwise and the mixture was warmed to rt. The precipitate was filtered, triturated with ether and dried to give the title compound as a yellow solid (1.03 g, 93%). $^1$H NMR (400 MHz, CD$_3$OD) δ 9.83 (s, 1H), 8.64-8.56 (m, 2H), 8.41 (d, J=7.0 Hz, 1H), 8.36 (d, J=8.8 Hz, 1H), 8.20 (d, J=9.03 Hz, 1H), 4.53 (s, 3H).

B. 6-bromo-2-methyl-1,2,3,4-tetrahydroisoquinoline

To a solution of 6-bromo-2-methylisoquinolinium trifluoromethanesulfonate (371 mg, 1 mmol) in methanol (10 mL) was added bromocresol green indicator. Sodium borohydride (93 mg, 2.5 mmol) was added and the reaction was stirred at rt. HCl in acetic acid (1M) was added periodically to maintain a yellow color. After 1 h, water (50 mL) was added and the solution was basified with NaOH (1M), extracted into CH$_2$Cl$_2$ (100 mL), dried over MgSO$_4$ and concentrated to give the title compound as a white solid (200 mg, 99%). $^1$H NMR (400 MHz, CDCl$_3$) δ 7.29-7.17 (m, 2H), 6.88 (d, J=8.0 Hz, 1H), 3.51 (s, 2H), 2.93-2.82 (m, 2H), 2.65 (t, J=5.8 Hz, 2H), 2.45 (s, 3H).

C. (E)-2-methyl-6-(2-(4,4,5,5-tetramethyl-1,3,2-dioxaborolan-2-yl)vinyl)-1,2,3,4-tetrahydroisoquinoline The title compound was synthesized according to the method of Example A51A, except substituting 6-bromo-2-methyl-1,2,3,4-tetrahydroisoquinoline (720 mg, 3.2 mmol). The title compound isolated as a brown oil (720 mg, 75%). MS ESI 300.2 [M+H]$^+$, calcd for [C$_{18}$H$_{26}$BNO$_2$+H]$^+$ 300.2.

D. (1R,2S)-2-(3-((E)-2-(2-methyl-1,2,3,4-tetrahydroisoquinolin-6-yl)vinyl)-1H-indazol-6-yl)spiro[cyclopropane-1,3'-indolin]-2'-one The title compound was synthesized according to the method of Example A51B, except substituting (1R,2S)-2-(3-iodo-1H-indazol-6-yl)[cyclopropane-1,3'-indolin]-2'-one (122 mg, 0.3 mmol) and (E)-2-methyl-6-(2-(4,4,5,5-tetramethyl-1,3,2-dioxaborolan-2-yl)vinyl)-1,2,3,4-tetrahydroisoquinoline (110 mg, 0.37 mmol). Purification by reverse phase preparatory HPLC gave the title compound as a yellow TFA salt (38 mg, 14%). $^1$H NMR (400 MHz, CD$_3$OD) δ 7.99 (d, J=8.3 Hz, 1H), 7.58 (d, J=7.8 Hz, 1H), 7.54 (s, 1H), 7.50-7.43 (m, 3H), 7.23 (d, J=8.0 Hz, 1H), 7.10-6.99 (m, 2H), 6.94 (d, J=7.8 Hz, 1H), 6.58 (t, J=7.5 Hz, 1H), 5.99 (d, J=7.8 Hz, 1H), 4.64-4.53 (m, 1H), 4.41-4.27 (m, 1H), 3.82-3.75 (m, 1H), 3.51-3.33 (m, 2H), 3.28-3.16 (m, 2H), 3.08 (s, 3H), 2.28-2.16 (m, 2H); MS ESI 447.3 [M+H]$^+$, calcd for [C$_{29}$H$_{26}$N$_4$O+H]$^+$ 447.2. [α]$^{23.6°}_D$=−147° (c 0.30, Methanol).

Example A75. (1R,2S)-5'-methoxy-2-(3-((E)-2-(2-methyl-1,2,3,4-tetrahydroisoquinolin-6-yl)vinyl)-1H-indazol-6-yl)spiro[cyclopropane-1,3'-indolin]-2'-one 2,2,2-trifluoroacetate salt

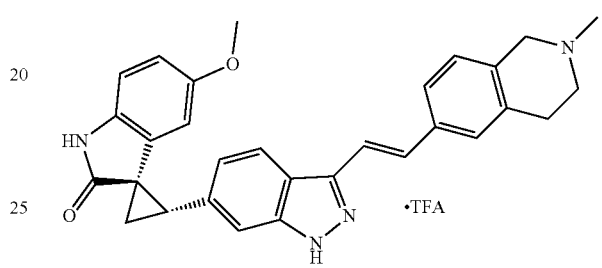

The title compound was synthesized according to the method of Example A51B, except substituting (E)-2-methyl-6-(2-(4,4,5,5-tetramethyl-1,3,2-dioxaborolan-2-yl)vinyl)-1,2,3,4-tetrahydroisoquinoline (134 mg, 0.45 mmol). Purification by reverse phase preparatory HPLC gave the title compound as a yellow TFA salt (42 mg, 25%). $^1$H NMR (400 MHz, CD$_3$OD) δ 8.01 (d, J=8.3 Hz, 1H), 7.58 (d, J=8.3 Hz, 1H), 7.54 (s, 1H), 7.48 (bs, 3H), 7.23 (d, J=8.0 Hz, 1H), 7.05 (d, J=7.8 Hz, 1H), 6.84 (d, J=8.5 Hz, 1H), 6.62 (d, J=8.8 Hz, 1H), 5.58 (s, 1H), 4.60-4.51 (m, 1H), 4.37-4.33 (m, 1H), 3.82-3.75 (m, 1H), 3.51-3.33 (m, 2H), 3.28-3.16 (m, 2H), 3.27 (s, 3H), 3.08 (s, 3H), 2.28-2.15 (m, 2H); MS ESI 477.3 [M+H]$^+$, calcd for [C$_{29}$H$_{26}$N$_4$O+H]$^+$ 477.2.

Example A76. (1R,2S)-2-(3-(2-methyl-1,2,3,4-tetrahydroisoquinolin-6-yl)-1H-indazol-6-yl)spiro[cyclopropane-1,3'-indolin]-2'-one 2,2,2-trifluoroacetate salt

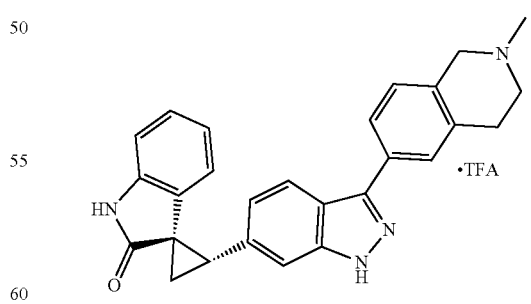

A. 2-methyl-6-(4,4,5,5-tetramethyl-1,3,2-dioxaborolan-2-yl)-1,2,3,4-tetrahydro isoquinoline The title compound was synthesized according to the method of Example A69 method A, except substituting 6-bromo-2-methyl-1,2,3,4-tetrahydroisoquinoline (450 mg, 2 mmol). Trituration with hexane gave the title compound as a brown solid (265 mg, 49%). MS ESI 274.1 [M+H]$^+$, calcd for [C$_{16}$H$_{26}$BNO$_3$+H]$^+$ 274.2.

B. (1R,2S)-2-(3-(2-methyl-1,2,3,4-tetrahydroisoquinolin-6-yl)-1H-indazol-6-yl)spiro[cyclopropane-1,3'-indolin]-2'-one The title compound was synthesized according to the method of Example A42B, except substituting (1R,2S)-2-(3-iodo-1H-indazol-6-yl)[cyclopropane-1,3'-indolin]-2'-one (64 mg, 0.15 mmol) and 2-methyl-6-(4,4,5,5-tetramethyl-1,3,2-dioxaborolan-2-yl)-1,2,3,4-tetrahydroisoquinoline (80 mg, 0.29 mmol). Purification by reverse phase preparatory HPLC gave the title compound as a yellow TFA salt (24 mg, 31%). $^1$H NMR (400 MHz, CD$_3$OD) δ 7.95-7.81 (m, 3H), 7.50 (s, 1H), 7.35 (d, J=8.3 Hz, 1H), 7.08-6.99 (m, 2H), 6.94 (d, J=7.5 Hz, 1H), 6.57 (t, J=7.5 Hz, 1H), 6.00 (d, J=7.5 Hz, 1H), 4.66-4.62 (m, 1H), 4.43-4.38 (m, 1H), 3.85-3.78 (m, 1H), 3.52-3.42 (m, 1H), 3.41-3.33 (m, 1H), 3.32-3.20 (m, 2H), 3.10 (s, 3H), 2.27-2.14 (m, 2H); MS ESI 421.3 [M+H]$^+$, calcd for [C$_{27}$H$_{24}$N$_4$O+H]$^+$ 421.2.

Example A77. (1R,2S)-2-(3-((E)-2-(2-(morpholinomethyl)thiazol-4-yl)vinyl)-1H-indazol-6-yl)spiro[cyclopropane-1,3'-indolin]-2'-one 2,2,2-trifluoroacetate salt

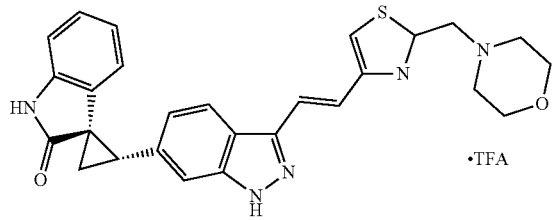 [SMILES: O=C1Nc2ccccc2[C@]12C[C@H]2c1ccc2c(/C=C/C3=CSC(CN4CCOCC4)N3)n[nH]c2c1]

A. (E)-4-((4-(2-(4,4,5,5-tetramethyl-1,3,2-dioxaborolan-2-yl)vinyl)thiazol-2-yl)methyl)morpholine To a solution of 4-((4-bromothiazol-2-yl)methyl)morpholine (125 mg, 0.5 mmol) and triethylamine (0.2 mL, 1.5 mmol) in DMF (1.5 mL) was added 4,4,5,5-tetramethyl-2-vinyl-1,3,2-dioxaborolane (0.15 mL, 1 mmol) and Pd(Ptert-Bu$_3$)$_2$ (8 mg, 0.002 mmol). The mixture was heated to 120° C. under microwave irradiation for 1 h. Ethyl acetate (50 mL) was added and the solution was washed with water (2×10 mL) and brine (10 mL), dried over MgSO$_4$ and concentrated to an orange oil (165 mg, 99%). $^1$H NMR (400 MHz, CDCl$_3$) δ 7.31 (d, J=18.0 Hz, 1H), 7.19 (s, 1H), 6.40 (d, J=18.0 Hz, 1H), 3.84 (s, 2H), 3.74 (bs, 4H), 2.61 (bs, 4H), 1.29 (s, 12H); MS ESI 337.1 [M+H]$^+$, calcd for [C$_{16}$H$_{25}$BN$_2$O$_3$S+H]$^+$ 337.2. [α]$^{22.8°}_D$=−169° (c 0.42, Methanol).

B. 1R,2S)-2-(3-((E)-2-(2-(morpholinomethyl)thiazol-4-yl)vinyl)-1H-indazol-6-yl)spiro[cyclopropane-1,3'-indolin]-2'-one The title compound was synthesized according to the method of Example A51B, except substituting (1R,2S)-2-(3-iodo-1H-indazol-6-yl) [cyclopropane-1,3'-indolin]-2'-one (100 mg, 0.25 mmol) and (E)-4-((4-(2-(4,4,5,5-tetramethyl-1,3,2-dioxaborolan-2-yl)vinyl)thiazol-2-yl)methyl)morpholine (100 mg, 0.3 mmol). Purification by reverse phase preparatory HPLC gave the title compound as a yellow TFA salt (50 mg, 35%). $^1$H NMR (CD$_3$OD) δ: 7.96 (d, J=8.3 Hz, 1H), 7.80 (d, J=16.3 Hz, 1H), 7.72 (s, 1H), 7.53 (d, J=16.3 Hz, 1H), 7.47 (s, 1H), 7.08-6.98 (m, 2H), 6.94 (d, J=7.5 Hz, 1H), 6.57 (t, J=7.4 Hz, 1H), 5.97 (d, J=7.3 Hz, 1H), 4.82 (s, 2H), 3.98 (bs, 4H), 3.53 (bs, 4H), 3.38-3.33 (m, 1H), 2.28-2.13 (m, 2H); MS ESI 484.3 [M+H]$^+$, calcd for [C$_{27}$H$_{25}$N$_5$O$_2$S+H]$^+$ 484.2.

Example A78. (1R,2S)-(E)-2-(3-(4-(1-methylpiperidin-4-yloxy)styryl)-1H-indazol-6-yl)spiro[cyclopropane-1,3'-indolin]-2'-one 2,2,2-trifluoroacetate salt

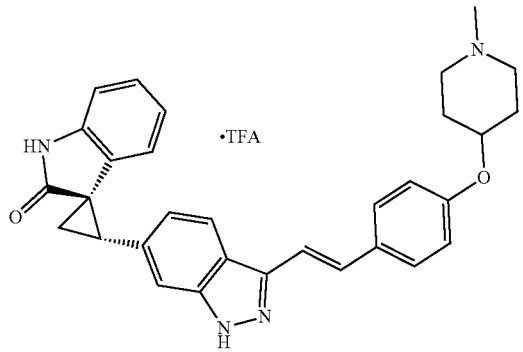 [SMILES: CN1CCC(Oc2ccc(/C=C/c3n[nH]c4cc([C@@H]5C[C@@]56C(=O)Nc5ccccc56)ccc34)cc2)CC1]

A. 4-(4-bromophenoxy)-1-methylpiperidine

Prepared according to the method of Example A64 method A, except substituting 4-(4-bromophenoxy)piperidine (256 mg, 1 mmol). The title compound was isolated as a white solid (270 mg, 99%). $^1$H NMR (CDCl$_3$) δ: 7.36 (d, J=8.3 Hz, 2H), 6.79 (d, J=8.3 Hz, 2H), 4.28 (bs, 1H), 2.73-2.65 (m, 2H), 2.32 (s, 3H), 2.32-2.25 (m, 2H), 2.05-1.95 (m, 2H), 1.86-1.80 (m, 2H).

B. (E)-1-methyl-4-(4-(2-(4,4,5,5-tetramethyl-1,3,2-dioxaborolan-2-yl)vinyl)phenoxy)piperidine The title compound was synthesized according to the method of Example A51A, except substituting 4-(4-bromophenoxy)-1-methylpiperidine (270 mg, 1 mmol). The title compound isolated as an orange oil (340 mg, 99%). MS ESI 344.2 [M+H]$^+$, calcd for [C$_{20}$H$_{30}$BNO$_3$+H]$^+$ 344.2.

C. (1R,2S)-2-(3-(4-(1-methylpiperidin-4-yloxy)styryl)-1H-indazol-6-yl)spiro[cyclopropane-1,3'-indolin]-2'-one The title compound was synthesized according to the method of Example A51B, except substituting (1R,2S)-2-(3-iodo-1H-indazol-6-yl)[cyclopropane-1,3'-indolin]-2'-one (100 mg, 0.25 mmol) and (E)-1-methyl-4-(4-(2-(4,4,5,5-tetramethyl-1,3,2-dioxaborolan-2-yl)vinyl)phenoxy)piperidine (105 mg, 0.3 mmol). Purification by reverse phase preparatory HPLC gave the title compound as a yellow TFA salt (35 mg, 25%). $^1$H NMR (CD$_3$OD) δ: 7.99-7.97 (m, 1H), 7.63-7.56 (m, 2H), 7.50-7.42 (m, 2H), 7.36-7.28 (m, 1H), 7.10-7.01 (m, 4H), 6.97-6.91 (m, 1H), 6.59 (t, J=7.7 Hz, 1H), 5.99 (d, J=7.8 Hz, 1H), 4.84-4.79 (m, 0.5H), 4.65-4.60 (m, 0.5H), 3.65-3.62 (m, 1H), 3.47-3.34 (m, 3H), 3.25-3.13 (m, 1H), 2.94 (s, 3H), 2.44-2.40 (m, 1H), 2.32-2.01 (m, 5H), 1.96-1.81 (m, 1H); MS ESI 491.2 [M+H]$^+$, calcd for [C$_{31}$H$_{30}$N$_4$O$_2$+H]$^+$ 491.3. [α]$^{22}_D$=−154° (c 0.43, MeOH).

Example A79. (1R,2S)-(E)-5'-methoxy-2-(3-(4-(1-methylpiperidin-4-yloxy)styryl)-1H-indazol-6-yl)spiro[cyclopropane-1,3'-indolin]-2'-one 2,2,2-trifluoroacetate salt

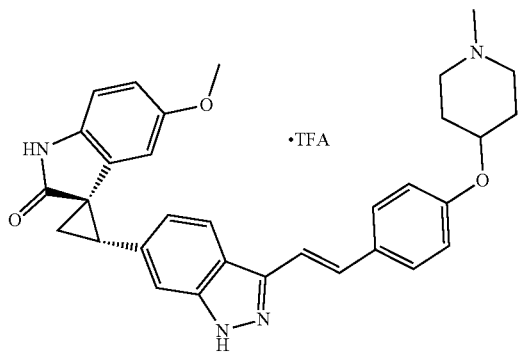 [SMILES: COc1ccc2c(c1)[C@]1(C[C@H]1c1ccc3c(/C=C/c4ccc(OC5CCN(C)CC5)cc4)n[nH]c3c1)C(=O)N2]

The title compound was synthesized according to the method of Example A51B, except substituting (E)-1-methyl-4-(4-(2-(4,4,5,5-tetramethyl-1,3,2-dioxaborolan-2-yl)vinyl)phenoxy)piperidine (105 mg, 0.3 mmol). Purification by reverse phase preparatory HPLC gave the title compound as a yellow TFA salt (36 mg, 25%). $^1$H NMR (CD$_3$OD) δ: 7.95 (d, J=8.8 Hz, 1H), 7.56-7.53 (m, 2H), 7.45-7.40 (m, 2H), 7.30-7.26 (m, 1H), 7.04-6.98 (m, 4H), 6.83 (d, J=8.3 Hz, 1H), 6.60 (d, J=8.3 Hz, 1H), 5.58 (s, 1H) 4.81-4.54 (m, 1H) 3.65-3.33 (m, 4H), 3.24 (s, 3H), 3.23-3.13 (m, 1H) 2.92 (s, 3H), 2.44-2.37 (m, 1H), 2.32-2.01 (m, 5H), 1.96-1.81 (m, 1H); MS ESI 521.3 [M+H]$^+$, calcd for [C$_{32}$H$_{32}$N$_4$O$_3$+H]$^+$ 521.2.

Example A80. (1R,2S)-(E)-2-(3-(4-(2-morpholino-propan-2-yl)styryl)-1H-indazol-6-yl)spiro[cyclopropane-1,3'-indolin]-2'-one 2,2,2-trifluoroacetate salt

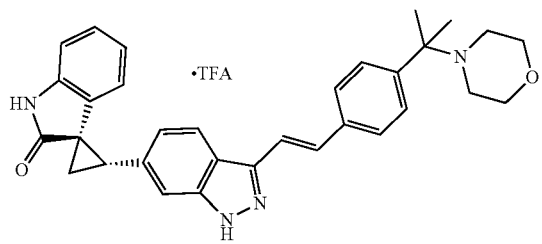 [SMILES: CC(C)(c1ccc(/C=C/c2n[nH]c3cc([C@@H]4C[C@@]45C(=O)Nc4ccccc45)ccc23)cc1)N1CCOCC1]

A. 2-methyl-2-morpholinopropanenitrile

Acetone cyanohydrin (4.3 g, 50 mmol) was dissolved into acetone (5 mL). Morpholine (4.3 g, 50 mmol) was added and the solution was stirred at rt for 24 h. The volatile solvents were removed in vacuo to give the title compound as a clear liquid in quantitative yield. MS ESI 155.0 [M+H]$^+$, calcd for [C$_8$H$_{14}$N$_2$O+H]$^+$ 155.1.

B. 4-(2-(4-bromophenyl)propan-2-yl)morpholine

Magnesium turnings (190 mg, 7.4 mmol) was added to dry THF (15 mL) under argon. 1,4-dibromobenzene (2.43 g, 10.3 mmol) was added and the solution was heated to reflux for 30 min 2-Methyl-2-morpholinopropanenitrile (1 g, 6.6 mmol) was dissolved into THF (30 mL) and added dropwise to the solution at reflux. The mixture was stirred for 2 h and cooled to rt. The reaction was quenched with sat. K$_2$CO$_3$ solution and extracted with CH$_2$Cl$_2$ (200 mL), dried over MgSO$_4$ and concentrated to an orange oil. The crude mixture was purified on a Biotage silica column (2-15% MeOH in CH$_2$Cl$_2$) to give the title compound as a yellow oil (204 mg, 10%). MS ESI 284.0, 286.0 [M+H]$^+$, calcd for [C$_{13}$H$_{18}$BrNO+H]$^+$ 284.1, 286.1.

C. (E)-4-(2-(4-(2-(4,4,5,5-tetramethyl-1,3,2-dioxa-borolan-2-yl)vinyl)phenyl)propan-2-yl)morpholine The title compound was synthesized according to the method of Example A51A, except substituting 4-(2-(4-bromophenyl)propan-2-yl)morpholine (200 mg, 0.7 mmol). The title compound isolated as an orange oil (140 mg, 40%). MS ESI 358.1 [M+H]$^+$, calcd for [C$_{21}$H$_{32}$BNO$_3$+H]$^+$ 358.2.

D. (1R,2S)-2-(3-(4-(2-morpholinopropan-2-yl)styryl)-1H-indazol-6-yl)spiro[cyclopropane-1,3'-indolin]-2'-one The title compound was synthesized according to the method of Example A51B, except substituting (1R,2S)-2-(3-iodo-1H-indazol-6-yl)[cyclopropane-1,3'-indolin]-2'-one (100 mg, 0.25 mmol) and (E)-1-methyl-4-(4-(2-(4,4,5,5-tetramethyl-1,3,2-dioxaborolan-2-yl)vinyl)phenoxy)piperidine (140 mg, 0.4 mmol). Purification by reverse phase preparatory HPLC gave the title compound as a yellow TFA salt (51 mg, 34%). $^1$H NMR (CD$_3$OD) δ: 7.98 (d, J=8.5 Hz, 1H), 7.80-7.76 (m, 2H), 7.70 (d, J=8.3 Hz, 2H), 7.52-7.46 (m, 3H), 7.08-6.98 (m, 2H), 6.94 (d, J=7.8 Hz, 1H), 6.56 (t, J=7.7 Hz, 1H), 5.98 (d, J=7.5 Hz, 1H), 4.06-3.96 (m, 2H), 3.83-3.73 (m, 2H), 3.35-3.29 (m, 3H), 3.13-3.08 (m, 2H), 2.26-2.14 (m, 2H), 1.90 (s, 6H); MS ESI 418.2 [M-C$_4$H$_8$NO]$^+$, calcd for [C$_{32}$H$_{32}$N$_4$O$_2$—C$_4$H$_8$NO]$^+$ 418.2. [α]$^{22.8°}_D$=−109° (c 0.32, Methanol).

Example A81. (1R,2S)-(E)-2-(3-(4-((1-methylpiperidin-4-yl)methyl)styryl)-1H-indazol-6-yl)spiro[cyclopropane-1,3'-indolin]-2'-one 2,2,2-trifluoroacetate salt

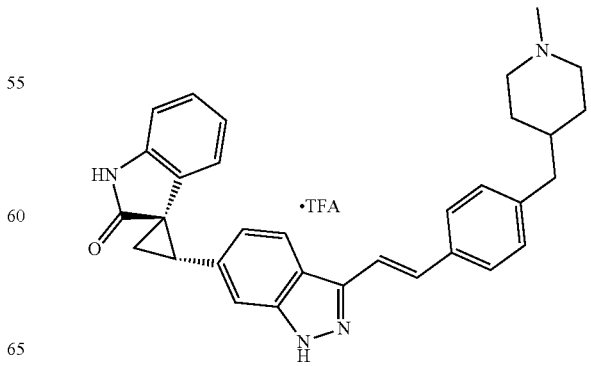

A. tert-butyl 4-(4-bromobenzyl)piperidine-1-carboxylate

To a solution of tert-butyl 4-methylenepiperidine-1-carboxylate (1 g, 5.1 mmol) was added 9-BBN solution (10.2 mL of 0.5 M solution, 5.1 mmol) and the mixture was heated to reflux for 1 h under argon. The solution was then cooled to rt and 1,4-iodobromobenzene (1.3 g, 4.7 mmol) was added, followed by $K_2CO_3$ (843 mg, 6.1 mmol), DMF (10 mL), water (1 mL) and Pd(dppf)Cl$_2$ (114 mg, 0.15 mmol). The solution was heated to 60° C. under argon for 3 h and cooled to rt. Ethyl acetate (250 mL) was added and the solution was washed with water (2×50 mL), brine (50 mL), dried over MgSO$_4$ and concentrated to dryness. The crude product was purified by Biotage silica gel column (50:50 Hexane/Ethyl acetate) to give the title compound as a yellow solid (1.2 g, 72%).

B. 4-(4-bromobenzyl)piperidine

To a solution of tert-butyl 4-(4-bromobenzyl)piperidine-1-carboxylate (780 mg, 2.2 mmol) in CH$_2$Cl$_2$ (15 mmol), was added TFA (0.5 mL) and the mixture was stirred at rt for 1 h. The solvent was removed in vacuo and the residue dissolved into CH$_2$Cl$_2$ (50 mL), washed with NaOH (0.1M, 10 mL), brine (10 mL), dried over MgSO$_4$ and concentrated to dryness to give the title compound as a beige solid (520 mg, 93%).

C. 4-(4-bromobenzyl)-1-methylpiperidine

Prepared according to the method of Example A69 method A, except substituting 4-(4-bromobenzyl)piperidine (520 mg, 2 mmol). The title compound was isolated as a brown solid (490 mg, 89%). $^1$H NMR (CDCl$_3$) δ 7.39 (d, J=7.5 Hz, 2H), 7.01 (d, J=7.8 Hz, 2H), 2.93 (d, J=11.0 Hz, 2H), 2.50 (d, J=6.8 Hz, 2H), 2.32 (s, 3H), 1.99-1.94 (m, 2H), 1.65-1.62 (m, 2H), 1.50-1.35 (m, 3H).

D. (E)-1-methyl-4-(4-(2-(4,4,5,5-tetramethyl-1,3,2-dioxaborolan-2-yl)vinyl)benzyl)piperidine The title compound was synthesized according to the method of Example A51A, except substituting 4-(4-bromobenzyl)-1-methylpiperidine (267 mg, 1 mmol). The title compound isolated as an orange oil (340 mg, 99%). MS ESI 342.2 [M+H]$^+$, calcd for [C$_{21}$H$_{32}$BNO$_2$+H]$^+$ 342.2.

E. (1R,2S)-2-(3-(4-((1-methylpiperidin-4-yl)methyl)styryl)-1H-indazol-6-yl)spiro[cyclopropane-1,3'-indolin]-2'-one The title compound was synthesized according to the method of Example A51B, except substituting (1R,2S)-2-(3-iodo-1H-indazol-6-yl) [cyclopropane-1,3'-indolin]-2'-one (100 mg, 0.25 mmol) and (E)-1-methyl-4-(4-(2-(4,4,5,5-tetramethyl-1,3,2-dioxaborolan-2-yl)vinyl)benzyl)piperidine (105 mg, 0.3 mmol). Purification by reverse phase preparatory HPLC gave the title compound as a yellow TFA salt (39 mg, 27%). $^1$H NMR (CD$_3$OD) δ: 7.97 (d, J=8.8 Hz, 1H), 7.56 (d, J=7.3 Hz, 2H), 7.51-7.37 (m, 3H), 7.22 (d, J=7.5 Hz, 2H), 7.08-7.01 (m, 2H), 6.94 (d, J=8.0 Hz, 1H), 6.57 (t, J=7.5 Hz, 1H), 5.99 (d, J=7.5 Hz, 1H), 3.50-3.47 (m, 2H), 3.37-3.31 (m, 1H), 2.97-2.92 (m, 2H), 2.83 (s, 3H), 2.63 (d, J=6.0 Hz, 2H), 2.26-2.14 (m, 2H), 1.96-1.81 (m, 3H), 1.56-1.41 (m, 2H); MS ESI 489.4 [M+H]$^+$, calcd for [C$_{32}$H$_{32}$N$_4$O+H]$^+$ 489.3. [α]$^{22.8°}_D$ −96° (c 0.26, Methanol).

Example A82. (1R,2S)-(E)-5'-methoxy-2-(3-(4-((1-methylpiperidin-4-yl)methyl)styryl)-1H-indazol-6-yl)spiro[cyclopropane-1,3'-indolin]-2'-one 2,2,2-trifluoroacetate salt

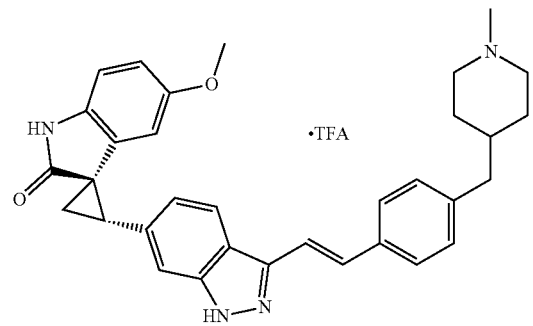 [SMILES: COc1ccc2c(c1)[C@]1(C[C@H]1c1ccc3c(/C=C/c4ccc(CC5CCN(C)CC5)cc4)n[nH]c3c1)C(=O)N2]

The title compound was synthesized according to the method of Example A51B, except substituting (E)-1-methyl-4-(4-(2-(4,4,5,5-tetramethyl-1,3,2-dioxaborolan-2-yl)vinyl)benzyl)piperidine (105 mg, 0.3 mmol). Purification by reverse phase preparatory HPLC gave the title compound as a yellow TFA salt (24 mg, 17%). $^1$H NMR (CD$_3$OD) δ: 7.97 (d, J=8.3 Hz, 1H), 7.54 (d, J=7.8 Hz, 2H), 7.51-7.36 (m, 3H), 7.20 (d, J=7.5 Hz, 2H), 7.01 (d, J=8.3 Hz, 1H), 6.83 (d, J=8.8 Hz, 1H), 6.60 (d, J=8.3 Hz, 1H), 5.59 (s, 1H), 3.50-3.47 (m, 2H), 3.37-3.31 (m, 1H), 3.25 (s, 3H), 2.97-2.92 (m, 2H), 2.83 (s, 3H), 2.62 (d, J=6.0 Hz, 2H), 2.26-2.14 (m, 2H), 1.96-1.81 (m, 3H), 1.53-1.44 (m, 2H); MS ESI 519.3 [M+H]$^+$, calcd for [C$_{33}$H$_{34}$N$_4$O$_2$+H]$^+$ 519.3. [α]$^{22.8°}_D$=−100° (c 0.29, Methanol).

Example A83. (1R,2S)-(E)-5'-methoxy-2-(3-(4-(pyrrolidin-1-ylmethyl)styryl)-1H-indazol-6-yl)spiro[cyclopropane-1,3'-indolin]-2'-one 2,2,2-trifluoroacetate

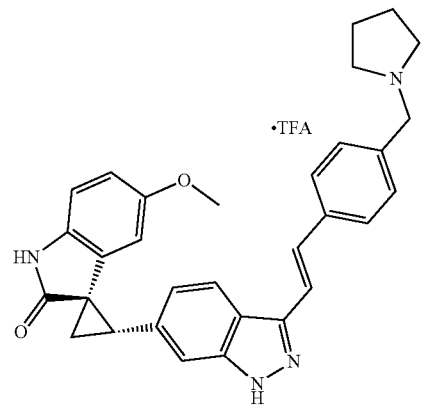 [SMILES: COc1ccc2c(c1)[C@]1(C[C@H]1c1ccc3c(/C=C/c4ccc(CN5CCCC5)cc4)n[nH]c3c1)C(=O)N2]

The title compound was synthesized according to the method of Example A51B, except substituting (E)-4-(4-(2-(4,4,5,5-tetramethyl-1,3,2-dioxaborolan-2-yl)vinyl)benzyl)pyrrolidine (50 mg, 0.16 mmol). Purification by reverse phase preparatory HPLC gave the title compound as a yellow TFA salt (19 mg, 21%). $^1$H NMR (CD$_3$OD) δ: 8.02 (d, J=8.3 Hz, 1H), 7.75 (d, J=7.8 Hz, 2H), 7.56-7.47 (m, 5H), 7.05 (d, J=8.5 Hz, 1H), 6.84 (d, J=8.5 Hz, 1H), 6.61 (d, J=8.5 Hz, 1H), 5.58 (s, 1H), 4.39 (s, 2H), 3.52 (bs., 2H), 3.37 (t, J=8.5 Hz, 1H), 3.27 (s, 3H), 3.25-3.16 (m, 2H), 2.27-2.14 (m, 4H), 2.03 (bs., 2H); MS ESI 491.3 [M+H]$^+$, calcd for [C$_{31}$H$_{30}$N$_4$O$_2$+H]$^+$ 491.2. [α]$^{24.2°}_D$=−117° (c 0.52, Methanol).

Example A84. (1R*,2R*)-(E)-2-(3-(4-((dimethylamino)methyl)styryl)-1H-indazol-6-yl)-5'-methoxyspiro[cyclopropane-1,3'-indolin]-2'-one

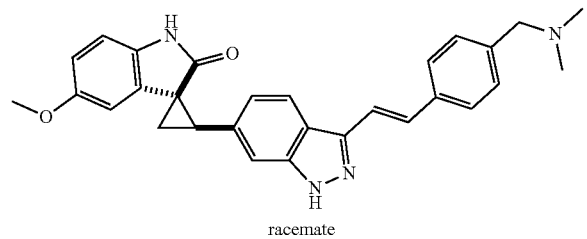

racemate

The minor diastereomer from the reaction of Example A34B was isolated as yellow-orange solid film (36 mg, 3%). $^1$H NMR (400 MHz, CD$_3$OD) δ ppm 7.99 (d, J=8.5 Hz, 1H), 7.75 (d, J=8.0 Hz, 2H), 7.56-7.46 (m, 5H), 7.15 (d, J=8.5 Hz, 1H), 6.87 (d, J=8.3 Hz, 1H), 6.82-6.72 (m, 2H), 4.31 (s, 2H), 3.81 (s, 3H), 3.39 (t, J=8.8 Hz, 1H), 2.87 (s, 6H), 2.41 (dd, J=8.4, 4.9 Hz, 1H), 2.23 (dd, J=8.8, 4.8 Hz, 1H); MS ESI [M+H]$^+$ 465.2, calcd for [C$_{29}$H$_{28}$N$_4$O$_2$+H]$^+$ 465.2.

Example A85. (1R*,2R*)-5'-methoxy-2-(3-((E)-2-(6-(4-methylpiperazin-1-yl)pyridin-3-yl)vinyl)-1H-indazol-6-yl)spiro[cyclopropane-1,3'-indolin]-2'-one

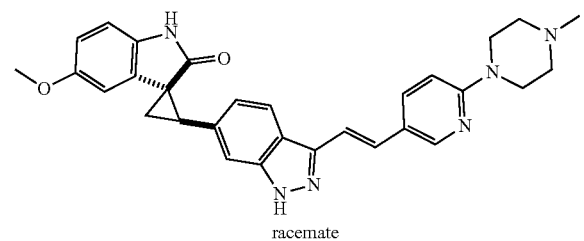

racemate

From two repeated batches of Example A31 using 5-methoxy-3-((3-((E)-2-(6-(4-methylpiperazin-1-yl)pyridin-3-yl)vinyl)-1H-indazol-6-yl)methylene)indolin-2-one (combined 491 mg, 1.0 mmol), purification using flash chromatography (silica gel, 1% Et$_3$N in CHCl$_3$/MeOH 96:4 to 92:8), followed by trituration with 1:1 Et$_2$O/CH$_2$Cl$_2$ gave the minor diastereomer title compound as a pale yellow solid (18 mg, 4%). $^1$H NMR (400 MHz, CDCl$_3$ with a few drops of CD$_3$OD) δ ppm 8.21 (s, 1H), 7.82 (d, J=8.5 Hz, 1H), 7.75 (d, J=8.5 Hz, 1H), 7.39 (s, 1H), 7.27 (d, J=17.3 Hz, 1H), 7.16 (d, J=17.3 Hz, 1H), 7.05 (d, J=8.8 Hz, 1H), 6.80 (d, J=8.3 Hz, 1H), 6.72 (d, J=8.8 Hz, 1H), 6.67 (d, J=9.3 Hz, 1H), 6.54 (s, 1H), 3.77 (s, 3H), 3.58 (bs, 4H), 3.18-3.27 (m, 1H), 2.57 (bs, 4H), 2.40 (dd, J=8.5, 5.3 Hz, 1H), 2.35 (bs, 3H), 2.09 (dd, J=9.0, 5.0 Hz, 1H); MS ESI 507.3 [M+H]$^+$, calcd for [C$_{30}$H$_{30}$N$_6$O$_2$+H]$^+$ 507.2.

Example A86. (1R*,2S*)-5'-amino-2-(3-(4-(4-methylpiperazin-1-yl)phenyl)-1H-indazol-6-yl)spiro[cyclopropane-1,3'-indolin]-2'-one

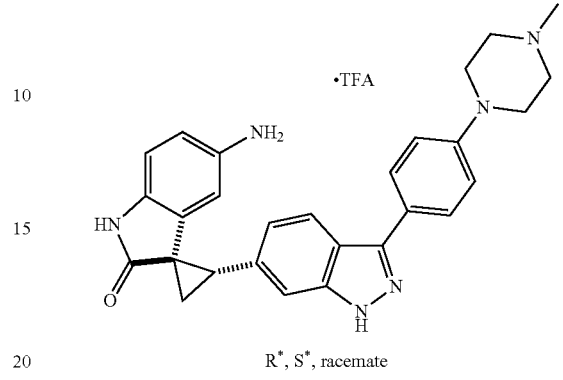

R*, S*, racemate

A. (E)-tert-butyl 3-((3-iodo-1H-indazol-6-yl)methylene)-2-oxoindolin-5-yl carbamate The title compound was synthesized according to the method described for (E)-3-((1H-indazol-5-yl)methylene)indolin-2-one, except substituting 3-iodo-1H-indazole-6-carbaldehyde (930 mg, 3.42 mmol) and tert-butyl 2-oxoindolin-5-ylcarbamate (809 mg, 3.26 mmol), the title compound was obtained as an orange solid (1.02 g, 62%); MS ESI 503.1 [M+H]$^+$, calcd for [C$_{21}$H$_{19}$IN$_4$O$_3$+H]$^+$ 503.06.

B. tert-butyl 2-(3-iodo-1H-indazol-6-yl)-2'-oxospiro[cyclopropane-1,3'-indoline]-5'-ylcarbamate The title compound was synthesized according to the method of Example A6, except substituting (E)-tert-butyl 3-((3-iodo-1H-indazol-6-yl)methylene)-2-oxoindolin-5-ylcarbamate (1.02 g, 2.03 mmol) to give a 1:1 mixture of diastereomers (196 mg, 19%); MS ESI 517.1 [M+H]$^+$, calcd for [C$_{22}$H$_{21}$IN$_4$O$_3$+H]$^+$ 517.07.

C. (1R*,2S*)-5'-amino-2-(3-(4-(4-methylpiperazin-1-yl)phenyl)-1H-indazol-6-yl)spiro[cyclopropane-1,3'-indolin]-2'-one The Suzuki coupling was executed according to the method in Example A45, except substituting tert-butyl 2-(3-iodo-1H-indazol-6-yl)-2'-oxospiro[cyclopropane-1,3'-indoline]-5'-ylcarbamate (70 mg, 0.136 mmol), 1-methyl-4-(4-(4,4,5,5-tetramethyl-1,3,2-dioxaborolan-2-yl)phenyl)piperazine (57 mg, 0.190 mmol). The resulting product was was dissolved into CH$_2$Cl$_2$ (1.0 mL) and TFA (50 uL) was added. After 1 h the reaction was complete, the solvent was removed and the residue purified by prep-HPLC to give a white powder (3.2 mg, 15%); $^1$H NMR (400 MHz, CD$_3$OD) δ 7.94 (d, J=8.6 Hz, 1H), 7.87 (d, J=8.4 Hz, 2H), 7.53 (s, 1H), 7.18 (d, J=8.8 Hz, 2H), 7.05-7.02 (m, 3H), 6.04 (s, 1H), 4.01-3.97 (bs, 2H), 3.75-3.65 (bs, 2H), 3.46 (t, J=8.4 Hz, 1H), 3.32-3.28 (bs, 2H), 3.18-3.08 (bs, 2H), 3.00 (s, 3H), 2.35-2.31 (m, 1H), 2.29-2.25 (m, 1H); MS ESI [M+H]$^+$ 465.1, calcd for [C$_{28}$H$_{28}$N$_6$O+H]$^+$ 465.24.

Example A87. (1R*,2S*)-(E)-1'-methyl-2-(3-(4-(morpholinomethyl)styryl)-1H-indazol-6-yl)spiro[cyclopropane-1,3'-indolin]-2'-one 2,2,2-trifluoroacetate

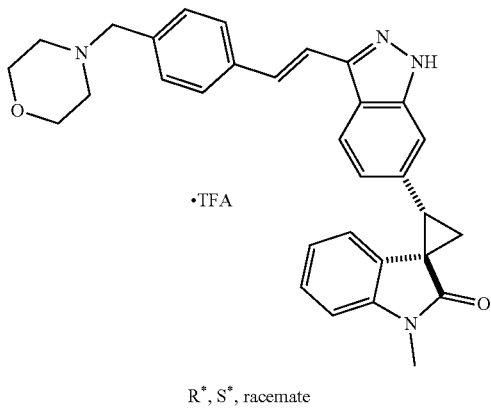

R*, S*, racemate

A. (E)-3-((3-iodo-1H-indazol-6-yl)methylene)-1-methylindolin-2-one

The title compound was synthesized according to the method described for (E)-3-((1H-indazol-5-yl)methylene)indolin-2-one, except substituting 3-iodo-1H-indazole-6-carbaldehyde (462 mg, 1.70 mmol) and 1-methylindolin-2-one (250 mg, 1.70 mmol), the title compound was obtained as a yellow-orange solid (545 mg, 80%); MS ESI 402.2 [M+H]+, calcd for [C$_{17}$H$_{12}$IN$_3$O+H]+ 402.01.

B. (1R*,2S*)-2-(3-iodo-1H-indazol-6-yl)-1'-methylspiro[cyclopropane-1,3'-indolin]-2'-one The title compound was synthesized according to the method of Example A6, except substituting (E)-3-((3-iodo-1H-indazol-6-yl)methylene)-1-methylindolin-2-one (545 mg, 1.36 mmol) to give the title compound as a 9:1 mixture of diastereomers (405 mg, 72%); MS ESI 416.0 [M+H]+, calcd for [C$_{18}$H$_{14}$IN$_3$O+H]+ 416.03.

C. (1R*,2S*)-(E)-1'-methyl-2-(3-(4-(morpholinomethyl)styryl)-1H-indazol-6-yl)spiro[cyclopropane-1,3'-indolin]-2'-one 2,2,2-trifluoroacetate The title compound was synthesized according to the method of Example A45, except substituting (1R*,2S*)-2-(3-iodo-1H-indazol-6-yl)-1'-methylspiro[cyclopropane-1,3'-indolin]-2'-one (30 mg, 0.072 mmol) and (E)-4-(4-(2-(4,4,5,5-tetramethyl-1,3,2-dioxaborolan-2-yl)vinyl)benzyl)morpholine (31 mg, 0.094 mmol). After Suzuki coupling, the solvent was removed and the residue was purified by prep-HPLC to give the title compound (16 mg, 45%); $^1$H NMR (400 MHz, CD$_3$OD) δ 8.00 (d, J=8.4 Hz, 1H), 7.77 (d, J=8.2 Hz, 2H), 7.54-7.46 (m, 5H), 7.14 (t, J=7.8 Hz, 1H), 7.02 (d, J=8.1 Hz, 2H), 6.64 (t, J=7.3 Hz, 1H), 6.02 (d, J=7.2 Hz, 1H), 4.38 (s, 2H), 4.08-4.04 (m, 2H), 3.75-3.69 (m, 2H), 3.43-3.34 (m, 6H), 3.27-3.19 (m, 2H), 2.29-2.25 (m, 1H), 2.22-2.18 (m, 1H); MS ESI [M+H]+ 491.3, calcd for [C$_{31}$H$_{30}$N$_4$O$_2$+H]+ 491.24.

Example A88. (1R*,2S*)-1'-methyl-2-(3-(4-(piperazin-1-yl)phenyl)-1H-indazol-6-yl)spiro[cyclopropane-1,3'-indolin]-2'-one 2,2,2-trifluoroacetate

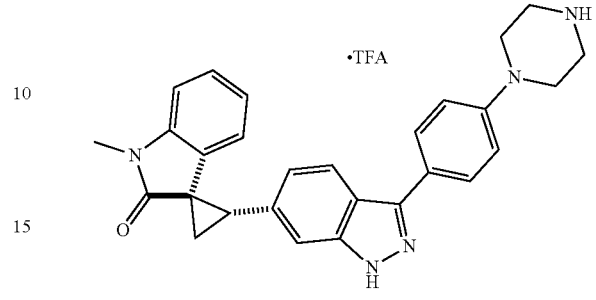

R*, S*, racemate

The title compound was synthesized according to the method of Example A45, except substituting (1R*,2S*)-2-(3-iodo-1H-indazol-6-yl)-1'-methylspiro[cyclopropane-1,3'-indolin]-2'-one (35 mg, 0.084 mmol) and tert-butyl 4-(4-(4,4,5,5-tetramethyl-1,3,2-dioxaborolan-2-yl)phenyl)piperazine-1-carboxylate (42 mg, 0.109 mmol). The solvent was removed and the Boc-protected amine purified by column chromatography (silica gel, CH$_2$Cl$_2$/MeOH, 95:5) to give an impure product which dissolved into CH$_2$Cl$_2$ (1.0 mL) and TFA (50 uL) was added. The reaction was stirred for 2 h, the solvent removed and the residue purified by prep-HPLC to give the title compound as a white powder (4.0 mg, 11%); $^1$H NMR (400 MHz, CD$_3$OD) δ 7.88-7.85 (m, 3H), 7.46 (s, 1H), 7.18-7.12 (m, 3H), 7.03-6.97 (m, 2H), 6.65 (t, J=7.7 Hz, 1H), 6.04 (d, J=7.5 Hz, 1H), 3.51-3.48 (m, 4H), 3.42-3.39 (m, 4H), 3.35 (s, 3H), 2.29-2.25 (m, 1H), 2.22-2.18 (m, 1H); MS ESI [M+H]+ 450.2, calcd for [C$_{28}$H$_{27}$N$_5$O+H]+ 450.23.

Example A89. (1R*,2S*)-(E)-1'-methyl-2-(3-(4-(piperazin-1-yl)styryl)-1H-indazol-6-yl)spiro[cyclopropane-1,3'-indolin]-2'-one 2,2,2-trifluoroacetate

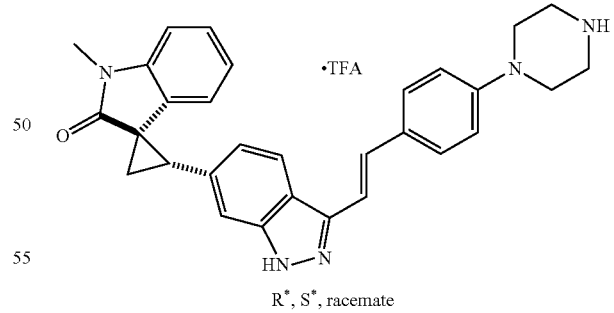

R*, S*, racemate

A. tert-butyl 4-(4-ethynylphenyl)piperazine-1-carboxylate

A microwave vial was charged with tert-butyl 4-(4-iodophenyl)piperazine-1-carboxylate (300 mg, 0.773 mmol), trimethylsilylacetylene (0.22 mL, 1.54 mmol), NEt$_3$ (3.0 mL), DMF (1.5 mL), CuI (15 mg, 0.080 mmol), and PdCl$_2$(PPh$_3$)$_2$ (27 mg, 0.039 mmol). The vial was capped and heated in the microwave at 100° C. for 1 h. After removing the NEt$_3$ in vacuo, the residue was extracted with EtOAc (15 mL). The organic layer was then washed with NaHCO$_3$ (sat.) (5 mL), H$_2$O (5 mL), brine (5 mL) and then dried over MgSO$_4$. The solvent was removed and then the material was dissolved into MeOH (4 mL) and THF (2 mL). K$_2$CO$_3$ (1.0 mL of a 1M solution) was added and the reaction stirred for 3 h. The solvent was removed and the residue extracted with EtOAc (15 mL). The organic layer was washed with brine (5 mL) and then dried over MgSO$_4$. The solvent was removed and the product dried under high vacuum to give the title compound as a brown solid (212 mg, 96%); MS ESI 287.0 [M+H]$^+$, calcd for [C$_{17}$H$_{22}$N$_2$O$_2$+H]$^+$ 287.18.

B. (E)-tert-butyl 4-(4-(2-(4,4,5,5-tetramethyl-1,3,2-dioxaborolan-2-yl)vinyl)phenyl)piperazine-1-carboxylate The title compound was synthesized according to the method of Example A42A, except substituting tert-butyl 4-(4-ethynylphenyl)piperazine-1-carboxylate (212 mg, 0.740 mmol) to give, after column chromatography (silica gel, Hexanes/EtOAc, 6:1 to 5:1), the title compound as a pale-yellow solid (137 mg, 45%); MS ESI 415.3 [M+H]$^+$, calcd for [C$_{23}$H$_{35}$BN$_2$O$_4$+H]$^+$ 415.28.

C. (1R*,2S*)-(E)-1'-methyl-2-(3-(4-(piperazin-1-yl)styryl)-1H-indazol-6-yl)spiro[cyclopropane-1,3'-indolin]-2'-one 2,2,2-trifluoroacetate The title compound was synthesized according to the method of Example A45, except substituting (1R*,2S*)-2-(3-iodo-1H-indazol-6-yl)-1'-methylspiro[cyclopropane-1,3'-indolin]-2'-one (37 mg, 0.090 mmol) and (E)-tert-butyl 4-(4-(2-(4,4,5,5-tetramethyl-1,3,2-dioxaborolan-2-yl)vinyl)phenyl)piperazine-1-carboxylate (45 mg, 0.109 mmol). The solvent was removed and the Boc-protected amine purified by column chromatography (silica gel, CH$_2$Cl$_2$/MeOH, 95:5) to give an impure product which dissolved into CH$_2$Cl$_2$ (2.0 mL) and TFA (200 uL) was added. The reaction was stirred for 2 h, the solvent removed and the residue purified by prep-HPLC to give the title compound as an off-white powder (2.0 mg, 4.0%); $^1$H NMR (400 MHz, CD$_3$OD) δ 7.97 (d, J=8.5 Hz, 1H), 7.56 (d, J=8.4 Hz, 2H), 7.46-7.41 (m, 2H), 7.30 (d, J=17 Hz, 1H), 7.15 (t, J=7.2 Hz, 1H), 7.06-6.99 (m, 4H), 6.65 (t, J=8.0 Hz, 1H), 6.02 (d, J=7.7 Hz, 1H), 3.49-3.44 (m, 4H), 3.40-3.31 (m, 8H), 2.28-2.25 (m, 1H), 2.21-2.18 (m, 1H); MS ESI [M+H]$^+$ 476.2, calcd for [C$_{30}$H$_{29}$N$_5$O+H]$^+$ 476.25.

Example A90. (1R,2S)-(E)-1'-methyl-2-(3-(4-(piperazin-1-yl)styryl)-1H-indazol-6-yl)spiro[cyclopropane-1,3'-indolin]-2'-one hydrochloride

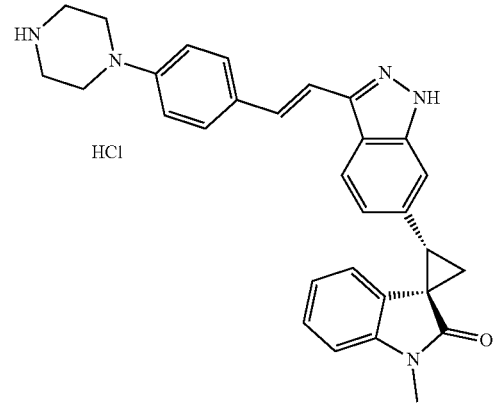 [SMILES: CN1C(=O)[C@@]2(C[C@H]2c2ccc3c(/C=C/c4ccc(N5CCNCC5)cc4)n[nH]c3c2)c2ccccc21 ; Cl]

The title compound was synthesized according to the method of Example A42B, except substituting (1R,2S)-2-(3-iodo-1H-indazol-6-yl)-1'-methylspiro[cyclopropane-1,3'-indolin]-2'-one (218 mg, 0.526 mmol) and (E)-tert-butyl 4-(4-(2-(4,4,5,5-tetramethyl-1,3,2-dioxaborolan-2-yl)vinyl)phenyl)piperazine-1-carboxylate (261 mg, 0.631 mmol). The Boc-protected intermediate was purified by column chromatography (silica gel, CH$_2$Cl$_2$/MeOH, 97:3 to 96:4) to give 218 mg, 72%. This material was dissolved into CH$_2$Cl$_2$ (6.0 mL) and TFA (1.0 mL) and stirred for 2 h, the solvent was removed and the residue purified by prep-HPLC which gave the TFA salt. This material was free-based by washing with NaHCO$_3$ (sat.) (10 mL) and extracting with EtOAc (2×50 mL). The HCl salt was prepared according to the method of A42B which gave, after drying, the title product (48 mg, 15%); Spectral data was identical to that obtained in Example A89. Optical Rotation: [α]$^{22}_D$=100° (c 0.43, MeOH).

Example A91. (1R*,2S*)-(E)-2-(3-(4-(piperazin-1-yl)styryl)-1H-indazol-6-yl)spiro[cyclopropane-1,3'-indolin]-2'-one 2,2,2-trifluoroacetate

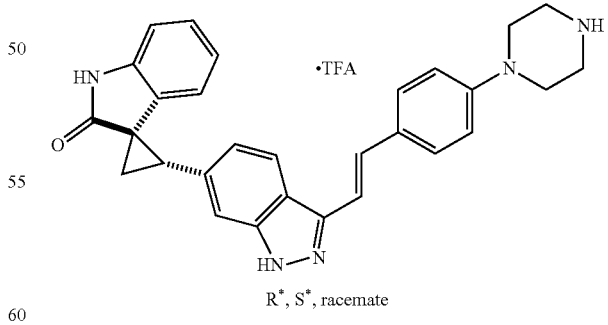

R*, S*, racemate

The title compound was synthesized according to the method of Example A45, except substituting (1R*,2S*)-2-(3-iodo-1H-indazol-6-yl)spiro[cyclopropane-1,3'-indolin]-2'-one (72 mg, 0.180 mmol) and (E)-tert-butyl 4-(4-(2-(4,4,5,5-tetramethyl-1,3,2-dioxaborolan-2-yl)vinyl)phenyl)piperazine-1-carboxylate (90 mg, 0.217 mmol). The solvent was removed and the residue purified by column chromatography (silica gel, hexanes/EtOAc, 2:1) to give 38 mg of the Boc-protected amine which dissolved into $CH_2Cl_2$ (2.0 mL) and TFA (0.1 mL) was added. The reaction was stirred for 3 h, the solvent was removed and the residue purified by prep-HPLC to yield the title compound (6.5 mg, 6.0%); $^1$H NMR (400 MHz, $CD_3OD$) δ 7.97 (d, J=8.1 Hz, 1H), 7.57 (d, J=8.6 Hz, 2H), 7.47-7.42 (m, 2H), 7.30 (d, J=17 Hz, 1H), 7.06-7.01 (m, 4H), 6.93 (d, J=7.6 Hz, 1H), 6.58 (t, J=7.6 Hz, 1H), 5.98 (d, J=8.0 Hz, 1H), 3.49-3.44 (m, 4H), 3.40-3.31 (m, 5H), 2.26-2.22 (m, 1H), 2.19-2.16 (m, 1H); MS ESI [M+H]$^+$ 462.2, calcd for $[C_{29}H_{27}N_5O+H]^+$ 462.23.

Example A92. (1R,2S)-(E)-2-(3-(4-(piperazin-1-yl)styryl)-1H-indazol-6-yl)spiro[cyclopropane-1,3'-indolin]-2'-one bis(2,2,2-trifluoroacetate)

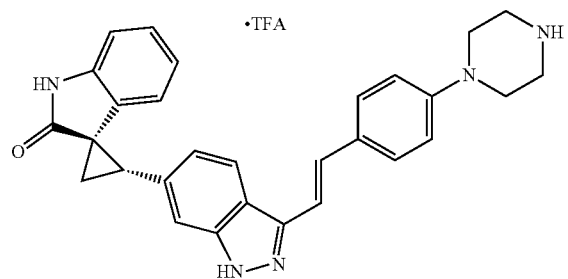 [SMILES: O=C1Nc2ccccc2[C@]12C[C@H]2c1ccc2c(/C=C/c3ccc(N4CCNCC4)cc3)n[nH]c2c1]

The title compound was synthesized according to the method of Example A91, except substituting (1R,2S)-2-(3-iodo-1H-indazol-6-yl)spiro[cyclopropane-1,3'-indolin]-2'-one (40 mg, 0.1 mmol). The title compound was isolated as a yellow solid (23 mg, 40%). The spectral data was identical to that obtained for Example A91.

Example A93. (1R*,2S*)-1'-methyl-2-(3-(6-(4-methylpiperazin-1-yl)pyridin-3-yl)-1H-indazol-6-yl)spiro[cyclopropane-1,3'-indolin]-2'-one bis(2,2,2-trifluoroacetate)

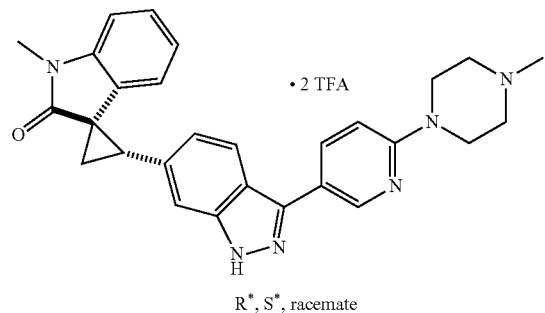

R*, S*, racemate

The title compound was synthesized according to the method of Example A45, except substituting (1R*,2S*)-2-(3-iodo-1H-indazol-6-yl)-1'-methylspiro[cyclopropane-1,3'-indolin]-2'-one (80 mg, 0.193 mmol) and 1-methyl-4-(5-(4,4,5,5-tetramethyl-1,3,2-dioxaborolan-2-yl)pyridin-2-yl)piperazine (76 mg, 0.251 mmol). The product was extracted with EtOAc (50 mL), the organic layer washed with saturated $NaHCO_3$ (5 mL), brine (5 mL) and then dried over $MgSO_4$. The solvent was removed and the residue purified by column chromatography (silica gel, $CH_2Cl_2$/MeOH/7N $NH_3$ in MeOH, 94:5:1) to give the product which was 90% pure by LC-MS, so was purified again by prep-HPLC to give a pale-yellow solid (6.6 mg, 7.3%); $^1$H NMR (400 MHz, $CD_3OD$) δ 8.73 (s, 1H), 8.22 (d, J=9.0 Hz, 1H), 7.84 (d, J=8.6, 1H), 7.48 (s, 1H), 7.16-7.11 (m, 2H), 7.03-6.98 (m, 2H), 6.64 (t, J=7.3 Hz, 1H), 6.03 (d, J=7.8 Hz, 1H), 3.70-3.15 (bs, 8H), 3.40-3.34 (m, 4H), 2.98 (s, 3H), 2.29-2.25 (m, 1H), 2.21-2.18 (m, 1H); MS ESI [M+H]$^+$ 465.2, calcd for $[C_{28}H_{28}N_6O+H]^+$ 465.24.

Example A94. (1R,2S)-(E)-1'-methyl-2-(3-(4-(piperidin-1-ylmethyl)styryl)-1H-indazol-6-yl)spiro[cyclopropane-1,3'-indolin]-2'-one hydrochloride

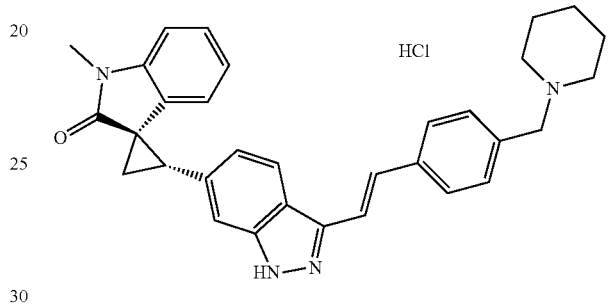

The title compound was synthesized according to the method of Example A42B, except substituting (1R,2S)-2-(3-iodo-1H-indazol-6-yl)-1'-methylspiro[cyclopropane-1,3'-indolin]-2'-one (594 mg, 1.43 mmol) and (E)-1-(4-(2-(4,4,5,5-tetramethyl-1,3,2-dioxaborolan-2-yl)vinyl)benzyl)piperidine (563 mg, 1.72 mmol). Purification by column chromatography (silica gel, $CH_2Cl_2$/MeOH/7N $NH_3$ in MeOH, 91:8:1) gave 443 mg, 63% of the free base as a pale orange solid. The HCl salt was prepared according to the method for A42B, which gave, after drying, the title product (378 mg, 50%); $^1$H NMR (400 MHz, $CD_3OD$) δ 8.01 (d, J=8.1 Hz, 1H), 7.76 (d, J=7.2 Hz, 2H), 7.54-7.47 (m, 5H), 7.15 (t, J=7.6 Hz, 1H), 7.05 (d, J=7.9 Hz, 2H), 6.64 (t, J=7.9 Hz, 1H), 6.02 (d, J=6.6 Hz, 1H), 4.31 (s, 2H), 3.48-3.45 (m, 2H), 3.39 (t, J=8.2 Hz, 1H), 3.36 (s, 3H), 3.01-2.95 (m, 2H), 2.29-2.26 (m, 1H), 2.22-2.19 (m, 1H), 1.99-1.72 (m, 5H), 1.57-1.50 (m, 1H); MS ESI [M+H]$^+$ 489.3, calcd for $[C_{32}H_{32}N_4O+H]^+$ 489.27. Optical Rotation: $[\alpha]^{22}_D$=−122° (c 0.49, MeOH).

Example A95. (1R*,2S*)-(E)-1'-methyl-2-(3-(4-(piperidin-1-ylmethyl)styryl)-1H-indazol-6-yl)spiro[cyclopropane-1,3'-indolin]-2'-one 2,2,2-trifluoroacetate

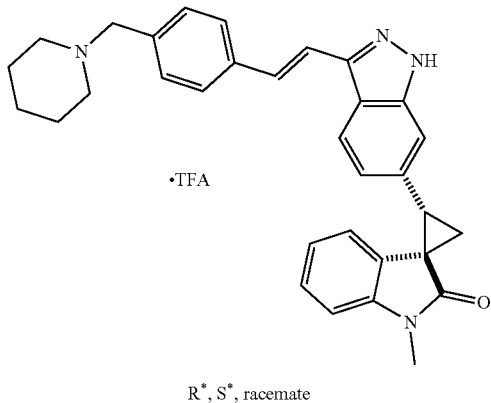

R*, S*, racemate

The title compound was synthesized according to the method of Example A43, except substituting (1R*,2S*)-2-(3-iodo-1H-indazol-6-yl)-1'-methylspiro[cyclopropane-1,3'-indolin]-2'-one (44 mg, 0.106 mmol) and (E)-1-(4-(2-(4,4,5,5-tetramethyl-1,3,2-dioxaborolan-2-yl)vinyl)benzyl)piperidine (45 mg, 0.138 mmol). Purification by prep-HPLC gave the title compound (6.5 mg, 10%); Spectral data was identical to that in obtained in Example A94.

Example A96. (1R*,2S*)-2-(3-(4-(4-isopropylpiperazin-1-yl)phenyl)-1H-indazol-6-yl)-5'-methoxyspiro[cyclopropane-1,3'-indolin]-2'-one

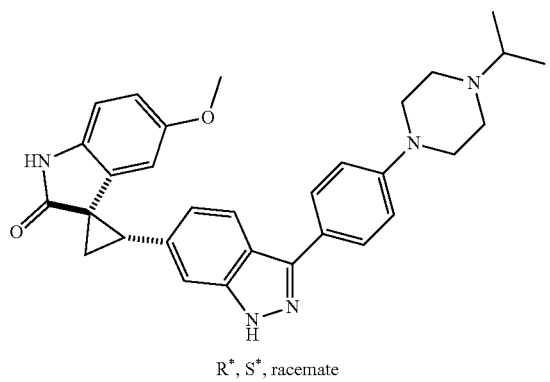

R*, S*, racemate

A. (1R*,2S*)-5'-methoxy-2-(3-(4-(piperazin-1-yl)phenyl)-1H-indazol-6 yl)spiro[cyclopropane-1,3'-indolin]-2'-one 2,2,2-trifluoroacetate The title compound was synthesized according to the method of Example A43, except substituting (1R*,2S*)-2-(3-iodo-1H-indazol-6-yl)-5'-methoxyspiro[cyclopropane-1,3'-indolin]-2'-one (200 mg, 0.464 mmol) and tert-butyl 4-(4-(4,4,5,5-tetramethyl-1,3,2-dioxaborolan-2-yl)phenyl)piperazine-1-carboxylate (234 mg, 0.603 mmol). The solvent was removed and the residue was purified by column chromatography (silica gel, $CH_2Cl_2$/MeOH, 96:4 to 94:6) which gave 183 mg of the Boc protected material. This material was dissolved into $CH_2Cl_2$ (6.0 mL) and TFA (0.60 mL) and the reaction stirred for 3 h, after which the solvent was removed and the product dried under high vacuum to give the title compound as a brown solid (190 mg, 70%); MS ESI [M+H]$^+$ 466.3, calcd for [$C_{28}H_{27}N_5O_2$+H]$^+$ 466.22.

B. (1R*,2S*)-2-(3-(4-(4-isopropylpiperazin-1-yl)phenyl)-1H-indazol-6-yl)-5'-methoxyspiro[cyclopropane-1,3'-indolin]-2'-one A solution of (1R*,2S*)-5'-methoxy-2-(3-(4-(piperazin-1-yl)phenyl)-1H-indazol-6-yl)spiro[cyclopropane-1,3'-indolin]-2'-one 2,2,2-trifluoroacetate (30 mg, 0.052 mmol) in 1,2-dichloroethane (0.5 mL), MeOH (0.1 mL) was treated with acetone (80 uL, 1.04 mmol) and NaBH(OAc)$_3$ (17 mg, 0.078 mmol) and the reaction was heated to 40° C. for 18 h. The solvent was removed and the residue purified by column chromatography (silica gel, $CH_2Cl_2$/MeOH/7N $NH_3$ in MeOH, 96:3:1) which gave an impure solid that was sonicated in $Et_2O$. The solvent was decanted off and the solid dried to give the title product as an off-white powder (12 mg, 46%); $^1$H NMR (400 MHz, DMSO-d$_6$) δ 12.99 (s, 1H), 10.44 (s, 1H), 7.91 (d, J=8.8 Hz, 1H), 7.81 (d, J=8.4 Hz, 2H), 7.47 (s, 1H), 7.06-6.99 (m, 3H), 6.74 (d, J=8.5 Hz, 1H), 6.57 (d, J=7.5 Hz, 1H), 5.69 (s, 1H), 3.29 (s, 3H), 3.25-3.15 (m, 4H), 2.67 (m, 2H), 2.65-2.55 (m, 4H), 2.35-2.32 (m, 1H), 2.22-1.98 (m, 1H), 1.01 (d, J=5.6 Hz, 6H); MS ESI [M+H]$^+$ 508.3, calcd for [$C_{31}H_{33}N_5O_2$+H]$^+$ 508.27.

Example A97. (1R,2S)-2-(3-(4-(4-isopropylpiperazin-1-yl)phenyl)-1H-indazol-6-yl)-5'-Methoxyspiro[cyclopropane-1,3'-indolin]-2'-one 2,2,2-trifluoroacetate

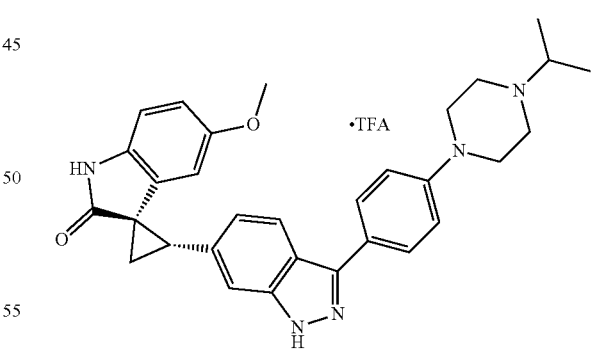

The title compound was synthesized according to the method of Example A51B, using 1-isopropyl-4-(4-(4,4,5,5-tetramethyl-1,3,2-dioxaborolan-2-yl)phenyl)piperazine (200 mg, 0.61 mmol). The crude reaction mixture was concentrated under reduced pressure to dryness, and purified by preparative HPLC to give the title compound as a white solid (130 mg, 44%). Spectral data was identical to that obtained for Example A96.

Optical Rotation: $[\alpha]^{22}_D = -94°$ (c 0.68, MeOH).

Example A98. (1R*,2S*)-2-(3-(4-(4-ethylpiperazin-1-yl)phenyl)-1H-indazol-6-yl)-5'-methoxyspiro[cyclopropane-1,3'-indolin]-2'-one 2,2,2-trifluoroacetate

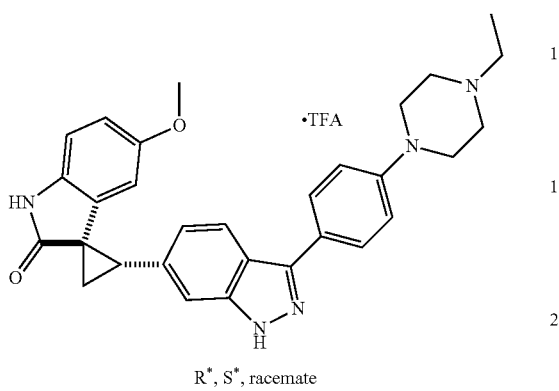

R*, S*, racemate

The title compound was synthesized according to the method of Example A96B, using (1R*,2S*)-5'-methoxy-2-(3-(4-(piperazin-1-yl)phenyl)-1H-indazol-6-yl)spiro [cyclopropane-1,3'-indolin]-2'-one 2,2,2-trifluoroacetate (40 mg, 0.069 mmol) and acetaldehyde (6.0 uL, 0.140 mmol). The crude reaction mixture was concentrated under reduced pressure to dryness, and purified by preparative HPLC to give the title compound as a white solid (3.0 mg, 7.0%); $^1$H NMR (400 MHz, CD$_3$OD) δ 7.91 (d, J=8.6 Hz, 1H), 7.87 (d, J=8.5 Hz, 2H), 7.49 (s, 1H), 7.17 (d, J=8.6 Hz, 2H), 7.02 (d, J=8.8 Hz, 1H), 6.82 (d, J=8.5 Hz, 1H), 6.60 (d, J=8.9 Hz, 1H), 5.60 (s, 1H), 4.02-4.92 (m, 2H), 3.74-3.64 (m, 2H), 3.38-3.22 (m, 5H), 3.28 (s, 3H), 3.14-3.05 (m, 2H), 2.26-2.22 (m, 1H), 2.20-2.16 (m, 1H), 1.41 (t, J=7.2 Hz, 3H); MS ESI [M+H]$^+$ 494.3, calcd for [C$_{30}$H$_{31}$N$_5$O$_2$+H]$^+$ 494.26.

Example A99. (1R,2S)-2-(3-(4-(4-ethylpiperazin-1-yl)phenyl)-1H-indazol-6-yl)-5'-methoxyspiro[cyclopropane-1,3'-indolin]-2'-one 2,2,2-trifluoroacetate

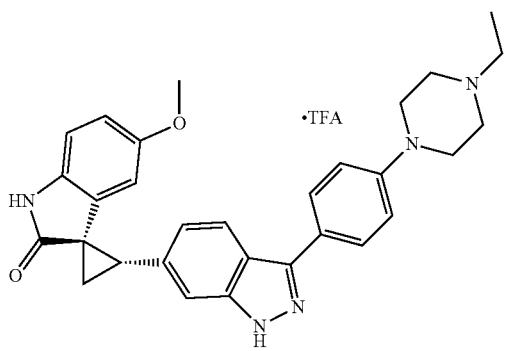 [SMILES: CCN1CCN(c2ccc(-c3n[nH]c4cc([C@@H]5C[C@@]56C(=O)Nc5ccc(OC)cc56)ccc34)cc2)CC1]

The title compound was synthesized according to the method of Example A42B, except substituting (1R,2S)-2-(3-iodo-1H-indazol-6-yl)-5'-methoxyspiro[cyclopropane-1,3'-indolin]-2'-one (719 mg, 1.67 mmol) and 1-ethyl-4-(4-(4,4,5,5-tetramethyl-1,3,2-dioxaborolan-2-yl)phenyl)piperazine (633 mg, 2.00 mmol). The mixture was purified by prep-HPLC which gave the title compound as a beige powder (180 mg, 19%). Spectral data was identical to that obtained in Example A98. Optical Rotation: $[\alpha]^{22}_D = -100°$ (c 0.55, MeOH).

Example A100. (1R*,2S*)-5'-methoxy-1'-methyl-2-(3-(4-(4-methylpiperazin-1-yl)phenyl)-1H-indazol-6-yl)spiro[cyclopropane-1,3'-indolin]-2'-one 2,2,2-trifluoroacetate

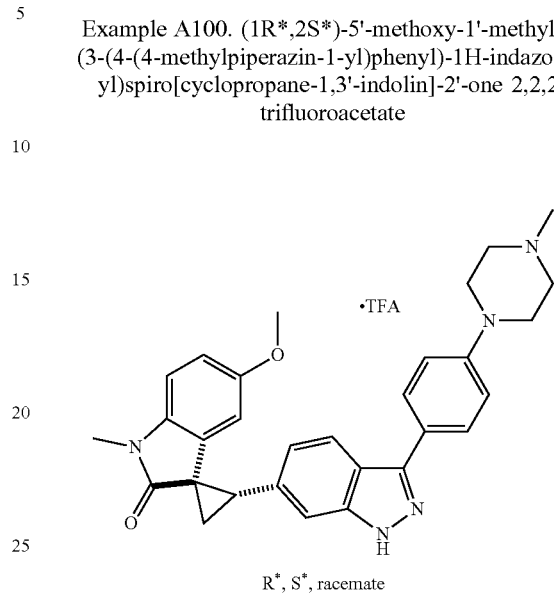

R*, S*, racemate

A. 5-methoxy-1-methylindolin-2-one

A dry round-bottom flask was charged with NaH (60% wt) (64 mg, 1.61 mmol) and toluene (2.0 mL). The suspension was heated to 100° C. and then 5-methoxyindolin-2-one (250 mg, 1.53 mmol) was added. After 30 min at 100° C., Me$_2$SO$_4$ (0.16 mL, 1.68 mmol) was added and the temperature maintained at 100° C. for 2.5 h. The reaction was cooled to room temperature and the solvent was removed in vacuo. The residue was purified by column chromatography (silica gel, hexanes/EtOAc, 3:1 to 2:1) to give the product as a beige solid (144 mg, 53%); MS ESI 164.1 [M+H]$^+$, calcd for [C$_9$H$_9$NO$_2$+H]$^+$ 164.07.

B. (1R*,2S*)-2-(3-iodo-1H-indazol-6-yl)-5'-methoxy-1'-methylspiro[cyclopropane-1,3'-indolin]-2'-one A vial was charged with 5-methoxy-1-methylindolin-2-one (144 mg, 0.813 mg), 3-iodo-1H-indazole-6-carbaldehyde (221 mg, 0.813 mmol), MeOH (4.0 mL), and piperidine (7 uL, 0.081 mmol). The mixture was reacted at 50° C. for 18 h. The resulting orange precipitate was filtered, washed with MeOH and then dried under high vacuum. The orange solid was then added to a suspension of NaH (60% wt.) (155 mg, 3.87 mmol), trimethylsulfoxonium iodide (284 mg, 1.29 mmol), and DMF (3.0 mL) that had been pre-stirred at room temperature for 30 minutes. This mixture was heated to 40° C. for 2 h. The reaction was cooled to 0° C., quenched with NH$_4$Cl (sat.) (2 mL) and extracted with EtOAc (100 mL). The organic layer was separated, washed with brine (10 mL) and dried over MgSO$_4$. The solvent was removed and the residue purified by column chromatography (silica gel, Hexanes/Acetone, 5:1 to 3:1) to give the title compound as a pink solid give (205 mg, 57%); MS ESI 446.0 [M+H]$^+$, calcd for [C$_{19}$H$_{16}$IN$_3$O$_2$+H]$^+$ 446.04.

C. (1R*,2S*)-5'-methoxy-1'-methyl-2-(3-(4-(4-methylpiperazin-1-yl)phenyl)-1H-indazol-6-yl)spiro[cyclopropane-1,3'-indolin]-2'-one 2,2,2-trifluoroacetate A microwave vial was charged with (1R*,2S*)-2-(3-iodo-1H-indazol-6-yl)-5'-methoxy-1'-methylspiro[cyclopropane-1,3'-indolin]-2'-one (35 mg, 0.079 mmol), 1-methyl-4-(4-(4,4,5,5-tetramethyl-1,3,2-dioxaborolan-2-yl)phenyl)piperazine (36 mg, 0.119 mmol), $Na_2CO_3$ (83 uL of 1M solution), and 1.0 mL of DME/water/EtOH (16:2:1). The mixture was purged briefly with $Ar_{(g)}$ then $PdCl_2(PPh_3)_2$ (6.0 mg, 0.0080 mmol) was added, the microwave vial capped and the reaction heated to 125° C. in the microwave for 1 h. The solvent was removed and the residue purified by prep-HPLC to give a pale-yellow solid (17 mg, 35%); $^1$H NMR (400 MHz, $CD_3OD$) δ 7.90 (d, J=8.4 Hz, 1H), 7.87 (d, J=8.4 Hz, 2H), 7.48 (s, 1H), 7.17 (d, J=8.4 Hz, 2H), 7.00 (d, J=8.2 Hz, 1H), 6.92 (d, J=8.8 Hz, 1H), 6.69 (dd, $J_1$=8.8 Hz, $J_2$=2.5 Hz, 1H), 5.64 (d, J=2.5 Hz, 1H), 4.01-3.95 (m, 2H), 3.66-3.58 (m, 2H), 3.42-3.33 (m, 9H), 3.18-3.09 (m, 2H), 2.99 (s, 3H), 2.29-2.25 (m, 1H), 2.23-2.18 (m, 1H); MS ESI $[M+H]^+$ 494.3, calcd for $[C_{30}H_{31}N_5O_2+H]^+$ 494.26.

Example A101. (1R,2S)-5'-methoxy-1'-methyl-2-(3-(4-(piperazin-1-yl)phenyl)-1H-indazol-6-yl)spiro[cyclopropane-1,3'-indolin]-2'-one 2,2,2-trifluoroacetate

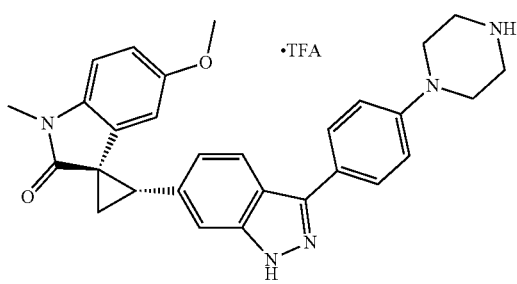 [SMILES: COc1ccc2c(c1)[C@]1(C[C@H]1c1ccc3c(-c4ccc(N5CCNCC5)cc4)n[nH]c3c1)C(=O)N2C]

The boc protected title compound was synthesized according to the method of Example A51B, except substituting (1R,2S)-2-(3-iodo-1H-indazol-6-yl)-S-methoxy-1'-methylspiro[cyclopropane-1,3'-indolin]-2'-one (600 mg, 1.35 mmol) and tert-butyl 4-(4-(4,4,5,5-tetramethyl-1,3,2-dioxaborolan-2-yl)phenyl)piperazine-1-carboxylate (534 mg, 1.37 mmol). The Boc protected compound was purified by column chromatography (silica gel, hexanes/EtOAc, 100:0 to 5:95) which gave 400 mg. This material was dissolved in $CH_2Cl_2$ (12 mL) and TFA (3 mL) and the reaction stirred for 3 h at which time the solvent was removed and the residue purified by prep-HPLC which yielded the title product as a pale-yellow solid (339 mg, 42%); $^1$H NMR (400 MHz, $CD_3OD$) δ 7.90 (d, J=8.2 Hz, 1H), 7.86 (d, J=8.4 Hz, 2H), 7.48 (s, 1H), 7.17 (d, J=8.4 Hz, 2H), 7.00 (d J=8.6 Hz, 1H,), 6.92 (d, J=8.5 Hz, 1H), 6.69 (d, J=8.6 Hz, 1H), 5.64 (s, 1H), 3.53-3.48 (m, 4H), 3.43-3.37 (m, 5H), 3.31 (s, 3H), 3.29 (s, 3H), 2.29-2.26 (m, 1H), 2.22-2.18 (m, 1H); MS ESI $[M+H]^+$ 480.3, calcd for $[C_{29}H_{29}N_5O_2+H]^+$ 480.24.

Optical Rotation: $[\alpha]^{22}_D$=–113° (c 0.62, MeOH).

Example A102. (1R,2S)-(E)-5'-methoxy-1'-methyl-2-(3-(4-(morpholinomethyl)styryl)-1H-indazol-6-yl)spiro[cyclopropane-1,3'-indolin]-2'-one hydrochloride

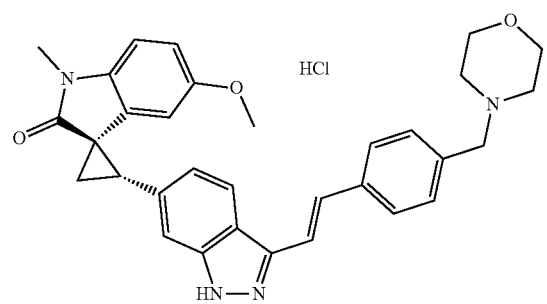 [SMILES: COc1ccc2c(c1)[C@]1(C[C@H]1c1ccc3c(/C=C/c4ccc(CN5CCOCC5)cc4)n[nH]c3c1)C(=O)N2C ; Cl]

The title compound was synthesized according to the method of Example A42B, except substituting (1R,2S)-2-(3-iodo-1H-indazol-6-yl)-5'-methoxy-1'-methylspiro[cyclopropane-1,3'-indolin]-2'-one (512 mg, 1.15 mmol) and (E)-4-(4-(2-(4,4,5,5-tetramethyl-1,3,2-dioxaborolan-2-yl)vinyl)benzyl)morpholine (454 mg, 1.38 mmol). Purification by column chromatography (silica gel, $CH_2Cl_2$/MeOH, 95:5 to 92:8) gave the free base as a yellow solid. The HCl salt was prepared according to the method of A42B, which gave after drying, the title product as a pale-yellow solid (346 mg, 54%); $^1$H NMR (400 MHz, $CD_3OD$) δ 8.02 (d, J=8.6 Hz, 1H), 7.77 (d, J=8.0 Hz, 2H), 7.56-7.49 (m, 5H), 7.04 (d, J=8.4 Hz, 1H), 6.92 (d, J=7.8 Hz, 1H), 6.69 (d, J=8.6 Hz, 1H), 5.63 (s, 1H), 4.39 (s, 2H), 4.08-4.05 (m, 2H), 3.77-3.71 (m, 2H), 3.35-3.23 (m, 11H), 2.27-2.25 (m, 1H), 2.22-2.19 (m, 1H); MS ESI $[M+H]^+$ 521.3, calcd for $[C_{32}H_{32}N_4O_3+H]^+$ 521.26. Optical Rotation: $[\alpha]^{22}_D$=–85° (c 0.59, MeOH).

Example A103. (1R*,2S*)-2-(3-(4-(2-(dimethylamino)ethoxy)phenyl)-1H-indazol-6-yl)-5'-methoxyspiro[cyclopropane-1,3'-indolin]-2'-one 2,2,2-trifluoroacetate

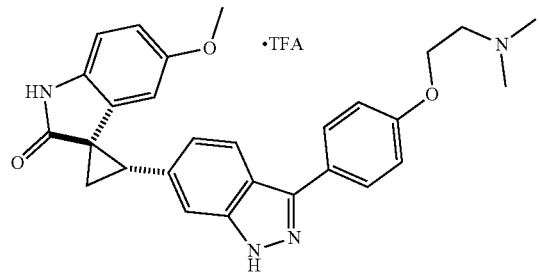

R*, S*, racemate

The title compound was synthesized according to the method of Example A42B, except substituting (1R*,2S*)-2-(3-iodo-1H-indazol-6-yl)-5'-methoxyspiro[cyclopropane-1,3'-indolin]-2'-one (30 mg, 0.070 mmol) and N,N-dimethyl-2-(4-(4,4,5,5-tetramethyl-1,3,2-dioxaborolan-2-yl)phenoxy)ethanamine (24 mg, 0.084 mmol). The product was extracted with EtOAc (20 mL), and the organic layer washed with saturated $NaHCO_3$ (5 mL), brine (5 mL) and then dried over $MgSO_4$. The solvent was removed and the residue was purified by prep-HPLC to give a pale-yellow solid (8.2 mg, 20%). Spectral data was identical to Example A69.

Example A104. (1R*,2S*)-5'-methoxy-1'-methyl-2-(3-(6-(4-methylpiperazin-1-yl)pyridin-3-yl)-1H-indazol-6-yl)spiro[cyclopropane-1,3'-indolin]-2'-one bis(2,2,2-trifluoroacetate)

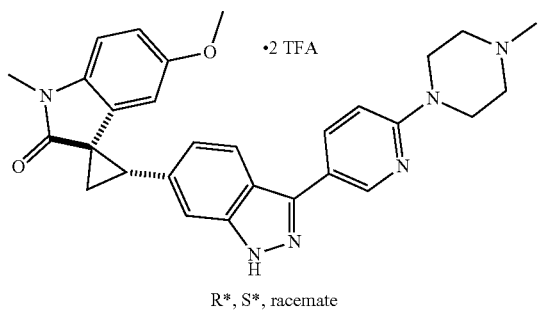

R*, S*, racemate

The title compound was synthesized according to the method of Example A42B, except substituting (1R*,2S*)-2-(3-iodo-1H-indazol-6-yl)-5'-methoxyspiro[cyclopropane-1,3'-indolin]-2'-one (50 mg, 0.112 mmol) and 1-methyl-4-(5-(4,4,5,5-tetramethyl-1,3,2-dioxaborolan-2-yl)pyridin-2-yl)piperazine (41 mg, 0.134 mmol). The product was extracted with EtOAc (20 mL), and the organic layer washed with saturated NaHCO$_3$ (5 mL), brine (5 mL) and then dried over MgSO$_4$. The solvent was removed and the residue purified by prep-HPLC to give a pale-yellow solid (10 mg, 15%); $^1$H NMR (400 MHz, CD$_3$OD) δ 8.75 (s, 1H), 8.20 (d, J=9.0 Hz, 1H), 7.87 (d, J=8.2 Hz, 1H), 7.51 (s, 1H), 7.11 (d, J=8.9 Hz, 1H), 7.03 (d, J=8.8 Hz, 1H), 6.92 (d, J=8.8 Hz, 1H), 6.70 (dd, J$_1$=9.0 Hz, J$_2$=2.3 Hz, 1H), 5.65 (d, J=2.4 Hz, 1H), 4.70-4.45 (bs, 2H), 3.75-3.50 (bs, 2H), 3.37 (m, 1H), 3.34 (s, 3H), 3.35-3.10 (bs, 7H), 2.98 (s, 3H), 2.30-2.25 (m, 1H), 2.23-2.18 (m, 1H); MS ESI [M+H]$^+$ 495.3, calcd for [C$_{29}$H$_{30}$N$_6$O$_2$+H]$^+$ 495.25.

Example A105. (1R,2S)-5'-methoxy-2-(3-((E)-2-(5-(morpholinomethyl)thiophen-2-yl)vinyl)-1H-indazol-6-yl)spiro[cyclopropane-L3'-indolin]-2'-one hydrochloride

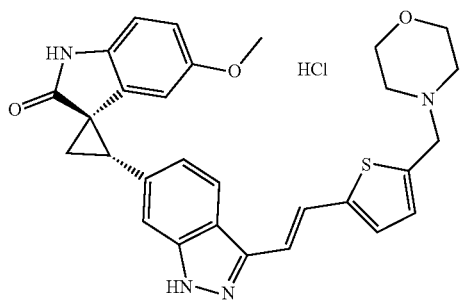 [SMILES: COc1ccc2c(c1)[C@]1(C[C@H]1c1ccc3c(/C=C/c4ccc(CN5CCOCC5)s4)n[nH]c3c1)C(=O)N2 ; Cl]

A. 5-ethynylthiophene-2-carbaldehyde

A solution of 5-bromothiophene-2-carbaldehyde (0.60 mL, 5.0 mmol), trimethylsilylacetylene (0.84 mL, 6.0 mmol), and diisopropylamine (5.0 mL) was purged briefly with Ar$_{(g)}$ then CuI (48 mg, 0.25 mmol) and PdCl$_2$(PPh$_3$)$_2$ (88 mg, 0.125 mmol) was added and the reaction heated to 60° C. for 18 h. The reaction was cooled to rt and diluted with Et$_2$O (100 mL). The solution was then washed with 0.2M HCl (10 mL), brine (10 mL), dried over MgSO$_4$, and the solvent removed in vacuo. The resulting residue was purified by column chromatography (silica gel, hexanes/EtOAc, 9:1) to give 237 mg, 23% of the trimethylsilyl protected alkyne. This material was then dissolved into MeOH (5.0 mL) and then KOH (1.2 mL of a 2M solution) was added. The mixture was stirred at 30° C. for 2 h, then extracted with CH$_2$Cl$_2$ (3×50 mL). The organic layer was washed with brine (10 mL), dried over MgSO$_4$, and the solvent removed to give the title compound (88 mg, 57%); $^1$H NMR (400 MHz, CDCl$_3$) δ 9.87 (s, 1H), 7.64 (d, J=3.9 Hz, 1H), 7.32 (d, J=3.9 Hz, 1H), 3.58 (s, 1H).

B. 4-((5-ethynylthiophen-2-yl)methyl)morpholine

To a solution of 5-ethynylthiophene-2-carbaldehyde (88 mg, 0.646 mmol), morpholine (56 uL, 0.646 mmol) in 1,2-dichloroethane (3.0 mL) was added a drop of AcOH. The mixture was stirred for 15 min and then NaBH(OAc)$_3$ (205 mg, 0.969 mmol) was added and stirred at room temperature for 18 h. The reaction was diluted with CH$_2$Cl$_2$ (30 mL) and washed with saturated NaHCO$_3$ (2×5 mL), brine (5 mL), and the organic layer dried over MgSO$_4$. The solvent was removed and the residue purified by column chromatography (silica gel, hexanes/EtOAc, 3:1) to give the title product (80 mg, 60%); MS ESI [M+H]$^+$ 208.08, calcd for [C$_{11}$H$_{13}$NOS+H]$^+$ 207.8.

C. (E)-4-((5-(2-(4,4,5,5-tetramethyl-1,3,2-dioxaborolan-2-yl)vinyl)thiophen-2-yl)methyl)morpholine The title compound was synthesized according to the method of Example A42A, except substituting 4-((5-ethynylthiophen-2-yl)methyl)morpholine (80 mg, 0.386 mmol) to give, after column chromatography (silica gel, Hexanes/EtOAc, 2:1 to 1:1), an orange oil (76 mg, 59%); MS ESI 336.0 [M+H]$^+$, calcd for [C$_{17}$H$_{26}$BNO$_3$S+H]$^+$ 336.18.

D. (1R,2S)-5'-methoxy-2-(3-((E)-2-(5-(morpholinomethyl)thiophen-2-yl)vinyl)-1H-indazol-6-yl)spiro[cyclopropane-1,3'-indolin]-2'-one hydrochloride The title compound was synthesized according to the method of Example A42B, except substituting (1R,2S)-2-(3-iodo-1H-indazol-6-yl)-5'-methoxyspiro[cyclopropane-1,3'-indolin]-2'-one (76 mg, 0.189 mmol) and (E)-4-((5-(2-(4,4,5,5-tetramethyl-1,3,2-dioxaborolan-2-yl)vinyl)thiophen-2-yl)methyl)morpholine (76 mg, 0.227 mmol). The product was extracted with EtOAc (50 mL), and the organic layer washed with saturated NaHCO$_3$ (5 mL), brine (5 mL) and then dried over MgSO$_4$. The solvent was removed and the residue purified by column chromatography (silica gel, CH$_2$Cl$_2$/MeOH, 95:5 to 93:7) to give 73 mg, 84% of the free base. To prepare the HCl salt, the free base was dissolved into THF (1.0 mL) and HCl (0.22 mL of 1M solution in Et$_2$O) was added. A precipitate immediately formed which was further precipitated by added Et$_2$O and then filtered, washed with Et$_2$O to give of a pale-yellow powder after drying (53 mg, 51%); $^1$H NMR (400 MHz, CD$_3$OD) δ 7.98 (d, J=8.3 Hz, 1H), 7.64 (d, J=16.3 Hz, 1H), 7.49 (s, 1H), 7.32-7.25 (m, 3H), 7.06 (d, J=8.6 Hz, 1H), 6.83 (d, J=8.5 Hz, 1H), 6.60 (dd, J₁=8.1 Hz, J₂=2.3 Hz, 1H), 5.57 (d, J=1.6 Hz, 1H), 4.62 (s, 2H), 4.11-4.08 (m, 2H), 3.80-3.71 (m, 2H), 3.49-3.46 (m, 2H), 3.36-3.20 (m, 3H), 3.26 (s, 3H), 2.26-2.22 (m, 1H), 2.20-2.16 (m, 1H); MS ESI [M+H]⁺ 513.1, calcd for [C₂₉H₂₈N₄O₃S+H]⁺ 513.20. Optical Rotation: [α]²²_D=–96° (c 0.54, MeOH).

Example A106. (1R,2S)-(E)-2-(3-(4-(((R)-3-fluoropyrrolidin-1-yl)methyl)styryl)-1H-indazol-6-yl)spiro[cyclopropane-1,3'-indolin]-2'-one 2,2,2-trifluoroacetate

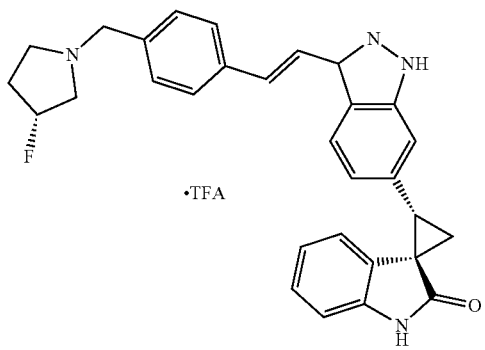 [SMILES: O=C1Nc2ccccc2[C@]12C[C@H]2c1ccc2c(c1)NNC2/C=C/c1ccc(CN2CC[C@@H](F)C2)cc1]

A. (R)-1-(4-bromobenzyl)-3-fluoropyrrolidine

The title compound was synthesized according to the method of Example A105B, except substituting (R)-3-fluoropyrrolidine hydrochloride (576 mg, 4.59 mmol) and 4-bromobenzaldehyde (849 mg, 4.59 mmol) which gave 1.09 g, 91% of a clear, colourless oil; MS ESI [M+H]⁺ 258.0, calcd for [C₁₁H₁₃BrFN+H]⁺ 258.03.

B. (3R)-3-fluoro-1-(4-((E)-2-(4,4,6-trimethyl-1,3,2-dioxaborinan-2-yl)vinyl)benzyl)pyrrolidine The title compound was synthesized according to the method of Example A51A, except substituting (R)-1-(4-bromobenzyl)-3-fluoropyrrolidine (1.07 g, 4.15 mmol) and 4,4,6-trimethyl-2-vinyl-1,3,2-dioxaborinane (0.77 mL, 4.57 mmol) which gave 1.40 g, 91% of a pale orange solid; MS ESI [M+H]⁺ 332.3, calcd for [C₁₉H₂₇BFNO₂+H]⁺ 332.22.

C. (1R,2S)-(E)-2-(3-(4-(((R)-3-fluoropyrrolidin-1-yl)methyl)styryl)-1H-indazol-6-yl)spiro[cyclopropane-1,3'-indolin]-2'-one 2,2,2-trifluoroacetate The title compound was synthesized according to the method of Example A42B, except substituting (1R,2S)-2-(3-iodo-1H-indazol-6-yl)spiro[cyclopropane-1,3'-indolin]-2'-one (630 mg, 1.57 mmol) and (3R)-3-fluoro-1-(4-((E)-2-(4,4,6-trimethyl-1,3,2-dioxaborinan-2-yl)vinyl)benzyl)pyrrolidine (622 mg, 1.88 mmol). The title product was obtained as a pale-yellow solid after prep-HPLC purification (338 mg, 48%); ¹H NMR (400 MHz, CD₃OD) δ 7.98 (d, 1H, J=8.3 Hz), 7.73 (d, 2H, J=7.80 Hz), 7.55-7.45 (m, 5H), 7.06-7.00 (m, 2H), 6.93 (d, 1H, J=7.7 Hz), 6.56 (t, 1H, J=7.5 Hz), 5.97 (d, 1H, J=7.5 Hz), 5.46 (d, 1H, J=52.4 Hz), 4.46 (s, 2H), 3.73-3.31 (m, 5H), 2.65-2.44 (m, 2H), 2.26-2.15 (m, 2H); MS ESI [M+H]⁺ 479.3, calcd for [C₃₀H₂₇FN₄O+H]⁺ 479.22. Optical Rotation: [α]²²_D=–125° (c 0.44, MeOH).

Example A107. (1R,2S)-2-(3-(imidazo[1,2-a]pyridin-6-yl)-1H-indazol-6-yl)-5'-methoxyspiro[cyclopropane-1,3'-indolin]-2'-one 2,2,2-trifluoroacetate

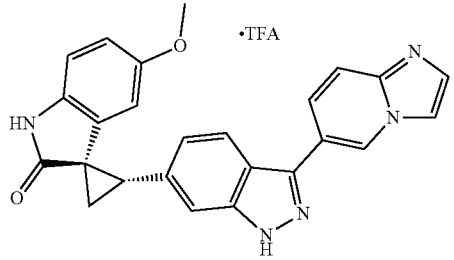 [SMILES: COc1ccc2c(c1)[C@]1(C[C@H]1c1ccc3c(-c4ccc5nccn5c4)n[nH]c3c1)C(=O)N2]

The title compound was synthesized according to the method of Example A42B, except substituting (1R,2S)-2-(3-iodo-1H-indazol-6-yl)-5'-methoxyspiro[cyclopropane-1,3'-indolin]-2'-one (75 mg, 0.187 mmol) and imidazo[1,2-a]pyridin-6-ylboronic acid (36 mg, 0.224 mmol). The title product was obtained as a white solid after prep-HPLC purification (33 mg, 33%); ¹H NMR (400 MHz, CD₃OD) δ 9.42 (s, 1H), 8.65 (d, 1H, J=9.4 Hz), 8.32 (s, 1H), 8.13-7.99 (m, 3H), 7.60 (s, 1H), 7.13 (d, 1H, J=7.8 Hz), 6.83 (d, 1H, J=7.6 Hz), 6.61 (d, 1H, J=7.0 Hz), 5.61 (s, 1H), 3.42-3.38 (m, 1H), 3.29 (s, 3H), 2.31-2.26 (m, 1H), 2.22-2.16 (m, 1H); MS ESI [M+H]⁺ 422.2, calcd for [C₂₅H₁₉N₅O₂+H]⁺ 422.16. Optical Rotation: [α]²²_D=–96° (c 0.52, MeOH).

Example A108. (1R,2S)-2-(3-(4-(2-(1H-imidazol-1-yl)ethoxy)phenyl)-1H-indazol-6-yl)-5'-methoxyspiro[cyclopropane-1,3'-indolin]-2'-one 2,2,2-trifluoroacetate

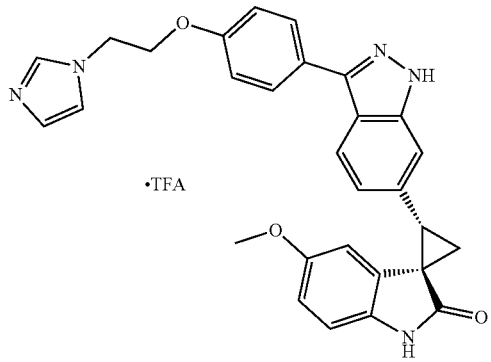 [SMILES: COc1ccc2c(c1)[C@]1(C[C@H]1c1ccc3c(-c4ccc(OCCn5ccnc5)cc4)n[nH]c3c1)C(=O)N2]

The title compound was synthesized according to the method of Example A42B, except substituting (1R,2S)-2-(3-iodo-1H-indazol-6-yl)-5'-methoxyspiro[cyclopropane-1,3'-indolin]-2'-one (75 mg, 0.187 mmol) and imidazo[1,2-a]pyridin-6-ylboronic acid (52 mg, 0.224 mmol). The title product was obtained as a white solid after prep-HPLC purification (45 mg, 40%); ¹H NMR (400 MHz, CD₃OD) δ 9.09 (s, 1H), 7.90-7.85 (m, 3H), 7.78 (s, 1H), 7.61 (s, 1H), 7.49 (s, 1H), 7.09 (d, 2H, J=7.8 Hz), 7.02 (d, 1H, J=8.5 Hz), 6.82 (d, 1H, J=8.5 Hz), 6.60 (d, 1H, J=7.7 Hz), 5.59 (s, 1H), 4.72-4.70 (m, 2H), 4.48-4.44 (m, 2H), 3.36 (t, 1H, J=8.8 Hz), 3.26 (s, 3H), 2.25-2.20 (m, 1H), 2.19-2.16 (m, 1H); MS ESI [M+H]⁺ 492.3, calcd for [C₂₉H₂₅N₅O₃+H]⁺ 492.20. Optical Rotation: [α]²²_D=–82° (c 0.43, MeOH).

Example A109. (1R,2S)-(E)-2-(3-(4-((dimethyl-amino)methyl)styryl)-1H-indazol-6-yl)-1'-methyl-spiro[cyclopropane-1,3'-indolin]-2'-one 2,2,2-trifluoroacetate

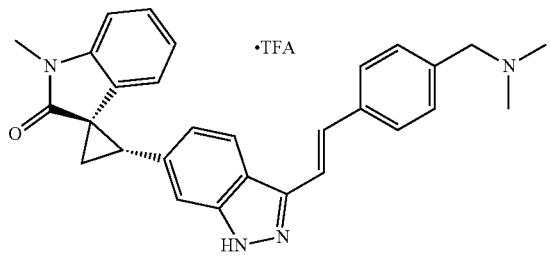 [SMILES: CN(C)Cc1ccc(/C=C/c2n[nH]c3cc([C@@H]4C[C@@]45C(=O)N(C)c4ccccc45)ccc23)cc1]

The title compound was synthesized according to the method of Example A42B, except substituting (1R,2S)-2-(3-iodo-1H-indazol-6-yl)-1'-methylspiro[cyclopropane-1,3'-indolin]-2'-one (134 mg, 0.322 mmol) and (E)-N,N-dimethyl-1-(4-(2-(4,4,5,5-tetramethyl-1,3,2-dioxaborolan-2-yl)vinyl)phenyl)methanamine (111 mg, 0.386 mmol). Purification by prep-HPLC resulted in a pale-yellow solid which was sonicated with Et$_2$O and filtered to give the title product (42 mg, 23%); $^1$H NMR (400 MHz, CD$_3$OD) δ 8.00 (d, 1H, J=8.0 Hz), 7.76 (d, 2H, J=7.6 Hz), 7.54-7.47 (m, 5H), 7.15 (t, 1H, J=8.2 Hz), 7.03 (d, 2H, J=7.8 Hz), 6.64 (t, 1H, J=7.5 Hz), 6.02 (d, 1H, J=7.0 Hz), 4.33 (s, 2H), 3.41-3.35 (m, 4H), 2.88 (s, 6H), 2.29-2.26 (m, 1H), 2.22-2.19 (m, 1H); MS ESI [M+H]$^+$ 449.2, calcd for [C$_{29}$H$_{28}$N$_4$O+H]$^+$ 449.23. Optical Rotation: [α]$^{22}_D$=−152° (c 0.42, MeOH).

Example A110. (1R,2S)-1'-methyl-2-(3-((E)-2-(6-(4-methylpiperazin-1-yl)pyridin-3-yl)vinyl)-1H-indazol-6-yl)spiro[cyclopropane-1,3'-indolin]-2'-one bis(2,2,2-trifluoroacetate)

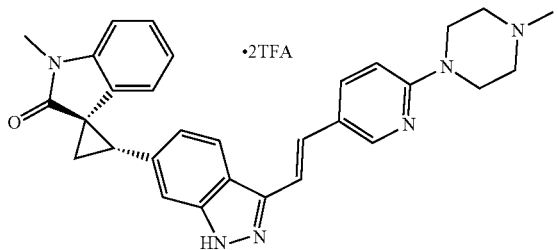 [SMILES: CN1CCN(c2ccc(/C=C/c3n[nH]c4cc([C@@H]5C[C@@]56C(=O)N(C)c5ccccc56)ccc34)cn2)CC1]

A. (E)-1-methyl-4-(5-(2-(4,4,5,5-tetramethyl-1,3,2-dioxaborolan-2-yl)vinyl)pyridin-2-yl)piperazine The title compound was synthesized according to the method of Example A51A, except substituting 1-(5-bromopyridin-2-yl)-4-methylpiperazine (55 mg, 0.216 mmol). After work-up obtained 58 mg of a crude material that was used for subsequent Suzuki coupling step; MS ESI [M+H]$^+$ 330.2, calcd for [C$_{18}$H$_{28}$BN$_3$O$_2$+H]$^+$ 330.24.

B. (1R,2S)-1'-methyl-2-(3-((E)-2-(6-(4-methylpiperazin-1-yl)pyridin-3-yl)vinyl)-1H-indazol-6-yl)spiro[cyclopropane-1,3'-indolin]-2'-one bis(2,2,2-trifluoroacetate)

The title compound was synthesized according to the method of Example A42B, except substituting (1R,2S)-2-(3-iodo-1H-indazol-6-yl)-1'-methylspiro[cyclopropane-1,3'-indolin]-2'-one (61 mg, 0.147 mmol) and (E)-1-methyl-4-(5-(2-(4,4,5,5-tetramethyl-1,3,2-dioxaborolan-2-yl)vinyl)pyridin-2-yl)piperazine (58 mg, 0.176 mmol). Purification by prep-HPLC resulted in a pale-yellow solid which was sonicated with Et$_2$O and filtered to give the title compound over two steps (21 mg, 14%); $^1$H NMR (400 MHz, CD$_3$OD) δ 8.35 (s, 1H), 8.05 (d, 1H, J=8.4 Hz), 7.98 (d, 1H, J=8.2 Hz), 7.44-7.33 (m, 3H), 7.14 (t, 1H, J=7.5 Hz), 7.06-6.99 (m, 3H), 6.63 (t, 1H, J=6.7 Hz), 6.02 (d, 1H, J=7.7 Hz), 4.60-4.30 (m, 4H), 3.60-3.08 (m, 4H), 3.47-3.33 (m, 4H), 2.97 (s, 3H), 2.28-2.25 (m, 1H), 2.21-2.18 (m, 1H); MS ESI [M+H]$^+$ 491.3, calcd for [C$_{30}$H$_{30}$N$_6$O+H]$^+$ 491.26.

Example A111. (1R,2S)-5'-methoxy-2-(3-((E)-2-(pyridin-4-yl)vinyl)-1H-indazol-6-yl)spiro[cyclopropane-1,3'-indolin]-2'-one 2,2,2-trifluoroacetate

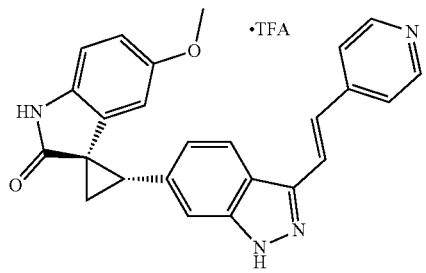 [SMILES: COc1ccc2c(c1)[C@]1(C[C@H]1c1ccc3c(/C=C/c4ccncc4)n[nH]c3c1)C(=O)N2]

A. (E)-4-(2-(4,4,5,5-tetramethyl-1,3,2-dioxaborolan-2-yl)vinyl)pyridine

The title compound was synthesized according to the method of Example A51A, except substituting 4-bromopyridine hydrochloride (500 mg, 2.57 mmol). After work-up obtained 130 mg of a crude material was used for subsequent Suzuki coupling step; MS ESI [M+H]$^+$ 231.1, calcd for [C$_{13}$H$_{18}$BNO$_2$+H]$^+$ 231.10.

B. (1R,2S)-5'-methoxy-2-(3-((E)-2-(pyridin-4-yl)vinyl)-1H-indazol-6-yl)spiro[cyclopropane-1,3'-indolin]-2'-one 2,2,2-trifluoroacetate The title compound was synthesized according to the method of Example A42B, except substituting (1R,2S)-2-(3-iodo-1H-indazol-6-yl)-5'-methoxyspiro[cyclopropane-1,3'-indolin]-2'-one (164 mg, 0.380 mmol) and (E)-4-(2-(4,4,5,5-tetramethyl-1,3,2-dioxaborolan-2-yl)vinyl)pyridine (130 mg, 0.450 mmol). Purified by column chromatography (silica gel, CH$_2$Cl$_2$/MeOH, 92:8 to 90:10) to give a solid which was titurated with Et$_2$O and filtered to give 59 mg, 30% of the free base. The TFA salt was prepared by dissolving free base into MeOH (6 mL) and H$_2$O (1 mL) and adding TFA (70 uL). The mixture was stirred for 10 minutes, the solvent was removed in vacuo and the residue was dried under high vacuum to give of title product (47 mg, 24%); $^1$H NMR (400 MHz, CD$_3$OD) δ 8.70 (d, 2H, J=5.2 Hz), 8.25 (d, 2H, J=4.3 Hz), 8.22-8.11 (m, 2H), 7.69 (d, 1H, J=16.0 Hz), 7.56 (s, 1H), 7.14 (d, 1H, J=8.8 Hz), 6.83 (d, 1H, J=9.0 Hz), 6.61 (d, 1H, J=8.1 Hz), 5.56 (s, 1H), 3.45-3.40 (m, 1H), 3.27 (s, 3H), 2.26-2.21 (m, 1H), 2.20-2.17 (m, 1H); MS ESI [M+H]$^+$ 409.2, calcd for [C$_{25}$H$_{20}$N$_4$O$_2$+H]$^+$ 409.17. Optical Rotation: [α]$^{22}_D$=−94° (c 0.51, MeOH).

Example A112. (1R,2S)-(E)-2-(3-(4-(((R)-3-fluoro-pyrrolidin-1-yl)methyl)styryl)-1H-indazol-6-yl)-5'-methoxyspiro[cyclopropane-1,3'-indolin]-2'-one 2,2,2-trifluoroacetate

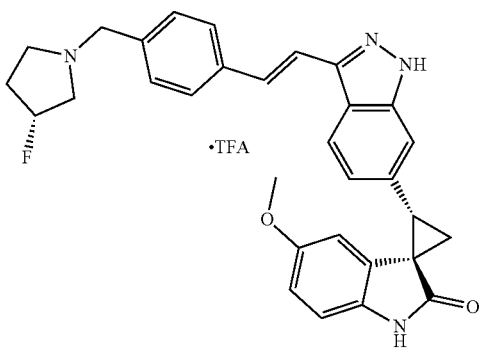 [SMILES: COc1ccc2c(c1)[C@]1(C[C@H]1c1ccc3c(/C=C/c4ccc(CN5CC[C@@H](F)C5)cc4)n[nH]c3c1)C(=O)N2]

The title compound was synthesized according to the method of Example A42B, except substituting (1R,2S)-2-(3-iodo-1H-indazol-6-yl)-5'-methoxyspiro[cyclopropane-1,3'-indolin]-2'-one (125 mg, 0.290 mmol) and (3R)-3-fluoro-1-(4-((E)-2-(4,4,6-trimethyl-1,3,2-dioxaborinan-2-yl)vinyl)benzyl)pyrrolidine (115 mg, 0.348 mmol). Purification by prep-HPLC gave 64 mg, 35% of the title compound as a beige solid; $^1$H NMR (400 MHz, CD$_3$OD) δ 8.01 (d, 1H, J=8.3 Hz), 7.75 (d, 2H, J=7.9 Hz), 7.55-7.48 (m, 5H), 7.04 (d, 1H, J=8.5 Hz), 6.82 (d, 1H, J=8.2 Hz), 6.60 (d, 1H, J=8.5 Hz), 5.58 (s, 1H), 5.46 (d, 1H, J=53.2 Hz), 4.46 (bs, 2H), 3.80-3.48 (m, 4H), 3.36 (t, 1H, J=8.8 Hz), 3.26 (s, 3H), 2.54-2.33 (m, 2H), 2.27-2.24 (m, 1H), 2.22-2.17 (m, 1H); MS ESI [M+H]$^+$ 509.3, calcd for [C$_{31}$H$_{29}$FN$_4$O$_2$+H]$^+$ 509.24. Optical Rotation: [α]$^{22}_D$=−91° (c 0.58, MeOH).

Example A113. (1R,2S)-2-(3-((E)-2-(2,3,4,5-tetra-hydrobenzo[f][1,4]oxazepin-7-yl)vinyl)-1H-indazol-6-yl)spiro[cyclopropane-1,3'-indolin]-2'-one 2,2,2-trifluoroacetate

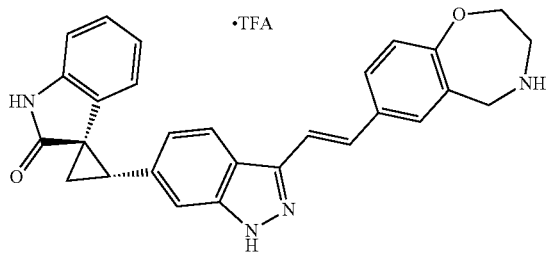 [SMILES: O=C1Nc2ccccc2[C@]12C[C@H]2c1ccc2c(/C=C/c3ccc4c(c3)CNCCO4)n[nH]c2c1]

The title compound was synthesized according to the method of Example A51B, by using (1R,2S)-2-(3-iodo-1H-indazol-6-yl)spiro[cyclopropane-1,3'-indolin]-2'-one (105 mg, 0.27 mmol) and (E)-tert-butyl 7-(2-(4,4,5,5-tetramethyl-1,3,2-dioxaborolan-2-yl)vinyl)-2,3-dihydrobenzo[f][1,4]oxazepine-4(5H)-carboxylate (130 mg, 0.32 mmol). The residue from the reaction was dissolved into CH$_2$Cl$_2$ (5 mL) and TFA (0.2 mL) was added and the mixture was stirred for 1 h and concentrated to dryness. Purification by preparative HPLC gave the title compound as a cream solid (40 mg, 30%). $^1$H NMR (400 MHz, CD$_3$OD) δ 7.97 (d, J=8.2 Hz, 1H), 7.68-7.64 (m, 2H), 7.50-7.39 (m, 3H), 7.16 (d, J=8.2 Hz, 1H), 7.07-7.01 (m, 2H), 6.94 (d, J=7.8 Hz, 1H), 6.57 (t, J=7.6 Hz, 1H), 5.98 (d, J=7.4 Hz, 1H), 4.45 (s, 2H), 4.39 (br. s, 2H), 3.68 (br. s, 2H), 3.39-3.33 (m, 1H) 2.25-2.16 (m, 2H); MS ESI 449.3 [M+H]$^+$, calcd for [C$_{28}$H$_{24}$N$_4$O$_2$+H]$^+$ 449.2.

Example A114. (1R,2S)-2-(3-((E)-1-(4-(morpholinomethyl)phenyl)prop-1-en-2-yl)-1H-indazol-6-yl)spiro[cyclopropane-1,3'-indolin]-2'-one 2,2,2-trifluoroacetate

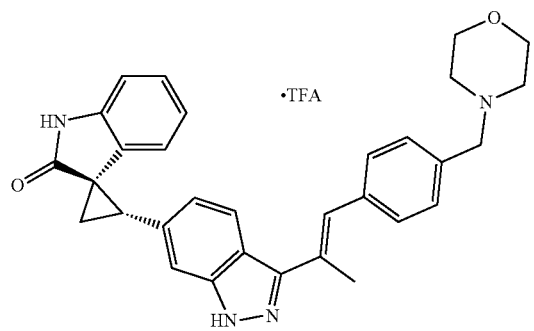 [SMILES: C/C(=C\c1ccc(CN2CCOCC2)cc1)c1n[nH]c2cc([C@@H]3C[C@@]34C(=O)Nc3ccccc34)ccc12]

A. (Z)-4-(4-(2-(4,4,5,5-tetramethyl-1,3,2-dioxaborolan-2-yl)prop-1-enyl)benzyl)morpholine An oven-dried round bottom flask was charged with 4-(4-ethynylbenzyl)morpholine (500 mg, 2.48 mmol) and THF (10 mL) and the solution cooled to −78° C. at which time n-BuLi (1.7 mL of a 1.6M solution in hexanes) was added. Stirred at −78° C. for 1 h and then MeI (0.46 mL, 7.44 mmol) was then added and the reaction was allowed to warm slowly to 0° C. over 2 h and then quenched with NH$_4$Cl$_{(sat.)}$ (5 mL). The product was extracted with Et$_2$O (250 mL) and the organic layers washed with brine (50 mL), and dried over MgSO$_4$. The solvent was removed to yield a clear oil which was 4:1 mixture of 4-(4-(prop-1-ynyl)benzyl)morpholine to 4-(4-ethynylbenzyl)morpholine. This crude mixture was hydroborated according to the method of A42A to yield the title compound after column chromatography (silica gel, hexanes/EtOAc, 3:1 to 1:1) as white solid (511 mg, 60%); MS ESI [M+H]$^+$ 344.2, calcd for [C$_{20}$H$_{30}$BNO$_3$+H]$^+$ 344.24.

B. (1R,2S)-5'-methoxy-2-(3-((E)-1-(4-(morpholinomethyl)phenyl)prop-1-en-2-yl)-1H-indazol-6-yl)spiro[cyclopropane-1,3'-indolin]-2'-one 2,2,2-trifluoroacetate The title compound was synthesized according to the method of Example A42B, except substituting (1R,2S)-2-(3-iodo-1H-indazol-6-yl)spiro[cyclopropane-1,3'-indolin]-2'-one (497 mg, 1.24 mmol) and (Z)-4-(4-(2-(4,4,5,5-tetramethyl-1,3,2-dioxaborolan-2-yl)prop-1-enyl)benzyl)morpholine (511 mg, 1.49 mmol). Purification by prep-HPLC gave the title compound as an off-white solid (176 mg, 23%); $^1$H NMR (400 MHz, CD$_3$OD) δ 7.85 (d, 1H, J=8.4 Hz), 7.54 (s, 4H), 7.43 (s, 1H), 7.25 (s, 1H), 7.01 (t, 1H, J=7.6 Hz), 6.95-6.90 (m, 2H), 6.53 (t, J=7.0 Hz), 5.96 (d, 1H, J=7.6 Hz), 4.37 (s, 2H), 4.09-3.99 (m, 2H), 3.80-3.73 (m, 2H), 3.45-3.30 (m, 3H), 3.27-3.17 (m, 2H), 2.41 (s, 3H), 2.20-2.14 (m, 2H); MS ESI [M+H]⁺ 491.3, calcd for [C$_{31}$H$_{30}$N$_4$O$_2$+H]⁺ 491.24. Optical Rotation: [α]$^{22}_D$=−129° (c 0.85, MeOH).

Example A115. (1R,2S)-(E)-1'-methyl-2-(3-(4-(pyrrolidin-1-ylmethyl)styryl)-1H-indazol-6-yl)spiro[cyclopropane-1,3'-indolin]-2'-one 2,2,2-trifluoroacetate

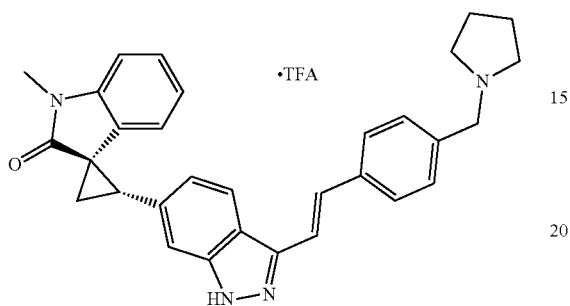

The title compound was synthesized according to the method of Example A42B, except substituting (1R,2S)-2-(3-iodo-1H-indazol-6-yl)-1'-methylspiro[cyclopropane-1,3'-indolin]-2'-one (147 mg, 0.353 mmol) and (E)-1-(4-(2-(4,4,5,5-tetramethyl-1,3,2-dioxaborolan-2-yl)vinyl)benzyl)pyrrolidine (133 mg, 0.424 mmol). Purification by prep-HPLC gave the title compound as an pale-yellow solid (46 mg, 22%); ¹H NMR (400 MHz, CD$_3$OD) δ 7.98 (d, 1H, J=8.7 Hz), 7.73 (d, 2H, J=7.4 Hz), 7.53-7.44 (m, 5H), 7.14 (t, 1H, J=7.2 Hz), 7.01 (d, 2H, J=7.9 Hz), 6.63 (t, 1H, J=7.4 Hz), 6.01 (d, 1H, J=7.6 Hz), 4.38 (s, 2H), 3.55-3.45 (m, 2H), 3.40-3.32 (m, 1H), 3.34 (s, 3H), 3.26-3.16 (m, 2H), 2.28-2.17 (m, 4H), 2.05-1.95 (m, 2H); MS ESI [M+H]⁺ 475.4, calcd for [C$_{31}$H$_{30}$N$_4$O+H]⁺ 475.25. Optical Rotation: [α]$^{22}_D$=−148° (c 0.40, MeOH).

Example A116. (1R,2S)-(E)-2-(3-(3,5-difluoro-4-(morpholinomethyl)styryl)-1H-indazol-6-yl)spiro[cyclopropane-1,3'-indolin]-2'-one 2,2,2-trifluoroacetate

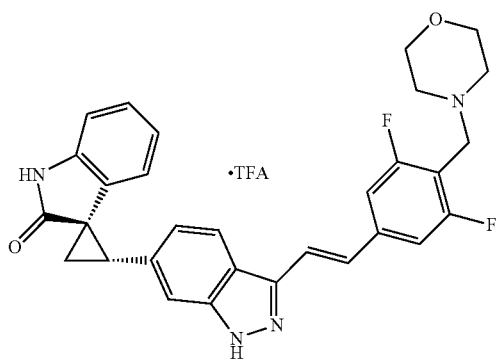 [SMILES: O=C1Nc2ccccc2[C@]12C[C@H]2c1ccc2c(/C=C/c3cc(F)c(CN4CCOCC4)c(F)c3)n[nH]c2c1]

The title compound was synthesized according to the method of Example A51B, by using (1R,2S)-2-(3-iodo-1H-indazol-6-yl)spiro[cyclopropane-1,3'-indolin]-2'-one (125 mg, 0.311 mmol) and (E)-4-(2,6-difluoro-4-(2-(4,4,5,5-tetramethyl-1,3,2-dioxaborolan-2-yl)vinyl)benzyl)morpholine (130.9 mg, 0.358 mmol). Purification by preparative HPLC gave the title compound as a cream solid (88 mg, 45%). ¹H NMR (400 MHz, CD$_3$OD) δ 7.94 (d, J=8.4 Hz, 1H), 7.56 (d, J=16.8 Hz, 1H), 7.46-7.42 (m, 4H), 7.04-6.99 (m, 2H), 6.92 (d, J=7.6 Hz, 1H), 6.53 (t, J=7.6 Hz, 1H), 5.95 (d, J=7.6 Hz, 1H), 4.48 (s, 2H), 4.08-3.84 (bm, 4H), 3.49-3.35 (bm, 5H), 2.26-2.23 (m, 1H), 2.21-2.17 (m, 1H); MS ESI 513.3 [M+H]⁺, calcd for [C$_{30}$H$_{26}$F$_2$N$_4$O$_2$+H]⁺ 513.21. Optical Rotation [α]$^{23}_D$=−121° (c 0.34, MeOH).

Example A117. (1R*,2S*)-2-(3-(6-(4-hydroxypiperidin-1-yl)pyridin-3-yl)-1H-indazol-6-yl)-5-methoxyspiro[cyclopropane-1,3'-indolin]-2'-one 2,2,2-trifluoroacetate

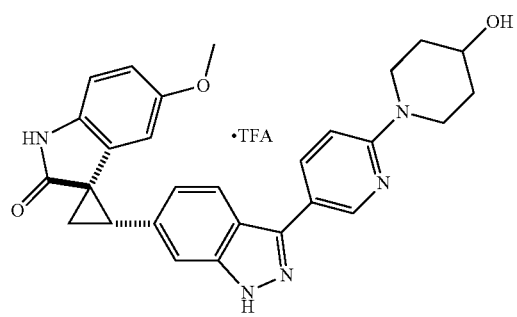

A. 1-(5-(6-((1R*,2S*)-5'-methoxy-2'-oxospiro[cyclopropane-1,3'-indoline]-2-yl)-1H-indazol-3-yl)pyridin-2-yl)piperidin-4-yl acetate The title compound was synthesized according to the method described for example A45 except reacting (1R*,2S*)-2-(3-iodo-1H-indazol-6-yl)-5'-methoxyspiro[cyclopropane-1,3'-indolin]-2'-one (20 mg, 0.046 mmol) with 1-(4-(4,4,5,5-tetramethyl-1,3,2-dioxaborolan-2-yl)phenyl)piperidin-4-yl acetate (18 mg, 0.051 mmol). Crude product was purified by flash chromatography using EtOAc/Hexanes (4:1 to 1:0) and MeOH/CH$_2$Cl$_2$ as eluent (10:90) to give the title compound as a white solid (39 mg, 33%). ¹H NMR (400 MHz, CDCl$_3$) δ 8.07 (dd, J=8.0, 4.0 Hz, 1H), 8.03 (s, 1H), 7.85 (d, J=8.0 Hz, 1H), 7.70 (d, J=8.0 Hz, 1H), 7.64 (d, J=8.0 Hz, 1H), 7.00 (d, J=12 Hz, 1H), 6.80 (d, J=8.0 Hz, 1H), 6.56 (dd, J=8.0, 4.0 Hz, 1H), 5.56 (s, 1H), 5.04-5.00 (m, 1H), 4.04-3.98 (m, 2H), 3.48-3.37 (m, 3H), 3.28 (s, 3H), 2.27-2.23 (m, 1H), 2.08 (s, 3H), 2.05-1.97 (m, 3H), 1.78-1.70 (m, 2H); MS ESI 524.4 [M+H]⁺, calcd for [C$_{30}$H$_{29}$N$_5$O$_4$+H]⁺ 524.22.

B. (1R*,2S*)-2-(3-(6-(4-hydroxypiperidin-1-yl)pyridin-3-yl)-1H-indazol-6-yl)-5'-methoxyspiro[cyclopropane-1,3'-indolin]-2'-one 2,2,2-trifluoroacetate A mixture of 1-(5-(6-((1R*,2S*)-5'-methoxy-2'-oxospiro[cyclopropane-1,3'-indoline]-2-yl)-1H-indazol-3-yl)pyridin-2-yl)piperidin-4-yl acetate (40 mg, 0.076 mmol) and aqueous NH$_4$OH (0.03 mL, 14 M) in MeOH (3 mL) was stirred at rt for 17 h. The crude reaction mixture was concentrated under reduced pressure to dryness, and the resulting crude product was purified by preparative HPLC to give the title compound as a yellow solid and as the TFA salt (23 mg, 62%). ¹H NMR (400 MHz, MeOD) δ 8.56 (dd, J=9.6, 2.0 Hz, 1H), 8.37 (d, J=1.6 Hz, 1H), 7.86 (d, J=8.5

Hz, 1H), 7.54 (s, 1H), 7.49 (d, J=9.6 Hz, 1H), 7.05 (d, J=8.5 Hz, 1H), 6.83 (d, J=8.4 Hz, 1H), 6.60 (dd, J=8.4, 2.4 Hz, 1H), 5.60 (d, J=2.3 Hz, 1H), 4.06-3.99 (m, 3H), 3.65-3.59 (m, 2H), 3.37-3.35 (m, 1H), 3.28 (s, 3H), 2.26-2.23 (m, 1H), 2.20-2.16 (m, 2H), 2.09-2.04 (m, 2H), 1.78-1.69 (m, 2H); MS ESI 482.3 [M+H]$^+$, calcd for [C$_{28}$H$_{27}$N$_5$O$_3$+H]$^+$ 482.21.

Example A118. (1R*,2S*)-2-(3-(4-(4-hydroxypiperidin-1-yl)phenyl)-1H-indazol-6-yl)-5'-methoxyspiro[cyclopropane-1,3'-indolin]-2'-one 2,2,2-trifluoroacetate

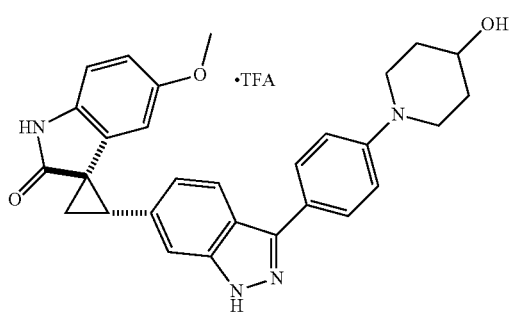

A. 1-(4-(6-((1R*,2S*)-5'-methoxy-2'-oxospiro[cyclopropane-1,3-indoline]-2-yl)-1H-indazol-3-yl)phenyl)piperidin-4-yl acetate The title compound was synthesized according to the method described for example A45 except reacting a (1R*, 2S*)-2-(3-iodo-1H-indazol-6-yl)-5'-methoxyspiro[cyclopropane-1,3'-indolin]-2'-one (76 mg, 0.18 mmol) with 1-(4-(4,4,5,5-tetramethyl-1,3,2-dioxaborolan-2-yl)phenyl)piperidin-4-yl acetate (67 mg, 0.19 mmol). Crude product was purified by flash chromatography using EtOAc/Hexanes (2:3 to 1:0) to give the title compound as a yellow solid (38 mg, 41%). MS ESI 523.3 [M+H]$^+$, calcd for [C$_{31}$H$_{30}$N$_4$O$_4$+H]$^+$ 523.23.

B. (1R*,2S*)-2-(3-(4-(4-hydroxypiperidin-1-yl)phenyl)-1H-indazol-6-yl)-5'-methoxy spiro[cyclopropane-1,3'-indolin]-2'-one 2,2,2-trifluoroacetate The title compound was synthesized according to the method described for Example A117, except substituting 1-(4-(6-((1R*,2S*)-5'-methoxy-2'-oxospiro[cyclopropane-1,3'-indoline]-2-yl)-1H-indazol-3-yl)phenyl)piperidin-4-yl acetate (38 mg, 0.073 mmol) and the reaction was stirred for 2 d. The crude reaction mixture was concentrated under reduced pressure to dryness, and the resulting crude product was purified by preparative HPLC to give the title compound as a yellow solid and as the TFA salt (23 mg, 62%). $^1$H NMR (400 MHz, MeOD) δ 8.11 (d, J=8.7 Hz, 2H), 7.95 (d, J=8.4 Hz, 1H), 7.65 (d, J=8.6 Hz, 2H), 7.54 (s, 1H), 7.06 (d, J=8.6 Hz, 1H), 6.83 (d, J=8.3 Hz, 1H), 6.62 (dd, J=8.2, 2.3 Hz, 1H), 5.60 (d, J=2.3 Hz, 1H), 4.09-4.05 (m, 1H), 3.89-3.85 (m, 2H), 3.56-3.52 (m, 2H), 3.40-3.35 (m, 1H), 3.27 (s, 3H), 2.28-2.18 (m, 4H), 2.20-1.99 (m, 2H); MS ESI 481.3 [M+H]$^+$, calcd for [C$_{29}$H$_{28}$N$_4$O$_3$+H]$^+$ 481.22.

Example A119. (1R*,2S*)-2-(3-(4-(4-(dimethylamino)piperidin-1-yl)phenyl)-1H-indazol-6-yl)-5'-methoxyspiro[cyclopropane-1,3'-indolin]-2'-one 2,2,2-trifluoroacetate

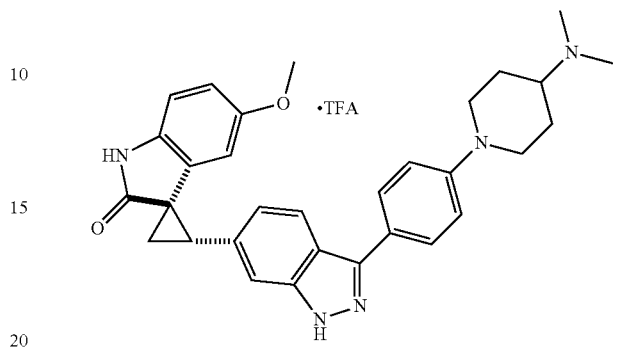

The title compound was synthesized according to the method of Example A43, except reacting (1R*,2S*)-2-(3-iodo-1H-indazol-6-yl)-5'-methoxyspiro[cyclopropane-1,3'-indolin]-2'-one (44 mg, 0.10 mmol) with N,N-dimethyl-1-(4-(4,4,5,5-tetramethyl-1,3,2-dioxaborolan-2-yl)phenyl)piperidin-4-amine (37 mg, 0.11 mmol). The crude reaction mixture was concentrated under reduced pressure to dryness, and purified by preparative HPLC to give the title compound as a yellow solid (6 mg, 12%). $^1$H NMR (400 MHz, MeOD) δ 7.91 (d, J=8.4 Hz, 1H), 7.84 (d, J=8.6 Hz, 2H), 7.49 (s, 1H), 7.16 (d, J=8.6 Hz, 2H), 7.02 (d, J=8.4 Hz, 1H), 6.83 (d, J=8.5 Hz, 1H), 6.61 (dd, J=8.4, 2.3 Hz, 1H), 5.61 (d, J=2.2 Hz, 1H), 4.03-4.00 (m, 2H), 3.44-3.37 (m, 2H), 3.27 (s, 3H), 2.93 (s, 6H), 2.93-2.88 (m, 2H), 2.27-2.19 (m, 4H), 1.93-1.83 (m, 2H); MS ESI 508.3 [M+H]$^+$, calcd for [C$_{31}$H$_{33}$N$_5$O$_2$+H]$^+$ 508.26.

Example A120. (1R,2S)-2-(3-(4-(4-(dimethylamino)piperidin-1-yl)phenyl)-1H-indazol-6-yl)-5'-methoxyspiro[cyclopropane-1,3'-indolin]-2'-one 2,2,2-trifluoroacetate

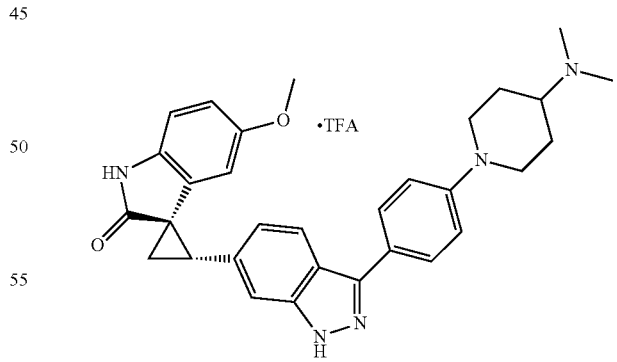

The title compound was synthesized according to the method of Example A43, except reacting (1R,2S)-2-(3-iodo-1H-indazol-6-yl)-5'-methoxyspiro[cyclopropane-1,3'-indolin]-2'-one (76 mg, 0.18 mmol) with 4-(4-isopropylpiperazin-1-yl)phenylboronic acid (48 mg, 0.19 mmol). The crude reaction mixture was concentrated under reduced pressure to dryness, and purified by preparative HPLC to give the title compound as a yellow solid (45 mg, 51%). $^1$H NMR (400 MHz, MeOD) δ 7.88 (d, J=8.7 Hz, 1H), 7.85 (d, J=8.8 Jz, 2H), 7.48 (s, 1H), 7.19 (d, J=8.6 Hz, 2H), 6.99 (d, J=8.5 Hz, 1H), 6.83 (d, J=8.5 Hz, 1H), 6.61 (dd, J=8.5, 2.4 Hz, 1H), 5.60 (d, J=2.2 Hz, 1H), 4.00-3.96 (m, 2H), 3.44-3.37 (m, 2H), 3.25 (s, 3H), 3.00-2.94 (m, 2H), 2.92 (s, 6H), 2.25-2.16 (m, 4H), 1.96-1.87 (m, 2H); MS ESI 508.3 [M+H]$^+$, calcd for [C$_{31}$H$_{33}$N$_5$O$_2$+H]$^+$ 508.26.

Example A121. (1R,2S)-5'-methoxy-2-(3-(4-(4-morpholinopiperidin-1-yl)phenyl)-1H-indazol-6-yl)spiro[cyclopropane-1,3'-indolin]-2'-one 2,2,2-trifluoroacetate

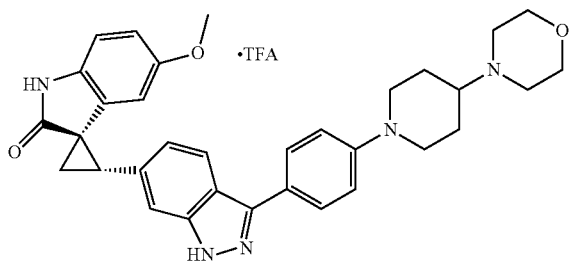 [SMILES: COc1ccc2c(c1)[C@]1(C[C@H]1c1ccc3c(-c4ccc(N5CCC(N6CCOCC6)CC5)cc4)n[nH]c3c1)C(=O)N2]

The title compound was synthesized according to the method of Example A51B, except reacting (1R,2S)-2-(3-iodo-1H-indazol-6-yl)-5'-methoxyspiro[cyclopropane-1,3'-indolin]-2'-one (118 mg, 0.27 mmol) with 4-(4-morpholinopiperidin-1-yl)phenylboronic acid (87 mg, 0.30 mmol). The crude reaction mixture was concentrated under reduced pressure to dryness, and purified by preparative HPLC to give the title compound as a yellow solid (59 mg, 33%). $^1$H NMR (400 MHz, MeOD) δ 7.84 (d, J=8.4 Hz, 3H), 7.47 (s, 1H), 7.18 (d, J=8.4 Hz, 2H), 6.97 (d, J=8.6 Hz, 1H), 6.82 (d, J=8.4 Hz, 1H), 6.59 (dd, J=8.5, 1.5 Hz, 1H), 5.60 (s, 1H), 4.16-4.03 (m, 2H), 4.00-3.92 (m, 2H), 3.82-3.72 (m, 2H), 3.58-3.48 (m, 2H), 3.46-3.33 (m, 2H), 3.25-3.13 (m 2H), 3.23 (s, 3H), 2.97 (t, J=12.0 Hz, 2H), 2.29-2.15 (m, 4H), 1.95-1.87 (m, 2H); MS ESI 550.3 [M+H]$^+$, calcd for [C$_{33}$H$_{35}$N$_5$O$_3$+H]$^+$ 550.27.

Optical Rotation: [α]$^{22}_D$=−111° (c 0.49, MeOH).

Example A122. (1R*,2S*)-5'-methoxy-2-(3-(4-(piperidin-4-yl)phenyl)-1H-indazol-6-yl)spiro[cyclopropane-1,3'-indolin]-2'-one 2,2,2-trifluoroacetate

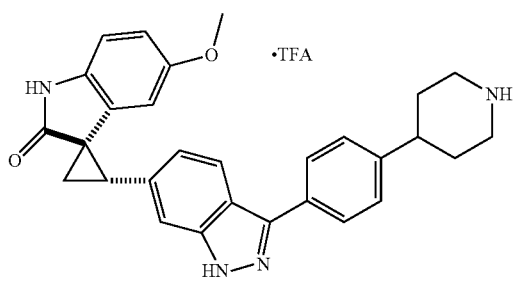

A. tert-butyl 4-(4-(6-((1R,2S)-5'-methoxy-2'-oxospiro[cyclopropane-1,3'-indoline]-2-yl)-1H-indazol-3-yl)phenyl)piperidine-1-carboxylate The title compound was synthesized according to the method of Example A43, except reacting a mixture of (1R*,2S*)-2-(3-iodo-1H-indazol-6-yl)-5'-methoxyspiro[cyclopropane-1,3'-indolin]-2'-one (192 mg, 0.446 mmol) with tert-butyl 4-(4-(4,4,5,5-tetramethyl-1,3,2-dioxaborolan-2-yl)phenyl)piperidine-1-carboxylate (190 mg, 0.49 mmol). The crude reaction mixture was concentrated under reduced pressure to dryness, and purified by flash chromatography using EtOAc/hexanes as eluent (1:4 to 7:3) to give the title compound as a yellow solid (239 mg, 80%). $^1$H NMR (400 MHz, MeOD) δ 7.93-7.90 (m, 3H), 7.36-7.34 (m, 3H), 7.02 (d, J=8.0 Jz, 1H), 6.80 (d, J=8.0 Hz, 1H), 6.58 (dd, J=8.0, 4.0 Hz, 1H), 5.55 (s, 1H), 4.39-4.20 (m, 2H), 3.35-3.46 (m, 1H), 3.29 (s, 3H), 2.89-2.79 (m, 2H), 2.76-2.67 (m, 1H), 2.08-2.02 (m 2H), 1.91-1.83 (m, 2H), 1.75-1.61 (m, 2H), 1.51 (s, 9H); MS ESI 565.3 [M+H]$^+$, calcd for [C$_{34}$H$_{36}$N$_4$O$_4$+H]$^+$ 565.27.

B. (1R*,2S*)-5'-methoxy-2-(3-(4-(piperidin-4-yl)phenyl)-1H-indazol-6-yl)spiro[cyclopropane-1,3'-indolin]-2'-one 2,2,2-trifluoroacetate To a solution of tert-butyl 4-(4-(6-((1R,2S)-5'-methoxy-2'-oxospiro[cyclopropane-1,3'-indoline]-2-yl)-1H-indazol-3-yl)phenyl)piperidine-1-carboxylate (102 mg, 0.181 mmol) in CH$_2$Cl$_2$ (5 mL) was added TFA (0.4 mL, 5.4 mmol). The resulting reaction mixture was stirred at rt for 2.5 h. The crude reaction mixture was concentrated under reduced pressure to dryness, and purified by preparative HPLC to give the title compound as a yellow solid (20 mg, 72%). $^1$H NMR (400 MHz, MeOD) δ 7.89 (d, J=8.2 Hz, 3H), 7.47 (s, 1H), 7.41 (d, J=8.2 Hz, 2H), 7.01 (d, J=8.6 Hz, 1H), 6.83 (d, J=8.4 Hz, 1H), 6.91 (dd, J=8.4, 2.4 Hz, 1H), 5.60 (d, J=2.3 Hz, 1H), 3.56-3.50 (m, 2H),), 3.39-3.32 (m, 1H), 3.25 (s, 3H), 3.17 (t, J=11.9 Hz, 2H), 3.02-2.92 (m, 1H), 2.25-2.22 (m, 1H), 2.19-2.01 (m, 3H), 2.02-1.91 (m, 2H); MS ESI 465.3 [M+H]$^+$, calcd for [C$_{29}$H$_{28}$N$_4$O$_2$+H]$^+$ 465.22.

Example A123. (1R,2S)-5'-methoxy-2-(3-(4-(1-methylpiperidin-4-yl)phenyl)-1H-indazol-6-yl)spiro[cyclopropane-1,3'-indolin]-2'-one hydrochloride

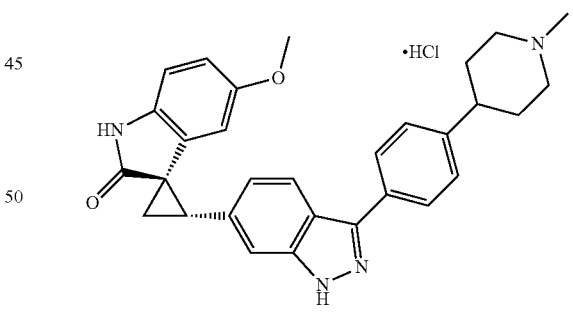

The title compound was synthesized according to the method of Example A51B, except reacting (1R,2S)-2-(3-iodo-1H-indazol-6-yl)-5'-methoxyspiro[cyclopropane-1,3'-indolin]-2'-one (195 mg, 0.45 mmol) with 1-methyl-4-(4-(4,4,5,5-tetramethyl-1,3,2-dioxaborolan-2-yl)phenyl)piperidine (150 mg, 0.50 mmol). The reaction was then allowed to cool to rt and was diluted with EtOAc and water was added. The resulting mixture was extracted with EtOAc and the combined organic extracts were washed with brine, dried over MgSO$_4$ and concentrated to give an orange solid.

The title compound was purified by silica gel chromatography (95:3:2 to 80:18:2 $CH_2Cl_2$/MeOH/$NH_3$) to yield a yellow solid. HCl (1M in diethyl ether, 0.15 mL, 0.15 mmol) was added in a dropwise manner to a solution of (1R,2S)-5'-methoxy-2-(3-(4-(1-methylpiperidin-4-yl)phenyl)-1H-indazol-6-yl)spiro[cyclopropane-1,3'-indolin]-2'-one in THF (2 mL). A brown precipitate formed and the solid was then filtered and freeze-dried to give the title compound as a white solid (43 mg, 17%). $^1$H NMR (400 MHz, $CD_3OD$) δ 7.95-7.92 (m, 3H), 7.52 (s, 1H), 7.44 (d, J=8.0 Hz, 2H), 7.05 (d, J=8.5 Hz, 1H), 6.83 (d, J=8.1 Hz, 1H), 6.62 (d, J=8.7 Hz, 1H), 5.61 (s, 1H), 3.67-3.64 (m, 2H),), 3.40-3.32 (m, 1H), 3.27 (s, 3H), 3.21 (t, J=12.8 Hz, 2H), 3.04-2.93 (m, 1H), 2.96 (s, 3H), 2.28-2.19 (m, 4H), 2.07-1.98 (m, 2H); MS ESI 479.4 $[M+H]^+$, calcd for $[C_{30}H_{30}N_4O_2+H]^+$ 479.24.

Optical Rotation: $[α]^{22}_D$=127° (c 0.37, MeOH).

Example A124. (1R,2S)-2-(3-(4-(4-fluoro-1-methylpiperidin-4-yl)phenyl)-1H-indazol-6-yl)-5'-methoxyspiro[cyclopropane-1,3'-indolin]-2'-one 2,2,2-trifluoroacetate

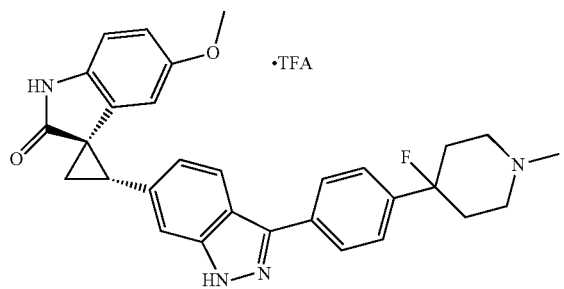 [SMILES: COc1ccc2c(c1)[C@]1(C[C@H]1c1ccc3c(-c4ccc(C5(F)CCN(C)CC5)cc4)n[nH]c3c1)C(=O)N2]

The title compound was synthesized according to the method of Example A51B, except reacting (1R,2S)-2-(3-iodo-1H-indazol-6-yl)-5'-methoxyspiro[cyclopropane-1,3'-indolin]-2'-one (180 mg, 0.45 mmol) with 1-methyl-4-(4-(4,4,5,5-tetramethyl-1,3,2-dioxaborolan-2-yl)phenyl)piperidine (150 mg, 0.50 mmol). The reaction was then allowed to cool to rt and was diluted with EtOAc and water was added. The resulting mixture was extracted with EtOAc and the combined organic extracts were washed with brine, dried over $MgSO_4$ and concentrated to give an orange solid. The title compound was purified by silica gel chromatography (95:5 to 75:25 $CH_2Cl_2$/MeOH) followed by preparative HPLC to yield a white solid. Water was added to the solid and was freeze-dried to give the title compound as a white solid (13 mg, 7%). $^1$H NMR (400 MHz, $CD_3OD$) δ 8.01 (d, J=8.0 Hz, 2H), 7.93 (d, J=8.4 Hz, 1H), 7.59 (d, J=8.1 Jz, 2H), 7.52 (s, 1H), 7.04 (d, J=8.3 Hz, 1H), 6.83 (d, J=8.4 Hz, 1H), 6.62 (d, J=8.2 Hz, 1H), 5.61 (s, 1H), 3.63-3.61 (m, 2H), 3.50-3.43 (m, 2H), 3.37 (t, J=8.5 Hz, 1H), 3.26 (s, 3H), 3.02 (s, 3H), 2.57-2.50 (m, 1H), 2.44-2.35 (m, 3H), 2.27-2.21 (m, 1H), 2.20-2.18 (m, 1H); $^{19}$F NMR (400 MHz, MeOD) δ -77.40, -160.82; MS ESI 497.3 $[M+H]^+$, calcd for $[C_{30}H_{29}FN_4O_2]^+$ 497.58.

Optical Rotation: $[α]^{22}_D$=-111° (c 0.37, MeOH).

Example A125. (1R,2S)-5'-methoxy-2-(3-(5-(morpholinomethyl)thiophen-3-yl)-1H-indazol-6-yl)spiro[cyclopropane-1,3'-indolin]-2'-one 2,2,2-trifluoroacetate

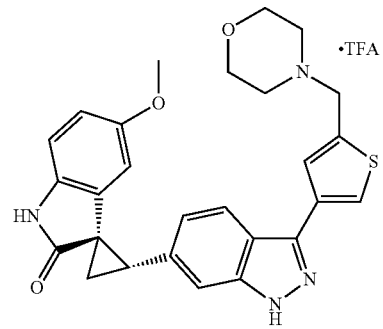 [SMILES: COc1ccc2c(c1)[C@]1(C[C@H]1c1ccc3c(-c4csc(CN5CCOCC5)c4)n[nH]c3c1)C(=O)N2]

The title compound was synthesized according to the method of Example A51B, except reacting (1R,2S)-2-(3-iodo-1H-indazol-6-yl)-5'-methoxyspiro[cyclopropane-1,3'-indolin]-2'-one (100 mg, 0.23 mmol) with 4-((4-(4,4,5,5-tetramethyl-1,3,2-dioxaborolan-2-yl)thiophen-2-yl)methyl)morpholine (79 mg, 0.26 mmol). The reaction was then allowed to cool to rt and was diluted with EtOAc and water was added. The resulting mixture was extracted with EtOAc and the combined organic extracts were dried over $MgSO_4$ and concentrated. The crude product was purified by preparative HPLC to give the title compound as a white solid (90 mg, 65%). $^1$H NMR (400 MHz, $CD_3OD$) δ 8.12 (s, 1H), 7.95 (m, 2H), 7.51 (s, 1H), 7.02 (d, J=8.5 Jz, 1H), 6.83 (d, J=8.5 Hz, 1H), 6.60 (d, J=8.6 Hz, 1H), 5.58 (s, 1H), 4.69 (s, 2H), 4.15-3.40 (m, 8H), 3.32-3.26 (m, 1H), 3.26 (s, 3H), 2.25-2.22 (m, 1H), 2.20-2.17 (m, 1H); MS ESI 487.3 $[M+H]^+$, calcd for $[C_{27}H_{26}N_4O_3S+H]^+$ 487.17.

Optical Rotation: $[α]^{22}_D$=-121° (c 0.36, MeOH).

Example A126. (1R,2S)-2-(3-(4-(cis-3,5-dimethylpiperazin-1-yl)phenyl)-1H-indazol-6-yl)-5'-methoxyspiro[cyclopropane-1,3'-indolin]-2'-one 2,2,2-trifluoroacetate

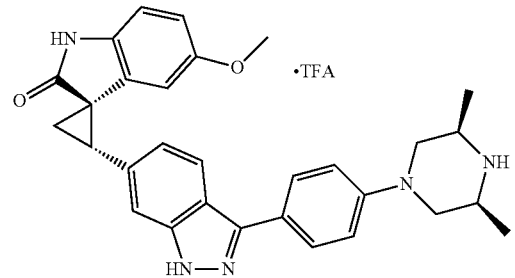 [SMILES: COc1ccc2c(c1)[C@]1(C[C@H]1c1ccc3c(-c4ccc(N5C[C@@H](C)N[C@@H](C)C5)cc4)n[nH]c3c1)C(=O)N2]

The title compound was synthesized according to the method of Example A42B, except reacting (1R,2S)-2-(3-iodo-1H-indazol-6-yl)-5'-methoxyspiro[cyclopropane-1,3'-indolin]-2'-one (91 mg, 0.21 mmol) with 4-(cis-3,5-dimethylpiperazin-1-yl)phenylboronic acid (59 mg, 0.25 mmol). The reaction was then allowed to cool to rt and was diluted with EtOAc and water was added. The resulting mixture was extracted with EtOAc and the combined organic extracts were dried over MgSO$_4$ and concentrated. The crude product was purified by preparative HPLC to give the title compound as a yellow solid (53 mg, 43%). $^1$H NMR (400 MHz, CD$_3$OD) δ 7.91 (d, J=8.6 Hz, 1H), 7.86 (d, J=8.5 Hz, 2H), 7.49 (s, 1H), 7.18 (d, J=8.7 Hz, 2H), 7.02 (d, J=8.5 Hz, 1H), 6.83 (d, J=8.4 Hz, 1H), 6.63 (d, J=8.4 Hz, 1H), 5.60 (s, 1H), 4.00-3.97 (m, 2H), 3.59-3.48 (m, 2H), 3.39-3.35 (m, 1H), 3.26 (s, 3H), 2.76 (t, J=12.2 Hz, 2H), 2.27-2.24 (m, 1H), 2.21-2.17 (m, 1H), 1.42 (d, J=6.5 Hz, 6H); MS ESI 494.4 [M+H]$^+$, calcd for [C$_{30}$H$_{31}$N$_5$O$_2$+H]$^+$ 494.60.

Optical Rotation: [α]$^{22}_D$=−116° (c 0.41, MeOH).

Example A127. (1R,2S)-2-(3-(4-((R)-3-(dimethylamino)pyrrolidin-1-yl)phenyl)-1H-indazol-6-yl)-5'-methoxyspiro[cyclopropane-1,3'-indolin]-2'-one 2,2,2-trifluoroacetate

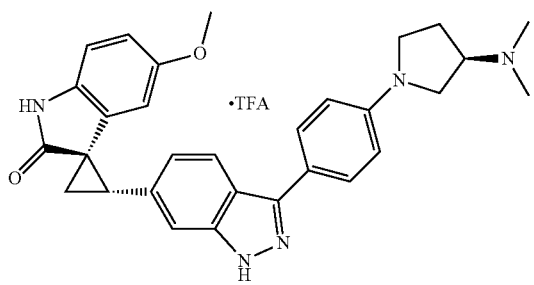 [SMILES: COc1ccc2c(c1)[C@]1(C[C@H]1c1ccc3c(-c4ccc(N5CC[C@@H](N(C)C)C5)cc4)n[nH]c3c1)C(=O)N2]

The title compound was synthesized according to the method of Example A51B, except reacting (1R,2S)-2-(3-iodo-1H-indazol-6-yl)-5'-methoxyspiro[cyclopropane-1,3'-indolin]-2'-one (108 mg, 0.25 mmol) with (R)—N,N-dimethyl-1-(4-(4,4,5,5-tetramethyl-1,3,2-dioxaborolan-2-yl)phenyl)pyrrolidin-3-amine (95 mg, 0.30 mmol). The reaction was then allowed to cool to room temperature and was diluted with EtOAc and water was added. The resulting mixture was extracted with EtOAc and the combined organic extracts were dried over MgSO$_4$ and concentrated. The crude product was purified by preparative HPLC twice to give the title compound as a yellow solid (31 mg, 25%). $^1$H NMR (400 MHz, CD$_3$OD) δ 7.89 (d, J=8.4 Hz, 1H), 7.81 (d, J=8.2 Hz, 2H), 7.47 (s, 1H), 7.00 (d, J=8.4 Jz, 1H), 6.83-6.81 (m, 3H), 6.61 (d, J=8.4 Hz, 1H), 5.61 (s, 1H), 4.09-4.04 (m, 1H), 3.80-3.75 (m, 1H), 3.71-3.61 (m, 2H), 3.45-3.36 (m, 2H), 3.26 (s, 3H), 3.00 (s, 6H), 2.66-2.55 (m, 1H), 2.36-2.29 (m, 1H), 2.26-2.23 (m, 1H), 2.20-2.17 (m, 1H); MS ESI 494.4 [M+H]$^+$, calcd for [C$_{30}$H$_{31}$N$_5$O$_2$+H]$^+$ 494.25.

Optical Rotation: [α]$^{22}_D$=−134° (c 0.38, MeOH).

Example A128. (1R,2S)-2-(3-(4-((S)-3-(dimethylamino)pyrrolidin-1-yl)phenyl)-1H-indazol-6-yl)-5'-methoxyspiro[cyclopropane-1,3'-indolin]-2'-one 2,2,2-trifluoroacetate

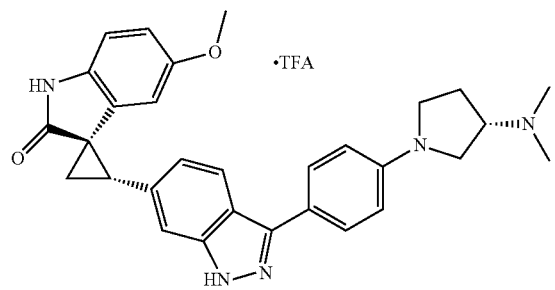 [SMILES: COc1ccc2c(c1)[C@]1(C[C@H]1c1ccc3c(-c4ccc(N5CC[C@H](N(C)C)C5)cc4)n[nH]c3c1)C(=O)N2]

The title compound was synthesized according to the method of Example A51B, except reacting (1R,2S)-2-(3-iodo-1H-indazol-6-yl)-5'-methoxyspiro[cyclopropane-1,3'-indolin]-2'-one (155 mg, 0.36 mmol) with (S)—N,N-dimethyl-1-(4-(4,4,5,5-tetramethyl-1,3,2-dioxaborolan-2-yl)phenyl)pyrrolidin-3-amine (125 mg, 0.40 mmol). The reaction was then allowed to cool to room temperature and was diluted with EtOAc and water was added. The resulting mixture was extracted with EtOAc and the combined organic extracts were dried over MgSO$_4$ and concentrated. The crude product was purified by silica gel chromatography (MeOH/CH$_2$Cl$_2$, 2:98 to 15:85) followed by preparative HPLC, and was freeze-dried to give the title compound as a yellow solid (53 mg, 25%). $^1$H NMR (400 MHz, CD$_3$OD) δ 7.85 (d, J=8.4 Hz, 1H), 7.78 (d, J=7.8 Hz, 2H), 7.46 (s, 1H), 6.96 (d, J=8.5 Hz, 1H), 6.84-6.78 (m, 3H), 6.59 (d, J=8.5 Hz, 1H), 5.60 (s, 1H), 4.06-4.01 (m, 1H), 3.76-3.72 (m, 1H), 3.67-3.59 (m, 2H), 3.42-3.32 (m, 2H), 3.24 (s, 3H), 2.98 (s, 6H), 2.63-2.52 (m, 1H), 2.35-2.28 (m, 1H), 2.26-2.21 (m, 1H), 2.18-2.15 (m, 1H); MS ESI 494.3 [M+H]$^+$, calcd for [C$_{30}$H$_{31}$N$_5$O$_2$+H]$^+$ 494.25.

Optical Rotation: [α]$^{22}_D$=−122° (c 0.37, MeOH).

Example A129. (1R,2S)-2-(3-(4-((2-(dimethylamino)ethyl)(methyl)amino)phenyl)-1H-indazol-6-yl)-5'-methoxyspiro[cyclopropane-1,3'-indolin]-2'-one 2,2,2-trifluoroacetate

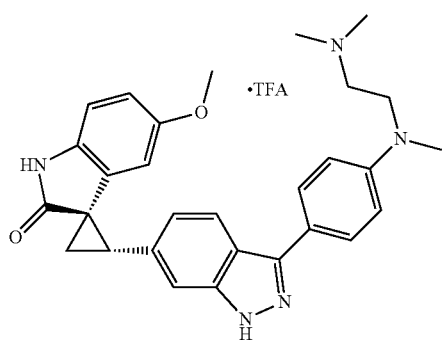 [SMILES: COc1ccc2c(c1)[C@]1(C[C@H]1c1ccc3c(-c4ccc(N(C)CCN(C)C)cc4)n[nH]c3c1)C(=O)N2]

The title compound was synthesized according to the method of Example A42B, except reacting (1R,2S)-2-(3-iodo-1H-indazol-6-yl)-5'-methoxyspiro[cyclopropane-1,3'-indolin]-2'-one (60 mg, 0.14 mmol) with N,N,N'-trimethyl- N'-(4-(4,4,5,5-tetramethyl-1,3,2-dioxaborolan-2-yl)phenyl)ethane-1,2-diamine (51 mg, 0.17 mmol). The reaction was then allowed to cool to rt and was diluted with EtOAc and water was added. The resulting mixture was extracted with EtOAc and the combined organic extracts were dried over MgSO$_4$ and concentrated. The crude product was purified by preparative HPLC and freezed-dried to give the title compound as a yellow solid (31 mg, 37%). $^1$H NMR (400 MHz, CD$_3$OD) δ 7.89 (d, J=8.5 Hz, 1H), 7.83 (d, J=7.9 Hz, 2H), 7.48 (s, 1H), 7.03-6.99 (m, 3H), 6.83 (d, J=8.7 Hz, 1H), 6.61 (d, J=8.6 Hz, 1H), 5.60 (s, 1H), 3.78 (t, J=6.8 Hz, 2H), 3.42-3.39 (m, 3H), 3.23 (s, 3H), 3.06 (s, 3H), 2.98 (s, 6H), 2.26-2.23 (m, 1H), 2.20-2.17 (m, 1H); MS ESI 482.4 [M+H]$^+$, calcd for [C$_{29}$H$_{31}$N$_5$O$_2$+H]$^+$ 482.25.

Optical Rotation: [α]$^{22}_D$=108° (c 0.46, MeOH).

Example A130. 3-(6-((1R*,2S*)-2'-oxospiro[cyclopropane-1,3'-indoline]-2-yl)-1H-indazol-3-yl)benzenesulfonamide

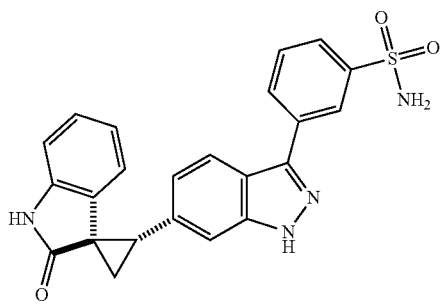

To a mixture of (1R*,2S*)-2-(3-iodo-1H-indazol-6-yl)spiro[cyclopropane-1,3'-indolin]-2'-one (80.2 mg, 0.2 mmol) and 3-(4,4,5,5-tetramethyl-1,3,2-dioxaborolan-2-yl)benzenesulfonamide (68.2 mg, 0.24 mmol) in DME (4 mL) was added 1 M Na$_2$CO$_3$ (0.24 mL, 0.24 mmol), followed by Pd(PPh$_3$)$_2$Cl$_2$ (14 mg, 0.02 mmol). The resulting mixture was purged with argon and microwaved 2 h at 120° C. It was diluted with H$_2$O, extracted with EtOAc and dried (Na$_2$SO$_4$). Removal of solvents provided an oil which was triturated with EtOAc/hex then MeOH/CH$_2$Cl$_2$/hex to give the title compound as a white solid (7 mg, 8%). $^1$H NMR (400 MHz, DMSO-d$_6$) δ 13.41 (s, 1H), 10.63 (s, 1H), 8.41 (s, 1H), 8.19 (d, J=6.8 Hz, 1H), 8.00 (d, J=8.4 Hz, 1H), 7.20 (d, J=8.0 Hz, 1H), 7.69 (t, J=7.6 Hz, 1H), 7.54 (s, 1H), 7.47 (s, 2H, NH$_2$), 7.08 (d, J=8.4 Hz, 1H), 7.00 (t, J=7.2 Hz, 1H), 6.85 (d, J=6.8 Hz, 1H), 6.54 (t, J=7.4 Hz, 1H), 6.05 (d, J=6.4 Hz, 1H), 3.22 (t, J=7.6 Hz, 1H), 2.38-2.30 (m, 1H), 2.05-1.98 (m, 1H); MS ESI 431.1 [M+H]$^+$, calcd for [C$_{23}$H$_{18}$N$_4$O$_3$S+H]$^+$ 431.1.

Example A131. (1R,2S)-(E)-2-(3-(4-((dimethylamino)methyl)styryl)-1H-indazol-6-yl)-1'-(2-methoxyethyl)spiro[cyclopropane-1,3'-indolin]-2'-one 2,2,2-trifluoroacetate

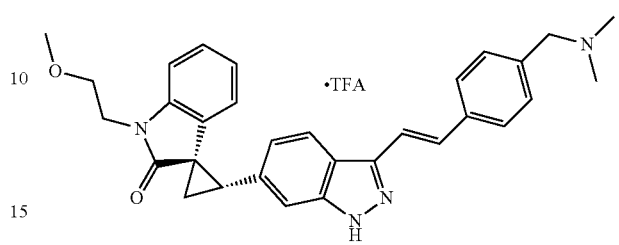

The title compound was synthesized according to the method of Example A51B, by using (1R,2S)-2-(3-iodo-1H-indazol-6-yl)-1'-(2-methoxyethyl)spiro[cyclopropane-1,3'-indolin]-2'-one (490 mg, 1.07 mmol) and (E)-N,N-dimethyl-1-(4-(2-(4,4,5,5-tetramethyl-1,3,2-dioxaborolan-2-yl)vinyl)benzyl)methanamine (321.7 mg, 1.12 mmol). Purification by preparative HPLC gave the title compound as a off-white solid (297 mg, 46%). $^1$H NMR (400 MHz, CD$_3$OD) δ 7.90 (d, J=8.0 Hz, 1H), 7.68 (d, J=7.6 Hz, 2H), 7.50-7.42 (m, 5H), 7.08-7.03 (m, 2H), 6.93 (d, J=8.4 Hz, 1H), 6.55 (t, J=7.6 Hz, 1H), 5.96 (d, J=7.6 Hz, 1H), 4.30 (s, 2H), 4.01 (t, J=4.8 Hz, 2H), 3.67 (t, J=5.2 Hz, 2H), 3.35-3.31 (m, 4H), 2.86 (s, 6H), 2.21-2.20 (m, 1H), 2.17-2.14 (m, 1H); MS ESI 493.4 [M+H]$^+$, calcd for [C$_{31}$H$_{32}$N$_4$O$_2$+H]$^+$ 493.26.

[α]$^{23}_D$=−169° (c 0.36, MeOH).

Example A132. (1R,2S)-5'-methoxy-2-(3-(3-(morpholinomethyl)styryl)-1H-indazol-6-yl)spiro[cyclopropane-1,3'-indolin]-2'-one 2,2,2-trifluoroacetate

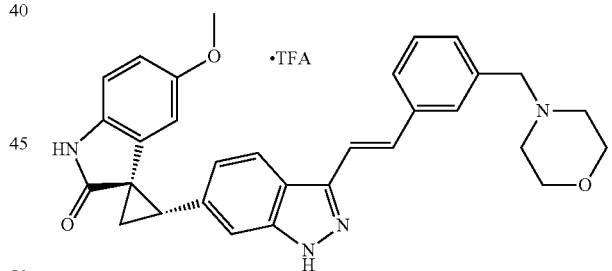

The title compound (163 mg, 67%, TFA salt) was obtained as a white solid from (1R,2S)-2-(3-iodo-1H-indazol-6-yl)-5'-methoxyspiro[cyclopropane-1,3'-indolin]-2'-one (172 mg, 0.4 mmol) and (E)-4-(3-(2-(4,4,5,5-tetramethyl-1,3,2-dioxaborolan-2-yl)vinyl)benzyl)morpholine (184 mg, 0.56 mmol) using the method for the preparation of Example A51B (PhCH$_3$/EtOH=8 mL/4 mL, 5 mol % Pd(PPh$_3$)$_4$, 125° C., 2 h). $^1$H NMR (400 MHz, CD$_3$OD) δ 7.89 (d, J=8.4 Hz, 1H), 7.72 (s, 1H), 7.67 (d, J=7.6 Hz, 1H), 7.50-7.37 (m, 5H), 6.93 (d, J=8.4 Hz, 1H), 6.80 (d, J=8.4 Hz, 1H), 6.56 (dd, J=8.4 Hz, J=2.4 Hz, 1H), 5.56 (d, J=2.0 Hz, 1H), 4.37 (s, 2H), 4.10-4.08 (m, 2H), 3.82-3.71 (m, 2H), 3.45-3.35 (m, 2H), 3.32 (t, J=8.2 Hz, 1H), 3.25-3.15 (m, 5H; s, 3H at 3.20 ppm and m, 2H overlapping), 2.20-2.10 (m, 2H); MS ESI 507.3 [M+H]$^+$, calcd for [C$_{31}$H$_{30}$N$_4$O$_3$+H]$^+$ 507.2.

Optical Rotation [α]$^{22}_D$=−89° (c 0.34, MeOH).

Example A133. (1R*,2S*)-5'-methoxy-2-(3-(3-(morpholinomethyl)styryl)-1H-indazol-6-yl)spiro[cyclopropane-1,3'-indolin]-2'-one 2,2,2-trifluoroacetate

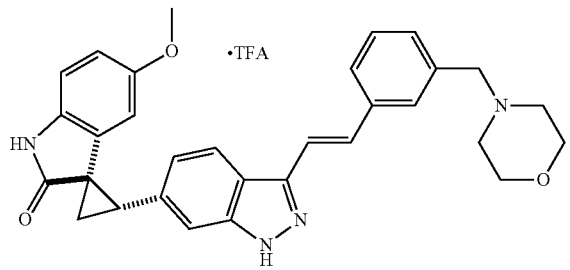

To a mixture of (1R*,2S*)-5'-methoxy-2-(3-vinyl-1H-indazol-6-yl)spiro[cyclopropane-1,3'-indolin]-2'-one (66 mg, 0.2 mmol), 4-(3-bromobenzyl)morpholine (56 mg, 0.22 mmol), Pd(OAc)$_2$ (2.2 mg, 0.01 mmol) and P(o-tol)$_3$ (6.7 mg, 0.022 mmol) in DMF (2 mL) was added $^i$Pr$_2$NEt (0.07 mL, 0.4 mmol). The resulting mixture was purged with argon, then microwaved 30 min at 150° C. The crude mixture was passed through a microfilter then purified by prep-HPLC to give the title compound (50 mg, 40%) as a light yellow foam. NMR indicated 13% branched isomer. Spectral data was identical to that in obtained in Example A132.

Example A134. (1R,2S)-2-(3-(3-((dimethylamino)methyl)styryl)-1H-indazol-6-yl)-5'-methoxyspiro[cyclopropane-1,3'-indolin]-2'-one 2,2,2-trifluoroacetate

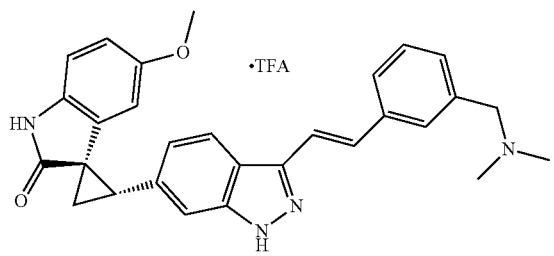 [SMILES: COc1ccc2c(c1)[C@]1(C[C@H]1c1ccc3c(/C=C/c4cccc(CN(C)C)c4)n[nH]c3c1)C(=O)N2]

The title compound (89 mg, 38%, TFA salt) was obtained as a pale yellow solid from (1R,2S)-2-(3-iodo-1H-indazol-6-yl)-5'-methoxyspiro[cyclopropane-1,3'-indolin]-2'-one (172 mg, 0.4 mmol) and (E)-N,N-dimethyl-1-(3-(2-(4,4,5,5-tetramethyl-1,3,2-dioxaborolan-2-yl)vinyl)phenyl)methanamine (161 mg, 0.56 mmol) using the method for the preparation of Example A51B (PhCH$_3$/EtOH=8 mL/4 mL, 5 mol % Pd(PPh$_3$)$_4$, 125° C., 2 h). $^1$H NMR (400 MHz, CD$_3$OD) δ 7.93 (d, J=8.4 Hz, 1H), 7.73 (s, 1H, partially overlapping with the peak at 7.70 ppm), 7.70 (d, J=8.0 Hz, 1H, partially overlapping with the peak at 7.73 ppm), 7.52-7.45 (m, 4H), 7.40 (d, J=7.6 Hz, 1H), 7.96 (d, J=8.4 Hz, 1H), 6.82 (d, J=8.4 Hz, 1H), 6.58 (dd, J=8.4 Hz, J=2.4 Hz, 1H), 5.57 (d, J=2.4 Hz, 1H), 4.34 (s, 2H), 3.33 (t, J=8.8 Hz, partially overlapping with MeOH residue, 1H), 3.23 (s, 3H), 2.89 (s, 6H), 2.22-2.12 (m, 2H); MS ESI 465.3 [M+H]$^+$, calcd for [C$_{29}$H$_{28}$N$_4$O$_2$+H]$^+$ 465.2.

Optical Rotation [α]$^{22}_D$=−82° (c 0.38, MeOH).

Example A135. (1R*,2S*)-2-(3-(3-((dimethylamino)methyl)styryl)-1H-indazol-6-yl)-5'-methoxyspiro[cyclopropane-1,3'-indolin]-2'-one 2,2,2-trifluoroacetate

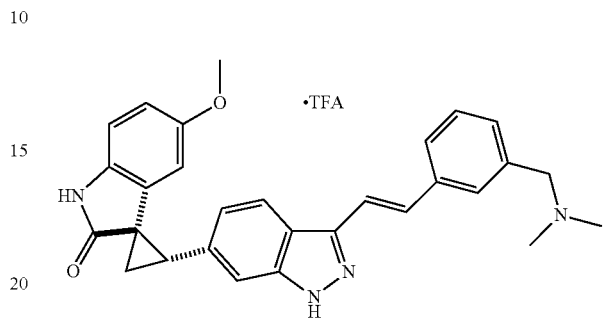

To a mixture of crude (1R*,2S*)-5'-methoxy-2-(3-vinyl-1H-indazol-6-yl)spiro[cyclopropane-1,3'-indolin]-2'-one (100 mg, 0.2 mmol), 1-(3-bromophenyl)-N,N-dimethylmethanamine (43 mg, 0.2 mmol), Pd(OAc)$_2$ (2.2 mg, 0.01 mmol) and P(o-tol)$_3$ (6.7 mg, 0.022 mmol) in DMF (2 mL) was added $^i$Pr$_2$NEt (0.07 mL, 0.4 mmol). The resulting mixture was purged with argon, then microwaved 30 min at 125° C. It was passed through a microfilter then purified by prep-HPLC to give the title compound as a light yellow solid. NMR indicated 7% branched isomer (43 mg, 37%). Spectral data was identical to that in obtained in Example A134.

Example A136. (1R*,2S*)-5'-methoxy-2-(3-(3-(morpholinomethyl)phenyl)-1H-indazol-6-yl)spiro[cyclopropane-1,3'-indolin]-2'-one 2,2,2-trifluoroacetate

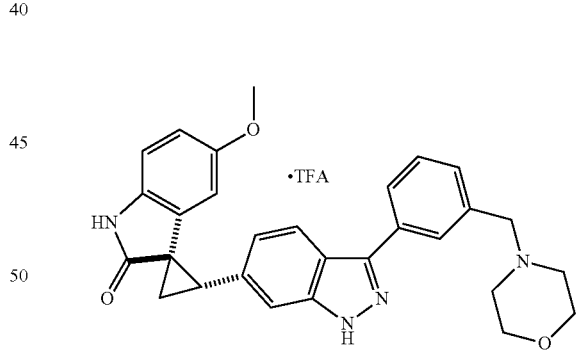

The title compound (61 mg, 51%, TFA salt) was obtained as a white solid from (1R*,2S*)-2-(3-iodo-1H-indazol-6-yl)-5'-methoxyspiro[cyclopropane-1,3'-indolin]-2'-one (86.2 mg, 0.2 mmol) and 4-(3-(4,4,5,5-tetramethyl-1,3,2-dioxaborolan-2-yl)benzyl) morpholine (91 mg, 0.3 mmol) using the method for the preparation of Example A51B (PhCH$_3$/EtOH=3 mL/1.5 mL, 2.5 mol % Pd(PPh$_3$)$_4$, 120° C., 2 h). $^1$H NMR (400 MHz, CD$_3$OD) δ 8.12 (s, 1H), 8.08 (d, J=8.0 Hz, 1H), 7.97 (d, J=8.4 Hz, 1H), 7.64 (t, J=7.6 Hz, 1H), 7.56 (d, J=7.6 Hz, 1H), 7.52 (s, 1H), 7.02 (d, J=8.4 Hz, 1H), 6.83 (d, J=8.4 Hz, 1H), 6.60 (dd, J=8.4 Hz, J=2.4 Hz, 1H), 5.59 (d, J=2.4 Hz, 1H), 4.71 (s, 2H), 4.10-4.00 (m, 2H), 3.80-3.70 (m, 2H), 3.48-3.40 (m, 2H), 3.35 (t, J=8.3 Hz, 1H, partially overlapping with MeOH residue), 3.30-3.20 (m, 5H; s, 3H at 3.26 ppm and m, 2H overlapping), 2.23 (dd, J=8.0 Hz, J=4.8 Hz, 1H), 2.17 (dd, J=9.2 Hz, 4.8 Hz, 1H); MS ESI 481.3 [M+H]$^+$, calcd for [C$_{29}$H$_{28}$N$_4$O$_3$+H]$^+$ 481.2.

Example A137. 4-((6-((1R*,2S*)-5'-methoxy-2'-oxospiro[cyclopropane-1,3'-indoline]-2-yl)-1H-indazol-3-yl)ethynyl)benzaldehyde

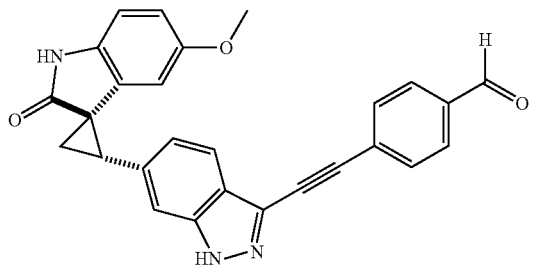

To a mixture of (1R*,2S*)-2-(3-iodo-1H-indazol-6-yl)-5'-methoxyspiro [cyclopropane-1,3'-indolin]-2'-one (862 mg, 2 mmol), 4-ethynylbenzaldehyde (286 mg, 2.2 mmol), Pd(PPh$_3$)$_2$Cl$_2$ (28 mg, 0.04 mmol, 2 mmol %) and CuI (15.3 mg, 0.08 mmol, 4 mmol %) in a 50 mL of flask was added DMF (6 mL) and Et$_3$N (10 mL). The resulting mixture was stirred at 100° C. (oil temp.) for 90 min. After removal of Et$_3$N, H$_2$O (20 mL) was added and the precipitates were collected by suction filtration. Crystals formed in the mother liquor were collected and dried to give the title compound (106 mg) as a yellow solid. The remaining residue was combined and purified by flash chromatography (gradient: EtOAc.hex 0 to 50% to 100%), followed by trituration with H$_2$O to give the title compound (440 mg) as a yellow solid. Total 546 mg (yield 63%). $^1$H NMR (400 MHz, DMSO-d$_6$) δ 13.63 (s, 1H), 10.44 (s, 1H), 10.05 (s, 1H), 7.98 (d, J=7.6 Hz, 2H), 7.87 (d, J=8.0 Hz, 2H), 7.79 (d, J=8.4 Hz, 1H), 7.57 (s, 1H), 7.10 (d, J=8.8 Hz, 1H), 6.75 (d, J=8.4 Hz, 1H), 6.58 (d, J=8.0 Hz, 1H), 5.63 (s, 1H), 3.29 (s, 3H), 3.22 (t, J=8.4 Hz, 1H), 2.40-2.33 (m, 1H), 1.99 (dd, J=8.8 Hz, 4.8 Hz, 1H); MS ESI 434.2 [M+H]$^+$, calcd for [C$_{27}$H$_{19}$N$_3$O$_3$+H]$^+$ 434.1.

Example A138. (1R*,2S*)-5'-methoxy-2-(3-((4-(morpholinomethyl)phenyl)ethynyl)-1H-indazol-6-yl)spiro[cyclopropane-1,3'-indolin]-2'-one 2,2,2-trifluoroacetate

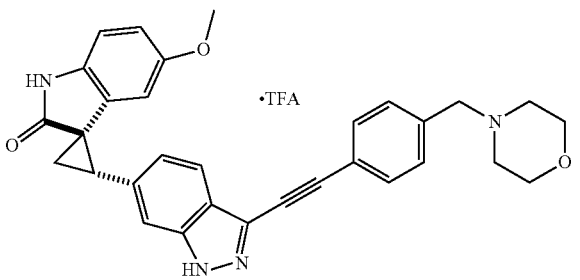

To a solution of Example A137 (43.3 mg, 0.1 mmol) in THF (5 mL) was added morpholine (0.05 mL, 0.5 mmol), followed by NaBH(OAc)$_3$ (33.5 mg, 0.15 mmol) and 2 drops of HOAc. The resulting mixture was stirred for 2 h at rt. LC-MS showed incompletion. Additional morpholine (0.05 mL) and NaBH(OAc)$_3$ (22.3 mg, 0.1 mmol) were added and the resulting mixture was stirred O/N at rt. Aqueous workup, followed by prep-HPLC purification gave the title compound as a white solid (23 mg, 37%). $^1$H NMR (400 MHz, CD$_3$OD) δ 7.75 (d, J=7.6 Hz, 3H), 7.59 (d, J=8.0 Hz, 2H), 7.53 (s, 1H), 7.08 (d, J=8.4 Hz, 1H), 6.84 (d, J=8.4 Hz, 1H), 6.62 (dd, J=8.6 Hz, J=2.6 Hz, 1H), 5.56 (d, J=2.4 Hz, 1H), 4.42 (s, 2H), 4.11-4.03 (m, 2H), 3.80-3.70 (m, 2H), 3.40-3.20 (m, 8H), 2.25 (dd, J=7.8 Hz, J=5.0 Hz, 1H), 2.18 (dd, J=8.8 Hz, J=4.8 Hz, 1H); MS ESI 505.3 [M+H]$^+$, calcd for [C$_{31}$H$_{28}$N$_4$O$_3$+H]$^+$ 505.2.

Example A139. (1R*,2S*)-5'-methoxy-2-(3-(4-(morpholinomethyl)phenyl)-1H-indazol-6-yl)spiro[cyclopropane-1,3'-indolin]-2'-one 2,2,2-trifluoroacetate

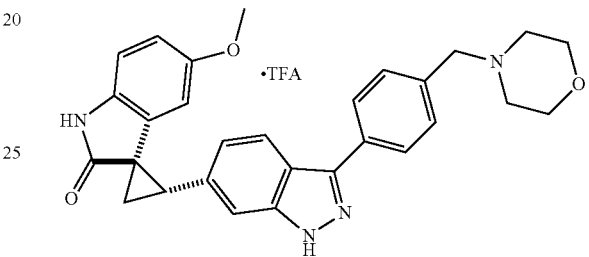

The title compound (46 mg, 39%, TFA salt) was obtained as a white solid from (1R*,2S*)-2-(3-iodo-1H-indazol-6-yl)-5'-methoxyspiro[cyclopropane-1,3'-indolin]-2'-one (86.2 mg, 0.2 mmol) and 4-(4-(4,4,5,5-tetramethyl-1,3,2-dioxaborolan-2-yl)benzyl)morpholine (60.6 mg, 0.2 mmol) using the method for the preparation of Example A51B (PhCH$_3$/EtOH=3 mL/1.5 mL, 2.5 mol % Pd(PPh$_3$)$_4$, 120° C., 2 h). $^1$H NMR (400 MHz, CD$_3$OD) δ 8.06 (d, J=8.4 Hz, 2H), 7.91 (d, J=8.4 Hz, 1H), 7.65 (d, J=8.0 Hz, 2H), 7.52 (s, 1H), 7.02 (d, J=8.4 Hz, 1H), 7.83 (d, J=8.4 Hz, 1H), 6.59 (dd, J=8.6 Hz, 2.6 Hz, 1H), 5.59 (d, J=2.4 Hz, 1H), 4.43 (s, 2H), 4.06 (d, J=13.2 Hz, 2H), 3.76 (t, J=11.8 Hz, 2H), 3.44 (d, J=12.0 Hz, 2H), 3.35 (t, J=8.4 Hz, 1H, partially overlapping with MeOH residue), 3.30-3.19 (m, 5H; s, 3H at 3.24 ppm and m, 2H overlapping), 2.23 (dd, J=7.8 Hz, 5.0 Hz, 1H), 2.17 (dd, J=9.2 Hz, 4.8 Hz, 1H); MS ESI 481.3 [M+H]$^+$, calcd for [C$_{29}$H$_{28}$N$_4$O$_3$+H]$^+$ 481.2.

Example A140. (1R*,2S*)-5'-methoxy-2-(3-(4-((4-methylpiperazin-1-yl)methyl)phenyl)-1H-indazol-6-yl)spiro[cyclopropane-1,3'-indolin]-2'-one bis-2,2,2-trifluoroacetate

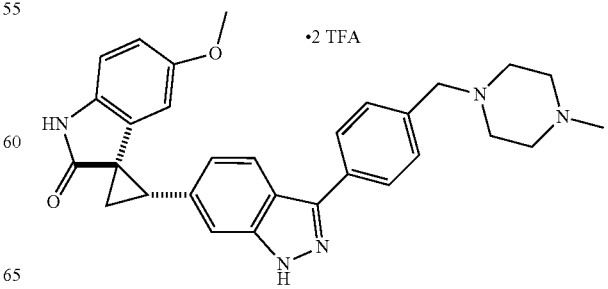

The title compound (35 mg, 24%, di-TFA salt) was obtained as a white semi-solid from (1R*,2S*)-2-(3-iodo-1H-indazol-6-yl)-5'-methoxyspiro[cyclopropane-1,3'-indolin]-2'-one (86.2 mg, 0.2 mmol) and 1-methyl-4-(4-(4,4,5,5-tetramethyl-1,3,2-dioxaborolan-2-yl)benzyl)piperazine (63.2 mg, 0.2 mmol) using the method for the preparation of Example A51B (PhCH$_3$/EtOH=3 mL/1.5 mL, 2.5 mol % Pd(PPh$_3$)$_4$, 120° C., 2 h). $^1$H NMR (400 MHz, CD$_3$OD) δ 8.00 (d, J=8.0 Hz, 2H), 7.91 (d, J=8.4 Hz, 1H), 7.60 (d, J=8.0 Hz, 2H), 7.51 (s, 1H), 7.02 (d, J=8.4 Hz, 1H), 6.83 (d, J=8.4 Hz, 1H), 6.60 (dd, J=8.4 Hz, 2.4 Hz, 1H), 5.59 (d, J=2.4 Hz, 1H), 4.17 (s, 2H), 3.54-3.44 (m, 4H), 3.36 (t, J=8.4 Hz, 1H), 3.33-3.26 (m, 4H), 3.25 (s, 3H), 2.94 (s, 3H), 2.24 (dd, J=8.0 Hz, 4.8 Hz, 1H), 2.18 (dd, J=8.8 Hz, 4.8 Hz, 1H); MS ESI 494.3 [M+H]$^+$, calcd for [C$_{30}$H$_{31}$N$_5$O$_2$+H]$^+$ 494.2.

Example A141. (1R*,2S*)-5'-ethyl-2-(3-(3-(morpholinomethyl)phenyl)-1H-indazol-6-yl)spiro[cyclopropane-1,3'-indolin]-2'-one 2,2,2-trifluoroacetate

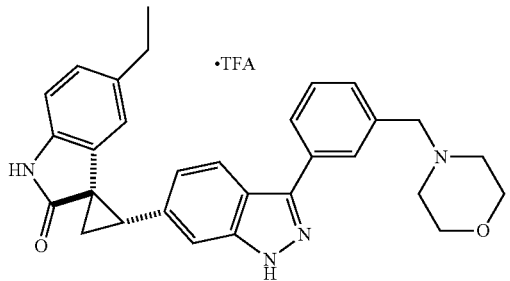

The title compound (42 mg, 35%, TFA salt) was obtained as a white solid from (1R*,2S*)-5'-ethyl-2-(3-iodo-1H-indazol-6-yl)spiro[cyclopropane-1,3'-indolin]-2'-one (85.8 mg, 0.2 mmol) and 4-(3-(4,4,5,5-tetramethyl-1,3,2-dioxaborolan-2-yl)benzyl) morpholine (66.7 mg, 0.22 mmol) using the method for the preparation of Example A51B (PhCH$_3$/EtOH=2 mL/1 mL, 2.5 mol % Pd(PPh$_3$)$_4$, 120° C., 2 h). $^1$H NMR (400 MHz, CD$_3$OD) δ 8.11 (s, 1H), 8.07 (d, J=8.0 Hz, 1H), 7.96 (d, J=8.4 Hz, 1H), 7.64 (t, J=7.8 Hz, 1H), 7.56 (d, J=7.6 Hz, 1H), 7.47 (s, 1H), 7.01 (d, J=8.8 Hz, 1H), 6.84 (d, J=8.0 Hz, 1H), 6.82 (d, J=8.0 Hz, 1H), 5.77 (s, 1H), 4.47 (s, 2H), 4.05 (d, J=12.4 Hz, 2H), 3.76 (t, J=11.8 Hz, 2H), 3.45 (d, J=11.6 Hz, 2H), 3.36-3.20 (m, 3H), 2.23-2.07 (m, 4H), 0.63 (t, J=7.4 Hz, 3H); MS ESI 479.3 [M+H]$^+$, calcd for [C$_{30}$H$_{30}$N$_4$O$_2$+H]$^+$ 479.2.

Example A142. (1R*,2S*)-5'-ethyl-2-(3-(4-(4-methylpiperazin-1-yl)phenyl)-1H-indazol-6-yl)spiro[cyclopropane-1,3'-indolin]-2'-one 2,2,2-trifluoroacetate

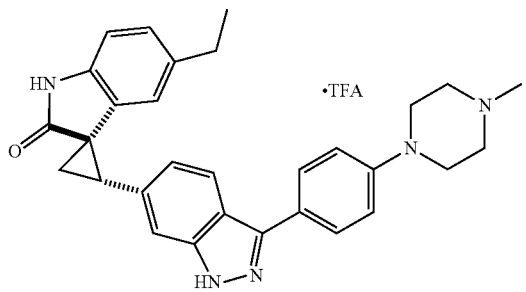

The title compound (52 mg, 44%, TFA salt) was obtained as a light yellow semi-solid from (1R*,2S*)-5'-ethyl-2-(3-iodo-1H-indazol-6-yl)spiro[cyclopropane-1,3'-indolin]-2'-one (85.8 mg, 0.2 mmol) and 1-methyl-4-(4-(4,4,5,5-tetramethyl-1,3,2-dioxaborolan-2-yl)phenyl)piperazine (72.5 mg, 0.24 mmol) using the method for the preparation of Example A51B (PhCH$_3$/EtOH=2 mL/1 mL, 2.5 mol % Pd(PPh$_3$)$_4$, 120° C., 2 h). $^1$H NMR (400 MHz, CD$_3$OD) δ 7.82 (d, J=8.4 Hz, 3H), 7.42 (s, 1H), 7.13 (d, J=8.4 Hz, 2H), 6.94 (d, J=8.8 Hz, 1H), 6.82 (t, J=8.8 Hz, 2H), 5.76 (s, 1H), 3.93 (d, J=12.4 Hz, 2H), 3.63 (d, J=11.6 Hz, 2H), 3.35-3.22 (m, 2H), 3.12 (t, J=12.4 Hz, 2H), 3.00 (s, 3H), 2.21-2.07 (m, 4H), 0.62 (t, J=7.6 Hz, 3H); MS ESI 478.3 [M+H]$^+$, calcd for [C$_{30}$H$_{31}$N$_5$O+H]$^+$ 478.3.

Example A143. (1R*,2S*)-5',6'-dimethoxy-2-(3-(3-(morpholinomethyl)phenyl)-1H-indazol-6-yl)spiro[cyclopropane-1,3'-indolin]-2'-one 2,2,2-trifluoroacetate

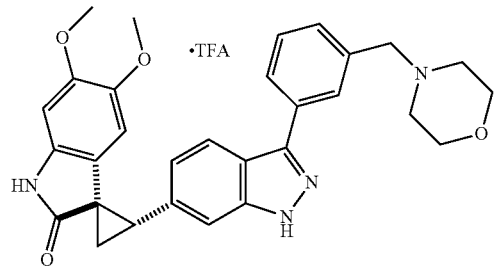

The title compound (50 mg, 58%, TFA salt) was obtained as a pale yellow solid from (1R*,2S*)-2-(3-iodo-1H-indazol-6-yl)-5',6'-dimethoxyspiro[cyclopropane-1,3'-indolin]-2'-one (92.2 mg, 0.2 mmol) and 4-(3-(4,4,5,5-tetramethyl-1,3,2-dioxaborolan-2-yl)benzyl)morpholine (60.6 mg, 0.2 mmol) using the method for the preparation of Example A51B (PhCH$_3$/EtOH=3 mL/1.5 mL, 2.5 mol % Pd(PPh$_3$)$_4$, 120° C., 2 h). $^1$H NMR (400 MHz, CD$_3$OD) δ 8.11 (s, 1H), 8.08 (d, J=7.6 Hz, 1H), 7.98 (d, J=8.4 Hz, 1H), 7.64 (t, J=7.8 Hz, 1H), 7.55 (d, J=7.6 Hz, 1H), 7.53 (s, 1H), 7.03 (d, J=8.4 Hz, 1H), 6.65 (s, 1H), 5.57 (s, 1H), 4.47 (s, 2H), 4.05 (d, J=12.4 Hz, 2H), 3.90-3.70 (m, 5H), 3.45 (d, J=12.4 Hz, 2H), 3.32-3.20 (m, 2H, partially overlapping with MeOH residue), 3.10 (s, 3H), 2.22 (dd, J=7.6 Hz, 5.0 Hz, 1H), 2.14 (dd, J=8.8 Hz, 4.8 Hz, 1H); MS ESI 511.3 [M+H]$^+$, calcd for [C$_{30}$H$_{30}$N$_4$O$_4$+H]$^+$ 511.2.

Example A144. (1R*,2S*)-5',6'-dimethoxy-2-(3-(4-(4-methylpiperazin-1-yl)phenyl)-1H-indazol-6-yl)spiro[cyclopropane-1,3'-indolin]-2'-one 2,2,2-trifluoroacetate

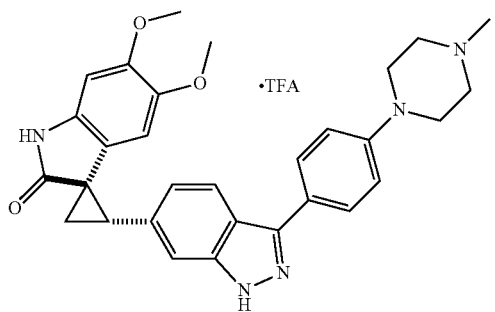

The title compound (36 mg, 29%, TFA salt) was obtained as a pale yellow solid from (1R*,2S*)-2-(3-iodo-1H-indazol-6-yl)-5',6'-dimethoxyspiro[cyclopropane-1,3'-indolin]-2'-one (92.2 mg, 0.2 mmol) and 1-methyl-4-(4-(4,4,5,5-tetramethyl-1,3,2-dioxaborolan-2-yl)phenyl)piperazine (60.4 mg, 0.2 mmol) using the method for the preparation of Example A51B (PhCH$_3$/EtOH=2 mL/1 mL, 2.5 mol % Pd(PPh$_3$)$_4$, 120° C., 2 h, then additional 1.25 mol % Pd(PPh$_3$)$_4$, 140° C., 30 min). $^1$H NMR (400 MHz, CD$_3$OD) δ 7.88-7.82 (m, 3H), 7.47 (s, 1H), 7.14 (d, J=8.8 Hz, 2H), 6.98 (d, J=8.8 Hz, 1H), 6.65 (s, 1H), 5.56 (s, 1H), 3.94 (d, J=13.2 Hz, 2H), 3.74 (s, 3H), 3.63 (d, J=10.2 Hz, 2H), 3.32-3.23 (m, 3H), 3.13 (d, J=12.8 Hz, 2H), 3.09 (s, 3H), 2.98 (s, 3H), 2.21 (dd, J=7.6 Hz, 4.8 Hz, 1H), 2.13 (dd, J=9.2 Hz, 4.8 Hz, 1H); MS ESI 510.3 [M+H]$^+$, calcd for [C$_{30}$H$_{31}$F$_3$N$_5$O$_3$+H]$^+$ 510.2.

Example A145. (1R*,2S*)-5'-methoxy-2-(3-((4-((4-methylpiperazin-1-yl)methyl)phenyl)ethynyl)-1H-indazol-6-yl)spiro[cyclopropane-1,3'-indolin]-2'-one bis(2,2,2-trifluoroacetate)

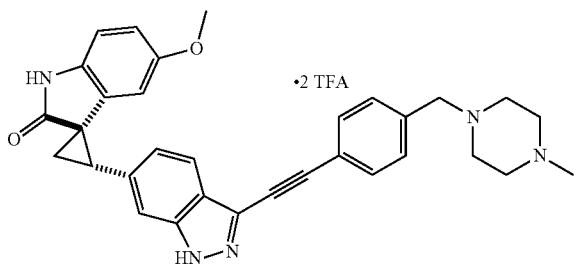

To a mixture of 4-((6-((1R*,2S*)-5'-methoxy-2'-oxospiro[cyclopropane-1,3'-indoline]-2-yl)-1H-indazol-3-yl)ethynyl)benzaldehyde (86.6 mg, 0.2 mmol) and N-methylpiperazine (0.045 mL, 0.4 mmol) in THF (5 mL) was added 2 drops of AcOH, followed by NaBH(OAc)$_3$ (64 mg, 0.3 mmol). The resulting mixture was stirred for 2 h at rt. Aqueous workup followed by prep-HPLC purification gave the title compound (25 mg, 17%, di-TFA salt) as a white solid. $^1$H NMR (400 MHz, CD$_3$OD) δ 7.95 (d, J=8.4 Hz, 1H), 7.66 (d, J=8.0 Hz, 2H), 7.52 (s, 1H), 7.50 (d, J=8.0 Hz, 2H), 7.07 (s, 1H), 6.84 (d, J=8.4 Hz, 1H), 6.32 (dd, J=8.8 Hz, 2.4 Hz, 1H), 5.56 (d, J=2.4 Hz, 1H), 4.02 (s, 2H), 3.50-3.40 (m, 4H), 3.36 (t, J=8.4 Hz, 1H), 3.28 (s, 3H), 3.28-3.16 (m, 4H), 2.94 (s, 3H), 2.24 (dd, J=8.0 Hz, 4.8 Hz, 1H), 2.18 (dd, J=8.8 Hz, 4.8 Hz, 1H); MS ESI 518.3 [M+H]$^+$, calcd for [C$_{32}$H$_{31}$N$_5$O$_2$+H]$^+$ 518.2.

Example A146. (1R,2S)-(E)-2-(3-(4-((diethylamino)methyl)-3,5-difluorostyryl)-1H-indazol-6-yl)-5'-methoxyspiro[cyclopropane-1,3'-indolin]-2'-one 2,2,2-trifluoroacetate

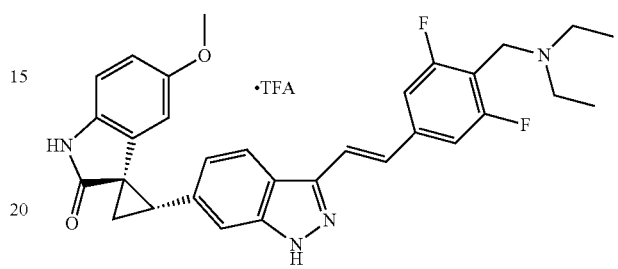

The title compound was synthesized according to the method of Example A51B, by using (1R,2S)-2-(3-iodo-1H-indazol-6-yl-)-5'-methoxyspiro[cyclopropane-1,3'-indolin]-2'-one (125 mg, 0.289 mmol) and (E)-N-(2,6-Difluoro-(4-(2-(4,4,5,5-tetramethyl-1,3,2-dioxaborolan-2-yl)vinyl)benzyl)N-ethylethanamine (122.2 mg, 0.347 mmol). Purification by preparative HPLC gave the title compound as a cream solid (59 mg, 31.6%). $^1$H NMR (400 MHz, CD$_3$OD) δ 7.99 (d, J=8.0 Hz, 1H), 7.59 (d, J=16.8 Hz, 1H), 7.50-7.45 (m, 4H), 7.03 (s, J=8.4 Hz, 1H), 6.82 (d, J=8.4 Hz, 1H), 6.59 (d, J=8.8 Hz, 1H), 5.57 (s, 1H), 4.46 (s, 2H), 3.37-3.28 (m, 5H), 3.25 (s, 3H), 2.25-2.22 (m, 1H), 2.19-2.17 (m, 1H), 1.26 (t, J=11.2 Hz, 6H); MS ESI 529.3 [M+H]$^+$, calcd for [C$_{31}$H$_{30}$F$_2$N$_4$O$_2$+H]$^+$ 529.2.

Optical Rotation: [α]$^{23}_D$=−80° (c 0.65, Methanol).

Example A147. (1R*,2S*)-(E)-2-(3-(4-((4-methylpiperazin-1-yl)methyl)styryl)-1H-indazol-6-yl)spiro[cyclopropane-1,3'-indolin]-2'-one bis-2,2,2-trifluoroacetate

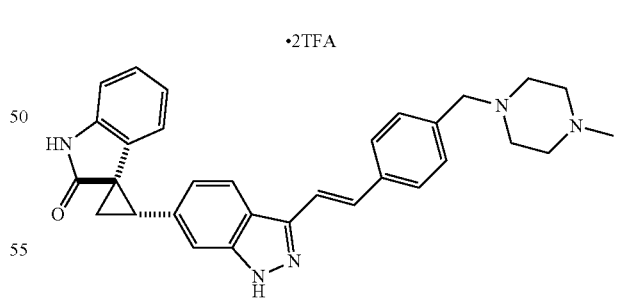

To a mixture of (1R*,2S*)-2-(3-vinyl-1H-indazol-6-yl)spiro[cyclopropane-1,3'-indolin]-2'-one (60.2 mg, 0.2 mmol) and 1-(4-bromobenzyl)-4-methylpiperazine (53.8 mg, 0.2 mmol) in DMF (2 mL) was added $^i$Pr$_2$NEt (0.07 mL), followed by Pd(OAc)$_2$ (2.2 mg, 0.01 mmol) and P(o-tol)$_3$ (6.7 mg, 0.022 mmol). The resulting mixture was purged with argon, and then microwaved 2 h at 100° C. LC-MS showed low conversion. Additional Pd(OAc)$_2$ (2.2 mg, 0.01 mmol) and P(o-tol)$_3$ (6.7 mg, 0.022 mmol) were added and the reaction mixture was purged with argon and microwaved 2 h at 125° C. Purification by prep-HPLC gave the title compound as a white solid (23 mg, 16%). ¹H NMR (400 MHz, CD₃OD) δ 7.99 (d, J=8.4 Hz, 1H), 7.71 (d, J=8.0 Hz, 2H), 7.53-7.46 (m, 5H), 7.05 (t, J=7.6 Hz, 1H, partially overlapping with the peak at 7.04 ppm), 7.04 (d, J=8.0 Hz, 1H, partially overlapping with the peak at 7.05 ppm), 6.94 (d, J=7.6 Hz, 1H), 6.58 (t, J=7.4 Hz, 1H), 5.99 (d, J=8.0 Hz, 1H), 4.19 (s, 2H), 3.60-3.30 (m, 9H), 2.95 (s, 3H), 2.24 (dd, J=7.6 Hz, 4.8 Hz, 1H), 2.18 (dd, J=9.0 Hz, J=4.6 Hz, 1H); MS ESI 490.3 [M+H]⁺, calcd for [C₃₁H₃₁N₅O+H]⁺ 490.3.

Example A148. (1R*,2S*)-5'-methoxy-2-(3-(4-(4-methylpiperazine-1-carbonyl) phenyl)-1H-indazol-6-yl)spiro[cyclopropane-1,3'-indolin]-2'-one 2,2,2-trifluoroacetate

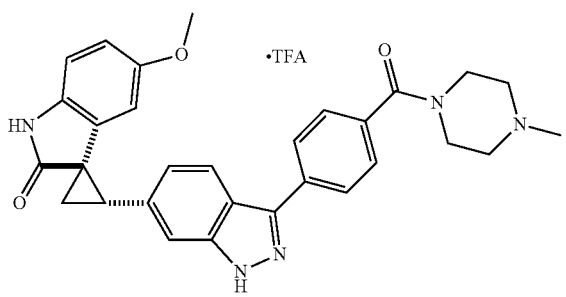

The title compound (67 mg, 54%, TFA salt) was obtained as a white solid from (1R*,2S*)-2-(3-iodo-1H-indazol-6-yl)-5'-methoxyspiro[cyclopropane-1,3'-indolin]-2'-one (86.2 mg, 0.2 mmol) and (4-methylpiperazin-1-yl)(4-(4,4,5,5-tetramethyl-1,3,2-dioxaborolan-2-yl)phenyl)methanone (66 mg, 0.2 mmol) using the method for the preparation of Example A51B (PhCH₃/EtOH=3 mL/1.5 mL, 2.5 mol % Pd(PPh₃)₄, 130° C., 2 h). ¹H NMR (400 MHz, CD₃OD) δ 7.99 (d, J=8.0 Hz, 2H), 7.80 (d, J=8.4 Hz, 1H), 7.59 (d, J=8.4 Hz, 2H), 7.48 (s, 1H), 6.92 (d, J=8.4 Hz, 1H), 6.80 (d, J=8.8 Hz, 1H), 6.55 (dd, J=8.4 Hz, J=2.4 Hz, 1H), 5.58 (d, J=2.0 Hz, 1H), 3.70-3.10 (m, 12H), 2.96 (s, 3H), 2.21-2.11 (m, 2H); MS ESI 508.3 [M+H]⁺, calcd for [C₃₀H₂₉N₅O₃+H]⁺ 508.2.

Example A149. (1R*,2S*)-5'-methoxy-2-(3-(3-(4-methylpiperazine-1-carbonyl) phenyl)-1H-indazol-6-yl)spiro[cyclopropane-1,3'-indolin]-2'-one 2,2,2-trifluoroacetate

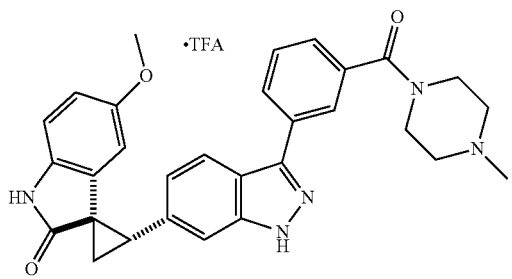

The title compound (72 mg, 58%, TFA salt) was obtained as a white solid from (1R*,2S*)-2-(3-iodo-1H-indazol-6-yl)-5'-methoxyspiro[cyclopropane-1,3'-indolin]-2'-one (86.2 mg, 0.2 mmol) and (4-methylpiperazin-1-yl)(3-(4,4,5,5-tetramethyl-1,3,2-dioxaborolan-2-yl)phenyl)methanone (66 mg, 0.2 mmol) using the method for the preparation of Example A51B (PhCH₃/EtOH=3 mL/1.5 mL, 2.5 mol % Pd(PPh₃)₄, 130° C., 2 h). ¹H NMR (400 MHz, CD₃OD) δ 8.02 (s, 1H, partially overlapping with the peak at 8.01 ppm), 8.01 (d, J=7.2 Hz, partially overlapping with the peak at 8.02 ppm, 1H), 7.83 (d, J=8.8 Hz, 1H), 7.48 (d, J=6.8 Hz, 1H, partially overlapping with the peak at 7.47 ppm), 7.47 (s, 1H, partially overlapping with the peak at 7.48 ppm), 6.93 (d, J=8.4 Hz, 1H), 6.81 (d, J=8.4 Hz, 1H), 6.56 (dd, J=8.4 Hz, J=2.4 Hz, 1H), 3.70-3.10 (m, 12H), 2.94 (s, 3H), 2.21-2.11 (m, 2H); MS ESI 508.3 [M+H]⁺, calcd for [C₃₀H₂₉N₅O₃+H]⁺ 508.2.

Example A150. (1R,2S)-2-(3-((E)-2-(6-methylpyridin-3-yl)vinyl)-1H-indazol-6-yl)spiro[cyclopropane-1,3'-indolin]-2'-one

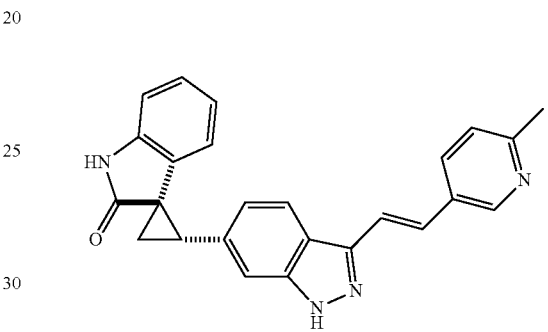

To a mixture of (1R*,2S*)-2-(3-vinyl-1H-indazol-6-yl)spiro[cyclopropane-1,3'-indolin]-2'-one (60.2 mg, 0.2 mmol) and 3-bromo-2-methylpyridine (34.4 mg, 0.2 mmol) in DMF (1.5 mL) was added ⁱPr₂NEt (0.07 mL), followed by Pd(OAc)₂ (2.2 mg, 0.01 mmol) and P(o-tol)₃ (6.7 mg, 0.022 mmol). The resulting mixture was purged with argon, and then microwaved 2 h at 125° C. Purification by prep-HPLC gave the title compound as a light yellow solid (25 mg, 25%). NMR indicated 6% of the branched isomer. ¹H NMR (400 MHz, CD₃OD) δ 8.90 (s, 1H), 7.74 (dd, J=8.4 Hz, 1.6 Hz, 1H), 8.02 (d, J=8.4 Hz, 1H), 7.87 (d, J=8.4 Hz, 1H), 7.78 (d, J=16.8 Hz, 1H), 7.55 (d, J=16.8 Hz, 1H), 7.49 (s, 1H), 7.07-7.00 (m, 2H), 6.94 (d, J=8.0 Hz, 1H), 6.55 (t, J=7.6 Hz, 1H), 5.97 (d, J=7.6 Hz, 1H), 3.34 (t, J=8.4 Hz, 1H, partially overlapping with MeOH residue), 2.78 (s, 3H), 2.23 (dd, J=7.6 Hz, J=4.8 Hz, 1H), 2.18 (dd, J=8.8 Hz, J=4.8 Hz, 1H); MS ESI 393.1 [M+H]⁺, calcd for [C₂₅H₂₀N₄O+H]⁺ 393.2.

Example A151. (1R,2S)-(E)-2-(3-(3-(morpholinomethyl)styryl)-1H-indazol-6-yl)spiro[cyclopropane-1,3'-indolin]-2'-one 2,2,2-trifluoroacetate

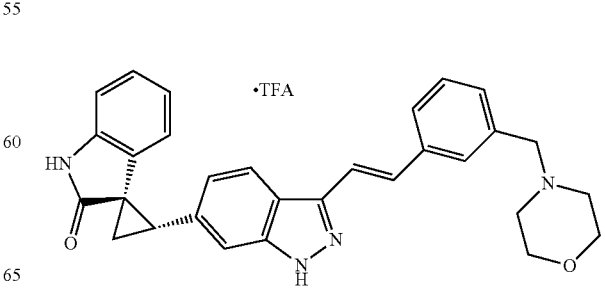

The title compound (158 mg, 67%, TFA salt) was obtained as a white solid from (1R,2S)-2-(3-iodo-1H-indazol-6-yl)-spiro[cyclopropane-1,3'-indolin]-2'-one (160 mg, 0.4 mmol) and (E)-4-(3-(2-(4,4,5,5-tetramethyl-1,3,2-dioxaborolan-2-yl)vinyl)benzyl) morpholine (184 mg, 0.56 mmol) using the method for the preparation of Example A51B (PhCH$_3$/EtOH=8 mL/4 mL, 5 mol % Pd(PPh$_3$)$_4$, 125° C., 2 h). $^1$H NMR (400 MHz, CD$_3$OD) δ 8.11 (s, 1H), 7.88 (d, J=8.4 Hz, 1H), 7.73 (s, 1H), 7.67 (d, J=8.0 Hz, 1H), 7.50-7.38 (m, 5H), 6.98 (t, J=7.8 Hz, 1H), 6.91 (d, J=8.0 Hz, 2H), 6.48 (t, J=7.6 Hz, 1H), 5.92 (d, J=7.2 Hz, 1H), 4.36 (s, 2H), 4.03 (d, J=11.6 Hz, 2H), 3.76 (t, J=12.0 Hz, 2H), 3.45-3.14 (m, 5H), 2.17-2.08 (m, 2H); MS ESI 477.3 [M+H]$^+$, calcd for [C$_{30}$H$_{28}$N$_4$O$_2$+H]$^+$ 477.2.

Optical Rotation [α]$^≤_D$=−144° (c 0.34, MeOH).

Example A152. (1R*,2S*)-(E)-2-(3-(3-(morpholinomethyl)styryl)-1H-indazol-6-yl)spiro[cyclopropane-1,3'-indolin]-2'-one 2,2,2-trifluoroacetate

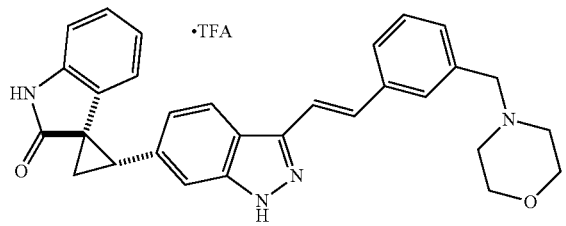

To a mixture of (1R*,2S*)-2-(3-vinyl-1H-indazol-6-yl)spiro[cyclopropane-1,3'-indolin]-2'-one (60.2 mg, 0.2 mmol) and 4-(3-bromobenzyl)morpholine (51.2 mg, 0.2 mmol) in DMF (1.5 mL) was added $^i$Pr$_2$NEt (0.07 mL), followed by Pd(OAc)$_2$ (2.2 mg, 0.01 mmol) and P(o-tol)$_3$ (6.7 mg, 0.022 mmol). The resulting mixture was purged with argon, and then microwaved 2 h at 125° C. Purification by prep-HPLC gave the title compound as a white solid (22 mg, 19%). NMR indicated 3% branched isomer. Spectral data was identical to that in obtained in Example A151.

Example A153. (1R*,2S*)-2-(3-(3-(morpholinomethyl)phenyl)-1H-indazol-6-yl)spiro[cyclopropane-1,3'-indolin]-2'-one 2,2,2-trifluoroacetate

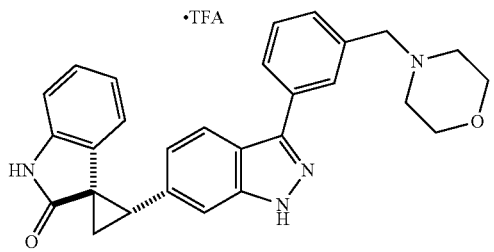

The title compound (40 mg, 44%, TFA salt) was obtained as a white solid from (1R*,2S*)-2-(3-iodo-1H-indazol-6-yl)-5'-methoxyspiro[cyclopropane-1,3'-indolin]-2'-one (80.2 mg, 0.2 mmol) and 4-(3-(4,4,5,5-tetramethyl-1,3,2-dioxaborolan-2-yl)benzyl) morpholine (60.6 mg, 0.2 mmol) using the method for the preparation of Example A51B (PhCH$_3$/EtOH=3 mL/1.5 mL, 2.5 mol % Pd(PPh$_3$)$_4$, 120° C., 2 h). $^1$H NMR (400 MHz, CD$_3$OD) δ 8.11 (s, 1H), 8.08 (d, J=8.0 Hz, 1H), 7.95 (d, J=8.1 Hz, 1H), 7.64 (t, J=7.8 Hz, 1H), 7.56 (d, J=7.6 Hz, 1H), 7.50 (s, 1H), 7.04 (t, J=8.0 Hz, 1H, partially overlapping with the peak at 7.00 ppm), 7.00 (d, J=8.4 Hz, 1H, partially overlapping with the peak at 7.04 ppm), 6.93 (d, J=7.6 Hz, 1H), 6.54 (t, J=7.6 Hz, 1H), 5.98 (d, J=7.6 Hz, 1H), 4.47 (s, 2H), 4.05 (d, J=11.2 Hz, 2H), 3.76 (t, J=10.4 Hz, 2H), 3.50-3.20 (m, 5H), 2.24-2.14 (m, 4H); MS ESI 415.2 [M+H]$^+$, calcd for [C$_{28}$H$_{26}$N$_4$O$_2$+H]$^+$ 415.2.

Example A154. (1R*,2S*)-2-(3-(4-(morpholinomethyl)phenyl)-1H-indazol-6-yl)spiro[cyclopropane-1,3'-indolin]-2'-one 2,2,2-trifluoroacetate

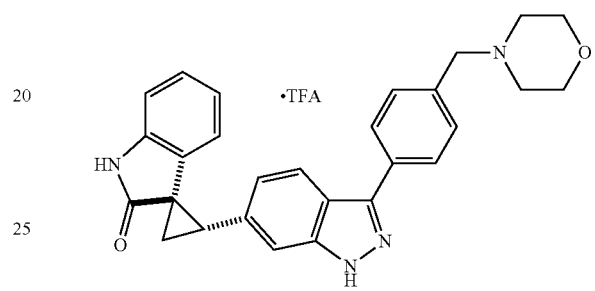

The title compound (59 mg, 44%, TFA salt) was obtained as a white solid from (1R*,2S*)-2-(3-iodo-1H-indazol-6-yl)-5'-methoxyspiro[cyclopropane-1,3'-indolin]-2'-one (80.2 mg, 0.2 mmol) and 4-(4-(4,4,5,5-tetramethyl-1,3,2-dioxaborolan-2-yl)benzyl)morpholine (60.6 mg, 0.2 mmol) using the method for the preparation of Example A51B (PhCH$_3$/EtOH=3 mL/1.5 mL, 2.5 mol % Pd(PPh$_3$)$_4$, 130° C., 2 h). $^1$H NMR (400 MHz, CD$_3$OD) δ 8.04 (d, J=8.0 Hz, 2H), 7.85 (d, J=8.4 Hz, 1H), 7.64 (d, J=8.0 Hz, 2H), 7.48 (s, 1H), 7.02 (t, J=7.6 Hz, 1H), 6.97 (d, J=8.4 Hz, 1H), 6.92 (d, J=7.6 Hz, 1H), 6.53 (t, J=7.4 Hz, 1H), 5.97 (d, J=7.2 Hz, 1H), 4.42 (s, 2H), 4.05 (d, J=11.6 Hz, 2H), 3.77 (t, J=11.2 Hz, 2H), 3.43 (d, J=10.2 Hz, 2H), 3.50-3.15 (m, 3H), 2.22-2.13 (m, 2H); MS ESI 415.2 [M+H]$^+$, calcd for [C$_{28}$H$_{26}$N$_4$O$_2$+H]$^+$ 415.2.

Example A155. (1R*,2S*)-2-(3-(4-((4-methylpiperazin-1-yl)methyl)phenyl)-1H-indazol-6-yl)spiro[cyclopropane-1,3'-indolin]-2'-one bis-2,2,2-trifluoroacetate

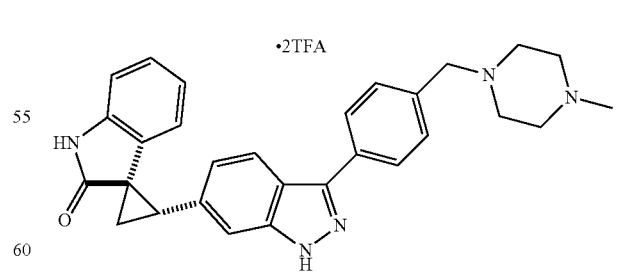

The title compound (57 mg, 41%, di-TFA salt) was obtained as a white solid from (1R*,2S*)-2-(3-iodo-1H-indazol-6-yl)-5'-methoxyspiro[cyclopropane-1,3'-indolin]-2'-one (80.2 mg, 0.2 mmol) and 1-methyl-4-(4-(4,4,5,5-tetramethyl-1,3,2-dioxaborolan-2-yl)benzyl)piperazine (63.2 mg, 0.2 mmol) using the method for the preparation of Example A51B (PhCH$_3$/EtOH=3 mL/1.5 mL, 2.5 mol % Pd(PPh$_3$)$_4$, 130° C., 2 h). $^1$H NMR (400 MHz, CD$_3$OD) δ 7.99 (d, J=8.0 Hz, 2H), 7.82 (d, J=8.4 Hz, 1H), 7.62 (d, J=8.0 Hz, 2H), 7.46 (s, 1H), 7.01 (t, J=7.6 Hz, 1H), 6.98-6.90 (m, 2H), 6.52 (t, J=7.6 Hz, 1H), 5.96 (d, J=7.6 Hz, 1H), 4.30 (s, 2H), 3.63-3.40 (m, 8H), 3.32-3.28 (m, 1H, partially buried under MeOH residue), 2.96 (s, 3H), 2.21-2.11 (m, 2H); MS ESI 464.2 [M+H]$^+$, calcd for [C$_{29}$H$_{29}$N$_5$O+H]$^+$ 464.2.

Example A156. (1R*,2S*)-2-(3-(4-(4-methylpiperazine-1-carbonyl)phenyl)-1H-indazol-6-yl)spiro[cyclopropane-1,3'-indolin]-2'-one 2,2,2-trifluoroacetate

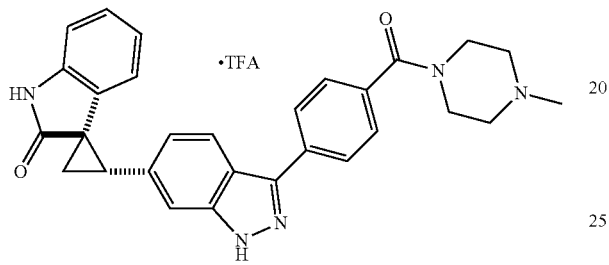

The title compound (60 mg, 51%, TFA salt) was obtained as a white solid from (1R*,2S*)-2-(3-iodo-1H-indazol-6-yl)-5'-methoxyspiro[cyclopropane-1,3'-indolin]-2'-one (80.2 mg, 0.2 mmol) and (4-methylpiperazin-1-yl)(4-(4,4,5,5-tetramethyl-1,3,2-dioxaborolan-2-yl)phenyl)methanone (66 mg, 0.2 mmol) using the method for the preparation of Example A51B (PhCH$_3$/EtOH=3 mL/1.5 mL, 2.5 mol % Pd(PPh$_3$)$_4$, 130° C., 2 h). $^1$H NMR (400 MHz, CD$_3$OD) δ 8.02 (d, J=8.0 Hz, 2H), 7.82 (d, J=8.4 Hz, 1H), 7.61 (d, J=8.4 Hz, 2H), 7.46 (s, 1H), 7.00 (t, J=7.6 Hz, 1H), 6.92 (d, J=8.0 Hz, 2H), 6.50 (t, J=7.6 Hz, 1H), 5.95 (d, J=7.6 Hz, 1H), 3.70-3.10 (m, 9H), 2.96 (s, 3H), 2.20-2.10 (m, 2H); MS ESI 478.3 [M+H]$^+$, calcd for [C$_{29}$H$_{27}$N$_5$O$_2$+H]$^+$ 478.3.

Example A157. (1R*,2S*)-2-(3-((E)-2-(6-(4-methylpiperazin-1-yl)pyridin-3-yl)vinyl)-1H-indazol-6-yl)spiro[cyclopropane-1,3'-indolin]-2'-one bis-2,2,2-trifluoroacetate

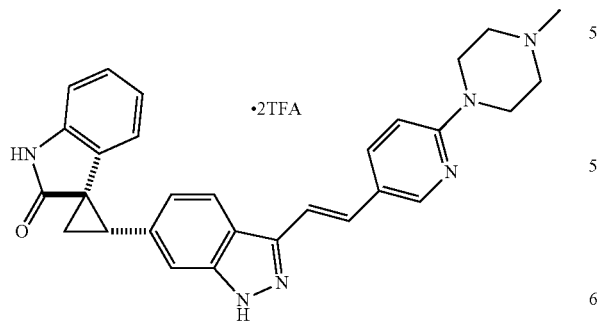

To a mixture of (1R*,2S*)-2-(3-vinyl-1H-indazol-6-yl)spiro[cyclopropane-1,3'-indolin]-2'-one (60 mg, 0.2 mmol) and 1-(5-bromopyridin-2-yl)-4-methylpiperazine (51 mg, 0.2 mmol) in DMF (1.5 mL) was added $^i$Pr$_2$NEt (0.07 mL), followed by Pd(OAc)$_2$ (2.2 mg, 0.01 mmol) and P(o-tol)$_3$ (6.7 mg, 0.022 mmol). The resulting mixture was purged with argon, and then microwaved 2 h at 125° C. Purification by prep-HPLC gave the title compound as a yellow solid (28 mg, 20%). $^1$H NMR (400 MHz, CD$_3$OD) δ 8.07 (d, J=1.6 Hz, 1H), 8.22 (dd, J=9.2 Hz2.0 Hz, 1H), 7.97 (d, J=8.4 Hz, 1H), 7.43 (d, J=16.4 Hz, 2H, partially overlapping with the peak at 7.41 ppm), 7.41 (s, 1H, partially overlapping with the peak at 7.43 ppm), 7.22 (d, J=9.2 Hz, 1H), 7.04 (t, J=7.8 Hz, partially overlapping with the peak at 7.01 ppm, 1H), 7.01 (d, J=8.8 Hz, partially overlapping with the peak at 7.04 ppm, 1H), 6.94 (d, J=7.6 Hz, 1H), 6.56 (t, J=7.6 Hz, 1H), 5.98 (d, J=7.6 Hz, 1H), 4.70-3.30 (m, 9H), 2.99 (s, 3H), 2.22 (dd, J=7.8 Hz, 5.0 Hz, 1H), 2.17 (dd, J=9.2 Hz, 4.4 Hz, 1H); MS ESI 477.2 [M+H]$^+$, calcd for [C$_{29}$H$_{28}$N$_6$O+H]$^+$ 477.2.

Example A158. (1R*,2S*)-2-(3-((E)-2-(2,6-dimethylpyridin-3-yl)vinyl)-1H-indazol-6-yl)spiro[cyclopropane-1,3'-indolin]-2'-one

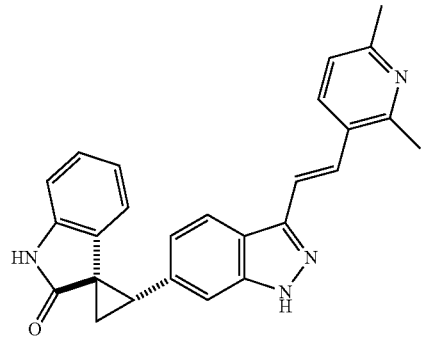

To a mixture of (1R*,2S*)-2-(3-vinyl-1H-indazol-6-yl)spiro[cyclopropane-1,3'-indolin]-2'-one (60 mg, 0.2 mmol) and 3-bromo-2,6-dimethylpyridine (37 mg, 0.2 mmol) in DMF (1.5 mL) was added $^i$Pr$_2$NEt (0.07 mL), followed by Pd(OAc)$_2$ (2.2 mg, 0.01 mmol) and P(o-tol)$_3$ (6.7 mg, 0.022 mmol). The resulting mixture was purged with argon, and then microwaved 2 h at 125° C. Purification by prep-HPLC gave the title compound as a light yellow solid (23 mg, 22%). NMR indicated 3% of the branched isomer. $^1$H NMR (400 MHz, CD$_3$OD) δ 8.73 (d, J=8.0 Hz, 1H), 7.97 (d, J=8.4 Hz, 1H), 7.72 (d, J=8.4 Hz, 1H, partially overlapping with the peak at 7.68 ppm), 7.68 (d, J=16.4 Hz, 1H, partially overlapping with the peak at 7.72 ppm), 7.59 (d, J=16.4 Hz, 1H), 7.50 (s, 1H), 7.06 (d, J=8.8 Hz, 1H, overlapping with the peak at 7.05 ppm), 7.05 (t, J=8.6 Hz, 1H, partially overlapping with the peak at 7.06 ppm), 6.94 (d, J=8.0 Hz, 1H), 6.56 (t, J=7.6 Hz, 1H), 5.98 (d, J=7.6 Hz, 1H), 3.35 (t, J=8.4 Hz, 1H), 2.86 (s, 3H), 2.76 (s, 3H), 2.24 (dd, J=7.6 Hz, 4.8 Hz, 1H), 2.18 (dd, J=9.0 Hz, 5.0 Hz, 1H); MS ESI 407.2 [M+H]$^+$, calcd for [C$_{26}$H$_{22}$N$_4$O+H]$^+$ 407.2.

Example A159. (1R*,2S*)-5'-methoxy-2-(3-(4-(2-morpholinoethyl)phenyl)-1H-indazol-6-yl)spiro[cyclopropane-1,3'-indolin]-2'-one 2,2,2-trifluoroacetate

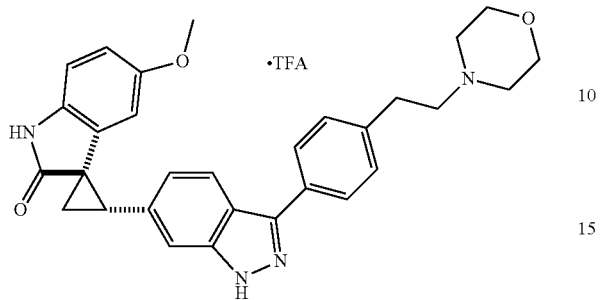

The title compound (27 mg, 22%, TFA salt) was obtained as a light yellow solid from (1R*,2S*)-2-(3-iodo-1H-indazol-6-yl)-5'-methoxyspiro[cyclopropane-1,3'-indolin]-2'-one (86.2 mg, 0.2 mmol) and 4-(4-(4,4,5,5-tetramethyl-1,3,2-dioxaborolan-2-yl)phenethyl)morpholine (63.4 mg, 0.2 mmol) using the method for the preparation of Example A51B (PhCH$_3$/EtOH=3 mL/1.5 mL, 2.5 mol % Pd(PPh$_3$)$_4$, 130° C., 2 h). $^1$H NMR (400 MHz, CD$_3$OD) δ 7.95-7.88 (m, 3H), 7.50 (s, 1H), 7.45 (d, J=8.0 Hz, 2H), 7.02 (d, J=8.4 Hz, 1H), 6.83 (d, J=8.4 Hz, 1H), 6.61 (dd, J=8.4 Hz, 2.4 Hz, 1H), 5.60 (d, J=2.4 Hz, 1H), 4.10 (d, J=12.4 Hz, 2H), 3.81 (t, J=12.2 Hz, 2H), 3.60 (d, J=12.4 Hz, 2H), 3.50-3.43 (m, 2H), 3.36 (t, J=8.4 Hz, 1H), 3.28-3.18 (m, 5H; s, 3H, OMe and m, 2H), 3.18-3.12 (m, 2H), 2.24 (dd, J=7.6 Hz, 4.8 Hz, 1H), 2.18 (dd, J=9.0 Hz, 4.6 Hz, 1H); MS ESI 495.3 [M+H]$^+$, calcd for [C$_{30}$H$_{30}$N$_4$O$_3$+H]$^+$ 495.2.

Example A160. 2-((1R*,2S*)-(E)-2-(3-(4-((dimethylamino)methyl)styryl)-1H-indazol-6-yl)-2'-oxospiro[cyclopropane-1,3'-indoline]-1'-yl)acetamide 2,2,2-trifluoroacetate

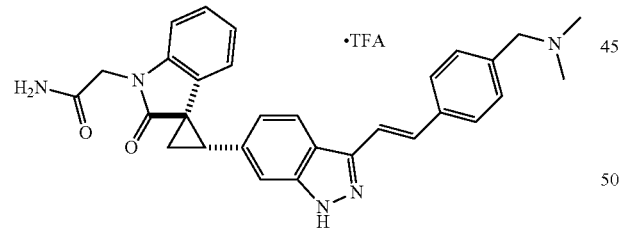

The title compound (79 mg, 33%, TFA salt) was obtained as a pale yellow solid from 2-((1R*,2S*)-2-(3-iodo-1H-indazol-6-yl)-2'-oxospiro[cyclopropane-1,3'-indoline]-1'-yl)acetamide (183 mg, 0.4 mmol) and (E)-N,N-dimethyl-1-(4-(2-(4,4,5,5-tetramethyl-1,3,2-dioxaborolan-2-yl)vinyl)phenyl)methanamine (161 mg, 0.56 mmol) using the method for the preparation of Example A51B (PhCH$_3$/EtOH=8 mL/4 mL, 5 mol % Pd(PPh$_3$)$_4$, 125° C., 2 h). $^1$H NMR (400 MHz, CD$_3$OD) δ 7.92 (d, J=8.4 Hz, 1H), 7.68 (d, J=8.0 Hz, 2H), 7.50-7.43 (m, 5H), 7.07 (t, J=8.2 Hz, 1H, partially overlapping with the peak at 7.04 ppm), 7.04 (d, J=9.2 Hz, partially overlapping with the peak at 7.07 ppm), 6.90 (d, J=8.0 Hz, 1H), 6.60 (t, J=7.6 Hz, 1H), 6.02 (d, J=7.6 Hz, 1H), 4.58-4.54 (m, 2H), 4.30 (s, 2H), 3.39 (t, J=8.4 Hz, 1H), 2.86 (s, 6H), 2.27-2.18 (m, 2H); MS ESI 492.3 [M+H]$^+$, calcd for [C$_{30}$H$_{29}$N$_5$O$_2$+H]$^+$ 492.2.

Example A161. (1R*,2S*)-2-(3-((E)-2-(2-methylpyridin-4-yl)vinyl)-1H-indazol-6-yl)spiro[cyclopropane-1,3'-indolin]-2'-one

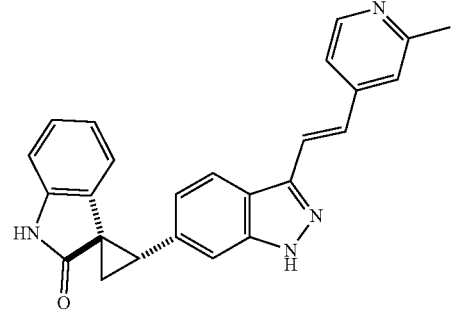

To a mixture of (1R*,2S*)-2-(3-vinyl-1H-indazol-6-yl)spiro[cyclopropane-1,3'-indolin]-2'-one (60.2 mg, 0.2 mmol) and 4-bromo-2-methylpyridine (34.4 mg, 0.2 mmol) in DMF (2 mL) was added $^i$Pr$_2$NEt (0.07 mL), followed by Pd(OAc)$_2$ (2.2 mg, 0.01 mmol) and P(o-tol)$_3$ (6.7 mg, 0.022 mmol). The resulting mixture was purged with argon, and then microwaved 2 h at 125° C. Purification by prep-HPLC gave the title compound as a yellow solid (23 mg, 23%). NMR indicated 7% of the branched isomer. $^1$H NMR (400 MHz, CD$_3$OD) δ 8.53 (d, J=6.4 Hz, 1H), 8.13-8.03 (m, 4H), 7.59 (d, J=16.4 Hz, 1H), 7.53 (s, 1H), 7.10 (d, J=8.4 Hz, 1H), 7.05 (t, J=7.6 Hz, 1H), 6.94 (d, J=8.4 Hz, 1H), 6.56 (t, J=7.6 Hz, 1H), 5.97 (d, J=7.6 Hz, 1H), 3.56 (t, J=8.0 Hz, 1H), 2.77 (s, 3H), 2.25 (dd, J=7.6 Hz, J=4.8 Hz, 1H), 2.18 (dd, J=9.2 Hz, 4.8 Hz, 1H); MS ESI 393.2 [M+H]$^+$, calcd for [C$_{25}$H$_{20}$N$_4$O+H]$^+$ 393.2.

Example A162. (1R*,2S*)-(E)-2-(3-(3-((dimethylamino)methyl)styryl)-1H-indazol-6-yl)spiro[cyclopropane-1,3'-indolin]-2'-one 2,2,2-trifluoroacetate

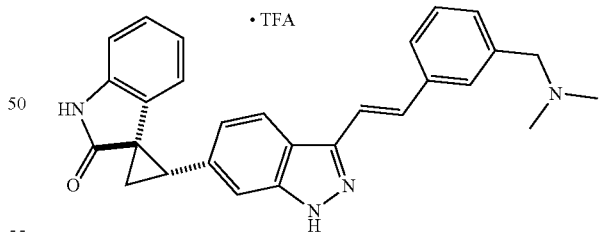

To a mixture of (1R*,2S*)-2-(3-vinyl-1H-indazol-6-yl)spiro[cyclopropane-1,3'-indolin]-2'-one (60.2 mg, 0.2 mmol) and 1-(3-bromophenyl)-N,N-dimethylmethanamine (42.8 mg, 0.2 mmol) in DMF (2 mL) was added $^i$Pr$_2$NEt (0.07 mL), followed by Pd(OAc)$_2$ (2.2 mg, 0.01 mmol) and P(o-tol)$_3$ (6.7 mg, 0.022 mmol). The resulting mixture was purged with argon, and then microwaved 2 h at 125° C. Purification by prep-HPLC gave the title compound (24 mg, 22%, TFA salt) as a white solid. NMR indicated 5% of the branched isomer. $^1$H NMR (400 MHz, CD$_3$OD) δ 7.99 (d, J=8.4 Hz, 1H), 7.78-7.75 (m, 2H), 7.55-7.49 (m, 3H), 7.47

(s, 1H), 7.41 (d, J=7.6 Hz, 1H), 7.08-7.00 (m, 2H), 6.94 (d, J=7.6 Hz, 1H), 6.57 (t, J=7.4 Hz, 1H), 5.98 (d, J=8.4 Hz, 1H), 4.36 (s, 2H), 3.35 (t, J=8.4 Hz, 1H, partially overlapping with MeOH residue), 2.90 (s, 6H), 2.23 (dd, J=8.0 Hz, J=4.8 Hz, 1H), 2.08 (dd, J=9.2 Hz, J=4.8 Hz, 1H); MS ESI 435.2 [M+H]$^+$, calcd for [C$_{28}$H$_{26}$N$_4$O+H]$^+$ 435.2.

Example A163. (1R*,2S*)-5'-methoxy-2-(3-((E)-2-(6-(piperazin-1-yl)pyridin-3-yl)vinyl)-1H-indazol-6-yl)spiro[cyclopropane-1,3'-indolin]-2'-one 2,2,2-trifluoroacetate

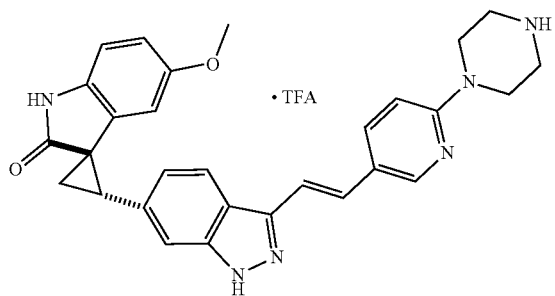

To a mixture of crude (1R*,2S*)-5'-methoxy-2-(3-vinyl-1H-indazol-6-yl)spiro [cyclopropane-1,3'-indolin]-2'-one (100 mg, 0.2 mmol) and 1-(5-bromopyridin-2-yl)piperazine (48 mg, 0.2 mmol) in DMF (2 mL) was added $^i$Pr$_2$NEt (0.07 mL), followed by Pd(OAc)$_2$ (2.2 mg, 0.01 mmol) and P(o-tol)$_3$ (6.7 mg, 0.022 mmol). The resulting mixture was purged with argon, and then microwaved 2 h at 125° C. Purification by prep-HPLC gave the title compound as a yellow solid (15.7 mg, 13%). $^1$H NMR (400 MHz, CD$_3$OD) δ 8.32-8.27 (m, 2H), 8.01 (d, J=8.4 Hz, 1H), 7.48 (s, 1H), 7.44 (s, 2H), 7.26 (d, J=9.2 Hz, 1H), 7.04 (d, J=8.4 Hz, 1H), 6.84 (d, J=8.8 Hz, 1H), 6.61 (dd, J=8.4 Hz, 2.4 Hz, 1H), 5.58 (d, J=2.0 Hz, 1H), 3.95 (t, J=5.2 Hz, 4H), 3.43 (t, J=5.2 Hz, 4H), 3.36 (t, J=8.0 Hz, 1H), 3.26 (s, 3H), 2.24 (dd, J=7.8 Hz, J=5.0 Hz, 1H), 2.18 (dd, J=9.0 Hz, 5.0 Hz, 1H); MS ESI 493.3 [M+H]$^+$, calcd for [C$_{29}$H$_{28}$N$_6$O$_2$+H]$^+$ 493.2.

Example A164. 2-((1R*,2S*)-(E)-2-(3-(3-((dimethylamino)methyl)styryl)-1H-indazol-6-yl)-2'-oxospiro[cyclopropane-1,3'-indoline]-1'-yl)acetamide 2,2,2-trifluoroacetate

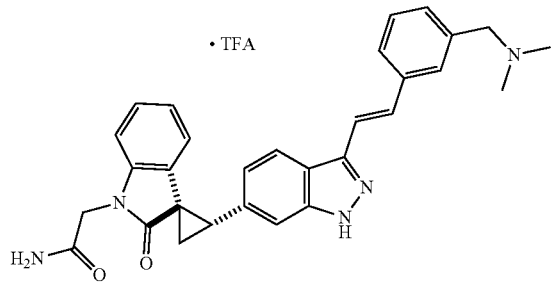

The title compound (6.9 mg, 23%, TFA salt) was obtained as a white solid from 2-((1R*,2S*)-2-(3-iodo-1H-indazol-6-yl)-2'-oxospiro[cyclopropane-1,3'-indoline]-1'-yl)acetamide (22.9 mg, 0.05 mmol) and (E)-N,N-dimethyl-1-(3-(2-(4,4,5,5-tetramethyl-1,3,2-dioxaborolan-2-yl)vinyl) phenyl)methanamine (21.6 mg, 0.075 mmol) using the method for the preparation of Example A51B (PhCH$_3$/EtOH=2 mL/1 mL, 4 mol % Pd(PPh$_3$)$_4$, 120° C., 2 h). $^1$H NMR (400 MHz, CD$_3$OD) δ 8.01 (d, J=8.4 Hz, 1H), 7.80 (s, 1H, partially overlapping with the peak at 7.79 ppm), 7.79 (d, J=9.2 Hz, 1H, partially overlapping with the peak at 7.80 ppm), 7.57-7.52 (m, 4H), 7.42 (d, J=7.2 Hz, 1H), 7.15-7.08 (m, 2H), 6.93 (d, J=8.0 Hz, 1H), 6.64 (t, J=7.8 Hz, 1H), 6.03 (d, J=7.6 Hz, 1H), 4.60 (d, J=16.4 Hz, 1H), 4.55 (d, J=17.2 Hz, 1H), 4.37 (s, 2H), 3.44 (t, J=8.6 Hz, 1H), 2.91 (s, 6H), 2.33-2.24 (m, 2H); MS ESI 492.3 [M+H]$^+$, calcd for [C$_{30}$H$_{29}$N$_5$O$_2$+H]$^+$ 492.2.

Example A165. 2-((1R*,2S*)-(E)-2'-oxo-2-(3-(4-(piperidin-1-ylmethyl)styryl)-1H-indazol-6-yl)spiro[cyclopropane-1,3'-indoline]-1'-yl)acetamide 2,2,2-trifluoroacetate

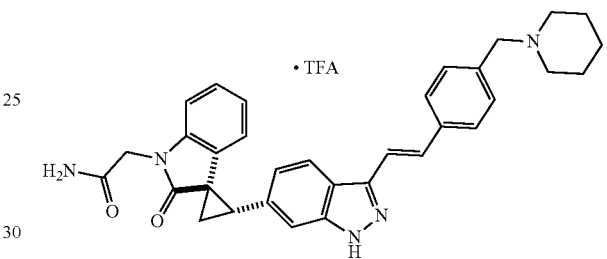

The title compound (12 mg, 37%, TFA salt) was obtained as a white solid from 2-((1R*,2S*)-2-(3-iodo-1H-indazol-6-yl)-2'-oxospiro[cyclopropane-1,3'-indoline]-1'-yl)acetamide (22.9 mg, 0.05 mmol) and (E)-1-(4-(2-(4,4,5,5-tetramethyl-1,3,2-dioxaborolan-2-yl)vinyl)benzyl)piperidine (24.6 mg, 0.075 mmol) using the method for the preparation of Example A51B (PhCH$_3$/EtOH=2 mL/1 mL, 4 mol % Pd(PPh$_3$)$_4$, 120° C., 2 h). $^1$H NMR (400 MHz, CD$_3$OD) δ 8.01 (d, J=8.4 Hz, 1H), 7.76 (d, J=8.4 Hz, 2H), 7.57-7.50 (m, 5H), 7.15-7.08 (m, 2H), 6.93 (d, J=8.0 Hz, 1H), 6.64 (t, J=7.4 Hz, 1H), 6.03 (d, J=7.6 Hz, 1H), 4.60 (d, J=16.8 Hz, 1H), 4.55 (d, J=16.8 Hz, 1H), 4.30 (s, 2H), 3.52-3.40 (m, 3H), 2.98 (t, J=11.6 Hz, 2H), 2.32-2.22 (m, 2H), 2.00-1.68 (m, 5H), 1.60-1.46 (m, 1H); MS ESI 532.4 [M+H]$^+$, calcd for [C$_{33}$H$_{33}$N$_5$O$_2$+H]$^+$ 532.3.

Example A166. (1R*,2S*)-2-(3-(4-((dimethylamino)methyl)phenyl)-1H-indazol-6-yl)-5'-methoxyspiro[cyclopropane-1,3'-indolin]-2'-one 2,2,2-trifluoroacetate

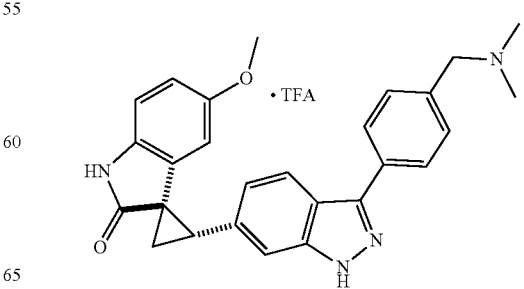

To a mixture of (1R*,2S*)-2-(3-iodo-1H-indazol-6-yl)-5'-methoxyspiro[cyclopropane-1,3'-indolin]-2'-one (172.4 mg, 0.4 mmol), 4-(4,4,5,5-tetramethyl-1,3,2-dioxaborolan-2-yl)benzaldehyde (93 mg, 0.4 mmol) in PhCH₃/EtOH (3 mL/1.5 mL) was added 1 M Na₂CO₃ (0.8 mL, 0.8 mmol), followed by Ph(PPh₃)₄ (11.6 mg, 0.01 mmol). The resulting mixture was purged with argon and then microwaved 2 h at 120° C. After aqueous workup (extraction with EtOAc) and removal of solvents, the residue was purified by prep-HPLC to give the crude Suzuki product aldehyde (105 mg) as a light yellow solid. It was mixed with Me₂NH (2 M in THF, 0.5 mL, 1 mmol) in DCE (8 mL). NaBH(OAc)₃ (106 mg, 0.5 mmol) were added, followed by HOAc (3 drops). The resulting mixture was stirred for 4 h at rt. After basic workup, it was purified by prep-HPLC to give the title compound as a white solid (41.5 mg, 19% over 2 steps, TFA salt). $^1$H NMR (400 MHz, CD₃OD) δ 8.06 (d, J=8.0 Hz, 2H), 7.91 (d, J=8.4 Hz, 1H), 7.63 (d, J=8.0 Hz, 2H), 7.52 (s, 1H), 7.02 (d, J=8.4 Hz, 1H), 6.83 (d, J=8.4 Hz, 1H), 6.06 (dd, J=8.4 Hz, 2.0 Hz, 1H), 5.60 (d, J=2.4 Hz, 1H), 3.35 (t, J=8.4 Hz, 1H, partially overlapping with MeOH residue), 3.25 (s, 3H), 2.91 (s, 6H), 2.23 (dd, J=7.8 Hz, J=5.0 Hz, 1H), 2.18 (dd, J=8.8 Hz, 4.8 Hz, 1H); MS ESI 439.2 [M+H]⁺, calcd for [C₂₇H₂₆N₄O₂+H]⁺ 439.2.

Example A167. (1R*,2S*)-(E)-2-(3-(4-((dimethylamino)methyl)styryl)-1H-indazol-6-yl)-5'-ethylspiro[cyclopropane-1,3'-indolin]-2'-one 2,2,2-trifluoroacetate

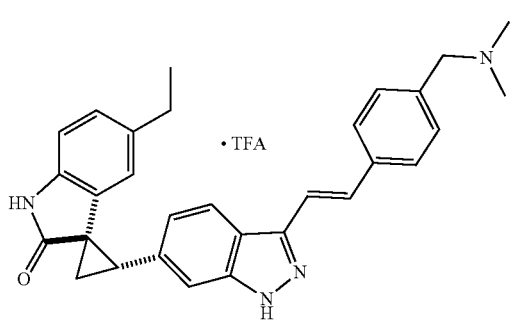

The title compound (19.5 mg, 34%, TFA salt) was obtained as a light yellow solid from (1*R,2S*)-2-(3-iodo-1H-indazol-6-yl)-5'-ethylspiro[cyclopropane-1,3'-indolin]-2'-one (42.9 mg, 0.1 mmol) and (E)-N,N-dimethyl-1-(4-(2-(4,4,5,5-tetramethyl-1,3,2-dioxaborolan-2-yl)vinyl)phenyl)methanamine (29 mg, 0.1 mmol) using the method for the preparation of Example A51B (PhCH₃/EtOH=2 mL/1 mL, 2.5 mol % Pd(PPh₃)₄, 120° C., 2 h). $^1$H NMR (400 MHz, CD₃OD) δ 8.01 (d, J=8.8 Hz, 1H), 7.76 (d, J=8.0 Hz, 2H), 7.54-7.50 (m, 4H), 7.44 (s, 1H), 7.04 (d, J=8.4 Hz, 1H), 6.86 (d, J=8.0 Hz, 1H), 6.82 (d, J=8.0 Hz, 1H), 5.77 (s, 1H), 4.33 (s, 2H), 3.34 (t, J=8.0 Hz, 1H, partially overlapping with MeOH residue), 2.88 (s, 6H), 2.25-2.10 (m, 4H), 0.65 (t, J=7.6 Hz, 3H); MS ESI 463.3 [M+H]⁺, calcd for [C₃₀H₃₀N₄O+H]⁺ 463.2.

Example A168. (1R*,2S*)-(E)-2-(3-(4-((dimethylamino)methyl)styryl)-1H-indazol-6-yl)-5',6'-dimethoxyspiro[cyclopropane-1,3'-indolin]-2'-one 2,2,2-trifluoroacetate

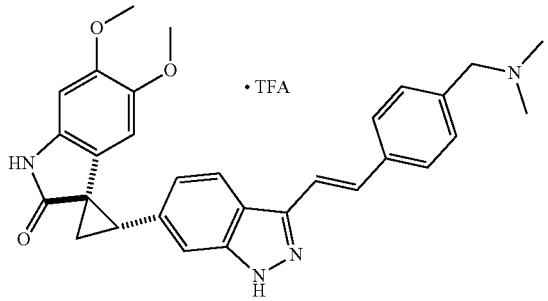

The title compound (7.5 mg, 12%, TFA salt) was obtained as a light yellow solid from (1R*,2S*)-2-(3-iodo-1H-indazol-6-yl)-5',6'-dimethoxyspiro[cyclopropane-1,3'-indolin]-2'-one (46.1 mg, 0.1 mmol) and (E)-N,N-dimethyl-1-(4-(2-(4,4,5,5-tetramethyl-1,3,2-dioxaborolan-2-yl)vinyl)phenyl)methanamine (29 mg, 0.1 mmol) using the method for the preparation of Example A51B (PhCH₃/EtOH=2 mL/1 mL, 2.5 mol % Pd(PPh₃)₄, 120° C., 2 h). $^1$H NMR (400 MHz, CD₃OD) δ 8.05 (d, J=8.4 Hz, 1H), 7.78 (d, J=8.0 Hz, 2H), 7.56-7.49 (m, 5H), 7.07 (d, J=8.0 Hz, 1H), 6.66 (s, 1H), 5.56 (s, 1H), 4.33 (s, 2H), 3.76 (s, 3H), 3.32 (t, J=8.2 Hz, 1H, partially overlapping with MeOH residue), 3.11 (s, 3H), 2.89 (s, 6H), 2.24 (dd, J=7.6 Hz, J=5.2 Hz, 1H), 2.15 (dd, J=9.2 Hz, J=4.8 Hz, 1H); MS ESI 495.3 [M+H]⁺, calcd for [C₃₀H₃₀N₄O₃+H]⁺ 495.2.

Example A169. (1R*,2S*)-(E)-2-(3-(4-((dimethylamino)methyl)styryl)-1H-indazol-6-yl)-5'-methylspiro[cyclopropane-1,3'-indolin]-2'-one 2,2,2-trifluoroacetate

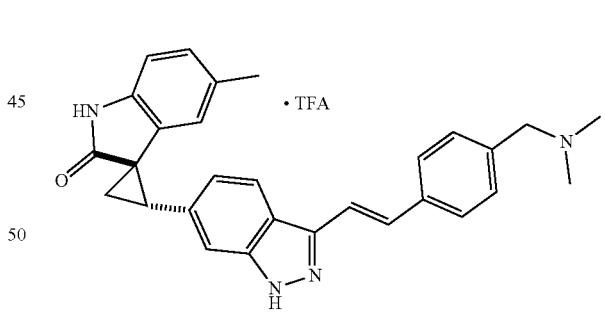

The title compound (27 mg, 48%, TFA salt) was obtained as a light yellow solid from (1*R,2S*)-2-(3-iodo-1H-indazol-6-yl)-5'-methylspiro[cyclopropane-1,3'-indolin]-2'-one (41.5 mg, 0.1 mmol) and (E)-N,N-dimethyl-1-(4-(2-(4,4,5,5-tetramethyl-1,3,2-dioxaborolan-2-yl)vinyl)phenyl)methanamine (43 mg, 0.15 mmol) using the method for the preparation of Example A51B (PhCH₃/EtOH=2 mL/1 mL, 2.5 mol % Pd(PPh₃)₄, 120° C., 2 h). $^1$H NMR (400 MHz, CD₃OD) δ 8.00 (d, J=8.4 Hz, 1H), 7.75 (d, J=8.0 Hz, 2H), 7.53 (s, 2H, partially overlapping with the peak at 7.52 ppm), 7.52 (d, J=8.8 Hz, 2H, partially overlapping with the peak at 7.53 ppm), 7.46 (s, 1H), 7.03 (d, J=8.4 Hz, 1H), 6.86 (d, J=8.0 Hz, 1H), 6.82 (d, J=7.6 Hz, 1H), 5.83 (s, 1H), 4.33

(s, 2H), 3.32 (t, J=8.4 Hz, 1H, partially overlapping with MeOH residue), 2.88 (s, 6H), 2.22-2.13 (m, 2H), 1.88 (s, 3H); MS ESI 449.2 [M+H]⁺, calcd for $[C_{29}H_{28}N_4O+H]^+$ 449.2.

Example A170. (1R*,2S*)-2-(3-(4-(4-methylpiperazin-1-yl)phenyl)-1H-indazol-6-yl)-5'-(trifluoromethyl)spiro[cyclopropane-1,3'-indolin]-2'-one 2,2,2-trifluoroacetate

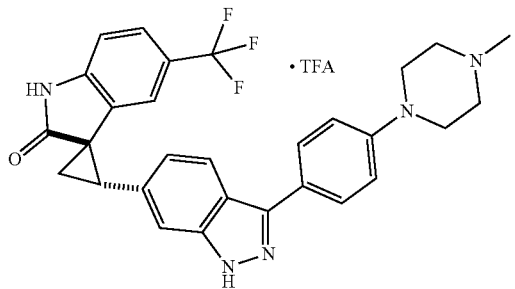

The title compound (28 mg, 50%, TFA salt) was obtained as a light yellow solid from (1R*,2S*)-2-(3-iodo-1H-indazol-6-yl)-5'-(trifluoromethyl)spiro[cyclopropane-1,3'-indolin]-2'-one (47 mg, 0.1 mmol) and 1-methyl-4-(4-(4,4,5,5-tetramethyl-1,3,2-dioxaborolan-2-yl)phenyl)piperazine (30 mg, 0.1 mmol) using the method for the preparation of Example A51B (PhCH₃/EtOH=2 mL/1 mL, 2.5 mol % Pd(PPh₃)₄, 125° C., 2 h then 130° C., 2 h). ¹H NMR (400 MHz, CD₃OD) δ 7.88 (d, J=8.4 Hz, 1H), 7.85 (d, J=8.8 Hz, 2H), 7.49 (s, 1H), 7.35 (d, J=8.0 Hz, 1H), 7.17 (d, J=8.4 Hz, 2H), 7.05 (d, J=8.0 Hz, 1H), 6.98 (d, J=8.4 Hz, 1H), 6.19 (s, 1H), 3.96 (d, J=13.6 Hz, 2H), 3.64 (d, J=11.6 Hz, 2H), 3.44 (t, J=8.4 Hz, 1H), 3.29 (t, J=11.6 Hz, partially overlapping with MeOH residue), 3.13 (t, J=12.4 Hz, 2H), 2.99 (s, 3H), 2.39 (dd, J=7.8 Hz, 5.0 Hz, 1H), 2.26 (dd, J=9.0 Hz, 5.0 Hz, 1H); MS ESI 518.3 [M+H]⁺, calcd for $[C_{29}H_{26}F_3N_5O+H]^+$ 518.2.

Example A171. (1R*,2S*)-(E)-5'-chloro-2-(3-(4-((dimethylamino)methyl)styryl)-1H-indazol-6-yl)spiro[cyclopropane-1,3'-indolin]-2'-one 2,2,2-trifluoroacetate

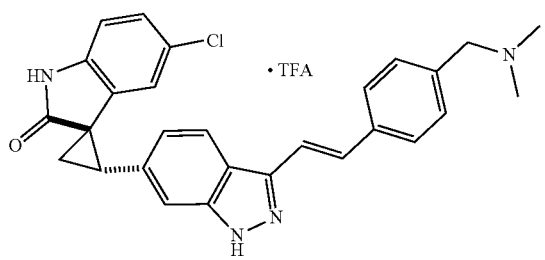

The title compound (29 mg, 50%, TFA salt) was obtained as a light yellow solid from (1R*,2S*)-5'-chloro-2-(3-iodo-1H-indazol-6-yl)spiro[cyclopropane-1,3'-indolin]-2'-one (43.6 mg, 0.1 mmol) and (E)-N,N-dimethyl-1-(4-(2-(4,4,5,5-tetramethyl-1,3,2-dioxaborolan-2-yl)vinyl)phenyl)methanamine (43 mg, 0.15 mmol) using the method for the preparation of Example A51B (PhCH₃/EtOH=2 mL/1 mL, 2.5 mol % Pd(PPh₃)₄, 120° C., 2 h). ¹H NMR (400 MHz, CD₃OD) δ 8.03 (d, J=8.4 Hz, 1H), 7.75 (d, J=8.0 Hz, 2H), 7.55-7.47 (m, 5H), 7.06-7.01 (m, 2H), 6.90 (d, J=8.4 Hz, 1H), 5.97 (s, 1H), 4.33 (s, 2H), 3.39 (t, J=8.4 Hz, 1H), 2.88 (s, 6H), 2.29 (dd, J=8.0 Hz, 5.2 Hz, 1H), 2.21 (dd, J=8.8 Hz, 4.8 Hz, 1H); MS ESI 469.3 [M+H]⁺, calcd for $[C_{28}H_{25}ClN_4O+H]^+$ 469.2.

Example A172. (1R*,2S*)-(E)-2-(3-(4-((dimethylamino)methyl)styryl)-1H-indazol-6-yl)spiro[cyclopropane-1,3'-pyrrolo[2,3-b]pyridin]-2'(1'H)-one 2,2,2-trifluoroacetate

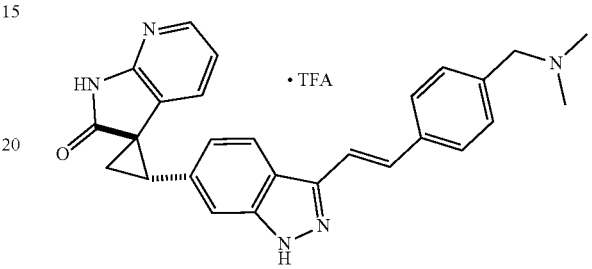

The title compound (17 mg, 31%, TFA salt) was obtained as a white solid from (1R*,2S*)-2-(3-iodo-1H-indazol-6-yl)spiro[cyclopropane-1,3'-pyrrolo [2,3-b]pyridin]-2'(1'H)-one (40.2 mg, 0.15 mmol) and (E)-N,N-dimethyl-1-(4-(2-(4,4,5,5-tetramethyl-1,3,2-dioxaborolan-2-yl)vinyl)phenyl)methanamine (43 mg, 0.1 mmol) using the method for the preparation of Example A51B (PhCH₃/EtOH=2 mL/1 mL, 2.5 mol % Pd(PPh₃)₄, 120° C., 2 h). ¹H NMR (400 MHz, CD₃OD) δ 8.04 (d, J=8.4 Hz, 1H), 7.93 (d, J=5.6 Hz, 1H), 7.77 (d, J=8.4 Hz, 2H), 7.56-7.50 (m, 5H), 7.07 (d, J=8.4 Hz, 1H), 6.65 (dd, J=7.2 Hz, J=5.4 Hz, 1H), 6.38 (d, J=7.2 Hz, 1H), 4.34 (s, 2H), 3.49 (t, J=8.4 Hz, 1H), 2.89 (s, 6H), 2.42 (dd, J=8.0 Hz, 5.2 Hz, 1H), 2.29 (dd, J=9.0 Hz, 5.0 Hz, 1H); MS ESI 436.2 [M+H]⁺, calcd for $[C_{27}H_{25}N_5O+H]^+$ 436.1.

Example A173. (1R*,2S*)-5'-methyl-2-(3-(4-(4-methylpiperazin-1-yl)phenyl)-1H-indazol-6-yl)spiro[cyclopropane-1,3'-indolin]-2'-one 2,2,2-trifluoroacetate

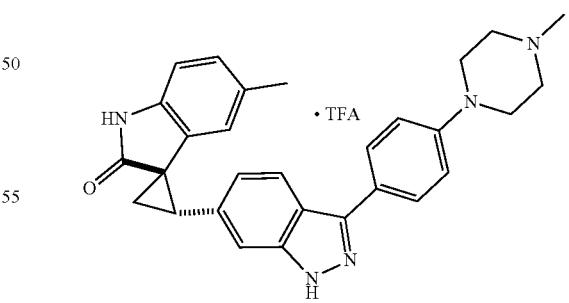

The title compound (57 mg, 50%, TFA salt) was obtained as a pale yellow solid from (1R*,2S*)-2-(3-iodo-1H-indazol-6-yl)-5'-methylspiro[cyclopropane-1,3'-indolin]-2'-one (145.5 mg, 0.3 mmol) and 1-methyl-4-(4-(4,4,5,5-tetramethyl-1,3,2-dioxaborolan-2-yl)phenyl)piperazine (60.4 mg, 0.2 mmol) using the method for the preparation of Example A51B (PhCH₃/EtOH=2 mL/1 mL, 2.5 mol % Pd(PPh₃)₄, 125° C., 2 h then 130° C., 2 h). $^1$H NMR (400 MHz, CD$_3$OD) δ 7.82 (d, J=7.2 Hz, 3H), 7.44 (s, 1H), 7.11 (d, J=8.4 Hz, 1H), 6.94 (d, J=7.2 Hz, 1H), 6.82 (d, J=8.0 Hz, 1H), 6.80 (d, J=8.0 Hz, 1H), 5.83 (s, 1H), 3.91 (d, J=13.6 Hz, 2H), 3.62 (d, J=11.6 Hz, 2H), 3.32-3.20 (m, 3H), 3.12 (t, J=12.4 Hz, 2H), 2.97 (s, 3H), 2.19-2.11 (m, 2H), 1.84 (s, 3H); MS ESI 464.3 [M+H]$^+$, calcd for [C$_{29}$H$_{29}$N$_5$O+H]$^+$ 464.2.

Example A174. (1R*,2S*)-(E)-5'-methoxy-2-(3-(4-(4-methylpiperazin-1-yl)styryl)-1H-indazol-6-yl) spiro[cyclopropane-1,3'-indolin]-2'-one 2,2,2-trifluoroacetate

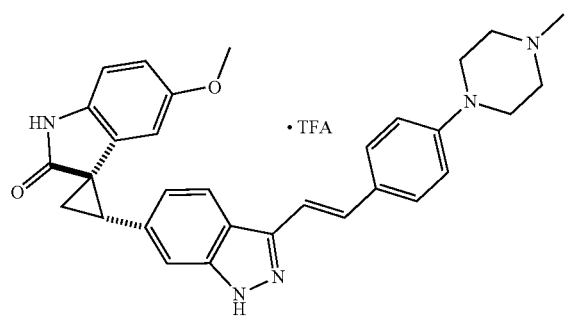

To a mixture of crude (1R*,2S*)-5'-methoxy-2-(3-vinyl-1H-indazol-6-yl)spiro [cyclopropane-1,3'-indolin]-2'-one (97 mg, 0.2 mmol) and 1-(4-bromophenyl)-4-methylpiperazine (51 mg, 0.2 mmol) in DMF (2 mL) was added $^i$Pr$_2$NEt (0.07 mL), followed by Pd(OAc)$_2$ (2.2 mg, 0.01 mmol) and P(o-tol)$_3$ (6.7 mg, 0.022 mmol). The resulting mixture was purged with argon, then microwaved 2 h at 125° C. Purification by prep-HPLC followed by trituration from MeOH gave the title compound (4 mg, 3%, TFA salt) as a white solid. $^1$H NMR (400 MHz, CD$_3$OD) δ 8.00 (d, J=8.0 Hz, 1H), 7.57 (d, J=8.0 Hz, 2H), 7.46 (s, 1H, partially overlapping with the peak at 7.44 ppm), 7.44 (d, J=16.4 Hz, 1H, partially overlapping with the peak at 7.46 ppm), 7.31 (d, J=16.8 Hz, 1H), 7.10-7.00 (m, 3H), 6.84 (d, J=8.4 Hz, 1H), 6.62 (d, J=7.2 Hz, 1H), 5.59 (s, 1H), 4.01-3.00 (m, 12H), 2.99 (s, 3H), 2.30-2.15 (m, 2H); MS ESI 506.3 [M+H]$^+$, calcd for [C$_{31}$H$_{31}$N$_5$O$_2$+H]$^+$ 506.2.

Example A175. (1R,2S)-(E)-5'-methoxy-2-(3-(4-(4-methylpiperazin-1-yl)styryl)-1H-indazol-6-yl)spiro [cyclopropane-1,3'-indolin]-2'-one 2,2,2-trifluoroacetate

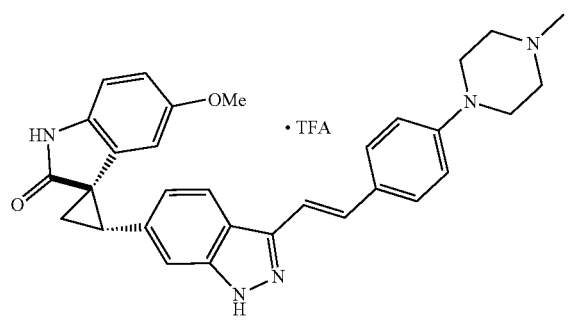 [SMILES: COc1ccc2c(c1)[C@]1(C[C@H]1c1ccc3c(/C=C/c4ccc(N5CCN(C)CC5)cc4)n[nH]c3c1)C(=O)N2]

The title compound was prepared in a similar manner to Example A51B using (1R,2S)-2-(3-iodo-1H-indazol-6-yl)-5'-methoxy spiro[cyclopropane-1,3'-indolin]-2'-one (36.0 mg, 0.083 mmol) and (E)-1-methyl-4-(4-(2-(4,4,5,5-tetramethyl-1,3,2-dioxaborolan-2-yl)vinyl)phenyl)piperazine (31.9 mg, 0.097 mmol). The reaction mixture was diluted with MeOH (3 mL) and poured onto a 20 cc PoraPak Rxn Cx cartridge. After rinsing with MeOH (20 mL), the title compound was eluted using 2M NH$_3$:MeOH (20 mL). After removal of the solvents in vacuo, the title compound was purified by preparative HPLC to yield the title compound as the TFA salt (yellow solid, 23.3 mg, 45%). $^1$H NMR was identical to Example A174; MS ESI 506.3 [M+H]$^+$, calcd for [C$_{31}$H$_{31}$N$_5$O$_2$+H]$^+$ 506.3.

Example A176. (1R*,2S*)-(E)-2-(3-(4-((dimethylamino)methyl)styryl)-1H-indazol-6-yl)-1'-isopentyl-spiro[cyclopropane-1,3'-indolin]-2'-one

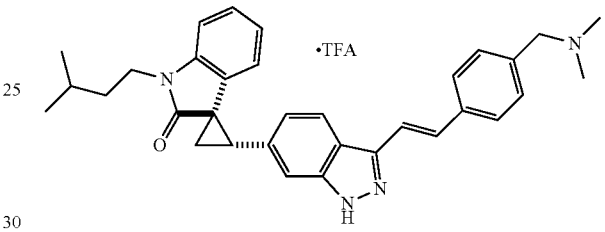

The title compound (7.5 mg, 15%) was obtained as a white solid (prep-HPLC then basified and triturated from MeOH) from (1R*,2S*)-2-(3-iodo-1H-indazol-6-yl)-1'-isopentylspiro[cyclopropane-1,3'-indolin]-2'-one (47 mg, 0.1 mmol) and (E)-N,N-dimethyl-1-(4-(2-(4,4,5,5-tetramethyl-1,3,2-dioxaborolan-2-yl)vinyl)phenyl)methanamine (43 mg, 0.15 mmol) using the method for the preparation of Example A51B (PhCH$_3$/EtOH=1 mL/1 mL, 2.5 mol % Pd(PPh$_3$)$_4$, 125° C., 2 h). $^1$H NMR (400 MHz, CD$_3$OD) δ 7.99 (d, J=8.4 Hz, 1H), 7.63 (d, J=8.0 Hz, 2H), 7.48 (d, J=8.4 Hz, 2H), 7.44 (s, 1H), 7.37 (d, J=8.0 Hz, 2H), 7.14 (t, J=7.8 Hz, 1H), 7.02 (d, J=8.0 Hz), 6.99 (d, J=8.0 Hz, 1H), 6.63 (t, J=7.6 Hz, 1H), 6.03 (d, J=7.6 Hz, 1H), 3.92 (t, J=7.2 Hz, 2H), 3.61 (s, 2H), 3.36 (t, J=8.8 Hz, 1H), 2.35 (s, 6H), 2.30-2.17 (m, 2H), 1.75-1.60 (m, 3H), 1.03 (dd, J=6.0 Hz, 2.0 Hz, 6H); MS ESI 505.4 [M+H]$^+$, calcd for [C$_{33}$H$_{36}$N$_4$O+H]$^+$ 505.3.

Example A177. (1R,2S)-(E)-5'-methoxy-2-(3-(4-(2-morpholinoethyl)styryl)-1H-indazol-6-yl)spiro[cyclopropane-1,3'-indolin]-2'-one 2,2,2-trifluoroacetate

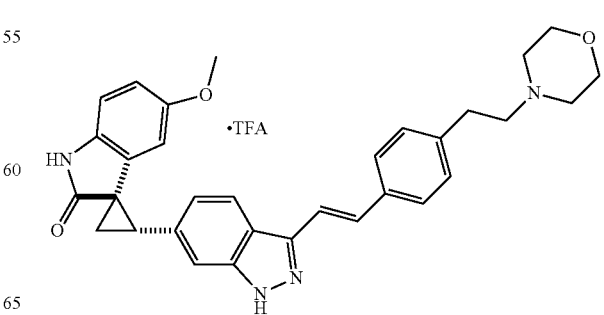

To a mixture of 4-(4-bromophenethyl)morpholine (731 mg, 2.71 mmol) and 4,4,5,5-tetramethyl-2-vinyl-1,3,2-dioxaborolane (0.5 mL, 2.95 mmol, 1.1 eq.) in a 20 mL microwave vial was added Et$_3$N (0.76 mL, 5.4 mmol, 2 eq.), followed by Pd(P$^t$Bu$_3$)$_2$ (14 mg, 0.027 mmol, 1 mol %). The resulting mixture was purged with argon, then capped and heated at 80° C. (oil temp.) for 2 h. After cooling to rt, the reaction was quenched with sat. NaHCO$_3$ (10 mL), H$_2$O (10 mL), extracted with EtOAc (30 mL×2) and dried over Na$_2$SO$_4$. After evaporation of the solvents, the residue was purified by Biotage column system (EtOAc/hex gradient: 0-100%) to give (E)-4-(4-(2-(4,4,5,5-tetramethyl-1,3,2-dioxaborolan-2-yl)vinyl)phenethyl)morpholine as a white solid (714 mg, 77%). $^1$H NMR (400 MHz, CDCl$_3$) δ 7.42 (d, J=8.0 Hz, 2H), 7.38 (d, J=19.0 Hz, 1H), 7.19 (d, J=7.8 Hz, 2H), 6.13 (d, J=18.3 Hz, 1H), 3.75 (t, J=4.4 Hz, 4H), 2.84-2.77 (m, 2H), 2.63-2.56 (m, 2H), 2.53 (br, pseudo s, 4H), 1.32 (s, 12H).

To a mixture of (1R,2S)-2-(3-iodo-1H-indazol-6-yl)-5'-methoxyspiro [cyclopropane-1,3'-indolin]-2'-one (172 mg, 0.4 mmol) and (E)-4-(4-(2-(4,4,5,5-tetramethyl-1,3,2-dioxaborolan-2-yl)vinyl)phenethyl)morpholine (138 mg, 0.4 mmol) in PhCH$_3$/EtOH (8 mL/4 mL) in a 20 mL microwave vial was added 1 M Na$_2$CO$_3$ (0.8 mL, 0.8 mmol), followed by Pd(PPh$_3$)$_4$ (23 mg, 0.02 mmol, 5 mol %). The resulting mixture was purged with argon, and then microwaved 2 h at 125° C. After cooling to rt, the mixture was diluted with H$_2$O (20 mL), extracted with EtOAc (30 mL×2) and dried over Na$_2$SO$_4$. After removal of the solvents, the residue was redissolved in DMF (4 mL) and purified by prep-HPLC to give the title compound as a pale yellow solid (115 mg, 45%). $^1$H NMR (400 MHz, CD$_3$OD) δ 7.90 (d, J=8.4 Hz, 1H), 7.53 (d, J=7.2 Hz, 2H), 7.43 (s, 1H), 7.37 (d, J=6.4 Hz, 2H), 7.28 (d, J=7.2 Hz, 2H), 6.95 (d, J=7.6 Hz, 1H), 6.81 (d, J=8.4 Hz, 1H), 6.57 (d, J=7.6 Hz, 1H), 5.57 (s, 1H), 4.06 (d, J=11.2 Hz, 2H), 3.80 (t, J=11.2 Hz, 2H), 3.56 (d, J=11.2 Hz, 2H), 3.38 (t, J=7.6 Hz, 2H), 3.27-3.12 (m, 5H), 3.09-3.05 (m, 2H) 2.20-2.10 (m, 2H); MS ESI 521.4 [M+H]$^+$, calcd for [C$_{32}$H$_{32}$N$_4$O$_3$+H]$^+$ 521.2.

Optical Rotation [α]$^{23}_D$=−90° (c 0.67, MeOH).

Example A178. (1R*,2S*)-(E)-5'-methoxy-2-(3-(4-(2-morpholinoethyl) styryl)-1H-indazol-6-yl)spiro [cyclopropane-1,3'-indolin]-2'-one 2,2,2-trifluoroacetate

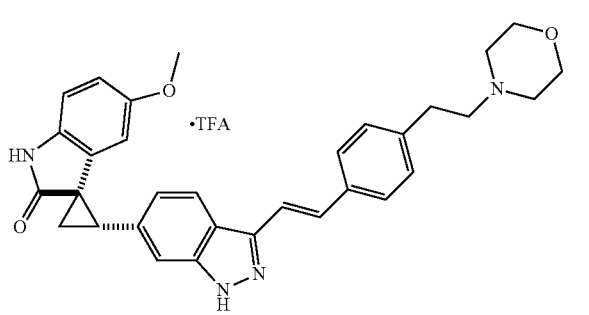

To a mixture of crude (1R*,2S*)-5'-methoxy-2-(3-vinyl-1H-indazol-6-yl)spiro[cyclopropane-1,3'-indolin]-2'-one (100 mg, 0.2 mmol) and 4-(4-bromophenethyl)morpholine (54 mg, 0.2 mmol) in DMF (2 mL) was added $^i$Pr$_2$NEt (0.07 mL), followed by Pd(OAc)$_2$ (2.2 mg, 0.01 mmol) and P(o-tol)$_3$ (6.7 mg, 0.022 mmol). The resulting mixture was purged with argon, and then microwaved 2 h at 125° C. The mixture was purification by prep-HPLC gave the title compound as a white solid 36 mg, 28%, TFA salt. Spectral data was identical to that in obtained in Example A177.

Example A179. (1R*,2S*)-(E)-5'-methoxy-2-(3-(4-(4-methylpiperazine-1-carbonyl)styryl)-1H-indazol-6-yl)spiro[cyclopropane-1,3'-indolin]-2'-one 2,2,2-trifluoroacetate

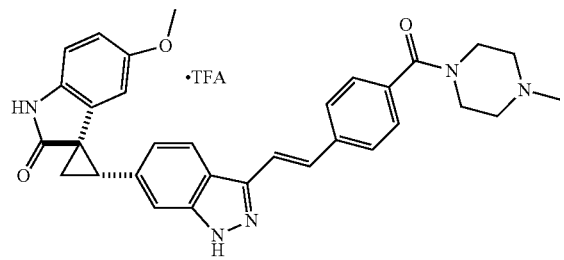

To a mixture of crude (1R*,2S*)-5'-methoxy-2-(3-vinyl-1H-indazol-6-yl)spiro [cyclopropane-1,3'-indolin]-2'-one (100 mg, 0.2 mmol) and (4-bromophenyl)(4-methylpiperazin-1-yl)methanone (56.6 mg, 0.2 mmol) in DMF (2 mL) was added $^i$Pr$_2$NEt (0.07 mL), followed by Pd(OAc)$_2$ (2.2 mg, 0.01 mmol) and P(o-tol)$_3$ (6.7 mg, 0.022 mmol). The resulting mixture was purged with argon, and then microwaved 2 h at 125° C. LC-MS showed incompletion and it was microwaved an additional 90 min at 130° C. Purification by prep-HPLC gave the title compound (32 mg, 25%) as a pale yellow solid. $^1$H NMR (400 MHz, CD$_3$OD) δ 7.97 (d, J=8.4 Hz, 1H), 7.71 (d, J=8.4 Hz, 2H), 7.55-7.45 (m, 5H), 7.01 (d, J=8.4 Hz, 1H), 6.83 (d, J=8.4 Hz, 1H), 6.59 (dd, J=8.4 Hz, 2.4 Hz, 1H), 5.58 (d, J=2.4 Hz, 1H), 3.65-3.10 (m, 12H), 2.96 (s, 3H), 2.25-2.14 (m, 2H); MS ESI 534.4 [M+H]$^+$, calcd for [C$_{32}$H$_{31}$N$_5$O$_3$+H]$^+$ 534.3.

Example A180. (1R*,2S*)-(E)-2-(3-(4-((dimethylamino)methyl)styryl)-1H-indazol-6-yl)-1'-(2-methoxyethyl)spiro[cyclopropane-1,3'-indolin]-2'-one 2,2,2-trifluoroacetate

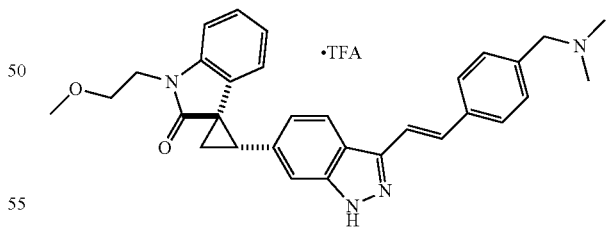

The title compound (30 mg, 25%, TFA salt) was obtained as a colorless sticky oil from (1R*,2S*)-2-(3-iodo-1H-indazol-6-yl)-1'-(2-methoxyethyl)spiro[cyclopropane-1,3'-indolin]-2'-one (92 mg, 0.2 mmol) and (E)-N,N-dimethyl-1-(4-(2-(4,4,5,5-tetramethyl-1,3,2-dioxaborolan-2-yl)vinyl)phenyl)methanamine (86 mg, 0.3 mmol) using the method for the preparation of Example A51B (PhCH$_3$/EtOH=3 mL/1.5 mL, 2.5 mol % Pd(PPh$_3$)$_4$, 120° C., 2 h). $^1$H NMR (400 MHz, CD$_3$OD) δ 7.99 (d, J=8.4 Hz, 1H), 7.75 (d, J=8.0 Hz, 2H), 7.55-7.45 (m, 5H), 7.13-7.07 (m, 2H), 7.01 (d, J=8.4 Hz, 1H), 6.61 (dd, J=8.0 Hz, 1H), 6.01 (d, J=7.2 Hz, 1H), 4.32 (s, 2H), 4.05 (t, J=5.4 Hz, 2H), 3.71 (t, J=5.6 Hz, 2H), 3.41-3.35 (m, 4H), 2.89 (s, 6H), 2.28-2.18 (m, 2H); MS ESI 493.4 [M+H]+, calcd for [C$_{31}$H$_{32}$N$_4$O$_2$+H]+ 493.3.

Example A181. (1R*,2S*)-2-(3-4E)-2-(5-((dimethylamino)methyl)thiophen-3-yl)vinyl)-1H-indazol-6-yl)-5'-methoxyspiro[cyclopropane-1,3'-indolin]-2'-one 2,2,2-trifluoroacetate

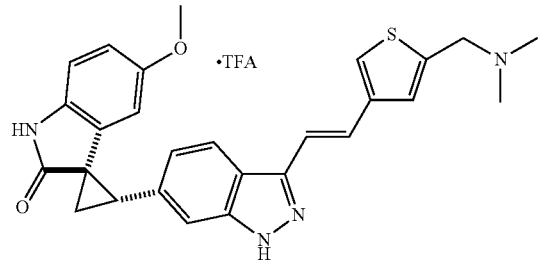 [SMILES: COc1ccc2c(c1)[C@]1(C[C@H]1c1ccc3c(/C=C/c4csc(CN(C)C)c4)n[nH]c3c1)C(=O)N2]

The title compound (147 mg, 35%, TFA salt) was obtained as a light yellow solid from (1R*,2S*)-2-(3-iodo-1H-indazol-6-yl)-5'-methoxyspiro[cyclopropane-1,3'-indolin]-2'-one (172 mg, 0.4 mmol) and (E)-N,N-dimethyl-1-(4-(2-(4,4,5,5-tetramethyl-1,3,2-dioxaborolan-2-yl)vinyl) thiophen-2-yl)methanamine (176 mg, 0.6 mmol) using the method for the preparation of Example A51B (PhCH$_3$/EtOH=8 mL/4 mL, 5 mol % Pd(PPh$_3$)$_4$, 125° C., 2 h). $^1$H NMR (400 MHz, CD$_3$OD) δ 7.82 (d, J=8.4 Hz, 1H), 7.63 (s, 1H), 7.56 (s, 1H), 7.42 (s, 1H), 7.37 (d, J=16.8 Hz, 1H), 7.24 (d, J=16.4 Hz, 1H), 6.90 (d, J=8.4 Hz, 1H), 6.81 (d, J=8.4 Hz, 1H), 6.55 (dd, J=8.2 Hz, 2.2 Hz, 1H), 5.55 (d, J=2.0 Hz, 1H), 4.53 (s, 2H), 3.31 (t, J=8.2 Hz, 1H), 3.20 (s, 3H), 2.90 (s, 6H), 2.20-2.10 (m, 2H); MS ESI 471.2 [M+H]+, calcd for [C$_{27}$H$_{26}$N$_4$O$_2$S+H]+ 471.2.

Example A182. (1R*,2S*)-5'-methoxy-2-(3-(4-(piperazin-1-yl)styryl)-1H-indazol-6-yl)spiro[cyclopropane-1,3'-indolin]-2'-one 2,2,2-trifluoroacetate

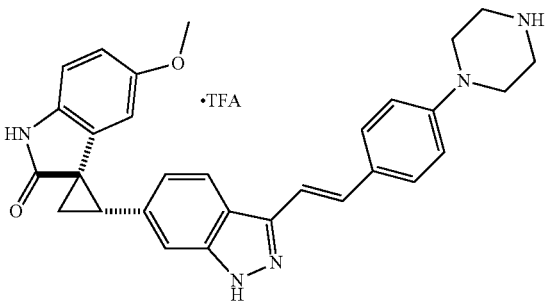

The title compound (42 mg, 35%, TFA salt) was obtained as a yellow solid from (1R*,2S*)-2-(3-iodo-1H-indazol-6-yl)-5'-methoxyspiro[cyclopropane-1,3'-indolin]-2'-one (86.2 mg, 0.2 mmol) and (E)-1-(4-(2-(4,4,5,5-tetramethyl-1,3,2-dioxaborolan-2-yl)vinyl)phenyl)piperazine (62.8 mg, 0.2 mmol) using the method for the preparation of Example A51B (PhCH$_3$/EtOH=3 mL/1.5 mL, 2.5 mol % Pd(PPh$_3$)$_4$, 125° C., 2 h). $^1$H NMR (400 MHz, CD$_3$OD) δ 7.89 (d, J=8.8 Hz, 1H), 7.50 (d, J=8.8 Hz, 2H), 7.47 (s, 1H), 7.35 (d, J=16.8 Hz, 1H), 7.22 (d, J=16.8 Hz, 1H), 7.02 (d, J=8.8 Hz, 2H), 6.96 (d, J=8.4 Hz, 1H), 6.86 (d, J=8.8 Hz, 1H), 6.60 (dd, J=8.6 Hz, J=2.2 Hz, 1H), 5.58 (s, 1H), 3.49-3.43 (m, 4H), 3.40-3.30 (m, 5H), 3.23 (s, 3H), 2.25-2.15 (m, 2H); MS ESI 492.3 [M+H]+, calcd for [C$_{30}$H$_{29}$N$_5$O$_2$+H]+ 492.2.

Example A183. (1R,2S)-5'-methoxy-2-(3-((E)-2-(5-(morpholinomethyl)thiophen-3-yl)vinyl)-1H-indazol-6-yl)spiro[cyclopropane-1,3'-indolin]-2'-one 2,2,2-trifluoroacetate

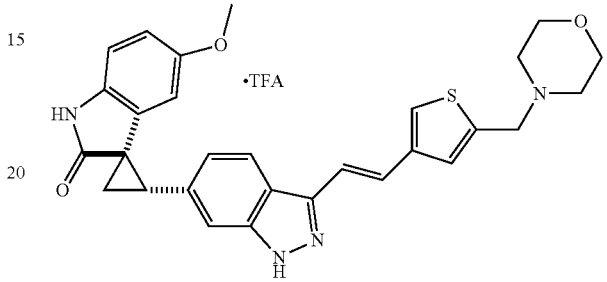

The title compound (413 mg, 66%, TFA salt) was obtained as a pale yellow solid from (1R,2S)-2-(3-iodo-1H-indazol-6-yl)-5'-methoxyspiro[cyclopropane-1,3'-indolin]-2'-one (514 mg, 1.2 mmol) and (E)-4-((4-(2-(4,4,5,5-tetramethyl-1,3,2-dioxaborolan-2-yl)vinyl)thiophen-2-yl)methyl) morpholine (442 mg, 1.32 mmol) using the method for the preparation of Example A51B (PhCH$_3$/EtOH=4.5 mL/9 mL, 1.67 mol % Pd(PPh$_3$)$_4$, 110° C., 2 h). $^1$H NMR (400 MHz, CD$_3$OD) δ 7.67 (d, J=8.4 Hz, 1H), 7.57 (s, 1H), 7.45 (s, 1H), 7.39 (s, 1H), 7.26 (d, J=16.4 Hz, 1H), 7.16 (d, J=16.4 Hz, 1H), 6.78 (d, J=8.4 Hz, 2H), 6.48 (d, J=8.4 Hz, 1H), 5.54 (s, 1H), 4.52 (s, 2H), 4.05-3.65 (m, 4H), 3.50-3.05 (m, 8H), 2.12-2.03 (m, 2H); MS ESI 513.3 [M+H]+, calcd for [C$_{29}$H$_{28}$N$_4$O$_3$S+H]+ 513.2.

Optical Rotation [α]$^{23}_D$=−92° (c 0.35, MeOH).

Example A184. (1R*,2S*)-5'-methoxy-2-(3-((E)-2-(5-(morpholinomethyl)thiophen-3-yl)vinyl)-1H-indazol-6-yl)spiro[cyclopropane-1,3'-indolin]-2'-one 2,2,2-trifluoroacetate

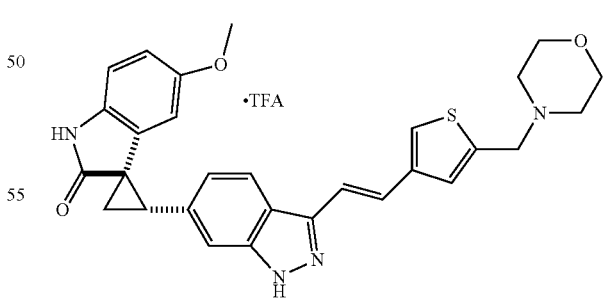

The title compound (129 mg, 52%, TFA salt) was obtained as a pale yellow solid from three identical batches of (1R*,2S*)-2-(3-iodo-1H-indazol-6-yl)-5'-methoxyspiro [cyclopropane-1,3'-indolin]-2'-one (172 mg, 0.4 mmol) and (E)-4-((4-(2-(4,4,5,5-tetramethyl-1,3,2-dioxaborolan-2-yl) vinyl)thiophen-2-yl)methyl)morpholine (136 mg, 0.44 mmol) using the method for the preparation of Example A51B (PhCH$_3$/EtOH=8 mL/4 mL, 5 mol % Pd(PPh$_3$)$_4$, 125° C., 2 h). Spectral data was identical to that in obtained in Example A183.

Example A185. (1R,2S)-(E)-2-(3-(4-trans-2,6-dimethylmorpholino)methyl)styryl)-1H-indazol-6-yl)-5'-methoxyspiro[cyclopropane-1,3'-indolin]-2'-one 2,2,2-trifluoroacetate

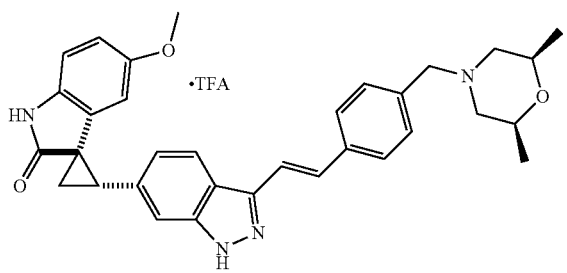

The title compound (445 mg, 57%, TFA salt) was obtained as a pale yellowish white solid from three identical batches of (1R,2S)-2-(3-iodo-1H-indazol-6-yl)-5'-methoxyspiro[cyclopropane-1,3'-indolin]-2'-one (172 mg, 0.4 mmol) and cis-2,6-dimethyl-4-(4-((E)-2-(4,4,5,5-tetramethyl-1,3,2-dioxaborolan-2-yl)vinyl)benzyl)morpholine (150 mg, 0.42 mmol) using the method for the preparation of Example A51B (PhCH$_3$/EtOH=9 mL/4.5 mL, 2.5 mol % Pd(PPh$_3$)$_4$, 110° C., 2 h). $^1$H NMR (400 MHz, CD$_3$OD) δ 7.75 (d, J=8.4 Hz, 1H), 7.57 (d, J=8.0 Hz, 2H), 7.46 (d, J=8.0 Hz, 2H), 7.42 (s, 1H), 7.35 (d, J=16.8 Hz, 1H), 7.30 (d, J=16.4 Hz, 1H), 6.82 (d, J=9.2 Hz, 1H, partially overlapping with the peak at 6.80 ppm), 6.80 (d, J=8.8 Hz, partially overlapping with the peak at 6.82 ppm), 6.51 (d, J=8.4 Hz, 1H), 5.19 (s, 1H), 4.28 (s, 2H), 3.92-3.80 (m, 2H), 3.40-3.30 (m, 2H), 3.27 (t, J=8.4 Hz, 1H), 3.15 (s, 3H), 2.70 (t, J=11.4 Hz, 2H), 2.15-2.05 (m, 2H), 1.18 (d, J=6.0 Hz, 6H); MS ESI 535.3 [M+H]$^+$, calcd for [C$_{33}$H$_{34}$N$_4$O$_3$+H]$^+$ 535.3.

Optical Rotation $[\alpha]^{23}_D$=−91° (c 0.31, MeOH).

Example A186. (1R*,2S*)-(E)-2-(3-(4-trans-2,6-dimethylmorpholino) methyl)styryl)-1H-indazol-6-yl)-5'-methoxyspiro[cyclopropane-1,3'-indolin]-2'-one 2,2,2-trifluoroacetate

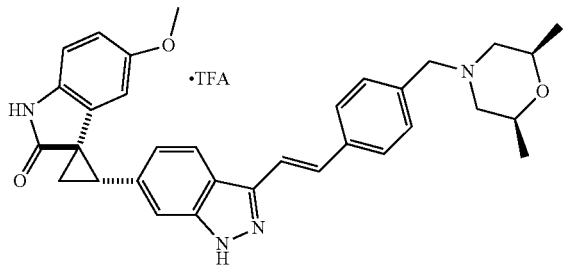

To a mixture of (1R*,2S*)-2-(3-iodo-1H-indazol-6-yl)-5'-methoxyspiro[cyclopropane-1,3'-indolin]-2'-one (431 mg, 1 mmol), (E)-4-(2-(4,4,5,5-tetramethyl-1,3,2-dioxaborolan-2-yl)vinyl)benzaldehyde (284 mg, 1.1 mmol) in PhCH$_3$/EtOH (8 mL/4 mL) was added 1 M Na$_2$CO$_3$ (2 mL, 2 mmol), followed by Ph(PPh$_3$)$_4$ (29 mg, 0.025 mmol). The resulting mixture was purged with argon and then microwaved 2 h at 125° C. After aqueous workup (extraction with EtOAc) and removal of solvents, the residue was redissolved in DCE/THF (45 mL/15 mL). Cis-2,6-dimethylmorpholine (115 mg, 1 mmol) and NaBH(OAc)$_3$ (254 mg, 1.2 mmol) were added, followed by AcOH (0.2 mL). The resulting mixture was stirred for 3 h at rt and quenched with sat. NaHCO$_3$ (20 mL), H$_2$O (20 mL), sat. brine (20 mL). The solution was extracted with EtOAc (60 mL×2) and dried over Na$_2$SO$_4$. After removal of solvent, the residue was purified by prep-HPLC to give the title compound as a pale yellow solid (132 mg, 20% over 2 steps). Spectral data was identical to that in obtained in Example A185.

Example A187. (1R,2S)-(E)-2-(3-(4-(4-ethylpiperazin-1-yl)styryl)-1H-indazol-6-yl)-5'-methoxyspiro[cyclopropane-1,3'-indolin]-2'-one 2,2,2-trifluoroacetate

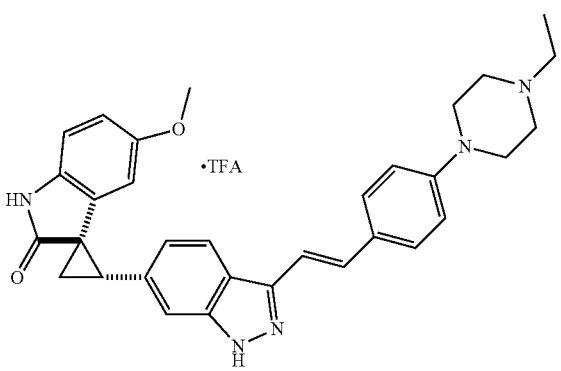

The title compound (414 mg, 55%, TFA salt) was obtained as a white solid (prep-HPLC, followed by trituration from MeOH) from three identical batches of (1R,2S)-2-(3-iodo-1H-indazol-6-yl)-5'-methoxyspiro[cyclopropane-1,3'-indolin]-2'-one (172 mg, 0.4 mmol) and (E)-1-ethyl-4-(4-(2-(4,4,5,5-tetramethyl-1,3,2-dioxaborolan-2-yl)vinyl)phenyl)piperazine (impure, 205 mg, 0.6 mmol) using the method for the preparation of Example A51B (PhCH$_3$/EtOH=6 mL/6 mL, 2.5 mol % Pd(PPh$_3$)$_4$, 110° C., 2 h). $^1$H NMR (400 MHz, CD$_3$OD) δ 7.96 (d, J=8.4 Hz, 1H), 7.53 (d, J=8.4 Hz, 2H), 7.45 (s, 1H), 7.41 (d, J=16.8 Hz, 1H), 7.28 (d, J=16.8 Hz, 1H), 7.03-6.98 (m, 3H), 6.83 (d, J=8.4 Hz, 1H), 6.60 (dd, J=8.4 Hz, 2.0 Hz, 1H), 5.59 (d, J=2.0 Hz, 1H), 3.91 (d, J=12.8 Hz, 2H), 3.66 (d, J=11.6 Hz, 2H), 3.35 (t, J=8.4 Hz, 1H, partially overlapping with MeOH residue), 3.29 (q, J=7.2 Hz, 2H, partially overlapping with the peak at 3.25 ppm), 3.25 (s, 3H, partially overlapping with the peaks at 3.29 ppm and 3.20 ppm), 3.20 (t, J=11.8 Hz, 2H, partially overlapping with the peak at 3.25 ppm), 3.08 (t, J=12.2 Hz, 2H), 2.25-2.15 (m, 2H), 1.39 (t, J=7.2 Hz, 3H); MS ESI 520.4 [M+H]$^+$, calcd for [C$_{32}$H$_{33}$N$_5$O$_2$+H]$^+$ 520.3.

Optical Rotation $[\alpha]^{23}_D$=−108° (c 0.37, MeOH).

Example A188. (1R*,2S*)-(E)-2-(3-(4-(4-ethylpiperazin-1-yl)styryl)-1H-indazol-6-yl)-5'-methoxyspiro[cyclopropane-1,3'-indolin]-2'-one 2,2,2-trifluoroacetate

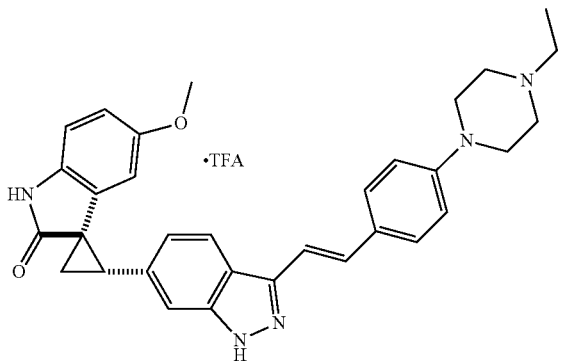

The title compound (53 mg, 42%, TFA salt) was obtained as a light yellow solid from (1R*,2S*)-2-(3-iodo-1H-indazol-6-yl)-5'-methoxyspiro[cyclopropane-1,3'-indolin]-2'-one (86.2 mg, 0.2 mmol) and (E)-1-ethyl-4-(4-(2-(4,4,5,5-tetramethyl-1,3,2-dioxaborolan-2-yl)vinyl)phenyl)piperazine (75 mg, 0.22 mmol) using the method for the preparation of Example A51B (PhCH$_3$/EtOH=3 mL/1.5 mL, 5 mol % Pd(PPh$_3$)$_4$, 125° C., 2 h). Spectral data was identical to that in obtained in Example A187.

Example A189. (1R*,2S*)-(E)-2-(3-(4-(4-isopropylpiperazin-1-yl)styryl)-1H-indazol-6-yl)-5'-methoxyspiro[cyclopropane-1,3'-indolin]-2'-one 2,2,2-trifluoroacetate

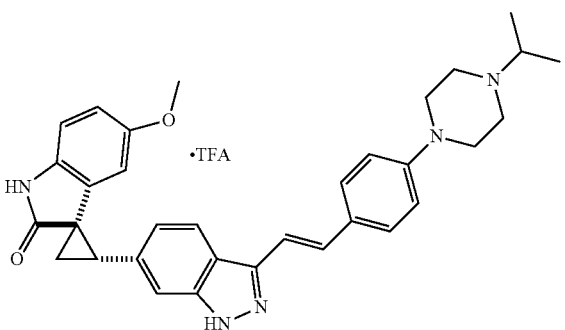

The title compound (85 mg, 66%, TFA salt) was obtained as a light yellow solid from (1R*,2S*)-2-(3-iodo-1H-indazol-6-yl)-5'-methoxyspiro[cyclopropane-1,3'-indolin]-2'-one (86.2 mg, 0.2 mmol) and (E)-1-isopropyl-4-(4-(2-(4,4,5,5-tetramethyl-1,3,2-dioxaborolan-2-yl)vinyl)phenyl)piperazine (78.3 mg, 0.22 mmol) using the method for the preparation of Example A51B (PhCH$_3$/EtOH=3 mL/1.5 mL, 5 mol % Pd(PPh$_3$)$_4$, 125° C., 2 h). $^1$H NMR (400 MHz, CD$_3$OD) δ 7.99 (d, J=8.8 Hz, 1H), 7.57 (d, J=8.0 Hz, 2H), 7.46 (s, 1H, partially overlapping with the peak at 7.44 ppm), 7.44 (d, J=16.4 Hz, 1H, partially overlapping with the peak at 7.46 ppm), 7.31 (d, J=16.4 Hz, 1H), 7.08-7.00 (m, 3H), 6.84 (d, J=8.4 Hz, 1H), 6.61 (d, J=8.0 Hz, 1H), 5.59 (s, 1H), 3.96 (d, J=13.6 Hz, 2H), 3.65-3.55 (m, 3H), 3.40-3.30 (m, 6H), 3.08 (t, J=9.0 Hz, 2H), 2.26-2.15 (m, 2H), 1.43 (d, J=5.6 Hz, 6H); MS ESI 534.4 [M+H]$^+$, calcd for [C$_{33}$H$_{35}$N$_5$O$_2$+H]$^+$ 534.3.

Example A190. (1R*,2S*)-2-(3-((E)-2-(2-ethylisoindolin-5-yl)vinyl)-1H-indazol-6-yl)-5'-methoxyspiro[cyclopropane-1,3'-indolin]-2'-one 2,2,2-trifluoroacetate

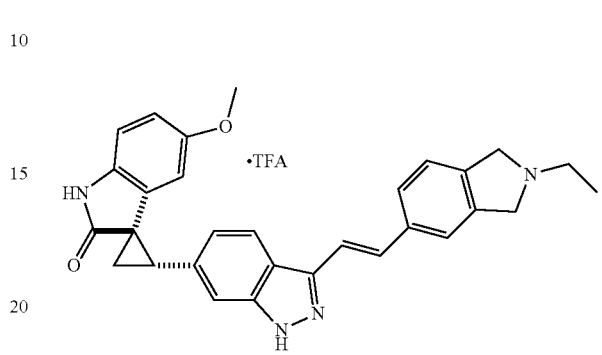

The title compound (54 mg, 46%, TFA salt) was obtained as a pale yellow semi-solid from (1R*,2S*)-2-(3-iodo-1H-indazol-6-yl)-5'-methoxyspiro[cyclopropane-1,3'-indolin]-2'-one (86.2 mg, 0.2 mmol) and crude (E)-2-methyl-5-(2-(4,4,5,5-tetramethyl-1,3,2-dioxaborolan-2-yl)vinyl)isoindoline (73.0 mg, 0.24 mmol) using the method for the preparation of Example A51B (PhCH$_3$/EtOH=3 mL/1.5 mL, 5 mol % Pd(PPh$_3$)$_4$, 125° C., 2 h). $^1$H NMR (400 MHz, CD$_3$OD) δ 7.93 (d, J=8.4 Hz, 1H), 7.61 (s, 1H, partially overlapping with the peak at 7.60 ppm), 7.60 (d, J=8.0 Hz, 1H, partially overlapping with the peak at 7.61 ppm), 7.48-7.37 (m, 4H), 6.90 (d, J=8.4 Hz, 1H), 6.83 (d, J=8.4 Hz, 1H), 6.59 (dd, J=8.4 Hz, 1.6 Hz, 1H), 5.58 (d, J=1.2 Hz, 1H), 4.95-4.80 (m, 2H), 4.60-4.54 (m, 2H), 3.50 (q, J=7.2 Hz, 2H), 3.31 (t, 1H, overlapping with MeOH residue), 3.24 (s, 3H), 2.23-2.13 (m, 2H), 1.44 (t, J=7.2 Hz, 1H); MS ESI 477.3 [M+H]$^+$, calcd for [C$_{30}$H$_{28}$N$_4$O$_2$+H]$^+$ 477.2.

Example A191. (1R,2S)-2-(3-(4-(4-(2-hydroxyethyl)piperazin-1-yl)phenyl)-1H-indazol-6-yl)-5'-methoxyspiro[cyclopropane-1,3'-indolin]-2'-one 2,2,2-trifluoroacetate

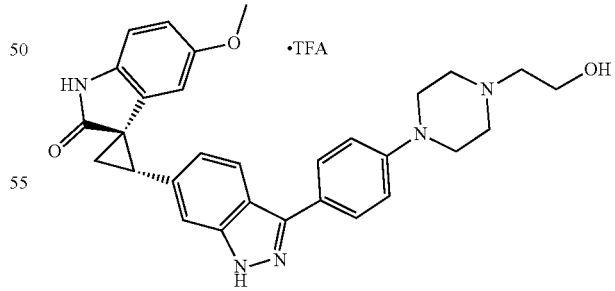

The title compound (42 mg, 34%, TFA salt) was obtained as a white solid from (1R,2S)-2-(3-iodo-1H-indazol-6-yl)-5'-methoxyspiro[cyclopropane-1,3'-indolin]-2'-one (86.2 mg, 0.2 mmol) and 2-(4-(4-(4,4,5,5-tetramethyl-1,3,2-dioxaborolan-2-yl)phenyl) piperazin-1-yl)ethanol (73.0 mg, 0.22 mmol) using the method for the preparation of Example A51B (PhCH$_3$/EtOH=3 mL/1.5 mL, 5 mol % Pd(PPh$_3$)$_4$, 125° C., 2 h). ¹H NMR (400 MHz, CD₃OD) δ 7.80 (d, J=8.4 Hz, 3H), 7.46 (s, 1H), 7.10 (d, J=8.4 Hz, 2H), 6.93 (d, J=8.4 Hz, 1H), 6.82 (d, J=8.4 Hz, 1H), 6.58 (dd, J=8.2 Hz, 1.8 Hz, 1H), 5.59 (s, 1H), 3.95-3.65 (m, 6H), 3.40-3.15 (m, 10H; OMe peak at 3.22 ppm), 2.23-2.13 (m, 2H); MS ESI 510.3 [M+H]⁺, calcd for [C₃₀H₃₁N₅O₃+H]⁺ 510.2.

Optical Rotation [α]$_D^{24}$=−92° (c 0.37, MeOH).

Example A192. (1R,2S)-2-(3-(4-(4-cyclopentylpiperazin-1-yl)phenyl)-1H-indazol-6-yl)-5'-methoxyspiro[cyclopropane-1,3'-indolin]-2'-one 2,2,2-trifluoroacetate

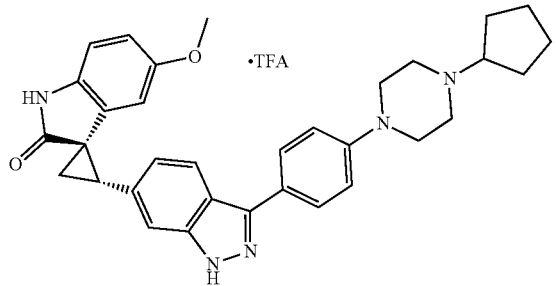 [SMILES: COc1ccc2c(c1)[C@]1(C[C@H]1c1ccc3c(-c4ccc(N5CCN(C6CCCC6)CC5)cc4)n[nH]c3c1)C(=O)N2]

The title compound (43 mg, 33%, TFA salt) was obtained as a white solid (prep-HPLC, followed by trituration from MeOH) from (1R,2S)-2-(3-iodo-1H-indazol-6-yl)-5'-methoxyspiro[cyclopropane-1,3'-indolin]-2'-one (86.2 mg, 0.2 mmol) and 1-cyclopentyl-4-(4-(4,4,5,5-tetramethyl-1,3,2-dioxaborolan-2-yl)phenyl)piperazine (78.3 mg, 0.22 mmol) using the method for the preparation of Example A51B (PhCH₃/EtOH=3 mL/1.5 mL, 5 mol % Pd(PPh₃)₄, 125° C., 2 h). ¹H NMR (400 MHz, DMSO-d₆) δ 13.07 (s, 1H), 10.44 (s, 1H), 9.58 (br, s, 1H), 7.91 (d, J=8.8 Hz, 1H), 7.88 (d, J=8.8 Hz, 2H), 7.50 (s. 1H), 7.14 (d, J=8.4 Hz, 2H), 7.20 (d, J=8.0 Hz, 1H), 6.74 (d, J=8.4 Hz, 1H), 6.57 (d, J=8.8 Hz, 1H), 5.70 (s, 1H), 3.94 (d, J=12.8 Hz, 1H), 3.62 (d, J=11.4 Hz, 1H), 3.29 (s, 3H), 3.26-3.14 (m, 3H), 3.01 (t, J=12.8 Hz, 2H), 2.36-2.30 (m, 2H), 2.10-1.97 (m, 3H), 1.77-1.53 (m, 6H); MS ESI 534.4 [M+H]⁺, calcd for [C₃₃H₃₅N₅O₂+H]⁺ 534.3.

Optical Rotation [α]$_D^{24}$=−116° (c 0.29, MeOH).

Example A193. (1R,2S)-2-(3-(4-(4-cyclohexylpiperazin-1-yl)phenyl)-1H-indazol-6-yl)-5'-methoxyspiro[cyclopropane-1,3'-indolin]-2'-one 2,2,2-trifluoroacetate

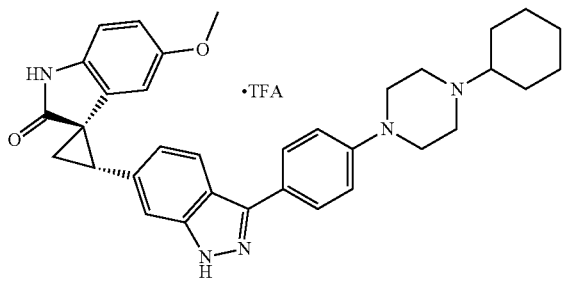 [SMILES: COc1ccc2c(c1)[C@]1(C[C@H]1c1ccc3c(-c4ccc(N5CCN(C6CCCCC6)CC5)cc4)n[nH]c3c1)C(=O)N2]

The title compound (56 mg, 42%, TFA salt) was obtained as a white solid from (1R,2S)-2-(3-iodo-1H-indazol-6-yl)-5'-methoxyspiro[cyclopropane-1,3'-indolin]-2'-one (86.2 mg, 0.2 mmol) and 1-cyclohexyl-4-(4-(4,4,5,5-tetramethyl-1,3,2-dioxaborolan-2-yl)phenyl)piperazine (81.4 mg, 0.22 mmol) using the method for the preparation of Example A51B (PhCH₃/EtOH=3 mL/1.5 mL, 5 mol % Pd(PPh₃)₄, 125° C., 2 h). ¹H NMR (400 MHz, CD₃OD) δ 7.92 (d, J=8.8 Hz, 1H), 7.88 (d, J=8.0 Hz, 2H), 7.49 (s, 1H), 7.18 (d, J=8.4 Hz, 2H), 7.03 (d, J=8.4 Hz, 1H), 6.84 (d, J=9.2 Hz, 1H), 6.62 (dd, J=8.4 Hz, 1H), 5.61 (s, 1H), 4.00 (d, J=12.4 Hz, 2H), 3.67 (d, J=11.6 Hz, 2H), 3.40-3.28 (m, 7H), 3.12 (t, J=12.2 Hz, 2H), 2.27-2.16 (m, 4H), 2.00 (d, J=12.4 Hz, 2H), 1.76 (d, J=13.6 Hz, 1H), 1.60-1.20 (m, 5H); MS ESI 548.4 [M+H]⁺, calcd for [C₃₄H₃₇N₅O₂+H]⁺ 548.3.

Optical Rotation [α]$_D^{23}$=−97° (c 0.21, MeOH).

Example A194. (1R,2S)-(E)-5'-methoxy-2-(3-(4-(2-morpholinoethoxy)styryl)-1H-indazol-6-yl)spiro[cyclopropane-1,3'-indolin]-2'-one 2,2,2-trifluoroacetate

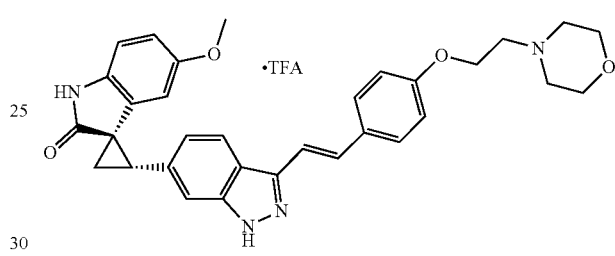

The title compound (431 mg, 66%, TFA salt) was obtained as a white solid from (1R,2S)-2-(3-iodo-1H-indazol-6-yl)-5'-methoxyspiro[cyclopropane-1,3'-indolin]-2'-one (431 mg, 1 mmol) and ((E)-4-(2-(4-(2-(4,4,5,5-tetramethyl-1,3,2-dioxaborolan-2-yl)vinyl)phenoxy)ethyl)morpholine (359 mg, 1 mmol) using the method for the preparation of Example A51B (PhCH₃/EtOH=4.5 mL/9 mL, 2 mol % Pd(PPh₃)₄, 125° C., 2 h). ¹H NMR (400 MHz, CD₃OD) δ 7.72 (d, J=8.4 Hz, 1H), 7.40-7.34 (m, 3H), 7.22 (d, J=16.4 Hz, 1H), 7.10 (d, J=16.4 Hz, 1H), 6.89 (d, J=8.0 Hz, 2H), 6.80 (d, J=10.0 Hz, 1H, partially overlapping with the peak at 6.78 ppm), 6.78 (d, J=9.2 Hz, 1H, partially overlapping with the peak at 6.80 ppm), 6.49 (d, J=8.4 Hz, 1H), 5.55 (s, 1H), 4.31 (s, 2H), 4.05-3.97 (m, 4H), 3.62-3.50 (m, 4H), 3.30-3.15 (m, 3H; t, J=8.2 Hz, 1H overlapping with m, 2H), 3.12 (s, 3H), 2.10-2.00 (m, 2H); MS ESI 537.4 [M+H]⁺, calcd for [C₃₂H₃₂N₄O₄+H]⁺ 537.2.

Optical Rotation [α]$_D^{23}$=−85° (c 0.24, MeOH).

Example A195. (1R,2S)-(E)-5'-methyl-2-(3-(4-(morpholinomethyl)styryl)-1H-indazol-6-yl)spiro[cyclopropane-1,3'-indolin]-2'-one 2,2,2-trifluoroacetate

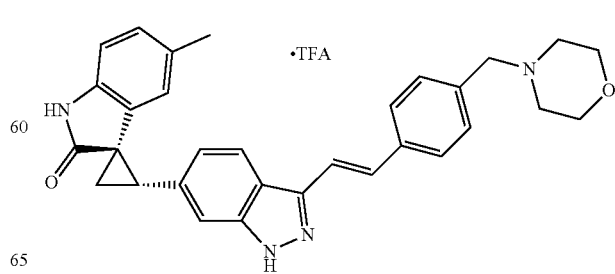

The title compound (470 mg, 78%, TFA salt) was obtained as a yellow solid from (1R,2S)-2-(3-iodo-1H-indazol-6-yl)-5'-methylspiro[cyclopropane-1,3'-indolin]-2'-one (415 mg, 1 mmol) and (E)-4-(4-(2-(4,4,5,5-tetramethyl-1,3,2-dioxaborolan-2-yl)vinyl) benzyl)morpholine (329 mg, 1 mmol) using the method for the preparation of Example A51B (PhCH$_3$/EtOH=4.5 mL/9 mL, 2 mol % Pd(PPh$_3$)$_4$, 110° C., 2 h). $^1$H NMR (400 MHz, CD$_3$OD) δ 7.73 (d, J=8.4 Hz, 1H), 7.53 (d, J=8.0 Hz, 2H), 7.44 (d, J=8.0 Hz, 2H), 7.38 (s, 1H), 7.32 (d, J=16.8 Hz, 1H), 7.27 (d, J=16.8 Hz, 1H), 6.82 (d, J=8.4 Hz, 1H), 6.77 (d, J=8.0 Hz, 1H), 6.73 (d, J=8.0 Hz, 1H), 5.78 (s, 1H), 4.29 (s, 2H), 3.99 (d, J=11.2 Hz, 2H), 3.75 (t, J=11.6 Hz, 2H), 3.42-3.32 (m, 2H), 3.21 (t, J=8.4 Hz, 1H), 3.18-3.08 (m, 2H), 2.09-2.01 (m, 2H), 1.72 (s, 3H); MS ESI 491.3 [M+H]$^+$, calcd for [C$_{31}$H$_{30}$N$_4$O$_2$+H]$^+$ 491.2.

Optical Rotation 89° [α]$^{23}_D$=−89° (c 0.28, MeOH).

Example A196. (1R*,2S*)-(E)-5'-methyl-2-(3-(4-(morpholinomethyl)styryl)-1H-indazol-6-yl)spiro[cyclopropane-1,3'-indolin]-2'-one 2,2,2-trifluoroacetate

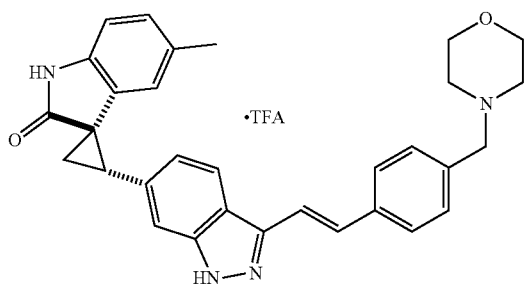

The title compound (27 mg, 22%, TFA salt) was obtained as a yellow solid from (1R*,2S*)-2-(3-iodo-1H-indazol-6-yl)-5'-methylspiro[cyclopropane-1,3'-indolin]-2'-one (83 mg, 0.2 mmol) and (E)-4-(4-(2-(4,4,5,5-tetramethyl-1,3,2-dioxaborolan-2-yl)vinyl)benzyl)morpholine (66 mg, 0.2 mmol) using the method for the preparation of Example A51B. Spectral data was identical to that in obtained in Example A195.

Example A197. (1R,2S)-5'-methoxy-2-(3-((E)-2-(pyridin-3-yl)vinyl)-1H-indazol-6-yl)spiro[cyclopropane-1,3'-indolin]-2'-one

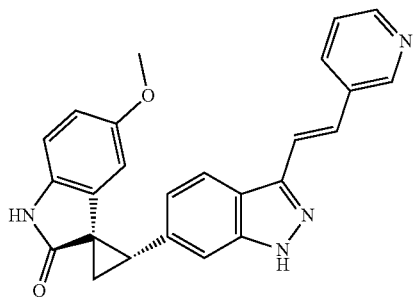

The title compound (113 mg, 55%) was obtained as a yellow solid from (1R,2S)-2-(3-iodo-1H-indazol-6-yl)-5'-methoxyspiro[cyclopropane-1,3'-indolin]-2'-one (216 mg, 0.5 mmol) and (E)-3-(2-(4,4,5,5-tetramethyl-1,3,2-dioxaborolan-2-yl)vinyl)pyridine (128 mg, 0.55 mmol) using the method for the preparation of Example A51B (PhCH$_3$/EtOH=8 mL/4 mL, 4 mol % Pd(PPh$_3$)$_4$, 125° C., 2 h). $^1$H NMR (400 MHz, DMSO-d$_6$) δ 11.31 (s, 1H), 10.45 (s, 1H), 9.04 (s, 1H), 8.62 (d, J=4.4 Hz, 1H), 8.54 (d, J=8.0 Hz, 1H), 8.12 (d, J=8.4 Hz, 1H), 7.81 (d, J=17.2 Hz, 1H), 7.75-7.70 (m, 1H), 7.58 (d, J=16.8 Hz, 1H), 7.51 (s, 1H), 7.08 (d, J=8.4 Hz, 1H), 6.75 (d, J=8.4 Hz, 1H), 6.57 (dd, J=8.0 Hz, 1H), 5.66 (s, 1H), 3.28 (s, 3H), 3.22 (t, J=8.4 Hz, 1H), 2.38-2.33 (m, 1H), 2.03-1.97 (m, 1H); MS ESI 409.2 [M+H]$^+$, calcd for [C$_{25}$H$_{20}$N$_4$O$_2$+H]$^+$ 409.2.

Optical Rotation [α]$^{23}_D$=−95° (c 0.21, MeOH).

Example A198. (1R,2S)-(E)-2-(3-(4-cis-2,6-dimethylmorpholino)methyl)styryl)-1H-indazol-6-yl)spiro[cyclopropane-1,3'-indolin]-2'-one 2,2,2-trifluoroacetate

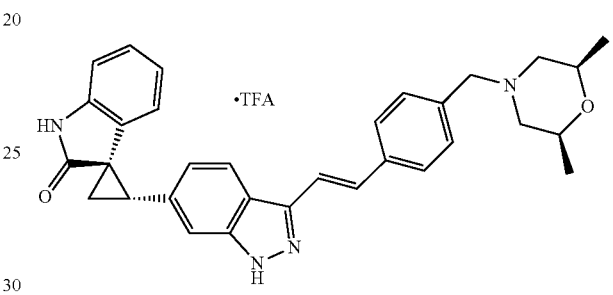

The title compound (284 mg, 57%, TFA salt) was obtained as a white solid from two batches of (1R,2S)-2-(3-iodo-1H-indazol-6-yl)spiro[cyclopropane-1,3'-indolin]-2'-one (160 mg, 0.4 mmol) and cis-2,6-dimethyl-4-((E)-2-(4,4,5,5-tetramethyl-1,3,2-dioxaborolan-2-yl)vinyl) benzyl)morpholine (157 mg, 0.42 mmol) using the method for the preparation of Example A51B (PhCH$_3$/EtOH=9 mL/4.5 mL, 2.5 mol % Pd(PPh$_3$)$_4$, 110° C., 2.5 h). $^1$H NMR (400 MHz, CD$_3$OD) δ 7.74 (d, J=8.4 Hz, 1H), 7.58 (d, J=8.0 Hz, 2H), 7.47 (d, J=7.6 Hz, 2H), 7.40-7.28 (m, 3H), 6.96-6.99 (m, 2H), 6.82 (d, J=8.4 Hz, 1H), 6.40 (t, J=7.4 Hz, 1H), 5.89 (d, J=7.6 Hz, 1H), 4.28 (s, 2H), 3.93-3.80 (m, 2H), 3.34 (d, J=13.6 Hz, 2H, overlapping with MeOH residue), 3.24 (t, J=7.6 Hz, 1H), 2.70 (t, J=7.4 Hz, 2H), 2.08 (p, J=7.6 Hz, 2H), 1.18 (d, J=6.0 Hz, 6H); MS ESI 505.3 [M+H]$^+$, calcd for [C$_{32}$H$_{32}$N$_4$O$_2$+H]$^+$ 505.3.

Optical Rotation [α]$^{23}_D$=−134° (c 0.27, MeOH).

Example A199. (1R,2S)-(E)-2-(3-(3-fluoro-4-(morpholinomethyl)styryl)-1H-indazol-6-yl)-5-methoxyspiro[cyclopropane-1,3'-indolin]-2'-one 2,2,2-trifluoroacetate

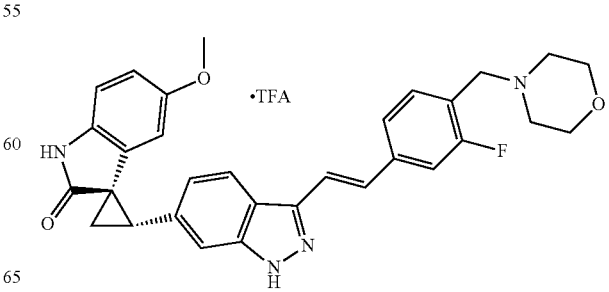

The title compound (154 mg, 60%, TFA salt) was obtained as a white solid from (1R,2S)-2-(3-iodo-1H-indazol-6-yl)-5'-methoxyspiro[cyclopropane-1,3'-indolin]-2'-one (172 mg, 0.4 mmol) and (E)-4-(2-fluoro-4-(2-(4,4,5,5-tetramethyl-1,3,2-dioxaborolan-2-yl)vinyl)benzyl)morpholine (145 mg, 0.42 mmol) using the method for the preparation of Example A51B (PhCH₃/EtOH=6 mL/6 mL, 2.5 mol % Pd(PPh₃)₄, 110° C., 2 h). ¹H NMR (400 MHz, CD₃OD) δ 7.78 (d, J=8.4 Hz, 1H), 7.52 (t, J=7.4 Hz, 1H), 7.45-7.35 (m, 4H), 7.29 (d, J=16.4 Hz, 1H), 6.87 (d, J=8.4 Hz, 1H), 6.80 (d, J=8.4 Hz, 1H), 6.54 (d, J=8.4 Hz, 1H), 5.56 (s, 1H), 4.40 (s, 2H), 4.10-3.90 (m, 4H), 3.50-3.20 (m, 5H), 3.18 (s, 3H), 2.18-2.08 (m, 2H); MS ESI 525.3 [M+H]⁺, calcd for [C₃₁H₂₉FN₄O₃+H]⁺ 525.2.

Optical Rotation [α]²³_D=88° (c 0.27, MeOH).

Example A200. (1R,2S)-(E)-2-(3-(3-fluoro-4-(morpholinomethyl)styryl)-1H-indazol-6-yl)spiro[cyclopropane-1,3'-indolin]-2'-one 2,2,2-trifluoroacetate

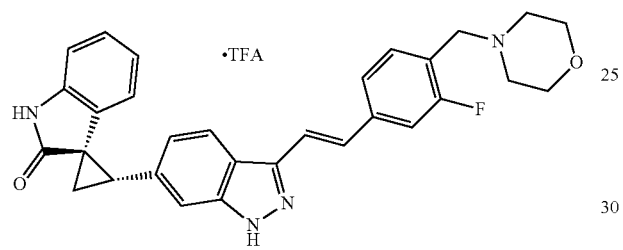

The title compound (228 mg, 75%, TFA salt) was obtained as a white solid from (1R,2S)-2-(3-iodo-1H-indazol-6-yl)spiro[cyclopropane-1,3'-indolin]-2'-one (200 mg, 0.5 mmol) and (E)-4-(2-fluoro-4-(2-(4,4,5,5-tetramethyl-1,3,2-dioxaborolan-2-yl)vinyl) benzyl)morpholine (190 mg, 0.55 mmol) using the method for the preparation of Example A51B (PhCH₃/EtOH=7 mL/7 mL, 2 mol % Pd(PPh₃)₄, 110° C., 2 h). ¹H NMR (400 MHz, CD₃OD) δ 7.50 (d, J=8.4 Hz, 1H), 7.49 (t, J=7.6 Hz, 1H), 7.40-7.30 (m, 4H), 7.24 (d, J=16.8 Hz, 1H), 6.97-6.82 (m, 3H), 6.42 (t, J=7.4 Hz, 1H), 5.90 (d, J=7.6 Hz, 1H), 4.36 (s, 2H), 4.10-3.70 (m, 4H), 3.50-3.15 (m, 5H), 2.12-2.03 (m, 2H); MS ESI 495.3 [M+H]⁺, calcd for [C₃₀H₂₇FN₄O₂+H]⁺ 495.2.

Optical Rotation [α]²³_D=−130° (c 0.40, MeOH).

Example A201. (1R,2S)-(E)-2-(3-(4-((cis-2,6-dimethylpiperidin-1-yl)methyl)styryl)-1H-indazol-6-yl)spiro[cyclopropane-1,3'-indolin]-2'-one 2,2,2-trifluoroacetate

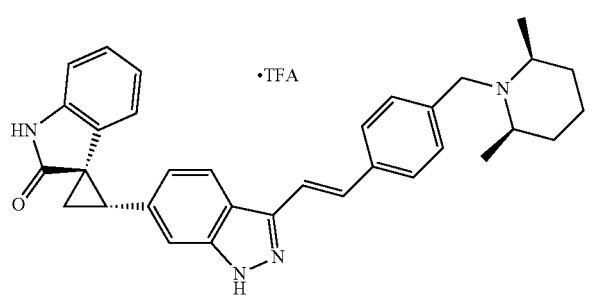 [SMILES: C[C@@H]1CCC[C@H](C)N1Cc1ccc(/C=C/c2n[nH]c3cc([C@@H]4C[C@@]45C(=O)Nc4ccccc45)ccc23)cc1]

The title compound (91 mg, 74%, TFA salt) was obtained as a light yellow solid from (1R,2S)-2-(3-iodo-1H-indazol-6-yl)spiro[cyclopropane-1,3'-indolin]-2'-one (80.2 mg, 0.2 mmol) and cis-2,6-dimethyl-1-(4-((E)-2-(4,4,5,5-tetramethyl-1,3,2-dioxaborolan-2-yl)vinyl)benzyl)piperidine (78.5 mg, 0.22 mmol) using the method for the preparation of Example A51B (PhCH₃/EtOH=1.5 mL/3 mL, 2 mol % Pd(PPh₃)₄, 110° C., 2 h). ¹H NMR (400 MHz, CD₃OD) δ 7.90 (d, J=8.4 Hz, 1H), 7.68-7.60 (s, 1H at 7.51 ppm and d, J=16.8 Hz, 1H at 7.50 ppm overlapping, 1H), 7.64 (d, J=8.8 Hz, 1H, partially overlapping with the peak at 7.66 ppm), 7.55-7.38 (m, 5H), 7.00 (t, J=7.6 Hz, 1H), 6.96-6.90 (m, 2H); 6.50 (t, J=7.6 Hz, 1H), 5.96 (d, J=7.2 Hz, 1H), 4.54 (s, 1.2H), 4.26 (s, 0.8H), 3.60-3.50 (m, 0.7H), 3.28 (t, J=8.0, 1H, partially overlapping with MeOH residue), 3.20-3.10 (m, 1.2H), 2.20-2.08 (m, 2H), 1.96-1.35 (m, 12H); MS ESI 503.3 [M+H]⁺, calcd for [C₃₃H₃₄N₄O+H]⁺ 503.3.

Optical Rotation [α]²³_D=−133° (c 0.22, MeOH).

Example A202. (1R,2S)-2-(3-((E)-2-(5-(morpholinomethyl)thiophen-3-yl)vinyl)-1H-indazol-6-yl)spiro[cyclopropane-1,3'-indolin]-2'-one 2,2,2-trifluoroacetate

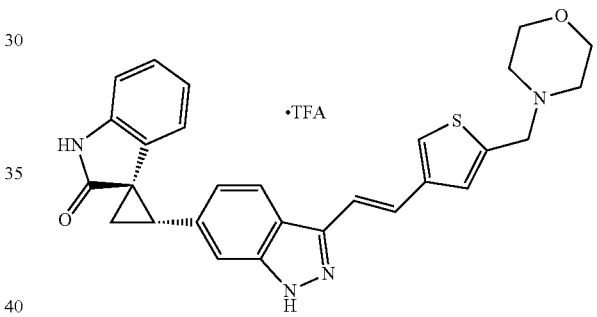

The title compound (76 mg, 64%, TFA salt) was obtained as an off white solid from (1R,2S)-2-(3-iodo-1H-indazol-6-yl)spiro[cyclopropane-1,3'-indolin]-2'-one (80 mg, 0.2 mmol) and (E)-4-((4-(2-(4,4,5,5-tetramethyl-1,3,2-dioxaborolan-2-yl)vinyl)thiophen-2-yl)methyl)morpholine (80 mg, 0.24 mmol) using the method for the preparation of Example A51B (PhCH₃/EtOH=1.5 mL/3 mL, 2 mol % Pd(PPh₃)₄, 110° C., 2 h). ¹H NMR (400 MHz, CD₃OD) δ 7.86 (d, J=8.4 Hz, 1H), 7.68 (s, 1H), 7.62 (s, 1H), 7.44-7.39 (d, J=16.4 Hz, 1H at 7.42 ppm and s, 1H at 7.42 ppm overlapping; 2H); 7.27 (d, J=16.8 Hz, 1H), 7.01 (d, J=7.6 Hz, 1H), 6.93 (d, J=7.2 Hz, 1H, partially overlapping with the peak at 6.92 ppm), 6.92 (d, J=6.8 Hz, 1H, partially overlapping with the peak at 6.93 ppm), 6.51 (t, J=7.6 Hz, 1H), 5.94 (d, J=7.6 Hz, 1H), 4.60 (s, 2H), 4.15-3.70 (m, 4H), 3.55-3.10 (m, 5H), 2.20-2.10 (m, 2H); MS ESI 483.3 [M+H]⁺, calcd for [C₂₈H₂₆N₄O₂S+H]⁺ 483.2.

Optical Rotation [α]²³_D=−133° (c 0.25, MeOH).

Example A203. (1R,2S)-(E)-2-(3-(4-((cis-2,6-dimethylpiperidin-1-yl)methyl)styryl)-1H-indazol-6-yl)-5'-methoxyspiro[cyclopropane-1,3'-indolin]-2'-one 2,2,2-trifluoroacetate

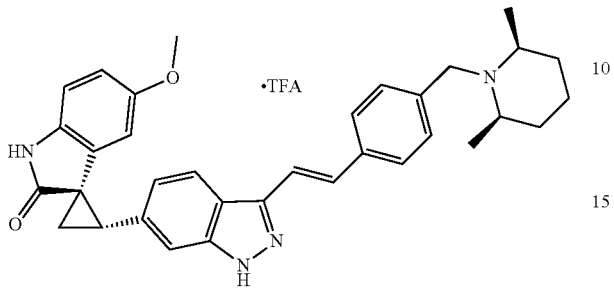

The title compound (78 mg, 60%, TFA salt) was obtained as a white solid from (1R,2S)-2-(3-iodo-1H-indazol-6-yl)-5'-methoxy spiro[cyclopropane-1,3'-indolin]-2'-one (86.2 mg, 0.2 mmol) and cis-2,6-dimethyl-1-(4-((E)-2-(4,4,5,5-tetramethyl-1,3,2-dioxaborolan-2-yl)vinyl)benzyl)piperidine (78.5 mg, 0.22 mmol) using the method for the preparation of Example A51B (PhCH$_3$/EtOH=1.5 mL/3 mL, 2 mol % Pd(PPh$_3$)$_4$, 110° C., 2 h). $^1$H NMR (400 MHz, CD$_3$OD) δ 7.91 (d, J=8.4 Hz, 1H), 7.68-7.63 (s, 1H at 7.66 ppm and d, J=16.4 Hz, 1H at 7.66 ppm overlapping; 2H), 7.53 (d, J=7.6 Hz, 1H), 7.50-7.40 (m, 4H), 6.96 (d, J=8.0 Hz, 1H), 6.82 (d, J=8.4 Hz, 1H), 6.57 (d, J=8.4 Hz, 1H), 5.58 (s, 1H), 4.56 (s, 1.2H), 4.28 (s, 0.8H), 3.60-3.50 (m, 0.7H), 3.31 (t, 1H, overlapping with MeOH residue), 3.23-3.13 (m, 4.3H; OMe and 1.3H), 2.22-2.12 (m, 2H), 2.00-1.35 (m, 12H); MS ESI 533.4 [M+H]$^+$, calcd for [C$_{34}$H$_{36}$N$_4$O$_2$+H]$^+$ 533.3.

Optical Rotation [α]$^{23}_D$=−93° (c 0.27, MeOH).

Example A204. (1R,2S)-(E)-2-(3-(4-(2-morpholinoethoxy)styryl)-1H-indazol-6-yl)spiro[cyclopropane-1,3'-indolin]-2'-one 2,2,2-trifluoroacetate

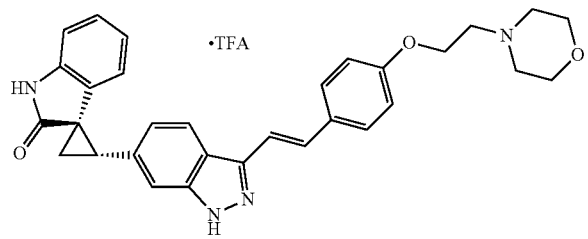 [SMILES: O=C1Nc2ccccc2[C@]12C[C@H]2c1ccc2c(/C=C/c3ccc(OCCN4CCOCC4)cc3)n[nH]c2c1]

The title compound (94 mg, 74%, TFA salt) was obtained as a light yellow solid from (1R,2S)-2-(3-iodo-1H-indazol-6-yl)spiro[cyclopropane-1,3'-indolin]-2'-one (80 mg, 0.2 mmol) and (E)-4-(2-(4-(2-(4,4,5,5-tetramethyl-1,3,2-dioxaborolan-2-yl)vinyl) phenoxy)ethyl)morpholine (72 mg, 0.2 mmol) using the method for the preparation of Example A51B (PhCH$_3$/EtOH=1.5 mL/3 mL, 2 mol % Pd(PPh$_3$)$_4$, 110° C., 2 h). $^1$H NMR (400 MHz, CD$_3$OD) δ 7.83 (d, J=8.4 Hz, 1H), 7.47 (d, J=8.0 Hz, 2H), 7.38 (s, 1H), 7.32 (d, J=16.8 Hz, 1H), 7.19 (d, J=16.4 Hz, 1H), 7.02-6.93 (m, 3H), 6.91 (d, J=7.2 Hz, 1H, partially overlapping with the peak at 6.89 ppm), 6.89 (d, J=8.0 Hz, 1H, partially overlapping with the peak at 6.91 ppm), 6.48 (t, J=7.2 Hz, 1H), 5.93 (d, J=7.6 Hz, 1H), 4.36 (t, J=4.0 Hz, 2H), 4.10-3.76 (m, 4H), 3.65-3.50 (m, 4H), 3.30-3.18 (m, 3H), 2.15-2.05 (m, 2H); MS ESI 507.3 [M+H]$^+$, calcd for [C$_{31}$H$_{30}$N$_4$O$_3$+H]$^+$ 507.2.

Optical Rotation [α]$^{23}_D$=−139° (c 0.29, MeOH).

Example A205. (1R,2S)-(E)-2-(3-(4-(2-morpholinoethyl)styryl)-1H-indazol-6-yl)spiro[cyclopropane-1,3'-indolin]-2'-one 2,2,2-trifluoroacetate

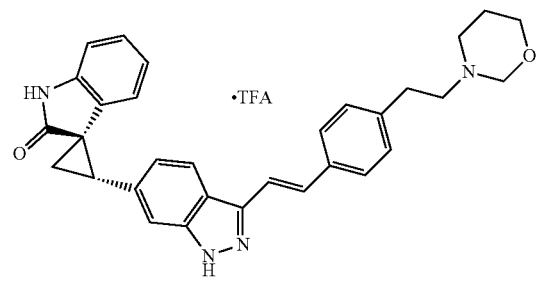 [SMILES: O=C1Nc2ccccc2[C@]12C[C@H]2c1ccc2c(/C=C/c3ccc(CCN4CCCOC4)cc3)n[nH]c2c1]

The title compound (89 mg, 74%, TFA salt) was obtained as a light yellow solid from (1R,2S)-2-(3-iodo-1H-indazol-6-yl)spiro[cyclopropane-1,3'-indolin]-2'-one (80 mg, 0.2 mmol) and (E)-4-(4-(2-(4,4,5,5-tetramethyl-1,3,2-dioxaborolan-2-yl)vinyl)phenethyl) morpholine (69 mg, 0.2 mmol) using the method for the preparation of Example A51B (PhCH$_3$/EtOH=1.5 mL/3 mL, 2 mol % Pd(PPh$_3$)$_4$, 110° C., 2 h). $^1$H NMR (400 MHz, CD$_3$OD) δ 7.86 (d, J=8.4 Hz, 1H), 7.50 (d, J=7.6 Hz, 2H), 7.37 (d, J=16.4 Hz, 2H), 7.34 (s, 1H), 7.26 (d, J=7.6 Hz, 2H), 6.97 (t, J=7.2 Hz, 1H), 6.91 (d, J=7.2 Hz, 2H), 6.49 (t, J=7.4 Hz, 1H), 5.94 (t, J=7.6 Hz, 1H), 4.04 (d, J=12.0 Hz, 2H), 3.80 (t, J=11.8 Hz, 2H), 3.54 (d, J=12.0 Hz, 2H), 3.36 (t, J=8.8 Hz, 2H), 3.27 (t, J=8.6 Hz, 1H), 3.15 (t, J=11.0 Hz, 2H), 3.05 (t, J=8.4 Hz, 2H), 2.16-2.06 (m, 2H); MS ESI 491.3 [M+H]$^+$, calcd for [C$_{31}$H$_{30}$N$_4$O$_2$+H]$^+$ 491.2.

Optical Rotation [α]$^{23}_D$=−141° (c 0.22, MeOH).

Example A206. (1R,2S)-(E)-2-(3-(4-((diethylamino)methyl)styryl)-1H-indazol-6-yl)-5'-methoxy spiro[cyclopropane-1,3'-indolin]-2'-one 2,2,2-trifluoroacetate

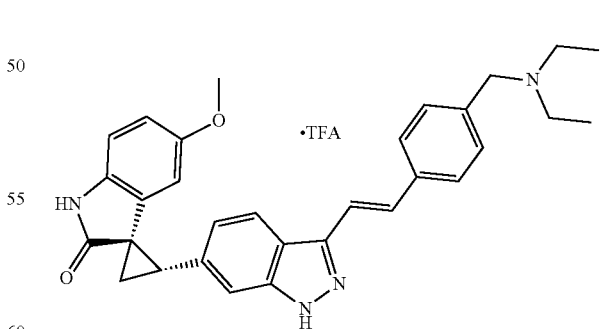

The title compound was synthesized according to the method of Example A51B, by using (1R,2S)-2-(3-iodo-1H-indazol-6-yl-)-5'-methoxyspiro[cyclopropane-1,3'-indolin]-2'-one (700 mg, 1.62 mmol) and (E)-N-ethyl-N-(4-(2-(4,4,5,5-tetramethyl-1,3,2-dioxaborolan-2-yl)vinyl)benzyl) ethanamine (588.5 mg, 1.86 mmol). Purification by preparative HPLC gave the title compound as a cream solid (448 mg, 46%). $^1$H NMR (400 MHz, CD$_3$OD) δ 8.02 (d, J=8.4 Hz, 1H), 7.75 (d, J=8.0 Hz, 2H), 7.54-7.49 (m, 5H), 7.04 (s, J=8.4 Hz, 1H), 6.82 (d, J=8.0 Hz, 1H), 6.60 (d, J=8.4 Hz, 1H), 5.58 (s, 1H), 4.36 (s, 2H), 3.36 (t, J=8.4 Hz, 1H), 3.31-3.18 (bm, 7H), 2.26-2.23 (m, 1H), 2.20-2.17 (m, 1H), 1.37 (t, J=7.2 Hz, 6H); MS ESI 493.4 [M+H]$^+$, calcd for [C$_{31}$H$_{32}$N$_4$O$_2$+H]$^+$ 493.26.

Optical Rotation: $[\alpha]^{22}_D$=−80° (c 0.286, Methanol).

Example A207. (1R*,2S*)-5'-fluoro-2-(3-((E)-2-(6-morpholinopyridin-3-yl)vinyl)-1H-indazol-6-yl)spiro[cyclopropane-1,3'-indolin]-2'-one 2,2,2-trifluoroacetate

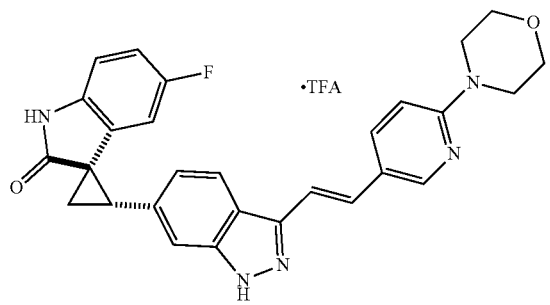

A. (E)-4-(5-(2-(4,4,5,5-tetramethyl-1,3,2-dioxaborolan-2-yl)vinyl)pyridin-2-yl)morpholine According to procedure for the synthesis of example A42A, by using 4-(5-ethylnylpyridin-2-yl)morpholine (90 mg, 0.478 mmol) and 4,4,5,5-tetramethyl-1,3,2-dioxaborolane (0.28 mL, 1.929 mmol) to give the title compound after purification using Biotage on KPNH SNAP 25 gm column with hexane:ethyl acetate (99:1 to 70:30) gradient as a cream solid (123 mg, 81%). $^1$H NMR (400 MHz, CDCl$_3$) δ 8.24 (d, J=1.6 Hz, 1H), 7.71 (dd, J=8.8 Hz, J=6.8 Hz 1H), 7.32 (s, 1H), 6.61 (d, J=9.2 Hz, 1H), 5.95 (d, J=18.4 Hz, 1H), 3.81 (t, J=4.4 Hz, 4H), 3.55 (t, J=5.2 Hz, 4H), 1.31 (s, 12H); MS ESI 317.0 [M+H]$^+$, calcd for [C$_{17}$H$_{25}$BN$_2$O$_3$+H]$^+$ 317.20.

B. (1R*,2S*)-5'-fluoro-2-(3-((E)-2-(6-morpholinopyridin-3-yl)vinyl)-1H-indazol-6-yl)spiro[cyclopropane-1,3'-indolin]-2'-one 2,2,2-trifluoroacetate The title compound was synthesized according to the method of Example A43, by substituting (1R*,2S*)-5'-fluoro-2-(3-iodo-1H-indazol-6-yl)spiro[cyclopropane-1,3'-indolin]-2'-one (50 mg, 0.119 mmol) and (E)-4-(5-(2-(4,4,5,5-tetramethyl-1,3,2-dioxaborolan-2-yl) vinyl)pyridin-2-yl)morpholine (46.1 mg, 0.131 mmol). Purification by preparative HPLC gave the title compound as a cream solid (15 mg, 21%). $^1$H NMR (400 MHz, CD$_3$OD) δ 8.48 (d, J=9.6 Hz, 1H), 8.15 (s, 1H), 8.04 (d, J=8.0 Hz, 1H), 7.55-7.44 (m, 4H), 7.04 (d, J=8.4 Hz, 1H), 6.91-6.88 (m, 1H), 6.81 (t, J=2.4 Hz, 1H), 5.73 (dd, J=8.8 Hz, 6.4 Hz, 1H), 3.89 (t, J=4.4 Hz, 4H), 3.71 (t, J=5.2 Hz, 4H), 3.40 (t, J=8.4 Hz, 1H), 2.32-2.28 (m, 1H), 2.24-2.20 (m, 1H); MS ESI 482.3 [M+H]$^+$, calcd for [C$_{28}$H$_{24}$FN$_5$O$_2$+H]$^+$ 482.19.

Example A208. (1R*,2S*)-(E)-2-(3-(4-((dimethylamino)methyl)styryl)-1H-indazol-6-yl)-5'-flurorospiro[cyclopropane-1,3'-indolin]-2'-one 2,2,2-trifluoroacetate

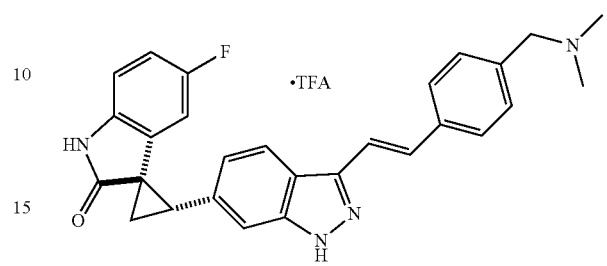

The title compound was synthesized according to the method of Example A51B, by using (1R*,2S*)-5'-fluoro-2-(3-iodo-1H-indazol-6-yl)spiro[cyclopropane-1,3'-indolin]-2'-one (75 mg, 0.178 mmol) and (E)-N,N-dimethyl-1(4-(2-(4,4,5,5-tetramethyl-1,3,2-dioxaborolan-2-yl)vinyl)benzyl) methanamine (63.9 mg, 0.222 mmol). Purification by preparative HPLC gave the title compound as a cream solid (42 mg, 41.4%). $^1$H NMR (400 MHz, CD$_3$OD) δ 8.04 (d, J=8.4 Hz, 1H), 7.77 (d, J=8.0 Hz, 2H), 7.57 (s, 2H), 7.56-7.50 (m, 3H), 7.05 (d, J=8.4 Hz, 1H), 6.91-6.88 (m, 1H), 6.82-6.77 (m, 1H), 5.77 (dd, J=8.8 Hz, J=2.4 Hz, 1H), 4.33 (s, 2H), 3.42-3.38 (m, 1H), 2.88 (s, 6H), 2.32-2.29 (m, 1H), 2.24-2.20 (m, 1H); MS ESI 453.2 [M+H]$^+$, calcd for [C$_{28}$H$_{25}$FN$_4$O+H]$^+$ 453.2.

Example A209. 1R*,2S*1-5'-(difluoromethoxy)-2-(3-(6-(4-methylpiperazine-1-yl)pyridine-3-yl)-1H-indazol-6-yl) spiro[cyclopropane-1,3'-indolin]-2'-one 2,2,2-trifluoroacetate

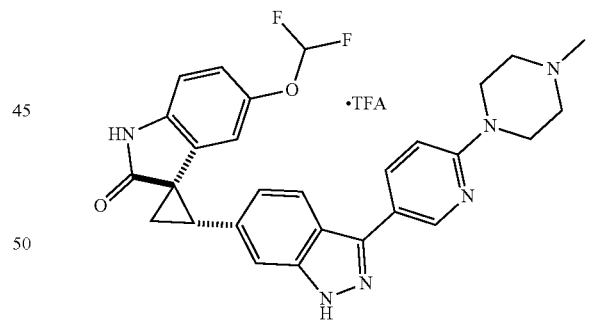

To a suspension of NaH (18.96 mg, 0.474 mmol) in DMF (1.0 mL) at room temperature was added trimethylsulfoxonium iodide (35.03 mg, 0.159 mmol). The resulting solid suspension was stirred at rt for 15 min followed by addition of (E)-5'-(difluoromethoxy)-3-((3-(6-(4-methylpiperazine-3-yl)-1H-indazol-6-1)methylene)-indolin-2-one (40 mg, 0.079 mmol) in single lot. The reaction mixture was then stirred at 55° C. for 18 h. The reaction was cooled to rt and quenched with saturated NH$_4$Cl sol. The mixture was extracted with EtOAc and the combined organic extracts were washed with brine, dried over MgSO$_4$ and concentrated to give yellow viscous oil. The crude product was purified by silica gel chromatography (98:2 to 94:6 CH$_2$Cl$_2$/

2N NH$_3$:MeOH) gradient to yield the title compound as an off-white solid. (11 mg, 26%). $^1$H NMR (400 MHz, CD$_3$OD) δ 8.66 (d, J=2.0 Hz, 1H), 8.10 (dd, J=8.8 Hz, J=2.4 Hz, 1H), 7.85 (d, J=8.4 Hz, 1H), 7.48 (s, 1H), 6.98 (t, J=9.2 Hz, 2H), 6.90 (d, J=8.8 Hz, 1H), 6.85 (d, J=2.0 Hz, 1H), 6.13 (t, J=74 Hz, 1H), 5.77 (d, J=2.0 Hz, 1H), 3.64 (bm, 4H), 3.41 (t, J=8.4 Hz, 1H), 2.60 (t, J=5.2 Hz, 4H), 2.40 (s, 3H), 2.33-2.29 (m, 1H), 2.24-2.21 (m, 1H); MS ESI 517.2 [M+H]$^+$, calcd for [C$_{28}$H$_{26}$F$_2$N$_6$O$_2$+H]$^+$ 517.21.

Example A210. 1R*,2S*1-5'-fluoro-2-(3-(6-(4-methylpiperazine-1-yl)pyridine-3-yl)-1H-indazol-6-yl)-spiro[cyclopropane-1,3'-indolin]-2'-one

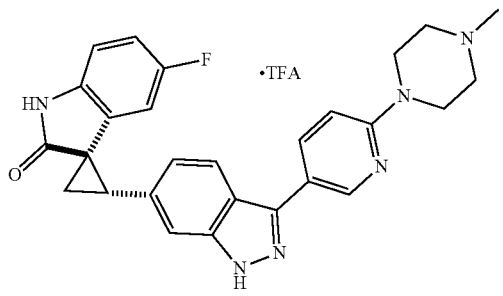

The title compound was synthesized according to Example A209, by using (E/Z)-5'-fluoro-3-((3-(6-(4-methylpiperazine-3-yl)-1H-indazol-6-yl)methylene)-indolin-2-one (100 mg, 0.0.22 mmol) to give the title compound as a cream solid (51.5 mg, 50%). $^1$H NMR (400 MHz, DMSO-d$_6$) δ 13.11 (s, 1H), 10.66 (s, 1H), 8.70 (s, 1H), 8.07 (d, J=9.2 Hz, 1H), 7.90 (d, J=8.4 Hz, 1H), 7.50 (s, 1H), 7.03-6.94 (m, 2H), 6.82 (d, J=6.0 Hz, 2H), 5.87 (d, J=8.4 Hz, 1H), 3.26 (bm, 4H), 2.21 (s, 3H), 2.45-2.39 (m, 5H), 2.05-2.01 (m, 1H); MS ESI 469.3 [M+H]$^+$, calcd for [C$_{27}$H$_{25}$FN$_6$O+H]$^+$ 469.21.

Example A211. (1R*,2S*)-(E)-2-(3-(4-((diethylamino)methyl)styryl)-1H-indazol-6-yl)spiro-[cyclopropane-1,3'-indolin]-2'-one 2,2,2-trifluoroacetate

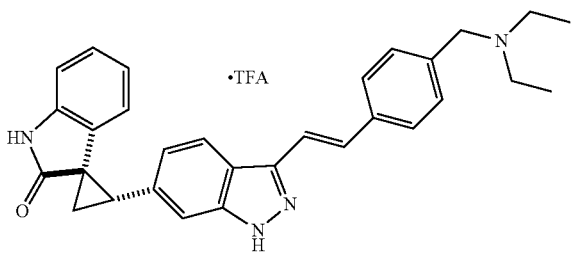

A. N-ethyl-N-(4-ethynylbenzyl)ethanamine

Sodium triacetoxyborohydride (1.22 g, 5.76 mmol) was added to a solution of 4-ethynylbenzaldehyde (0.50 g, 3.84 mmol) in 1,2-dichloroethane (18.75 mL) at rt. Diethylamine (0.61 mL, 5.76 mmol) and acetic acid (0.12 mL, 1.92 mmol) were then added under N$_2$ atmosphere to the mixture at rt and the reaction was stirred for 18 h. The reaction was quenched with sat. sodium bicarbonate solution (10 mL) and the mixture was stirred for 15 min. Dichloromethane (18.75 mL) was then added and the layers were separated. The aqueous layer was extracted using dichloromethane (10 mL), and the combined organic layers were washed with brine and dried over sodium sulfate. The solvent was then removed under vacuum at 40° C./200 mbar. The resultant oily residue was purified by silica gel column chromatography using dichloromethane: methanol (100 to 90:10) gradient to give the title compound as pale yellow thick oil (0.455 g, 63.2%). $^1$H NMR (400 MHz, CDCl$_3$) δ 7.46 (d, J=8.0 Hz, 2H), 7.76 (d, J=7.6 Hz, 2H), 3.78 (s, 2H), 3.08 (s, 1H), 2.72-2.66 (m, 4H), 1.13 (t, J=7.2 Hz, 6H); MS ESI 187.9 [M+H]$^+$, calcd for [C$_{13}$H$_{17}$N+H]$^+$ 187.14.

B. (E)-N-ethyl-N-(4-(2-(4,4,5,5-tetramethyl-1,3,2-dioxaborolan-2-yl)vinyl)benzyl)ethananamine According to procedure for the synthesis of example A42A, by using N-ethyl-N-(4-ethynylbenzyl)ethanamine (0.70 g, 3.73 mmol) and 4,4,5,5-tetramethyl-1,3,2-dioxaborolane (1.62 mL, 11.21 mmol) to give the title compound as a yellowish orange oil (1.02 g, 86%). $^1$H NMR (400 MHz, CDCl$_3$) δ 7.43-7.35 (m, 3H), 7.30-7.27 (m, 2H), 6.12 (d, J=18.4 Hz, 1H), 3.56 (s, 2H), 2.54-2.49 (m, 4H), 1.32 (s, 12H), 1.04 (t, J=7.2 Hz, 6H); MS ESI 316.1 [M+H]$^+$, calcd for [C$_{29}$H$_{30}$BNO$_2$+H]$^+$ 316.24.

This intermediate can also be prepared by the following method:

According to procedure for the synthesis of Example A211A, by using (E)-4-(2-(4,4,5,5-tetramethyl-1,3,2-dooxaborolan-2-yl)vinyl)benzaldehyde (1.93 g, 7.48 mmol), sodium triacetoxyborohydride (2.38 g, 11.22 mmol) and diethylamine (1.16 mL, 11.22 mmol) to give the title compound after purification using Biotage on SNAP 25 g column with hexane:ethylacetate (100 to 72:25) gradient as a pale yellow thick oil (1.55 g, 66%).

D. (1R*,2S*)-2-(3-(4-((diethylamino)methyl)styryl)-1H-indazol-6-yl)spiro-[cyclopropane-1,3'-indolin]-2'-one 2,2,2-trifluoroacetate The title compound was synthesized according to the method of Example A51B, by using (1R*,2S*)-2-(3-iodo-1H-indazol-6-yl-)spiro[cyclopropane-1,3'-indolin]-2'-one (70.0 mg, 0.174 mmol) and (E)-N-ethyl-N-(4-(2-(4,4,5,5-tetramethyl-1,3,2-dioxaborolan-2-yl)vinyl)benzyl)ethanamine (68.76 mg, 0.218 mmol). Purification by preparative HPLC gave the title compound as a cream solid (29 mg, 29%). $^1$H NMR (400 MHz, CD$_3$OD) δ 8.01 (d, J=8.4 Hz, 1H), 7.76 (d, J=8.0 Hz, 2H), 7.56-7.52 (m, 4H), 7.48 (s, 1H), 7.04 (d, J=7.2 Hz, 2H), 6.93 (d, J=7.6 Hz, 1H), 6.58 (t, J=7.2 Hz, 1H), 5.98 (d, J=7.6 Hz, 1H), 4.36 (s, 2H), 3.29-3.17 (m, 5H), 2.25 (t, J=4.8 Hz, 1H), 2.21-2.17 (m, 1H), 1.37 (t, J=7.2 Hz, 6H); MS ESI 463.3 [M+H]$^+$, calcd for [C$_{30}$H$_{30}$N$_4$O+H]$^+$ 463.25.

Example A212. (1R,2S)-(E)-2-(3-(4-((diethylamino)methyl)styryl)-1H-indazol-6-yl)spiro-[cyclopropane-1,3'-indolin]-2'-one 2,2,2-trifluoroacetate

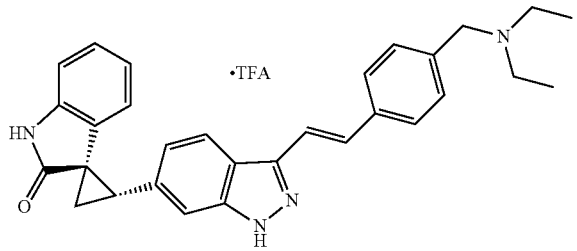 [SMILES: CCN(CC)Cc1ccc(/C=C/c2n[nH]c3cc([C@@H]4C[C@@]45C(=O)Nc4ccccc45)ccc23)cc1]

The title compound was synthesized according to the method of Example A51B, by using (1R,2S)-2-(3-iodo-1H-indazol-6-yl-)spiro[cyclopropane-1,3'-indolin]-2'-one (600 mg, 1.50 mmol) and (E)-N-ethyl-N-(4-(2-(4,4,5,5-tetramethyl-1,3,2-dioxaborolan-2-yl) vinyl) benzyl)ethanamine (589.3 mg, 1.87 mmol). Purification by preparative HPLC gave the title compound as a cream solid (360 mg, 42%). Spectral data was identical to that obtained for Example A211D.

Optical Rotation: $[\alpha]^{23}_D = -194°$ (c 0.577, Methanol).

Example A213. (1R*,2S*)-5'-methoxy-2-(3-((E)-2-(6-morpholinopyridin-3-yl)vinyl)-1H-indazol-6-yl)spiro[cyclopropane-1,3'-indolin]-2'-one 2,2,2-trifluoroacetate

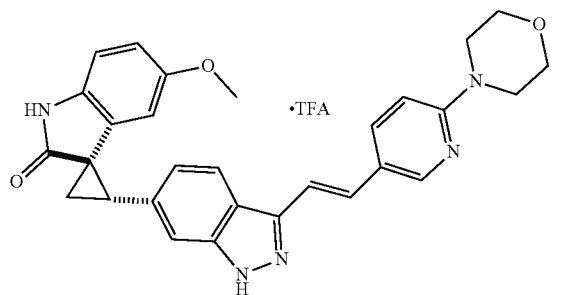

The title compound was synthesized according to the method of Example A43, by substituting (1R*,2S*)-2-(3-iodo-1H-indazol-6-yl-)5'-methoxy spiro[cyclopropane-1,3'-indolin]-2'-one (50 mg, 0.115 mmol) and (E)-4-(5-(2-(4,4,5,5-tetramethyl-1,3,2-dioxaborolan-2-yl)vinyl)pyridin-2-yl)morpholine (44.8 mg, 0.127 mmol). Purification by preparative HPLC gave the title compound as a cream solid (12.5 mg, 18%). $^1$H NMR (400 MHz, CD$_3$OD) δ 8.48 (d, J=9.6 Hz, 1H), 8.15 (s, 1H), 8.03 (d, J=8.4 Hz, 1H), 7.55-7.44 (m, 4H), 7.05 (d, J=8.4 Hz, 1H), 6.83 (d, J=8.4 Hz, 1H), 6.62 (dd, J=8.4 Hz, J=6.4 Hz, 1H), 5.57 (d, J=2.4 Hz, 1H), 3.89 (t, J=4.4 Hz, 4H), 3.71 (t, J=5.2 Hz, 4H), 3.37 (t, J=8.4 Hz, 1H), 3.27 (s, 3H), 2.26-2.23 (m, 1H), 2.21-2.18 (m, 1H); MS ESI 494.3 [M+H]$^+$, calcd for [C$_{29}$H$_{27}$N$_5$O$_3$+H]$^+$ 494.21.

Example A214. (1R*,2S*)-(E)-5'-difluoromethoxy-2-(3-(4-((dimethylamino)methyl)styryl)-1H-indazol-6-yl)spiro[cyclopropane-1,3'-indolin]-2'-one 2,2,2-trifluoroacetate

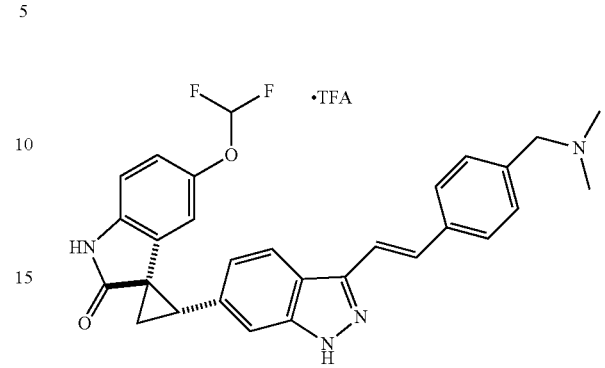

The title compound was synthesized according to the method of Example A51B, by using (1R*,2S*)-5'-difluoromethoxy-2-(3-iodo-1H-indazol-6-yl)spiro[cyclopropane-1,3'-indolin]-2'-one (75 mg, 0.16 mmol) and (E)-N,N-dimethyl-1(4-(2-(4,4,5,5-tetra methyl-1,3,2-dioxaborolan-2-yl) vinyl)benzyl)methanamine (57.63 mg, 0.20 mmol). Purification by preparative HPLC gave the title compound as a off-white solid (38 mg, 39%). $^1$H NMR (400 MHz, CD$_3$OD) 8.03 (d, J=8.4 Hz, 1H), 7.76 (d, J=8.0 Hz, 1H), 7.55-7.48 (m, 5H), 7.03 (d, J=8.4 Hz, 1H), 6.91 (d, J=8.4 Hz, 1H), 6.84 (d, J=8.4 Hz, 1H), 6.14 (t, J=74.4 Hz, 1H), 5.77 (s, 1H), 4.33 (s, 2H), 3.41 (t, J=8.4 Hz, 1H), 2.88 (s, 6H), 2.33-2.30 (m, 1H), 2.25-2.21 (m, 1H), MS ESI 501.2 [M+H]$^+$, calcd for [C$_{29}$H$_{26}$F$_2$N$_4$O$_2$+H]$^+$ 501.21.

Example A215. (1R*,2S*)-(E)-2-(3-(4-((dimethylamino)methyl)-3,5-difluorostyryl)-1H-indazol-6-yl)-5'-methoxyspiro[cyclopropane-1,3'-indolin]-2'-one 2,2,2-trifluoro acetate

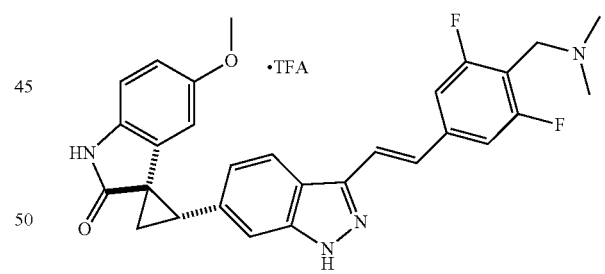

A mixture of (1R*,2S*)-5'-methoxy-2-(3-vinyl-1H-indazol-6-yl)spiro [cyclopropane-1,3'-indolin]-2'-one (50.0 mg, 0.15 mmol), 1-(4-bromo-2,6-difluorophenyl)-N,N-dimethylmethanamine (41.51 mg, 0.165 mmol), Pd(OAc)$_2$ (1.69 mg, 0.0075 mmol), P(oTol)$_3$ (5.0 mg, 0.016 mmol) and DIPEA (39.0 mg, 0.30 mmol) in DMF (1.0 mL) was sealed and heated with stirring under microwave irradiation at 125° C. for 2 h. The reaction was then diluted with ethyl acetate (20 mL) and water (5 mL) and the layers were separated. The aqueous layer was extracted using ethyl acetate (10 mL), and the combined ethyl acetate layer was washed with brine (4.0 mL) and was dried over sodium sulfate and then concentrated vacuum at 40° C./100 mbar to yield a yellowish residue. The crude product was purified by prep. HPLC to give the title compound as a pale yellow solid (9.5 mg, 10%). $^1$H NMR (400 MHz, CD$_3$OD) δ 7.80 (d, J=8.4 Hz, 1H), 7.47 (s, 1H), 7.43 (d, J=16.4 Hz, 1H), 7.30-7.25 (m, 3H), 6.87 (d, J=8.4 Hz, 1H), 6.79 (d, J=8.4 Hz, 1H), 6.53 (d, J=8.8 Hz, 1H), 5.56 (s, 1H), 4.43 (s, 2H), 3.28 (t, J=10.0 Hz, 1H), 3.19 (s, 3H), 2.96 (s, 6H), 2.18-21.2 (m, 2H); MS ESI 501.3 [M+H]$^+$, calcd for [C$_{29}$H$_{26}$F$_2$N$_4$O$_2$+H]$^+$ 501.21.

Example A216. (1R,2S)-(E)-2-(3-(4-((dimethylamino)methyl)-3,5-difluorostyryl)-1H-indazol-6-yl)-5'-methoxyspiro[cyclopropane-1,3'-indolin]-2'-one 2,2,2-trifluoroacetate

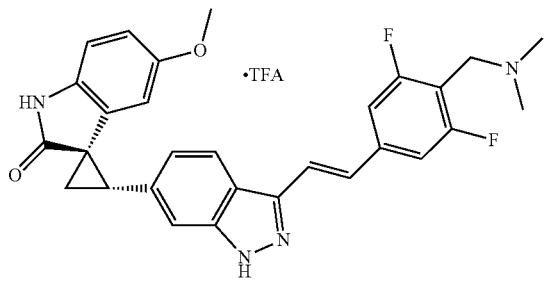 [SMILES: COc1ccc2c(c1)[C@]1(C[C@H]1c1ccc3c(/C=C/c4cc(F)c(CN(C)C)c(F)c4)n[nH]c3c1)C(=O)N2]

A. (E)-1-(2,6-difluoro-4-(2-(4,4,5,5-tetramethyl-1,3,2-dioxaorolan-2-yl)vinyl)phenyl)-N,N-dimethylmethanamine This intermediate was prepared via 2 different synthetic methods.
Method 1.

a. 1-(4-bromo-2,6-difluorophenyl)-N,N-dimethylmethanamine

According to procedure for the synthesis of Example A211A, by using 4-bromo-2,6-difluorobenzaldehyde (500 mg, 2.26 mmol), sodium triacetoxyborohydride (959 mg, 4.52 mmol) and 2M dimethylamine solution (2.626 mL, 4.52 mmol) to give the title compound as a colorless oil (452 mg, 79%). $^1$H NMR (400 MHz, CDCl$_3$) δ 7.09 (d, J=6.8 Hz, 2H), 3.54 (s, 2H), 2.26 (s, 6H); MS ESI 249.9 [M+H]$^+$, calcd for [C$_9$H$_{10}$BrF$_2$N+H]$^+$ 249.0.

b. 1-(4-ethylnyl-2,6-difluorophenyl)-N,N-dimethylmethanamine

A mixture of 1-(4-bromo-2,6-difluorophenyl)-N,N-dimethylmethanamine (0.45 g, 1.79 mmol), trimethylsilylacetylene (0.356 mL, 2.24 mmol), Pd(PPh$_3$)$_2$Cl$_2$ (50.49 mg, 0.071 mmol), CuI (3.42 mg, 0.017 mmol) and DIPEA (0.46 mL, 2.69 mmol) in DMF (3.0 mL) was sealed under argon atmosphere and heated with stirring under microwave irradiation at 100° C. for 2 h. The reaction was diluted with methanol (9 mL) and the resulting precipitate was filtered off. The mother liquor was concentrated under vacuum at 45° C./75 mbar to give a brown, thick oil. The residue was purified on Biotage using SNAP 25 g column with hexane: ethyl acetate (100 to 80:20) gradient to give yellow oil as a trimethylsilyl ether (0.250 g, 52%); MS ESI 268.0 [M+H]$^+$, calcd for [C$_{14}$H$_{19}$F$_2$NSi+H]$^+$ 268.13.
Deprotection of above trimethylsilyl ether was carried out in methanol (10 mL) and 10% K$_2$CO$_3$ solution (1.67 mL) at rt for 1.5 h. The solvents were removed in vacuo below 40° C. and then water (5 mL) was added at room temperature. The product was extracted using dichloromethane (2×15 mL) and the combined organic layers were washed with brine and dried over sodium sulfate. The solvent was removed under vacuum at 40° C./200 mbar to give brownish oil, which was purified on Biotage using SNAP 25 g column with hexane:ethyl acetate (100 to 75:75) gradient to give yellow oil (98 mg, 54%). $^1$H NMR (400 MHz, CDCl$_3$) δ 7.04 (d, J=6.8 Hz, 2H), 3.68 (s, 2H), 3.17 (s, 1H), 2.35 (s, 6H); MS ESI 195.8 [M+H]$^+$, calcd for [C$_1$H$_{11}$F$_2$N+H]$^+$ 195.09.

c. (E)-1-(2,6-difluoro-4-(2-(4,4,5,5-tetramethyl-1,3,2-dioxaorolan-2-yl)vinyl)phenyl)-N,N-dimethylmethanamine According to procedure for the synthesis of example A42A, by using 1-(4-ethylnyl-2,6-difluorophenyl)-N,N-dimethylmethanamine (97 mg, 0.496 mmol) and 4,4,5,5-tetramethyl-1,3,2-dioxaborolane (0.21 mL, 1.488 mmol) to give the title compound after purification on Biotage using KPNH SNAP 25 gm column with hexane:ethyl acetate (100 to 50:50) gradient as a brown semi solid (67 mg, 41%). $^1$H NMR (400 MHz, CDCl$_3$) δ 7.24 (d, J=18.4 Hz, 1H), 6.99 (d, J=7.6 Hz, 2H), 6.13 (d, J=18.4 Hz, 1H), 3.57 (s, 2H), 2.28 (s, 6H), 1.32 (s, 12H); MS ESI 324.2 [M+H]$^+$, calcd for [C$_{17}$H$_{24}$BrF$_2$NO$_2$+H]$^+$ 323.19.
Method 2 a. (E)-2,6-difluoro-4-(2-(4,4,5,5-tetramethyl-1,3,2-dioxaborolan-2-yl)vinyl)benzaldehyde According to procedure for the synthesis of example A51A, by using 4-bromo-2,6-difluorobenzaldehyde (1.10 g, 4.98 mmol) and 4,4,5,5-tetramethyl-2-vinyl-1,3,2-dioxaborolane (0.97 mL, 5.72 mmol) to give the title compound as a colorless oil (1.10 g, 76%). $^1$H NMR (400 MHz, CDCl$_3$) δ 10.31 (s, 1H), 7.05 (d, J=9.6 Hz, 2H), 7.22 (d, J=8.8 Hz, 1H), 6.28 (d, J=18.8 Hz, 1H), 1.33 (s, 12H); MS ESI 295.1 [M+H]$^+$, calcd for [C$_{15}$H$_{17}$BF$_2$O$_3$+H]$^+$ 295.13.

b. (E)-1-(2,6-difluoro-4-(2-(4,4,5,5-tetramethyl-1,3,2-dioxaorolan-2-yl)vinyl)phenyl)-N,N-dimethylmethanamine According to procedure for the synthesis of example A211A, by using (E)-2,6-difluoro-4-(2-(4,4,5,5-tetramethyl-1,3,2-dioxaborolan-2-yl)vinyl)benzaldehyde (1.10 g, 3.74 mmol), sodium triacetoxyborohydride (1.19 g, 5.61 mmol) and 2M dimethylamine solution (3.74 mL, 7.48 mmol) to give the title compound as a colorless thick oil (0.571 g, 47%). $^1$H NMR (400 MHz, CDCl$_3$) δ 7.24 (d, J=18.4 Hz, 1H), 6.99 (d, J=7.6 Hz, 2H), 6.13 (d, J=18.4 Hz, 1H), 3.57 (s, 2H), 2.28 (s, 6H), 1.32 (s, 12H); MS ESI 324.2 [M+H]$^+$, calcd for [C$_{17}$H$_{24}$BrF$_2$NO$_2$+H]$^+$ 323.19.

B. (1R,2S)-2-(3-(4-((dimethylamino)methyl)-3,5-difluorostyryl)-1H-indazol-6-yl)-5'-methoxyspiro[cyclopropane-1,3'-indolin]-2'-one 2,2,2-trifluoroacetate The title compound was synthesized according to the method of Example A51B, by using (1R,2S)-2-(3-iodo-1H-indazol-6-yl-)-5'-methoxyspiro[cyclopropane-1,3'-indolin]-2'-one (500 mg, 1.15 mmol) and (E)-1-(2,6-difluoro-4-(2-(4,4,5,5-tetramethyl-1,3,2-dioxaborolan-2-yl)vinyl)phenyl)-

N,N-dimethylmethanamine (393.4 mg, 1.21 mmol). Purification by preparative HPLC gave the title compound as a cream solid (400 mg, 56.1%). Spectral data was identical for that obtained in Example A215.

Optical Rotation: $[\alpha]^{22}_D = -88°$ (c 0.354, Methanol).

Example A217. (1R*,2S*)-(E)-2-(3-(3,5-difluoro-4-(morpholinomethyl)styryl-1H-indazol-6-yl)-5'-methoxyspiro[cyclopropane-1,3'-indolin]-2'-one 2,2,2-trifluoroacetate

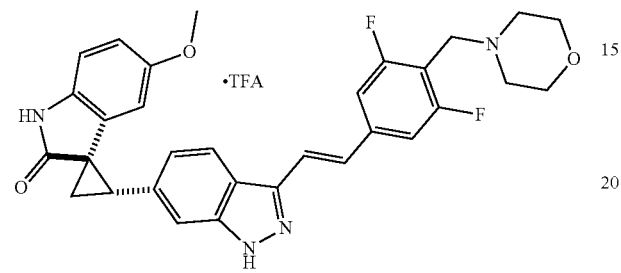

A. 1-(4-bromo-2,6-difluorophenyl)-morpholine

According to procedure for the synthesis of Example A211A by using 4-bromo-2,6-difluorobenzaldehyde (1.0 g, 4.52 mmol), sodiumtriacetoxyborohydride (1.438 g, 6.78 mmol) and morpholine (0.59 mL, 6.78 mmol) to give the title compound as a pale yellow oil (1.30 g, 98.4%). $^1$H NMR (400 MHz, CDCl$_3$) δ 7.09 (d, J=6.4 Hz, 2H), 3.69 (d, J=4.4 Hz, 4H), 3.63 (s, 2H), 2.49 (bm, 4H); MS ESI 292.1 [M+H]$^+$, calcd for [C$_{11}$H$_{12}$BrF$_2$NO+H]$^+$ 293.0.

B. 1-(4-ethylnyl-2,6-difluorophenyl)morpholine

According to procedure for the synthesis of Example A216A method 1b, by using 1-(4-bromo-2,6-difluorophenyl)-morpholine (1.32 g, 4.51 mmol) to give the title compound as a light brown oil (0.65 g, 60%). $^1$H NMR (400 MHz, CDCl$_3$) δ 7.02 (d, J=7.2 Hz, 2H), 3.71-3.67 (m, 6H), 3.16 (s, 1H), 2.50 (bm, 4H); MS ESI 238.0 [M+H]$^+$, calcd for [C$_{13}$H$_{13}$F$_2$NO+H]$^+$ 238.10.

C. (E)-4-(2,6-difluoro-4-(2-(4,4,5,5-tetramethyl-1,3,2-dioxaborolan-2-yl)vinyl)benzyl)morpholine According to procedure for the synthesis of example A42A, by using 1-(4-ethylnyl-2,6-difluorophenyl)morpholine (0.97 g, 4.08 mmol) and 4,4,5,5-tetramethyl-1,3,2-dioxaborolane (1.78 mL, 12.24 mmol) to give the title compound as a cream solid (1.21 g, 81%). $^1$H NMR (400 MHz, CDCl$_3$) δ 7.23 (d, J=18.4 Hz, 1H), 6.99 (d, J=7.6 Hz, 2H), 6.13 (d, J=18.4 Hz, 1H), 3.59-3.66 (m, 6H), 2.51 (bm, 4H), 1.32 (s, 12H); MS ESI 366.1 [M+H]$^+$, calcd for [C$_{19}$H$_{26}$BF$_2$NO$_3$+H]$^+$ 366.2.

D. (1R*,2S*)-2-(3-(3,5-difluoro-4-(morpholinomethyl)styryl-1H-indazol-6-yl)-5'-methoxyspiro[cyclopropane-1,3'-indolin]-2'-one 2,2,2-trifluoroacetate The title compound was synthesized according to the method of Example A51B, by using (1R*,2S*)-2-(3-iodo-1H-indazol-6-yl-)-5'-methoxyspiro[cyclopropane-1,3'-indolin]-2'-one (60 mg, 0.139 mmol) and (E)-4-(2,6-difluoro-4-(2-(4,4,5,5-tetramethyl-1,3,2-dioxaborolan-2-yl)vinyl)benzyl)morpholine (58.44 mg, 0.16 mmol). Purification by preparative HPLC gave the title compound as a cream solid (29 mg, 27%). $^1$H NMR (400 MHz, CD$_3$OD) δ 8.03 (d, J=8.8 Hz, 1H), 7.63 (d, J=16.8 Hz, 1H), 7.52-7.49 (m, 4H), 7.06 (s, J=8.4 Hz, 1H), 6.82 (d, J=8.4 Hz, 1H), 6.60 (d, J=8.8 Hz, 1H), 5.57 (s, 1H), 4.51 (s, 2H), 4.10-3.72 (bm, 4H), 3.47-3.42 (bm, 5H), 3.26 (s, 3H), 2.26-2.23 (m, 1H), 2.21-2.17 (m, 1H); MS ESI 543.3 [M+H]$^+$, calcd for [C$_{31}$H$_{28}$F$_2$N$_4$O$_3$+H]$^+$ 543.22.

Example A218. (1R,2S)-(E)-2-(3-(3,5-difluoro-4-(morpholinomethyl)styryl)-1H-indazol-6-yl)-5'-methoxyspiro[cyclopropane-1,3'-indolin]-2'-one 2,2,2-trifluoroacetate

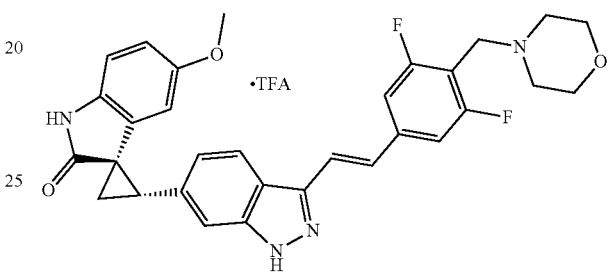

The title compound was synthesized according to the method of Example A51B, by substituting (1R,2S)-2-(3-iodo-1H-indazol-6-yl-)-5'-methoxyspiro[cyclopropane-1,3'-indolin]-2'-one (600 mg, 1.50 mmol) and (E)-4-(2,(4,4,5,5-tetramethyl-1,3,2-dioxaborolan-2-yl)vinyl)benzyl)morpholine (579.6 mg, 1.06 mmol). Purification by preparative HPLC gave the title compound as a cream solid (345 mg, 40%). Spectral data was identical for that obtained in Example A217.

Optical Rotation: $[\alpha]^{22}_D = -74°$ (c 0.34, Methanol).

Example A219. 1R*,2S*)-(E)-5'-fluoro-2-(3-(4-(morpholinomethyl)styryl-1H-indazol-6-yl)spiro[cyclopropane-1,3'-indolin]-2'-one 2,2,2-trifluoroacetate

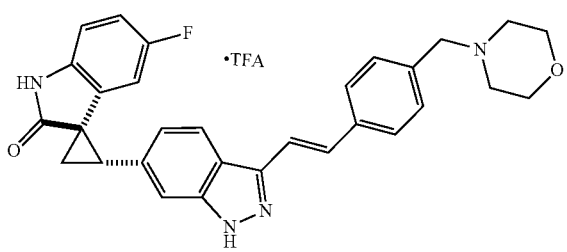

The title compound was synthesized according to the method of Example A51B, by using (1R*,2S*)-5'-fluoro-2-(3-iodo-1H-indazol-6-yl)spiro[cyclopropane-1,3'-indolin]-2'-one (60.0 mg, 0.139 mmol) and (E)-4-(4-(2-(4,4,5,5-tetramethyl-1,3,2-dioxaborolan-2-yl)vinyl)benzyl)morpholine (54.83 mg, 0.173 mmol). Purification by preparative HPLC gave the title compound as a cream solid (31.0 mg, 37%). $^1$H NMR (400 MHz, CD$_3$OD) δ 8.04 (d, J=8.8 Hz, 1H), 7.77 (d, J=7.2 Hz, 2H), 7.59-7.52 (m, 5H), 7.05 (d, J=8.0 Hz, 1H), 6.91-6.88 (m, 1H), 6.79 (t, J=8.0 Hz, 1H), 5.74 (d, J=8.8 Hz, 1H), 4.39 (s, 2H), 4.08-4.05 (bm, 2H), 3.76-3.70 (bt, 2H), 3.42-3.35 (m, 3H), 3.26-3.23 (bm, 2H), 2.30 (t, J=5.6 Hz, 1H), 2.24-2.20 (m, 1H); MS ESI 495.3 [M+H]$^+$, calcd for [C$_{30}$H$_{27}$FN$_4$O$_2$+H]$^+$ 495.22.

Example A220. (1R,2S)-(E)-5'-fluoro-2-(3-(4-(morpholinomethyl)styryl-1H-indazol-6-yl)spiro[cyclopropane-1,3'-indolin]-2'-one 2,2,2-trifluoroacetate

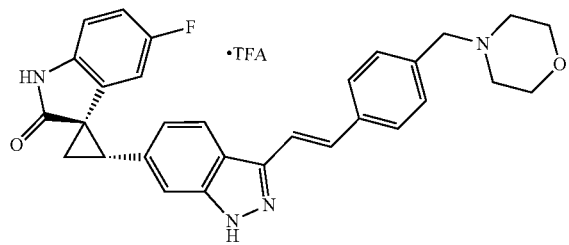 [SMILES: O=C1Nc2ccc(F)cc2[C@]12C[C@H]2c1ccc2c(/C=C/c3ccc(CN4CCOCC4)cc3)n[nH]c2c1]

The title compound was synthesized according to the method of Example A51B, by using (1R,2S)-5'-fluoro-2-(3-iodo-1H-indazol-6-yl)spiro[cyclopropane-1,3'-indolin]-2'-one (240 mg, 0.571 mmol) and (E)-4-(4-(2-(4,4,5,5-tetramethyl-1,3,2-dioxaborolan-2-yl) vinyl) benzyl) morpholine (216.7 mg, 0.658 mmol). Purification by preparative HPLC gave the title compound as a cream solid (230 mg, 66%). Spectral data was identical to that obtained for Example A219.

Optical Rotation: [α]$^{22}_D$=136° (c 0.404, Methanol).

Example A221. (1R,2S)-(E)-2-(3-(4-((diethylamino)methyl)-3,5-difluorostyryl)-1H-indazol-6-yl)spiro[cyclopropane-1,3'-indolin]-2'-one 2,2,2-trifluoroacetate

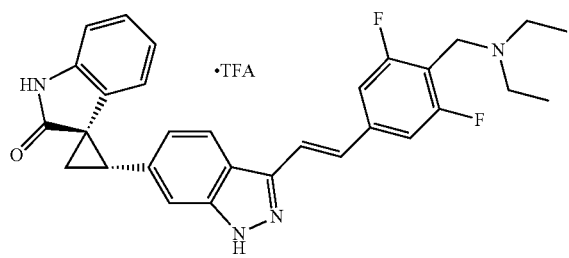 [SMILES: CCN(CC)Cc1c(F)cc(/C=C/c2n[nH]c3cc([C@@H]4C[C@@]45C(=O)Nc4ccccc45)ccc23)cc1F]

A.
N-(4-bromo-2,6-difluorobenzyl-)N-ethylethanamine

According to procedure for the synthesis of Example A211A, by using 4-bromo-2,6-difluorobenzaldehyde (610 mg, 2.76 mmol), sodium triacetoxyborohydride (883.35 mg, 4.15 mmol) and diethylamine (425.21 mmL, 4.15 mmol) to give the title compound as a colorless oil (660 mg, 86%). $^1$H NMR (400 MHz, CDCl$_3$) δ 7.06 (d, J=6.4 Hz, 2H), 3.61 (s, 2H), 2.55-2.50 (m, 4H), 1.07 (t, J=6.8 Hz, 6H); MS ESI 279.9 [M+H]$^+$, calcd for [C$_{11}$H$_{14}$BrF$_2$N+H]$^+$ 278.03.

B.
N-ethyl-N-(4-ethynyl-2,6-difluorobenzyl)ethanamine

According to procedure for the synthesis of Example A216A method 1b, by using N-(4-bromo-2,6-difluorobenzyl-)N-ethylethanamine (660 mg, 2.37 mmol) to give the title compound as a light brown oil (252 mg, 48%). $^1$H NMR (400 MHz, CDCl$_3$) δ 6.99 (d, J=7.2 Hz, 2H), 3.67 (s, 2H), 3.13 (s, 1H), 2.57-2.51 (m, 4H), 1.08 (t, J=7.2 Hz, 6H); MS ESI 224.0 [M+H]$^+$, calcd for [C$_{13}$H$_{15}$F$_2$N+H]$^+$ 224.12.

C: (E)-N-(2,6-Difluoro-(4-(2-(4,4,5,5-tetramethyl-1,3,2-dioxaborolan-2-yl)vinyl)benzyl)N-ethylethanamine According to procedure for the synthesis of example A42A, by using N-ethyl-N-(4-ethynyl-2,6-difluorobenzyl)ethanamine (252 mg, 1.12 mmol) and 4,4,5,5-tetramethyl-1,3,2-dioxaborolane (0.493 mL, 3.36 mmol) to give the title compound as a cream semi solid (410 mg, 90%). $^1$H NMR (400 MHz, CDCl$_3$) δ 7.24 (d, J=13.2 Hz, 1H), 6.97 (d, J=7.6 Hz, 2H), 6.12 (d, J=17.6 Hz, 1H), 3.67 (s, 2H), 2.58-2.52 (m, 4H), 1.32 (s, 12H), 1.08 (t, J=6.8 Hz, 6H); MS ESI 352.2 [M+H]$^+$, calcd for [C$_{27}$H$_{26}$N$_6$O$_2$+H]$^+$ 351.22.

This intermediate can also be prepared by the following method:

According to procedure for the synthesis of Example A211A, by using (E)-2,6-difluoro-4-(2-(4,4,5,5-tetramethyl-1,3,2-dioxaborolan-2-yl)vinyl)benzaldehyde (1.10 g, 3.74 mmol), sodium triacetoxyborohydride (1.19 g, 5.61 mmol) and diethylamine (0.58 mL, 5.61 mmol) to give the title compound as a cream color solid (0.54 g, 41%).

C. (1R,2S)-2-(3-(4-((diethylamino)methyl)-3,5-difluorostyryl)-1H-indazol-6-yl)spiro[cyclopropane-1,3'-indolin]-2'-one 2,2,2-trifluoroacetate The title compound was synthesized according to the method of Example A51B, by using (1R,2S)-2-(3-iodo-1H-indazol-6-yl-)-spiro[cyclopropane-1,3'-indolin]-2'-one (125 mg, 0.311 mmol) and (E)-N-(2,6-difluoro-(4-(2-(4,4,5,5-tetramethyl-1,3,2-dioxaborolan-2-yl)vinyl)benzyl)-N-ethylethanamine (131.4 mg, 0.373 mmol). Purification by preparative HPLC gave the title compound as a cream solid (54 mg, 28.4%). $^1$H NMR (400 MHz, CD$_3$OD) δ 7.98 (d, J=8.0 Hz, 1H), 7.59 (d, J=16.4 Hz, 1H), 7.55-7.45 (m, 4H), 7.04 (d, J=8.0 Hz, 2H), 6.92 (d, J=8.0 Hz, 1H), 6.55 (t, J=7.6 Hz, 1H), 5.96 (d, J=7.6 Hz, 1H), 4.46 (s, 2H), 3.35-3.28 (m, 5H), 2.24-2.21 (m, 1H), 2.19-2.15 (m, 1H), 1.42 (t, J=6.8 Hz, 6H); MS ESI 499.4 [M+H]$^+$, calcd for [C$_{30}$H$_{28}$F$_2$NO$_4$+H]$^+$ 499.23.

Optical Rotation: [α]$^{22}_D$=−126° (c 0.46, Methanol).

Example A222. (1R,2S)-5'-methoxy-2-(3-(4-(1-methylpiperidin-4-yloxy)phenyl)-1H-indazol-6-yl)spiro[cyclopropane-1,3'-indolin]-2'-one 2,2,2-trifluoroacetate salt

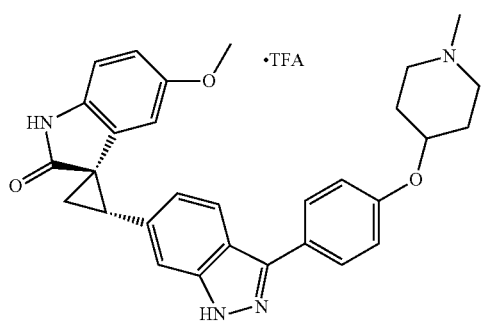 [SMILES: COc1ccc2c(c1)[C@]1(C[C@H]1c1ccc3c(-c4ccc(OC5CCN(C)CC5)cc4)n[nH]c3c1)C(=O)N2]

B. 1-methyl-4-(4-(4,4,5,5-tetramethyl-1,3,2-dioxa-borolan-2-yl)phenoxy)piperidine The title compound was synthesized according to the method described for the synthesis of 1-(4-(4,4,5,5-tetramethyl-1,3,2-dioxaborolan-2-yl)phenyl)piperidin-4-yl acetate, except substituting 4-(4-bromophenoxy)-1-methylpiperidine (300 mg, 1.11 mmol). The reaction was then allowed to cool to rt and was diluted with EtOAc and water was added. The resulting mixture was extracted with EtOAc and the combined organic extracts were washed with brine, dried over $MgSO_4$ and concentrated to give the crude product. Crude product was purified by flash chromatography using $MeOH/CH_2Cl_2$ (2:98 to 15:85) to give the title compound as a brown solid (200 mg, 57%). $^1H$ NMR (400 MHz, $CD_3OD$) δ 7.68 (d, J=7.6 Hz, 2H), 6.94 (d, J=7.7 Hz, 2H), 4.53 (br s, 1H), 2.94-2.91 (m, 2H), 2.58-2.50 (m, 2H), 2.40 (s, 3H), 2.18-2.00 (m, 2H), 1.93-1.78 (m, 2H), 1.34 (m, 12H); MS ESI 318.1 $[M+H]^+$, calcd for $[C_{18}H_{28}BNO_3+H]^+$ 318.22.

C. (1R,2S)-5'-methoxy-2-(3-(4-(1-methylpiperidin-4-yloxy)phenyl)-1H-indazol-6-yl)spiro[cyclopropane-1,3'-indolin]-2'-one 2,2,2-trifluoroacetate salt The title compound was synthesized according to the method of Example A51B, except substituting 1-methyl-4-(4-(4,4,5,5-tetramethyl-1,3,2-dioxaborolan-2-yl)phenoxy)piperidine (160 mg, 0.51 mmol). Purification by reverse phase preparatory HPLC gave the title compound as a white TFA salt (119 mg, 42%). $^1H$ NMR ($CD_3OD$) δ: 7.92-7.87 (m, 3H), 7.50 (s, 1H), 7.20-7.13 (m, 2H), 7.03 (d, J=8.7 Hz, 1H), 6.83 (d, J=7.9 Hz, 1H), 6.62 (d, J=8.1 Hz, 1H), 5.61 (s, 1H), 3.67-3.63 (m, 1H) 3.49-3.35 (m, 4H), 3.26 (s, 3H), 2.96 (s, 3H), 2.47-2.43 (m, 1H), 2.342.07-2.01 (m, 5H), 1.95-1.87 (m, 1H); MS ESI 495.4 $[M+H]^+$, calcd for $[C_{30}H_{30}N_4O_3+H]^+$ 495.23.

Optical Rotation: $[α]^{23}_D$=−113° (c 0.44, MeOH).

Example B: PLK4 Inhibition Assay

Active PLK4 was purified from an *E. coli* expression system as an amino terminal GST fusion of residues 1-391 of human PLK4. The protein was purified from clarified cell extracts after induction at 15° C. overnight using glutathione sepharose, gel permeation chromatography, and ion exchange (Resource Q). The resulting protein was dephosphorylated with lambda phosphatase (NEB cat #P0753), and resolved from the phosphatase using gluthione sepharose. The dephosphorylated GST-PLK4 was stored in aliquots at −80° C. until use.

PLK4 activity was measured using an indirect ELISA detection system. Dephosphorylated GST-PLK4 (4 nM) was incubated in the presence of 15 μM ATP (Sigma cat #A7699), 50 mM HEPES-$Na^{2+}$ pH 7.4, 10 mM $MgCl_2$, 0.01% Brij 35 (Sigma cat #03-3170), in a 96 well microtitre plate pre-coated with MBP (Millipore cat #30-011). The reaction was allowed to proceed for 30 minutes, followed by 5 washes of the plate with Wash Buffer (50 mM TRIS-Cl pH 7.4 and 0.2% Tween 20), and incubation for 30 minutes with a 1:3000 dilution of primary antibody (Cell Signaling cat #9381). The plate was washed 5 times with Wash Buffer, incubated for 30 minutes in the presence of secondary antibody coupled to horse radish peroxidase (BioRad cat #1721019, 1:3000 concentration), washed an additional 5 times with Wash Buffer, and incubated in the presence of TMB substrate (Sigma cat #T0440). The colourimetric reaction was allowed to continue for 5 minutes, followed by addition of stop solution (0.5 N sulphuric acid), and quantified by detection at 450 nm with either a monochromatic or filter based plate reader (Molecular Devices M5 or Beckman DTX880, respectively).

Compound inhibition was determined at either a fixed concentration (10 μM) or at a variable inhibitor concentration (typically 50 μM to 0.1 μM in a 10 point dose response titration). Compounds were pre-incubated in the presence of enzyme for 15 minutes prior to addition of ATP and the activity remaining quantified using the above described activity assay. The % Inhibition of a compound was determined using the following formula; % Inhibition=100×(1−(experimental value−background value)/(high activity control−background value)). The $IC_{50}$ value was determined using a non-linear 4 point logistic curve fit (XLfit4, IDBS) with the formula; $(A+(B/(1+((x/C)^D))))$, where A=background value, B=range, C=inflection point, D=curve fit parameter.

Example C: PLK1 Inhibition Assay

PLK1 inhibition was determined using the Z-Lyte assay kit from Invitrogen (cat #PV3802). The assay was performed using the recommended manufacturer's instructions with 25 μM ATP and 8 nM PLK1 (Invitrogen cat #PV3501). The % inhibition values were determined according to the manufacturer's directions and $IC_{50}$ values were obtained using a non-linear 4 point logistic curve fit (XLfit4, IDBS)

Example D: PLK2 Inhibition Assay

PLK2 inhibition was determined using the Z-Lyte assay kit from Invitrogen (cat #PV3802). The assay was performed using the recommended manufacturer's instructions with 60 μM ATP and 133 nM PLK2 (Invitrogen cat #PV4204). The % inhibition values were determined according to the manufacturer's directions and $IC_{50}$ values were obtained using a non-linear 4 point logistic curve fit (XLfit4, IDBS)

Example E: PLK3 Inhibition Assay

PLK3 inhibition was determined using the Z-Lyte assay kit from Invitrogen (cat #PV3802). The assay was performed using the recommended manufacturer's instructions with 100 μM ATP and 21 nM PLK3 (Invitrogen cat #PV3812). The % inhibition values were determined according to the manufacturer's directions and $IC_{50}$ values were obtained using a non-linear 4 point logistic curve fit (XLfit4, IDBS).

Example F: Aurora A Inhibition Assay

Aurora A inhibition was determined using the Z-Lyte assay kit from Invitrogen. The assay was performed using the recommended manufacturer's instructions with 20 μM ATP and 12 nM Aurora A (Invitrogen cat #PV3612). The % inhibition values were determined according to the manufacturer's directions and $IC_{50}$ values were obtained using a non-linear 4 point logistic curve fit (XLfit4, IDBS)

Example G: Aurora B Inhibition Assay

Aurora B inhibition was determined using the Z-Lyte assay kit from Invitrogen. The assay was performed using the recommended manufacturer's instructions with 128 μM ATP and 28 nM Aurora B (Invitrogen cat #PV3970). The % inhibition values were determined according to the manufacturer's directions and $IC_{50}$ values were obtained using a non-linear 4 point logistic curve fit (XLfit4, IDBS)

In Table 1, $IC_{50}$ values for PLK4, Aurora A and Aurora B Kinases are indicated as "A," "B," and "C," for those less than or equal to 0.1 µM; those greater than 0.1 µM and less than or equal to 1 µM; and those greater than 1 µM, respectively. The relative inhibition percentages at a dose of 1 µM are indicated as "X" and "Y" for those equal to or greater than 50% inhibition and those less than 50% inhibition, respectively. As shown in Table 1, numerous compounds of the invention are effective PLK4 inhibitors. With respect to PLK1, PLK2 and PLK3, Examples A22 and A23 did not show greater than 50% inhibition at 10 µM. In addition, a number of compounds of the invention also inhibit Aurora kinases, in particular Aurora B kinase.

TABLE 1

Inhibition Data of PLK4, Aurora A and Aurora B Kinases

| Compound # | PLK4 | Aurora A | Aurora B |
|---|---|---|---|
| Example A1 | C | — | — |
| Example A2 | C | Y | C |
| Example A3 | C | — | — |
| Example A4 | B | — | — |
| Example A5 | C | — | — |
| Example A6 | A | Y | B |
| Example A7 | A | Y | B |
| Example A8 | C | — | — |
| Example A9 | B | Y | B |
| Example A10 | B | Y | B |
| Example A11 | C | Y | C |
| Example A12 | B | — | — |
| Example A13 | A | Y | A |
| Example A15 | A | Y | C |
| Example A16 | A | Y | A |
| Example A17 | A | Y | B |
| Example A18 | A | B | A |
| Example A19 | A | Y | A |
| Example A20 | A | Y | A |
| Example A21 | A | Y | A |
| Example A22 | A | A | A |
| Example A23 | A | A | A |
| Example A24 | A | X | A |
| Example A25 | B | X | B |
| Example A26 | A | X | A |
| Example A27 | A | Y | A |
| Example A28 | A | X | A |
| Example A29 | A | X | A |
| Example A30 | A | X | A |
| Example A31 | A | X | A |
| Example A32 | A | — | — |
| Example A33 | A | — | A |
| Example A34 | A | X | A |
| Example A35 | A | B | A |
| Example A36 | A | X | A |
| Example A37 | A | Y | A |
| Example A38 | A | Y | A |
| Example A39 | A | — | A |
| Example A40 | B | Y | B |
| Example A41 | A | X | A |
| Example A42 | A | X | A |
| Example A43 | A | Y | A |
| Example A44 | A | Y | B |
| Example A45 | A | Y | B |
| Example A46 | A | — | — |
| Example A47 | A | Y | B |
| Example A48 | A | Y | A |
| Example A49 | A | Y | A |
| Example A50 | A | Y | A |
| Example A51 | A | A | A |
| Example A52 | A | Y | A |
| Example A53 | A | X | A |
| Example A54 | A | X | B |
| Example A55 | A | X | A |
| Example A56 | A | A | A |
| Example A57 | A | X | B |
| Example A58 | A | X | A |
| Example A59 | A | X | A |
| Example A60 | A | X | B |
| Example A61 | A | X | A |
| Example A62 | A | X | A |
| Example A63 | A | X | A |
| Example A64 | A | X | A |
| Example A65 | A | X | A |
| Example A66 | A | X | A |
| Example A67 | A | Y | A |
| Example A68 | A | Y | A |
| Example A69 | A | Y | A |
| Example A70 | A | Y | A |
| Example A71 | A | Y | A |
| Example A72 | A | X | A |
| Example A73 | A | X | A |
| Example A74 | A | X | A |
| Example A75 | A | X | A |
| Example A76 | A | Y | A |
| Example A77 | A | — | — |
| Example A78 | A | X | A |
| Example A79 | A | X | A |
| Example A80 | A | X | B |
| Example A81 | A | X | A |
| Example A82 | A | X | A |
| Example A83 | A | X | A |
| Example A84 | A | X | B |
| Example A85 | A | — | — |
| Example A86 | A | X | B |
| Example A87 | A | X | A |
| Example A88 | B | — | — |
| Example A89 | A | X | A |
| Example A90 | A | X | A |
| Example A91 | A | X | A |
| Example A92 | A | X | A |
| Example A93 | A | X | A |
| Example A94 | A | X | A |
| Example A95 | A | X | A |
| Example A96 | A | Y | A |
| Example A97 | A | Y | A |
| Example A98 | A | Y | A |
| Example A99 | A | Y | A |
| Example A100 | A | Y | A |
| Example A101 | A | Y | A |
| Example A102 | A | X | A |
| Example A103 | A | Y | A |
| Example A104 | A | Y | A |
| Example A105 | A | X | A |
| Example A106 | A | X | A |
| Example A107 | A | Y | A |
| Example A108 | A | Y | A |
| Example A109 | A | X | A |
| Example A110 | A | X | A |
| Example A111 | A | X | A |
| Example A112 | A | X | A |
| Example A113 | A | X | — |
| Example A114 | A | — | — |
| Example A115 | A | Y | — |
| Example A116 | A | X | A |
| Example A117 | A | Y | B |
| Example A118 | A | — | — |
| Example A119 | A | Y | A |
| Example A120 | A | Y | A |
| Example A121 | A | Y | A |
| Example A122 | A | Y | A |
| Example A123 | A | Y | A |
| Example A124 | A | — | — |
| Example A125 | A | — | — |
| Example A126 | A | Y | A |

TABLE 1-continued

Inhibition Data of PLK4, Aurora A and Aurora B Kinases

| Compound # | IC50 Ranges | | |
|---|---|---|---|
| | PLK4 | Aurora A | Aurora B |
| Example A127 | A | X | A |
| Example A128 | A | — | — |
| Example A129 | A | Y | A |
| Example A130 | A | Y | B |
| Example A131 | A | X | A |
| Example A132 | A | B | A |
| Example A133 | A | X | A |
| Example A134 | A | B | A |
| Example A135 | A | X | A |
| Example A136 | A | Y | A |
| Example A137 | A | Y | A |
| Example A138 | A | X | A |
| Example A139 | A | Y | A |
| Example A140 | A | Y | A |
| Example A141 | C | Y | C |
| Example A142 | A | Y | A |
| Example A143 | C | — | — |
| Example A144 | B | — | — |
| Example A145 | A | Y | B |
| Example A146 | A | Y | A |
| Example A147 | A | X | B |
| Example A148 | A | Y | B |
| Example A149 | A | Y | C |
| Example A150 | A | X | A |
| Example A151 | A | A | A |
| Example A152 | A | X | B |
| Example A153 | B | — | — |
| Example A154 | A | X | B |
| Example A155 | A | Y | B |
| Example A156 | A | Y | B |
| Example A157 | A | X | — |
| Example A158 | A | X | A |
| Example A159 | A | Y | A |
| Example A160 | A | X | A |
| Example A161 | A | X | A |
| Example A162 | A | X | A |
| Example A163 | A | X | A |
| Example A164 | A | X | A |
| Example A165 | A | X | A |
| Example A166 | A | Y | A |
| Example A167 | A | X | A |
| Example A168 | A | Y | A |
| Example A169 | A | X | A |
| Example A170 | B | — | — |
| Example A171 | A | A | A |
| Example A172 | A | | A |
| Example A173 | A | Y | A |
| Example A174 | A | X | A |
| Example A175 | A | Y | A |
| Example A176 | A | X | B |
| Example A177 | A | X | A |
| Example A178 | A | A | A |
| Example A179 | A | A | A |
| Example A180 | A | A | A |
| Example A181 | A | X | A |
| Example A182 | A | X | A |
| Example A183 | A | X | A |
| Example A184 | A | X | A |
| Example A185 | A | X | A |
| Example A186 | A | X | A |
| Example A187 | A | X | A |
| Example A188 | A | X | A |
| Example A189 | A | X | A |
| Example A190 | A | X | A |
| Example A191 | A | Y | A |
| Example A192 | A | Y | A |
| Example A193 | A | Y | A |
| Example A194 | A | X | A |
| Example A195 | A | X | — |
| Example A196 | A | X | A |
| Example A197 | A | X | A |
| Example A198 | A | X | A |
| Example A199 | A | X | A |
| Example A200 | A | X | A |
| Example A201 | A | X | A |
| Example A202 | A | X | A |
| Example A203 | A | X | A |
| Example A204 | A | X | A |
| Example A205 | A | X | A |
| Example A206 | A | X | A |
| Example A207 | A | X | A |
| Example A208 | A | X | A |
| Example A209 | A | Y | A |
| Example A210 | A | X | A |
| Example A211 | A | X | A |
| Example A212 | A | X | A |
| Example A213 | A | X | A |
| Example A214 | A | X | A |
| Example A215 | A | A | A |
| Example A216 | A | X | A |
| Example A217 | A | X | A |
| Example A218 | A | X | A |
| Example A219 | A | X | A |
| Example A220 | A | X | A |
| Example A221 | A | X | A |

Example H: FLT3 Inhibition Assay

The enzymatic activity of FLT3 was determined using the Z-Lyte assay kit from Invitrogen (Invitrogen cat #PV3191). The assay was performed using the recommended manufacturer's instructions with 117.5 µM ATP and 1 nM FLT3 (Invitrogen cat #PV3182). The % inhibition values were determined according to the manufacturer's directions and $IC_{50}$ values were obtained using a non-linear 4 point logistic curve fit (XLfit4, IDBS). In Table 2, $IC_{50}$ values for FLT3 inhibition are indicated as "A," "B," and "C," for those less than or equal to 0.1 µM; those greater than 0.1 µM and less than or equal to 1 µM; and those greater than 1 µM, respectively, for selected compounds of the invention.

TABLE 2

Inhibition Data of Flt3

| Compound # | $IC_{50}$ Ranges |
|---|---|
| Example A16 | A |
| Example A24 | A |
| Example A33 | A |
| Example A39 | A |
| Example A42 | A |
| Example A44 | C |
| Example A45 | C |
| Example A47 | C |
| Example A56 | A |
| Example A58 | A |
| Example A68 | B |
| Example A71 | B |
| Example A97 | A |
| Example A99 | A |
| Example A112 | B |
| Example A126 | B |
| Example A128 | B |
| Example A129 | B |
| Example A131 | C |
| Example A132 | A |
| Example A134 | A |
| Example A136 | C |
| Example A138 | B |
| Example A141 | C |
| Example A149 | C |

TABLE 2-continued

Inhibition Data of Flt3

| Compound # | $IC_{50}$ Ranges |
|---|---|
| Example A154 | B |
| Example A175 | A |
| Example A185 | B |
| Example A192 | B |
| Example A217 | A |

Example I: Kinase Selectivity Assays

The inhibitory activity of selected compounds of the invention was evaluated against a panel of 45 different kinase enzymes by CEREP, France. The assays were performed using standard HTRF assay methods as documented by CEREP against the human orthologues of Abl kinase, Akt1/PKBa, AMPKa, BMX kinase (Etk), Brk, CaMK2a, CaMK4, CDC2/CDK1 (cycB), CHK1, CHK2, c-Met kinase, CSK, EphB4 kinase, ERK1, ERK2 (P42mapk), FGFR2 kinase, FGFR4 kinase, FLT-1 kinase (VEGFR1), FLT-3 kinase, Fyn kinase, IGF1R kinase, IRK (InsR), JNK 2, KDR kinase (VEGFR2), Lck kinase, Lyn kinase, MAPKAPK2, MEK1/MAP2K1, p38a kinase, p38d kinase, p38 g kinase, PDGFRb kinase, PDK1, PKA, PKCa, PKCb1, PKCb2, PKCg, Ret kinase, ROCK2, RSK2, Src kinase, Syk, and TRKA (Table 3). The % Inhibition was determined by the formula; % Inhibition=100×(1−(experimental value−background value)/(high activity control−background value)).

TABLE 3

Percent Inhibition Values For Examples A2, A13, A22 & A26 at 10 μM Concentration

| Kinase | Example A2 % Inhibition @ 10 uM | Example A13 % Inhibition @ 10 uM | Example A22 % Inhibition @ 10 uM | Example A26 % Inhibition @ 10 uM |
|---|---|---|---|---|
| Abl | 3 | 91 | 97 | 100 |
| Akt1/PKBalpha | −2 | −2 | −1 | −4 |
| AMPKalpha | 57 | 8 | 82 | 69 |
| BMX (Etk) | −3 | 3 | 71 | 39 |
| Brk | 1 | −1 | 41 | 53 |
| CaMK2alpha | 41 | 1 | 82 | 9 |
| CaMK4 | 7 | −6 | −8 | −4 |
| CDC2/CDK1 | 57 | 5 | 93 | 60 |
| CHK1 | −4 | −9 | 37 | 43 |
| CHK2 | −10 | −5 | 4 | −3 |
| c-Met | 15 | −8 | 97 | 61 |
| CSK | 9 | 10 | 99 | 75 |
| EphB4 | 11 | 0 | 99 | 65 |
| ERK1 | 4 | −3 | 8 | 1 |
| ERK (P42mapk) | 9 | 2 | 11 | 2 |
| FGFR4 | 0 | −20 | 56 | −12 |
| FLT-1 (VEGFR1) | 1 | 22 | 82 | 30 |
| FLT-3 | 62 | 86 | 100 | 102 |
| Fyn | 7 | 2 | 87 | 55 |
| IGF1R | 20 | −3 | 22 | 0 |
| IRK (InsR) | 4 | −2 | 21 | 5 |
| JNK 2 | −2 | 11 | 32 | 5 |
| KDR (VEGFR2) | 14 | 6 | 98 | 58 |
| Lck | 17 | 71 | 97 | 100 |
| Lyn | 26 | 15 | 99 | 86 |
| MAPKAPK2 | −4 | −10 | 4 | 2 |
| MEK1/MAP2K1 | 4 | −2 | 12 | −2 |
| p38alpha | 6 | −28 | 32 | −22 |
| p38delta | −10 | 1 | −22 | 5 |
| p38gamma | 4 | −1 | −15 | −5 |
| PDGFRbeta | 4 | 3 | 88 | 59 |
| PDK1 | 4 | −2 | 69 | 2 |
| PKA | 0 | −2 | −6 | −7 |
| PKCalpha | −2 | 3 | 7 | 6 |
| PKCbeta 1 | 1 | −2 | 0 | −2 |
| PKCbeta 2 | 4 | −2 | 11 | 26 |
| PKCgamma | 7 | 3 | 8 | 10 |
| Ret | 14 | 10 | 99 | 86 |
| ROCK2 | 39 | −8 | 88 | 32 |
| RSK2 | 17 | 1 | 48 | 22 |
| Src | −10 | 13 | 26 | 51 |
| Syk | — | −1 | — | — |
| TRKA | 54 | 93 | 100 | 101 |

Table 3 above shows the percent inhibition values obtained for Examples A2, A13, A22 and A24 at 10 μM concentration. From this inhibition data it is apparent that certain kinases, e.g. Abl, CSK, FLT-3, Lck, Lyn, Ret and TRKA kinase are inhibited by compounds of the invention. These activities may impart additional therapeutic benefit to these compounds.

The inhibitory activity of selected compounds of the invention was evaluated against a panel of 284 different kinase enzymes by Millipore Corporation. The % Inhibition was determined by the formula; % Inhibition=100×(1−(experimental value−background value)/(high activity control−background value)).

TABLE 4

Percent Inhibition Values for Examples A33, A39 and A42 at 0.1 μM Concentration

| Kinase | % Inhibition @ 0.1 μM | | |
|---|---|---|---|
| | A33 | A39 | A42 |
| Abl | 72 | 68 | 77 |
| Abl (m) | 96 | 82 | 92 |
| Abl (H396P) | 93 | 77 | 93 |
| Abl (M351T) | 95 | 77 | 91 |
| Abl (Q252H) | 83 | 59 | 83 |
| Abl (T315I) | 94 | 90 | 98 |
| Abl (Y253F) | 78 | 43 | 75 |
| ALK | 32 | 20 | 64 |
| Arg | 94 | 61 | 89 |
| Arg (m) | 96 | 58 | 90 |
| ARK5 | 67 | 23 | 86 |
| Aurora-A | 96 | 70 | 100 |
| Aurora-B | 100 | 102 | 101 |
| Bmx | 68 | 35 | 92 |
| EphA1 | 22 | 17 | 61 |
| EphB1 | 34 | 15 | 54 |
| FGFR1 | 87 | 10 | 96 |
| FGFR1 (V561M) | 91 | 18 | 91 |
| FGFR2 | 82 | 34 | 88 |
| FGFR2 (N549H) | 75 | 38 | 87 |
| FGFR3 | 91 | 60 | 90 |
| Flt3 | 28 | 2 | 54 |
| GCK | 51 | 16 | 80 |
| IRAK1 | 24 | 49 | 52 |
| Itk | 34 | 9 | 82 |
| Lck | 48 | −3 | 77 |

TABLE 4-continued

Percent Inhibition Values for Examples A33, A39 and A42 at 0.1 μM Concentration

| Kinase | % Inhibition @ 0.1 μM | | |
|---|---|---|---|
| | A33 | A39 | A42 |
| Lck activated | 41 | 62 | 90 |
| MuSK | 18 | 72 | 90 |
| Ret (V804L) | 43 | 24 | 60 |
| Ron | 42 | 3 | 62 |
| Ros | 23 | 17 | 93 |
| Tie2 | 83 | 32 | 98 |
| Tie2 (R849W) | 40 | 38 | 83 |
| Tie2 (Y897S) | 49 | 40 | 92 |
| TrkA | 97 | 93 | 100 |
| TrkB | 98 | 70 | 101 |

Table 4 above shows the percent inhibition values obtained for Examples A33, A39, and A42 at 0.1 μM concentration. From the panel of 284 kinases, only examples which showed greater than 50% inhibition at 0.1 μM are reported in Table 4. From this inhibition data it is apparent that certain kinases, e.g. Ab1, Arg, AurA, AurB, FGFR3, TrkA and TRKB kinase are inhibited by compounds of the invention. These activities may impart additional therapeutic benefit to these compounds.

Example J: Cancer Cell Line Data of Compounds of the Invention

Breast cancer cells (MCF-7, MDA-MB-468, HCC1954), colon cancer cells (SW620) and lung cancer cells (A549), together with human mammary epithelial primary cells (HMEC), were seeded (1000 to 4000 per 80 μl per well depending on the cell growth rate) into 96 well plates, 24 hours before compound overlay. Compounds were prepared as 10 mM stock solutions in 100% DMSO which were diluted with DMEM (Dulbecco's Modified Eagle's Medium) cell growth Medium (Invitrogen, Burlington, ON, Canada) containing 10% FBS (Fetal Bovine Serum) to concentrations ranging from 50 nM to 250 μM. Aliquots (20 μl) from each concentration were overlaid to 80 μl of the pre-seeded cells in the 96 well plates to make final concentrations of 10 nM to 50 μM. The cells were cultured for 5 days before the Sulforhodamine B assay (SRB) was performed to determine the compound's cell growth inhibition activity.

Sulforhodamine B (purchased from Sigma, Oakville, ON, Canada) is a water-soluble dye that binds to the basic amino acids of the cellular proteins. Thus, colorimetric measurement of the bound dye provides an estimate of the total protein mass that is related to the cell number. the cells are fixed in situ by gently aspirating off the culture media and adding 50 μl ice cold 10% Trichloroacetic Acid (TCA) per well and incubate at 4° C. for 30-60 min. The plates are washed with water five times and allowed to air dry for 5 min. Addition of 50 μl 0.4% (w/v) SRB solution in 1% (v/v) acetic acid to each well and incubatation for 30 min at RT completes the staining reaction. Following staining, plates are washed four times with 1% acetic acid to remove unbound dye and then allowed to air dry for 5 min. The stain is solubilized with 100 μl of 10 mM Tris pH 10.5 per well. Absorbance is read at 570 nm.

The percentage (%) of relative growth inhibition was calculated by comparing to DMSO treated only cells (100%). $GI_{50}$'s were determined for compounds with cytotoxic activity. The $GI_{50}$ was calculated using GraphPad PRISM software (GraphPad Software, Inc., San Diego, Calif., USA). $GI_{50}$ (growth inhibition) is the compound concentration that causes 50% inhibition of cell growth.

In Table 5 below, $GI_{50}$ value ranges for several compound examples against a luminal breast cancer cell line (MCF-7), two basal breast cancer cell line (MDA-MB-468, HCC1954), a lung cancer cell line (A549), a colon cancer cell line (SW-620) and primary breast cells (HMEC) are given. The example compounds demonstrated varying growth inhibition/cell killing activity against cancer cells of luminal breast cancer and basal breast cancer cell, lung cancer and colon cancer. In general, these compounds showed less or little activity against normal cells as exemplified by HMEC. The $GI_{50}$ ranges are indicated as "A," "B," "C," and "D," for values less than or equal to 0.1 μM; those greater than 0.1 μM and less than or equal to 1 μM; those greater than 1 μM and less than or equal to 10 μM; and those greater than 10 μM, respectively.

TABLE 5

Cell Growth Inhibition Data

| Example # | Cell Line $GI_{50}$ Range | | | | | |
|---|---|---|---|---|---|---|
| | MCF-7 | MDA-MB-468 | A-549 | SW-620 | HCC-1954 | HMEC |
| A2 | D | D | D | D | D | — |
| A4 | C | C | D | C | C | — |
| A6 | B | B | B | B | B | — |
| A7 | B | B | B | B | B | — |
| A13 | A | B | A | A | B | D |
| A14 | A | A | A | A | C | — |
| A15 | C | C | C | C | C | — |
| A16 | A | B | A | C | C | D |
| A17 | C | C | C | C | — | — |
| A18 | B | B | C | C | C | — |
| A19 | B | B | B | C | B | — |
| A20 | C | B | C | D | C | — |
| A21 | A | B | C | C | D | — |
| A22 | B | B | B | B | C | D |
| A23 | A | A | A | A | C | D |
| A24 | B | A | A | A | | D |
| A25 | C | B | B | C | D | — |
| A26 | B | B | B | B | C | — |
| A27 | C | B | C | C | C | — |
| A28 | C | A | C | A | C | — |
| A29 | C | A | B | B | C | C |
| A30 | C | B | B | B | C | C |
| A31 | A | A | A | B | C | — |
| A33 | A | A | A | A | A | D |
| A34 | — | — | — | B | C | — |
| A35 | A | A | A | A | C | D |
| A37 | D | B | A | A | D | — |
| A38 | B | A | A | B | D | — |
| A39 | A | A | A | A | C | D |
| A41 | A | A | A | C | C | — |
| A42 | A | A | A | A | B | D |
| A43 | C | C | C | C | D | — |
| A45 | C | B | B | C | D | — |
| A46 | C | C | C | D | D | — |
| A47 | C | C | C | C | C | — |
| A48 | A | A | A | C | C | — |
| A49 | A | A | A | C | C | — |
| A50 | C | B | B | C | D | — |
| A51 | A | A | A | A | A | — |
| A52 | C | C | B | C | C | — |
| A55 | B | A | A | B | C | — |
| A56 | B | A | A | A | B | D |
| A57 | B | B | B | B | C | — |
| A58 | D | A | A | A | C | D |
| A59 | — | A | A | A | C | D |
| A60 | A | A | A | B | | — |
| A60 | B | A | A | A | A | C |
| A61 | C | A | A | A | C | — |

TABLE 5-continued

Cell Growth Inhibition Data

Cell Line GI$_{50}$ Range

| Example # | MCF-7 | MDA-MB-468 | A-549 | SW-620 | HCC-1954 | HMEC |
|---|---|---|---|---|---|---|
| A62 | A | A | A |  | C | — |
| A63 | A | A | A | A | C | — |
| A64 | A | A | A | A | B | — |
| A65 | B | A | A | A | A | D |
| A65 | A | A | A | A | B | — |
| A67 | A | A | A | A | A | — |
| A68 | A | A | A | A | A | — |
| A69 | A | A | A | A | B | — |
| A70 | C | B | B | C | C | — |
| A71 | B | B | B | B | B | — |
| A72 | B | A | A | A | C | — |
| A73 | C | A | A | A | C | — |
| A74 | C | A | A | A | C | — |
| A75 | B | A | A | A | D | — |
| A76 | B | B | B | C | C | — |
| A77 | C | B | B | B | C | — |
| A78 | C | A | A | A | B | — |
| A79 | B | A | A | A | C | — |
| A83 | C | A | A | A | C | — |
| A86 | D | C | C | C | D | — |
| A87 | A | A | A | B | C | — |
| A89 | C | A | A | B | C | — |
| A90 | A | A | A | A | B | — |
| A91 | A | A | A | A | C | — |
| A92 | A | A | A | A | B | D |
| A93 | C | C | C | C | C | — |
| A94 | A | A | A | A | B | — |
| A95 | C | A | A | A | C | — |
| A96 | A | A | A | A | C | — |
| A97 | A | A | A | A | B | D |
| A98 | B | A | A | A | D | — |
| A99 | A | A | A | A | B | D |
| A100 | B | B | A | A | C | — |
| A101 | B | A | A | B | C | — |
| A102 | C | A | A | B | D | — |
| A103 | A | A | A | A | C | — |
| A104 | B | B | A | B | B | — |
| A105 | A | A | A | A | A | D |
| A106 | D | A | A | A | A | C |
| A107 | C | B | C | C | D | — |
| A108 | B | B | B | C | C | — |
| A109 | A | A | A | A | A | — |
| A110 | A | A | A | A | A | — |
| A111 | D | A | A | B | D | — |
| A112 | A | A | A | A | C | — |
| A115 | C | A | A | A | B | — |
| A116 | A | A | A | B | B | — |
| A117 | C | B | C | D | D | — |
| A118 | C | B | C | C | D | — |
| A119 | A | A | A | A | B | — |
| A120 | A | A | A | A | B | D |
| A121 | B | B | B | C | C | — |
| A122 | A | A | A | A | B | — |
| A123 | B | A | B | B | C | — |
| A124 | B | B | A | B | C | — |
| A126 | A | A | A | A | C | — |
| A127 | C | A | A | A | C | — |
| A129 | A | A | A | A | C | — |
| A130 | C | C | D | D | D | — |
| A131 | C | A | A | A | B | — |
| A132 | B | A | A | A | C | D |
| A133 | A | A | A | B | D | — |
| A134 | A | A | A | A | B | D |
| A135 | A | A | A | B | D | — |
| A136 | C | C | C | D | D | — |
| A138 | B | B | B | C | C | — |
| A139 | B | B | B | C | C | — |
| A140 | A | A | A | C | C | — |
| A145 | B | B | B | C | C | — |
| A146 | C | A | A | A | C | — |
| A147 | A | A | A | B | C | — |
| A148 | B | B | B | C | D | — |
| A149 | C | C | D | D | D | — |
| A150 | B | B | B | B | D | — |
| A151 | B | B | A | B | C | D |
| A152 | B | A | A | B | C | — |
| A154 | C | C | C | D | D | — |
| A155 | C | C | C | C | D | — |
| A157 | C | A | A | B | C | — |
| A158 | C | A | B | B | D | — |
| A159 | B | B | B | C | D | — |
| A160 | C | A | A | A | A | D |
| A161 | C | B | B | B | C | — |
| A162 | B | A | A | B | C | — |
| A163 | A | A | A | A | C | — |
| A165 | C | A | A | A | C | — |
| A166 | C | B | B | B | D | — |
| A167 | B | A | A | A | C | — |
| A168 | B | B | A | B | B | — |
| A169 | A | A | A |  | C | — |
| A171 | A | A | A | A | C | — |
| A172 | B | A | A | A | C | — |
| A173 | B | B | B | B | B | — |
| A174 | A | A | A | A | B | — |
| A175 | B | A | A | A | B | C |
| A176 | B | A | A | A | B | — |
| A177 | A | A | A | A | A | — |
| A178 | A | A | A | A | B | — |
| A179 | A | A | A | A | C | — |
| A180 | B | A | A | A | B | — |
| A181 | A | A | A | A | B | — |
| A182 | A | A | A | A | A | — |
| A183 | A | A | A | A | C | — |
| A184 | B | A | A | A | D | — |
| A185 | A | A | A | B | A | — |
| A186 | B | A | A | A | C | — |
| A187 | A | A | A | A | B | — |
| A188 | A | A | A | A | B | — |
| A189 | A | A | A | A | A | C |
| A190 | A | A | A | A | A | C |
| A191 | C | A | A | B | C | D |
| A192 | B | A | A | A | B | D |
| A193 | B | A | A | B | A | C |
| A194 | A | A | A | B | D | D |
| A196 | A | A | A | A | B | — |
| A197 | A | A | A | A | B | — |
| A198 | A | A | A | B | A | — |
| A199 | A | A | A | A | D | — |
| A200 | D | A | A | A | C | — |
| A201 | B | A | A | A | B | — |
| A202 | C | A | A | A | C | — |
| A203 | A | A | A | A | C | — |
| A204 | C | A | A | A | D | — |
| A205 | B | A | A | A | B | — |
| A206 | A | A | A | A | C | — |
| A207 | B | B | A | A | C | — |
| A208 | B | A | A | A | B | — |
| A209 | B | B | B | C | C | — |
| A210 | B | B | B | B | C | — |
| A211 | B | A | A | B | C | — |
| A212 | A | A | A | A | C | — |
| A213 | C | A | A | A | D | — |
| A214 | A | A | A | C | C | — |
| A215 | A | A | A | A | A | — |
| A216 | B | A | A | A | C | — |
| A217 | A | A | A | B | B | — |
| A218 | A | A | A | B | A | — |
| A219 | B | A | A | A | B | — |
| A220 | B | A | A | A | D | — |
| A221 | D | A | A | B | C | — |

In addition to the cell lines tested as described above, selected compounds have been assayed against an extended panel. These include: breast cancer cell lines (T47 D, MDA-MB-231, HS578T, BT474, SKBR3, HCC1954), a lung cancer cell line (H358), brain cancer cell lines (A172, Hs683, SK-N-SH), Colon cancer cell lines (Colo 205, CT-15, HCT116+/−, HCT116+/+), ovarian cancer cell lines (OVCAR-3, SK-OV-3, SW 626), a melanoma cell line (518A2), a prostate cancer cell line (PC-3) and an immortalized breast cell line (184A1). The sulforhodamine B assay (SRB) described above was use to assay test compounds against the extended panel (Table 6). The $GI_{50}$ ranges are indicated as "A," "B," "C," and "D," for values less than or equal to 0.1 µM; those greater than 0.1 µM and less than or equal to 1 µM; those greater than 1 µM and less than or equal to 50 µM; and those greater than 50 µM, respectively.

TABLE 6

Cell Growth Inhibition Data

| Cell line | $GI_{50}$ Range Example # | | |
|---|---|---|---|
| | A13 | A22 | A23 |
| T47 D | C | C | A |
| MDA-MB-231 | A | B | A |
| HS578T | C | B | A |
| BT474 | C | C | C |
| SKBR3 | C | C | C |
| H358 | A | C | A |
| A172 | A | B | A |
| Hs683 | A | B | A |
| SK-N-SH | D | C | A |
| Colo 205 | A | B | A |
| HCT-15 | C | B | C |
| HCT116+/− | C | C | C |
| HCT116+/+ | C | C | C |
| OVCAR-3 | A | C | A |
| SK-OV-3 | C | C | C |
| SW 626 | C | C | C |
| 518A2 | A | B | A |
| PC-3 | C | C | C |
| 184A1 | B | C | C |

Example K: In Vitro Angiogenesis Assay

Certain compounds of the invention exhibited micromolar and submicromolar activity against Receptor Tyrosine Kinaseas (RTKs) such as FGFR2, VEGFR1, VEGFR2 and PDGFDbeta. Activity against these RTKs can result in antiangiogenic activity which is associated with slowed tumor growth and/or tumor regression. To measure the antiangiogenic effects of compounds of the invention, selected examples were tested in an angiogenesis assay as described below. Note that compound Examples A13, A22 and A23 showed anti-agiogenic effects at submicromolar concentrations (FIGS. 1 and 2).

HUV-EC-C cells were obtained from the American Type Culture Collection (ATCC, CRL-1730), and were used at early passage for the assay. The in vitro Angiogenesis Assay Kit (Chemicon) was used according to the manufacturer's recommendation. An ice-cold mixture of ECMatrix was transferred into a precooled 96-well plate. After the matrix solution had solidified (>1 hr incubation at 37° C.), 8,000 cells were mixed with the appropriate inhibitor concentration (in 100 microliters EGM-2) and plated into each well. The clinical antiangiogenic, Sutent was used as a positive control in comparison to a compound of the invention, A13. After incubation at 37° C. for 4 hr, tube formation was inspected. Two methods, pattern recognition and branch point counting, were used to quantify the progression of angiogenesis and expressed as a percentage of the control tube count (FIGS. 1 and 2).

While this invention has been particularly shown and described with reference to example embodiments thereof, it will be understood by those skilled in the art that various changes in form and details may be made therein without departing from the scope of the invention encompassed by the appended claims.

What is claimed is:

1. A method of alleviating or ameliorating one or more symptoms of cancer in a subject with prostate cancer, comprising administering to a subject an effective amount of a compound represented by the following structural formula:

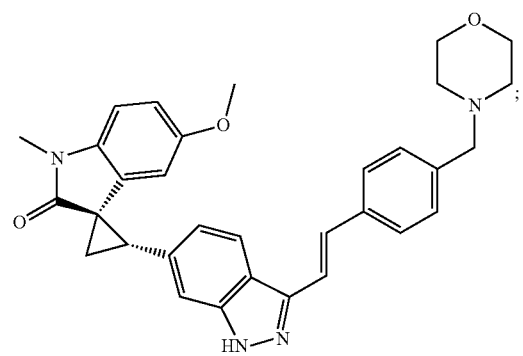 [SMILES: COc1ccc2c(c1)[C@]1(C[C@H]1c1ccc3c(/C=C/c4ccc(CN5CCOCC5)cc4)n[nH]c3c1)C(=O)N2C]

or a pharmaceutically acceptable salt thereof.

2. The method of claim 1, further comprising co-administering an additional therapeutic agent.

3. A method of alleviating or ameliorating one or more symptoms of cancer in a subject with prostate cancer, comprising administering to a subject an effective amount of a compound represented by the following structural formula:

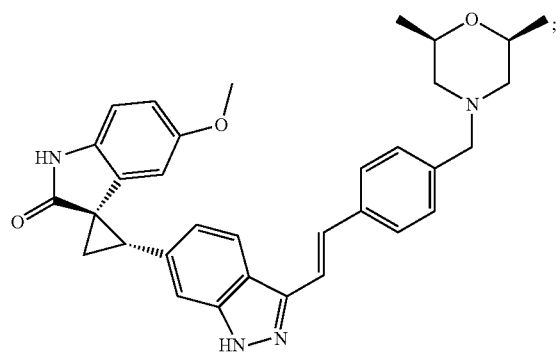 [SMILES: COc1ccc2c(c1)[C@]1(C[C@H]1c1ccc3c(/C=C/c4ccc(CN5C[C@@H](C)O[C@@H](C)C5)cc4)n[nH]c3c1)C(=O)N2]

or a pharmaceutically acceptable salt thereof.

4. The method of claim 3, further comprising co-administering an additional therapeutic agent.

5. A method of alleviating or ameliorating one or more symptoms of cancer in a subject with prostate cancer, comprising administering to a subject an effective amount of a compound represented by the following structural formula:

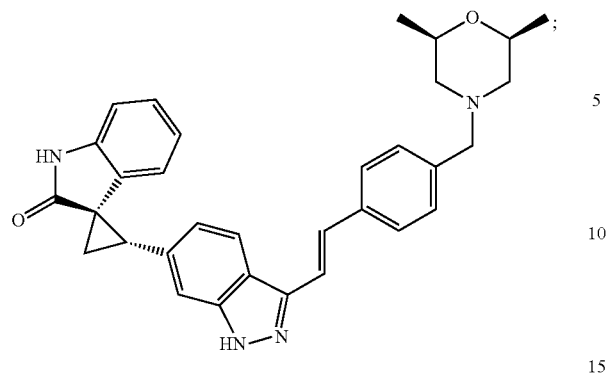
or a pharmaceutically acceptable salt thereof.
6. The method of claim 5, further comprising co-administering an additional therapeutic agent.
\* \* \* \* \*